United States Patent
Grice et al.

(10) Patent No.: US 11,149,037 B2
(45) Date of Patent: Oct. 19, 2021

(54) PYRAZOLE MAGL INHIBITORS

(71) Applicant: H. Lundbeck A/S, Valby (DK)

(72) Inventors: Cheryl A. Grice, Encinitas, CA (US); Olivia D. Weber, San Diego, CA (US); Daniel J. Buzard, San Diego, CA (US); Michael B. Shaghafi, San Diego, CA (US); John J. M. Wiener, La Jolla, CA (US); Justin S. Cisar, San Diego, CA (US); Katharine K. Duncan, San Diego, CA (US)

(73) Assignee: H. LUNDBECK A/S, Valby (DK)

( * ) Notice: Subject to any disclaimer, the term of this patent is extended or adjusted under 35 U.S.C. 154(b) by 0 days.

(21) Appl. No.: 16/615,746

(22) PCT Filed: May 22, 2018

(86) PCT No.: PCT/US2018/033964
§ 371 (c)(1),
(2) Date: Nov. 21, 2019

(87) PCT Pub. No.: WO2018/217809
PCT Pub. Date: Nov. 29, 2018

(65) Prior Publication Data
US 2020/0087304 A1    Mar. 19, 2020

Related U.S. Application Data

(60) Provisional application No. 62/510,223, filed on May 23, 2017.

(51) Int. Cl.
| | | |
|---|---|---|
| *A61K 31/4155* | (2006.01) |
| *A61K 31/438* | (2006.01) |
| *A61K 31/4439* | (2006.01) |
| *A61K 31/496* | (2006.01) |
| *A61P 25/00* | (2006.01) |
| *C07D 401/06* | (2006.01) |
| *C07D 401/12* | (2006.01) |
| *C07D 401/14* | (2006.01) |
| *C07D 403/06* | (2006.01) |
| *C07D 403/12* | (2006.01) |
| *C07D 403/14* | (2006.01) |
| *C07D 409/14* | (2006.01) |
| *C07D 413/14* | (2006.01) |
| *C07D 417/14* | (2006.01) |
| *C07D 471/04* | (2006.01) |
| *C07D 471/10* | (2006.01) |
| *C07D 487/04* | (2006.01) |
| *C07D 487/10* | (2006.01) |
| *C07D 491/048* | (2006.01) |
| *C07D 491/08* | (2006.01) |
| *C07D 519/00* | (2006.01) |
| *C07D 498/08* | (2006.01) |

(52) U.S. Cl.
CPC ......... *C07D 471/10* (2013.01); *C07D 401/06* (2013.01); *C07D 401/14* (2013.01); *C07D 403/06* (2013.01); *C07D 403/14* (2013.01); *C07D 409/14* (2013.01); *C07D 413/14* (2013.01); *C07D 417/14* (2013.01); *C07D 471/04* (2013.01); *C07D 487/04* (2013.01); *C07D 487/10* (2013.01); *C07D 491/048* (2013.01); *C07D 498/08* (2013.01); *C07D 519/00* (2013.01)

(58) Field of Classification Search
CPC .............. A61K 31/4155; A61K 31/438; A61K 31/4439; A61K 31/496; A61P 25/00; C07D 401/06; C07D 401/12; C07D 401/14; C07D 403/06; C07D 403/12; C07D 403/14; C07D 409/14; C07D 413/14; C07D 417/14; C07D 471/04; C07D 471/10; C07D 487/04; C07D 487/10; C07D 491/048; C07D 491/08; C07D 519/00
See application file for complete search history.

(56) References Cited

U.S. PATENT DOCUMENTS

| | | |
|---|---|---|
| 3,308,130 A | 3/1967 | Bousquet |
| 7,772,236 B2 | 8/2010 | Beavers et al. |
| 10,266,497 B2 | 4/2019 | Grice et al. |
| 10,323,038 B2 | 6/2019 | Grice et al. |
| 10,385,057 B2 | 8/2019 | Grice et al. |
| 10,519,134 B2 | 12/2019 | Grice et al. |

(Continued)

FOREIGN PATENT DOCUMENTS

| | | |
|---|---|---|
| WO | WO-2010074588 A2 | 7/2010 |
| WO | WO-2013078771 A1 | 6/2013 |

(Continued)

OTHER PUBLICATIONS

Sawant et al., Necessity of Establishing Chemical Integrity of Polymorphs of Drug Substance Using a Combination of NMR, PLC, Elemental Analysis, and Solid-State Characterization Techniques: Case Studies, Organic Process Research & Development, vol. 17, pp. 519-532 (Year: 2013).*

(Continued)

*Primary Examiner* — Brenda L Coleman
(74) *Attorney, Agent, or Firm* — Wilson Sonsini Goodrich & Rosati

(57) ABSTRACT

Provided herein are pyrazole compounds and pharmaceutical compositions comprising said compounds. The subject compounds and compositions are useful as modulators of MAGL. Furthermore, the subject compounds and compositions are useful for the treatment of pain.

24 Claims, No Drawings

(56) References Cited

U.S. PATENT DOCUMENTS

| | | | |
|---|---|---|---|
| 10,927,105 | B1 | 2/2021 | Grice et al. |
| 2003/0013712 | A1 | 1/2003 | Tullis et al. |
| 2006/0183780 | A1 | 8/2006 | Hallberg et al. |
| 2007/0027328 | A1* | 2/2007 | Aronhime ............... A61P 3/06 548/537 |
| 2011/0172230 | A1 | 7/2011 | Ishii et al. |
| 2012/0065191 | A1 | 3/2012 | Kiss et al. |
| 2014/0018318 | A1 | 1/2014 | Cravatt et al. |
| 2015/0051211 | A1 | 2/2015 | Ji et al. |
| 2016/0318864 | A1 | 11/2016 | Koike et al. |
| 2017/0029390 | A1 | 2/2017 | Butler et al. |
| 2017/0190669 | A1 | 7/2017 | Boger et al. |
| 2018/0344729 | A1 | 12/2018 | Cravatt et al. |
| 2021/0053960 | A1 | 2/2021 | Grice |

FOREIGN PATENT DOCUMENTS

| | | | |
|---|---|---|---|
| WO | WO-2015179559 | A2 | 11/2015 |
| WO | WO-2016014975 | A2 | 1/2016 |
| WO | WO-2017087854 | A1 | 5/2017 |
| WO | WO-2017087858 | A1 | 5/2017 |
| WO | WO-2017087863 | A1 | 5/2017 |
| WO | WO-2017096315 | A1 | 6/2017 |
| WO | WO-2018217805 | A1 | 11/2018 |
| WO | WO-2018217809 | A1 | 11/2018 |

OTHER PUBLICATIONS

Baggelaar et al. Development of an activity-based probe and in silico design reveal highly selective inhibitors for diacylglycerol lipase-α in brain. Angew Chem Int Ed Engl 52(46):12081-12085 (2013).
Berge et al. Pharmaceutical Salts. Journal of Pharmaceutical Sciences 66(1):1-19 (Jan. 1977).
Blankman et al. A comprehensive profile of brain enzymes that hydrolyze the endocannabinoid 2-arachidonoylglycerol. Chem. Biol. 14:1347-1356 (2007).
Bundgaard et al. Design of Prodrugs pp. 7-9, 21-24 (1985).
Fleisher et al. Improved oral drug delivery: solubility limitations overcome by the use of prodrugs. Advanced Drug Delivery Reviews 19:115-130 (1996).
Horig et al. From bench to clinic and back: Perspective on the 1st IQPC Translational Research conference. J Trans Med 2(1):44 (2004).
Hsu et al. Development and Optimization of Piperidyl-1,2,3-Triazole Ureas as Selective Chemical Probes of Endocannabinoid Biosynthesis. J Med Chem 56:8257-8269 (2013).
Hsu et al. Discovery and optimization of piperidyl-1,2,3-triazole ureas as potent, selective, and in vivo-active inhibitors of a/β-hydrolase domain containing 6 (ABHD6). J Med Chem 56:8270-8279 (2012).
Hsu et al. Supporting Information for Development and Optimization of Piperidyl-1,2,3-Triazole Ureas as Selective Chemical Probes of Endocannabinoid Biosynthesis. J Med Chem 56:8257-8269, S1-S18 (2013).
Janssen et al. Discovery of glycine sulfonamides as dual inhibitors of sn-1-diacylglycerol lipase α and α/β-hydrolase domain 6. J Med Chem 57(15):6610-6622 (2014).

Kohnz et al. Chemical approaches to therapeutically target the metabolism and signaling of the endocannabinoid 2-AG and eicosanoids. Chem Soc Rev 43(19):6859-6869 (2014).
Korhonen et al. Piperazine and piperidine carboxamides and carbamates as inhibitors of fatty acid amide hydrolase (FAAH) and monoacylglycerol lipase (MAGL). Bioorg Med Chem 22(23):6694-6705 (2014).
Long et al. Selective blockade of 2-arachidonoylglycerol hydrolysis produces cannabinoid behavioral effects. Nat Chem Biol. 5(1):37-44 (2009).
Lysenko et al. Monoacylglycerol lipase inhibitor JZL184 improves behavior and neural properties in Ts65Dn mice, a model of down syndrome. PLoS One 9(12):e114521 (2013).
Morren et al. The filaricidal derivatives of 1-methylpiperazine. Bulletin des Societes Chimiques Belges 59(3-4):228-237 (1950).
Mulvihill et al. Therapeutic potential of monoacylglycerol lipase inhibitors. Life Sci 92(8-9):492-497 (2013).
Niphakis et al. O-Hydroxyacetamide Carbamates as a Highly Potent and Selective Class of Endocannabinoid Hydrolase Inhibitors. ACS Chem. Neurosci. 3(5):418-426 (2012/Web2011).
Ogasawara et al. Rapid and profound rewiring of brain lipid signaling networks by acute diacylglycerol lipase inhibition. PNAS USA 113(1):26-33 (2016).
Otrubova et al. Discovery libraries targeting the major enzyme classes: the serine hydrolases. Bioorg Med Chem Lett 24(16):3807-3813 (2014).
PCT/US2015/031834 International Search Report and Written Opinion dated Apr. 20, 2016.
PCT/US2016/062862 International Search Report and Written Opinion dated Jan. 27, 2017.
PCT/US2016/062868 International Search Report and Written Opinion dated Jan. 30, 2017.
PCT/US2016/062873 International Search Report and Written Opinion dated Jan. 27, 2017.
PCT/US2016/064844 International Search Report and Written Opinion dated Feb. 15, 2017.
PCT/US2018/033959 International Search Report and Written Opinion dated Jul. 23, 2018.
PCT/US2018/033964 International Preliminary Report on Patentability dated Dec. 5, 2019.
PCT/US2018/033964 International Search Report and Written Opinion dated Sep. 13, 2018.
PCT/US2018/033964 Invitation to Pay Additional Fees dated Jul. 20, 2018.
Schafer et al. Failure is an option: learning from unsuccessful proof-of-concept trials. Drug Discov Today 13(21-22):913-916 (2008).
U.S. Appl. No. 15/312,998 Office Action dated Nov. 2, 2017.
U.S. Appl. No. 15/778,207 Office Action dated Jun. 6, 2019.
Van Den Nieuwendijk et al. Synthesis of Eight 1-Deoxynojirimycin Isomers from a Single Chiral Cyanohydrin. Eur JOC 18:3437-3446 (2012).
Van Den Nieuwendijk et al. Synthesis of L-altro-1-deoxynojirimycin, D-allo-1-deoxynojirimycin, and D-galacto-1-deoxynojirimycin from a single chiral cyanohydrin. Org lett 12(17):3957-3959 (2010).
Van Der Wel et al. A natural substrate-based fluorescence assay for inhibitor screening on diacylglycerol lipase α. J Lipid Res 56(4):927-935 (2015).
U.S. Appl. No. 16/615,747 Office Action dated Jun. 21, 2021.

* cited by examiner

PYRAZOLE MAGL INHIBITORS

CROSS-REFERENCE

This application is a US National Stage entry of PCT application PCT/US2018/33964, filed on May 22, 2018, which claims the benefit of U.S. Provisional Application No. 62/510,223, filed on May 23, 2017, which is are herein incorporated by reference in its their entirety.

BACKGROUND

Monoacylglycerol lipase (MAGL) is an enzyme responsible for hydrolyzing endocannabinoids such as 2-AG (2-arachidonoylglycerol), an arachidonate based lipid, in the nervous system. Fatty acid amide hydrolase (FAAH) is another enzyme responsible for hydrolyzing endocannabinoids such as anandamide.

BRIEF SUMMARY OF THE INVENTION

This disclosure provides, for example, compounds and compositions which are modulators of MAGL, and their use as medicinal agents, processes for their preparation, and pharmaceutical compositions that include disclosed compounds as at least one active ingredient. The disclosure also provides for the use of disclosed compounds as medicaments and/or in the manufacture of medicaments for the inhibition of MAGL activity in warm-blooded animals such as humans.

In one aspect is a compound of Formula (I):

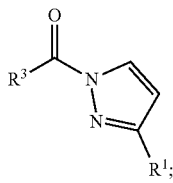

Formula (I)

wherein:
$R^1$ is $-N(R^2)C(O)R^{15}$ or $-N(H)SO_2R^{15}$;
$R^2$ is H or $C_{1-6}$alkyl;
$R^3$ is

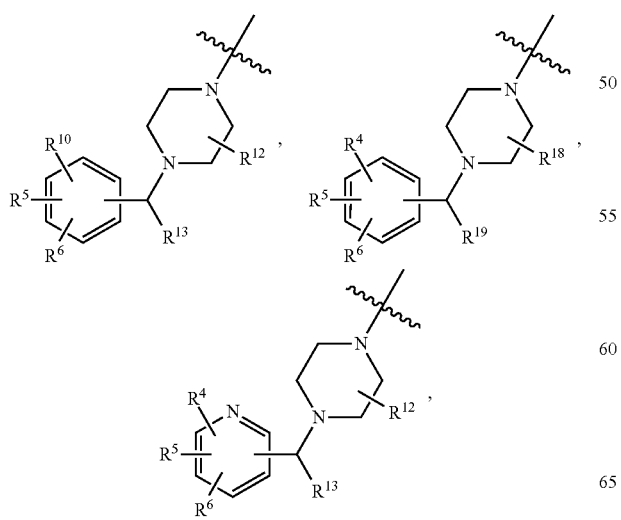

-continued

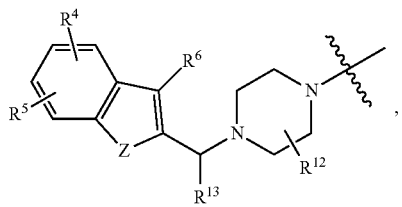

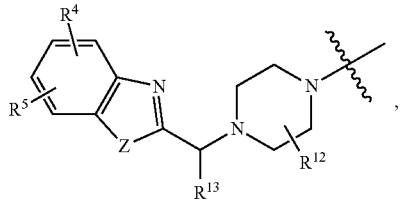

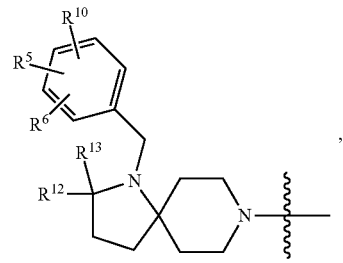

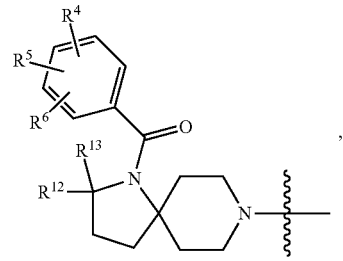

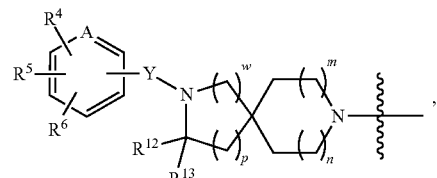

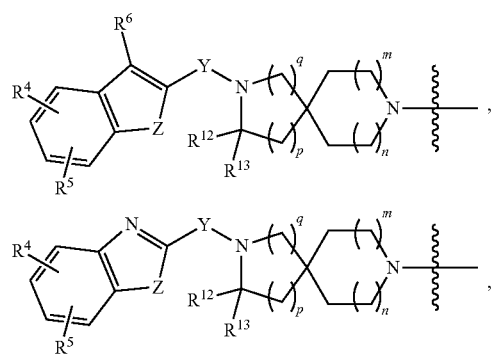

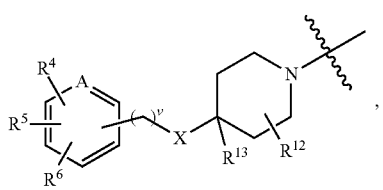

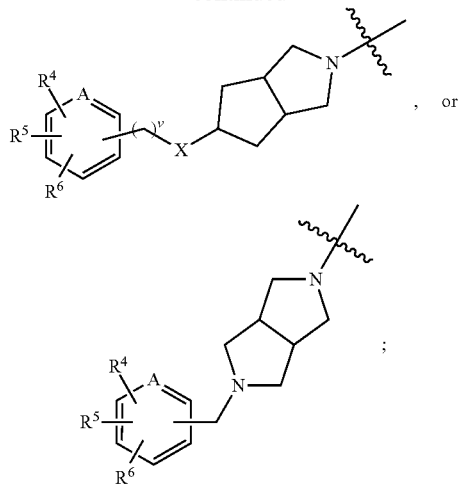

, or

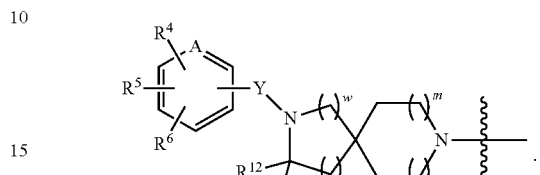

;

A is N or C(H);
X is —O—, —N($R^{16}$)—, or —$CH_2$N($R^{16}$)$CH_2$—;
Y is —$CH_2$— or —C(O)—;
Z is —S—, —O—, or —N($R^{20}$)—;
$R^4$ is H, halogen, —$OR^7$, $C_{1-6}$alkyl, $C_{1-6}$alkyl-OH, $C_{2-6}$alkenyl, $C_{2-6}$alkynyl, —O—$C_{3-8}$cycloalkyl, —O—$C_{3-8}$cycloalkyl-OH, —N(H)—$C_{1-6}$alkyl-$CO_2$H, —$SO_2R^{17}$, —$CO_2R^8$, —C(O)$NR^8R^9$, $C_{3-8}$cycloalkyl, $C_{2-9}$heterocycloalkyl, —$C_{1-6}$alkyl-$C_{2-9}$heterocycloalkyl, $C_{6-10}$aryl, $C_{1-9}$heteroaryl, wherein $C_{3-8}$cycloalkyl, $C_{2-9}$heterocycloalkyl, —$C_{1-6}$alkyl-$C_{2-9}$heterocycloalkyl, $C_{6-10}$aryl, $C_{1-9}$heteroaryl are optionally substituted with 1 or 2 $R^{14}$;
$R^5$ is H, —CN, halogen, $C_{1-6}$alkyl, $C_{1-6}$haloalkoxy, or phenyl;
$R^6$ is H, halogen, or $C_{1-6}$alkyl;
$R^7$ is H, $C_{1-6}$alkyl, $C_{1-6}$haloalkyl, $C_{3-8}$cycloalkyl, $C_{2-9}$heterocycloalkyl, $C_{6-10}$aryl, or $C_{1-9}$heteroaryl, wherein $C_{2-9}$heterocycloalkyl, $C_{6-10}$aryl, or $C_{1-9}$heteroaryl are optionally substituted with 1 or 2 $R^{14}$;
each $R^8$ and each $R^9$ are independently selected from H and $C_{1-6}$alkyl; or $R^8$ and $R^9$ together with the nitrogen to which they are attached are combined to form a heterocycloalkyl ring;
$R^{10}$ is —O—$C_{1-6}$haloalkyl, —O—$C_{1-6}$alkyl-$CO_2$H, —O—$C_{3-8}$cycloalkyl, —O—$C_{3-8}$cycloalkyl-$CO_2$H, —N(H)—$C_{1-6}$alkyl-$CO_2$H, or —$SO_2R^{17}$;
$R^{12}$ is H, halogen, or $C_{1-6}$alkyl;
$R^{13}$ is H or $C_{1-6}$alkyl;
each $R^{14}$ is independently selected from halogen, —OH, oxo, $C_{1-6}$alkyl, $C_{1-6}$haloalkyl, $C_{1-6}$alkoxy, —$C_{1-6}$alkyl-OH, $C_{3-8}$cycloalkyl, —$CO_2R^8$, —C(O)$NR^8R^9$, —C(O)—$C_{1-6}$alkyl, —C(O)—$C_{1-6}$alkyl-OH, —$SO_2$—$C_{1-6}$alkyl, —N($R^8$)$SO_2$—$C_{1-6}$alkyl, and —N($R^8$)C(O)—$C_{1-6}$alkyl;
$R^{15}$ is $C_{1-6}$alkyl or $C_{3-8}$cycloalkyl;
$R^{16}$ is H, $C_{1-6}$alkyl, —C(O)—$C_{1-6}$alkyl, or —$CH_2CO_2H$;
$R^{17}$ is $C_{1-6}$alkyl or $C_{3-8}$cycloalkyl;
$R^{18}$ and $R^{19}$ are independently selected from H and $C_{1-6}$alkyl, wherein $R^{18}$ and $R^{19}$ are not both H;
$R^{20}$ is H or $C_{1-6}$alkyl;
v is 0 or 1;
n is 0 or 1;
m is 0 or 1;
p is 0, 1, or 2;
q is 0, 1, or 2; and
w is 1 or 2;
or a solvate, hydrate, tautomer, N-oxide, stereoisomer, or pharmaceutically acceptable salt thereof.

In some embodiments is a compound of Formula (I), or a solvate, hydrate, tautomer, N-oxide, stereoisomer, or pharmaceutically acceptable salt thereof, wherein $R^3$ is

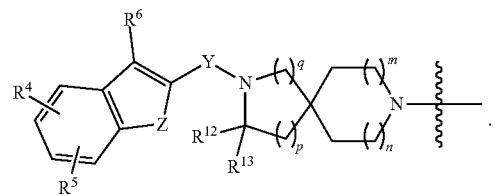

In another embodiment is a compound of Formula (I), or a solvate, hydrate, tautomer, N-oxide, stereoisomer, or pharmaceutically acceptable salt thereof, wherein m is 1, n is 1, p is 1, and w is 1. In another embodiment is a compound of Formula (I), or a solvate, hydrate, tautomer, N-oxide, stereoisomer, or pharmaceutically acceptable salt thereof, wherein m is 0, n is 1, p is 1, and w is 2. In another embodiment is a compound of Formula (I), or a solvate, hydrate, tautomer, N-oxide, stereoisomer, or pharmaceutically acceptable salt thereof, wherein m is 1, n is 1, p is 0, and w is 1. In another embodiment is a compound of Formula (I), or a solvate, hydrate, tautomer, N-oxide, stereoisomer, or pharmaceutically acceptable salt thereof, wherein A is C(H). In another embodiment is a compound of Formula (I), or a solvate, hydrate, tautomer, N-oxide, stereoisomer, or pharmaceutically acceptable salt thereof, wherein A is N. In some embodiments is a compound of Formula (I), or a solvate, hydrate, tautomer, N-oxide, stereoisomer, or pharmaceutically acceptable salt thereof, wherein $R^3$ is In another embodiment is a compound of Formula (I), or a solvate, hydrate, tautomer, N-oxide, stereoisomer, or pharmaceutically acceptable salt thereof, wherein m is 1, n is 1, q is 1, and p is 1. In another embodiment is a compound of Formula (I), or a solvate, hydrate, tautomer, N-oxide, stereoisomer, or pharmaceutically acceptable salt thereof, wherein m is 0, n is 1, q is 2, and p is 1. In another embodiment is a compound of Formula (I), or a solvate, hydrate, tautomer, N-oxide, stereoisomer, or pharmaceutically acceptable salt thereof, wherein m is 1, n is 1, q is 0, and p is 2. In another embodiment is a compound of Formula (I), or a solvate, hydrate, tautomer, N-oxide, stereoisomer, or pharmaceutically acceptable salt thereof, wherein m is 1, n is 1, q is 1, and p is 0. In another embodiment is a compound of Formula (I), or a solvate, hydrate, tautomer, N-oxide, stereoisomer, or pharmaceutically acceptable salt thereof, wherein Z is —S—. In another embodiment is a compound of Formula (I), or a solvate, hydrate, tautomer, N-oxide, stereoisomer, or pharmaceutically acceptable salt thereof, wherein Z is —N(H)—. In another embodiment is a compound of Formula (I), or a solvate, hydrate, tautomer, N-oxide, stereoisomer, or pharmaceutically acceptable salt thereof, wherein Y is —CH$_2$—. In another embodiment is a compound of Formula (I), or a solvate, hydrate, tautomer, N-oxide, stereoisomer, or pharmaceutically acceptable salt thereof, wherein Y is —C(O)—. In another embodiment is a compound of Formula (I), or a solvate, hydrate, tautomer, N-oxide, stereoisomer, or pharmaceutically acceptable salt thereof, wherein R$^3$ is

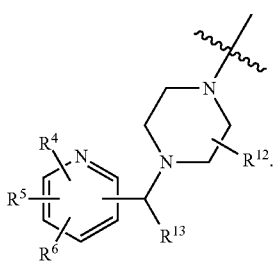

In another embodiment is a compound of Formula (I), or a solvate, hydrate, tautomer, N-oxide, stereoisomer, or pharmaceutically acceptable salt thereof, wherein R$^3$ is

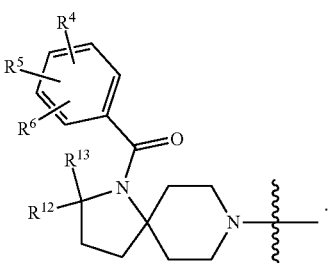

In another embodiment is a compound of Formula (I), or a solvate, hydrate, tautomer, N-oxide, stereoisomer, or pharmaceutically acceptable salt thereof, wherein R$^6$ is H. In another embodiment is a compound of Formula (I), or a solvate, hydrate, tautomer, N-oxide, stereoisomer, or pharmaceutically acceptable salt thereof, wherein R$^3$ is

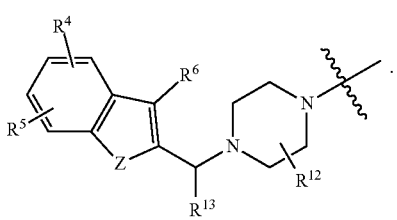

In another embodiment is a compound of Formula (I), or a solvate, hydrate, tautomer, N-oxide, stereoisomer, or pharmaceutically acceptable salt thereof, wherein R$^3$ is

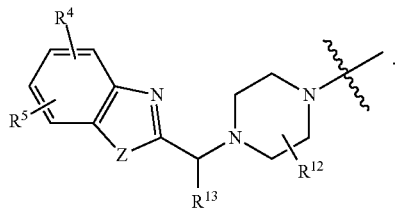

In another embodiment is a compound of Formula (I), or a solvate, hydrate, tautomer, N-oxide, stereoisomer, or pharmaceutically acceptable salt thereof, wherein Z is —S—. In another embodiment is a compound of Formula (I), or a solvate, hydrate, tautomer, N-oxide, stereoisomer, or pharmaceutically acceptable salt thereof, wherein Z is —N(H)—. In another embodiment is a compound of Formula (I), or a solvate, hydrate, tautomer, N-oxide, stereoisomer, or pharmaceutically acceptable salt thereof, wherein R$^{13}$ is H. In another embodiment is a compound of Formula (I), or a solvate, hydrate, tautomer, N-oxide, stereoisomer, or pharmaceutically acceptable salt thereof, wherein R$^{12}$ is H. In another embodiment is a compound of Formula (I), or a solvate, hydrate, tautomer, N-oxide, stereoisomer, or pharmaceutically acceptable salt thereof, wherein R$^3$ is

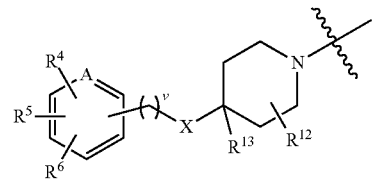

In another embodiment is a compound of Formula (I), or a solvate, hydrate, tautomer, N-oxide, stereoisomer, or pharmaceutically acceptable salt thereof, wherein R$^{13}$ is H. In another embodiment is a compound of Formula (I), or a solvate, hydrate, tautomer, N-oxide, stereoisomer, or pharmaceutically acceptable salt thereof, wherein R$^{13}$ is —CH$_3$. In another embodiment is a compound of Formula (I), or a solvate, hydrate, tautomer, N-oxide, stereoisomer, or pharmaceutically acceptable salt thereof, wherein R$^{12}$ is H. In another embodiment is a compound of Formula (I), or a solvate, hydrate, tautomer, N-oxide, stereoisomer, or pharmaceutically acceptable salt thereof, wherein R$^3$ is

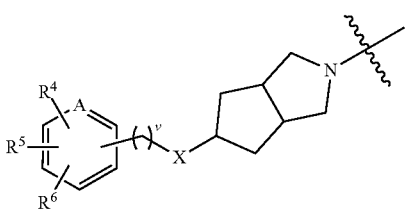

In another embodiment is a compound of Formula (I), or a solvate, hydrate, tautomer, N-oxide, stereoisomer, or pharmaceutically acceptable salt thereof, wherein v is 0. In another embodiment is a compound of Formula (I), or a solvate, hydrate, tautomer, N-oxide, stereoisomer, or pharmaceutically acceptable salt thereof, wherein v is 1. In another embodiment is a compound of Formula (I), or a solvate, hydrate, tautomer, N-oxide, stereoisomer, or pharmaceutically acceptable salt thereof, wherein X is —O—. In another embodiment is a compound of Formula (I), or a solvate, hydrate, tautomer, N-oxide, stereoisomer, or pharmaceutically acceptable salt thereof, wherein X is —N(CH₃)—. In another embodiment is a compound of Formula (I), or a solvate, hydrate, tautomer, N-oxide, stereoisomer, or pharmaceutically acceptable salt thereof, wherein $R^3$ is

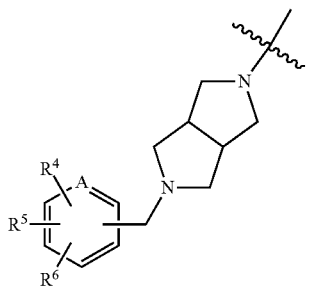

In another embodiment is a compound of Formula (I), or a solvate, hydrate, tautomer, N-oxide, stereoisomer, or pharmaceutically acceptable salt thereof, wherein A is C(H). In another embodiment is a compound of Formula (I), or a solvate, hydrate, tautomer, N-oxide, stereoisomer, or pharmaceutically acceptable salt thereof, wherein A is N. In another embodiment is a compound of Formula (I), or a solvate, hydrate, tautomer, N-oxide, stereoisomer, or pharmaceutically acceptable salt thereof, wherein $R^3$ is

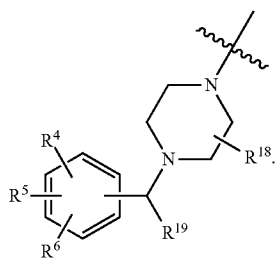

In another embodiment is a compound of Formula (I), or a solvate, hydrate, tautomer, N-oxide, stereoisomer, or pharmaceutically acceptable salt thereof, wherein $R^{18}$ is $C_{1-6}$alkyl. In another embodiment is a compound of Formula (I), or a solvate, hydrate, tautomer, N-oxide, stereoisomer, or pharmaceutically acceptable salt thereof, wherein $R^{18}$ is —CH₃ and $R^{19}$ is H. In another embodiment is a compound of Formula (I), or a solvate, hydrate, tautomer, N-oxide, stereoisomer, or pharmaceutically acceptable salt thereof, wherein $R^{19}$ is $C_{1-6}$alkyl. In another embodiment is a compound of Formula (I), or a solvate, hydrate, tautomer, N-oxide, stereoisomer, or pharmaceutically acceptable salt thereof, wherein $R^{18}$ is H and $R^{19}$ is —CH₃. In another embodiment is a compound of Formula (I), or a solvate, hydrate, tautomer, N-oxide, stereoisomer, or pharmaceutically acceptable salt thereof, wherein $R^6$ is H. In another embodiment is a compound of Formula (I), or a solvate, hydrate, tautomer, N-oxide, stereoisomer, or pharmaceutically acceptable salt thereof, wherein $R^4$ is halogen, —OR⁷, $C_{1-6}$alkyl-OH, —N(H)—$C_{1-6}$alkyl-CO₂H, $C_{2-6}$alkynyl, $C_{1-6}$haloalkyl, —CO₂R⁸, —C(O)NR⁸R⁹, $C_{3-8}$cycloalkyl, $C_{2-9}$heterocycloalkyl, $C_{6-10}$aryl, or $C_{1-9}$heteroaryl, wherein $C_{3-8}$cycloalkyl, $C_{2-9}$heterocycloalkyl, $C_{6-10}$aryl, or $C_{1-9}$heteroaryl are optionally substituted with 1 or 2 $R^{14}$. In another embodiment is a compound of Formula (I), or a solvate, hydrate, tautomer, N-oxide, stereoisomer, or pharmaceutically acceptable salt thereof, wherein $R^4$ is halogen, —OR⁷, —N(H)—$C_{1-6}$alkyl-CO₂H, $C_{1-6}$haloalkyl, —C(O)NR⁸R⁹, $C_{3-8}$cycloalkyl, $C_{2-9}$heterocycloalkyl, or $C_{1-9}$heteroaryl, wherein $C_{2-9}$heterocycloalkyl or $C_{1-9}$heteroaryl are optionally substituted with 1 or 2 $R^{14}$. In another embodiment is a compound of Formula (I), or a solvate, hydrate, tautomer, N-oxide, stereoisomer, or pharmaceutically acceptable salt thereof, wherein $R^4$ is halogen. In another embodiment is a compound of Formula (I), or a solvate, hydrate, tautomer, N-oxide, stereoisomer, or pharmaceutically acceptable salt thereof, wherein $R^4$ is —Cl. In another embodiment is a compound of Formula (I), or a solvate, hydrate, tautomer, N-oxide, stereoisomer, or pharmaceutically acceptable salt thereof, wherein $R^4$ is $C_{1-6}$haloalkyl. In another embodiment is a compound of Formula (I), or a solvate, hydrate, tautomer, N-oxide, stereoisomer, or pharmaceutically acceptable salt thereof, wherein $R^4$ is —CF₃. In another embodiment is a compound of Formula (I), or a solvate, hydrate, tautomer, N-oxide, stereoisomer, or pharmaceutically acceptable salt thereof, wherein $R^4$ is —N(H)—$C_{1-6}$alkyl-CO₂H. In another embodiment is a compound of Formula (I), or a solvate, hydrate, tautomer, N-oxide, stereoisomer, or pharmaceutically acceptable salt thereof, wherein $R^4$ is —OR⁷. In another embodiment is a compound of Formula (I), or a solvate, hydrate, tautomer, N-oxide, stereoisomer, or pharmaceutically acceptable salt thereof, wherein $R^7$ is unsubstituted $C_{3-8}$cycloalkyl or $C_{6-10}$aryl optionally substituted with halogen. In another embodiment is a compound of Formula (I), or a solvate, hydrate, tautomer, N-oxide, stereoisomer, or pharmaceutically acceptable salt thereof, wherein $R^4$ is $C_{2-9}$heterocycloalkyl optionally substituted with 1 or 2 $R^{14}$. In another embodiment is a compound of Formula (I), or a solvate, hydrate, tautomer, N-oxide, stereoisomer, or pharmaceutically acceptable salt thereof, wherein $R^4$ is an unsubstituted $C_{2-9}$heterocycloalkyl. In another embodiment is a compound of Formula (I), or a solvate, hydrate, tautomer, N-oxide, stereoisomer, or pharmaceutically acceptable salt thereof, wherein $R^4$ is $C_{2-9}$heterocycloalkyl substituted with 1 or 2 $R^{14}$. In another embodiment is a compound of Formula (I), or a solvate, hydrate, tautomer, N-oxide, stereoisomer, or pharmaceutically acceptable salt thereof, wherein $R^4$ is

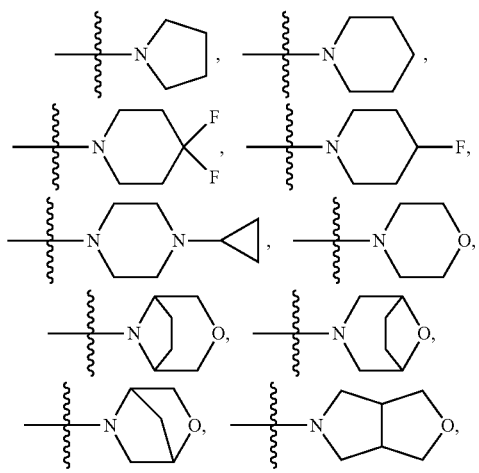

-continued

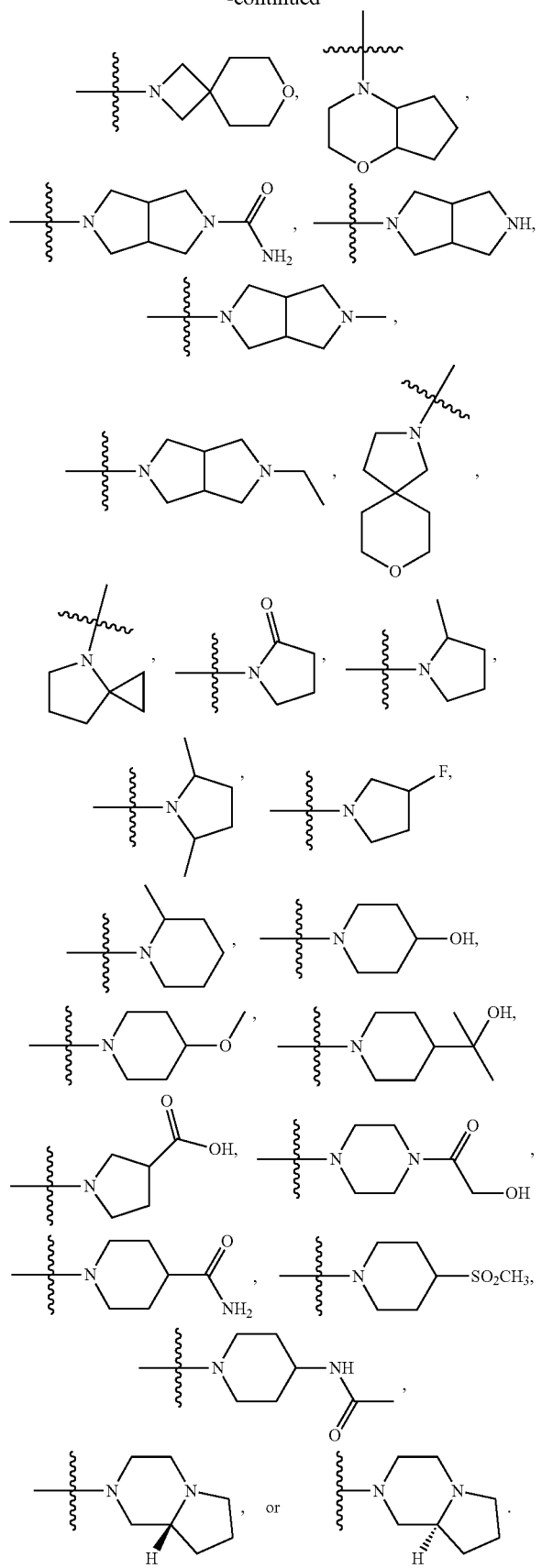

In another embodiment is a compound of Formula (I), or a solvate, hydrate, tautomer, N-oxide, stereoisomer, or pharmaceutically acceptable salt thereof, wherein $R^4$ is $C_{1-9}$heteroaryl optionally substituted with 1 or 2 $R^{14}$. In another embodiment is a compound of Formula (I), or a solvate, hydrate, tautomer, N-oxide, stereoisomer, or pharmaceutically acceptable salt thereof, wherein $R^4$ is an unsubstituted $C_{1-9}$heteroaryl. In another embodiment is a compound of Formula (I), or a solvate, hydrate, tautomer, N-oxide, stereoisomer, or pharmaceutically acceptable salt thereof, wherein $R^4$ is $C_{2-9}$heteroaryl substituted with 1 or 2 $R^{14}$. In another embodiment is a compound of Formula (I), or a solvate, hydrate, tautomer, N-oxide, stereoisomer, or pharmaceutically acceptable salt thereof, wherein $R^4$ is

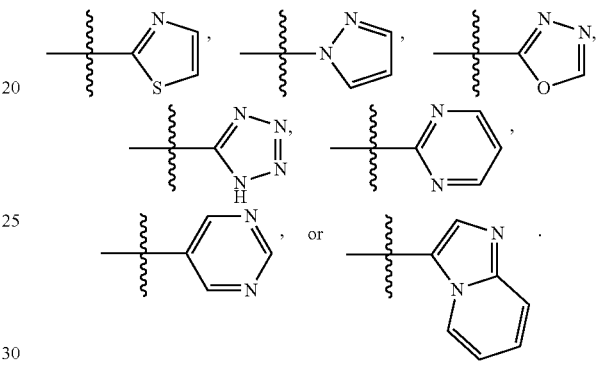

In another embodiment is a compound of Formula (I), or a solvate, hydrate, tautomer, N-oxide, stereoisomer, or pharmaceutically acceptable salt thereof, wherein $R^4$ is —C(O)NH$_2$. In another embodiment is a compound of Formula (I), or a solvate, hydrate, tautomer, N-oxide, stereoisomer, or pharmaceutically acceptable salt thereof, wherein $R^3$ is

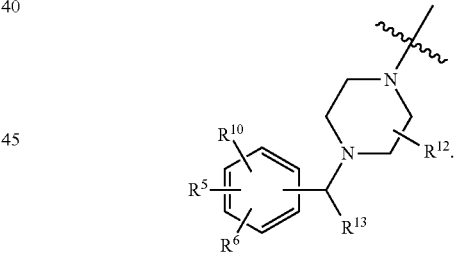

In another embodiment is a compound of Formula (I), or a solvate, hydrate, tautomer, N-oxide, stereoisomer, or pharmaceutically acceptable salt thereof, wherein $R^3$ is

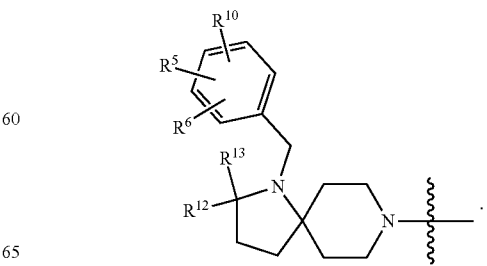

In another embodiment is a compound of Formula (I), or a solvate, hydrate, tautomer, N-oxide, stereoisomer, or pharmaceutically acceptable salt thereof, wherein $R^{10}$ is —O—$C_{1-6}$alkyl-$CO_2H$. In another embodiment is a compound of Formula (I), or a solvate, hydrate, tautomer, N-oxide, stereoisomer, or pharmaceutically acceptable salt thereof, wherein $R^{10}$ is —$OCH_2CO_2H$ or —$OCH_2CH_2CH_2CO_2H$. In another embodiment is a compound of Formula (I), or a solvate, hydrate, tautomer, N-oxide, stereoisomer, or pharmaceutically acceptable salt thereof, wherein $R^{10}$ is —N(H)—$C_{1-6}$alkyl-$CO_2H$. In another embodiment is a compound of Formula (I), or a solvate, hydrate, tautomer, N-oxide, stereoisomer, or pharmaceutically acceptable salt thereof, wherein $R^{10}$ is —N(H)$CH_2CO_2H$, —N(H)$CH_2CH_2CO_2H$, or —N(H)$CH_2CH_2CH_2CO_2H$. In another embodiment is a compound of Formula (I), or a solvate, hydrate, tautomer, N-oxide, stereoisomer, or pharmaceutically acceptable salt thereof, wherein $R^6$ is H. In another embodiment is a compound of Formula (I), or a solvate, hydrate, tautomer, N-oxide, stereoisomer, or pharmaceutically acceptable salt thereof, wherein $R^5$ is H, —CN, halogen, $C_{1-6}$alkyl, $C_{1-6}$haloalkyl, or $C_{1-6}$haloalkoxy. In another embodiment is a compound of Formula (I), or a solvate, hydrate, tautomer, N-oxide, stereoisomer, or pharmaceutically acceptable salt thereof, wherein $R^5$ is H. In another embodiment is a compound of Formula (I), or a solvate, hydrate, tautomer, N-oxide, stereoisomer, or pharmaceutically acceptable salt thereof, wherein $R^5$ is halogen. In another embodiment is a compound of Formula (I), or a solvate, hydrate, tautomer, N-oxide, stereoisomer, or pharmaceutically acceptable salt thereof, wherein $R^5$ is —Cl. In another embodiment is a compound of Formula (I), or a solvate, hydrate, tautomer, N-oxide, stereoisomer, or pharmaceutically acceptable salt thereof, wherein $R^5$ is $C_{1-6}$haloalkyl. In another embodiment is a compound of Formula (I), or a solvate, hydrate, tautomer, N-oxide, stereoisomer, or pharmaceutically acceptable salt thereof, wherein $R^5$ is —$CF_3$. In another embodiment is a compound of Formula (I), or a solvate, hydrate, tautomer, N-oxide, stereoisomer, or pharmaceutically acceptable salt thereof, wherein $R^1$ is —N($R^2$)C(O)$R^{15}$. In another embodiment is a compound of Formula (I), or a solvate, hydrate, tautomer, N-oxide, stereoisomer, or pharmaceutically acceptable salt thereof, wherein $R^2$ is H. In another embodiment is a compound of Formula (I), or a solvate, hydrate, tautomer, N-oxide, stereoisomer, or pharmaceutically acceptable salt thereof, wherein $R^{15}$ is $C_{1-6}$alkyl. In another embodiment is a compound of Formula (I), or a solvate, hydrate, tautomer, N-oxide, stereoisomer, or pharmaceutically acceptable salt thereof, wherein $R^{15}$ is —$CH_3$. In another embodiment is a compound of Formula (I), or a solvate, hydrate, tautomer, N-oxide, stereoisomer, or pharmaceutically acceptable salt thereof, wherein $R^1$ is —N(H)$SO_2R^{15}$. In another embodiment is a compound of Formula (I), or a solvate, hydrate, tautomer, N-oxide, stereoisomer, or pharmaceutically acceptable salt thereof, wherein $R^{15}$ is $C_{1-6}$alkyl. In another embodiment is a compound of Formula (I), or a solvate, hydrate, tautomer, N-oxide, stereoisomer, or pharmaceutically acceptable salt thereof, wherein $R^{15}$ is —$CH_3$.

In another embodiment is a pharmaceutical composition comprising a compound of Formula (I) described herein, or a solvate, hydrate, tautomer, N-oxide, or a pharmaceutically acceptable salt thereof, and at least one pharmaceutically acceptable excipient.

In another embodiment is a method of treating pain in a patient in need thereof, comprising administering to the patient a therapeutically effective amount of a compound of Formula (I) described herein, or a solvate, hydrate, tautomer, N-oxide, or a pharmaceutically acceptable salt thereof. In another embodiment is a method of treating neuropathic pain in a patient in need thereof, comprising administering to the patient a therapeutically effective amount of a compound of Formula (I) described herein, or a solvate, hydrate, tautomer, N-oxide, or a pharmaceutically acceptable salt thereof. In another embodiment is a method of treating inflammatory pain in a patient in need thereof, comprising administering to the patient a therapeutically effective amount of a compound of Formula (I) described herein, or a solvate, hydrate, tautomer, N-oxide, or a pharmaceutically acceptable salt thereof.

In another embodiment is a method of treating a disease or disorder in a patient comprising administering to the patient in need thereof a therapeutically effective amount of a compound of Formula (I) described herein, or a solvate, hydrate, tautomer, N-oxide, or a pharmaceutically acceptable salt thereof, wherein the disease is selected from migraine, epilepsy/seizure disorder, neuromyelitis optica (NMO), Tourette syndrome, persistent motor tic disorder, persistent vocal tic disorder, and abdominal pain associated with irritable bowel syndrome. In another embodiment is a method of treating migraine in a patient in need thereof, comprising administering to the patient a therapeutically effective amount of a compound of Formula (I) described herein, or a solvate, hydrate, tautomer, N-oxide, or a pharmaceutically acceptable salt thereof. In another embodiment is a method of treating epilepsy/seizure disorder in a patient in need thereof, comprising administering to the patient a therapeutically effective amount of a compound of Formula (I) described herein, or a solvate, hydrate, tautomer, N-oxide, or a pharmaceutically acceptable salt thereof. In another embodiment is a method of treating neuromyelitis optica (NMO) in a patient in need thereof, comprising administering to the patient a therapeutically effective amount of a compound of Formula (I) described herein, or a solvate, hydrate, tautomer, N-oxide, or a pharmaceutically acceptable salt thereof. In another embodiment is a method of treating Tourette syndrome in a patient in need thereof, comprising administering to the patient a therapeutically effective amount of a compound of Formula (I) described herein, or a solvate, hydrate, tautomer, N-oxide, or a pharmaceutically acceptable salt thereof. In another embodiment is a method of treating persistent motor tic disorder in a patient in need thereof, comprising administering to the patient a therapeutically effective amount of a compound of Formula (I) described herein, or a solvate, hydrate, tautomer, N-oxide, or a pharmaceutically acceptable salt thereof. In another embodiment is a method of treating persistent vocal tic disorder in a patient in need thereof, comprising administering to the patient a therapeutically effective amount of a compound of Formula (I) described herein, or a solvate, hydrate, tautomer, N-oxide, or a pharmaceutically acceptable salt thereof. In another embodiment is a method of treating abdominal pain associated with irritable bowel syndrome in a patient in need thereof, comprising administering to the patient a therapeutically effective amount of a compound of Formula (I) described herein, or a solvate, hydrate, tautomer, N-oxide, or a pharmaceutically acceptable salt thereof.

DETAILED DESCRIPTION OF THE INVENTION

This disclosure is directed, at least in part, to modulators or inhibitors of MAGL. For example, provided herein are compounds capable of inhibiting MAGL.

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range varies between 1% and 15% of the stated number or numerical range. The term "comprising" (and related terms such as "comprise" or "comprises" or "having" or "including") is not intended to exclude that which in other certain embodiments, for example, an embodiment of any composition of matter, composition, method, or process, or the like, described herein, may "consist of" or "consist essentially of" the described features.

Definitions

As used in the specification and appended claims, unless specified to the contrary, the following terms have the meaning indicated below.

As used herein, $C_1$-$C_x$ includes $C_1$-$C_2$, $C_1$-$C_3$ ... $C_1$-$C_x$. $C_1$-$C_x$ refers to the number of carbon atoms that make up the moiety to which it designates (excluding optional substituents).

"Amino" refers to the —$NH_2$ radical.

"Cyano" refers to the —CN radical.

"Nitro" refers to the —$NO_2$ radical.

"Oxa" refers to the —O— radical.

"Oxo" refers to the =O radical.

"Thioxo" refers to the =S radical.

"Imino" refers to the =N—H radical.

"Oximo" refers to the =N—OH radical.

"Alkyl" or "alkylene" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises one to six carbon atoms (e.g., $C_1$-$C_6$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), and 1-pentyl (n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, —$OR^a$, —$SR^a$, —OC(O)—$R^f$, —$N(R^a)_2$, —C(O)$R^a$, —C(O)O$R^a$, —C(O)N($R^a$)$_2$, —$N(R^a)$C(O)O$R^f$, —OC(O)—N$R^aR^f$, —$N(R^a)$C(O)$R^f$, —$N(R^a)$S(O)$_tR^f$ (where t is 1 or 2), —S(O)$_t$O$R^a$ (where t is 1 or 2), —S(O)$_tR^f$ (where t is 1 or 2) and —S(O)$_t$N($R^a$)$_2$ (where t is 1 or 2) where each $R^a$ is independently hydrogen, alkyl, haloalkyl, cycloalkyl, aryl, aralkyl, heterocycloalkyl, heteroaryl, or heteroarylalkyl, and each $R^f$ is independently alkyl, haloalkyl, cycloalkyl, aryl, aralkyl, heterocycloalkyl, heteroaryl, or heteroarylalkyl.

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —$OR^a$, —$SR^a$, —OC(O)—$R^f$, —$N(R^a)_2$, —C(O)$R^a$, —C(O)O$R^a$, —C(O)N($R^a$)$_2$, —$N(R^a)$C(O)O$R^f$, —OC(O)—N$R^aR^f$, —$N(R^a)$C(O)$R^f$, —$N(R^a)$S(O)$_tR^f$ (where t is 1 or 2), —S(O)$_t$O$R^a$ (where t is 1 or 2), —S(O)$_tR^f$ (where t is 1 or 2) and —S(O)$_t$N($R^a$)$_2$ (where t is 1 or 2) where each $R^a$ is independently hydrogen, alkyl, haloalkyl, cycloalkyl, aryl, aralkyl, heterocycloalkyl, heteroaryl, or heteroarylalkyl, and each $R^f$ is independently alkyl, haloalkyl, cycloalkyl, aryl, aralkyl, heterocycloalkyl, heteroaryl, or heteroarylalkyl.

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl has two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —$OR^a$, —$SR^a$, —OC(O)—$R^f$, —$N(R^a)_2$, —C(O)$R^a$, —C(O)O$R^a$, —C(O)N($R^a$)$_2$, —$N(R^a)$C(O)O$R^f$, —OC(O)—N$R^aR^f$, —$N(R^a)$C(O)$R^f$, —$N(R^a)$S(O)$_tR^f$ (where t is 1 or 2), —S(O)$_t$O$R^a$ (where t is 1 or 2), —S(O)$_tR^f$ (where t is 1 or 2) and —S(O)$_t$N($R^a$)$_2$ (where t is 1 or 2) where each $R^a$ is independently hydrogen, alkyl, haloalkyl, cycloalkyl, aryl, aralkyl, heterocycloalkyl, heteroaryl, or heteroarylalkyl, and each $R^f$ is independently alkyl, haloalkyl, cycloalkyl, aryl, aralkyl, heterocycloalkyl, heteroaryl, or heteroarylalkyl.

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from six to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents selected from alkyl, alkenyl, alkynyl, halo, haloalkyl, cyano, nitro, aryl, aralkyl, aralkenyl, aralkynyl, cycloalkyl, heterocycloalkyl, heteroaryl, heteroarylalkyl, —$R^b$—$OR^a$, —$R^b$—$OC(O)$—$R^a$, —$R^b$—$OC(O)$—$OR^a$, —$R^b$—$OC(O)$—$N(R^a)_2$, —$R^b$—$N(R^a)_2$, —$R^b$—$C(O)R^a$, —$R^b$—$C(O)OR^a$, —$R^b$—$C(O)N(R^a)_2$, —$R^b$—$O$—$R^c$—$C(O)N(R^a)_2$, —$R^b$—$N(R^a)C(O)OR^a$, —$R^b$—$N(R^a)C(O)R^a$, —$R^b$—$N(R^a)S(O)_tR^a$ (where t is 1 or 2), —$R^b$—$S(O)_tOR^a$ (where t is 1 or 2), —$R^b$—$S(O)_tR^a$ (where t is 1 or 2), and —$R^b$—$S(O)_tN(R^a)_2$ (where t is 1 or 2), where each $R^a$ is independently hydrogen, alkyl, haloalkyl, cycloalkyl, cycloalkylalkyl, aryl, aralkyl, heterocycloalkyl, heteroaryl, or heteroarylalkyl, each $R^b$ is independently a direct bond or a straight or branched alkylene or alkenylene chain, and $R^c$ is a straight or branched alkylene or alkenylene chain.

"Aryloxy" refers to a radical bonded through an oxygen atom of the formula —O-aryl, where aryl is as defined above.

"Aralkyl" refers to a radical of the formula —$R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkyloxy" refers to a radical bonded through an oxygen atom of the formula —O-aralkyl, where aralkyl is as defined above.

"Aralkenyl" refers to a radical of the formula $R^d$-aryl where $R^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —$R^e$-aryl, where $R^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Cycloalkyl" refers to a stable non-aromatic monocyclic or polycyclic hydrocarbon radical consisting solely of carbon and hydrogen atoms, which includes fused or bridged ring systems, having from three to fifteen carbon atoms. In certain embodiments, a cycloalkyl comprises three to ten carbon atoms. In other embodiments, a cycloalkyl comprises five to seven carbon atoms. The cycloalkyl is attached to the rest of the molecule by a single bond. Cycloalkyls are saturated, (i.e., containing single C—C bonds only) or partially unsaturated (i.e., containing one or more double bonds or triple bonds.) Examples of monocyclic cycloalkyls include, e.g., cyclopropyl, cyclobutyl, cyclopentyl, cyclohexyl, cycloheptyl, and cyclooctyl. In certain embodiments, a cycloalkyl comprises three to eight carbon atoms (e.g., $C_3$-$C_8$ cycloalkyl). In other embodiments, a cycloalkyl comprises three to seven carbon atoms (e.g., $C_3$-$C_7$ cycloalkyl). In other embodiments, a cycloalkyl comprises three to six carbon atoms (e.g., $C_3$-$C_6$ cycloalkyl). In other embodiments, a cycloalkyl comprises three to five carbon atoms (e.g., $C_3$-$C_5$ cycloalkyl). In other embodiments, a cycloalkyl comprises three to four carbon atoms (e.g., $C_3$-$C_4$ cycloalkyl). A partially unsaturated cycloalkyl is also referred to as "cycloalkenyl." Examples of monocyclic cycloalkenyls include, e.g., cyclopentenyl, cyclohexenyl, cycloheptenyl, and cyclooctenyl. Polycyclic cycloalkyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless stated otherwise specifically in the specification, the term "cycloalkyl" is meant to include cycloalkyl radicals that are optionally substituted by one or more substituents selected from alkyl, alkenyl, alkynyl, halo, haloalkyl, oxo, thioxo, cyano, nitro, aryl, aralkyl, aralkenyl, aralkynyl, cycloalkyl, heterocycloalkyl, heteroaryl, heteroarylalkyl, —$R^b$—$OR^a$, —$R^b$—$OC(O)$—$R^a$, —$R^b$—$OC(O)$—$OR^a$, —$R^b$—$OC(O)$—$N(R^a)_2$, —$R^b$—$N(R^a)_2$, —$R^b$—$C(O)R^a$, —$R^b$—$C(O)OR^a$, —$R^b$—$C(O)N(R^a)_2$, —$R^b$—$O$—$R^c$—$C(O)N(R^a)_2$, —$R^b$—$N(R^a)C(O)OR^a$, —$R^b$—$N(R^a)C(O)R^a$, —$R^b$—$N(R^a)S(O)_tR^a$ (where t is 1 or 2), —$R^b$—$S(O)_tOR^a$ (where t is 1 or 2), —$R^b$—$S(O)_tR^a$ (where t is 1 or 2), and —$R^b$—$S(O)_tN(R^a)_2$ (where t is 1 or 2), where each $R^a$ is independently hydrogen, alkyl, haloalkyl, cycloalkyl, cycloalkylalkyl, aryl, aralkyl, heterocycloalkyl, heteroaryl, or heteroarylalkyl, each $R^b$ is independently a direct bond or a straight or branched alkylene or alkenylene chain, and $R^c$ is a straight or branched alkylene or alkenylene chain.

"Halo" or "halogen" refers to bromo, chloro, fluoro or iodo substituents.

"Haloalkyl" refers to an alkyl radical, as defined above, that is substituted by one or more halo radicals, as defined above.

"Haloalkoxy" refers to an alkoxy radical, as defined above, that is substituted by one or more halo radicals, as defined above.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. The alkyl part of the fluoroalkyl radical are optionally substituted as defined above for an alkyl group.

"Heterocycloalkyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocycloalkyl radical is a monocyclic, bicyclic, tricyclic, or tetracyclic ring system, which include fused, spiro, or bridged ring systems. The heteroatoms in the heterocycloalkyl radical are optionally oxidized. One or more nitrogen atoms, if present, are optionally quaternized. The heterocycloalkyl radical is partially or fully saturated. In some embodiments, the heterocycloalkyl is attached to the rest of the molecule through any atom of the ring(s). Examples of such heterocycloalkyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxothiomorpholinyl, and 1,1-dioxo-thiomorpholinyl. Unless stated otherwise specifically in the specification, the term "heterocycloalkyl" is meant to include heterocycloalkyl radicals as defined above that are optionally substituted by one or more substituents selected from alkyl, alkenyl, alkynyl, halo, haloalkyl, oxo, thioxo, cyano, nitro, aryl, aralkyl, aralkenyl, aralkynyl, cycloalkyl, heterocycloalkyl, heteroaryl, heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$ (where t is 1 or 2), —$R^b$—S(O)$_t$$OR^a$ (where t is 1 or 2), —$R^b$—S(O)$_t$$R^a$ (where t is 1 or 2), and —$R^b$—S(O)$_t$N($R^a$)$_2$ (where t is 1 or 2), where each $R^a$ is independently hydrogen, alkyl, haloalkyl, cycloalkyl, cycloalkylalkyl, aryl, aralkyl, heterocycloalkyl, heteroaryl, or heteroarylalkyl, each $R^b$ is independently a direct bond or a straight or branched alkylene or alkenylene chain, and $R^c$ is a straight or branched alkylene or alkenylene chain.

"Heteroaryl" refers to a radical derived from a 3- to 18-membered aromatic ring radical that comprises one to seventeen carbon atoms and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Unless stated otherwise specifically in the specification, the term "heteroaryl" is meant to include heteroaryl radicals as defined above which are optionally substituted by one or more substituents selected from alkyl, alkenyl, alkynyl, halo, haloalkyl, oxo, thioxo, cyano, nitro, aryl, aralkyl, aralkenyl, aralkynyl, cycloalkyl, heterocycloalkyl, heteroaryl, heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$N($R^a$)C(O)$R^a$, —$R^b$—N($R^a$)S(O)$_t$$R^a$ (where t is 1 or 2), —$R^b$—S(O)$_t$$OR^a$ (where t is 1 or 2), —$R^b$—S(O)$_t$$R^a$ (where t is 1 or 2), and —$R^b$—S(O)$_t$N($R^a$)$_2$ (where t is 1 or 2), where each $R^a$ is independently hydrogen, alkyl, haloalkyl, cycloalkyl, cycloalkylalkyl, aryl, aralkyl, heterocycloalkyl, heteroaryl, or heteroarylalkyl, each $R^b$ is independently a direct bond or a straight or branched alkylene or alkenylene chain, and $R^c$ is a straight or branched alkylene or alkenylene chain.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroaryloxy" refers to radical bonded through an oxygen atom of the formula —O-heteroaryl, where heteroaryl is as defined above.

"Heteroarylalkyl" refers to a radical of the formula —$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula —O—$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

In some embodiments, the compounds disclosed herein contain one or more asymmetric centers and thus give rise to enantiomers, diastereomers, and other stereoisomeric forms that are defined, in terms of absolute stereochemistry, as (R)- or (S)-. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

A "tautomer" refers to a molecule wherein a proton shift from one atom of a molecule to another atom of the same molecule is possible. In certain embodiments, the compounds presented herein exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

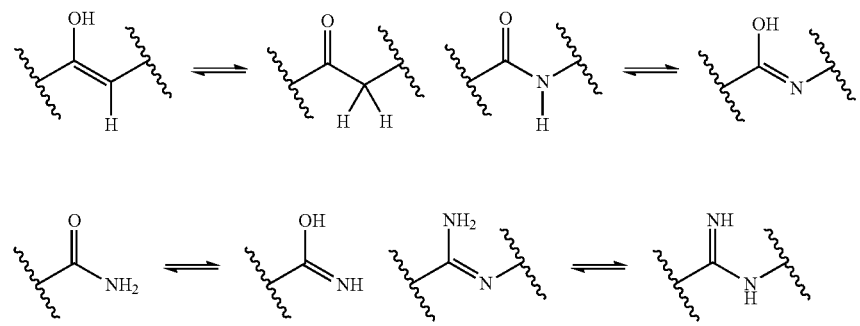

-continued

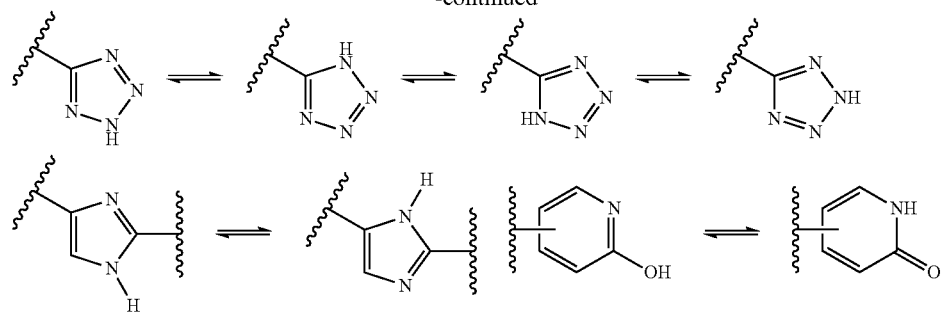

"Optional" or "optionally" means that a subsequently described event or circumstance may or may not occur and that the description includes instances when the event or circumstance occurs and instances in which it does not. For example, "optionally substituted aryl" means that the aryl radical are or are not substituted and that the description includes both substituted aryl radicals and aryl radicals having no substitution.

"Pharmaceutically acceptable salt" includes both acid and base addition salts. A pharmaceutically acceptable salt of any one of the pyrazole compounds described herein is intended to encompass any and all pharmaceutically suitable salt forms. Preferred pharmaceutically acceptable salts of the compounds described herein are pharmaceutically acceptable acid addition salts, and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science*, 66:1-19 (1997)). Acid addition salts of basic compounds are prepared by contacting the free base forms with a sufficient amount of the desired acid to produce the salt.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. In some embodiments, pharmaceutically acceptable base addition salts are formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts, and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins, and the like. See Berge et al., supra.

As used herein, "treatment" or "treating" or "palliating" or "ameliorating" are used interchangeably herein. These terms refer to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is still afflicted with the underlying disorder. For prophylactic benefit, the compositions are administered to a patient at risk of developing a particular disease, or to a patient reporting one or more of the physiological symptoms of a disease, even though a diagnosis of this disease has not been made.

Compounds

The compounds of Formula (I), (Ia), (Ib), (Ic), (Id), (Ie), (If), (Ig), (Ih), (Ii), (Ij), (Ik), (Il), or (Im) described herein which are modulators of MAGL. In some embodiments, the compounds are inhibitors of MAGL. The compounds of Formula (I), (Ia), (Ib), (Ic), (Id), (Ie), (If), (Ig), (Ih), (Ii), (Ij), (Ik), (Il), or (Im) described herein, and compositions comprising these compounds, are useful for the treatment of pain. In some embodiments, the compounds of Formula (I), (Ia), (Ib), (Ic), (Id), (Ie), (If), (Ig), (Ih), (Ii), (Ij), (Ik), (Il), or (Im) described herein, and compositions comprising these compounds, are useful for the treatment of pain, multiple sclerosis, Alzheimer's disease, and/or inflammatory bowel disease.

In some embodiments is a compound of Formula (I):
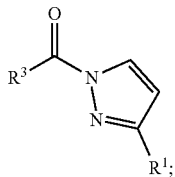
Formula (I)
wherein:
$R^1$ is —N($R^2$)C(O)$R^{15}$ or —N(H)SO$_2$$R^{15}$;
$R^2$ is H or $C_{1-6}$alkyl;
$R^3$ is
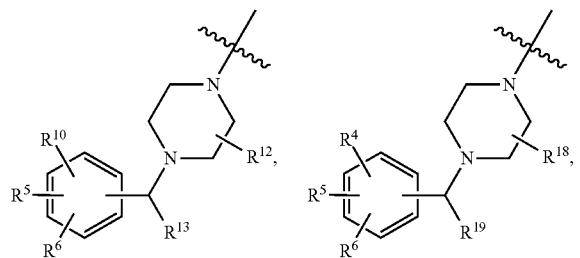
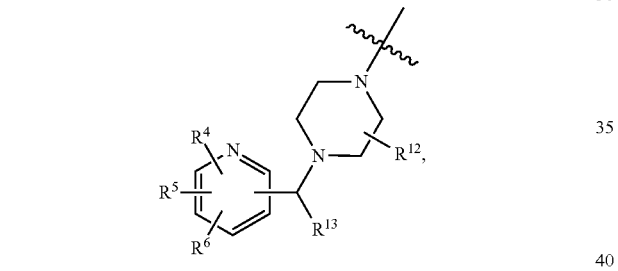
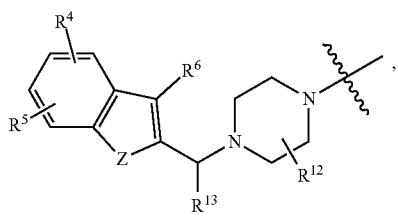
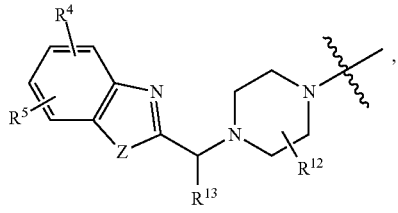
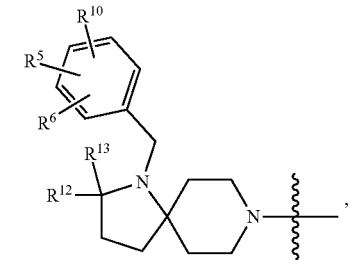
-continued
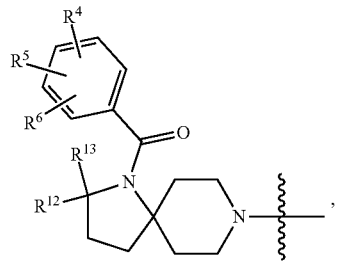
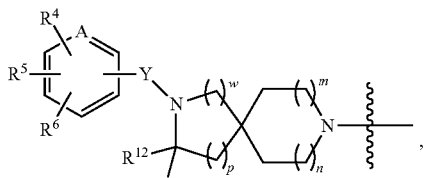
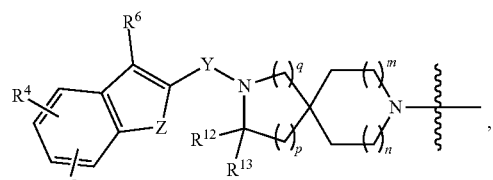
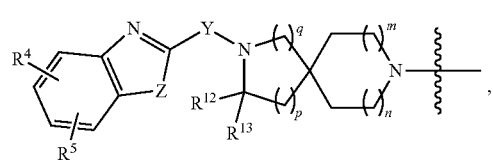
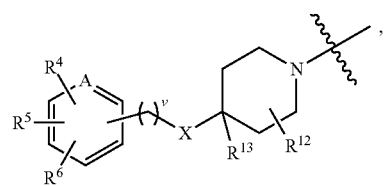
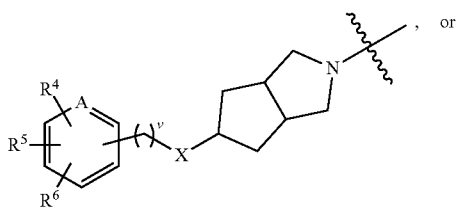
, or
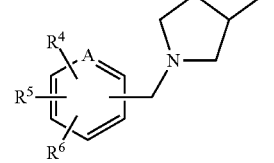
;

A is N or C(H);

X is —O—, —N($R_{16}$)—, or —$CH_2$N($R^{16}$)$CH_2$—;

Y is —$CH_2$— or —C(O)—;

Z is —S—, —O—, or —N($R^{20}$)—;

$R^4$ is H, halogen, —$OR^7$, $C_{1-6}$alkyl, $C_{1-6}$alkyl-OH, $C_{2-6}$alkenyl, $C_{2-6}$alkynyl, $C_{1-6}$haloalkyl, —O—$C_{3-8}$cycloalkyl, —O—$C_{3-8}$cycloalkyl-OH, —N(H)—$C_{1-6}$alkyl-$CO_2$H, —$SO_2R^{17}$, —$CO_2R^8$, —C(O)$NR^8R^9$, $C_{3-8}$cycloalkyl, $C_{2-9}$heterocycloalkyl, —$C_{1-6}$alkyl-$C_{2-9}$heterocycloalkyl, $C_{6-10}$aryl, $C_{1-9}$heteroaryl, wherein $C_{3-8}$cycloalkyl, $C_{2-9}$heterocycloalkyl, —$C_{1-6}$alkyl-$C_{2-9}$heterocycloalkyl, $C_{6-10}$aryl, $C_{1-9}$heteroaryl are optionally substituted with 1 or 2 $R^{14}$;

$R^5$ is H, —CN, halogen, $C_{1-6}$alkyl, $C_{1-6}$haloalkyl, $C_{1-6}$haloalkoxy, or phenyl;

$R^6$ is H, halogen, or $C_{1-6}$alkyl;

$R^7$ is H, $C_{1-6}$alkyl, $C_{1-6}$haloalkyl, $C_{3-8}$cycloalkyl, $C_{2-9}$heterocycloalkyl, $C_{6-10}$aryl, or $C_{1-9}$heteroaryl, wherein $C_{2-9}$heterocycloalkyl, $C_{6-10}$aryl, or $C_{1-9}$heteroaryl are optionally substituted with 1 or 2 $R^{14}$;

each $R^8$ and each $R^9$ are independently selected from H and $C_{1-6}$alkyl; or $R^8$ and $R^9$ together with the nitrogen to which they are attached are combined to form a heterocycloalkyl ring;

$R^{10}$ is —O—$C_{1-6}$haloalkyl, —O—$C_{1-6}$alkyl-$CO_2$H, —O—$C_{3-8}$cycloalkyl, —O—$C_{3-8}$cycloalkyl-$CO_2$H, —N(H)—$C_{1-6}$alkyl-$CO_2$H, or —$SO_2R^{17}$;

$R^{12}$ is H, halogen, or $C_{1-6}$alkyl;

$R^{13}$ is H or $C_{1-6}$alkyl;

each $R^{14}$ is independently selected from halogen, —OH, oxo, $C_{1-6}$alkyl, $C_{1-6}$haloalkyl, $C_{1-6}$alkoxy, —$C_{1-6}$alkyl-OH, $C_{3-8}$cycloalkyl, —$CO_2R^8$, —C(O)$NR^8R^9$, —C(O)—$C_{1-6}$alkyl, —C(O)—$C_{1-6}$alkyl-OH, —$SO_2$—$C_{1-6}$alkyl, —N($R^8$)$SO_2$—$C_{1-6}$alkyl, and —N($R^8$)C(O)—$C_{1-6}$alkyl;

$R^{15}$ is $C_{1-6}$alkyl or $C_{3-8}$cycloalkyl;

$R^{16}$ is H, $C_{1-6}$alkyl, —C(O)—$C_{1-6}$alkyl, or —$CH_2CO_2$H;

$R^{17}$ is $C_{1-6}$alkyl or $C_{3-8}$cycloalkyl;

$R^{18}$ and $R^{19}$ are independently selected from H and $C_{1-6}$alkyl, wherein $R^{18}$ and $R^{19}$ are not both H;

$R^{20}$ is H or $C_{1-6}$alkyl;

v is 0 or 1;

n is 0 or 1;

m is 0 or 1;

p is 0, 1, or 2;

q is 0, 1, or 2; and w is 1 or 2;

or a solvate, hydrate, tautomer, N-oxide, stereoisomer, or pharmaceutically acceptable salt thereof.

In another embodiment is a compound of Formula (I), or a solvate, hydrate, tautomer, N-oxide, stereoisomer, or pharmaceutically acceptable salt thereof, wherein $R^1$ is —N($R^2$)C(O)$R^{15}$. In another embodiment is a compound of Formula (I), or a solvate, hydrate, tautomer, N-oxide, stereoisomer, or pharmaceutically acceptable salt thereof, wherein $R^1$ is —N($R^2$)C(O)$R^{15}$ and $R^2$ is H. In another embodiment is a compound of Formula (I), or a solvate, hydrate, tautomer, N-oxide, stereoisomer, or pharmaceutically acceptable salt thereof, wherein $R^1$ is —N(H)C(O)$R^{15}$ and $R^{15}$ is $C_{1-6}$alkyl. In another embodiment is a compound of Formula (I), or a solvate, hydrate, tautomer, N-oxide, stereoisomer, or pharmaceutically acceptable salt thereof, wherein $R^1$ is —N(H)C(O)$R^{15}$ and $R^{15}$ is —$CH_3$. In another embodiment is a compound of Formula (I), or a solvate, hydrate, tautomer, N-oxide, stereoisomer, or pharmaceutically acceptable salt thereof, wherein $R^1$ is —N(H)C(O)$R^{15}$ and $R^{15}$ is $C_{3-8}$cycloalkyl. In another embodiment is a compound of Formula (I), or a solvate, hydrate, tautomer, N-oxide, stereoisomer, or pharmaceutically acceptable salt thereof, wherein $R^1$ is —N($R^2$)C(O)$R^{15}$ and $R^2$ is $C_{1-6}$alkyl. In another embodiment is a compound of Formula (I), or a solvate, hydrate, tautomer, N-oxide, stereoisomer, or pharmaceutically acceptable salt thereof, wherein $R^1$ is —N($R^2$)C(O)$R^{15}$ and $R^2$ is —$CH_3$. In another embodiment is a compound of Formula (I), or a solvate, hydrate, tautomer, N-oxide, stereoisomer, or pharmaceutically acceptable salt thereof, wherein $R^1$ is —N($CH_3$)C(O)$R^{15}$ and $R^{15}$ is $C_{1-6}$alkyl. In another embodiment is a compound of Formula (I), or a solvate, hydrate, tautomer, N-oxide, stereoisomer, or pharmaceutically acceptable salt thereof, wherein $R^1$ is —N($CH_3$)C(O)$R^{15}$ and $R^{15}$ is —$CH_3$. In another embodiment is a compound of Formula (I), or a solvate, hydrate, tautomer, N-oxide, stereoisomer, or pharmaceutically acceptable salt thereof, wherein $R^1$ is —N($CH_3$)C(O)$R^{15}$ and $R^{15}$ is $C_{3-8}$cycloalkyl. In another embodiment is a compound of Formula (I), or a solvate, hydrate, tautomer, N-oxide, stereoisomer, or pharmaceutically acceptable salt thereof, wherein $R^1$ is —N(H)$SO_2R^{15}$. In another embodiment is a compound of Formula (I), or a solvate, hydrate, tautomer, N-oxide, stereoisomer, or pharmaceutically acceptable salt thereof, wherein $R^1$ is —N(H)$SO_2R^{15}$ and $R^{15}$ is $C_{1-6}$alkyl. In another embodiment is a compound of Formula (I), or a solvate, hydrate, tautomer, N-oxide, stereoisomer, or pharmaceutically acceptable salt thereof, wherein $R^1$ is —N(H)$SO_2R^{15}$ and $R^{15}$ is —$CH_3$. In another embodiment is a compound of Formula (I), or a solvate, hydrate, tautomer, N-oxide, stereoisomer, or pharmaceutically acceptable salt thereof, wherein $R^1$ is —N(H)$SO_2R^{15}$ and $R^{15}$ is $C_{3-8}$cycloalkyl.

In another embodiment is a compound of Formula (I), or a solvate, hydrate, tautomer, N-oxide, stereoisomer, or pharmaceutically acceptable salt thereof, wherein $R^3$ is

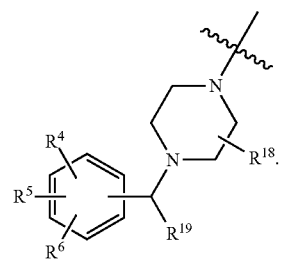

In another embodiment is a compound of Formula (I), or a solvate, hydrate, tautomer, N-oxide, stereoisomer, or pharmaceutically acceptable salt thereof, wherein $R^3$ is

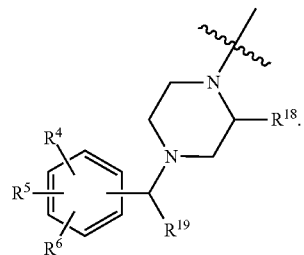

In another embodiment is a compound of Formula (I), or a solvate, hydrate, tautomer, N-oxide, stereoisomer, or pharmaceutically acceptable salt thereof, wherein $R^3$ is

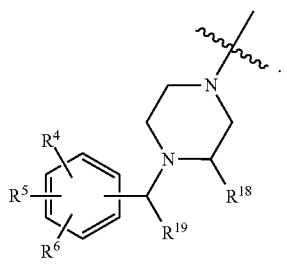

In another embodiment is a compound of Formula (I), or a solvate, hydrate, tautomer, N-oxide, stereoisomer, or pharmaceutically acceptable salt thereof, wherein $R^{18}$ is $C_{1-6}$alkyl. In another embodiment is a compound of Formula (I), or a solvate, hydrate, tautomer, N-oxide, stereoisomer, or pharmaceutically acceptable salt thereof, wherein $R^{18}$ is $C_{1-6}$alkyl and $R^{19}$ is H. In another embodiment is a compound of Formula (I), or a solvate, hydrate, tautomer, N-oxide, stereoisomer, or pharmaceutically acceptable salt thereof, wherein $R^{18}$ is —CH$_3$ and $R^{19}$ is H. In another embodiment is a compound of Formula (I), or a solvate, hydrate, tautomer, N-oxide, stereoisomer, or pharmaceutically acceptable salt thereof, wherein $R^{19}$ is $C_{1-6}$alkyl. In another embodiment is a compound of Formula (I), or a solvate, hydrate, tautomer, N-oxide, stereoisomer, or pharmaceutically acceptable salt thereof, wherein $R^{18}$ is H and $R^{19}$ is $C_{1-6}$alkyl. In another embodiment is a compound of Formula (I), or a solvate, hydrate, tautomer, N-oxide, stereoisomer, or pharmaceutically acceptable salt thereof, wherein $R^{18}$ is H and $R^{19}$ is —CH$_3$. In another embodiment is a compound of Formula (I), or a solvate, hydrate, tautomer, N-oxide, stereoisomer, or pharmaceutically acceptable salt thereof, wherein $R^{18}$ and $R^{19}$ are $C_{1-6}$alkyl. In another embodiment is a compound of Formula (I), or a solvate, hydrate, tautomer, N-oxide, stereoisomer, or pharmaceutically acceptable salt thereof, wherein $R^{18}$ and $R^{19}$ are —CH$_3$.

In another embodiment is a compound of Formula (I), or a solvate, hydrate, tautomer, N-oxide, stereoisomer, or pharmaceutically acceptable salt thereof, wherein $R^3$ is

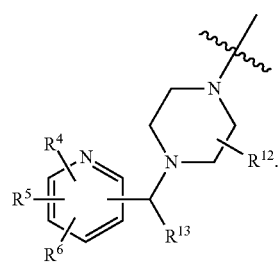

In another embodiment is a compound of Formula (I), or a solvate, hydrate, tautomer, N-oxide, stereoisomer, or pharmaceutically acceptable salt thereof, wherein $R^3$ is

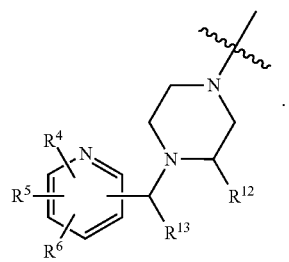

In another embodiment is a compound of Formula (I), or a solvate, hydrate, tautomer, N-oxide, stereoisomer, or pharmaceutically acceptable salt thereof, wherein $R^3$ is

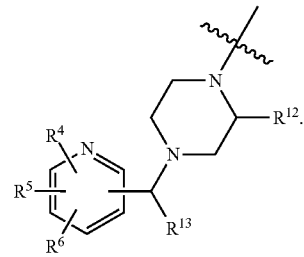

In another embodiment is a compound of Formula (I), or a solvate, hydrate, tautomer, N-oxide, stereoisomer, or pharmaceutically acceptable salt thereof, wherein $R^3$ is

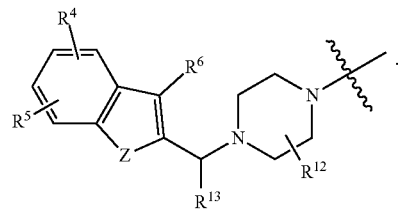

In another embodiment is a compound of Formula (I), or a solvate, hydrate, tautomer, N-oxide, stereoisomer, or pharmaceutically acceptable salt thereof, wherein $R^3$ is

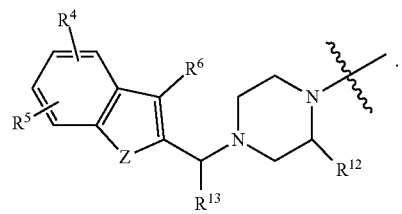

In another embodiment is a compound of Formula (I), or a solvate, hydrate, tautomer, N-oxide, stereoisomer, or pharmaceutically acceptable salt thereof, wherein $R^3$ is

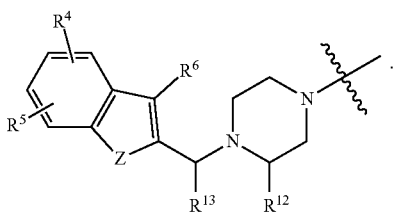

In another embodiment is a compound of Formula (I), or a solvate, hydrate, tautomer, N-oxide, stereoisomer, or pharmaceutically acceptable salt thereof, wherein $R^3$ is

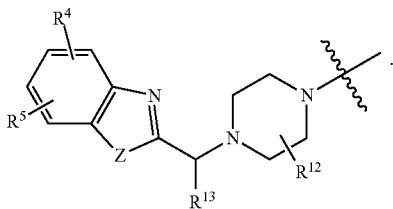

In another embodiment is a compound of Formula (I), or a solvate, hydrate, tautomer, N-oxide, stereoisomer, or pharmaceutically acceptable salt thereof, wherein $R^3$ is

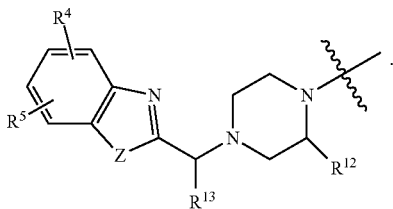

In another embodiment is a compound of Formula (I), or a solvate, hydrate, tautomer, N-oxide, stereoisomer, or pharmaceutically acceptable salt thereof, wherein $R^3$ is

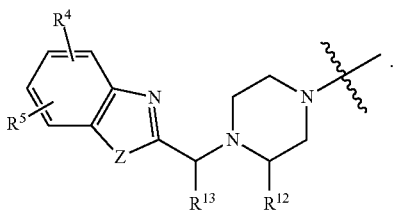

In another embodiment is a compound of Formula (I), or a solvate, hydrate, tautomer, N-oxide, stereoisomer, or pharmaceutically acceptable salt thereof, wherein Z is —S—. In another embodiment is a compound of Formula (I), or a solvate, hydrate, tautomer, N-oxide, stereoisomer, or pharmaceutically acceptable salt thereof, wherein Z is —O—. In another embodiment is a compound of Formula (I), or a solvate, hydrate, tautomer, N-oxide, stereoisomer, or pharmaceutically acceptable salt thereof, wherein Z is —N($R^{20}$)—. In another embodiment is a compound of Formula (I), or a solvate, hydrate, tautomer, N-oxide, stereoisomer, or pharmaceutically acceptable salt thereof, wherein Z is —N(H)—. In another embodiment is a compound of Formula (I), or a solvate, hydrate, tautomer, N-oxide, stereoisomer, or pharmaceutically acceptable salt thereof, wherein $R^3$ is

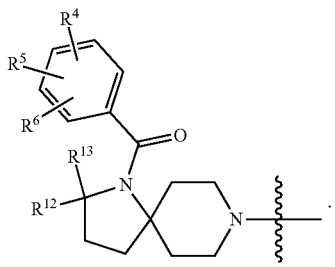

In another embodiment is a compound of Formula (I), or a solvate, hydrate, tautomer, N-oxide, stereoisomer, or pharmaceutically acceptable salt thereof, wherein $R^{12}$ is H and $R^{13}$ is H. In another embodiment is a compound of Formula (I), or a solvate, hydrate, tautomer, N-oxide, stereoisomer, or pharmaceutically acceptable salt thereof, wherein $R^{12}$ is $C_{1-6}$alkyl and $R^{13}$ is H. In another embodiment is a compound of Formula (I), or a solvate, hydrate, tautomer, N-oxide, stereoisomer, or pharmaceutically acceptable salt thereof, wherein $R^{12}$ is —$CH_3$ and $R^{13}$ is H. In another embodiment is a compound of Formula (I), or a solvate, hydrate, tautomer, N-oxide, stereoisomer, or pharmaceutically acceptable salt thereof, wherein $R^{12}$ is H and $R^{13}$ is $C_{1-6}$alkyl. In another embodiment is a compound of Formula (I), or a solvate, hydrate, tautomer, N-oxide, stereoisomer, or pharmaceutically acceptable salt thereof, wherein $R^{12}$ is H and $R^{13}$ is —$CH_3$. In another embodiment is a compound of Formula (I), or a solvate, hydrate, tautomer, N-oxide, stereoisomer, or pharmaceutically acceptable salt thereof, wherein $R^{12}$ is $C_{1-6}$alkyl and $R^{13}$ is $C_{1-6}$alkyl. In another embodiment is a compound of Formula (I), or a solvate, hydrate, tautomer, N-oxide, stereoisomer, or pharmaceutically acceptable salt thereof, wherein $R^{12}$ is —$CH_3$ and $R^{13}$ is —$CH_3$.

In another embodiment is a compound of Formula (I), or a solvate, hydrate, tautomer, N-oxide, stereoisomer, or pharmaceutically acceptable salt thereof, wherein $R^3$ is

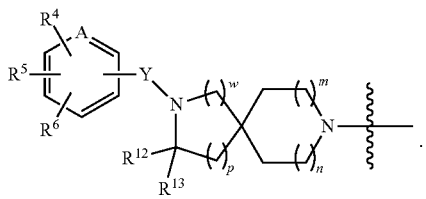

In another embodiment is a compound of Formula (I), or a solvate, hydrate, tautomer, N-oxide, stereoisomer, or pharmaceutically acceptable salt thereof, wherein m is 1, n is 1, p is 1, and w is 1. In another embodiment is a compound of Formula (I), or a solvate, hydrate, tautomer, N-oxide, stereoisomer, or pharmaceutically acceptable salt thereof, wherein m is 0, n is 1, p is 1, and w is 2. In another embodiment is a compound of Formula (I), or a solvate, hydrate, tautomer, N-oxide, stereoisomer, or pharmaceutically acceptable salt thereof, wherein m is 1, n is 1, p is 0, and w is 1. In another embodiment is a compound of Formula (I), or a solvate, hydrate, tautomer, N-oxide, stereoisomer, or pharmaceutically acceptable salt thereof, wherein A is C(H). In another embodiment is a compound of Formula (I), or a solvate, hydrate, tautomer, N-oxide, stereoisomer, or pharmaceutically acceptable salt thereof, wherein A is N. In another embodiment is a compound of Formula (I), or a solvate, hydrate, tautomer, N-oxide, stereoisomer, or pharmaceutically acceptable salt thereof, wherein $R^3$ is

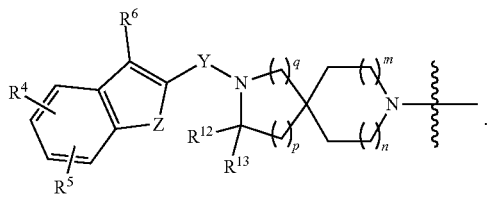

In another embodiment is a compound of Formula (I), or a solvate, hydrate, tautomer, N-oxide, stereoisomer, or pharmaceutically acceptable salt thereof, wherein $R^3$ is

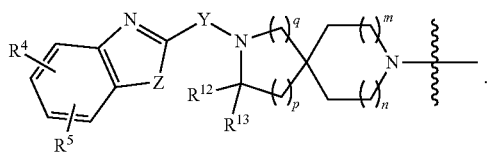

In another embodiment is a compound of Formula (I), or a solvate, hydrate, tautomer, N-oxide, stereoisomer, or pharmaceutically acceptable salt thereof, wherein Z is —S—. In another embodiment is a compound of Formula (I), or a solvate, hydrate, tautomer, N-oxide, stereoisomer, or pharmaceutically acceptable salt thereof, wherein Z is —O—. In another embodiment is a compound of Formula (I), or a solvate, hydrate, tautomer, N-oxide, stereoisomer, or pharmaceutically acceptable salt thereof, wherein Z is —N($R^{20}$)—. In another embodiment is a compound of Formula (I), or a solvate, hydrate, tautomer, N-oxide, stereoisomer, or pharmaceutically acceptable salt thereof, wherein Z is —N(H)—. In another embodiment is a compound of Formula (I), or a solvate, hydrate, tautomer, N-oxide, stereoisomer, or pharmaceutically acceptable salt thereof, wherein Z is —N($CH_3$)—. In another embodiment is a compound of Formula (I), or a solvate, hydrate, tautomer, N-oxide, stereoisomer, or pharmaceutically acceptable salt thereof, wherein Y is —$CH_2$—. In another embodiment is a compound of Formula (I), or a solvate, hydrate, tautomer, N-oxide, stereoisomer, or pharmaceutically acceptable salt thereof, wherein Y is —C(O)—. In another embodiment is a compound of Formula (I), or a solvate, hydrate, tautomer, N-oxide, stereoisomer, or pharmaceutically acceptable salt thereof, wherein m is 1, n is 1, q is 1, and p is 1. In another embodiment is a compound of Formula (I), or a solvate, hydrate, tautomer, N-oxide, stereoisomer, or pharmaceutically acceptable salt thereof, wherein m is 0, n is 1, q is 2, and p is 1. In another embodiment is a compound of Formula (I), or a solvate, hydrate, tautomer, N-oxide, stereoisomer, or pharmaceutically acceptable salt thereof, wherein m is 1, n is 1, q is 0, and p is 2. In another embodiment is a compound of Formula (I), or a solvate, hydrate, tautomer, N-oxide, stereoisomer, or pharmaceutically acceptable salt thereof, wherein m is 1, n is 1, q is 1, and p is 0. In another embodiment is a compound of Formula (I), or a solvate, hydrate, tautomer, N-oxide, stereoisomer, or pharmaceutically acceptable salt thereof, wherein m is 0, n is 0, q is 2, and p is 1. In another embodiment is a compound of Formula (I), or a solvate, hydrate, tautomer, N-oxide, stereoisomer, or pharmaceutically acceptable salt thereof, wherein $R^{12}$ is H and $R^{13}$ is H. In another embodiment is a compound of Formula (I), or a solvate, hydrate, tautomer, N-oxide, stereoisomer, or pharmaceutically acceptable salt thereof, wherein $R^{12}$ is $C_{1-6}$alkyl and $R^{13}$ is H. In another embodiment is a compound of Formula (I), or a solvate, hydrate, tautomer, N-oxide, stereoisomer, or pharmaceutically acceptable salt thereof, wherein $R^{12}$ is —$CH_3$ and $R^{13}$ is H. In another embodiment is a compound of Formula (I), or a solvate, hydrate, tautomer, N-oxide, stereoisomer, or pharmaceutically acceptable salt thereof, wherein $R^{12}$ is H and $R^{13}$ is $C_{1-6}$alkyl. In another embodiment is a compound of Formula (I), or a solvate, hydrate, tautomer, N-oxide, stereoisomer, or pharmaceutically acceptable salt thereof, wherein $R^{12}$ is H and $R^{13}$ is —$CH_3$. In another embodiment is a compound of Formula (I), or a solvate, hydrate, tautomer, N-oxide, stereoisomer, or pharmaceutically acceptable salt thereof, wherein $R^{12}$ is $C_{1-6}$alkyl and $R^{13}$ is $C_{1-6}$alkyl. In another embodiment is a compound of Formula (I), or a solvate, hydrate, tautomer, N-oxide, stereoisomer, or pharmaceutically acceptable salt thereof, wherein $R^{12}$ is —$CH_3$ and $R^{13}$ is —$CH_3$.

In another embodiment is a compound of Formula (I), or a solvate, hydrate, tautomer, N-oxide, stereoisomer, or pharmaceutically acceptable salt thereof, wherein $R^3$ is

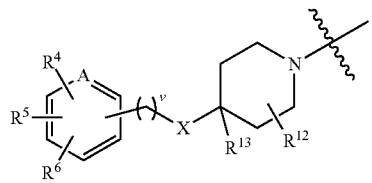

In another embodiment is a compound of Formula (I), or a solvate, hydrate, tautomer, N-oxide, stereoisomer, or pharmaceutically acceptable salt thereof, wherein $R^3$ is

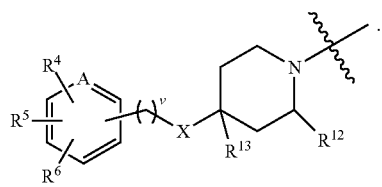

In another embodiment is a compound of Formula (I), or a solvate, hydrate, tautomer, N-oxide, stereoisomer, or pharmaceutically acceptable salt thereof, wherein $R^3$ is

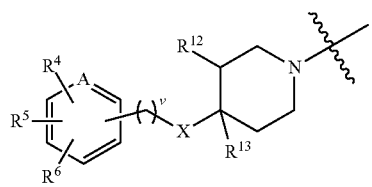

In another embodiment is a compound of Formula (I), or a solvate, hydrate, tautomer, N-oxide, stereoisomer, or pharmaceutically acceptable salt thereof, wherein $R^{12}$ is $C_{1-6}$alkyl and $R^{13}$ is H. In another embodiment is a compound of Formula (I), or a solvate, hydrate, tautomer, N-oxide, stereoisomer, or pharmaceutically acceptable salt thereof, wherein $R^{12}$ is —$CH_3$ and $R^{13}$ is H. In another embodiment is a compound of Formula (I), or a solvate, hydrate, tautomer, N-oxide, stereoisomer, or pharmaceutically acceptable salt thereof, wherein $R^{12}$ is H and $R^{13}$ is $C_{1-6}$alkyl. In another embodiment is a compound of Formula (I), or a solvate, hydrate, tautomer, N-oxide, stereoisomer, or pharmaceutically acceptable salt thereof, wherein $R^{12}$ is H and $R^{13}$ is —$CH_3$. In another embodiment is a compound of Formula (I), or a solvate, hydrate, tautomer, N-oxide, stereoisomer, or pharmaceutically acceptable salt thereof, wherein $R^{12}$ is $C_{1-6}$alkyl and $R^{13}$ is $C_{1-6}$alkyl. In another embodiment is a compound of Formula (I), or a solvate, hydrate, tautomer, N-oxide, stereoisomer, or pharmaceutically acceptable salt thereof, wherein $R^{12}$ is —$CH_3$ and $R^{13}$ is —$CH_3$. In another embodiment is a compound of Formula (I), or a solvate, hydrate, tautomer, N-oxide, stereoisomer, or pharmaceutically acceptable salt thereof, wherein $R^3$ is In another embodiment is a compound of Formula (I), or a solvate, hydrate, tautomer, N-oxide, stereoisomer, or pharmaceutically acceptable salt thereof, wherein X is —O—. In another embodiment is a compound of Formula (I), or a solvate, hydrate, tautomer, N-oxide, stereoisomer, or pharmaceutically acceptable salt thereof, wherein X is —N($R^{16}$)—. In another embodiment is a compound of Formula (I), or a solvate, hydrate, tautomer, N-oxide, stereoisomer, or pharmaceutically acceptable salt thereof, wherein X is —N(H)—. In another embodiment is a compound of Formula (I), or a solvate, hydrate, tautomer, N-oxide, stereoisomer, or pharmaceutically acceptable salt thereof, wherein X is —N($CH_3$)—. In another embodiment is a compound of Formula (I), or a solvate, hydrate, tautomer, N-oxide, stereoisomer, or pharmaceutically acceptable salt thereof, wherein X is —$CH_2$N($R^{16}$)$CH_2$—. In another embodiment is a compound of Formula (I), or a solvate, hydrate, tautomer, N-oxide, stereoisomer, or pharmaceutically acceptable salt thereof, wherein X is —$CH_2$N(H)$CH_2$—. In another embodiment is a compound of Formula (I), or a solvate, hydrate, tautomer, N-oxide, stereoisomer, or pharmaceutically acceptable salt thereof, wherein X is —$CH_2$N($CH_3$)$CH_2$—. In another embodiment is a compound of Formula (I), or a solvate, hydrate, tautomer, N-oxide, stereoisomer, or pharmaceutically acceptable salt thereof, wherein A is N. In another embodiment is a compound of Formula (I), or a solvate, hydrate, tautomer, N-oxide, stereoisomer, or pharmaceutically acceptable salt thereof, wherein A is C(H). In another embodiment is a compound of Formula (I), or a solvate, hydrate, tautomer, N-oxide, stereoisomer, or pharmaceutically acceptable salt thereof, wherein v is 0. In another embodiment is a compound of Formula (I), or a solvate, hydrate, tautomer, N-oxide, stereoisomer, or pharmaceutically acceptable salt thereof, wherein v is 1. In another embodiment is a compound of Formula (I), or a solvate, hydrate, tautomer, N-oxide, stereoisomer, or pharmaceutically acceptable salt thereof, wherein $R^3$ is In another embodiment is a compound of Formula (I), or a solvate, hydrate, tautomer, N-oxide, stereoisomer, or pharmaceutically acceptable salt thereof, wherein $R^4$ is halogen, —$OR^7$, $C_{1-6}$alkyl-OH, —N(H)—$C_{1-6}$alkyl-$CO_2$H, $C_{2-6}$alkynyl, $C_{1-6}$haloalkyl, —$CO_2R^8$, —C(O)$NR^8R^9$, $C_{3-8}$cycloalkyl, $C_{2-9}$heterocycloalkyl, $C_{6-10}$aryl, or $C_{1-9}$heteroaryl, wherein $C_{3-8}$cycloalkyl, $C_{2-9}$heterocycloalkyl, $C_{6-10}$aryl, or $C_{1-9}$heteroaryl are optionally substituted with 1 or 2 $R^{14}$. In another embodiment is a compound of Formula (I), or a solvate, hydrate, tautomer, N-oxide, stereoisomer, or pharmaceutically acceptable salt thereof, wherein $R^4$ is halogen, —$OR^7$, —N(H)—$C_{1-6}$alkyl-$CO_2$H, $C_{1-6}$haloalkyl, —C(O)$NR^8R^9$, $C_{3-8}$cycloalkyl, $C_{2-9}$heterocycloalkyl, or $C_{1-9}$heteroaryl, wherein $C_{2-9}$heterocycloalkyl or $C_{1-9}$heteroaryl are optionally substituted with 1 or 2 $R^{14}$. In another embodiment is a compound of Formula (I), or a solvate, hydrate, tautomer, N-oxide, stereoisomer, or pharmaceutically acceptable salt thereof, wherein $R^4$ is halogen. In another embodiment is a compound of Formula (I), or a solvate, hydrate, tautomer, N-oxide, stereoisomer, or pharmaceutically acceptable salt thereof, wherein $R^4$ is —Cl. In another embodiment is a compound of Formula (I), or a solvate, hydrate, tautomer, N-oxide, stereoisomer, or pharmaceutically acceptable salt thereof, wherein $R^4$ is $C_{1-6}$haloalkyl. In another embodiment is a compound of Formula (I), or a solvate, hydrate, tautomer, N-oxide, stereoisomer, or pharmaceutically acceptable salt thereof, wherein $R^4$ is —$CF_3$. In another embodiment is a compound of Formula (I), or a solvate, hydrate, tautomer, N-oxide, stereoisomer, or pharmaceutically acceptable salt thereof, wherein $R^4$ is —N(H)—$C_{1-6}$alkyl-$CO_2$H. In another embodiment is a compound of Formula (I), or a solvate, hydrate, tautomer, N-oxide, stereoisomer, or pharmaceutically acceptable salt thereof, wherein $R^4$ is —N(H)$CH_2CO_2$H. In another embodiment is a compound of Formula (I), or a solvate, hydrate, tautomer, N-oxide, stereoisomer, or pharmaceutically acceptable salt thereof, wherein $R^4$ is —N(H)$CH_2CH_2CO_2$H. In another embodiment is a compound of Formula (I), or a solvate, hydrate, tautomer, N-oxide, stereoisomer, or pharmaceutically acceptable salt thereof, wherein $R^4$ is —N(H)$CH_2CH_2CH_2CO_2$H. In another embodiment is a compound of Formula (I), or a solvate, hydrate, tautomer, N-oxide, stereoisomer, or pharmaceutically acceptable salt thereof, wherein $R^4$ is —C(O)$NR^8R^9$. In another embodiment is a compound of Formula (I), or a solvate, hydrate, tautomer, N-oxide, stereoisomer, or pharmaceutically acceptable salt thereof, wherein $R^4$ is —C(O)$NH_2$. In another embodiment is a compound of Formula (I), or a solvate, hydrate, tautomer, N-oxide, stereoisomer, or pharmaceutically acceptable salt thereof, wherein $R^4$ is $C_{3-8}$cycloalkyl. In another embodiment is a compound of Formula (I), or a solvate, hydrate, tautomer, N-oxide, stereoisomer, or pharmaceutically acceptable salt thereof, wherein $R^4$ is —$OR^7$. In another embodiment is a compound of Formula (I), or a solvate, hydrate, tautomer, N-oxide, stereoisomer, or pharmaceutically acceptable salt thereof, wherein $R^4$ is —$OR^7$ and $R^7$ is unsubstituted $C_{3-8}$cycloalkyl or $C_{6-10}$aryl optionally substituted with halogen. In another embodiment is a compound of Formula (I), or a solvate, hydrate, tautomer, N-oxide, stereoisomer, or pharmaceutically acceptable salt thereof, wherein $R^4$ is —$OR^7$ and $R^7$ is unsubstituted $C_{3-8}$cycloalkyl. In another embodiment is a compound of Formula (I), or a solvate, hydrate, tautomer, N-oxide, stereoisomer, or pharmaceutically acceptable salt thereof, wherein $R^4$ is —$OR^7$ and $R^7$ is phenyl optionally substituted with halogen. In another embodiment is a compound of Formula (I), or a solvate, hydrate, tautomer, N-oxide, stereoisomer, or pharmaceutically acceptable salt thereof, wherein $R^4$ is —$OR^7$ and $R^7$ is phenyl substituted with halogen. In another embodiment is a compound of Formula (I), or a solvate, hydrate, tautomer, N-oxide, stereoisomer, or pharmaceutically acceptable salt thereof, wherein $R^4$ is —$OR^7$ and $R^7$ is phenyl substituted with —Cl. In another embodiment is a compound of Formula (I), or a solvate, hydrate, tautomer, N-oxide, stereoisomer, or pharmaceutically acceptable salt thereof, wherein $R^4$ is $C_{2-9}$heterocycloalkyl optionally substituted with 1 or 2 $R^{14}$. In another embodiment is a compound of Formula (I), or a solvate, hydrate, tautomer, N-oxide, stereoisomer, or pharmaceutically acceptable salt thereof, wherein $R^4$ is an unsubstituted $C_{2-9}$heterocycloalkyl. In another embodiment is a compound of Formula (I), or a solvate, hydrate, tautomer, N-oxide, stereoisomer, or pharmaceutically acceptable salt thereof, wherein $R^4$ is $C_{2-9}$heterocycloalkyl substituted with 1 or 2 $R^{14}$. In another embodiment is a compound of Formula (I), or a solvate, hydrate, tautomer, N-oxide, stereoisomer, or pharmaceutically acceptable salt thereof, wherein $R^4$ is $C_{4-5}$heterocycloalkyl optionally substituted with 1 or 2 $R^{14}$, wherein the $C_{4-5}$heterocycloalkyl is a monocyclic heterocycloalkyl selected from pyrrolidine, piperidine, piperazine, and morpholine. In another embodiment is a compound of Formula (I), or a solvate, hydrate, tautomer, N-oxide, stereoisomer, or pharmaceutically acceptable salt thereof, wherein $R^4$ is $C_{5-9}$heterocycloalkyl optionally substituted with 1 or 2 $R^{14}$, wherein the $C_{5-9}$heterocycloalkyl is a bicyclic heterocycloalkyl. In another embodiment is a compound of Formula (I), or a solvate, hydrate, tautomer, N-oxide, stereoisomer, or pharmaceutically acceptable salt thereof, wherein $R^4$ is $C_{5-9}$heterocycloalkyl optionally substituted with 1 or 2 $R^{14}$, wherein the $C_{5-9}$heterocycloalkyl is a spirocyclic heterocycloalkyl. In another embodiment is a compound of Formula (I), or a solvate, hydrate, tautomer, N-oxide, stereoisomer, or pharmaceutically acceptable salt thereof, wherein $R^4$ is

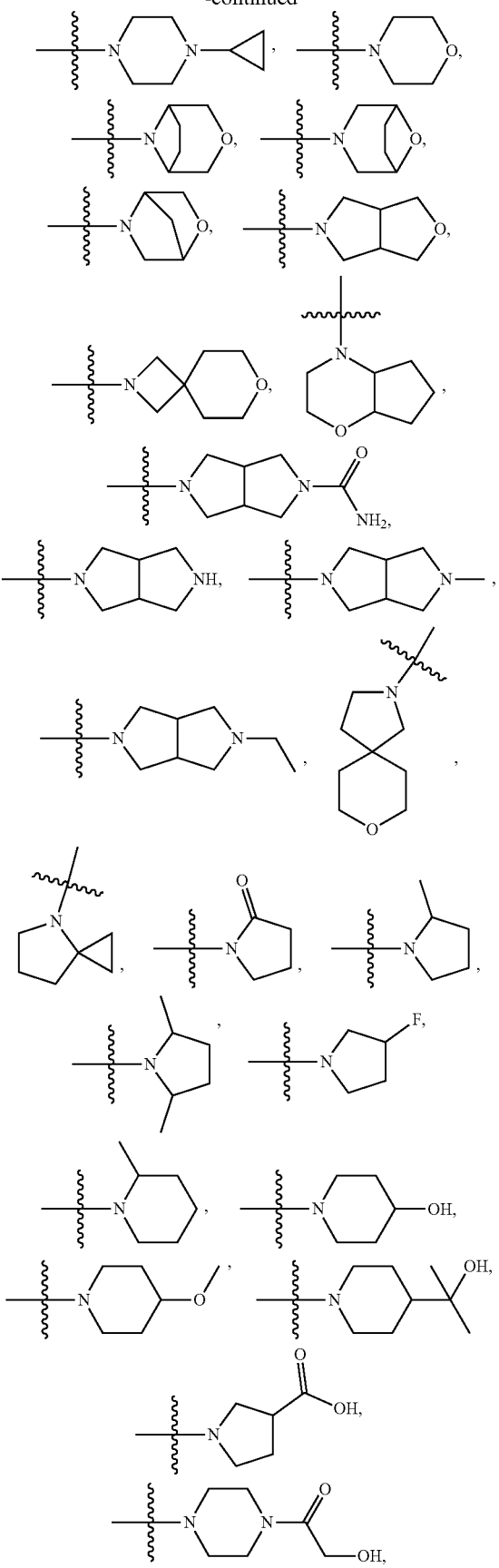

-continued

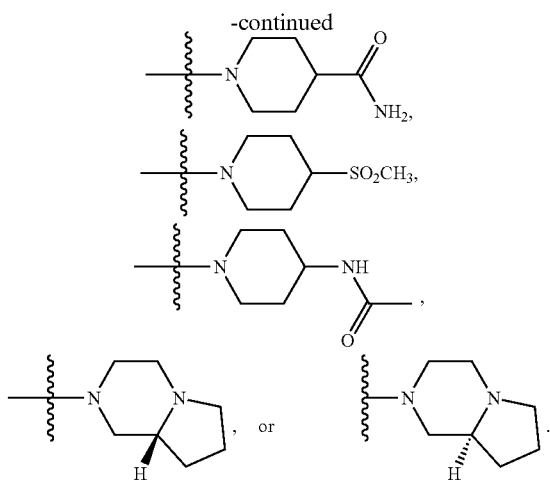

In another embodiment is a compound of Formula (I), or a solvate, hydrate, tautomer, N-oxide, stereoisomer, or pharmaceutically acceptable salt thereof, wherein $R^4$ is $C_{1-9}$heteroaryl optionally substituted with 1 or 2 $R^{14}$. In another embodiment is a compound of Formula (I), or a solvate, hydrate, tautomer, N-oxide, stereoisomer, or pharmaceutically acceptable salt thereof, wherein $R^4$ is an unsubstituted $C_{1-9}$heteroaryl. In another embodiment is a compound of Formula (I), or a solvate, hydrate, tautomer, N-oxide, stereoisomer, or pharmaceutically acceptable salt thereof, wherein $R^4$ is $C_{2-9}$heteroaryl substituted with 1 or 2 $R^{14}$. In another embodiment is a compound of Formula (I), or a solvate, hydrate, tautomer, N-oxide, stereoisomer, or pharmaceutically acceptable salt thereof, wherein $R^4$ is $C_{2-9}$heteroaryl optionally substituted with 1 or 2 $R^{14}$, wherein the $C_{2-9}$heteroaryl is selected from pyrrole, furan, thiophene, thiazole, pyrazole, oxazole, oxadiazole, thiadiazole, pyridine, pyrimidine, pyrazine, indole, benzothiophene, benzofuran, and imidazopyridine. In another embodiment is a compound of Formula (I), or a solvate, hydrate, tautomer, N-oxide, stereoisomer, or pharmaceutically acceptable salt thereof, wherein $R^4$ is

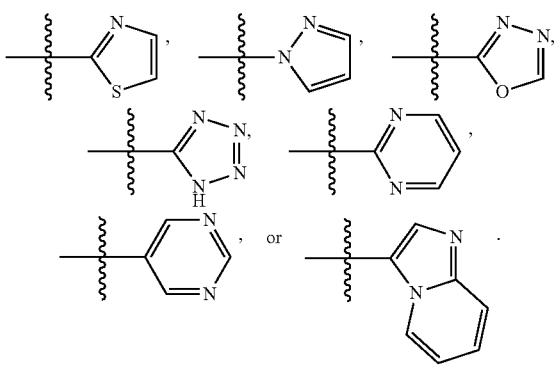

In another embodiment is a compound of Formula (I), or a solvate, hydrate, tautomer, N-oxide, stereoisomer, or pharmaceutically acceptable salt thereof, wherein $R^5$ is H, CN, halogen, $C_{1-6}$alkyl, $C_{1-6}$haloalkyl, or $C_{1-6}$haloalkoxy. In another embodiment is a compound of Formula (I), or a solvate, hydrate, tautomer, N-oxide, stereoisomer, or pharmaceutically acceptable salt thereof, wherein $R^5$ is H. In another embodiment is a compound of Formula (I), or a solvate, hydrate, tautomer, N-oxide, stereoisomer, or pharmaceutically acceptable salt thereof, wherein $R^5$ is —CN. In another embodiment is a compound of Formula (I), or a solvate, hydrate, tautomer, N-oxide, stereoisomer, or pharmaceutically acceptable salt thereof, wherein $R^5$ is halogen. In another embodiment is a compound of Formula (I), or a solvate, hydrate, tautomer, N-oxide, stereoisomer, or pharmaceutically acceptable salt thereof, wherein $R^5$ is —Cl. In another embodiment is a compound of Formula (I), or a solvate, hydrate, tautomer, N-oxide, stereoisomer, or pharmaceutically acceptable salt thereof, wherein $R^5$ is —F. In another embodiment is a compound of Formula (I), or a solvate, hydrate, tautomer, N-oxide, stereoisomer, or pharmaceutically acceptable salt thereof, wherein $R^5$ is $C_{1-6}$alkyl. In another embodiment is a compound of Formula (I), or a solvate, hydrate, tautomer, N-oxide, stereoisomer, or pharmaceutically acceptable salt thereof, wherein $R^5$ is —$CH_3$. In another embodiment is a compound of Formula (I), or a solvate, hydrate, tautomer, N-oxide, stereoisomer, or pharmaceutically acceptable salt thereof, wherein $R^5$ is $C_{1-6}$haloalkyl. In another embodiment is a compound of Formula (I), or a solvate, hydrate, tautomer, N-oxide, stereoisomer, or pharmaceutically acceptable salt thereof, wherein $R^5$ is —$CF_3$. In another embodiment is a compound of Formula (I), or a solvate, hydrate, tautomer, N-oxide, stereoisomer, or pharmaceutically acceptable salt thereof, wherein $R^5$ is $C_{1-6}$haloalkoxy. In another embodiment is a compound of Formula (I), or a solvate, hydrate, tautomer, N-oxide, stereoisomer, or pharmaceutically acceptable salt thereof, wherein $R^5$ is —$OCF_3$. In another embodiment is a compound of Formula (I), or a solvate, hydrate, tautomer, N-oxide, stereoisomer, or pharmaceutically acceptable salt thereof, wherein $R^6$ is H. In another embodiment is a compound of Formula (I), or a solvate, hydrate, tautomer, N-oxide, stereoisomer, or pharmaceutically acceptable salt thereof, wherein $R^6$ is halogen. In another embodiment is a compound of Formula (I), or a solvate, hydrate, tautomer, N-oxide, stereoisomer, or pharmaceutically acceptable salt thereof, wherein $R^6$ is —Cl. In another embodiment is a compound of Formula (I), or a solvate, hydrate, tautomer, N-oxide, stereoisomer, or pharmaceutically acceptable salt thereof, wherein $R^6$ is —F. In another embodiment is a compound of Formula (I), or a solvate, hydrate, tautomer, N-oxide, stereoisomer, or pharmaceutically acceptable salt thereof, wherein $R^6$ is $C_{1-6}$alkyl. In another embodiment is a compound of Formula (I), or a solvate, hydrate, tautomer, N-oxide, stereoisomer, or pharmaceutically acceptable salt thereof, wherein $R^6$ is —$CH_3$.

In another embodiment is a compound of Formula (I), or a solvate, hydrate, tautomer, N-oxide, stereoisomer, or pharmaceutically acceptable salt thereof, wherein $R^3$ is

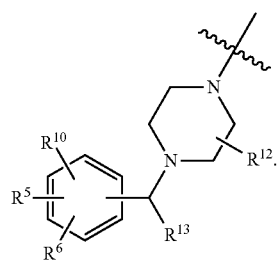

In another embodiment is a compound of Formula (I), or a solvate, hydrate, tautomer, N-oxide, stereoisomer, or pharmaceutically acceptable salt thereof, wherein $R^3$ is

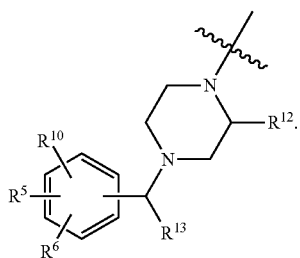

In another embodiment is a compound of Formula (I), or a solvate, hydrate, tautomer, N-oxide, stereoisomer, or pharmaceutically acceptable salt thereof, wherein $R^3$ is

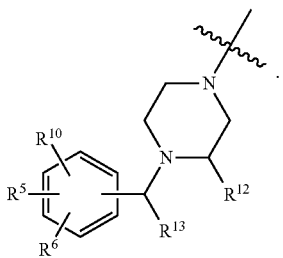

In another embodiment is a compound of Formula (I), or a solvate, hydrate, tautomer, N-oxide, stereoisomer, or pharmaceutically acceptable salt thereof, wherein $R^3$ is

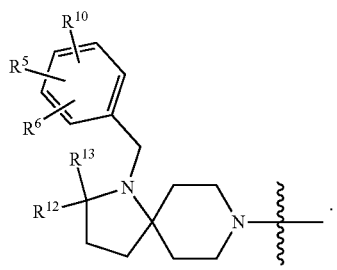

In another embodiment is a compound of Formula (I), or a solvate, hydrate, tautomer, N-oxide, stereoisomer, or pharmaceutically acceptable salt thereof, wherein $R^{10}$ is —O—$C_{1-6}$alkyl-$CO_2H$. In another embodiment is a compound of Formula (I), or a solvate, hydrate, tautomer, N-oxide, stereoisomer, or pharmaceutically acceptable salt thereof, wherein $R^{10}$ is —OCH$_2$CO$_2$H. In another embodiment is a compound of Formula (I), or a solvate, hydrate, tautomer, N-oxide, stereoisomer, or pharmaceutically acceptable salt thereof, wherein $R^{10}$ is —OCH$_2$CH$_2$CO$_2$H. In another embodiment is a compound of Formula (I), or a solvate, hydrate, tautomer, N-oxide, stereoisomer, or pharmaceutically acceptable salt thereof, wherein $R^{10}$ is —OCH$_2$CH$_2$CH$_2$CO$_2$H. In another embodiment is a compound of Formula (I), or a solvate, hydrate, tautomer, N-oxide, stereoisomer, or pharmaceutically acceptable salt thereof, wherein $R^{10}$ is —N(H)—$C_{1-6}$alkyl-CO$_2$H. In another embodiment is a compound of Formula (I), or a solvate, hydrate, tautomer, N-oxide, stereoisomer, or pharmaceutically acceptable salt thereof, wherein $R^{10}$ is —N(H)CH$_2$CO$_2$H. In another embodiment is a compound of Formula (I), or a solvate, hydrate, tautomer, N-oxide, stereoisomer, or pharmaceutically acceptable salt thereof, wherein $R^{10}$ is —N(H)CH$_2$CH$_2$CO$_2$H. In another embodiment is a compound of Formula (I), or a solvate, hydrate, tautomer, N-oxide, stereoisomer, or pharmaceutically acceptable salt thereof, wherein $R^{10}$ is —N(H)CH$_2$CH$_2$CH$_2$CO$_2$H. In another embodiment is a compound of Formula (I), or a solvate, hydrate, tautomer, N-oxide, stereoisomer, or pharmaceutically acceptable salt thereof, wherein $R^{10}$ is —O—$C_{1-6}$haloalkyl. In another embodiment is a compound of Formula (I), or a solvate, hydrate, tautomer, N-oxide, stereoisomer, or pharmaceutically acceptable salt thereof, wherein $R^{10}$ is —OCF$_3$. In another embodiment is a compound of Formula (I), or a solvate, hydrate, tautomer, N-oxide, stereoisomer, or pharmaceutically acceptable salt thereof, wherein $R^{10}$ is —O—$C_{3-8}$cycloalkyl. In another embodiment is a compound of Formula (I), or a solvate, hydrate, tautomer, N-oxide, stereoisomer, or pharmaceutically acceptable salt thereof, wherein $R^{10}$ is —O—$C_{3-8}$cycloalkyl-CO$_2$H. In another embodiment is a compound of Formula (I), or a solvate, hydrate, tautomer, N-oxide, stereoisomer, or pharmaceutically acceptable salt thereof, wherein $R^{10}$ is —SO$_2$R$^{17}$. In another embodiment is a compound of Formula (I), or a solvate, hydrate, tautomer, N-oxide, stereoisomer, or pharmaceutically acceptable salt thereof, wherein $R^{10}$ is —SO$_2$R$^{17}$ and $R^{17}$ is $C_{1-6}$alkyl. In another embodiment is a compound of Formula (I), or a solvate, hydrate, tautomer, N-oxide, stereoisomer, or pharmaceutically acceptable salt thereof, wherein $R^{10}$ is —SO$_2$R$^{17}$ and $R^{17}$ is —CH$_3$. In another embodiment is a compound of Formula (I), or a solvate, hydrate, tautomer, N-oxide, stereoisomer, or pharmaceutically acceptable salt thereof, wherein $R^{10}$ is —SO$_2$R$^{17}$ and $R^{17}$ is $C_{3-8}$cycloalkyl. In another embodiment is a compound of Formula (I), or a solvate, hydrate, tautomer, N-oxide, stereoisomer, or pharmaceutically acceptable salt thereof, wherein $R^5$ is H, CN, halogen, $C_{1-6}$alkyl, $C_{1-6}$haloalkyl, or $C_{1-6}$haloalkoxy. In another embodiment is a compound of Formula (I), or a solvate, hydrate, tautomer, N-oxide, stereoisomer, or pharmaceutically acceptable salt thereof, wherein $R^5$ is H. In another embodiment is a compound of Formula (I), or a solvate, hydrate, tautomer, N-oxide, stereoisomer, or pharmaceutically acceptable salt thereof, wherein $R^5$ is —CN. In another embodiment is a compound of Formula (I), or a solvate, hydrate, tautomer, N-oxide, stereoisomer, or pharmaceutically acceptable salt thereof, wherein $R^5$ is halogen. In another embodiment is a compound of Formula (I), or a solvate, hydrate, tautomer, N-oxide, stereoisomer, or pharmaceutically acceptable salt thereof, wherein $R^5$ is —Cl. In another embodiment is a compound of Formula (I), or a solvate, hydrate, tautomer, N-oxide, stereoisomer, or pharmaceutically acceptable salt thereof, wherein $R^5$ is —F. In another embodiment is a compound of Formula (I), or a solvate, hydrate, tautomer, N-oxide, stereoisomer, or pharmaceutically acceptable salt thereof, wherein $R^5$ is $C_{1-6}$alkyl. In another embodiment is a compound of Formula (I), or a solvate, hydrate, tautomer, N-oxide, stereoisomer, or pharmaceutically acceptable salt thereof, wherein $R^5$ is —CH$_3$. In another embodiment is a compound of Formula (I), or a solvate, hydrate, tautomer, N-oxide, stereoisomer, or pharmaceutically acceptable salt thereof, wherein $R^5$ is $C_{1-6}$haloalkyl. In another embodiment is a compound of Formula (I), or a solvate, hydrate, tautomer, N-oxide, stereoisomer, or pharmaceutically acceptable salt thereof, wherein $R^5$ is —CF$_3$. In another embodiment is a compound of Formula (I), or a solvate, hydrate, tautomer, N-oxide, stereoisomer, or pharmaceutically acceptable salt thereof, wherein $R^5$ is $C_{1-6}$haloalkoxy. In another embodiment is a compound of Formula (I), or a solvate, hydrate, tautomer, N-oxide, stereoisomer, or pharmaceutically acceptable salt thereof, wherein $R^5$ is —OCF$_3$. In another embodiment is a compound of Formula (I), or a solvate, hydrate, tautomer, N-oxide, stereoisomer, or pharmaceutically acceptable salt thereof, wherein $R^6$ is H. In another embodiment is a compound of Formula (I), or a solvate, hydrate, tautomer, N-oxide, stereoisomer, or pharmaceutically acceptable salt thereof, wherein $R^6$ is halogen. In another embodiment is a compound of Formula (I), or a solvate, hydrate, tautomer, N-oxide, stereoisomer, or pharmaceutically acceptable salt thereof, wherein $R^6$ is —Cl. In another embodiment is a compound of Formula (I), or a solvate, hydrate, tautomer, N-oxide, stereoisomer, or pharmaceutically acceptable salt thereof, wherein $R^6$ is —F. In another embodiment is a compound of Formula (I), or a solvate, hydrate, tautomer, N-oxide, stereoisomer, or pharmaceutically acceptable salt thereof, wherein $R^6$ is C$_{1-6}$alkyl. In another embodiment is a compound of Formula (I), or a solvate, hydrate, tautomer, N-oxide, stereoisomer, or pharmaceutically acceptable salt thereof, wherein $R^6$ is —CH$_3$.

In another embodiment is a compound of Formula (I) having the structure of Formula (Ia):

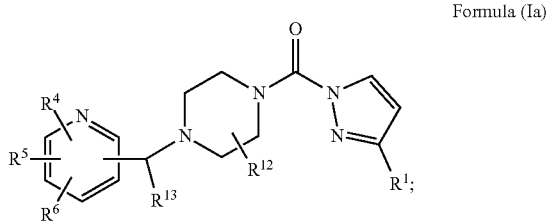

Formula (Ia)

wherein:
$R^1$ is —N(R$^2$)C(O)R$^{15}$ or —N(H)SO$_2$R$^{15}$;
$R^2$ is H or C$_{1-6}$alkyl;
$R^4$ is H, halogen, —OR$^7$, C$_{1-6}$ alkyl, C$_{1-6}$alkyl-OH, C$_{2-6}$alkenyl, C$_{2-6}$alkynyl, C$_{1-6}$haloalkyl, —O—C$_{3-8}$cycloalkyl, —O—C$_{3-8}$cycloalkyl-OH, —N(H)—C$_{1-6}$alkyl-CO$_2$H, —SO$_2$R$^{17}$, —CO$_2$R$^8$, —C(O)NR$^8$R$^9$, C$_{3-8}$cycloalkyl, C$_{2-9}$heterocycloalkyl, —C$_{1-6}$alkyl-C$_{2-9}$heterocycloalkyl, C$_{6-10}$aryl, C$_{1-9}$heteroaryl, wherein C$_{3-8}$cycloalkyl, C$_{2-9}$heterocycloalkyl, —C$_{1-6}$alkyl-C$_{2-9}$heterocycloalkyl, C$_{6-10}$aryl, C$_{1-9}$heteroaryl are optionally substituted with 1 or 2 R$^{14}$;
$R^5$ is H, —CN, halogen, C$_{1-6}$alkyl, C$_{1-6}$haloalkyl, C$_{1-6}$haloalkoxy, or phenyl;
$R^6$ is H, halogen, or C$_{1-6}$alkyl;
$R^7$ is H, C$_{1-6}$alkyl, C$_{1-6}$haloalkyl, C$_{3-8}$cycloalkyl, C$_{2-9}$heterocycloalkyl, C$_{6-10}$aryl, or C$_{1-9}$heteroaryl, wherein C$_{2-9}$heterocycloalkyl, C$_{6-10}$aryl, or C$_{1-9}$heteroaryl are optionally substituted with 1 or 2 R$^{14}$;
each R$^8$ and each R$^9$ are independently selected from H and C$_{1-6}$alkyl; or R$^8$ and R$^9$ together with the nitrogen to which they are attached are combined to form a heterocycloalkyl ring;
$R^{12}$ is H, halogen, or C$_{1-6}$alkyl;
$R^{13}$ is H or C$_{1-6}$alkyl;
each R$^{14}$ is independently selected from halogen, —OH, oxo, C$_{1-6}$alkyl, C$_{1-6}$haloalkyl, C$_{1-6}$alkoxy, —C$_{1-6}$alkyl-OH, C$_{3-8}$cycloalkyl, —CO$_2$R$^8$, —C(O)NR$^8$R$^9$, —C(O)—C$_{1-6}$alkyl, —C(O)—C$_{1-6}$alkyl-OH, —SO$_2$—C$_{1-6}$alkyl, —N(R$^8$)SO$_2$—C$_{1-6}$alkyl, and —N(R$^8$)C(O)—C$_{1-6}$alkyl;

$R^{15}$ is C$_{1-6}$alkyl or C$_{3-8}$cycloalkyl; and
$R^{17}$ is C$_{1-6}$alkyl or C$_{3-8}$cycloalkyl;
or a solvate, hydrate, tautomer, N-oxide, stereoisomer, or pharmaceutically acceptable salt thereof.

In another embodiment is a compound of Formula (Ia), or a solvate, hydrate, tautomer, N-oxide, stereoisomer, or pharmaceutically acceptable salt thereof, having the structure

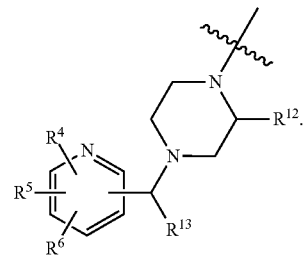

In another embodiment is a compound of Formula (Ia), or a solvate, hydrate, tautomer, N-oxide, stereoisomer, or pharmaceutically acceptable salt thereof, having the structure

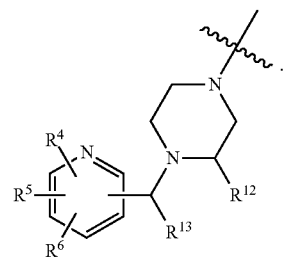

In another embodiment is a compound of Formula (Ia), or a solvate, hydrate, tautomer, N-oxide, stereoisomer, or pharmaceutically acceptable salt thereof, wherein $R^1$ is —N(R$^2$)C(O)R$^{15}$. In another embodiment is a compound of Formula (Ia), or a solvate, hydrate, tautomer, N-oxide, stereoisomer, or pharmaceutically acceptable salt thereof, wherein $R^1$ is —N(R$^2$)C(O)R$^{15}$ and $R^2$ is H. In another embodiment is a compound of Formula (Ia), or a solvate, hydrate, tautomer, N-oxide, stereoisomer, or pharmaceutically acceptable salt thereof, wherein $R^1$ is —N(H)C(O)R$^{15}$ and $R^{15}$ is C$_{1-6}$alkyl. In another embodiment is a compound of Formula (Ia), or a solvate, hydrate, tautomer, N-oxide, stereoisomer, or pharmaceutically acceptable salt thereof, wherein $R^1$ is —N(H)C(O)R$^{15}$ and $R^{15}$ is —CH$_3$. In another embodiment is a compound of Formula (Ia), or a solvate, hydrate, tautomer, N-oxide, stereoisomer, or pharmaceutically acceptable salt thereof, wherein $R^1$ is —N(H)C(O)R$^{15}$ and $R^{15}$ is C$_{3-8}$cycloalkyl. In another embodiment is a compound of Formula (Ia), or a solvate, hydrate, tautomer, N-oxide, stereoisomer, or pharmaceutically acceptable salt thereof, wherein $R^1$ is —N(R$^2$)C(O)R$^{15}$ and $R^2$ is C$_{1-6}$alkyl. In another embodiment is a compound of Formula (Ia), or a solvate, hydrate, tautomer, N-oxide, stereoisomer, or pharmaceutically acceptable salt thereof, wherein $R^1$ is —N(R$^2$)C(O)R$^{15}$ and $R^2$ is —CH$_3$. In another embodiment is a compound of Formula (Ia), or a solvate, hydrate, tautomer, N-oxide, stereoisomer, or pharmaceutically acceptable salt thereof, wherein $R^1$ is —N(CH$_3$)C(O)R$^{15}$ and $R^{15}$ is C$_{1-6}$alkyl. In another embodiment is a compound of Formula (Ia), or a solvate, hydrate, tautomer, N-oxide, stereoisomer, or pharmaceutically acceptable salt thereof, wherein $R^1$ is —N(CH$_3$)C(O)R$^{15}$ and $R^{15}$ is —CH$_3$. In another embodiment is a compound of Formula (Ia), or a solvate, hydrate, tautomer, N-oxide, stereoisomer, or pharmaceutically acceptable salt thereof, wherein $R^1$ is —N(CH$_3$)C(O)R$^{15}$ and $R^{15}$ is $C_{3-8}$cycloalkyl. In another embodiment is a compound of Formula (Ia), or a solvate, hydrate, tautomer, N-oxide, stereoisomer, or pharmaceutically acceptable salt thereof, wherein $R^1$ is —N(H)SO$_2$R$^{15}$. In another embodiment is a compound of Formula (Ia), or a solvate, hydrate, tautomer, N-oxide, stereoisomer, or pharmaceutically acceptable salt thereof, wherein $R^1$ is —N(H)SO$_2$R$^{15}$ and $R^{15}$ is $C_{1-6}$alkyl. In another embodiment is a compound of Formula (Ia), or a solvate, hydrate, tautomer, N-oxide, stereoisomer, or pharmaceutically acceptable salt thereof, wherein $R^1$ is —N(H)SO$_2$R$^{15}$ and $R^{15}$ is —CH$_3$. In another embodiment is a compound of Formula (Ia), or a solvate, hydrate, tautomer, N-oxide, stereoisomer, or pharmaceutically acceptable salt thereof, wherein $R^1$ is —N(H)SO$_2$R$^{15}$ and $R^{15}$ is $C_{3-8}$cycloalkyl.

In another embodiment is a compound of Formula (Ia), or a solvate, hydrate, tautomer, N-oxide, stereoisomer, or pharmaceutically acceptable salt thereof, wherein $R^4$ is halogen, —OR$^7$, $C_{1-6}$alkyl-OH, —N(H)—C$_{1-6}$alkyl-CO$_2$H, $C_{2-6}$alkynyl, $C_{1-6}$haloalkyl, —CO$_2$R$^8$, —C(O)NR$^8$R$^9$, $C_{3-8}$cycloalkyl, $C_{2-9}$heterocycloalkyl, $C_{6-10}$aryl, or $C_{1-9}$heteroaryl, wherein $C_{3-8}$cycloalkyl, $C_{2-9}$heterocycloalkyl, $C_{6-10}$aryl, or $C_{1-9}$heteroaryl are optionally substituted with 1 or 2 R$^{14}$. In another embodiment is a compound of Formula (Ia), or a solvate, hydrate, tautomer, N-oxide, stereoisomer, or pharmaceutically acceptable salt thereof, wherein $R^4$ is halogen, —OR$^7$, —N(H)—C$_{1-6}$alkyl-CO$_2$H, $C_{1-6}$haloalkyl, —C(O)NR$^8$R$^9$, $C_{3-8}$cycloalkyl, $C_{2-9}$heterocycloalkyl, or $C_{1-9}$heteroaryl, wherein $C_{2-9}$heterocycloalkyl or $C_{1-9}$heteroaryl are optionally substituted with 1 or 2 R$^{14}$. In another embodiment is a compound of Formula (Ia), or a solvate, hydrate, tautomer, N-oxide, stereoisomer, or pharmaceutically acceptable salt thereof, wherein $R^4$ is halogen. In another embodiment is a compound of Formula (Ia), or a solvate, hydrate, tautomer, N-oxide, stereoisomer, or pharmaceutically acceptable salt thereof, wherein $R^4$ is —Cl. In another embodiment is a compound of Formula (Ia), or a solvate, hydrate, tautomer, N-oxide, stereoisomer, or pharmaceutically acceptable salt thereof, wherein $R^4$ is $C_{1-6}$haloalkyl. In another embodiment is a compound of Formula (Ia), or a solvate, hydrate, tautomer, N-oxide, stereoisomer, or pharmaceutically acceptable salt thereof, wherein $R^4$ is —CF$_3$. In another embodiment is a compound of Formula (Ia), or a solvate, hydrate, tautomer, N-oxide, stereoisomer, or pharmaceutically acceptable salt thereof, wherein $R^4$ is —N(H)—C$_{1-6}$alkyl-CO$_2$H. In another embodiment is a compound of Formula (Ia), or a solvate, hydrate, tautomer, N-oxide, stereoisomer, or pharmaceutically acceptable salt thereof, wherein $R^4$ is —N(H)CH$_2$CO$_2$H. In another embodiment is a compound of Formula (Ia), or a solvate, hydrate, tautomer, N-oxide, stereoisomer, or pharmaceutically acceptable salt thereof, wherein $R^4$ is —N(H)CH$_2$CH$_2$CO$_2$H. In another embodiment is a compound of Formula (Ia), or a solvate, hydrate, tautomer, N-oxide, stereoisomer, or pharmaceutically acceptable salt thereof, wherein $R^4$ is —N(H)CH$_2$CH$_2$CH$_2$CO$_2$H. In another embodiment is a compound of Formula (Ia), or a solvate, hydrate, tautomer, N-oxide, stereoisomer, or pharmaceutically acceptable salt thereof, wherein $R^4$ is —C(O)NR$^8$R$^9$. In another embodiment is a compound of Formula (Ia), or a solvate, hydrate, tautomer, N-oxide, stereoisomer, or pharmaceutically acceptable salt thereof, wherein $R^4$ is —C(O)NH$_2$. In another embodiment is a compound of Formula (Ia), or a solvate, hydrate, tautomer, N-oxide, stereoisomer, or pharmaceutically acceptable salt thereof, wherein $R^4$ is $C_{3-8}$cycloalkyl. In another embodiment is a compound of Formula (Ia), or a solvate, hydrate, tautomer, N-oxide, stereoisomer, or pharmaceutically acceptable salt thereof, wherein $R^4$ is —OR$^7$. In another embodiment is a compound of Formula (Ia), or a solvate, hydrate, tautomer, N-oxide, stereoisomer, or pharmaceutically acceptable salt thereof, wherein $R^4$ is —OR$^7$ and $R^7$ is unsubstituted $C_{3-8}$cycloalkyl or $C_{6-10}$aryl optionally substituted with halogen. In another embodiment is a compound of Formula (Ia), or a solvate, hydrate, tautomer, N-oxide, stereoisomer, or pharmaceutically acceptable salt thereof, wherein $R^4$ is —OR$^7$ and $R^7$ is unsubstituted $C_{3-8}$cycloalkyl. In another embodiment is a compound of Formula (Ia), or a solvate, hydrate, tautomer, N-oxide, stereoisomer, or pharmaceutically acceptable salt thereof, wherein $R^4$ is —OR$^7$ and $R^7$ is phenyl optionally substituted with halogen. In another embodiment is a compound of Formula (Ia), or a solvate, hydrate, tautomer, N-oxide, stereoisomer, or pharmaceutically acceptable salt thereof, wherein $R^4$ is —OR$^7$ and $R^7$ is phenyl substituted with halogen. In another embodiment is a compound of Formula (Ia), or a solvate, hydrate, tautomer, N-oxide, stereoisomer, or pharmaceutically acceptable salt thereof, wherein $R^4$ is —OR$^7$ and $R^7$ is phenyl substituted with —Cl. In another embodiment is a compound of Formula (Ia), or a solvate, hydrate, tautomer, N-oxide, stereoisomer, or pharmaceutically acceptable salt thereof, wherein $R^4$ is $C_{2-9}$heterocycloalkyl optionally substituted with 1 or 2 R$^{14}$. In another embodiment is a compound of Formula (Ia), or a solvate, hydrate, tautomer, N-oxide, stereoisomer, or pharmaceutically acceptable salt thereof, wherein $R^4$ is an unsubstituted $C_{2-9}$heterocycloalkyl. In another embodiment is a compound of Formula (Ia), or a solvate, hydrate, tautomer, N-oxide, stereoisomer, or pharmaceutically acceptable salt thereof, wherein $R^4$ is $C_{2-9}$heterocycloalkyl substituted with 1 or 2 R$^{14}$. In another embodiment is a compound of Formula (Ia), or a solvate, hydrate, tautomer, N-oxide, stereoisomer, or pharmaceutically acceptable salt thereof, wherein $R^4$ is $C_{4-5}$heterocycloalkyl optionally substituted with 1 or 2 R$^{14}$, wherein the $C_{4-5}$heterocycloalkyl is a monocyclic heterocycloalkyl selected from pyrrolidine, piperidine, piperazine, and morpholine. In another embodiment is a compound of Formula (Ia), or a solvate, hydrate, tautomer, N-oxide, stereoisomer, or pharmaceutically acceptable salt thereof, wherein $R^4$ is $C_{5-9}$heterocycloalkyl optionally substituted with 1 or 2 R$^{14}$, wherein the $C_{5-9}$heterocycloalkyl is a bicyclic heterocycloalkyl. In another embodiment is a compound of Formula (Ia), or a solvate, hydrate, tautomer, N-oxide, stereoisomer, or pharmaceutically acceptable salt thereof, wherein $R^4$ is $C_{5-9}$heterocycloalkyl optionally substituted with 1 or 2 R$^{14}$, wherein the $C_{5-9}$heterocycloalkyl is a spirocyclic heterocycloalkyl. In another embodiment is a compound of Formula (Ia), or a solvate, hydrate, tautomer, N-oxide, stereoisomer, or pharmaceutically acceptable salt thereof, wherein $R^4$ is

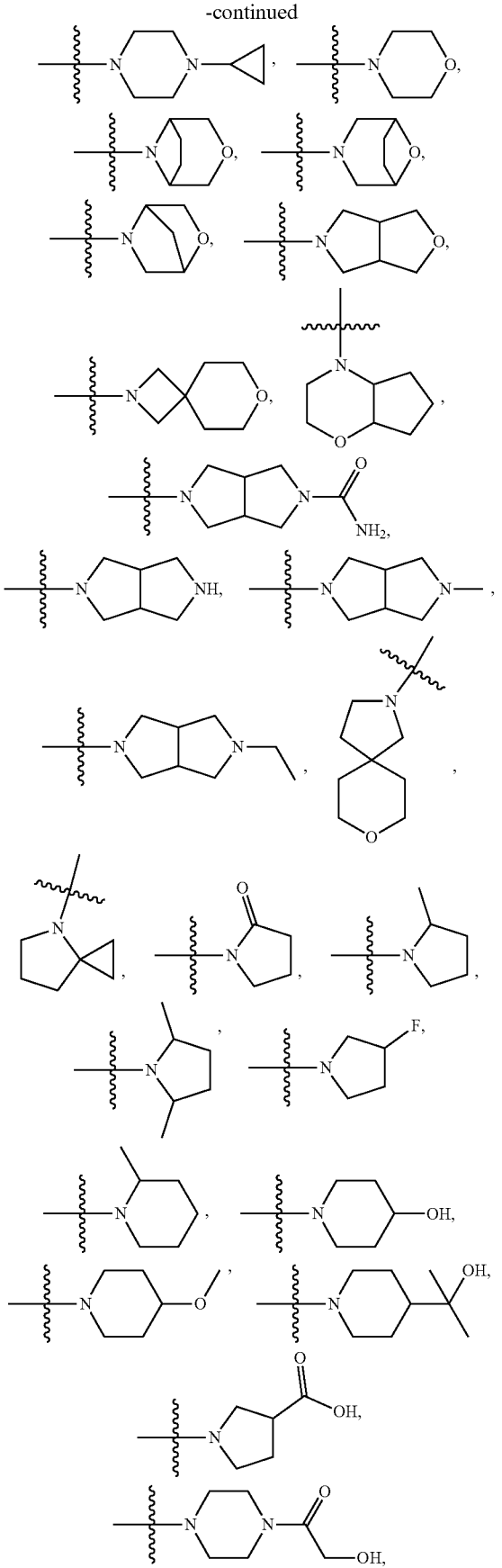

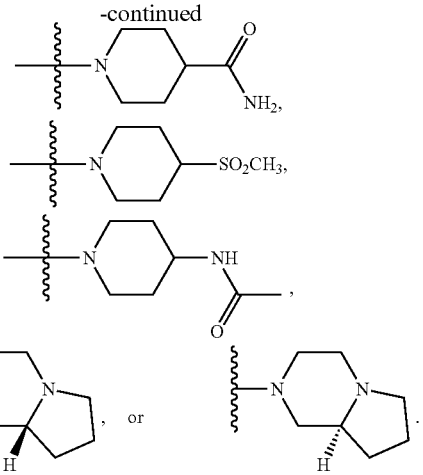

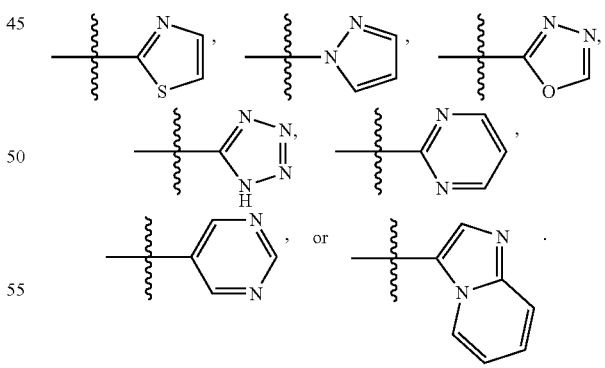

In another embodiment is a compound of Formula (Ia), or a solvate, hydrate, tautomer, N-oxide, stereoisomer, or pharmaceutically acceptable salt thereof, wherein $R^4$ is $C_{1-9}$heteroaryl optionally substituted with 1 or 2 $R^{14}$. In another embodiment is a compound of Formula (Ia), or a solvate, hydrate, tautomer, N-oxide, stereoisomer, or pharmaceutically acceptable salt thereof, wherein $R^4$ is an unsubstituted $C_{1-9}$heteroaryl. In another embodiment is a compound of Formula (Ia), or a solvate, hydrate, tautomer, N-oxide, stereoisomer, or pharmaceutically acceptable salt thereof, wherein $R^4$ is $C_{2-9}$heteroaryl substituted with 1 or 2 $R^{14}$. In another embodiment is a compound of Formula (Ia), or a solvate, hydrate, tautomer, N-oxide, stereoisomer, or pharmaceutically acceptable salt thereof, wherein $R^4$ is $C_{2-9}$heteroaryl optionally substituted with 1 or 2 $R^{14}$, wherein the $C_{2-9}$heteroaryl is selected from pyrrole, furan, thiophene, thiazole, pyrazole, oxazole, oxadiazole, thiadiazole, pyridine, pyrimidine, pyrazine, indole, benzothiophene, benzofuran, and imidazopyridine. In another embodiment is a compound of Formula (Ia), or a solvate, hydrate, tautomer, N-oxide, stereoisomer, or pharmaceutically acceptable salt thereof, wherein $R^4$ is In another embodiment is a compound of Formula (Ia), or a solvate, hydrate, tautomer, N-oxide, stereoisomer, or pharmaceutically acceptable salt thereof, wherein $R^5$ is H, CN, halogen, $C_{1-6}$alkyl, $C_{1-6}$haloalkyl, or $C_{1-6}$haloalkoxy. In another embodiment is a compound of Formula (Ia), or a solvate, hydrate, tautomer, N-oxide, stereoisomer, or pharmaceutically acceptable salt thereof, wherein $R^5$ is H. In another embodiment is a compound of Formula (Ia), or a solvate, hydrate, tautomer, N-oxide, stereoisomer, or pharmaceutically acceptable salt thereof, wherein $R^5$ is —CN. In another embodiment is a compound of Formula (Ia), or a solvate, hydrate, tautomer, N-oxide, stereoisomer, or pharmaceutically acceptable salt thereof, wherein $R^5$ is halogen. In another embodiment is a compound of Formula (Ia), or a solvate, hydrate, tautomer, N-oxide, stereoisomer, or pharmaceutically acceptable salt thereof, wherein $R^5$ is —Cl. In another embodiment is a compound of Formula (Ia), or a solvate, hydrate, tautomer, N-oxide, stereoisomer, or pharmaceutically acceptable salt thereof, wherein $R^5$ is —F. In another embodiment is a compound of Formula (Ia), or a solvate, hydrate, tautomer, N-oxide, stereoisomer, or pharmaceutically acceptable salt thereof, wherein $R^5$ is $C_{1-6}$alkyl. In another embodiment is a compound of Formula (Ia), or a solvate, hydrate, tautomer, N-oxide, stereoisomer, or pharmaceutically acceptable salt thereof, wherein $R^5$ is —CH$_3$. In another embodiment is a compound of Formula (Ia), or a solvate, hydrate, tautomer, N-oxide, stereoisomer, or pharmaceutically acceptable salt thereof, wherein $R^5$ is $C_{1-6}$haloalkyl. In another embodiment is a compound of Formula (Ia), or a solvate, hydrate, tautomer, N-oxide, stereoisomer, or pharmaceutically acceptable salt thereof, wherein $R^5$ is —CF$_3$. In another embodiment is a compound of Formula (Ia), or a solvate, hydrate, tautomer, N-oxide, stereoisomer, or pharmaceutically acceptable salt thereof, wherein $R^5$ is $C_{1-6}$haloalkoxy. In another embodiment is a compound of Formula (Ia), or a solvate, hydrate, tautomer, N-oxide, stereoisomer, or pharmaceutically acceptable salt thereof, wherein $R^5$ is —OCF$_3$. In another embodiment is a compound of Formula (Ia), or a solvate, hydrate, tautomer, N-oxide, stereoisomer, or pharmaceutically acceptable salt thereof, wherein $R^6$ is H. In another embodiment is a compound of Formula (Ia), or a solvate, hydrate, tautomer, N-oxide, stereoisomer, or pharmaceutically acceptable salt thereof, wherein $R^6$ is halogen. In another embodiment is a compound of Formula (Ia), or a solvate, hydrate, tautomer, N-oxide, stereoisomer, or pharmaceutically acceptable salt thereof, wherein $R^6$ is —Cl. In another embodiment is a compound of Formula (Ia), or a solvate, hydrate, tautomer, N-oxide, stereoisomer, or pharmaceutically acceptable salt thereof, wherein $R^6$ is —F. In another embodiment is a compound of Formula (Ia), or a solvate, hydrate, tautomer, N-oxide, stereoisomer, or pharmaceutically acceptable salt thereof, wherein $R^6$ is $C_{1-6}$alkyl. In another embodiment is a compound of Formula (Ia), or a solvate, hydrate, tautomer, N-oxide, stereoisomer, or pharmaceutically acceptable salt thereof, wherein $R^6$ is —CH$_3$.

In another embodiment is a compound of Formula (Ia), or a solvate, hydrate, tautomer, N-oxide, stereoisomer, or pharmaceutically acceptable salt thereof, wherein $R^{12}$ is H. In another embodiment is a compound of Formula (Ia), or a solvate, hydrate, tautomer, N-oxide, stereoisomer, or pharmaceutically acceptable salt thereof, wherein $R^{12}$ is $C_{1-6}$alkyl. In another embodiment is a compound of Formula (Ia), or a solvate, hydrate, tautomer, N-oxide, stereoisomer, or pharmaceutically acceptable salt thereof, wherein $R^{12}$ is —CH$_3$. In another embodiment is a compound of Formula (Ia), or a solvate, hydrate, tautomer, N-oxide, stereoisomer, or pharmaceutically acceptable salt thereof, wherein $R^{13}$ is H. In another embodiment is a compound of Formula (Ia), or a solvate, hydrate, tautomer, N-oxide, stereoisomer, or pharmaceutically acceptable salt thereof, wherein $R^{13}$ is $C_{1-6}$alkyl. In another embodiment is a compound of Formula (Ia), or a solvate, hydrate, tautomer, N-oxide, stereoisomer, or pharmaceutically acceptable salt thereof, wherein $R^{13}$ is —CH$_3$. In another embodiment is a compound of Formula (Ia), or a solvate, hydrate, tautomer, N-oxide, stereoisomer, or pharmaceutically acceptable salt thereof, wherein $R^{12}$ is H and $R^{13}$ is H. In another embodiment is a compound of Formula (Ia), or a solvate, hydrate, tautomer, N-oxide, stereoisomer, or pharmaceutically acceptable salt thereof, wherein $R^{12}$ is H and $R^{13}$ is $C_{1-6}$alkyl. In another embodiment is a compound of Formula (Ia), or a solvate, hydrate, tautomer, N-oxide, stereoisomer, or pharmaceutically acceptable salt thereof, wherein $R^{12}$ is H and $R^{13}$ is —CH$_3$. In another embodiment is a compound of Formula (Ia), or a solvate, hydrate, tautomer, N-oxide, stereoisomer, or pharmaceutically acceptable salt thereof, wherein $R^{12}$ is $C_{1-6}$alkyl and $R^{13}$ is H. In another embodiment is a compound of Formula (Ia), or a solvate, hydrate, tautomer, N-oxide, stereoisomer, or pharmaceutically acceptable salt thereof, wherein $R^{12}$ is —CH$_3$ and $R^{13}$ is H. In another embodiment is a compound of Formula (Ia), or a solvate, hydrate, tautomer, N-oxide, stereoisomer, or pharmaceutically acceptable salt thereof, wherein $R^{12}$ is $C_{1-6}$alkyl and $R^{13}$ is $C_{1-6}$alkyl. In another embodiment is a compound of Formula (Ia), or a solvate, hydrate, tautomer, N-oxide, stereoisomer, or pharmaceutically acceptable salt thereof, wherein $R^{12}$ is —CH$_3$ and $R^{13}$ is —CH$_3$.

In another embodiment is a compound of Formula (I) having the structure of Formula (Ib):

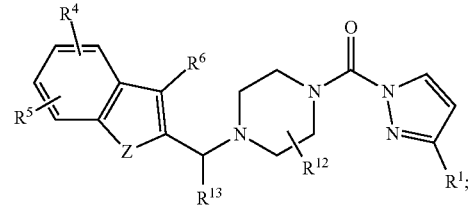

Formula (Ib)

wherein:
$R^1$ is —N(R$^2$)C(O)R$^{15}$ or —N(H)SO$_2$R$^{15}$;
$R^2$ is H or $C_{1-6}$alkyl;
Z is —S—, —O—, or —N(R$^{20}$)—;
$R^4$ is H, halogen, —OR$^7$, $C_{1-6}$alkyl, $C_{1-6}$alkyl-OH, $C_{2-6}$alkenyl, $C_{2-6}$alkynyl, $C_{1-6}$haloalkyl, —O—$C_{3-8}$cycloalkyl, —O—$C_{3-8}$cycloalkyl-OH, —N(H)—$C_{1-6}$alkyl-CO$_2$H, —SO$_2$R$^{17}$, —CO$_2$R$^8$, —C(O)NR$^8$R$^9$, $C_{3-8}$cycloalkyl, $C_{2-9}$heterocycloalkyl, —$C_{1-6}$alkyl-$C_{2-9}$heterocycloalkyl, $C_{6-10}$aryl, $C_{1-9}$heteroaryl, wherein $C_{3-8}$cycloalkyl, $C_{2-9}$heterocycloalkyl, —$C_{1-6}$alkyl-$C_{2-9}$heterocycloalkyl, $C_{6-10}$aryl, $C_{1-9}$heteroaryl are optionally substituted with 1 or 2 $R^{14}$;
$R^5$ is H, —CN, halogen, $C_{1-6}$alkyl, $C_{1-6}$haloalkoxy, or phenyl;
$R^6$ is H, halogen, or $C_{1-6}$alkyl;
$R^7$ is H, $C_{1-6}$alkyl, $C_{1-6}$haloalkyl, $C_{3-8}$cycloalkyl, $C_{2-9}$heterocycloalkyl, $C_{6-10}$aryl, or $C_{1-9}$heteroaryl, wherein $C_{2-9}$heterocycloalkyl, $C_{6-10}$aryl, or $C_{1-9}$heteroaryl are optionally substituted with 1 or 2 $R^{14}$;
each $R^8$ and each $R^9$ are independently selected from H and $C_{1-6}$alkyl; or $R^8$ and $R^9$ together with the nitrogen to which they are attached are combined to form a heterocycloalkyl ring;
$R^{12}$ is H, halogen, or $C_{1-6}$alkyl;
$R^{13}$ is H or $C_{1-6}$alkyl;
each $R^{14}$ is independently selected from halogen, —OH, oxo, $C_{1-6}$alkyl, $C_{1-6}$haloalkyl, $C_{1-6}$alkoxy, —$C_{1-6}$alkyl-OH, $C_{3-8}$cycloalkyl, —CO$_2$R$^8$, —C(O)NR$^8$R$^9$, —C(O)—C$_{1-6}$alkyl, —C(O)—C$_{1-6}$alkyl-OH, —SO$_2$—C$_{1-6}$alkyl, —N(R$^8$)SO$_2$—C$_{1-6}$alkyl, and —N(R$^8$)C(O)—C$_{1-6}$alkyl;

R$^{15}$ is C$_{1-6}$alkyl or C$_{3-8}$cycloalkyl;

R$^{17}$ is C$_{1-6}$alkyl or C$_{3-8}$cycloalkyl; and

R$^{20}$ is H or C$_{1-6}$alkyl;

or a solvate, hydrate, tautomer, N-oxide, stereoisomer, or pharmaceutically acceptable salt thereof.

In another embodiment is a compound of Formula (Ib), or a solvate, hydrate, tautomer, N-oxide, stereoisomer, or pharmaceutically acceptable salt thereof, having the structure

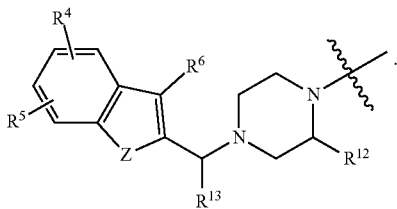

In another embodiment is a compound of Formula (Ib), or a solvate, hydrate, tautomer, N-oxide, stereoisomer, or pharmaceutically acceptable salt thereof, having the structure

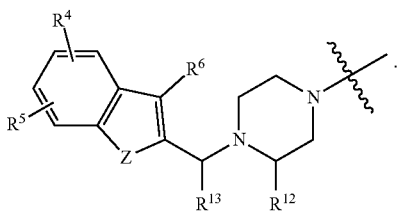

In another embodiment is a compound of Formula (Ib), or a solvate, hydrate, tautomer, N-oxide, stereoisomer, or pharmaceutically acceptable salt thereof, wherein Z is —S—. In another embodiment is a compound of Formula (Ib), or a solvate, hydrate, tautomer, N-oxide, stereoisomer, or pharmaceutically acceptable salt thereof, wherein Z is —O—. In another embodiment is a compound of Formula (Ib), or a solvate, hydrate, tautomer, N-oxide, stereoisomer, or pharmaceutically acceptable salt thereof, wherein Z is —N(R$^{20}$)—. In another embodiment is a compound of Formula (Ib), or a solvate, hydrate, tautomer, N-oxide, stereoisomer, or pharmaceutically acceptable salt thereof, wherein Z is —N(H)—. In another embodiment is a compound of Formula (Ib), or a solvate, hydrate, tautomer, N-oxide, stereoisomer, or pharmaceutically acceptable salt thereof, wherein Z is —N(CH$_3$)—.

In another embodiment is a compound of Formula (Ib), or a solvate, hydrate, tautomer, N-oxide, stereoisomer, or pharmaceutically acceptable salt thereof, wherein R$^1$ is —N(R$^2$)C(O)R$^{15}$. In another embodiment is a compound of Formula (Ib), or a solvate, hydrate, tautomer, N-oxide, stereoisomer, or pharmaceutically acceptable salt thereof, wherein R$^1$ is —N(R$^2$)C(O)R$^{15}$ and R$^2$ is H. In another embodiment is a compound of Formula (Ib), or a solvate, hydrate, tautomer, N-oxide, stereoisomer, or pharmaceutically acceptable salt thereof, wherein R$^1$ is —N(H)C(O)R$^{15}$ and R$^{15}$ is C$_{1-6}$alkyl. In another embodiment is a compound of Formula (Ib), or a solvate, hydrate, tautomer, N-oxide, stereoisomer, or pharmaceutically acceptable salt thereof, wherein R$^1$ is —N(H)C(O)R$^{15}$ and R$^{15}$ is —CH$_3$. In another embodiment is a compound of Formula (Ib), or a solvate, hydrate, tautomer, N-oxide, stereoisomer, or pharmaceutically acceptable salt thereof, wherein R$^1$ is —N(H)C(O)R$^{15}$ and R$^{15}$ is C$_{3-8}$cycloalkyl. In another embodiment is a compound of Formula (Ib), or a solvate, hydrate, tautomer, N-oxide, stereoisomer, or pharmaceutically acceptable salt thereof, wherein R$^1$ is —N(R$^2$)C(O)R$^{15}$ and R$^2$ is C$_{1-6}$alkyl. In another embodiment is a compound of Formula (Ib), or a solvate, hydrate, tautomer, N-oxide, stereoisomer, or pharmaceutically acceptable salt thereof, wherein R$^1$ is —N(R$^2$)C(O)R$^{15}$ and R$^2$ is —CH$_3$. In another embodiment is a compound of Formula (Ib), or a solvate, hydrate, tautomer, N-oxide, stereoisomer, or pharmaceutically acceptable salt thereof, wherein R$^1$ is —N(CH$_3$)C(O)R$^{15}$ and R$^{15}$ is C$_{1-6}$alkyl. In another embodiment is a compound of Formula (Ib), or a solvate, hydrate, tautomer, N-oxide, stereoisomer, or pharmaceutically acceptable salt thereof, wherein R$^1$ is —N(CH$_3$)C(O)R$^{15}$ and R$^{15}$ is —CH$_3$. In another embodiment is a compound of Formula (Ib), or a solvate, hydrate, tautomer, N-oxide, stereoisomer, or pharmaceutically acceptable salt thereof, wherein R$^1$ is —N(CH$_3$)C(O)R$^{15}$ and R$^{15}$ is C$_{3-8}$cycloalkyl. In another embodiment is a compound of Formula (Ib), or a solvate, hydrate, tautomer, N-oxide, stereoisomer, or pharmaceutically acceptable salt thereof, wherein R$^1$ is —N(H)SO$_2$R$^{15}$. In another embodiment is a compound of Formula (Ib), or a solvate, hydrate, tautomer, N-oxide, stereoisomer, or pharmaceutically acceptable salt thereof, wherein R$^1$ is —N(H)SO$_2$R$^{15}$ and R$^{15}$ is C$_{1-6}$alkyl. In another embodiment is a compound of Formula (Ib), or a solvate, hydrate, tautomer, N-oxide, stereoisomer, or pharmaceutically acceptable salt thereof, wherein R$^1$ is —N(H)SO$_2$R$^{15}$ and R$^{15}$ is —CH$_3$. In another embodiment is a compound of Formula (Ib), or a solvate, hydrate, tautomer, N-oxide, stereoisomer, or pharmaceutically acceptable salt thereof, wherein R$^1$ is —N(H)SO$_2$R$^{15}$ and R$^{15}$ is C$_{3-8}$cycloalkyl.

In another embodiment is a compound of Formula (Ib), or a solvate, hydrate, tautomer, N-oxide, stereoisomer, or pharmaceutically acceptable salt thereof, wherein R$^4$ is halogen, —OR$^7$, C$_{1-6}$alkyl-OH, —N(H)—C$_{1-6}$alkyl-CO$_2$H, C$_{2-6}$alkynyl, C$_{1-6}$haloalkyl, —CO$_2$R$^8$, —C(O)NR$^8$R$^9$, C$_{3-8}$cycloalkyl, C$_{2-9}$heterocycloalkyl, C$_{6-10}$aryl, or C$_{1-9}$heteroaryl, wherein C$_{3-8}$cycloalkyl, C$_{2-9}$heterocycloalkyl, C$_{6-10}$aryl, or C$_{1-9}$heteroaryl are optionally substituted with 1 or 2 R$^{14}$. In another embodiment is a compound of Formula (Ib), or a solvate, hydrate, tautomer, N-oxide, stereoisomer, or pharmaceutically acceptable salt thereof, wherein R$^4$ is halogen, —OR$^7$, —N(H)—C$_{1-6}$alkyl-CO$_2$H, C$_{1-6}$haloalkyl, —C(O)NR$^8$R$^9$, C$_{3-8}$cycloalkyl, C$_{2-9}$heterocycloalkyl, or C$_{1-9}$heteroaryl, wherein C$_{2-9}$heterocycloalkyl or C$_{1-9}$heteroaryl are optionally substituted with 1 or 2 R$^{14}$. In another embodiment is a compound of Formula (Ib), or a solvate, hydrate, tautomer, N-oxide, stereoisomer, or pharmaceutically acceptable salt thereof, wherein R$^4$ is halogen. In another embodiment is a compound of Formula (Ib), or a solvate, hydrate, tautomer, N-oxide, stereoisomer, or pharmaceutically acceptable salt thereof, wherein R$^4$ is —Cl. In another embodiment is a compound of Formula (Ib), or a solvate, hydrate, tautomer, N-oxide, stereoisomer, or pharmaceutically acceptable salt thereof, wherein R$^4$ is C$_{1-6}$haloalkyl. In another embodiment is a compound of Formula (Ib), or a solvate, hydrate, tautomer, N-oxide, stereoisomer, or pharmaceutically acceptable salt thereof, wherein R$^4$ is —CF$_3$. In another embodiment is a compound of Formula (Ib), or a solvate, hydrate, tautomer, N-oxide, stereoisomer, or pharmaceutically acceptable salt thereof, wherein R$^4$ is —N(H)—C$_{1-6}$alkyl-CO$_2$H. In another embodiment is a compound of Formula (Ib), or a solvate, hydrate, tautomer, N-oxide, stereoisomer, or pharmaceutically acceptable salt thereof, wherein $R^4$ is —N(H)CH$_2$CO$_2$H. In another embodiment is a compound of Formula (Ib), or a solvate, hydrate, tautomer, N-oxide, stereoisomer, or pharmaceutically acceptable salt thereof, wherein $R^4$ is —N(H) CH$_2$CH$_2$CO$_2$H. In another embodiment is a compound of Formula (Ib), or a solvate, hydrate, tautomer, N-oxide, stereoisomer, or pharmaceutically acceptable salt thereof, wherein $R^4$ is —N(H)CH$_2$CH$_2$CH$_2$CO$_2$H. In another embodiment is a compound of Formula (Ib), or a solvate, hydrate, tautomer, N-oxide, stereoisomer, or pharmaceutically acceptable salt thereof, wherein $R^4$ is —C(O)NR$^8$R$^9$. In another embodiment is a compound of Formula (Ib), or a solvate, hydrate, tautomer, N-oxide, stereoisomer, or pharmaceutically acceptable salt thereof, wherein $R^4$ is —C(O) NH$_2$. In another embodiment is a compound of Formula (Ib), or a solvate, hydrate, tautomer, N-oxide, stereoisomer, or pharmaceutically acceptable salt thereof, wherein $R^4$ is $C_{3-8}$cycloalkyl. In another embodiment is a compound of Formula (Ib), or a solvate, hydrate, tautomer, N-oxide, stereoisomer, or pharmaceutically acceptable salt thereof, wherein $R^4$ is —OR$^7$. In another embodiment is a compound of Formula (Ib), or a solvate, hydrate, tautomer, N-oxide, stereoisomer, or pharmaceutically acceptable salt thereof, wherein $R^4$ is —OR$^7$ and $R^7$ is unsubstituted $C_{3-8}$cycloalkyl or $C_{6-10}$aryl optionally substituted with halogen. In another embodiment is a compound of Formula (Ib), or a solvate, hydrate, tautomer, N-oxide, stereoisomer, or pharmaceutically acceptable salt thereof, wherein $R^4$ is —OR$^7$ and $R^7$ is unsubstituted $C_{3-8}$cycloalkyl. In another embodiment is a compound of Formula (Ib), or a solvate, hydrate, tautomer, N-oxide, stereoisomer, or pharmaceutically acceptable salt thereof, wherein $R^4$ is —OR$^7$ and $R^7$ is phenyl optionally substituted with halogen. In another embodiment is a compound of Formula (Ib), or a solvate, hydrate, tautomer, N-oxide, stereoisomer, or pharmaceutically acceptable salt thereof, wherein $R^4$ is —OR$^7$ and $R^7$ is phenyl substituted with halogen. In another embodiment is a compound of Formula (Ib), or a solvate, hydrate, tautomer, N-oxide, stereoisomer, or pharmaceutically acceptable salt thereof, wherein $R^4$ is —OR$^7$ and $R^7$ is phenyl substituted with —Cl. In another embodiment is a compound of Formula (Ib), or a solvate, hydrate, tautomer, N-oxide, stereoisomer, or pharmaceutically acceptable salt thereof, wherein $R^4$ is $C_{2-9}$heterocycloalkyl optionally substituted with 1 or 2 $R^{14}$. In another embodiment is a compound of Formula (Ib), or a solvate, hydrate, tautomer, N-oxide, stereoisomer, or pharmaceutically acceptable salt thereof, wherein $R^4$ is an unsubstituted $C_{2-9}$heterocycloalkyl. In another embodiment is a compound of Formula (Ib), or a solvate, hydrate, tautomer, N-oxide, stereoisomer, or pharmaceutically acceptable salt thereof, wherein $R^4$ is $C_{2-9}$heterocycloalkyl substituted with 1 or 2 $R^{14}$. In another embodiment is a compound of Formula (Ib), or a solvate, hydrate, tautomer, N-oxide, stereoisomer, or pharmaceutically acceptable salt thereof, wherein $R^4$ is $C_{4-5}$heterocycloalkyl optionally substituted with 1 or 2 $R^{14}$, wherein the $C_{4-5}$heterocycloalkyl is a monocyclic heterocycloalkyl selected from pyrrolidine, piperidine, piperazine, and morpholine. In another embodiment is a compound of Formula (Ib), or a solvate, hydrate, tautomer, N-oxide, stereoisomer, or pharmaceutically acceptable salt thereof, wherein $R^4$ is $C_{5-9}$heterocycloalkyl optionally substituted with 1 or 2 $R^{14}$, wherein the $C_{5-9}$heterocycloalkyl is a bicyclic heterocycloalkyl. In another embodiment is a compound of Formula (Ib), or a solvate, hydrate, tautomer, N-oxide, stereoisomer, or pharmaceutically acceptable salt thereof, wherein $R^4$ is $C_{5-9}$heterocycloalkyl optionally substituted with 1 or 2 $R^{14}$, wherein the $C_{5-9}$heterocycloalkyl is a spirocyclic heterocycloalkyl. In another embodiment is a compound of Formula (Ib), or a solvate, hydrate, tautomer, N-oxide, stereoisomer, or pharmaceutically acceptable salt thereof, wherein $R^4$ is

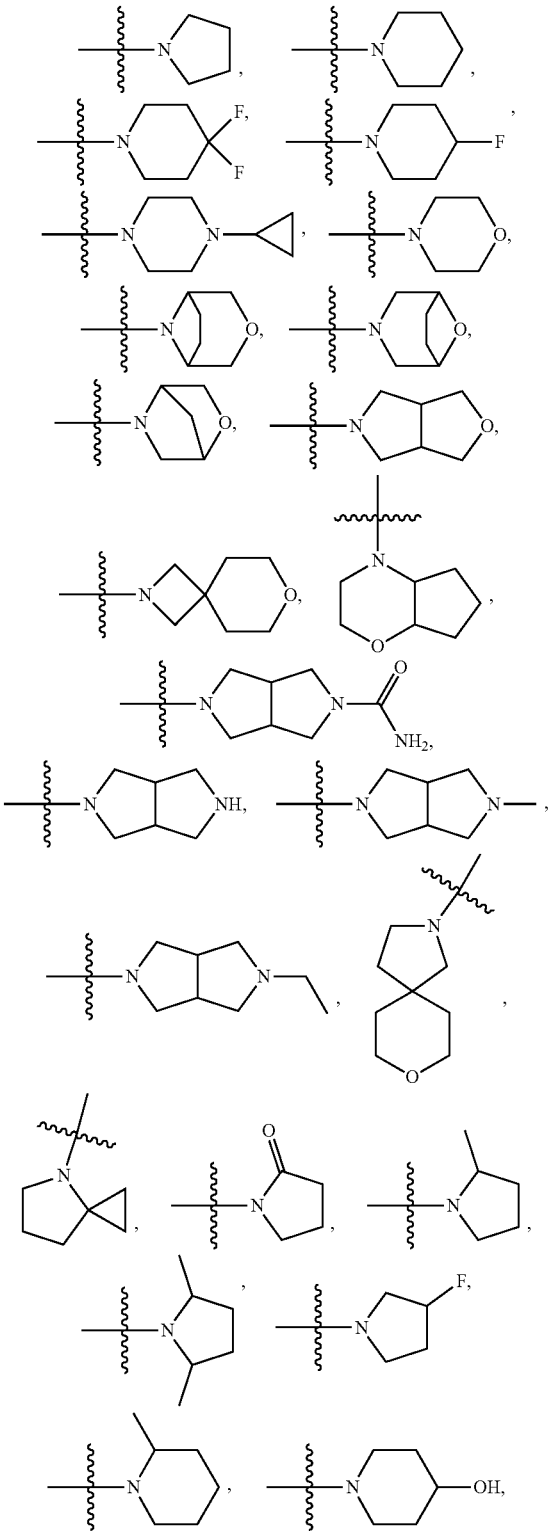

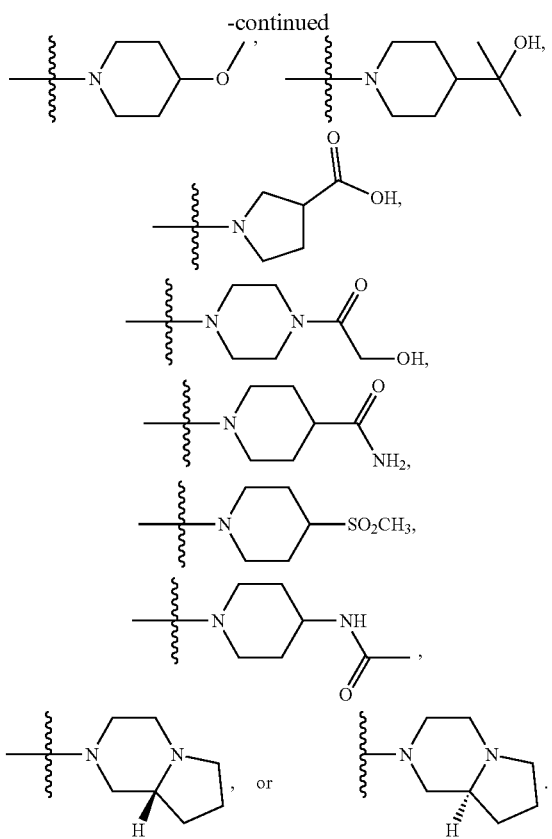

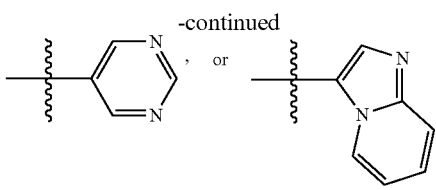

In another embodiment is a compound of Formula (Ib), or a solvate, hydrate, tautomer, N-oxide, stereoisomer, or pharmaceutically acceptable salt thereof, wherein $R^4$ is $C_{1-9}$heteroaryl optionally substituted with 1 or 2 $R^{14}$. In another embodiment is a compound of Formula (Ib), or a solvate, hydrate, tautomer, N-oxide, stereoisomer, or pharmaceutically acceptable salt thereof, wherein $R^4$ is an unsubstituted $C_{1-9}$heteroaryl. In another embodiment is a compound of Formula (Ib), or a solvate, hydrate, tautomer, N-oxide, stereoisomer, or pharmaceutically acceptable salt thereof, wherein $R^4$ is $C_{2-9}$heteroaryl substituted with 1 or 2 $R^{14}$. In another embodiment is a compound of Formula (Ib), or a solvate, hydrate, tautomer, N-oxide, stereoisomer, or pharmaceutically acceptable salt thereof, wherein $R^4$ is $C_{2-9}$heteroaryl optionally substituted with 1 or 2 $R^{14}$, wherein the $C_{2-9}$heteroaryl is selected from pyrrole, furan, thiophene, thiazole, pyrazole, oxazole, oxadiazole, thiadiazole, pyridine, pyrimidine, pyrazine, indole, benzothiophene, benzofuran, and imidazopyridine. In another embodiment is a compound of Formula (Ib), or a solvate, hydrate, tautomer, N-oxide, stereoisomer, or pharmaceutically acceptable salt thereof, wherein $R^4$ is In another embodiment is a compound of Formula (Ib), or a solvate, hydrate, tautomer, N-oxide, stereoisomer, or pharmaceutically acceptable salt thereof, wherein $R^5$ is H, CN, halogen, $C_{1-6}$alkyl, $C_{1-6}$haloalkyl, or $C_{1-6}$haloalkoxy. In another embodiment is a compound of Formula (Ib), or a solvate, hydrate, tautomer, N-oxide, stereoisomer, or pharmaceutically acceptable salt thereof, wherein $R^5$ is H. In another embodiment is a compound of Formula (Ib), or a solvate, hydrate, tautomer, N-oxide, stereoisomer, or pharmaceutically acceptable salt thereof, wherein $R^5$ is —CN. In another embodiment is a compound of Formula (Ib), or a solvate, hydrate, tautomer, N-oxide, stereoisomer, or pharmaceutically acceptable salt thereof, wherein $R^5$ is halogen. In another embodiment is a compound of Formula (Ib), or a solvate, hydrate, tautomer, N-oxide, stereoisomer, or pharmaceutically acceptable salt thereof, wherein $R^5$ is —Cl. In another embodiment is a compound of Formula (Ib), or a solvate, hydrate, tautomer, N-oxide, stereoisomer, or pharmaceutically acceptable salt thereof, wherein $R^5$ is —F. In another embodiment is a compound of Formula (Ib), or a solvate, hydrate, tautomer, N-oxide, stereoisomer, or pharmaceutically acceptable salt thereof, wherein $R^5$ is $C_{1-6}$alkyl. In another embodiment is a compound of Formula (Ib), or a solvate, hydrate, tautomer, N-oxide, stereoisomer, or pharmaceutically acceptable salt thereof, wherein $R^5$ is —$CH_3$. In another embodiment is a compound of Formula (Ib), or a solvate, hydrate, tautomer, N-oxide, stereoisomer, or pharmaceutically acceptable salt thereof, wherein $R^5$ is $C_{1-6}$haloalkyl. In another embodiment is a compound of Formula (Ib), or a solvate, hydrate, tautomer, N-oxide, stereoisomer, or pharmaceutically acceptable salt thereof, wherein $R^5$ is —$CF_3$. In another embodiment is a compound of Formula (Ib), or a solvate, hydrate, tautomer, N-oxide, stereoisomer, or pharmaceutically acceptable salt thereof, wherein $R^5$ is $C_{1-6}$haloalkoxy. In another embodiment is a compound of Formula (Ib), or a solvate, hydrate, tautomer, N-oxide, stereoisomer, or pharmaceutically acceptable salt thereof, wherein $R^5$ is —$OCF_3$. In another embodiment is a compound of Formula (Ib), or a solvate, hydrate, tautomer, N-oxide, stereoisomer, or pharmaceutically acceptable salt thereof, wherein $R^6$ is H. In another embodiment is a compound of Formula (Ib), or a solvate, hydrate, tautomer, N-oxide, stereoisomer, or pharmaceutically acceptable salt thereof, wherein $R^6$ is halogen. In another embodiment is a compound of Formula (Ib), or a solvate, hydrate, tautomer, N-oxide, stereoisomer, or pharmaceutically acceptable salt thereof, wherein $R^6$ is —Cl. In another embodiment is a compound of Formula (Ib), or a solvate, hydrate, tautomer, N-oxide, stereoisomer, or pharmaceutically acceptable salt thereof, wherein $R^6$ is —F. In another embodiment is a compound of Formula (Ib), or a solvate, hydrate, tautomer, N-oxide, stereoisomer, or pharmaceutically acceptable salt thereof, wherein $R^6$ is $C_{1-6}$alkyl. In another embodiment is a compound of Formula (Ib), or a solvate, hydrate, tautomer, N-oxide, stereoisomer, or pharmaceutically acceptable salt thereof, wherein $R^6$ is —$CH_3$.

In another embodiment is a compound of Formula (Ib), or a solvate, hydrate, tautomer, N-oxide, stereoisomer, or pharmaceutically acceptable salt thereof, wherein $R^{12}$ is H. In another embodiment is a compound of Formula (Ib), or a solvate, hydrate, tautomer, N-oxide, stereoisomer, or pharmaceutically acceptable salt thereof, wherein $R^{12}$ is $C_{1-6}$alkyl. In another embodiment is a compound of Formula (Ib), or a solvate, hydrate, tautomer, N-oxide, stereoisomer, or pharmaceutically acceptable salt thereof, wherein $R^{12}$ is —$CH_3$. In another embodiment is a compound of Formula (Ib), or a solvate, hydrate, tautomer, N-oxide, stereoisomer, or pharmaceutically acceptable salt thereof, wherein $R^{13}$ is H. In another embodiment is a compound of Formula (Ib), or a solvate, hydrate, tautomer, N-oxide, stereoisomer, or pharmaceutically acceptable salt thereof, wherein $R^{13}$ is $C_{1-6}$alkyl. In another embodiment is a compound of Formula (Ib), or a solvate, hydrate, tautomer, N-oxide, stereoisomer, or pharmaceutically acceptable salt thereof, wherein $R^{13}$ is —$CH_3$. In another embodiment is a compound of Formula (Ib), or a solvate, hydrate, tautomer, N-oxide, stereoisomer, or pharmaceutically acceptable salt thereof, wherein $R^{12}$ is H and $R^{13}$ is H. In another embodiment is a compound of Formula (Ib), or a solvate, hydrate, tautomer, N-oxide, stereoisomer, or pharmaceutically acceptable salt thereof, wherein $R^{12}$ is H and $R^{13}$ is $C_{1-6}$alkyl. In another embodiment is a compound of Formula (Ib), or a solvate, hydrate, tautomer, N-oxide, stereoisomer, or pharmaceutically acceptable salt thereof, wherein $R^{12}$ is H and $R^{13}$ is —$CH_3$. In another embodiment is a compound of Formula (Ib), or a solvate, hydrate, tautomer, N-oxide, stereoisomer, or pharmaceutically acceptable salt thereof, wherein $R^{12}$ is $C_{1-6}$alkyl and $R^{13}$ is H. In another embodiment is a compound of Formula (Ib), or a solvate, hydrate, tautomer, N-oxide, stereoisomer, or pharmaceutically acceptable salt thereof, wherein $R^{12}$ is —$CH_3$ and $R^{13}$ is H. In another embodiment is a compound of Formula (Ib), or a solvate, hydrate, tautomer, N-oxide, stereoisomer, or pharmaceutically acceptable salt thereof, wherein $R^{12}$ is $C_{1-6}$alkyl and $R^{13}$ is $C_{1-6}$alkyl. In another embodiment is a compound of Formula (Ib), or a solvate, hydrate, tautomer, N-oxide, stereoisomer, or pharmaceutically acceptable salt thereof, wherein $R^{12}$ is —$CH_3$ and $R^{13}$ is —$CH_3$.

In another embodiment is a compound of Formula (I) having the structure of Formula (Ic):

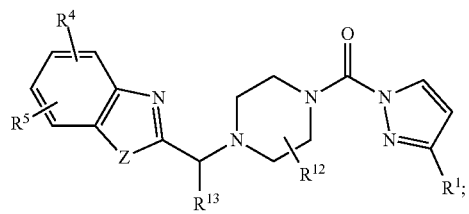

Formula (Ic)

wherein:
$R^1$ is —$N(R^2)C(O)R^{15}$ or —$N(H)SO_2R^{15}$;
$R^2$ is H or $C_{1-6}$alkyl;
Z is —S—, —O—, or —$N(R^{20})$—;
$R^4$ is H, halogen, —$OR^7$, $C_{1-6}$alkyl, $C_{1-6}$alkyl-OH, $C_{2-6}$alkenyl, $C_{2-6}$alkynyl, $C_{1-6}$haloalkyl, —O—$C_{3-8}$cycloalkyl, —O—$C_{3-8}$cycloalkyl-OH, —N(H)—$C_{1-6}$alkyl-$CO_2H$, —$SO_2R^{17}$, —$CO_2R^8$, —$C(O)NR^8R^9$, $C_{3-8}$cycloalkyl, $C_{2-9}$heterocycloalkyl, —$C_{1-6}$alkyl-$C_{2-9}$heterocycloalkyl, $C_{6-10}$aryl, $C_{1-9}$heteroaryl, wherein $C_{3-8}$cycloalkyl, $C_{2-9}$heterocycloalkyl, —$C_{1-6}$alkyl-$C_{2-9}$heterocycloalkyl, $C_{6-10}$aryl, $C_{1-9}$heteroaryl are optionally substituted with 1 or 2 $R^{14}$;
$R^5$ is H, —CN, halogen, $C_{1-6}$alkyl, $C_{1-6}$haloalkyl, $C_{1-6}$haloalkoxy, or phenyl;
$R^7$ is H, $C_{1-6}$alkyl, $C_{1-6}$haloalkyl, $C_{3-8}$cycloalkyl, $C_{2-9}$heterocycloalkyl, $C_{6-10}$aryl, or $C_{1-9}$heteroaryl, wherein $C_{2-9}$heterocycloalkyl, $C_{6-10}$aryl, or $C_{1-9}$heteroaryl are optionally substituted with 1 or 2 $R^{14}$;
each $R^8$ and each $R^9$ are independently selected from H and $C_{1-6}$alkyl; or $R^8$ and $R^9$ together with the nitrogen to which they are attached are combined to form a heterocycloalkyl ring;
$R^{12}$ is H, halogen, or $C_{1-6}$alkyl;
$R^{13}$ is H or $C_{1-6}$alkyl;
each $R^{14}$ is independently selected from halogen, —OH, oxo, $C_{1-6}$alkyl, $C_{1-6}$haloalkyl, $C_{1-6}$alkoxy, —$C_{1-6}$alkyl-OH, $C_{3-8}$cycloalkyl, —$CO_2R^8$, —$C(O)NR^8R^9$, —$C(O)$—$C_{1-6}$alkyl, —$C(O)$—$C_{1-6}$alkyl-OH, —$SO_2$—$C_{1-6}$alkyl, —$N(R^8)SO_2$—$C_{1-6}$alkyl, and —$N(R^8)C(O)$—$C_{1-6}$alkyl;
$R^{15}$ is $C_{1-6}$alkyl or $C_{3-8}$cycloalkyl;
$R^{17}$ is $C_{1-6}$alkyl or $C_{3-8}$cycloalkyl; and
$R^{20}$ is H or $C_{1-6}$alkyl;
or a solvate, hydrate, tautomer, N-oxide, stereoisomer, or pharmaceutically acceptable salt thereof.

In another embodiment is a compound of Formula (Ic), or a solvate, hydrate, tautomer, N-oxide, stereoisomer, or pharmaceutically acceptable salt thereof, having the structure

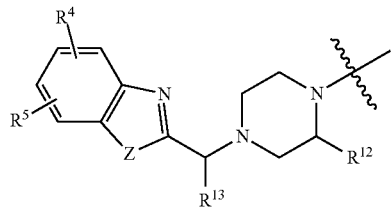

In another embodiment is a compound of Formula (Ic), or a solvate, hydrate, tautomer, N-oxide, stereoisomer, or pharmaceutically acceptable salt thereof, having the structure

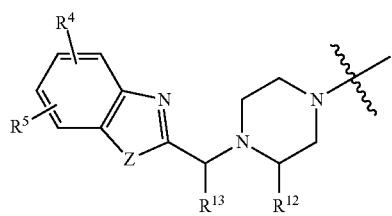

In another embodiment is a compound of Formula (Ic), or a solvate, hydrate, tautomer, N-oxide, stereoisomer, or pharmaceutically acceptable salt thereof, wherein Z is —S—. In another embodiment is a compound of Formula (Ic), or a solvate, hydrate, tautomer, N-oxide, stereoisomer, or pharmaceutically acceptable salt thereof, wherein Z is —O—. In another embodiment is a compound of Formula (Ic), or a solvate, hydrate, tautomer, N-oxide, stereoisomer, or pharmaceutically acceptable salt thereof, wherein Z is —$N(R^{20})$—. In another embodiment is a compound of Formula (Ic), or a solvate, hydrate, tautomer, N-oxide, stereoisomer, or pharmaceutically acceptable salt thereof, wherein Z is —N(H)—. In another embodiment is a compound of Formula (Ic), or a solvate, hydrate, tautomer, N-oxide, stereoisomer, or pharmaceutically acceptable salt thereof, wherein Z is —N(CH$_3$)—.

In another embodiment is a compound of Formula (Ic), or a solvate, hydrate, tautomer, N-oxide, stereoisomer, or pharmaceutically acceptable salt thereof, wherein R$^1$ is —N(R$^2$)C(O)R$^{15}$. In another embodiment is a compound of Formula (Ic), or a solvate, hydrate, tautomer, N-oxide, stereoisomer, or pharmaceutically acceptable salt thereof, wherein R$^1$ is —N(R$^2$)C(O)R$^{15}$ and R$^2$ is H. In another embodiment is a compound of Formula (Ic), or a solvate, hydrate, tautomer, N-oxide, stereoisomer, or pharmaceutically acceptable salt thereof, wherein R$^1$ is —N(H)C(O)R$^{15}$ and R$^{15}$ is C$_{1-6}$alkyl. In another embodiment is a compound of Formula (Ic), or a solvate, hydrate, tautomer, N-oxide, stereoisomer, or pharmaceutically acceptable salt thereof, wherein R$^1$ is —N(H)C(O)R$^{15}$ and R$^{15}$ is —CH$_3$. In another embodiment is a compound of Formula (Ic), or a solvate, hydrate, tautomer, N-oxide, stereoisomer, or pharmaceutically acceptable salt thereof, wherein R$^1$ is —N(H)C(O)R$^{15}$ and R$^{15}$ is C$_{3-8}$cycloalkyl. In another embodiment is a compound of Formula (Ic), or a solvate, hydrate, tautomer, N-oxide, stereoisomer, or pharmaceutically acceptable salt thereof, wherein R$^1$ is —N(R$^2$)C(O)R$^{15}$ and R$^2$ is C$_{1-6}$alkyl. In another embodiment is a compound of Formula (Ic), or a solvate, hydrate, tautomer, N-oxide, stereoisomer, or pharmaceutically acceptable salt thereof, wherein R$^1$ is —N(R$^2$)C(O)R$^{15}$ and R$^2$ is —CH$_3$. In another embodiment is a compound of Formula (Ic), or a solvate, hydrate, tautomer, N-oxide, stereoisomer, or pharmaceutically acceptable salt thereof, wherein R$^1$ is —N(CH$_3$)C(O)R$^{15}$ and R$^{15}$ is C$_{1-6}$alkyl. In another embodiment is a compound of Formula (Ic), or a solvate, hydrate, tautomer, N-oxide, stereoisomer, or pharmaceutically acceptable salt thereof, wherein R$^1$ is —N(CH$_3$)C(O)R$^{15}$ and R$^{15}$ is —CH$_3$. In another embodiment is a compound of Formula (Ic), or a solvate, hydrate, tautomer, N-oxide, stereoisomer, or pharmaceutically acceptable salt thereof, wherein R$^1$ is —N(CH$_3$)C(O)R$^{15}$ and R$^{15}$ is C$_{3-8}$cycloalkyl. In another embodiment is a compound of Formula (Ic), or a solvate, hydrate, tautomer, N-oxide, stereoisomer, or pharmaceutically acceptable salt thereof, wherein R$^1$ is —N(H)SO$_2$R$^{15}$. In another embodiment is a compound of Formula (Ic), or a solvate, hydrate, tautomer, N-oxide, stereoisomer, or pharmaceutically acceptable salt thereof, wherein R$^1$ is —N(H)SO$_2$R$^{15}$ and R$^{15}$ is C$_{1-6}$alkyl. In another embodiment is a compound of Formula (Ic), or a solvate, hydrate, tautomer, N-oxide, stereoisomer, or pharmaceutically acceptable salt thereof, wherein R$^1$ is —N(H)SO$_2$R$^{15}$ and R$^{15}$ is —CH$_3$. In another embodiment is a compound of Formula (Ic), or a solvate, hydrate, tautomer, N-oxide, stereoisomer, or pharmaceutically acceptable salt thereof, wherein R$^2$ is —N(H)SO$_2$R$^{15}$ and R$^{15}$ is C$_{3-8}$cycloalkyl.

In another embodiment is a compound of Formula (Ic), or a solvate, hydrate, tautomer, N-oxide, stereoisomer, or pharmaceutically acceptable salt thereof, wherein R$^4$ is halogen, —OR$^7$, C$_{1-6}$alkyl-OH, —N(H)—C$_{1-6}$alkyl-CO$_2$H, C$_{2-6}$alkynyl, C$_{1-6}$haloalkyl, —CO$_2$R$^8$, —C(O)NR$^8$R$^9$, C$_{3-8}$cycloalkyl, C$_{2-9}$heterocycloalkyl, C$_{6-10}$aryl, or C$_{1-9}$heteroaryl, wherein C$_{3-8}$cycloalkyl, C$_{2-9}$heterocycloalkyl, C$_{6-10}$aryl, or C$_{1-9}$heteroaryl are optionally substituted with 1 or 2 R$^{14}$. In another embodiment is a compound of Formula (Ic), or a solvate, hydrate, tautomer, N-oxide, stereoisomer, or pharmaceutically acceptable salt thereof, wherein R$^4$ is halogen, —OR$^7$, —N(H)—C$_{1-6}$alkyl-CO$_2$H, C$_{1-6}$haloalkyl, —C(O)NR$^8$R$^9$, C$_{3-8}$cycloalkyl, C$_{2-9}$heterocycloalkyl, or C$_{1-9}$heteroaryl, wherein C$_{2-9}$heterocycloalkyl or C$_{1-9}$heteroaryl are optionally substituted with 1 or 2 R$^{14}$. In another embodiment is a compound of Formula (Ic), or a solvate, hydrate, tautomer, N-oxide, stereoisomer, or pharmaceutically acceptable salt thereof, wherein R$^4$ is halogen. In another embodiment is a compound of Formula (Ic), or a solvate, hydrate, tautomer, N-oxide, stereoisomer, or pharmaceutically acceptable salt thereof, wherein R$^4$ is —Cl. In another embodiment is a compound of Formula (Ic), or a solvate, hydrate, tautomer, N-oxide, stereoisomer, or pharmaceutically acceptable salt thereof, wherein R$^4$ is C$_{1-6}$haloalkyl. In another embodiment is a compound of Formula (Ic), or a solvate, hydrate, tautomer, N-oxide, stereoisomer, or pharmaceutically acceptable salt thereof, wherein R$^4$ is —CF$_3$. In another embodiment is a compound of Formula (Ic), or a solvate, hydrate, tautomer, N-oxide, stereoisomer, or pharmaceutically acceptable salt thereof, wherein R$^4$ is —N(H)—C$_{1-6}$alkyl-CO$_2$H. In another embodiment is a compound of Formula (Ic), or a solvate, hydrate, tautomer, N-oxide, stereoisomer, or pharmaceutically acceptable salt thereof, wherein R$^4$ is —N(H)CH$_2$CO$_2$H. In another embodiment is a compound of Formula (Ic), or a solvate, hydrate, tautomer, N-oxide, stereoisomer, or pharmaceutically acceptable salt thereof, wherein R$^4$ is —N(H)CH$_2$CH$_2$CO$_2$H. In another embodiment is a compound of Formula (Ic), or a solvate, hydrate, tautomer, N-oxide, stereoisomer, or pharmaceutically acceptable salt thereof, wherein R$^4$ is —N(H)CH$_2$CH$_2$CH$_2$CO$_2$H. In another embodiment is a compound of Formula (Ic), or a solvate, hydrate, tautomer, N-oxide, stereoisomer, or pharmaceutically acceptable salt thereof, wherein R$^4$ is —C(O)NR$^8$R$^9$. In another embodiment is a compound of Formula (Ic), or a solvate, hydrate, tautomer, N-oxide, stereoisomer, or pharmaceutically acceptable salt thereof, wherein R$^4$ is —C(O)NH$_2$. In another embodiment is a compound of Formula (Ic), or a solvate, hydrate, tautomer, N-oxide, stereoisomer, or pharmaceutically acceptable salt thereof, wherein R$^4$ is C$_{3-8}$cycloalkyl. In another embodiment is a compound of Formula (Ic), or a solvate, hydrate, tautomer, N-oxide, stereoisomer, or pharmaceutically acceptable salt thereof, wherein R$^4$ is —OR$^7$. In another embodiment is a compound of Formula (Ic), or a solvate, hydrate, tautomer, N-oxide, stereoisomer, or pharmaceutically acceptable salt thereof, wherein R$^4$ is —OR$^7$ and R$^7$ is unsubstituted C$_{3-8}$cycloalkyl or C$_{6-10}$aryl optionally substituted with halogen. In another embodiment is a compound of Formula (Ic), or a solvate, hydrate, tautomer, N-oxide, stereoisomer, or pharmaceutically acceptable salt thereof, wherein R$^4$ is —OR$^7$ and R$^7$ is unsubstituted C$_{3-8}$cycloalkyl. In another embodiment is a compound of Formula (Ic), or a solvate, hydrate, tautomer, N-oxide, stereoisomer, or pharmaceutically acceptable salt thereof, wherein R$^4$ is —OR$^7$ and R$^7$ is phenyl optionally substituted with halogen. In another embodiment is a compound of Formula (Ic), or a solvate, hydrate, tautomer, N-oxide, stereoisomer, or pharmaceutically acceptable salt thereof, wherein R$^4$ is —OR$^7$ and R$^7$ is phenyl substituted with halogen. In another embodiment is a compound of Formula (Ic), or a solvate, hydrate, tautomer, N-oxide, stereoisomer, or pharmaceutically acceptable salt thereof, wherein R$^4$ is —OR$^7$ and R$^7$ is phenyl substituted with —Cl. In another embodiment is a compound of Formula (Ic), or a solvate, hydrate, tautomer, N-oxide, stereoisomer, or pharmaceutically acceptable salt thereof, wherein R$^4$ is C$_{2-9}$heterocycloalkyl optionally substituted with 1 or 2 R$^{14}$. In another embodiment is a compound of Formula (Ic), or a solvate, hydrate, tautomer, N-oxide, stereoisomer, or pharmaceutically acceptable salt thereof, wherein R$^4$ is an unsubstituted C$_{2-9}$heterocycloalkyl. In another embodiment is a compound of Formula (Ic), or a solvate, hydrate, tautomer, N-oxide, stereoisomer, or pharmaceutically acceptable salt thereof, wherein $R^4$ is $C_{2-9}$heterocycloalkyl substituted with 1 or 2 $R^{14}$. In another embodiment is a compound of Formula (Ic), or a solvate, hydrate, tautomer, N-oxide, stereoisomer, or pharmaceutically acceptable salt thereof, wherein $R^4$ is $C_{4-5}$heterocycloalkyl optionally substituted with 1 or 2 $R^{14}$, wherein the $C_{4-5}$heterocycloalkyl is a monocyclic heterocycloalkyl selected from pyrrolidine, piperidine, piperazine, and morpholine. In another embodiment is a compound of Formula (Ic), or a solvate, hydrate, tautomer, N-oxide, stereoisomer, or pharmaceutically acceptable salt thereof, wherein $R^4$ is $C_{5-9}$heterocycloalkyl optionally substituted with 1 or 2 $R^{14}$, wherein the $C_{5-9}$heterocycloalkyl is a bicyclic heterocycloalkyl. In another embodiment is a compound of Formula (Ic), or a solvate, hydrate, tautomer, N-oxide, stereoisomer, or pharmaceutically acceptable salt thereof, wherein $R^4$ is $C_{5-9}$heterocycloalkyl optionally substituted with 1 or 2 $R^{14}$, wherein the $C_{5-9}$heterocycloalkyl is a spirocyclic heterocycloalkyl. In another embodiment is a compound of Formula (Ic), or a solvate, hydrate, tautomer, N-oxide, stereoisomer, or pharmaceutically acceptable salt thereof, wherein $R^4$ is

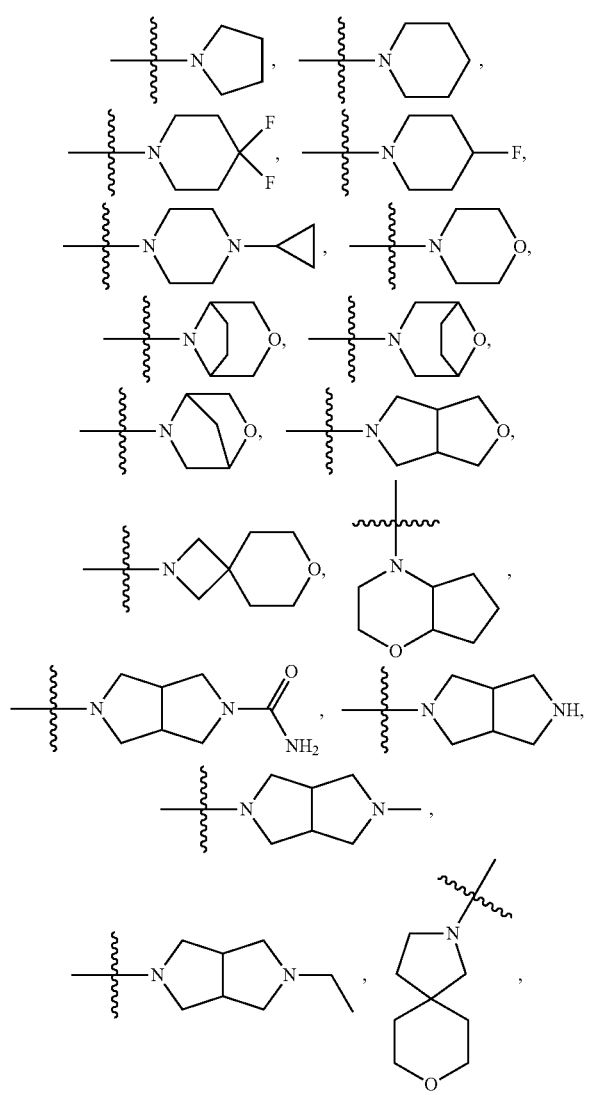

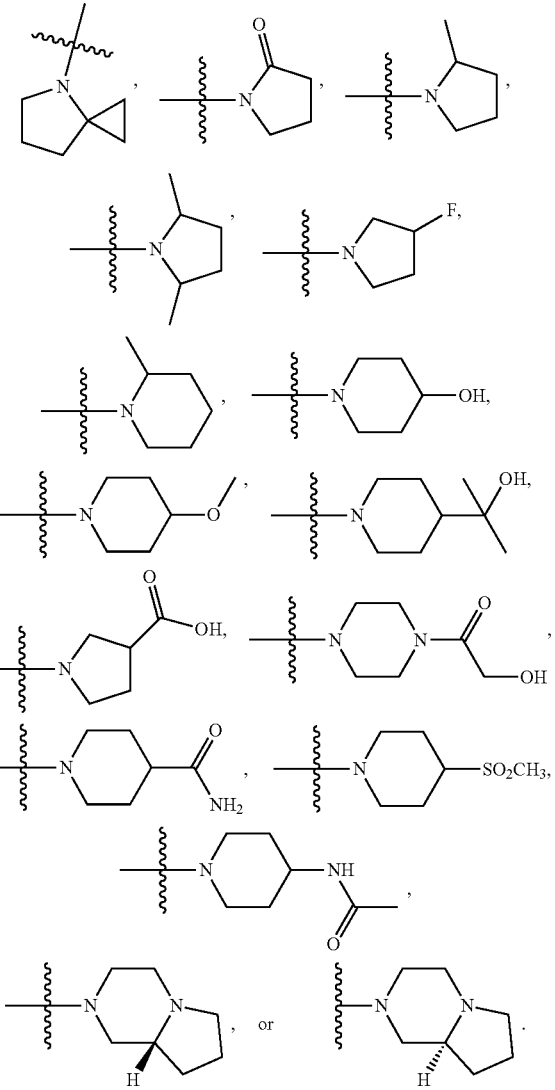

In another embodiment is a compound of Formula (Ic), or a solvate, hydrate, tautomer, N-oxide, stereoisomer, or pharmaceutically acceptable salt thereof, wherein $R^4$ is $C_{1-9}$heteroaryl optionally substituted with 1 or 2 $R^{14}$. In another embodiment is a compound of Formula (Ic), or a solvate, hydrate, tautomer, N-oxide, stereoisomer, or pharmaceutically acceptable salt thereof, wherein $R^4$ is an unsubstituted $C_{1-9}$heteroaryl. In another embodiment is a compound of Formula (Ic), or a solvate, hydrate, tautomer, N-oxide, stereoisomer, or pharmaceutically acceptable salt thereof, wherein $R^4$ is $C_{2-9}$heteroaryl substituted with 1 or 2 $R^{14}$. In another embodiment is a compound of Formula (Ic), or a solvate, hydrate, tautomer, N-oxide, stereoisomer, or pharmaceutically acceptable salt thereof, wherein $R^4$ is $C_{2-9}$heteroaryl optionally substituted with 1 or 2 $R^{14}$, wherein the $C_{2-9}$heteroaryl is selected from pyrrole, furan, thiophene, thiazole, pyrazole, oxazole, oxadiazole, thiadiazole, pyridine, pyrimidine, pyrazine, indole, benzothiophene, benzofuran, and imidazopyridine. In another embodiment is a compound of Formula (Ic), or a solvate, hydrate, tautomer, N-oxide, stereoisomer, or pharmaceutically acceptable salt thereof, wherein $R^4$ is

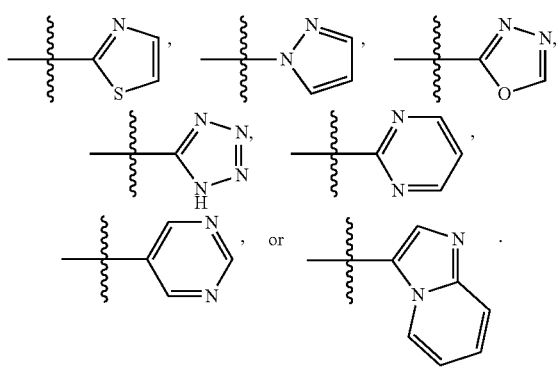

In another embodiment is a compound of Formula (Ic), or a solvate, hydrate, tautomer, N-oxide, stereoisomer, or pharmaceutically acceptable salt thereof, wherein $R^5$ is H, CN, halogen, $C_{1-6}$alkyl, $C_{1-6}$haloalkyl, or $C_{1-6}$haloalkoxy. In another embodiment is a compound of Formula (Ic), or a solvate, hydrate, tautomer, N-oxide, stereoisomer, or pharmaceutically acceptable salt thereof, wherein $R^5$ is H. In another embodiment is a compound of Formula (Ic), or a solvate, hydrate, tautomer, N-oxide, stereoisomer, or pharmaceutically acceptable salt thereof, wherein $R^5$ is —CN. In another embodiment is a compound of Formula (Ic), or a solvate, hydrate, tautomer, N-oxide, stereoisomer, or pharmaceutically acceptable salt thereof, wherein $R^5$ is halogen. In another embodiment is a compound of Formula (Ic), or a solvate, hydrate, tautomer, N-oxide, stereoisomer, or pharmaceutically acceptable salt thereof, wherein $R^5$ is —Cl. In another embodiment is a compound of Formula (Ic), or a solvate, hydrate, tautomer, N-oxide, stereoisomer, or pharmaceutically acceptable salt thereof, wherein $R^5$ is —F. In another embodiment is a compound of Formula (Ic), or a solvate, hydrate, tautomer, N-oxide, stereoisomer, or pharmaceutically acceptable salt thereof, wherein $R^5$ is $C_{1-6}$alkyl. In another embodiment is a compound of Formula (Ic), or a solvate, hydrate, tautomer, N-oxide, stereoisomer, or pharmaceutically acceptable salt thereof, wherein $R^5$ is —$CH_3$. In another embodiment is a compound of Formula (Ic), or a solvate, hydrate, tautomer, N-oxide, stereoisomer, or pharmaceutically acceptable salt thereof, wherein $R^5$ is $C_{1-6}$haloalkyl. In another embodiment is a compound of Formula (Ic), or a solvate, hydrate, tautomer, N-oxide, stereoisomer, or pharmaceutically acceptable salt thereof, wherein $R^5$ is —$CF_3$. In another embodiment is a compound of Formula (Ic), or a solvate, hydrate, tautomer, N-oxide, stereoisomer, or pharmaceutically acceptable salt thereof, wherein $R^5$ is $C_{1-6}$haloalkoxy. In another embodiment is a compound of Formula (Ic), or a solvate, hydrate, tautomer, N-oxide, stereoisomer, or pharmaceutically acceptable salt thereof, wherein $R^5$ is —$OCF_3$.

In another embodiment is a compound of Formula (Ic), or a solvate, hydrate, tautomer, N-oxide, stereoisomer, or pharmaceutically acceptable salt thereof, wherein $R^{12}$ is H. In another embodiment is a compound of Formula (Ic), or a solvate, hydrate, tautomer, N-oxide, stereoisomer, or pharmaceutically acceptable salt thereof, wherein $R^{12}$ is $C_{1-6}$alkyl. In another embodiment is a compound of Formula (Ic), or a solvate, hydrate, tautomer, N-oxide, stereoisomer, or pharmaceutically acceptable salt thereof, wherein $R^{12}$ is —$CH_3$. In another embodiment is a compound of Formula (Ic), or a solvate, hydrate, tautomer, N-oxide, stereoisomer, or pharmaceutically acceptable salt thereof, wherein $R^{13}$ is H. In another embodiment is a compound of Formula (Ic), or a solvate, hydrate, tautomer, N-oxide, stereoisomer, or pharmaceutically acceptable salt thereof, wherein $R^{13}$ is $C_{1-6}$alkyl. In another embodiment is a compound of Formula (Ic), or a solvate, hydrate, tautomer, N-oxide, stereoisomer, or pharmaceutically acceptable salt thereof, wherein $R^{13}$ is —$CH_3$. In another embodiment is a compound of Formula (Ic), or a solvate, hydrate, tautomer, N-oxide, stereoisomer, or pharmaceutically acceptable salt thereof, wherein $R^{12}$ is H and $R^{13}$ is H. In another embodiment is a compound of Formula (Ic), or a solvate, hydrate, tautomer, N-oxide, stereoisomer, or pharmaceutically acceptable salt thereof, wherein $R^{12}$ is H and $R^{13}$ is $C_{1-6}$alkyl. In another embodiment is a compound of Formula (Ic), or a solvate, hydrate, tautomer, N-oxide, stereoisomer, or pharmaceutically acceptable salt thereof, wherein $R^{12}$ is H and $R^{13}$ is —$CH_3$. In another embodiment is a compound of Formula (Ic), or a solvate, hydrate, tautomer, N-oxide, stereoisomer, or pharmaceutically acceptable salt thereof, wherein $R^{12}$ is $C_{1-6}$alkyl and $R^{13}$ is H. In another embodiment is a compound of Formula (Ic), or a solvate, hydrate, tautomer, N-oxide, stereoisomer, or pharmaceutically acceptable salt thereof, wherein $R^{12}$ is —$CH_3$ and $R^{13}$ is H. In another embodiment is a compound of Formula (Ic), or a solvate, hydrate, tautomer, N-oxide, stereoisomer, or pharmaceutically acceptable salt thereof, wherein $R^{12}$ is $C_{1-6}$alkyl and $R^{13}$ is $C_{1-6}$alkyl. In another embodiment is a compound of Formula (Ic), or a solvate, hydrate, tautomer, N-oxide, stereoisomer, or pharmaceutically acceptable salt thereof, wherein $R^{12}$ is —$CH_3$ and $R^{13}$ is —$CH_3$.

In another embodiment is a compound of Formula (I) having the structure of Formula (Id):

Formula (Id)

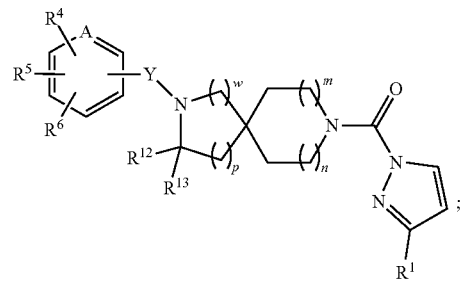

wherein:
$R^1$ is —N($R^2$)C(O)$R^{15}$ or —N(H)$SO_2R^{15}$;
$R^2$ is H or $C_{1-6}$alkyl;
A is N or C(H);
Y is —$CH_2$— or —C(O)—;
$R^4$ is H, halogen, —$OR^7$, $C_{1-6}$alkyl, $C_{1-6}$alkyl-OH, $C_{2-6}$alkenyl, $C_{2-6}$alkynyl, $C_{1-6}$haloalkyl, —O—$C_{3-8}$cycloalkyl, —O—$C_{3-8}$cycloalkyl-OH, —N(H)—$C_{1-6}$alkyl-$CO_2H$, —$SO_2R^{17}$, —$CO_2R^8$, —C(O)NR$^8$R$^9$, $C_{3-8}$cycloalkyl, $C_{2-9}$heterocycloalkyl, —$C_{1-6}$alkyl-$C_{2-9}$heterocycloalkyl, $C_{6-10}$aryl, $C_{1-9}$heteroaryl, wherein $C_{3-8}$cycloalkyl, $C_{2-9}$heterocycloalkyl, —$C_{1-6}$alkyl-$C_{2-9}$heterocycloalkyl, $C_{6-10}$aryl, $C_{1-9}$heteroaryl are optionally substituted with 1 or 2 $R^{14}$;
$R^5$ is H, —CN, halogen, $C_{1-6}$alkyl, $C_{1-6}$haloalkyl, $C_{1-6}$haloalkoxy, or phenyl;
$R^6$ is H, halogen, or $C_{1-6}$alkyl;
$R^7$ is H, $C_{1-6}$alkyl, $C_{1-6}$haloalkyl, $C_{3-8}$cycloalkyl, $C_{2-9}$heterocycloalkyl, $C_{6-10}$aryl, or $C_{1-9}$heteroaryl, wherein $C_{2-9}$heterocycloalkyl, $C_{6-10}$aryl, or $C_{1-9}$heteroaryl are optionally substituted with 1 or 2 $R^{14}$;

each $R^8$ and each $R^9$ are independently selected from H and $C_{1-6}$alkyl; or $R^8$ and $R^9$ together with the nitrogen to which they are attached are combined to form a heterocycloalkyl ring;

$R^{12}$ is H, halogen, or $C_{1-6}$alkyl;

$R^{13}$ is H or $C_{1-6}$alkyl;

each $R^{14}$ is independently selected from halogen, —OH, oxo, $C_{1-6}$alkyl, $C_{1-6}$haloalkyl, $C_{1-6}$alkoxy, —$C_{1-6}$alkyl-OH, $C_{3-8}$cycloalkyl, —$CO_2R^8$, —$C(O)NR^8R^9$, —$C(O)$—$C_{1-6}$alkyl, —$C(O)$—$C_{1-6}$alkyl-OH, —$SO_2$—$C_{1-6}$alkyl, —$N(R^8)SO_2$—$C_{1-6}$alkyl, and —$N(R^8)C(O)$—$C_{1-6}$alkyl;

$R^{15}$ is $C_{1-6}$alkyl or $C_{3-8}$cycloalkyl;

$R^{17}$ is $C_{1-6}$alkyl or $C_{3-8}$cycloalkyl;

n is 0 or 1;

m is 0 or 1;

p is 0, 1, or 2; and w is 1 or 2;

or a solvate, hydrate, tautomer, N-oxide, stereoisomer, or pharmaceutically acceptable salt thereof.

In another embodiment is a compound of Formula (Id), or a solvate, hydrate, tautomer, N-oxide, stereoisomer, or pharmaceutically acceptable salt thereof, wherein $R^1$ is —$N(R^2)C(O)R^{15}$. In another embodiment is a compound of Formula (Id), or a solvate, hydrate, tautomer, N-oxide, stereoisomer, or pharmaceutically acceptable salt thereof, wherein $R^1$ is —$N(R^2)C(O)R^{15}$ and $R^2$ is H. In another embodiment is a compound of Formula (Id), or a solvate, hydrate, tautomer, N-oxide, stereoisomer, or pharmaceutically acceptable salt thereof, wherein $R^1$ is —$N(H)C(O)R^{15}$ and $R^{15}$ is $C_{1-6}$alkyl. In another embodiment is a compound of Formula (Id), or a solvate, hydrate, tautomer, N-oxide, stereoisomer, or pharmaceutically acceptable salt thereof, wherein $R^1$ is —$N(H)C(O)R^{15}$ and $R^{15}$ is —$CH_3$. In another embodiment is a compound of Formula (Id), or a solvate, hydrate, tautomer, N-oxide, stereoisomer, or pharmaceutically acceptable salt thereof, wherein $R^1$ is —$N(H)C(O)R^{15}$ and $R^{15}$ is $C_{3-8}$cycloalkyl. In another embodiment is a compound of Formula (Id), or a solvate, hydrate, tautomer, N-oxide, stereoisomer, or pharmaceutically acceptable salt thereof, wherein $R^1$ is —$N(R^2)C(O)R^{15}$ and $R^2$ is $C_{1-6}$alkyl. In another embodiment is a compound of Formula (Id), or a solvate, hydrate, tautomer, N-oxide, stereoisomer, or pharmaceutically acceptable salt thereof, wherein $R^1$ is —$N(R^2)C(O)R^{15}$ and $R^2$ is —$CH_3$. In another embodiment is a compound of Formula (Id), or a solvate, hydrate, tautomer, N-oxide, stereoisomer, or pharmaceutically acceptable salt thereof, wherein $R^1$ is —$N(CH_3)C(O)R^{15}$ and $R^{15}$ is $C_{1-6}$alkyl. In another embodiment is a compound of Formula (Id), or a solvate, hydrate, tautomer, N-oxide, stereoisomer, or pharmaceutically acceptable salt thereof, wherein $R^1$ is —$N(CH_3)C(O)R^{15}$ and $R^{15}$ is —$CH_3$. In another embodiment is a compound of Formula (Id), or a solvate, hydrate, tautomer, N-oxide, stereoisomer, or pharmaceutically acceptable salt thereof, wherein $R^1$ is —$N(CH_3)C(O)R^{15}$ and $R^{15}$ is $C_{3-8}$cycloalkyl. In another embodiment is a compound of Formula (Id), or a solvate, hydrate, tautomer, N-oxide, stereoisomer, or pharmaceutically acceptable salt thereof, wherein $R^1$ is —$N(H)SO_2R^{15}$. In another embodiment is a compound of Formula (Id), or a solvate, hydrate, tautomer, N-oxide, stereoisomer, or pharmaceutically acceptable salt thereof, wherein $R^1$ is —$N(H)SO_2R^{15}$ and $R^{15}$ is $C_{1-6}$alkyl. In another embodiment is a compound of Formula (Id), or a solvate, hydrate, tautomer, N-oxide, stereoisomer, or pharmaceutically acceptable salt thereof, wherein $R^1$ is —$N(H)SO_2R^{15}$ and $R^{15}$ is —$CH_3$. In another embodiment is a compound of Formula (Id), or a solvate, hydrate, tautomer, N-oxide, stereoisomer, or pharmaceutically acceptable salt thereof, wherein $R^1$ is —$N(H)SO_2R^{15}$ and $R^{15}$ is $C_{3-8}$cycloalkyl.

In another embodiment is a compound of Formula (Id), or a solvate, hydrate, tautomer, N-oxide, stereoisomer, or pharmaceutically acceptable salt thereof, wherein m is 1, n is 1, p is 1, and w is 1. In another embodiment is a compound of Formula (Id), or a solvate, hydrate, tautomer, N-oxide, stereoisomer, or pharmaceutically acceptable salt thereof, wherein m is 0, n is 1, p is 1, and w is 2. In another embodiment is a compound of Formula (Id), or a solvate, hydrate, tautomer, N-oxide, stereoisomer, or pharmaceutically acceptable salt thereof, wherein m is 1, n is 1, p is 0, and w is 1.

In another embodiment is a compound of Formula (Id), or a solvate, hydrate, tautomer, N-oxide, stereoisomer, or pharmaceutically acceptable salt thereof, wherein A is C(H). In another embodiment is a compound of Formula (Id), or a solvate, hydrate, tautomer, N-oxide, stereoisomer, or pharmaceutically acceptable salt thereof, wherein A is N.

In another embodiment is a compound of Formula (Id), or a solvate, hydrate, tautomer, N-oxide, stereoisomer, or pharmaceutically acceptable salt thereof, wherein Y is —$CH_2$—. In another embodiment is a compound of Formula (Id), or a solvate, hydrate, tautomer, N-oxide, stereoisomer, or pharmaceutically acceptable salt thereof, wherein Y is —$C(O)$—.

In another embodiment is a compound of Formula (Id), or a solvate, hydrate, tautomer, N-oxide, stereoisomer, or pharmaceutically acceptable salt thereof, wherein $R^{12}$ is H. In another embodiment is a compound of Formula (Id), or a solvate, hydrate, tautomer, N-oxide, stereoisomer, or pharmaceutically acceptable salt thereof, wherein $R^{12}$ is $C_{1-6}$alkyl. In another embodiment is a compound of Formula (Id), or a solvate, hydrate, tautomer, N-oxide, stereoisomer, or pharmaceutically acceptable salt thereof, wherein $R^{12}$ is —$CH_3$. In another embodiment is a compound of Formula (Id), or a solvate, hydrate, tautomer, N-oxide, stereoisomer, or pharmaceutically acceptable salt thereof, wherein $R^{13}$ is H. In another embodiment is a compound of Formula (Id), or a solvate, hydrate, tautomer, N-oxide, stereoisomer, or pharmaceutically acceptable salt thereof, wherein $R^{13}$ is $C_{1-6}$alkyl. In another embodiment is a compound of Formula (Id), or a solvate, hydrate, tautomer, N-oxide, stereoisomer, or pharmaceutically acceptable salt thereof, wherein $R^{13}$ is —$CH_3$. In another embodiment is a compound of Formula (Id), or a solvate, hydrate, tautomer, N-oxide, stereoisomer, or pharmaceutically acceptable salt thereof, wherein $R^{12}$ is H and $R^{13}$ is H. In another embodiment is a compound of Formula (Id), or a solvate, hydrate, tautomer, N-oxide, stereoisomer, or pharmaceutically acceptable salt thereof, wherein $R^{12}$ is H and $R^{13}$ is $C_{1-6}$alkyl. In another embodiment is a compound of Formula (Id), or a solvate, hydrate, tautomer, N-oxide, stereoisomer, or pharmaceutically acceptable salt thereof, wherein $R^{12}$ is H and $R^{13}$ is —$CH_3$. In another embodiment is a compound of Formula (Id), or a solvate, hydrate, tautomer, N-oxide, stereoisomer, or pharmaceutically acceptable salt thereof, wherein $R^{12}$ is $C_{1-6}$alkyl and $R^{13}$ is H. In another embodiment is a compound of Formula (Id), or a solvate, hydrate, tautomer, N-oxide, stereoisomer, or pharmaceutically acceptable salt thereof, wherein $R^{12}$ is —$CH_3$ and $R^{13}$ is H. In another embodiment is a compound of Formula (Id), or a solvate, hydrate, tautomer, N-oxide, stereoisomer, or pharmaceutically acceptable salt thereof, wherein $R^{12}$ is $C_{1-6}$alkyl and $R^{13}$ is $C_{1-6}$alkyl. In another embodiment is a compound of Formula (Id), or a solvate, hydrate, tautomer, N-oxide, stereoisomer, or pharmaceutically acceptable salt thereof, wherein $R^{12}$ is —$CH_3$ and $R^{13}$ is —$CH_3$.

In another embodiment is a compound of Formula (Id), or a solvate, hydrate, tautomer, N-oxide, stereoisomer, or pharmaceutically acceptable salt thereof, wherein $R^4$ is halogen, —$OR^7$, $C_{1-6}$alkyl-OH, —N(H)—$C_{1-6}$alkyl-$CO_2H$, $C_{2-6}$alkynyl, $C_{1-6}$haloalkyl, —$CO_2R^8$, —C(O)$NR^8R^9$, $C_{3-8}$cycloalkyl, $C_{2-9}$heterocycloalkyl, $C_{6-10}$aryl, or $C_{1-9}$heteroaryl, wherein $C_{3-8}$cycloalkyl, $C_{2-9}$heterocycloalkyl, $C_{6-10}$aryl, or $C_{1-9}$heteroaryl are optionally substituted with 1 or 2 $R^{14}$. In another embodiment is a compound of Formula (Id), or a solvate, hydrate, tautomer, N-oxide, stereoisomer, or pharmaceutically acceptable salt thereof, wherein $R^4$ is halogen, —$OR^7$, —N(H)—$C_{1-6}$alkyl-$CO_2H$, $C_{1-6}$haloalkyl, —C(O)$NR^8R^9$, $C_{3-8}$cycloalkyl, $C_{2-9}$heterocycloalkyl, or $C_{1-9}$heteroaryl, wherein $C_{2-9}$heterocycloalkyl or $C_{1-9}$heteroaryl are optionally substituted with 1 or 2 $R^{14}$. In another embodiment is a compound of Formula (Id), or a solvate, hydrate, tautomer, N-oxide, stereoisomer, or pharmaceutically acceptable salt thereof, wherein $R^4$ is halogen. In another embodiment is a compound of Formula (Id), or a solvate, hydrate, tautomer, N-oxide, stereoisomer, or pharmaceutically acceptable salt thereof, wherein $R^4$ is —Cl. In another embodiment is a compound of Formula (Id), or a solvate, hydrate, tautomer, N-oxide, stereoisomer, or pharmaceutically acceptable salt thereof, wherein $R^4$ is $C_{1-6}$haloalkyl. In another embodiment is a compound of Formula (Id), or a solvate, hydrate, tautomer, N-oxide, stereoisomer, or pharmaceutically acceptable salt thereof, wherein $R^4$ is —$CF_3$. In another embodiment is a compound of Formula (Id), or a solvate, hydrate, tautomer, N-oxide, stereoisomer, or pharmaceutically acceptable salt thereof, wherein $R^4$ is —N(H)—$C_{1-6}$alkyl-$CO_2H$. In another embodiment is a compound of Formula (Id), or a solvate, hydrate, tautomer, N-oxide, stereoisomer, or pharmaceutically acceptable salt thereof, wherein $R^4$ is —N(H)$CH_2CO_2H$. In another embodiment is a compound of Formula (Id), or a solvate, hydrate, tautomer, N-oxide, stereoisomer, or pharmaceutically acceptable salt thereof, wherein $R^4$ is —N(H)$CH_2CH_2CO_2H$. In another embodiment is a compound of Formula (Id), or a solvate, hydrate, tautomer, N-oxide, stereoisomer, or pharmaceutically acceptable salt thereof, wherein $R^4$ is —N(H)$CH_2CH_2CH_2CO_2H$. In another embodiment is a compound of Formula (Id), or a solvate, hydrate, tautomer, N-oxide, stereoisomer, or pharmaceutically acceptable salt thereof, wherein $R^4$ is —C(O)$NR^8R^9$. In another embodiment is a compound of Formula (Id), or a solvate, hydrate, tautomer, N-oxide, stereoisomer, or pharmaceutically acceptable salt thereof, wherein $R^4$ is —C(O)$NH_2$. In another embodiment is a compound of Formula (Id), or a solvate, hydrate, tautomer, N-oxide, stereoisomer, or pharmaceutically acceptable salt thereof, wherein $R^4$ is $C_{3-8}$cycloalkyl. In another embodiment is a compound of Formula (Id), or a solvate, hydrate, tautomer, N-oxide, stereoisomer, or pharmaceutically acceptable salt thereof, wherein $R^4$ is —$OR^7$. In another embodiment is a compound of Formula (Id), or a solvate, hydrate, tautomer, N-oxide, stereoisomer, or pharmaceutically acceptable salt thereof, wherein $R^4$ is —$OR^7$ and $R^7$ is unsubstituted $C_{3-8}$cycloalkyl or $C_{6-10}$aryl optionally substituted with halogen. In another embodiment is a compound of Formula (Id), or a solvate, hydrate, tautomer, N-oxide, stereoisomer, or pharmaceutically acceptable salt thereof, wherein $R^4$ is —$OR^7$ and $R^7$ is unsubstituted $C_{3-8}$cycloalkyl. In another embodiment is a compound of Formula (Id), or a solvate, hydrate, tautomer, N-oxide, stereoisomer, or pharmaceutically acceptable salt thereof, wherein $R^4$ is —$OR^7$ and $R^7$ is phenyl optionally substituted with halogen. In another embodiment is a compound of Formula (Id), or a solvate, hydrate, tautomer, N-oxide, stereoisomer, or pharmaceutically acceptable salt thereof, wherein $R^4$ is —$OR^7$ and $R^7$ is phenyl substituted with halogen. In another embodiment is a compound of Formula (Id), or a solvate, hydrate, tautomer, N-oxide, stereoisomer, or pharmaceutically acceptable salt thereof, wherein $R^4$ is —$OR^7$ and $R^7$ is phenyl substituted with —Cl. In another embodiment is a compound of Formula (Id), or a solvate, hydrate, tautomer, N-oxide, stereoisomer, or pharmaceutically acceptable salt thereof, wherein $R^4$ is $C_{2-9}$heterocycloalkyl optionally substituted with 1 or 2 $R^{14}$. In another embodiment is a compound of Formula (Id), or a solvate, hydrate, tautomer, N-oxide, stereoisomer, or pharmaceutically acceptable salt thereof, wherein $R^4$ is an unsubstituted $C_{2-9}$heterocycloalkyl. In another embodiment is a compound of Formula (Id), or a solvate, hydrate, tautomer, N-oxide, stereoisomer, or pharmaceutically acceptable salt thereof, wherein $R^4$ is $C_{2-9}$heterocycloalkyl substituted with 1 or 2 $R^{14}$. In another embodiment is a compound of Formula (Id), or a solvate, hydrate, tautomer, N-oxide, stereoisomer, or pharmaceutically acceptable salt thereof, wherein $R^4$ is $C_{4-5}$heterocycloalkyl optionally substituted with 1 or 2 $R^{14}$, wherein the $C_{4-5}$heterocycloalkyl is a monocyclic heterocycloalkyl selected from pyrrolidine, piperidine, piperazine, and morpholine. In another embodiment is a compound of Formula (Id), or a solvate, hydrate, tautomer, N-oxide, stereoisomer, or pharmaceutically acceptable salt thereof, wherein $R^4$ is $C_{5-9}$heterocycloalkyl optionally substituted with 1 or 2 $R^{14}$, wherein the $C_{5-9}$heterocycloalkyl is a bicyclic heterocycloalkyl. In another embodiment is a compound of Formula (Id), or a solvate, hydrate, tautomer, N-oxide, stereoisomer, or pharmaceutically acceptable salt thereof, wherein $R^4$ is $C_{5-9}$heterocycloalkyl optionally substituted with 1 or 2 $R^{14}$, wherein the $C_{5-9}$heterocycloalkyl is a spirocyclic heterocycloalkyl. In another embodiment is a compound of Formula (Id), or a solvate, hydrate, tautomer, N-oxide, stereoisomer, or pharmaceutically acceptable salt thereof, wherein $R^4$ is

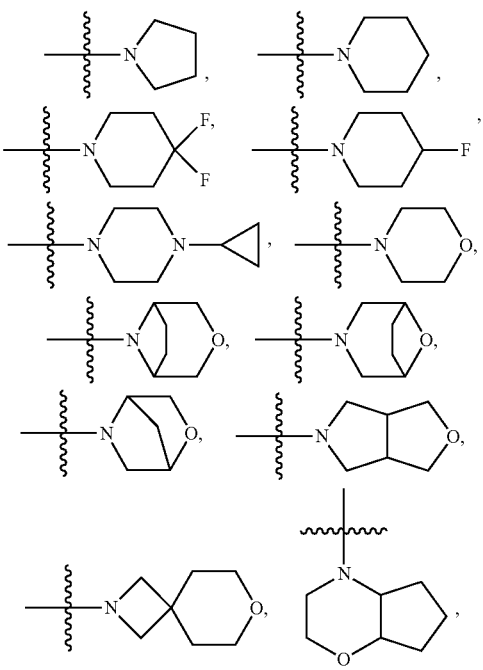

-continued

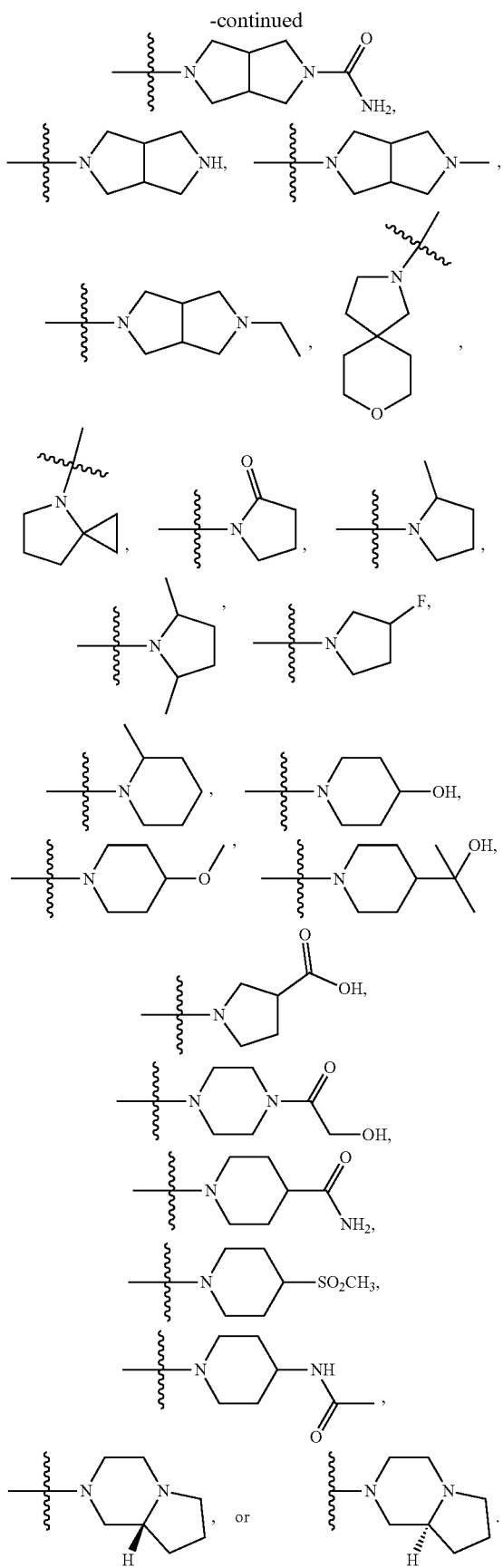

In another embodiment is a compound of Formula (Id), or a solvate, hydrate, tautomer, N-oxide, stereoisomer, or pharmaceutically acceptable salt thereof, wherein $R^4$ is $C_{1-9}$heteroaryl optionally substituted with 1 or 2 $R^{14}$. In another embodiment is a compound of Formula (Id), or a solvate, hydrate, tautomer, N-oxide, stereoisomer, or pharmaceutically acceptable salt thereof, wherein $R^4$ is an unsubstituted $C_{1-9}$heteroaryl. In another embodiment is a compound of Formula (Id), or a solvate, hydrate, tautomer, N-oxide, stereoisomer, or pharmaceutically acceptable salt thereof, wherein $R^4$ is $C_{2-9}$heteroaryl substituted with 1 or 2 $R^{14}$. In another embodiment is a compound of Formula (Id), or a solvate, hydrate, tautomer, N-oxide, stereoisomer, or pharmaceutically acceptable salt thereof, wherein $R^4$ is $C_{2-9}$heteroaryl optionally substituted with 1 or 2 $R^{14}$, wherein the $C_{2-9}$heteroaryl is selected from pyrrole, furan, thiophene, thiazole, pyrazole, oxazole, oxadiazole, thiadiazole, pyridine, pyrimidine, pyrazine, indole, benzothiophene, benzofuran, and imidazopyridine. In another embodiment is a compound of Formula (Id), or a solvate, hydrate, tautomer, N-oxide, stereoisomer, or pharmaceutically acceptable salt thereof, wherein $R^4$ is

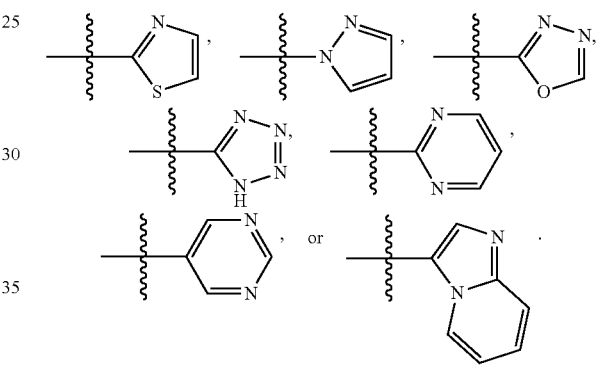

In another embodiment is a compound of Formula (Id), or a solvate, hydrate, tautomer, N-oxide, stereoisomer, or pharmaceutically acceptable salt thereof, wherein $R^5$ is H, CN, halogen, $C_{1-6}$alkyl, $C_{1-6}$haloalkyl, or $C_{1-6}$haloalkoxy. In another embodiment is a compound of Formula (Id), or a solvate, hydrate, tautomer, N-oxide, stereoisomer, or pharmaceutically acceptable salt thereof, wherein $R^5$ is H. In another embodiment is a compound of Formula (Id), or a solvate, hydrate, tautomer, N-oxide, stereoisomer, or pharmaceutically acceptable salt thereof, wherein $R^5$ is —CN. In another embodiment is a compound of Formula (Id), or a solvate, hydrate, tautomer, N-oxide, stereoisomer, or pharmaceutically acceptable salt thereof, wherein $R^5$ is halogen. In another embodiment is a compound of Formula (Id), or a solvate, hydrate, tautomer, N-oxide, stereoisomer, or pharmaceutically acceptable salt thereof, wherein $R^5$ is —Cl. In another embodiment is a compound of Formula (Id), or a solvate, hydrate, tautomer, N-oxide, stereoisomer, or pharmaceutically acceptable salt thereof, wherein $R^5$ is —F. In another embodiment is a compound of Formula (Id), or a solvate, hydrate, tautomer, N-oxide, stereoisomer, or pharmaceutically acceptable salt thereof, wherein $R^5$ is $C_{1-6}$alkyl. In another embodiment is a compound of Formula (Id), or a solvate, hydrate, tautomer, N-oxide, stereoisomer, or pharmaceutically acceptable salt thereof, wherein $R^5$ is —$CH_3$. In another embodiment is a compound of Formula (Id), or a solvate, hydrate, tautomer, N-oxide, stereoisomer, or pharmaceutically acceptable salt thereof, wherein $R^5$ is $C_{1-6}$haloalkyl. In another embodiment is a compound of Formula (Id), or a solvate, hydrate, tautomer, N-oxide, stereoisomer, or pharmaceutically acceptable salt thereof, wherein $R^5$ is —$CF_3$. In another embodiment is a compound of Formula (Id), or a solvate, hydrate, tautomer, N-oxide, stereoisomer, or pharmaceutically acceptable salt thereof, wherein $R^5$ is $C_{1-6}$haloalkoxy. In another embodiment is a compound of Formula (Id), or a solvate, hydrate, tautomer, N-oxide, stereoisomer, or pharmaceutically acceptable salt thereof, wherein $R^5$ is —$OCF_3$. In another embodiment is a compound of Formula (Id), or a solvate, hydrate, tautomer, N-oxide, stereoisomer, or pharmaceutically acceptable salt thereof, wherein $R^6$ is H. In another embodiment is a compound of Formula (Id), or a solvate, hydrate, tautomer, N-oxide, stereoisomer, or pharmaceutically acceptable salt thereof, wherein $R^6$ is halogen. In another embodiment is a compound of Formula (Id), or a solvate, hydrate, tautomer, N-oxide, stereoisomer, or pharmaceutically acceptable salt thereof, wherein $R^6$ is —Cl. In another embodiment is a compound of Formula (Id), or a solvate, hydrate, tautomer, N-oxide, stereoisomer, or pharmaceutically acceptable salt thereof, wherein $R^6$ is —F. In another embodiment is a compound of Formula (Id), or a solvate, hydrate, tautomer, N-oxide, stereoisomer, or pharmaceutically acceptable salt thereof, wherein $R^6$ is $C_{1-6}$alkyl. In another embodiment is a compound of Formula (Id), or a solvate, hydrate, tautomer, N-oxide, stereoisomer, or pharmaceutically acceptable salt thereof, wherein $R^6$ is —$CH_3$.

In another embodiment is a compound of Formula (I) having the structure of Formula (Ie):

Formula (Ie)

wherein:
$R^1$ is —$N(R^2)C(O)R^{15}$ or —$N(H)SO_2R^{15}$;
$R^2$ is H or $C_{1-6}$alkyl;
Y is —$CH_2$— or —C(O)—;
Z is —S—, —O—, or —$N(R^{20})$—;
$R^4$ is H, halogen, —$OR^7$, $C_{1-6}$alkyl, $C_{1-6}$alkyl-OH, $C_{2-6}$alkenyl, $C_{2-6}$alkynyl, $C_{1-6}$haloalkyl, —O—$C_{3-8}$cycloalkyl, —O—$C_{3-8}$cycloalkyl-OH, —N(H)—$C_{1-6}$alkyl-$CO_2$H, —$SO_2R^{17}$, —$CO_2R^8$, —$C(O)NR^8R^9$, $C_{3-8}$cycloalkyl, $C_{2-9}$heterocycloalkyl, —$C_{1-6}$alkyl-$C_{2-9}$heterocycloalkyl, $C_{6-10}$aryl, $C_{1-9}$heteroaryl, wherein $C_{3-8}$cycloalkyl, $C_{2-9}$heterocycloalkyl, —$C_{1-6}$alkyl-$C_{2-9}$heterocycloalkyl, $C_{6-10}$aryl, $C_{1-9}$heteroaryl are optionally substituted with 1 or 2 $R^{14}$;
$R^5$ is H, —CN, halogen, $C_{1-6}$alkyl, $C_{1-6}$haloalkyl, $C_{1-6}$haloalkoxy, or phenyl;
$R^6$ is H, halogen, or $C_{1-6}$alkyl;
$R^7$ is H, $C_{1-6}$alkyl, $C_{1-6}$haloalkyl, $C_{3-8}$cycloalkyl, $C_{2-9}$heterocycloalkyl, $C_{6-10}$aryl, or $C_{1-9}$heteroaryl, wherein $C_{2-9}$heterocycloalkyl, $C_{6-10}$aryl, or $C_{1-9}$heteroaryl are optionally substituted with 1 or 2 $R^{14}$;

each $R^8$ and each $R^9$ are independently selected from H and $C_{1-6}$alkyl; or $R^8$ and $R^9$ together with the nitrogen to which they are attached are combined to form a heterocycloalkyl ring;
$R^{12}$ is H, halogen, or $C_{1-6}$alkyl;
$R^{13}$ is H or $C_{1-6}$alkyl;
each $R^{14}$ is independently selected from halogen, —OH, oxo, $C_{1-6}$alkyl, $C_{1-6}$haloalkyl, $C_{1-6}$alkoxy, —$C_{1-6}$alkyl-OH, $C_{3-8}$cycloalkyl, —$CO_2R^8$, —$C(O)NR^8R^9$, —C(O)—$C_{1-6}$alkyl, —$C(O)C_{1-6}$alkyl-OH, —$SO_2$—$C_{1-6}$alkyl, —$N(R^8)SO_2$—$C_{1-6}$alkyl, and —$N(R^8)C(O)$—$C_{1-6}$alkyl;
$R^{15}$ is $C_{1-6}$alkyl or $C_{3-8}$cycloalkyl;
$R^{17}$ is $C_{1-6}$alkyl or $C_{3-8}$cycloalkyl;
$R^{20}$ is H or $C_{1-6}$alkyl;
n is 0 or 1;
m is 0 or 1;
p is 0, 1, or 2; and
q is 0, 1, or 2;
or a solvate, hydrate, tautomer, N-oxide, stereoisomer, or pharmaceutically acceptable salt thereof.

In another embodiment is a compound of Formula (Ie), or a solvate, hydrate, tautomer, N-oxide, stereoisomer, or pharmaceutically acceptable salt thereof, wherein $R^1$ is —$N(R^2)C(O)R^{15}$. In another embodiment is a compound of Formula (Ie), or a solvate, hydrate, tautomer, N-oxide, stereoisomer, or pharmaceutically acceptable salt thereof, wherein $R^1$ is —$N(R^2)C(O)R^{15}$ and $R^2$ is H. In another embodiment is a compound of Formula (Ie), or a solvate, hydrate, tautomer, N-oxide, stereoisomer, or pharmaceutically acceptable salt thereof, wherein $R^1$ is —$N(H)C(O)R^{15}$ and $R^{15}$ is $C_{1-6}$alkyl. In another embodiment is a compound of Formula (Ie), or a solvate, hydrate, tautomer, N-oxide, stereoisomer, or pharmaceutically acceptable salt thereof, wherein $R^1$ is —$N(H)C(O)R^{15}$ and $R^{15}$ is —$CH_3$. In another embodiment is a compound of Formula (Ie), or a solvate, hydrate, tautomer, N-oxide, stereoisomer, or pharmaceutically acceptable salt thereof, wherein $R^1$ is —$N(H)C(O)R^{15}$ and $R^{15}$ is $C_{3-8}$cycloalkyl. In another embodiment is a compound of Formula (Ie), or a solvate, hydrate, tautomer, N-oxide, stereoisomer, or pharmaceutically acceptable salt thereof, wherein $R^1$ is —$N(R^2)C(O)R^{15}$ and $R^2$ is $C_{1-6}$alkyl. In another embodiment is a compound of Formula (Ie), or a solvate, hydrate, tautomer, N-oxide, stereoisomer, or pharmaceutically acceptable salt thereof, wherein $R^1$ is —$N(R^2)C(O)R^{15}$ and $R^2$ is —$CH_3$. In another embodiment is a compound of Formula (Ie), or a solvate, hydrate, tautomer, N-oxide, stereoisomer, or pharmaceutically acceptable salt thereof, wherein $R^1$ is —$N(CH_3)C(O)R^{15}$ and $R^{15}$ is $C_{1-6}$alkyl. In another embodiment is a compound of Formula (Ie), or a solvate, hydrate, tautomer, N-oxide, stereoisomer, or pharmaceutically acceptable salt thereof, wherein $R^1$ is —$N(CH_3)C(O)R^{15}$ and $R^{15}$ is —$CH_3$. In another embodiment is a compound of Formula (Ie), or a solvate, hydrate, tautomer, N-oxide, stereoisomer, or pharmaceutically acceptable salt thereof, wherein $R^1$ is —$N(CH_3)C(O)R^{15}$ and $R^{15}$ is $C_{3-8}$cycloalkyl. In another embodiment is a compound of Formula (Ie), or a solvate, hydrate, tautomer, N-oxide, stereoisomer, or pharmaceutically acceptable salt thereof, wherein $R^1$ is —$N(H)SO_2R^{15}$. In another embodiment is a compound of Formula (Ie), or a solvate, hydrate, tautomer, N-oxide, stereoisomer, or pharmaceutically acceptable salt thereof, wherein $R^1$ is —$N(H)SO_2R^{15}$ and $R^{15}$ is $C_{1-6}$alkyl. In another embodiment is a compound of Formula (Ie), or a solvate, hydrate, tautomer, N-oxide, stereoisomer, or pharmaceutically acceptable salt thereof, wherein $R^1$ is —$N(H)SO_2R^{15}$ and $R^{15}$ is —$CH_3$. In another embodiment is a compound of Formula (Ie), or a solvate, hydrate, tautomer, N-oxide, stereoisomer, or pharmaceutically acceptable salt thereof, wherein $R^1$ is —N(H)SO$_2$R$^{15}$ and $R^{15}$ is $C_{3-8}$cycloalkyl.

In another embodiment is a compound of Formula (Ie), or a solvate, hydrate, tautomer, N-oxide, stereoisomer, or pharmaceutically acceptable salt thereof, wherein m is 1, n is 1, q is 1, and p is 1. In another embodiment is a compound of Formula (Ie), or a solvate, hydrate, tautomer, N-oxide, stereoisomer, or pharmaceutically acceptable salt thereof, wherein m is 0, n is 1, q is 2, and p is 1. In another embodiment is a compound of Formula (Ie), or a solvate, hydrate, tautomer, N-oxide, stereoisomer, or pharmaceutically acceptable salt thereof, wherein m is 1, n is 1, q is 0, and p is 2. In another embodiment is a compound of Formula (Ie), or a solvate, hydrate, tautomer, N-oxide, stereoisomer, or pharmaceutically acceptable salt thereof, wherein m is 1, n is 1, q is 1, and p is 0. In another embodiment is a compound of Formula (Ie), or a solvate, hydrate, tautomer, N-oxide, stereoisomer, or pharmaceutically acceptable salt thereof, wherein m is 0, n is 0, q is 2, and p is 1.

In another embodiment is a compound of Formula (Ie), or a solvate, hydrate, tautomer, N-oxide, stereoisomer, or pharmaceutically acceptable salt thereof, wherein Y is —CH$_2$—. In another embodiment is a compound of Formula (Ie), or a solvate, hydrate, tautomer, N-oxide, stereoisomer, or pharmaceutically acceptable salt thereof, wherein Y is —C(O)—.

In another embodiment is a compound of Formula (Ie), or a solvate, hydrate, tautomer, N-oxide, stereoisomer, or pharmaceutically acceptable salt thereof, wherein Z is —S—. In another embodiment is a compound of Formula (Ie), or a solvate, hydrate, tautomer, N-oxide, stereoisomer, or pharmaceutically acceptable salt thereof, wherein Z is —O—. In another embodiment is a compound of Formula (Ie), or a solvate, hydrate, tautomer, N-oxide, stereoisomer, or pharmaceutically acceptable salt thereof, wherein Z is —N(R$^{20}$)—. In another embodiment is a compound of Formula (Ie), or a solvate, hydrate, tautomer, N-oxide, stereoisomer, or pharmaceutically acceptable salt thereof, wherein Z is —N(H)—. In another embodiment is a compound of Formula (Ie), or a solvate, hydrate, tautomer, N-oxide, stereoisomer, or pharmaceutically acceptable salt thereof, wherein Z is —N(CH$_3$)—.

In another embodiment is a compound of Formula (Ie), or a solvate, hydrate, tautomer, N-oxide, stereoisomer, or pharmaceutically acceptable salt thereof, wherein $R^{12}$ is H. In another embodiment is a compound of Formula (Ie), or a solvate, hydrate, tautomer, N-oxide, stereoisomer, or pharmaceutically acceptable salt thereof, wherein $R^{12}$ is $C_{1-6}$alkyl. In another embodiment is a compound of Formula (Ie), or a solvate, hydrate, tautomer, N-oxide, stereoisomer, or pharmaceutically acceptable salt thereof, wherein $R^{12}$ is —CH$_3$. In another embodiment is a compound of Formula (Ie), or a solvate, hydrate, tautomer, N-oxide, stereoisomer, or pharmaceutically acceptable salt thereof, wherein $R^{13}$ is H. In another embodiment is a compound of Formula (Ie), or a solvate, hydrate, tautomer, N-oxide, stereoisomer, or pharmaceutically acceptable salt thereof, wherein $R^{13}$ is $C_{1-6}$alkyl. In another embodiment is a compound of Formula (Ie), or a solvate, hydrate, tautomer, N-oxide, stereoisomer, or pharmaceutically acceptable salt thereof, wherein $R^{13}$ is —CH$_3$. In another embodiment is a compound of Formula (Ie), or a solvate, hydrate, tautomer, N-oxide, stereoisomer, or pharmaceutically acceptable salt thereof, wherein $R^{12}$ is H and $R^{13}$ is H. In another embodiment is a compound of Formula (Ie), or a solvate, hydrate, tautomer, N-oxide, stereoisomer, or pharmaceutically acceptable salt thereof, wherein $R^{12}$ is H and $R^{13}$ is $C_{1-6}$alkyl. In another embodiment is a compound of Formula (Ie), or a solvate, hydrate, tautomer, N-oxide, stereoisomer, or pharmaceutically acceptable salt thereof, wherein $R^{12}$ is H and $R^{13}$ is —CH$_3$. In another embodiment is a compound of Formula (Ie), or a solvate, hydrate, tautomer, N-oxide, stereoisomer, or pharmaceutically acceptable salt thereof, wherein $R^{12}$ is $C_{1-6}$alkyl and $R^{13}$ is H. In another embodiment is a compound of Formula (Ie), or a solvate, hydrate, tautomer, N-oxide, stereoisomer, or pharmaceutically acceptable salt thereof, wherein $R^{12}$ is —CH$_3$ and $R^{13}$ is H. In another embodiment is a compound of Formula (Ie), or a solvate, hydrate, tautomer, N-oxide, stereoisomer, or pharmaceutically acceptable salt thereof, wherein $R^{12}$ is $C_{1-6}$alkyl and $R^{13}$ is $C_{1-6}$alkyl. In another embodiment is a compound of Formula (Ie), or a solvate, hydrate, tautomer, N-oxide, stereoisomer, or pharmaceutically acceptable salt thereof, wherein $R^{12}$ is —CH$_3$ and $R^{13}$ is —CH$_3$.

In another embodiment is a compound of Formula (Ie), or a solvate, hydrate, tautomer, N-oxide, stereoisomer, or pharmaceutically acceptable salt thereof, wherein $R^4$ is halogen, —OR$^7$, $C_{1-6}$alkyl-OH, —N(H)—$C_{1-6}$alkyl-CO$_2$H, $C_{2-6}$alkynyl, $C_{1-6}$haloalkyl, —CO$_2$R$^8$, —C(O)NR$^8$R$^9$, $C_{3-8}$cycloalkyl, $C_{2-9}$heterocycloalkyl, $C_{6-10}$aryl, or $C_{1-9}$heteroaryl, wherein $C_{3-8}$cycloalkyl, $C_{2-9}$heterocycloalkyl, $C_{6-10}$aryl, or $C_{1-9}$heteroaryl are optionally substituted with 1 or 2 $R^{14}$. In another embodiment is a compound of Formula (Ie), or a solvate, hydrate, tautomer, N-oxide, stereoisomer, or pharmaceutically acceptable salt thereof, wherein $R^4$ is halogen, —OR$^7$, —N(H)—$C_{1-6}$alkyl-CO$_2$H, $C_{1-6}$haloalkyl, —C(O)NR$^8$R$^9$, $C_{3-8}$cycloalkyl, $C_{2-9}$heterocycloalkyl, or $C_{1-9}$heteroaryl, wherein $C_{2-9}$heterocycloalkyl or $C_{1-9}$heteroaryl are optionally substituted with 1 or 2 $R^{14}$. In another embodiment is a compound of Formula (Ie), or a solvate, hydrate, tautomer, N-oxide, stereoisomer, or pharmaceutically acceptable salt thereof, wherein $R^4$ is halogen. In another embodiment is a compound of Formula (Ie), or a solvate, hydrate, tautomer, N-oxide, stereoisomer, or pharmaceutically acceptable salt thereof, wherein $R^4$ is —Cl. In another embodiment is a compound of Formula (Ie), or a solvate, hydrate, tautomer, N-oxide, stereoisomer, or pharmaceutically acceptable salt thereof, wherein $R^4$ is $C_{1-6}$haloalkyl. In another embodiment is a compound of Formula (Ie), or a solvate, hydrate, tautomer, N-oxide, stereoisomer, or pharmaceutically acceptable salt thereof, wherein $R^4$ is —CF$_3$. In another embodiment is a compound of Formula (Ie), or a solvate, hydrate, tautomer, N-oxide, stereoisomer, or pharmaceutically acceptable salt thereof, wherein $R^4$ is —N(H)—$C_{1-6}$alkyl-CO$_2$H. In another embodiment is a compound of Formula (Ie), or a solvate, hydrate, tautomer, N-oxide, stereoisomer, or pharmaceutically acceptable salt thereof, wherein $R^4$ is —N(H)CH$_2$CO$_2$H. In another embodiment is a compound of Formula (Ie), or a solvate, hydrate, tautomer, N-oxide, stereoisomer, or pharmaceutically acceptable salt thereof, wherein $R^4$ is —N(H)CH$_2$CH$_2$CO$_2$H. In another embodiment is a compound of Formula (Ie), or a solvate, hydrate, tautomer, N-oxide, stereoisomer, or pharmaceutically acceptable salt thereof, wherein $R^4$ is —N(H)CH$_2$CH$_2$CH$_2$CO$_2$H. In another embodiment is a compound of Formula (Ie), or a solvate, hydrate, tautomer, N-oxide, stereoisomer, or pharmaceutically acceptable salt thereof, wherein $R^4$ is —C(O)NR$^8$R$^9$. In another embodiment is a compound of Formula (Ie), or a solvate, hydrate, tautomer, N-oxide, stereoisomer, or pharmaceutically acceptable salt thereof, wherein $R^4$ is —C(O)NH$_2$. In another embodiment is a compound of Formula (Ie), or a solvate, hydrate, tautomer, N-oxide, stereoisomer, or pharmaceutically acceptable salt thereof, wherein $R^4$ is $C_{3-8}$cycloalkyl. In another embodiment is a compound of Formula (Ie), or a solvate, hydrate, tautomer, N-oxide, stereoisomer, or pharmaceutically acceptable salt thereof, wherein $R^4$ is —$OR^7$. In another embodiment is a compound of Formula (Ie), or a solvate, hydrate, tautomer, N-oxide, stereoisomer, or pharmaceutically acceptable salt thereof, wherein $R^4$ is —$OR^7$ and $R^7$ is unsubstituted $C_{3-8}$cycloalkyl or $C_{6-10}$aryl optionally substituted with halogen. In another embodiment is a compound of Formula (Ie), or a solvate, hydrate, tautomer, N-oxide, stereoisomer, or pharmaceutically acceptable salt thereof, wherein $R^4$ is —$OR^7$ and $R^7$ is unsubstituted $C_{3-8}$cycloalkyl. In another embodiment is a compound of Formula (Ie), or a solvate, hydrate, tautomer, N-oxide, stereoisomer, or pharmaceutically acceptable salt thereof, wherein $R^4$ is —$OR^7$ and $R^7$ is phenyl optionally substituted with halogen. In another embodiment is a compound of Formula (Ie), or a solvate, hydrate, tautomer, N-oxide, stereoisomer, or pharmaceutically acceptable salt thereof, wherein $R^4$ is —$OR^7$ and $R^7$ is phenyl substituted with halogen. In another embodiment is a compound of Formula (Ie), or a solvate, hydrate, tautomer, N-oxide, stereoisomer, or pharmaceutically acceptable salt thereof, wherein $R^4$ is —$OR^7$ and $R^7$ is phenyl substituted with —Cl. In another embodiment is a compound of Formula (Ie), or a solvate, hydrate, tautomer, N-oxide, stereoisomer, or pharmaceutically acceptable salt thereof, wherein $R^4$ is $C_{2-9}$heterocycloalkyl optionally substituted with 1 or 2 $R^{14}$. In another embodiment is a compound of Formula (Ie), or a solvate, hydrate, tautomer, N-oxide, stereoisomer, or pharmaceutically acceptable salt thereof, wherein $R^4$ is an unsubstituted $C_{2-9}$heterocycloalkyl. In another embodiment is a compound of Formula (Ie), or a solvate, hydrate, tautomer, N-oxide, stereoisomer, or pharmaceutically acceptable salt thereof, wherein $R^4$ is $C_{2-9}$heterocycloalkyl substituted with 1 or 2 $R^{14}$. In another embodiment is a compound of Formula (Ie), or a solvate, hydrate, tautomer, N-oxide, stereoisomer, or pharmaceutically acceptable salt thereof, wherein $R^4$ is $C_{4-5}$heterocycloalkyl optionally substituted with 1 or 2 $R^{14}$, wherein the $C_{4-5}$heterocycloalkyl is a monocyclic heterocycloalkyl selected from pyrrolidine, piperidine, piperazine, and morpholine. In another embodiment is a compound of Formula (Ie), or a solvate, hydrate, tautomer, N-oxide, stereoisomer, or pharmaceutically acceptable salt thereof, wherein $R^4$ is $C_{5-9}$heterocycloalkyl optionally substituted with 1 or 2 $R^{14}$, wherein the $C_{5-9}$heterocycloalkyl is a bicyclic heterocycloalkyl. In another embodiment is a compound of Formula (Ie), or a solvate, hydrate, tautomer, N-oxide, stereoisomer, or pharmaceutically acceptable salt thereof, wherein $R^4$ is $C_{5-9}$heterocycloalkyl optionally substituted with 1 or 2 $R^{14}$, wherein the $C_{5-9}$heterocycloalkyl is a spirocyclic heterocycloalkyl. In another embodiment is a compound of Formula (Ie), or a solvate, hydrate, tautomer, N-oxide, stereoisomer, or pharmaceutically acceptable salt thereof, wherein $R^4$ is

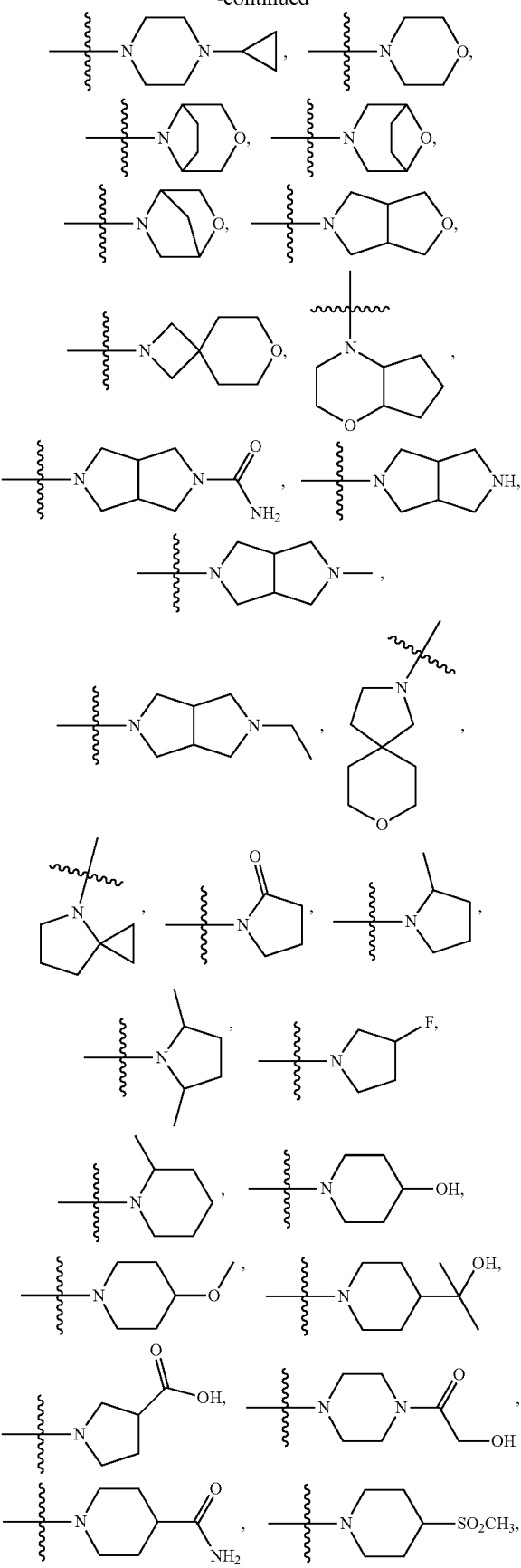

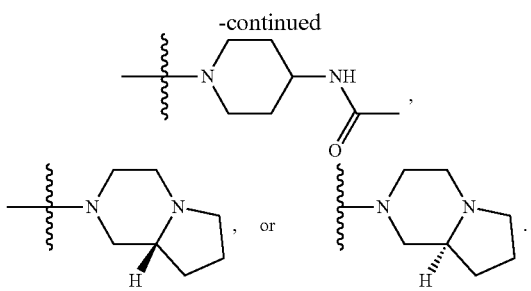

In another embodiment is a compound of Formula (Ie), or a solvate, hydrate, tautomer, N-oxide, stereoisomer, or pharmaceutically acceptable salt thereof, wherein $R^4$ is $C_{1-9}$heteroaryl optionally substituted with 1 or 2 $R^{14}$. In another embodiment is a compound of Formula (Ie), or a solvate, hydrate, tautomer, N-oxide, stereoisomer, or pharmaceutically acceptable salt thereof, wherein $R^4$ is an unsubstituted $C_{1-9}$heteroaryl. In another embodiment is a compound of Formula (Ie), or a solvate, hydrate, tautomer, N-oxide, stereoisomer, or pharmaceutically acceptable salt thereof, wherein $R^4$ is $C_{2-9}$heteroaryl substituted with 1 or 2 $R^{14}$. In another embodiment is a compound of Formula (Ie), or a solvate, hydrate, tautomer, N-oxide, stereoisomer, or pharmaceutically acceptable salt thereof, wherein $R^4$ is $C_{2-9}$heteroaryl optionally substituted with 1 or 2 $R^{14}$, wherein the $C_{2-9}$heteroaryl is selected from pyrrole, furan, thiophene, thiazole, pyrazole, oxazole, oxadiazole, thiadiazole, pyridine, pyrimidine, pyrazine, indole, benzothiophene, benzofuran, and imidazopyridine. In another embodiment is a compound of Formula (Ie), or a solvate, hydrate, tautomer, N-oxide, stereoisomer, or pharmaceutically acceptable salt thereof, wherein $R^4$ is

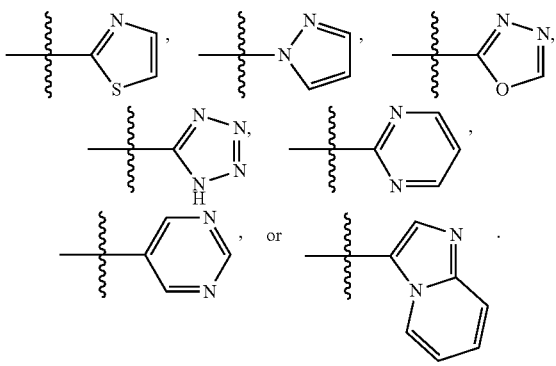

In another embodiment is a compound of Formula (Ie), or a solvate, hydrate, tautomer, N-oxide, stereoisomer, or pharmaceutically acceptable salt thereof, wherein $R^5$ is H, CN, halogen, $C_{1-6}$alkyl, $C_{1-6}$haloalkyl, or $C_{1-6}$haloalkoxy. In another embodiment is a compound of Formula (Ie), or a solvate, hydrate, tautomer, N-oxide, stereoisomer, or pharmaceutically acceptable salt thereof, wherein $R^5$ is H. In another embodiment is a compound of Formula (Ie), or a solvate, hydrate, tautomer, N-oxide, stereoisomer, or pharmaceutically acceptable salt thereof, wherein $R^5$ is —CN. In another embodiment is a compound of Formula (Ie), or a solvate, hydrate, tautomer, N-oxide, stereoisomer, or pharmaceutically acceptable salt thereof, wherein $R^5$ is halogen. In another embodiment is a compound of Formula (Ie), or a solvate, hydrate, tautomer, N-oxide, stereoisomer, or phar- maceutically acceptable salt thereof, wherein $R^5$ is —Cl. In another embodiment is a compound of Formula (Ie), or a solvate, hydrate, tautomer, N-oxide, stereoisomer, or pharmaceutically acceptable salt thereof, wherein $R^5$ is —F. In another embodiment is a compound of Formula (Ie), or a solvate, hydrate, tautomer, N-oxide, stereoisomer, or pharmaceutically acceptable salt thereof, wherein $R^5$ is $C_{1-6}$alkyl. In another embodiment is a compound of Formula (Ie), or a solvate, hydrate, tautomer, N-oxide, stereoisomer, or pharmaceutically acceptable salt thereof, wherein $R^5$ is —$CH_3$. In another embodiment is a compound of Formula (Ie), or a solvate, hydrate, tautomer, N-oxide, stereoisomer, or pharmaceutically acceptable salt thereof, wherein $R^5$ is $C_{1-6}$haloalkyl. In another embodiment is a compound of Formula (Ie), or a solvate, hydrate, tautomer, N-oxide, stereoisomer, or pharmaceutically acceptable salt thereof, wherein $R^5$ is —$CF_3$. In another embodiment is a compound of Formula (Ie), or a solvate, hydrate, tautomer, N-oxide, stereoisomer, or pharmaceutically acceptable salt thereof, wherein $R^5$ is $C_{1-6}$haloalkoxy. In another embodiment is a compound of Formula (Ie), or a solvate, hydrate, tautomer, N-oxide, stereoisomer, or pharmaceutically acceptable salt thereof, wherein $R^5$ is —$OCF_3$. In another embodiment is a compound of Formula (Ie), or a solvate, hydrate, tautomer, N-oxide, stereoisomer, or pharmaceutically acceptable salt thereof, wherein $R^6$ is H. In another embodiment is a compound of Formula (Ie), or a solvate, hydrate, tautomer, N-oxide, stereoisomer, or pharmaceutically acceptable salt thereof, wherein $R^6$ is halogen. In another embodiment is a compound of Formula (Ie), or a solvate, hydrate, tautomer, N-oxide, stereoisomer, or pharmaceutically acceptable salt thereof, wherein $R^6$ is —Cl. In another embodiment is a compound of Formula (Ie), or a solvate, hydrate, tautomer, N-oxide, stereoisomer, or pharmaceutically acceptable salt thereof, wherein $R^6$ is —F. In another embodiment is a compound of Formula (Ie), or a solvate, hydrate, tautomer, N-oxide, stereoisomer, or pharmaceutically acceptable salt thereof, wherein $R^6$ is $C_{1-6}$alkyl. In another embodiment is a compound of Formula (Ie), or a solvate, hydrate, tautomer, N-oxide, stereoisomer, or pharmaceutically acceptable salt thereof, wherein $R^6$ is —$CH_3$.

In another embodiment is a compound of Formula (I) having the structure of Formula (If):

Formula (If)

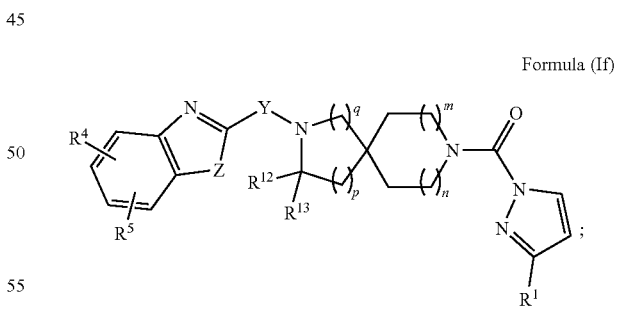

wherein:
$R^1$ is —$N(R^2)C(O)R^{15}$ or —$N(H)SO_2R^{15}$;
$R^2$ is H or $C_{1-6}$alkyl;
Y is —$CH_2$— or —C(O)—;
Z is —S—, —O—, or —$N(R^{20})$—;
$R^4$ is H, halogen, —$OR^7$, $C_{1-6}$alkyl, $C_{1-6}$alkyl-OH, $C_{2-6}$alkenyl, $C_{2-6}$alkynyl, $C_{1-6}$haloalkyl, —O—$C_{3-8}$cycloalkyl, —O—$C_{3-8}$cycloalkyl-OH, —N(H)—$C_{1-6}$alkyl-$CO_2$H, —$SO_2R^{17}$, —$CO_2R^8$, —$C(O)NR^8R^9$, $C_{3-8}$cycloalkyl, $C_{2-9}$heterocycloalkyl, —$C_{1-6}$alkyl-$C_{2-9}$ heterocycloalkyl, $C_{6-10}$aryl, $C_{1-9}$heteroaryl, wherein $C_{3-8}$cycloalkyl, $C_{2-9}$heterocycloalkyl, —$C_{1-6}$alkyl-$C_{2-9}$heterocycloalkyl, $C_{6-10}$aryl, $C_{1-9}$heteroaryl are optionally substituted with 1 or 2 $R^{14}$;

$R^5$ is H, —CN, halogen, $C_{1-6}$alkyl, $C_{1-6}$haloalkyl, $C_{1-6}$haloalkoxy, or phenyl;

$R^7$ is H, $C_{1-6}$alkyl, $C_{1-6}$haloalkyl, $C_{3-8}$cycloalkyl, $C_{2-9}$heterocycloalkyl, $C_{6-10}$aryl, or $C_{1-9}$heteroaryl, wherein $C_{2-9}$heterocycloalkyl, $C_{6-10}$aryl, or $C_{1-9}$heteroaryl are optionally substituted with 1 or 2 $R^{14}$;

each $R^8$ and each $R^9$ are independently selected from H and $C_{1-6}$alkyl; or $R^8$ and $R^9$ together with the nitrogen to which they are attached are combined to form a heterocycloalkyl ring;

$R^{12}$ is H, halogen, or $C_{1-6}$alkyl;

$R^{13}$ is H or $C_{1-6}$alkyl;

each $R^{14}$ is independently selected from halogen, —OH, oxo, $C_{1-6}$alkyl, $C_{1-6}$haloalkyl, $C_{1-6}$alkoxy, —$C_{1-6}$alkyl-OH, $C_{3-8}$cycloalkyl, —$CO_2R^8$, —$C(O)NR^8R^9$, —$C(O)$—$C_{1-6}$alkyl, —$C(O)$—$C_{1-6}$alkyl-OH, —$SO_2$—$C_{1-6}$alkyl, —$N(R^8)SO_2$—$C_{1-6}$alkyl, and —$N(R^8)C(O)$—$C_{1-6}$alkyl;

$R^{15}$ is $C_{1-6}$alkyl or $C_{3-8}$cycloalkyl;

$R^{17}$ is $C_{1-6}$alkyl or $C_{3-8}$cycloalkyl;

$R^{20}$ is H or $C_{1-6}$alkyl;

n is 0 or 1;

m is 0 or 1;

p is 0, 1, or 2; and q is 0, 1, or 2;

or a solvate, hydrate, tautomer, N-oxide, stereoisomer, or pharmaceutically acceptable salt thereof.

In another embodiment is a compound of Formula (If), or a solvate, hydrate, tautomer, N-oxide, stereoisomer, or pharmaceutically acceptable salt thereof, wherein $R^1$ is —$N(R^2)C(O)R^{15}$. In another embodiment is a compound of Formula (If), or a solvate, hydrate, tautomer, N-oxide, stereoisomer, or pharmaceutically acceptable salt thereof, wherein $R^1$ is —$N(R^2)C(O)R^{15}$ and $R^2$ is H. In another embodiment is a compound of Formula (If), or a solvate, hydrate, tautomer, N-oxide, stereoisomer, or pharmaceutically acceptable salt thereof, wherein $R^1$ is —$N(H)C(O)R^{15}$ and $R^{15}$ is $C_{1-6}$alkyl. In another embodiment is a compound of Formula (If), or a solvate, hydrate, tautomer, N-oxide, stereoisomer, or pharmaceutically acceptable salt thereof, wherein $R^1$ is —$N(H)C(O)R^{15}$ and $R^{15}$ is —$CH_3$. In another embodiment is a compound of Formula (If), or a solvate, hydrate, tautomer, N-oxide, stereoisomer, or pharmaceutically acceptable salt thereof, wherein $R^1$ is —$N(H)C(O)R^{15}$ and $R^{15}$ is $C_{3-8}$cycloalkyl. In another embodiment is a compound of Formula (If), or a solvate, hydrate, tautomer, N-oxide, stereoisomer, or pharmaceutically acceptable salt thereof, wherein $R^1$ is —$N(R^2)C(O)R^{15}$ and $R^2$ is $C_{1-6}$alkyl. In another embodiment is a compound of Formula (If), or a solvate, hydrate, tautomer, N-oxide, stereoisomer, or pharmaceutically acceptable salt thereof, wherein $R^1$ is —$N(R^2)C(O)R^{15}$ and $R^2$ is —$CH_3$. In another embodiment is a compound of Formula (If), or a solvate, hydrate, tautomer, N-oxide, stereoisomer, or pharmaceutically acceptable salt thereof, wherein $R^1$ is —$N(CH_3)C(O)R^{15}$ and $R^{15}$ is $C_{1-6}$alkyl. In another embodiment is a compound of Formula (If), or a solvate, hydrate, tautomer, N-oxide, stereoisomer, or pharmaceutically acceptable salt thereof, wherein $R^1$ is —$N(CH_3)C(O)R^{15}$ and $R^{15}$ is —$CH_3$. In another embodiment is a compound of Formula (If), or a solvate, hydrate, tautomer, N-oxide, stereoisomer, or pharmaceutically acceptable salt thereof, wherein $R^1$ is —$N(CH_3)C(O)R^{15}$ and $R^{15}$ is $C_{3-8}$cycloalkyl. In another embodiment is a compound of Formula (If), or a solvate, hydrate, tautomer, N-oxide, stereoisomer, or pharmaceutically acceptable salt thereof, wherein $R^1$ is —$N(H)SO_2R^{15}$. In another embodiment is a compound of Formula (If), or a solvate, hydrate, tautomer, N-oxide, stereoisomer, or pharmaceutically acceptable salt thereof, wherein $R^1$ is —$N(H)SO_2R^{15}$ and $R^{15}$ is $C_{1-6}$alkyl. In another embodiment is a compound of Formula (If), or a solvate, hydrate, tautomer, N-oxide, stereoisomer, or pharmaceutically acceptable salt thereof, wherein $R^1$ is —$N(H)SO_2R^{15}$ and $R^{15}$ is —$CH_3$. In another embodiment is a compound of Formula (If), or a solvate, hydrate, tautomer, N-oxide, stereoisomer, or pharmaceutically acceptable salt thereof, wherein $R^1$ is —$N(H)SO_2R^{15}$ and $R^{15}$ is $C_{3-8}$cycloalkyl.

In another embodiment is a compound of Formula (If), or a solvate, hydrate, tautomer, N-oxide, stereoisomer, or pharmaceutically acceptable salt thereof, wherein m is 1, n is 1, q is 1, and p is 1. In another embodiment is a compound of Formula (If), or a solvate, hydrate, tautomer, N-oxide, stereoisomer, or pharmaceutically acceptable salt thereof, wherein m is 0, n is 1, q is 2, and p is 1. In another embodiment is a compound of Formula (If), or a solvate, hydrate, tautomer, N-oxide, stereoisomer, or pharmaceutically acceptable salt thereof, wherein m is 1, n is 1, q is 0, and p is 2. In another embodiment is a compound of Formula (If), or a solvate, hydrate, tautomer, N-oxide, stereoisomer, or pharmaceutically acceptable salt thereof, wherein m is 1, n is 1, q is 1, and p is 0. In another embodiment is a compound of Formula (If), or a solvate, hydrate, tautomer, N-oxide, stereoisomer, or pharmaceutically acceptable salt thereof, wherein m is 0, n is 0, q is 2, and p is 1.

In another embodiment is a compound of Formula (If), or a solvate, hydrate, tautomer, N-oxide, stereoisomer, or pharmaceutically acceptable salt thereof, wherein Y is —$CH_2$—. In another embodiment is a compound of Formula (If), or a solvate, hydrate, tautomer, N-oxide, stereoisomer, or pharmaceutically acceptable salt thereof, wherein Y is —$C(O)$—.

In another embodiment is a compound of Formula (If), or a solvate, hydrate, tautomer, N-oxide, stereoisomer, or pharmaceutically acceptable salt thereof, wherein Z is —S—. In another embodiment is a compound of Formula (If), or a solvate, hydrate, tautomer, N-oxide, stereoisomer, or pharmaceutically acceptable salt thereof, wherein Z is —O—. In another embodiment is a compound of Formula (If), or a solvate, hydrate, tautomer, N-oxide, stereoisomer, or pharmaceutically acceptable salt thereof, wherein Z is —$N(R^{20})$—. In another embodiment is a compound of Formula (If), or a solvate, hydrate, tautomer, N-oxide, stereoisomer, or pharmaceutically acceptable salt thereof, wherein Z is —$N(H)$—. In another embodiment is a compound of Formula (If), or a solvate, hydrate, tautomer, N-oxide, stereoisomer, or pharmaceutically acceptable salt thereof, wherein Z is —$N(CH_3)$—.

In another embodiment is a compound of Formula (If), or a solvate, hydrate, tautomer, N-oxide, stereoisomer, or pharmaceutically acceptable salt thereof, wherein $R^{12}$ is H. In another embodiment is a compound of Formula (If), or a solvate, hydrate, tautomer, N-oxide, stereoisomer, or pharmaceutically acceptable salt thereof, wherein $R^{12}$ is $C_{1-6}$alkyl. In another embodiment is a compound of Formula (If), or a solvate, hydrate, tautomer, N-oxide, stereoisomer, or pharmaceutically acceptable salt thereof, wherein $R^{12}$ is —$CH_3$. In another embodiment is a compound of Formula (If), or a solvate, hydrate, tautomer, N-oxide, stereoisomer, or pharmaceutically acceptable salt thereof, wherein $R^{13}$ is H. In another embodiment is a compound of Formula (If), or a solvate, hydrate, tautomer, N-oxide, stereoisomer, or pharmaceutically acceptable salt thereof, wherein $R^{13}$ is $C_{1-6}$alkyl. In another embodiment is a compound of Formula (If), or a solvate, hydrate, tautomer, N-oxide, stereoisomer, or pharmaceutically acceptable salt thereof, wherein $R^{13}$ is —$CH_3$. In another embodiment is a compound of Formula (If), or a solvate, hydrate, tautomer, N-oxide, stereoisomer, or pharmaceutically acceptable salt thereof, wherein $R^{12}$ is H and $R^{13}$ is H. In another embodiment is a compound of Formula (If), or a solvate, hydrate, tautomer, N-oxide, stereoisomer, or pharmaceutically acceptable salt thereof, wherein $R^{12}$ is H and $R^{13}$ is $C_{1-6}$alkyl. In another embodiment is a compound of Formula (If), or a solvate, hydrate, tautomer, N-oxide, stereoisomer, or pharmaceutically acceptable salt thereof, wherein $R^{12}$ is H and $R^{13}$ is —$CH_3$. In another embodiment is a compound of Formula (If), or a solvate, hydrate, tautomer, N-oxide, stereoisomer, or pharmaceutically acceptable salt thereof, wherein $R^{12}$ is $C_{1-6}$alkyl and $R^{13}$ is H. In another embodiment is a compound of Formula (If), or a solvate, hydrate, tautomer, N-oxide, stereoisomer, or pharmaceutically acceptable salt thereof, wherein $R^{12}$ is —$CH_3$ and $R^{13}$ is H. In another embodiment is a compound of Formula (If), or a solvate, hydrate, tautomer, N-oxide, stereoisomer, or pharmaceutically acceptable salt thereof, wherein $R^{12}$ is $C_{1-6}$alkyl and $R^{13}$ is $C_{1-6}$alkyl. In another embodiment is a compound of Formula (If), or a solvate, hydrate, tautomer, N-oxide, stereoisomer, or pharmaceutically acceptable salt thereof, wherein $R^{12}$ is —$CH_3$ and $R^{13}$ is —$CH_3$.

In another embodiment is a compound of Formula (If), or a solvate, hydrate, tautomer, N-oxide, stereoisomer, or pharmaceutically acceptable salt thereof, wherein $R^4$ is halogen, —$OR^7$, $C_{1-6}$ alkyl-OH, —N(H)—$C_{1-6}$alkyl-$CO_2$H, $C_{2-6}$alkynyl, $C_{1-6}$haloalkyl, —$CO_2R^8$, —C(O)$NR^8R^9$, $C_{3-8}$cycloalkyl, $C_{2-9}$heterocycloalkyl, $C_{6-10}$aryl, or $C_{1-9}$heteroaryl, wherein $C_{3-8}$cycloalkyl, $C_{2-9}$heterocycloalkyl, $C_{6-10}$aryl, or $C_{1-9}$heteroaryl are optionally substituted with 1 or 2 $R^{14}$. In another embodiment is a compound of Formula (If), or a solvate, hydrate, tautomer, N-oxide, stereoisomer, or pharmaceutically acceptable salt thereof, wherein $R^4$ is halogen, —$OR^7$, —N(H)—$C_{1-6}$alkyl-$CO_2$H, $C_{1-6}$haloalkyl, —C(O)$NR^8R^9$, $C_{3-8}$cycloalkyl, $C_{2-9}$heterocycloalkyl, or $C_{1-9}$heteroaryl, wherein $C_{2-9}$heterocycloalkyl or $C_{1-9}$heteroaryl are optionally substituted with 1 or 2 $R^{14}$. In another embodiment is a compound of Formula (If), or a solvate, hydrate, tautomer, N-oxide, stereoisomer, or pharmaceutically acceptable salt thereof, wherein $R^4$ is halogen. In another embodiment is a compound of Formula (If), or a solvate, hydrate, tautomer, N-oxide, stereoisomer, or pharmaceutically acceptable salt thereof, wherein $R^4$ is —Cl. In another embodiment is a compound of Formula (If), or a solvate, hydrate, tautomer, N-oxide, stereoisomer, or pharmaceutically acceptable salt thereof, wherein $R^4$ is $C_{1-6}$haloalkyl. In another embodiment is a compound of Formula (If), or a solvate, hydrate, tautomer, N-oxide, stereoisomer, or pharmaceutically acceptable salt thereof, wherein $R^4$ is —$CF_3$. In another embodiment is a compound of Formula (If), or a solvate, hydrate, tautomer, N-oxide, stereoisomer, or pharmaceutically acceptable salt thereof, wherein $R^4$ is —N(H)—$C_{1-6}$alkyl-$CO_2$H. In another embodiment is a compound of Formula (If), or a solvate, hydrate, tautomer, N-oxide, stereoisomer, or pharmaceutically acceptable salt thereof, wherein $R^4$ is —N(H)$CH_2CO_2$H. In another embodiment is a compound of Formula (If), or a solvate, hydrate, tautomer, N-oxide, stereoisomer, or pharmaceutically acceptable salt thereof, wherein $R^4$ is —N(H)$CH_2CH_2CO_2$H. In another embodiment is a compound of Formula (If), or a solvate, hydrate, tautomer, N-oxide, stereoisomer, or pharmaceutically acceptable salt thereof, wherein $R^4$ is —N(H)$CH_2CH_2CH_2CO_2$H. In another embodiment is a compound of Formula (If), or a solvate, hydrate, tautomer, N-oxide, stereoisomer, or pharmaceutically acceptable salt thereof, wherein $R^4$ is —C(O)$NR^8R^9$. In another embodiment is a compound of Formula (If), or a solvate, hydrate, tautomer, N-oxide, stereoisomer, or pharmaceutically acceptable salt thereof, wherein $R^4$ is —C(O)$NH_2$. In another embodiment is a compound of Formula (If), or a solvate, hydrate, tautomer, N-oxide, stereoisomer, or pharmaceutically acceptable salt thereof, wherein $R^4$ is $C_{3-8}$cycloalkyl. In another embodiment is a compound of Formula (If), or a solvate, hydrate, tautomer, N-oxide, stereoisomer, or pharmaceutically acceptable salt thereof, wherein $R^4$ is —$OR^7$. In another embodiment is a compound of Formula (If), or a solvate, hydrate, tautomer, N-oxide, stereoisomer, or pharmaceutically acceptable salt thereof, wherein $R^4$ is —$OR^7$ and $R^7$ is unsubstituted $C_{3-8}$cycloalkyl or $C_{6-10}$aryl optionally substituted with halogen. In another embodiment is a compound of Formula (If), or a solvate, hydrate, tautomer, N-oxide, stereoisomer, or pharmaceutically acceptable salt thereof, wherein $R^4$ is —$OR^7$ and $R^7$ is unsubstituted $C_{3-8}$cycloalkyl. In another embodiment is a compound of Formula (If), or a solvate, hydrate, tautomer, N-oxide, stereoisomer, or pharmaceutically acceptable salt thereof, wherein $R^4$ is —$OR^7$ and $R^7$ is phenyl optionally substituted with halogen. In another embodiment is a compound of Formula (If), or a solvate, hydrate, tautomer, N-oxide, stereoisomer, or pharmaceutically acceptable salt thereof, wherein $R^4$ is —$OR^7$ and $R^7$ is phenyl substituted with halogen. In another embodiment is a compound of Formula (If), or a solvate, hydrate, tautomer, N-oxide, stereoisomer, or pharmaceutically acceptable salt thereof, wherein $R^4$ is —$OR^7$ and $R^7$ is phenyl substituted with —Cl. In another embodiment is a compound of Formula (If), or a solvate, hydrate, tautomer, N-oxide, stereoisomer, or pharmaceutically acceptable salt thereof, wherein $R^4$ is $C_{2-9}$heterocycloalkyl optionally substituted with 1 or 2 $R^{14}$. In another embodiment is a compound of Formula (If), or a solvate, hydrate, tautomer, N-oxide, stereoisomer, or pharmaceutically acceptable salt thereof, wherein $R^4$ is an unsubstituted $C_{2-9}$heterocycloalkyl. In another embodiment is a compound of Formula (If), or a solvate, hydrate, tautomer, N-oxide, stereoisomer, or pharmaceutically acceptable salt thereof, wherein $R^4$ is $C_{2-9}$heterocycloalkyl substituted with 1 or 2 $R^{14}$. In another embodiment is a compound of Formula (If), or a solvate, hydrate, tautomer, N-oxide, stereoisomer, or pharmaceutically acceptable salt thereof, wherein $R^4$ is $C_{4-5}$heterocycloalkyl optionally substituted with 1 or 2 $R^{14}$, wherein the $C_{4-5}$heterocycloalkyl is a monocyclic heterocycloalkyl selected from pyrrolidine, piperidine, piperazine, and morpholine. In another embodiment is a compound of Formula (If), or a solvate, hydrate, tautomer, N-oxide, stereoisomer, or pharmaceutically acceptable salt thereof, wherein $R^4$ is $C_{5-9}$heterocycloalkyl optionally substituted with 1 or 2 $R^{14}$, wherein the $C_{5-9}$heterocycloalkyl is a bicyclic heterocycloalkyl. In another embodiment is a compound of Formula (If), or a solvate, hydrate, tautomer, N-oxide, stereoisomer, or pharmaceutically acceptable salt thereof, wherein $R^4$ is $C_{5-9}$heterocycloalkyl optionally substituted with 1 or 2 $R^{14}$, wherein the $C_{5-9}$heterocycloalkyl is a spirocyclic heterocycloalkyl. In another embodiment is a compound of Formula (If), or a solvate, hydrate, tautomer, N-oxide, stereoisomer, or pharmaceutically acceptable salt thereof, wherein $R^4$ is

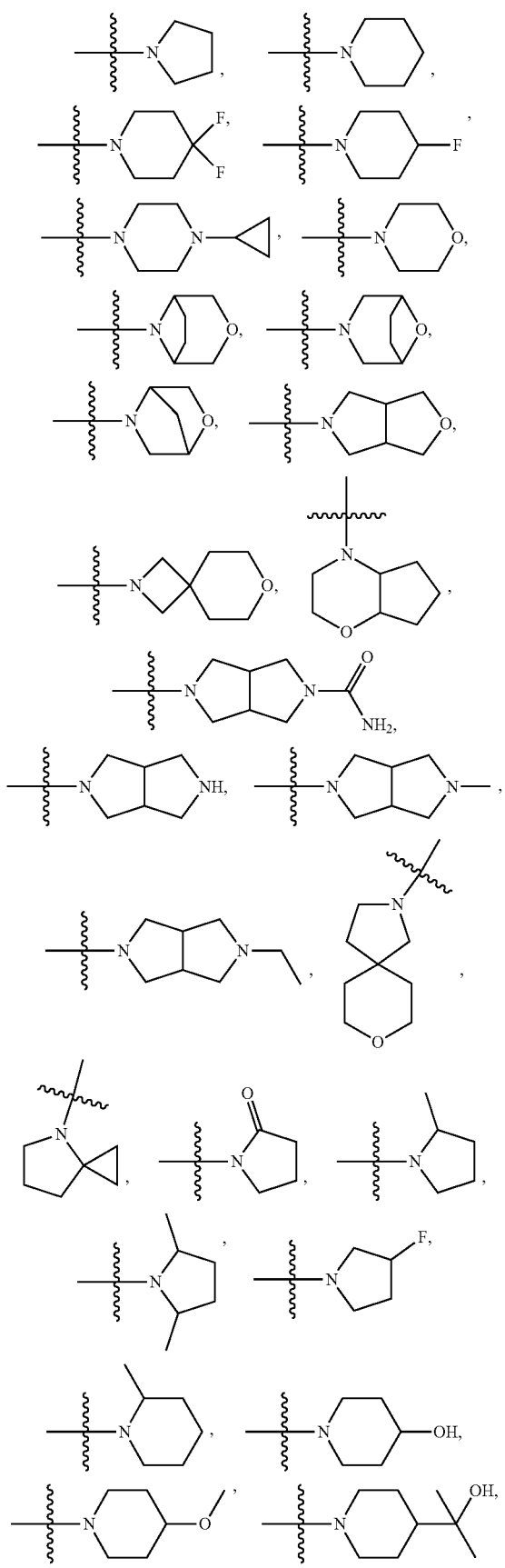
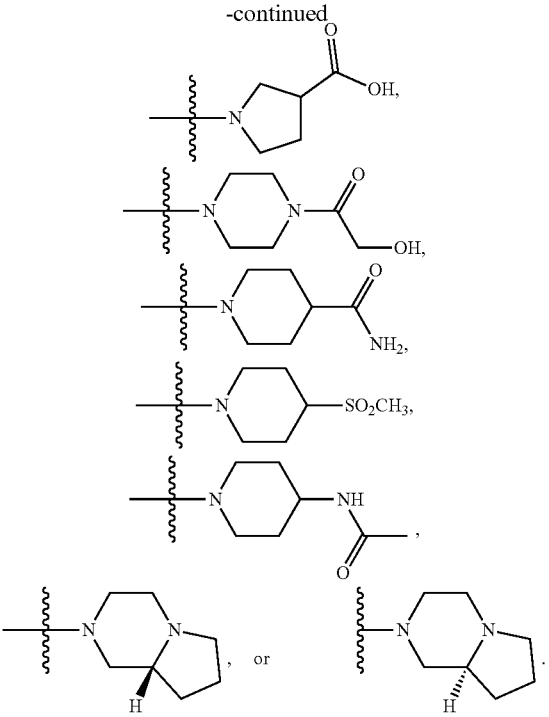

In another embodiment is a compound of Formula (If), or a solvate, hydrate, tautomer, N-oxide, stereoisomer, or pharmaceutically acceptable salt thereof, wherein $R^4$ is $C_{1-9}$heteroaryl optionally substituted with 1 or 2 $R^{14}$. In another embodiment is a compound of Formula (If), or a solvate, hydrate, tautomer, N-oxide, stereoisomer, or pharmaceutically acceptable salt thereof, wherein $R^4$ is an unsubstituted $C_{1-9}$heteroaryl. In another embodiment is a compound of Formula (If), or a solvate, hydrate, tautomer, N-oxide, stereoisomer, or pharmaceutically acceptable salt thereof, wherein $R^4$ is $C_{2-9}$heteroaryl substituted with 1 or 2 $R^{14}$. In another embodiment is a compound of Formula (If), or a solvate, hydrate, tautomer, N-oxide, stereoisomer, or pharmaceutically acceptable salt thereof, wherein $R^4$ is $C_{2-9}$heteroaryl optionally substituted with 1 or 2 $R^{14}$, wherein the $C_{2-9}$heteroaryl is selected from pyrrole, furan, thiophene, thiazole, pyrazole, oxazole, oxadiazole, thiadiazole, pyridine, pyrimidine, pyrazine, indole, benzothiophene, benzofuran, and imidazopyridine. In another embodiment is a compound of Formula (If), or a solvate, hydrate, tautomer, N-oxide, stereoisomer, or pharmaceutically acceptable salt thereof, wherein $R^4$ is

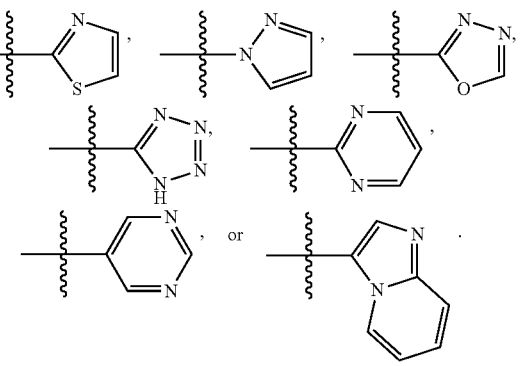

In another embodiment is a compound of Formula (If), or a solvate, hydrate, tautomer, N-oxide, stereoisomer, or pharmaceutically acceptable salt thereof, wherein $R^5$ is H, CN, halogen, $C_{1-6}$alkyl, $C_{1-6}$haloalkyl, or $C_{1-6}$haloalkoxy. In another embodiment is a compound of Formula (If), or a solvate, hydrate, tautomer, N-oxide, stereoisomer, or pharmaceutically acceptable salt thereof, wherein $R^5$ is H. In another embodiment is a compound of Formula (If), or a solvate, hydrate, tautomer, N-oxide, stereoisomer, or pharmaceutically acceptable salt thereof, wherein $R^5$ is —CN. In another embodiment is a compound of Formula (If), or a solvate, hydrate, tautomer, N-oxide, stereoisomer, or pharmaceutically acceptable salt thereof, wherein $R^5$ is halogen. In another embodiment is a compound of Formula (If), or a solvate, hydrate, tautomer, N-oxide, stereoisomer, or pharmaceutically acceptable salt thereof, wherein $R^5$ is —Cl. In another embodiment is a compound of Formula (If), or a solvate, hydrate, tautomer, N-oxide, stereoisomer, or pharmaceutically acceptable salt thereof, wherein $R^5$ is —F. In another embodiment is a compound of Formula (If), or a solvate, hydrate, tautomer, N-oxide, stereoisomer, or pharmaceutically acceptable salt thereof, wherein $R^5$ is $C_{1-6}$alkyl. In another embodiment is a compound of Formula (If), or a solvate, hydrate, tautomer, N-oxide, stereoisomer, or pharmaceutically acceptable salt thereof, wherein $R^5$ is —CH$_3$. In another embodiment is a compound of Formula (If), or a solvate, hydrate, tautomer, N-oxide, stereoisomer, or pharmaceutically acceptable salt thereof, wherein $R^5$ is $C_{1-6}$haloalkyl. In another embodiment is a compound of Formula (If), or a solvate, hydrate, tautomer, N-oxide, stereoisomer, or pharmaceutically acceptable salt thereof, wherein $R^5$ is —CF$_3$. In another embodiment is a compound of Formula (If), or a solvate, hydrate, tautomer, N-oxide, stereoisomer, or pharmaceutically acceptable salt thereof, wherein $R^5$ is $C_{1-6}$haloalkoxy. In another embodiment is a compound of Formula (If), or a solvate, hydrate, tautomer, N-oxide, stereoisomer, or pharmaceutically acceptable salt thereof, wherein $R^5$ is —OCF$_3$.

In another embodiment is a compound of Formula (I) having the structure of Formula (Ig):

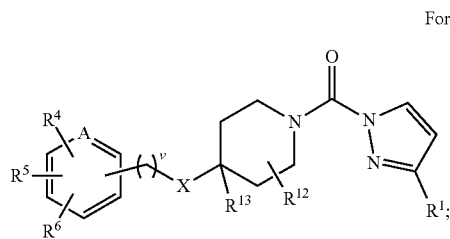

Formula (Ig)

wherein:
$R^1$ is —N($R^2$)C(O)$R^{15}$ or —N(H)SO$_2R^{15}$;
$R^2$ is H or $C_{1-6}$alkyl;
A is N or C(H);
X is —O—, —N($R^{16}$)—, or —CH$_2$N($R^{16}$)CH$_2$—;
$R^4$ is H, halogen, —OR$^7$, $C_{1-6}$alkyl, $C_{1-6}$alkyl-OH, $C_{2-6}$alkenyl, $C_{2-6}$alkynyl, $C_{1-6}$haloalkyl, —O—$C_{3-8}$cycloalkyl, —O—$C_{3-8}$cycloalkyl-OH, —N(H)—$C_{1-6}$alkyl-CO$_2$H, —SO$_2R^{17}$, —CO$_2R^8$, —C(O)NR$^8R^9$, $C_{3-8}$cycloalkyl, $C_{2-9}$heterocycloalkyl, —$C_{1-6}$alkyl-$C_{2-9}$heterocycloalkyl, $C_{6-10}$aryl, $C_{1-9}$heteroaryl, wherein $C_{3-8}$cycloalkyl, $C_{2-9}$heterocycloalkyl, —$C_{1-6}$alkyl-$C_{2-9}$heterocycloalkyl, $C_{6-10}$aryl, $C_{1-9}$heteroaryl are optionally substituted with 1 or 2 $R^{14}$;

$R^5$ is H, —CN, halogen, $C_{1-6}$alkyl, $C_{1-6}$haloalkyl, $C_{1-6}$haloalkoxy, or phenyl;
$R^6$ is H, halogen, or $C_{1-6}$alkyl;
$R^7$ is H, $C_{1-6}$alkyl, $C_{1-6}$haloalkyl, $C_{3-8}$cycloalkyl, $C_{2-9}$heterocycloalkyl, $C_{6-10}$aryl, or $C_{1-9}$heteroaryl, wherein $C_{2-9}$heterocycloalkyl, $C_{6-10}$aryl, or $C_{1-9}$heteroaryl are optionally substituted with 1 or 2 $R^{14}$;
each $R^8$ and each $R^9$ are independently selected from H and $C_{1-6}$alkyl; or $R^8$ and $R^9$ together with the nitrogen to which they are attached are combined to form a heterocycloalkyl ring;
$R^{12}$ is H, halogen, or $C_{1-6}$alkyl;
$R^{13}$ is H or $C_{1-6}$alkyl;
each $R^{14}$ is independently selected from halogen, —OH, oxo, $C_{1-6}$alkyl, $C_{1-6}$haloalkyl, $C_{1-6}$alkoxy, —$C_{1-6}$alkyl-OH, $C_{3-8}$cycloalkyl, —CO$_2R^8$, —C(O)NR$^8R^9$, —C(O)—$C_{1-6}$alkyl, —C(O)—$C_{1-6}$alkyl-OH, —SO$_2$—$C_{1-6}$alkyl, —N($R^8$)SO$_2$—$C_{1-6}$alkyl, and —N($R^8$)C(O)—$C_{1-6}$alkyl;
$R^{15}$ is $C_{1-6}$alkyl or $C_{3-8}$cycloalkyl;
$R^{16}$ is H, $C_{1-6}$alkyl, —C(O)—$C_{1-6}$alkyl, or —CH$_2$CO$_2$H;
$R^{17}$ is $C_{1-6}$alkyl or $C_{3-8}$cycloalkyl; and
v is 0 or 1;
or a solvate, hydrate, tautomer, N-oxide, stereoisomer, or pharmaceutically acceptable salt thereof.

In another embodiment is a compound of Formula (Ib), or a solvate, hydrate, tautomer, N-oxide, stereoisomer, or pharmaceutically acceptable salt thereof, having the structure

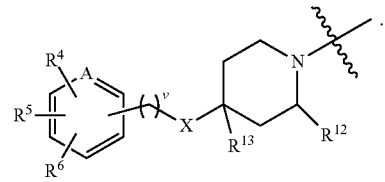

In another embodiment is a compound of Formula (Ib), or a solvate, hydrate, tautomer, N-oxide, stereoisomer, or pharmaceutically acceptable salt thereof, having the structure

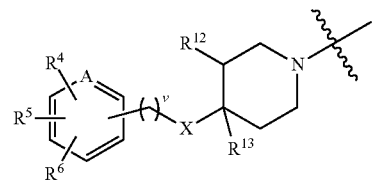

In another embodiment is a compound of Formula (Ig), or a solvate, hydrate, tautomer, N-oxide, stereoisomer, or pharmaceutically acceptable salt thereof, wherein $R^1$ is —N($R^2$)C(O)$R^{15}$. In another embodiment is a compound of Formula (Ig), or a solvate, hydrate, tautomer, N-oxide, stereoisomer, or pharmaceutically acceptable salt thereof, wherein $R^1$ is —N($R^2$)C(O)$R^{15}$ and $R^2$ is H. In another embodiment is a compound of Formula (Ig), or a solvate, hydrate, tautomer, N-oxide, stereoisomer, or pharmaceutically acceptable salt thereof, wherein $R^1$ is —N(H)C(O)$R^{15}$ and $R^{15}$ is $C_{1-6}$alkyl. In another embodiment is a compound of Formula (Ig), or a solvate, hydrate, tautomer, N-oxide, stereoisomer, or pharmaceutically acceptable salt thereof, wherein $R^1$ is —N(H)C(O)$R^{15}$ and $R^{15}$ is —CH$_3$. In another embodiment is a compound of Formula (Ig), or a solvate, hydrate, tautomer, N-oxide, stereoisomer, or pharmaceutically acceptable salt thereof, wherein $R^1$ is —N(H)C(O)$R^{15}$ and $R^{15}$ is $C_{3-8}$cycloalkyl. In another embodiment is a compound of Formula (Ig), or a solvate, hydrate, tautomer, N-oxide, stereoisomer, or pharmaceutically acceptable salt thereof, wherein $R^1$ is —N($R^2$)C(O)$R^{15}$ and $R^2$ is $C_{1-6}$alkyl. In another embodiment is a compound of Formula (Ig), or a solvate, hydrate, tautomer, N-oxide, stereoisomer, or pharmaceutically acceptable salt thereof, wherein $R^1$ is —N($R^2$)C(O)$R^{15}$ and $R^2$ is —CH$_3$. In another embodiment is a compound of Formula (Ig), or a solvate, hydrate, tautomer, N-oxide, stereoisomer, or pharmaceutically acceptable salt thereof, wherein $R^1$ is —N(CH$_3$)C(O)$R^{15}$ and $R^{15}$ is $C_{1-6}$alkyl. In another embodiment is a compound of Formula (Ig), or a solvate, hydrate, tautomer, N-oxide, stereoisomer, or pharmaceutically acceptable salt thereof, wherein $R^1$ is —N(CH$_3$)C(O)$R^{15}$ and $R^{15}$ is —CH$_3$. In another embodiment is a compound of Formula (Ig), or a solvate, hydrate, tautomer, N-oxide, stereoisomer, or pharmaceutically acceptable salt thereof, wherein $R^1$ is —N(CH$_3$)C(O)$R^{15}$ and $R^{15}$ is $C_{3-8}$cycloalkyl. In another embodiment is a compound of Formula (Ig), or a solvate, hydrate, tautomer, N-oxide, stereoisomer, or pharmaceutically acceptable salt thereof, wherein $R^1$ is —N(H)SO$_2$$R^{15}$. In another embodiment is a compound of Formula (Ig), or a solvate, hydrate, tautomer, N-oxide, stereoisomer, or pharmaceutically acceptable salt thereof, wherein $R^1$ is —N(H)SO$_2$$R^{15}$ and $R^{15}$ is $C_{1-6}$alkyl. In another embodiment is a compound of Formula (Ig), or a solvate, hydrate, tautomer, N-oxide, stereoisomer, or pharmaceutically acceptable salt thereof, wherein $R^1$ is —N(H)SO$_2$$R^{15}$ and $R^{15}$ is —CH$_3$. In another embodiment is a compound of Formula (Ig), or a solvate, hydrate, tautomer, N-oxide, stereoisomer, or pharmaceutically acceptable salt thereof, wherein $R^1$ is —N(H)SO$_2$$R^{15}$ and $R^{15}$ is $C_{3-8}$cycloalkyl.

In another embodiment is a compound of Formula (Ig), or a solvate, hydrate, tautomer, N-oxide, stereoisomer, or pharmaceutically acceptable salt thereof, wherein X is —O—. In another embodiment is a compound of Formula (Ig), or a solvate, hydrate, tautomer, N-oxide, stereoisomer, or pharmaceutically acceptable salt thereof, wherein X is —N($R^{16}$)—. In another embodiment is a compound of Formula (Ig), or a solvate, hydrate, tautomer, N-oxide, stereoisomer, or pharmaceutically acceptable salt thereof, wherein X is —N(H)—. In another embodiment is a compound of Formula (Ig), or a solvate, hydrate, tautomer, N-oxide, stereoisomer, or pharmaceutically acceptable salt thereof, wherein X is —N(CH$_3$)—. In another embodiment is a compound of Formula (Ig), or a solvate, hydrate, tautomer, N-oxide, stereoisomer, or pharmaceutically acceptable salt thereof, wherein X is —CH$_2$N($R^{16}$)CH$_2$—. In another embodiment is a compound of Formula (Ig), or a solvate, hydrate, tautomer, N-oxide, stereoisomer, or pharmaceutically acceptable salt thereof, wherein X is —CH$_2$N(H)CH$_2$—. In another embodiment is a compound of Formula (Ig), or a solvate, hydrate, tautomer, N-oxide, stereoisomer, or pharmaceutically acceptable salt thereof, wherein X is —CH$_2$N(CH$_3$)CH$_2$—.

In another embodiment is a compound of Formula (Ig), or a solvate, hydrate, tautomer, N-oxide, stereoisomer, or pharmaceutically acceptable salt thereof, wherein A is N. In another embodiment is a compound of Formula (Ig), or a solvate, hydrate, tautomer, N-oxide, stereoisomer, or pharmaceutically acceptable salt thereof, wherein A is C(H).

In another embodiment is a compound of Formula (Ig), or a solvate, hydrate, tautomer, N-oxide, stereoisomer, or pharmaceutically acceptable salt thereof, wherein v is 0. In another embodiment is a compound of Formula (Ig), or a solvate, hydrate, tautomer, N-oxide, stereoisomer, or pharmaceutically acceptable salt thereof, wherein v is 1.

In another embodiment is a compound of Formula (Ig), or a solvate, hydrate, tautomer, N-oxide, stereoisomer, or pharmaceutically acceptable salt thereof, wherein $R^4$ is halogen, —OR$^7$, $C_{1-6}$alkyl-OH, —N(H)—$C_{1-6}$alkyl-CO$_2$H, $C_{2-6}$alkynyl, $C_{1-6}$haloalkyl, —CO$_2$$R^8$, —C(O)NR$^8$$R^9$, $C_{3-8}$cycloalkyl, $C_{2-9}$heterocycloalkyl, $C_{6-10}$aryl, or $C_{1-9}$heteroaryl, wherein $C_{3-8}$cycloalkyl, $C_{2-9}$heterocycloalkyl, $C_{6-10}$aryl, or $C_{1-9}$heteroaryl are optionally substituted with 1 or 2 $R^{14}$. In another embodiment is a compound of Formula (Ig), or a solvate, hydrate, tautomer, N-oxide, stereoisomer, or pharmaceutically acceptable salt thereof, wherein $R^4$ is halogen, —OR$^7$, —N(H)—$C_{1-6}$alkyl-CO$_2$H, $C_{1-6}$haloalkyl, —C(O)NR$^8$$R^9$, $C_{3-8}$cycloalkyl, $C_{2-9}$heterocycloalkyl, or $C_{1-9}$heteroaryl, wherein $C_{2-9}$heterocycloalkyl or $C_{1-9}$heteroaryl are optionally substituted with 1 or 2 $R^{14}$. In another embodiment is a compound of Formula (Ig), or a solvate, hydrate, tautomer, N-oxide, stereoisomer, or pharmaceutically acceptable salt thereof, wherein $R^4$ is halogen. In another embodiment is a compound of Formula (Ig), or a solvate, hydrate, tautomer, N-oxide, stereoisomer, or pharmaceutically acceptable salt thereof, wherein $R^4$ is —Cl. In another embodiment is a compound of Formula (Ig), or a solvate, hydrate, tautomer, N-oxide, stereoisomer, or pharmaceutically acceptable salt thereof, wherein $R^4$ is $C_{1-6}$haloalkyl. In another embodiment is a compound of Formula (Ig), or a solvate, hydrate, tautomer, N-oxide, stereoisomer, or pharmaceutically acceptable salt thereof, wherein $R^4$ is —CF$_3$. In another embodiment is a compound of Formula (Ig), or a solvate, hydrate, tautomer, N-oxide, stereoisomer, or pharmaceutically acceptable salt thereof, wherein $R^4$ is —N(H)—$C_{1-6}$alkyl-CO$_2$H. In another embodiment is a compound of Formula (Ig), or a solvate, hydrate, tautomer, N-oxide, stereoisomer, or pharmaceutically acceptable salt thereof, wherein $R^4$ is —N(H)CH$_2$CO$_2$H. In another embodiment is a compound of Formula (Ig), or a solvate, hydrate, tautomer, N-oxide, stereoisomer, or pharmaceutically acceptable salt thereof, wherein $R^4$ is —N(H)CH$_2$CH$_2$CO$_2$H. In another embodiment is a compound of Formula (Ig), or a solvate, hydrate, tautomer, N-oxide, stereoisomer, or pharmaceutically acceptable salt thereof, wherein $R^4$ is —N(H)CH$_2$CH$_2$CH$_2$CO$_2$H. In another embodiment is a compound of Formula (Ig), or a solvate, hydrate, tautomer, N-oxide, stereoisomer, or pharmaceutically acceptable salt thereof, wherein $R^4$ is —C(O)NR$^8$$R^9$. In another embodiment is a compound of Formula (Ig), or a solvate, hydrate, tautomer, N-oxide, stereoisomer, or pharmaceutically acceptable salt thereof, wherein $R^4$ is —C(O)NH$_2$. In another embodiment is a compound of Formula (Ig), or a solvate, hydrate, tautomer, N-oxide, stereoisomer, or pharmaceutically acceptable salt thereof, wherein $R^4$ is $C_{3-8}$cycloalkyl. In another embodiment is a compound of Formula (Ig), or a solvate, hydrate, tautomer, N-oxide, stereoisomer, or pharmaceutically acceptable salt thereof, wherein $R^4$ is —OR$^7$. In another embodiment is a compound of Formula (Ig), or a solvate, hydrate, tautomer, N-oxide, stereoisomer, or pharmaceutically acceptable salt thereof, wherein $R^4$ is —OR$^7$ and $R^7$ is unsubstituted $C_{3-8}$cycloalkyl or $C_{6-10}$aryl optionally substituted with halogen. In another embodiment is a compound of Formula (Ig), or a solvate, hydrate, tautomer, N-oxide, stereoisomer, or pharmaceutically acceptable salt thereof, wherein $R^4$ is —OR$^7$ and $R^7$ is unsubstituted $C_{3-8}$cycloalkyl. In another embodiment is a compound of Formula (Ig), or a solvate, hydrate, tautomer, N-oxide, stereoisomer, or pharmaceutically acceptable salt thereof, wherein $R^4$ is —$OR^7$ and $R^7$ is phenyl optionally substituted with halogen. In another embodiment is a compound of Formula (Ig), or a solvate, hydrate, tautomer, N-oxide, stereoisomer, or pharmaceutically acceptable salt thereof, wherein $R^4$ is —$OR^7$ and $R^7$ is phenyl substituted with halogen. In another embodiment is a compound of Formula (Ig), or a solvate, hydrate, tautomer, N-oxide, stereoisomer, or pharmaceutically acceptable salt thereof, wherein $R^4$ is —$OR^7$ and $R^7$ is phenyl substituted with —Cl. In another embodiment is a compound of Formula (Ig), or a solvate, hydrate, tautomer, N-oxide, stereoisomer, or pharmaceutically acceptable salt thereof, wherein $R^4$ is $C_{2-9}$heterocycloalkyl optionally substituted with 1 or 2 $R^{14}$. In another embodiment is a compound of Formula (Ig), or a solvate, hydrate, tautomer, N-oxide, stereoisomer, or pharmaceutically acceptable salt thereof, wherein $R^4$ is an unsubstituted $C_{2-9}$heterocycloalkyl. In another embodiment is a compound of Formula (Ig), or a solvate, hydrate, tautomer, N-oxide, stereoisomer, or pharmaceutically acceptable salt thereof, wherein $R^4$ is $C_{2-9}$heterocycloalkyl substituted with 1 or 2 $R^{14}$. In another embodiment is a compound of Formula (Ig), or a solvate, hydrate, tautomer, N-oxide, stereoisomer, or pharmaceutically acceptable salt thereof, wherein $R^4$ is $C_{4-5}$heterocycloalkyl optionally substituted with 1 or 2 $R^{14}$, wherein the $C_{4-5}$heterocycloalkyl is a monocyclic heterocycloalkyl selected from pyrrolidine, piperidine, piperazine, and morpholine. In another embodiment is a compound of Formula (Ig), or a solvate, hydrate, tautomer, N-oxide, stereoisomer, or pharmaceutically acceptable salt thereof, wherein $R^4$ is $C_{5-9}$heterocycloalkyl optionally substituted with 1 or 2 $R^{14}$, wherein the $C_{5-9}$heterocycloalkyl is a bicyclic heterocycloalkyl. In another embodiment is a compound of Formula (Ig), or a solvate, hydrate, tautomer, N-oxide, stereoisomer, or pharmaceutically acceptable salt thereof, wherein $R^4$ is $C_{5-9}$heterocycloalkyl optionally substituted with 1 or 2 $R^{14}$, wherein the $C_{5-9}$heterocycloalkyl is a spirocyclic heterocycloalkyl. In another embodiment is a compound of Formula (Ig), or a solvate, hydrate, tautomer, N-oxide, stereoisomer, or pharmaceutically acceptable salt thereof, wherein $R^4$ is

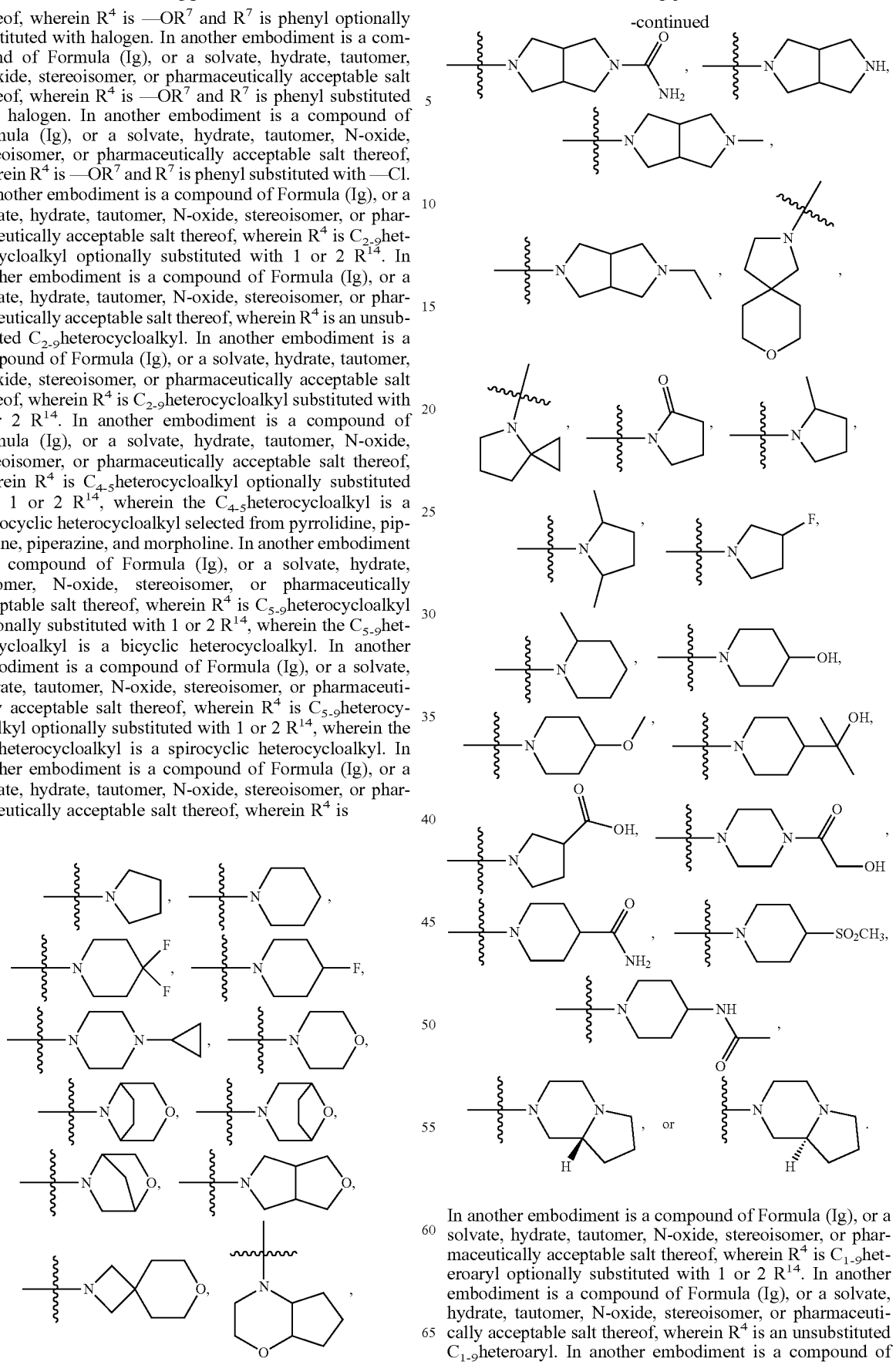

In another embodiment is a compound of Formula (Ig), or a solvate, hydrate, tautomer, N-oxide, stereoisomer, or pharmaceutically acceptable salt thereof, wherein $R^4$ is $C_{1-9}$heteroaryl optionally substituted with 1 or 2 $R^{14}$. In another embodiment is a compound of Formula (Ig), or a solvate, hydrate, tautomer, N-oxide, stereoisomer, or pharmaceutically acceptable salt thereof, wherein $R^4$ is an unsubstituted $C_{1-9}$heteroaryl. In another embodiment is a compound of Formula (Ig), or a solvate, hydrate, tautomer, N-oxide, stereoisomer, or pharmaceutically acceptable salt thereof, wherein $R^4$ is $C_{2-9}$heteroaryl substituted with 1 or 2 $R^{14}$. In another embodiment is a compound of Formula (Ig), or a solvate, hydrate, tautomer, N-oxide, stereoisomer, or pharmaceutically acceptable salt thereof, wherein $R^4$ is $C_{2-9}$heteroaryl optionally substituted with 1 or 2 $R^{14}$, wherein the $C_{2-9}$heteroaryl is selected from pyrrole, furan, thiophene, thiazole, pyrazole, oxazole, oxadiazole, thiadiazole, pyridine, pyrimidine, pyrazine, indole, benzothiophene, benzofuran, and imidazopyridine. In another embodiment is a compound of Formula (Ig), or a solvate, hydrate, tautomer, N-oxide, stereoisomer, or pharmaceutically acceptable salt thereof, wherein $R^4$ is

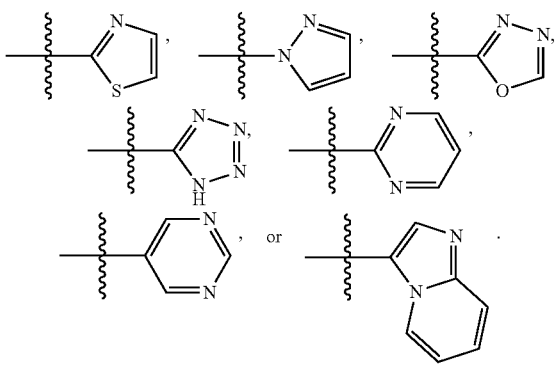

In another embodiment is a compound of Formula (Ig), or a solvate, hydrate, tautomer, N-oxide, stereoisomer, or pharmaceutically acceptable salt thereof, wherein $R^5$ is H, CN, halogen, $C_{1-6}$alkyl, $C_{1-6}$haloalkyl, or $C_{1-6}$haloalkoxy. In another embodiment is a compound of Formula (Ig), or a solvate, hydrate, tautomer, N-oxide, stereoisomer, or pharmaceutically acceptable salt thereof, wherein $R^5$ is H. In another embodiment is a compound of Formula (Ig), or a solvate, hydrate, tautomer, N-oxide, stereoisomer, or pharmaceutically acceptable salt thereof, wherein $R^5$ is —CN. In another embodiment is a compound of Formula (Ig), or a solvate, hydrate, tautomer, N-oxide, stereoisomer, or pharmaceutically acceptable salt thereof, wherein $R^5$ is halogen. In another embodiment is a compound of Formula (Ig), or a solvate, hydrate, tautomer, N-oxide, stereoisomer, or pharmaceutically acceptable salt thereof, wherein $R^5$ is —Cl. In another embodiment is a compound of Formula (Ig), or a solvate, hydrate, tautomer, N-oxide, stereoisomer, or pharmaceutically acceptable salt thereof, wherein $R^5$ is —F. In another embodiment is a compound of Formula (Ig), or a solvate, hydrate, tautomer, N-oxide, stereoisomer, or pharmaceutically acceptable salt thereof, wherein $R^5$ is $C_{1-6}$alkyl. In another embodiment is a compound of Formula (Ig), or a solvate, hydrate, tautomer, N-oxide, stereoisomer, or pharmaceutically acceptable salt thereof, wherein $R^5$ is —CH$_3$. In another embodiment is a compound of Formula (Ig), or a solvate, hydrate, tautomer, N-oxide, stereoisomer, or pharmaceutically acceptable salt thereof, wherein $R^5$ is $C_{1-6}$haloalkyl. In another embodiment is a compound of Formula (Ig), or a solvate, hydrate, tautomer, N-oxide, stereoisomer, or pharmaceutically acceptable salt thereof, wherein $R^5$ is —CF$_3$. In another embodiment is a compound of Formula (Ig), or a solvate, hydrate, tautomer, N-oxide, stereoisomer, or pharmaceutically acceptable salt thereof, wherein $R^5$ is $C_{1-6}$haloalkoxy. In another embodiment is a compound of Formula (Ig), or a solvate, hydrate, tautomer, N-oxide, stereoisomer, or pharmaceutically acceptable salt thereof, wherein $R^5$ is —OCF$_3$. In another embodiment is a compound of Formula (Ig), or a solvate, hydrate, tautomer, N-oxide, stereoisomer, or pharmaceutically acceptable salt thereof, wherein $R^6$ is H. In another embodiment is a compound of Formula (Ig), or a solvate, hydrate, tautomer, N-oxide, stereoisomer, or pharmaceutically acceptable salt thereof, wherein $R^6$ is halogen. In another embodiment is a compound of Formula (Ig), or a solvate, hydrate, tautomer, N-oxide, stereoisomer, or pharmaceutically acceptable salt thereof, wherein $R^6$ is —Cl. In another embodiment is a compound of Formula (Ig), or a solvate, hydrate, tautomer, N-oxide, stereoisomer, or pharmaceutically acceptable salt thereof, wherein $R^6$ is —F. In another embodiment is a compound of Formula (Ig), or a solvate, hydrate, tautomer, N-oxide, stereoisomer, or pharmaceutically acceptable salt thereof, wherein $R^6$ is $C_{1-6}$alkyl. In another embodiment is a compound of Formula (Ig), or a solvate, hydrate, tautomer, N-oxide, stereoisomer, or pharmaceutically acceptable salt thereof, wherein $R^6$ is —CH$_3$.

In another embodiment is a compound of Formula (Ig), or a solvate, hydrate, tautomer, N-oxide, stereoisomer, or pharmaceutically acceptable salt thereof, wherein $R^{12}$ is H. In another embodiment is a compound of Formula (Ig), or a solvate, hydrate, tautomer, N-oxide, stereoisomer, or pharmaceutically acceptable salt thereof, wherein $R^{12}$ is $C_{1-6}$alkyl. In another embodiment is a compound of Formula (Ig), or a solvate, hydrate, tautomer, N-oxide, stereoisomer, or pharmaceutically acceptable salt thereof, wherein $R^{12}$ is —CH$_3$. In another embodiment is a compound of Formula (Ig), or a solvate, hydrate, tautomer, N-oxide, stereoisomer, or pharmaceutically acceptable salt thereof, wherein $R^{13}$ is H. In another embodiment is a compound of Formula (Ig), or a solvate, hydrate, tautomer, N-oxide, stereoisomer, or pharmaceutically acceptable salt thereof, wherein $R^{13}$ is $C_{1-6}$alkyl. In another embodiment is a compound of Formula (Ig), or a solvate, hydrate, tautomer, N-oxide, stereoisomer, or pharmaceutically acceptable salt thereof, wherein $R^{13}$ is —CH$_3$. In another embodiment is a compound of Formula (Ig), or a solvate, hydrate, tautomer, N-oxide, stereoisomer, or pharmaceutically acceptable salt thereof, wherein $R^{12}$ is H and $R^{13}$ is H. In another embodiment is a compound of Formula (Ig), or a solvate, hydrate, tautomer, N-oxide, stereoisomer, or pharmaceutically acceptable salt thereof, wherein $R^{12}$ is H and $R^{13}$ is $C_{1-6}$alkyl. In another embodiment is a compound of Formula (Ig), or a solvate, hydrate, tautomer, N-oxide, stereoisomer, or pharmaceutically acceptable salt thereof, wherein $R^{12}$ is H and $R^{13}$ is —CH$_3$. In another embodiment is a compound of Formula (Ig), or a solvate, hydrate, tautomer, N-oxide, stereoisomer, or pharmaceutically acceptable salt thereof, wherein $R^{12}$ is $C_{1-6}$alkyl and $R^{13}$ is H. In another embodiment is a compound of Formula (Ig), or a solvate, hydrate, tautomer, N-oxide, stereoisomer, or pharmaceutically acceptable salt thereof, wherein $R^{12}$ is —CH$_3$ and $R^{13}$ is H. In another embodiment is a compound of Formula (Ig), or a solvate, hydrate, tautomer, N-oxide, stereoisomer, or pharmaceutically acceptable salt thereof, wherein $R^{12}$ is $C_{1-6}$alkyl and $R^{13}$ is $C_{1-6}$alkyl. In another embodiment is a compound of Formula (Ig), or a solvate, hydrate, tautomer, N-oxide, stereoisomer, or pharmaceutically acceptable salt thereof, wherein $R^{12}$ is —CH$_3$ and $R^{13}$ is —CH$_3$.

In another embodiment is a compound of Formula (I) having the structure of Formula (Ih):

Formula (Ih)

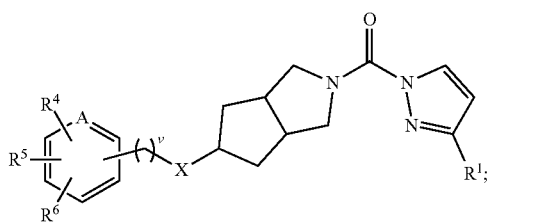

wherein:
R$^1$ is —N(R$^2$)C(O)R$^{15}$ or —N(H)SO$_2$R$^{15}$;
R$^2$ is H or C$_{1-6}$alkyl;
A is N or C(H);
X is —O—, —N(R$^{16}$)—, or —CH$_2$N(R$^{16}$)CH$_2$—;
R$^4$ is H, halogen, —OR$^7$, C$_{1-6}$alkyl, C$_{1-6}$alkyl-OH, C$_{2-6}$alkenyl, C$_{2-6}$alkynyl, C$_{1-6}$haloalkyl, —O—C$_{3-8}$cycloalkyl, —O—C$_{3-8}$cycloalkyl-OH, —N(H)—C$_{1-6}$alkyl-CO$_2$H, —SO$_2$R$^{17}$, —CO$_2$R$^8$, —C(O)NR$^8$R$^9$, C$_{3-8}$cycloalkyl, C$_{2-9}$heterocycloalkyl, —C$_{1-6}$alkyl-C$_{2-9}$heterocycloalkyl, C$_{6-10}$aryl, C$_{1-9}$heteroaryl, wherein C$_{3-8}$cycloalkyl, C$_{2-9}$heterocycloalkyl, —C$_{1-6}$alkyl-C$_{2-9}$heterocycloalkyl, C$_{6-10}$aryl, C$_{1-9}$heteroaryl are optionally substituted with 1 or 2 R$^{14}$;
R$^5$ is H, —CN, halogen, C$_{1-6}$alkyl, C$_{1-6}$haloalkyl, C$_{1-6}$haloalkoxy, or phenyl; R$^6$ is H, halogen, or C$_{1-6}$alkyl;
R$^7$ is H, C$_{1-6}$alkyl, C$_{1-6}$haloalkyl, C$_{3-8}$cycloalkyl, C$_{2-9}$heterocycloalkyl, C$_{6-10}$aryl, or C$_{1-9}$heteroaryl, wherein C$_{2-9}$heterocycloalkyl, C$_{6-10}$aryl, or C$_{1-9}$heteroaryl are optionally substituted with 1 or 2 R$^4$;
each R$^8$ and each R$^9$ are independently selected from H and C$_{1-6}$alkyl; or R$^8$ and R$^9$ together with the nitrogen to which they are attached are combined to form a heterocycloalkyl ring;
each R$^{14}$ is independently selected from halogen, —OH, oxo, C$_{1-6}$alkyl, C$_{1-6}$haloalkyl, C$_{1-6}$alkoxy, —C$_{1-6}$alkyl-OH, C$_{3-8}$cycloalkyl, —CO$_2$R$^8$, —C(O)NR$^8$R$^9$, —C(O)—C$_{1-6}$alkyl, —C(O)—C$_{1-6}$alkyl-OH, —SO$_2$—C$_{1-6}$alkyl, —N(R$^8$)SO$_2$—C$_{1-6}$alkyl, and —N(R$^8$)C(O)—C$_{1-6}$alkyl;
R$^{15}$ is C$_{1-6}$alkyl or C$_{3-8}$cycloalkyl;
R$^{16}$ is H, C$_{1-6}$alkyl, —C(O)—C$_{1-6}$alkyl, or —CH$_2$CO$_2$H;
R$^{17}$ is C$_{1-6}$alkyl or C$_{3-8}$cycloalkyl; and
v is 0 or 1;
or a solvate, hydrate, tautomer, N-oxide, stereoisomer, or pharmaceutically acceptable salt thereof.

In another embodiment is a compound of Formula (Ih), or a solvate, hydrate, tautomer, N-oxide, stereoisomer, or pharmaceutically acceptable salt thereof, wherein R$^1$ is —N(R$^2$)C(O)R$^{15}$. In another embodiment is a compound of Formula (Ih), or a solvate, hydrate, tautomer, N-oxide, stereoisomer, or pharmaceutically acceptable salt thereof, wherein R$^1$ is —N(R$^2$)C(O)R$^{15}$ and R$^2$ is H. In another embodiment is a compound of Formula (Ih), or a solvate, hydrate, tautomer, N-oxide, stereoisomer, or pharmaceutically acceptable salt thereof, wherein R$^1$ is —N(H)C(O)R$^{15}$ and R$^{15}$ is C$_{1-6}$alkyl. In another embodiment is a compound of Formula (Ih), or a solvate, hydrate, tautomer, N-oxide, stereoisomer, or pharmaceutically acceptable salt thereof, wherein R$^1$ is —N(H)C(O)R$^{15}$ and R$^{15}$ is —CH$_3$. In another embodiment is a compound of Formula (Ih), or a solvate, hydrate, tautomer, N-oxide, stereoisomer, or pharmaceutically acceptable salt thereof, wherein R$^1$ is —N(H)C(O)R$^{15}$ and R$^{15}$ is C$_{3-8}$cycloalkyl. In another embodiment is a compound of Formula (Ih), or a solvate, hydrate, tautomer, N-oxide, stereoisomer, or pharmaceutically acceptable salt thereof, wherein R$^1$ is —N(R$^2$)C(O)R$^{15}$ and R$^2$ is C$_{1-6}$alkyl. In another embodiment is a compound of Formula (Ih), or a solvate, hydrate, tautomer, N-oxide, stereoisomer, or pharmaceutically acceptable salt thereof, wherein R$^1$ is —N(R$^2$)C(O)R$^{15}$ and R$^2$ is —CH$_3$. In another embodiment is a compound of Formula (Ih), or a solvate, hydrate, tautomer, N-oxide, stereoisomer, or pharmaceutically acceptable salt thereof, wherein R$^1$ is —N(CH$_3$)C(O)R$^{15}$ and R$^{15}$ is C$_{1-6}$alkyl. In another embodiment is a compound of Formula (Ih), or a solvate, hydrate, tautomer, N-oxide, stereoisomer, or pharmaceutically acceptable salt thereof, wherein R$^1$ is —N(CH$_3$)C(O)R$^{15}$ and R$^{15}$ is —CH$_3$. In another embodiment is a compound of Formula (Ih), or a solvate, hydrate, tautomer, N-oxide, stereoisomer, or pharmaceutically acceptable salt thereof, wherein R$^1$ is —N(CH$_3$)C(O)R$^{15}$ and R$^{15}$ is C$_{3-8}$cycloalkyl. In another embodiment is a compound of Formula (Ih), or a solvate, hydrate, tautomer, N-oxide, stereoisomer, or pharmaceutically acceptable salt thereof, wherein R$^1$ is —N(H)SO$_2$R$^{15}$. In another embodiment is a compound of Formula (Ih), or a solvate, hydrate, tautomer, N-oxide, stereoisomer, or pharmaceutically acceptable salt thereof, wherein R$^1$ is —N(H)SO$_2$R$^{15}$ and R$^{15}$ is C$_{1-6}$alkyl. In another embodiment is a compound of Formula (Ih), or a solvate, hydrate, tautomer, N-oxide, stereoisomer, or pharmaceutically acceptable salt thereof, wherein R$^1$ is —N(H)SO$_2$R$^{15}$ and R$^{15}$ is —CH$_3$. In another embodiment is a compound of Formula (Ih), or a solvate, hydrate, tautomer, N-oxide, stereoisomer, or pharmaceutically acceptable salt thereof, wherein R$^1$ is —N(H)SO$_2$R$^{15}$ and R$^{15}$ is C$_{3-8}$cycloalkyl.

In another embodiment is a compound of Formula (Ih), or a solvate, hydrate, tautomer, N-oxide, stereoisomer, or pharmaceutically acceptable salt thereof, wherein X is —O—. In another embodiment is a compound of Formula (Ih), or a solvate, hydrate, tautomer, N-oxide, stereoisomer, or pharmaceutically acceptable salt thereof, wherein X is —N(R$^{16}$)—. In another embodiment is a compound of Formula (Ih), or a solvate, hydrate, tautomer, N-oxide, stereoisomer, or pharmaceutically acceptable salt thereof, wherein X is —N(H)—. In another embodiment is a compound of Formula (Ih), or a solvate, hydrate, tautomer, N-oxide, stereoisomer, or pharmaceutically acceptable salt thereof, wherein X is —N(CH$_3$)—. In another embodiment is a compound of Formula (Ih), or a solvate, hydrate, tautomer, N-oxide, stereoisomer, or pharmaceutically acceptable salt thereof, wherein X is —CH$_2$N(R$^{16}$)CH$_2$—. In another embodiment is a compound of Formula (Ih), or a solvate, hydrate, tautomer, N-oxide, stereoisomer, or pharmaceutically acceptable salt thereof, wherein X is —CH$_2$N(H)CH$_2$—. In another embodiment is a compound of Formula (Ih), or a solvate, hydrate, tautomer, N-oxide, stereoisomer, or pharmaceutically acceptable salt thereof, wherein X is —CH$_2$N(CH$_3$)CH$_2$—.

In another embodiment is a compound of Formula (Ih), or a solvate, hydrate, tautomer, N-oxide, stereoisomer, or pharmaceutically acceptable salt thereof, wherein A is N. In another embodiment is a compound of Formula (Ih), or a solvate, hydrate, tautomer, N-oxide, stereoisomer, or pharmaceutically acceptable salt thereof, wherein A is C(H).

In another embodiment is a compound of Formula (Ih), or a solvate, hydrate, tautomer, N-oxide, stereoisomer, or pharmaceutically acceptable salt thereof, wherein v is 0. In another embodiment is a compound of Formula (Ih), or a solvate, hydrate, tautomer, N-oxide, stereoisomer, or pharmaceutically acceptable salt thereof, wherein v is 1.

In another embodiment is a compound of Formula (Ih), or a solvate, hydrate, tautomer, N-oxide, stereoisomer, or pharmaceutically acceptable salt thereof, wherein $R^4$ is halogen, —$OR^7$, $C_{1-6}$alkyl-OH, —N(H)—$C_{1-6}$alkyl-$CO_2$H, $C_{2-6}$alkynyl, $C_{1-6}$haloalkyl, —$CO_2R^8$, —C(O)$NR^8R^9$, $C_{3-8}$cycloalkyl, $C_{2-9}$heterocycloalkyl, $C_{6-10}$aryl, or $C_{1-9}$heteroaryl, wherein $C_{3-8}$cycloalkyl, $C_{2-9}$heterocycloalkyl, $C_{6-10}$aryl, or $C_{1-9}$heteroaryl are optionally substituted with 1 or 2 $R^{14}$. In another embodiment is a compound of Formula (Ih), or a solvate, hydrate, tautomer, N-oxide, stereoisomer, or pharmaceutically acceptable salt thereof, wherein $R^4$ is halogen, —$OR^7$, —N(H)—$C_{1-6}$alkyl-$CO_2$H, $C_{1-6}$haloalkyl, —C(O)$NR^8R^9$, $C_{3-8}$cycloalkyl, $C_{2-9}$heterocycloalkyl, or $C_{1-9}$heteroaryl, wherein $C_{2-9}$heterocycloalkyl or $C_{1-9}$heteroaryl are optionally substituted with 1 or 2 $R^{14}$. In another embodiment is a compound of Formula (Ih), or a solvate, hydrate, tautomer, N-oxide, stereoisomer, or pharmaceutically acceptable salt thereof, wherein $R^4$ is halogen. In another embodiment is a compound of Formula (Ih), or a solvate, hydrate, tautomer, N-oxide, stereoisomer, or pharmaceutically acceptable salt thereof, wherein $R^4$ is —Cl. In another embodiment is a compound of Formula (Ih), or a solvate, hydrate, tautomer, N-oxide, stereoisomer, or pharmaceutically acceptable salt thereof, wherein $R^4$ is $C_{1-6}$haloalkyl. In another embodiment is a compound of Formula (Ih), or a solvate, hydrate, tautomer, N-oxide, stereoisomer, or pharmaceutically acceptable salt thereof, wherein $R^4$ is —$CF_3$. In another embodiment is a compound of Formula (Ih), or a solvate, hydrate, tautomer, N-oxide, stereoisomer, or pharmaceutically acceptable salt thereof, wherein $R^4$ is —N(H)—$C_{1-6}$alkyl-$CO_2$H. In another embodiment is a compound of Formula (Ih), or a solvate, hydrate, tautomer, N-oxide, stereoisomer, or pharmaceutically acceptable salt thereof, wherein $R^4$ is —N(H)$CH_2CO_2$H. In another embodiment is a compound of Formula (Ih), or a solvate, hydrate, tautomer, N-oxide, stereoisomer, or pharmaceutically acceptable salt thereof, wherein $R^4$ is —N(H)$CH_2CH_2CO_2$H. In another embodiment is a compound of Formula (Ih), or a solvate, hydrate, tautomer, N-oxide, stereoisomer, or pharmaceutically acceptable salt thereof, wherein $R^4$ is —N(H)$CH_2CH_2CH_2CO_2$H. In another embodiment is a compound of Formula (Ih), or a solvate, hydrate, tautomer, N-oxide, stereoisomer, or pharmaceutically acceptable salt thereof, wherein $R^4$ is —C(O)$NR^8R^9$. In another embodiment is a compound of Formula (Ih), or a solvate, hydrate, tautomer, N-oxide, stereoisomer, or pharmaceutically acceptable salt thereof, wherein $R^4$ is —C(O)$NH_2$. In another embodiment is a compound of Formula (Ih), or a solvate, hydrate, tautomer, N-oxide, stereoisomer, or pharmaceutically acceptable salt thereof, wherein $R^4$ is $C_{3-8}$cycloalkyl. In another embodiment is a compound of Formula (Ih), or a solvate, hydrate, tautomer, N-oxide, stereoisomer, or pharmaceutically acceptable salt thereof, wherein $R^4$ is —$OR^7$. In another embodiment is a compound of Formula (Ih), or a solvate, hydrate, tautomer, N-oxide, stereoisomer, or pharmaceutically acceptable salt thereof, wherein $R^4$ is —$OR^7$ and $R^7$ is unsubstituted $C_{3-8}$cycloalkyl or $C_{6-10}$aryl optionally substituted with halogen. In another embodiment is a compound of Formula (Ih), or a solvate, hydrate, tautomer, N-oxide, stereoisomer, or pharmaceutically acceptable salt thereof, wherein $R^4$ is —$OR^7$ and $R^7$ is unsubstituted $C_{3-8}$cycloalkyl. In another embodiment is a compound of Formula (Ih), or a solvate, hydrate, tautomer, N-oxide, stereoisomer, or pharmaceutically acceptable salt thereof, wherein $R^4$ is —$OR^7$ and $R^7$ is phenyl optionally substituted with halogen. In another embodiment is a compound of Formula (Ih), or a solvate, hydrate, tautomer, N-oxide, stereoisomer, or pharmaceutically acceptable salt thereof, wherein $R^4$ is —$OR^7$ and $R^7$ is phenyl substituted with halogen. In another embodiment is a compound of Formula (Ih), or a solvate, hydrate, tautomer, N-oxide, stereoisomer, or pharmaceutically acceptable salt thereof, wherein $R^4$ is —$OR^7$ and $R^7$ is phenyl substituted with —Cl. In another embodiment is a compound of Formula (Ih), or a solvate, hydrate, tautomer, N-oxide, stereoisomer, or pharmaceutically acceptable salt thereof, wherein $R^4$ is $C_{2-9}$heterocycloalkyl optionally substituted with 1 or 2 $R^{14}$. In another embodiment is a compound of Formula (Ih), or a solvate, hydrate, tautomer, N-oxide, stereoisomer, or pharmaceutically acceptable salt thereof, wherein $R^4$ is an unsubstituted $C_{2-9}$heterocycloalkyl. In another embodiment is a compound of Formula (Ih), or a solvate, hydrate, tautomer, N-oxide, stereoisomer, or pharmaceutically acceptable salt thereof, wherein $R^4$ is $C_{2-9}$heterocycloalkyl substituted with 1 or 2 $R^{14}$. In another embodiment is a compound of Formula (Ih), or a solvate, hydrate, tautomer, N-oxide, stereoisomer, or pharmaceutically acceptable salt thereof, wherein $R^4$ is $C_{4-5}$heterocycloalkyl optionally substituted with 1 or 2 $R^{14}$, wherein the $C_{4-5}$heterocycloalkyl is a monocyclic heterocycloalkyl selected from pyrrolidine, piperidine, piperazine, and morpholine. In another embodiment is a compound of Formula (Ih), or a solvate, hydrate, tautomer, N-oxide, stereoisomer, or pharmaceutically acceptable salt thereof, wherein $R^4$ is $C_{5-9}$heterocycloalkyl optionally substituted with 1 or 2 $R^{14}$, wherein the $C_{5-9}$heterocycloalkyl is a bicyclic heterocycloalkyl. In another embodiment is a compound of Formula (Ih), or a solvate, hydrate, tautomer, N-oxide, stereoisomer, or pharmaceutically acceptable salt thereof, wherein $R^4$ is $C_{5-9}$heterocycloalkyl optionally substituted with 1 or 2 $R^{14}$, wherein the $C_{5-9}$heterocycloalkyl is a spirocyclic heterocycloalkyl. In another embodiment is a compound of Formula (Ih), or a solvate, hydrate, tautomer, N-oxide, stereoisomer, or pharmaceutically acceptable salt thereof, wherein $R^4$ is

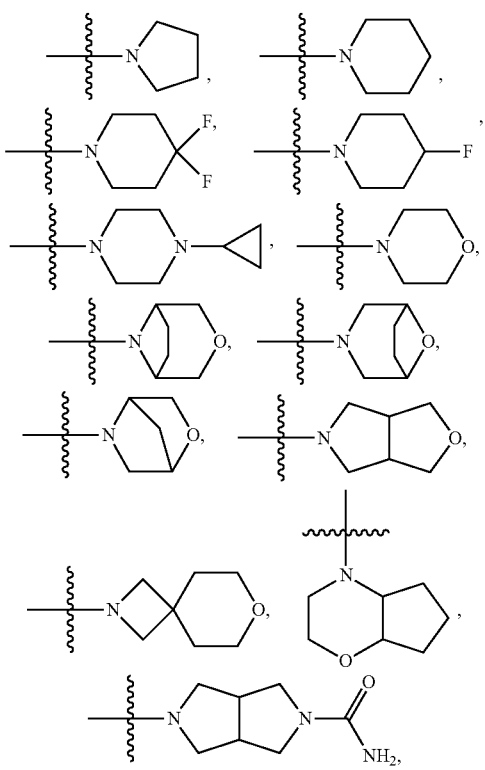

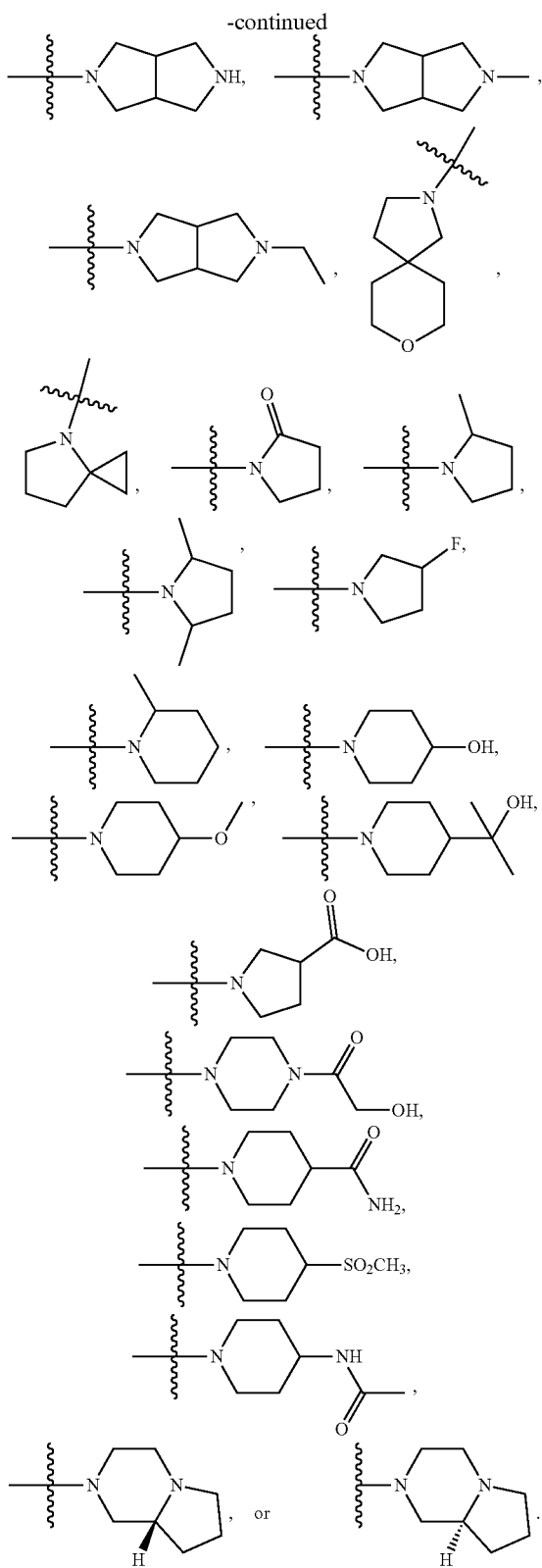

In another embodiment is a compound of Formula (Ih), or a solvate, hydrate, tautomer, N-oxide, stereoisomer, or pharmaceutically acceptable salt thereof, wherein $R^4$ is $C_{1-9}$heteroaryl optionally substituted with 1 or 2 $R^{14}$. In another embodiment is a compound of Formula (Ih), or a solvate, hydrate, tautomer, N-oxide, stereoisomer, or pharmaceutically acceptable salt thereof, wherein $R^4$ is an unsubstituted $C_{1-9}$heteroaryl. In another embodiment is a compound of Formula (Ih), or a solvate, hydrate, tautomer, N-oxide, stereoisomer, or pharmaceutically acceptable salt thereof, wherein $R^4$ is $C_{2-9}$heteroaryl substituted with 1 or 2 $R^{14}$. In another embodiment is a compound of Formula (Ih), or a solvate, hydrate, tautomer, N-oxide, stereoisomer, or pharmaceutically acceptable salt thereof, wherein $R^4$ is $C_{2-9}$heteroaryl optionally substituted with 1 or 2 $R^{14}$, wherein the $C_{2-9}$heteroaryl is selected from pyrrole, furan, thiophene, thiazole, pyrazole, oxazole, oxadiazole, thiadiazole, pyridine, pyrimidine, pyrazine, indole, benzothiophene, benzofuran, and imidazopyridine. In another embodiment is a compound of Formula (Ih), or a solvate, hydrate, tautomer, N-oxide, stereoisomer, or pharmaceutically acceptable salt thereof, wherein $R^4$ is

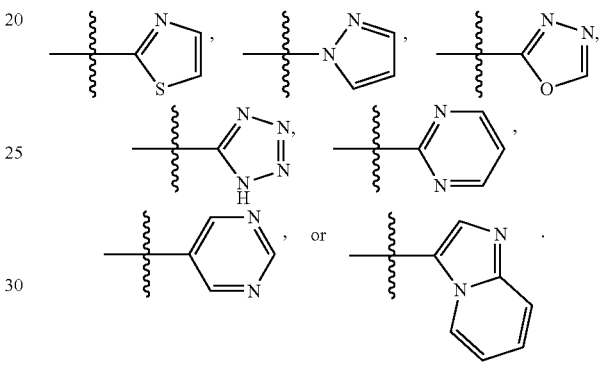

In another embodiment is a compound of Formula (Ih), or a solvate, hydrate, tautomer, N-oxide, stereoisomer, or pharmaceutically acceptable salt thereof, wherein $R^5$ is H, CN, halogen, $C_{1-6}$alkyl, $C_{1-6}$haloalkyl, or $C_{1-6}$haloalkoxy. In another embodiment is a compound of Formula (Ih), or a solvate, hydrate, tautomer, N-oxide, stereoisomer, or pharmaceutically acceptable salt thereof, wherein $R^5$ is H. In another embodiment is a compound of Formula (Ih), or a solvate, hydrate, tautomer, N-oxide, stereoisomer, or pharmaceutically acceptable salt thereof, wherein $R^5$ is —CN. In another embodiment is a compound of Formula (Ih), or a solvate, hydrate, tautomer, N-oxide, stereoisomer, or pharmaceutically acceptable salt thereof, wherein $R^5$ is halogen. In another embodiment is a compound of Formula (Ih), or a solvate, hydrate, tautomer, N-oxide, stereoisomer, or pharmaceutically acceptable salt thereof, wherein $R^5$ is —Cl. In another embodiment is a compound of Formula (Ih), or a solvate, hydrate, tautomer, N-oxide, stereoisomer, or pharmaceutically acceptable salt thereof, wherein $R^5$ is —F. In another embodiment is a compound of Formula (Ih), or a solvate, hydrate, tautomer, N-oxide, stereoisomer, or pharmaceutically acceptable salt thereof, wherein $R^5$ is $C_{1-6}$alkyl. In another embodiment is a compound of Formula (Ih), or a solvate, hydrate, tautomer, N-oxide, stereoisomer, or pharmaceutically acceptable salt thereof, wherein $R^5$ is —CH$_3$. In another embodiment is a compound of Formula (Ih), or a solvate, hydrate, tautomer, N-oxide, stereoisomer, or pharmaceutically acceptable salt thereof, wherein $R^5$ is $C_{1-6}$haloalkyl. In another embodiment is a compound of Formula (Ih), or a solvate, hydrate, tautomer, N-oxide, stereoisomer, or pharmaceutically acceptable salt thereof, wherein $R^5$ is —CF$_3$. In another embodiment is a compound of Formula (Ih), or a solvate, hydrate, tautomer, N-oxide, stereoisomer, or pharmaceutically acceptable salt thereof, wherein $R^5$ is $C_{1-6}$haloalkoxy. In another embodiment is a compound of Formula (Ih), or a solvate, hydrate, tautomer, N-oxide, stereoisomer, or pharmaceutically acceptable salt thereof, wherein $R^5$ is —$OCF_3$. In another embodiment is a compound of Formula (Ih), or a solvate, hydrate, tautomer, N-oxide, stereoisomer, or pharmaceutically acceptable salt thereof, wherein $R^6$ is H. In another embodiment is a compound of Formula (Ih), or a solvate, hydrate, tautomer, N-oxide, stereoisomer, or pharmaceutically acceptable salt thereof, wherein $R^6$ is halogen. In another embodiment is a compound of Formula (Ih), or a solvate, hydrate, tautomer, N-oxide, stereoisomer, or pharmaceutically acceptable salt thereof, wherein $R^6$ is —Cl. In another embodiment is a compound of Formula (Ih), or a solvate, hydrate, tautomer, N-oxide, stereoisomer, or pharmaceutically acceptable salt thereof, wherein $R^6$ is —F. In another embodiment is a compound of Formula (Ih), or a solvate, hydrate, tautomer, N-oxide, stereoisomer, or pharmaceutically acceptable salt thereof, wherein $R^6$ is $C_{1-6}$alkyl. In another embodiment is a compound of Formula (Ih), or a solvate, hydrate, tautomer, N-oxide, stereoisomer, or pharmaceutically acceptable salt thereof, wherein $R^6$ is —$CH_3$.

In another embodiment is a compound of Formula (I) having the structure of Formula (Ii):

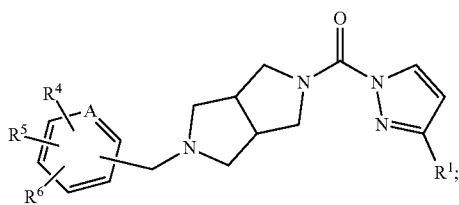

Formula (Ii)

wherein:
$R^1$ is —$N(R^2)C(O)R^{15}$ or —$N(H)SO_2R^{15}$;
$R^2$ is H or $C_{1-6}$alkyl;
$R^4$ is H, halogen, —$OR^7$, $C_{1-6}$alkyl, $C_{1-6}$alkyl-OH, $C_{2-6}$alkenyl, $C_{2-6}$alkynyl, $C_{1-6}$haloalkyl, —O—$C_{3-8}$cycloalkyl, —O—$C_{3-8}$cycloalkyl-OH, —N(H)—$C_{1-6}$alkyl-$CO_2$H, —$SO_2R^{17}$, —$CO_2R^8$, —$C(O)NR^8R^9$, $C_{3-8}$cycloalkyl, $C_{2-9}$heterocycloalkyl, —$C_{1-6}$alkyl-$C_{2-9}$heterocycloalkyl, $C_{6-10}$aryl, $C_{1-9}$heteroaryl, wherein $C_{3-8}$cycloalkyl, $C_{2-9}$heterocycloalkyl, —$C_{1-6}$alkyl-$C_{2-9}$heterocycloalkyl, $C_{6-10}$aryl, $C_{1-9}$heteroaryl are optionally substituted with 1 or 2 $R^{14}$;
$R^5$ is H, —CN, halogen, $C_{1-6}$alkyl, $C_{1-6}$haloalkyl, $C_{1-6}$haloalkoxy, or phenyl;
$R^6$ is H, halogen, or $C_{1-6}$alkyl;
$R^7$ is H, $C_{1-6}$alkyl, $C_{1-6}$haloalkyl, $C_{3-8}$cycloalkyl, $C_{2-9}$heterocycloalkyl, $C_{6-10}$aryl, or $C_{1-9}$heteroaryl, wherein $C_{2-9}$heterocycloalkyl, $C_{6-10}$aryl, or $C_{1-9}$heteroaryl are optionally substituted with 1 or 2 $R^{14}$;
each $R^8$ and each $R^9$ are independently selected from H and $C_{1-6}$alkyl; or $R^8$ and $R^9$ together with the nitrogen to which they are attached are combined to form a heterocycloalkyl ring;
each $R^{14}$ is independently selected from halogen, —OH, oxo, $C_{1-6}$alkyl, $C_{1-6}$haloalkyl, $C_{1-6}$alkoxy, —$C_{1-6}$alkyl-OH, $C_{3-8}$cycloalkyl, —$CO_2R^8$, —$C(O)NR^8R^9$, —C(O)—$C_{1-6}$alkyl, —C(O)—$C_{1-6}$alkyl-OH, —$SO_2$—$C_{1-6}$alkyl, —$N(R^8)SO_2$—$C_{1-6}$alkyl, and —$N(R^8)C(O)$—$C_{1-6}$alkyl;

$R^{15}$ is $C_{1-6}$alkyl or $C_{3-8}$cycloalkyl; and
$R^{17}$ is $C_{1-6}$alkyl or $C_{3-8}$cycloalkyl;
or a solvate, hydrate, tautomer, N-oxide, stereoisomer, or pharmaceutically acceptable salt thereof.

In another embodiment is a compound of Formula (Ii), or a solvate, hydrate, tautomer, N-oxide, stereoisomer, or pharmaceutically acceptable salt thereof, wherein $R^1$ is —$N(R^2)C(O)R^{15}$. In another embodiment is a compound of Formula (Ii), or a solvate, hydrate, tautomer, N-oxide, stereoisomer, or pharmaceutically acceptable salt thereof, wherein $R^1$ is —$N(R^2)C(O)R^{15}$ and $R^2$ is H. In another embodiment is a compound of Formula (Ii), or a solvate, hydrate, tautomer, N-oxide, stereoisomer, or pharmaceutically acceptable salt thereof, wherein $R^1$ is —$N(H)C(O)R^{15}$ and $R^{15}$ is $C_{1-6}$alkyl. In another embodiment is a compound of Formula (Ii), or a solvate, hydrate, tautomer, N-oxide, stereoisomer, or pharmaceutically acceptable salt thereof, wherein $R^1$ is —$N(H)C(O)R^{15}$ and $R^{15}$ is —$CH_3$. In another embodiment is a compound of Formula (Ii), or a solvate, hydrate, tautomer, N-oxide, stereoisomer, or pharmaceutically acceptable salt thereof, wherein $R^1$ is —$N(H)C(O)R^{15}$ and $R^{15}$ is $C_{3-8}$cycloalkyl. In another embodiment is a compound of Formula (Ii), or a solvate, hydrate, tautomer, N-oxide, stereoisomer, or pharmaceutically acceptable salt thereof, wherein $R^1$ is —$N(R^2)C(O)R^{15}$ and $R^2$ is $C_{1-6}$alkyl. In another embodiment is a compound of Formula (Ii), or a solvate, hydrate, tautomer, N-oxide, stereoisomer, or pharmaceutically acceptable salt thereof, wherein $R^1$ is —$N(R^2)C(O)R^{15}$ and $R^2$ is —$CH_3$. In another embodiment is a compound of Formula (Ii), or a solvate, hydrate, tautomer, N-oxide, stereoisomer, or pharmaceutically acceptable salt thereof, wherein $R^1$ is —$N(CH_3)C(O)R^{15}$ and $R^{15}$ is $C_{1-6}$alkyl. In another embodiment is a compound of Formula (Ii), or a solvate, hydrate, tautomer, N-oxide, stereoisomer, or pharmaceutically acceptable salt thereof, wherein $R^1$ is —$N(CH_3)C(O)R^{15}$ and $R^{15}$ is —$CH_3$. In another embodiment is a compound of Formula (Ii), or a solvate, hydrate, tautomer, N-oxide, stereoisomer, or pharmaceutically acceptable salt thereof, wherein $R^1$ is —$N(CH_3)C(O)R^{15}$ and $R^{15}$ is $C_{3-8}$cycloalkyl. In another embodiment is a compound of Formula (Ii), or a solvate, hydrate, tautomer, N-oxide, stereoisomer, or pharmaceutically acceptable salt thereof, wherein $R^1$ is —$N(H)SO_2R^{15}$. In another embodiment is a compound of Formula (Ii), or a solvate, hydrate, tautomer, N-oxide, stereoisomer, or pharmaceutically acceptable salt thereof, wherein $R^1$ is —$N(H)SO_2R^{15}$ and $R^{15}$ is $C_{1-6}$alkyl. In another embodiment is a compound of Formula (Ii), or a solvate, hydrate, tautomer, N-oxide, stereoisomer, or pharmaceutically acceptable salt thereof, wherein $R^1$ is —$N(H)SO_2R^{15}$ and $R^{15}$ is —$CH_3$. In another embodiment is a compound of Formula (Ii), or a solvate, hydrate, tautomer, N-oxide, stereoisomer, or pharmaceutically acceptable salt thereof, wherein $R^1$ is —$N(H)SO_2R^{15}$ and $R^{15}$ is $C_{3-8}$cycloalkyl.

In another embodiment is a compound of Formula (Ii), or a solvate, hydrate, tautomer, N-oxide, stereoisomer, or pharmaceutically acceptable salt thereof, wherein $R^4$ is halogen, —$OR^7$, $C_{1-6}$alkyl-OH, —N(H)—$C_{1-6}$alkyl-$CO_2$H, $C_{2-6}$alkynyl, $C_{1-6}$haloalkyl, —$CO_2R^8$, —$C(O)NR^8R^9$, $C_{3-8}$cycloalkyl, $C_{2-9}$heterocycloalkyl, $C_{6-10}$aryl, or $C_{1-9}$heteroaryl, wherein $C_{3-8}$cycloalkyl, $C_{2-9}$heterocycloalkyl, $C_{6-10}$aryl, or $C_{1-9}$heteroaryl are optionally substituted with 1 or 2 $R^{14}$. In another embodiment is a compound of Formula (Ii), or a solvate, hydrate, tautomer, N-oxide, stereoisomer, or pharmaceutically acceptable salt thereof, wherein $R^4$ is halogen, —$OR^7$, —N(H)—$C_{1-6}$alkyl-$CO_2$H, $C_{1-6}$haloalkyl, —$C(O)NR^8R^9$, $C_{3-8}$cycloalkyl, $C_{2-9}$heterocycloalkyl, or $C_{1-9}$heteroaryl, wherein $C_{2-9}$heterocycloalkyl or $C_{1-9}$heteroaryl are optionally substituted with 1 or 2 $R^{14}$. In another embodiment is a compound of Formula (Ii), or a solvate, hydrate, tautomer, N-oxide, stereoisomer, or pharmaceutically acceptable salt thereof, wherein $R^4$ is halogen. In another embodiment is a compound of Formula (Ii), or a solvate, hydrate, tautomer, N-oxide, stereoisomer, or pharmaceutically acceptable salt thereof, wherein $R^4$ is —Cl. In another embodiment is a compound of Formula (Ii), or a solvate, hydrate, tautomer, N-oxide, stereoisomer, or pharmaceutically acceptable salt thereof, wherein $R^4$ is $C_{1-6}$haloalkyl. In another embodiment is a compound of Formula (Ii), or a solvate, hydrate, tautomer, N-oxide, stereoisomer, or pharmaceutically acceptable salt thereof, wherein $R^4$ is —$CF_3$. In another embodiment is a compound of Formula (Ii), or a solvate, hydrate, tautomer, N-oxide, stereoisomer, or pharmaceutically acceptable salt thereof, wherein $R^4$ is —N(H)—$C_{1-6}$alkyl-$CO_2$H. In another embodiment is a compound of Formula (Ii), or a solvate, hydrate, tautomer, N-oxide, stereoisomer, or pharmaceutically acceptable salt thereof, wherein $R^4$ is —N(H)$CH_2CO_2$H. In another embodiment is a compound of Formula (Ii), or a solvate, hydrate, tautomer, N-oxide, stereoisomer, or pharmaceutically acceptable salt thereof, wherein $R^4$ is —N(H)$CH_2CH_2CO_2$H. In another embodiment is a compound of Formula (Ii), or a solvate, hydrate, tautomer, N-oxide, stereoisomer, or pharmaceutically acceptable salt thereof, wherein $R^4$ is —N(H)$CH_2CH_2CH_2CO_2$H. In another embodiment is a compound of Formula (Ii), or a solvate, hydrate, tautomer, N-oxide, stereoisomer, or pharmaceutically acceptable salt thereof, wherein $R^4$ is —C(O)$NR^8R^9$. In another embodiment is a compound of Formula (Ii), or a solvate, hydrate, tautomer, N-oxide, stereoisomer, or pharmaceutically acceptable salt thereof, wherein $R^4$ is —C(O)$NH_2$. In another embodiment is a compound of Formula (Ii), or a solvate, hydrate, tautomer, N-oxide, stereoisomer, or pharmaceutically acceptable salt thereof, wherein $R^4$ is $C_{3-8}$cycloalkyl. In another embodiment is a compound of Formula (Ii), or a solvate, hydrate, tautomer, N-oxide, stereoisomer, or pharmaceutically acceptable salt thereof, wherein $R^4$ is —$OR^7$. In another embodiment is a compound of Formula (Ii), or a solvate, hydrate, tautomer, N-oxide, stereoisomer, or pharmaceutically acceptable salt thereof, wherein $R^4$ is —$OR^7$ and $R^7$ is unsubstituted $C_{3-8}$cycloalkyl or $C_{6-10}$aryl optionally substituted with halogen. In another embodiment is a compound of Formula (Ii), or a solvate, hydrate, tautomer, N-oxide, stereoisomer, or pharmaceutically acceptable salt thereof, wherein $R^4$ is —$OR^7$ and $R^7$ is unsubstituted $C_{3-8}$cycloalkyl. In another embodiment is a compound of Formula (Ii), or a solvate, hydrate, tautomer, N-oxide, stereoisomer, or pharmaceutically acceptable salt thereof, wherein $R^4$ is —$OR^7$ and $R^7$ is phenyl optionally substituted with halogen. In another embodiment is a compound of Formula (Ii), or a solvate, hydrate, tautomer, N-oxide, stereoisomer, or pharmaceutically acceptable salt thereof, wherein $R^4$ is —$OR^7$ and $R^7$ is phenyl substituted with halogen. In another embodiment is a compound of Formula (Ii), or a solvate, hydrate, tautomer, N-oxide, stereoisomer, or pharmaceutically acceptable salt thereof, wherein $R^4$ is —$OR^7$ and $R^7$ is phenyl substituted with —Cl. In another embodiment is a compound of Formula (Ii), or a solvate, hydrate, tautomer, N-oxide, stereoisomer, or pharmaceutically acceptable salt thereof, wherein $R^4$ is $C_{2-9}$heterocycloalkyl optionally substituted with 1 or 2 $R^{14}$. In another embodiment is a compound of Formula (Ii), or a solvate, hydrate, tautomer, N-oxide, stereoisomer, or pharmaceutically acceptable salt thereof, wherein $R^4$ is an unsubstituted $C_{2-9}$heterocycloalkyl. In another embodiment is a compound of Formula (Ii), or a solvate, hydrate, tautomer, N-oxide, stereoisomer, or pharmaceutically acceptable salt thereof, wherein $R^4$ is $C_{2-9}$heterocycloalkyl substituted with 1 or 2 $R^{14}$. In another embodiment is a compound of Formula (Ii), or a solvate, hydrate, tautomer, N-oxide, stereoisomer, or pharmaceutically acceptable salt thereof, wherein $R^4$ is $C_{4-5}$heterocycloalkyl optionally substituted with 1 or 2 $R^{14}$, wherein the $C_{4-5}$heterocycloalkyl is a monocyclic heterocycloalkyl selected from pyrrolidine, piperidine, piperazine, and morpholine. In another embodiment is a compound of Formula (Ii), or a solvate, hydrate, tautomer, N-oxide, stereoisomer, or pharmaceutically acceptable salt thereof, wherein $R^4$ is $C_{5-9}$heterocycloalkyl optionally substituted with 1 or 2 $R^{14}$, wherein the $C_{5-9}$heterocycloalkyl is a bicyclic heterocycloalkyl. In another embodiment is a compound of Formula (Ii), or a solvate, hydrate, tautomer, N-oxide, stereoisomer, or pharmaceutically acceptable salt thereof, wherein $R^4$ is $C_{5-9}$heterocycloalkyl optionally substituted with 1 or 2 $R^{14}$, wherein the $C_{5-9}$heterocycloalkyl is a spirocyclic heterocycloalkyl. In another embodiment is a compound of Formula (Ii), or a solvate, hydrate, tautomer, N-oxide, stereoisomer, or pharmaceutically acceptable salt thereof, wherein $R^4$ is

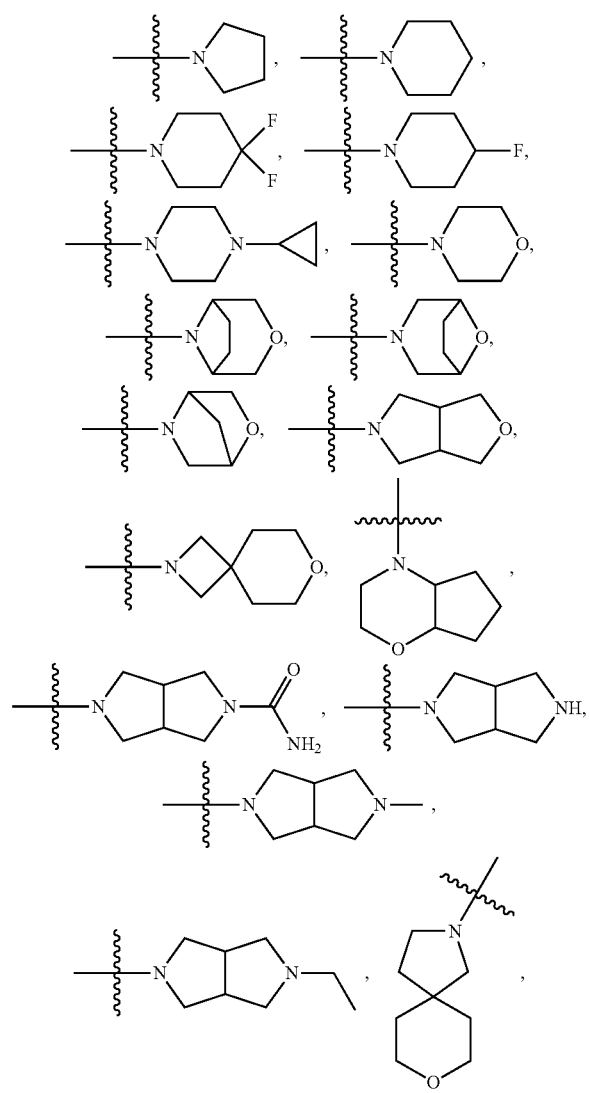

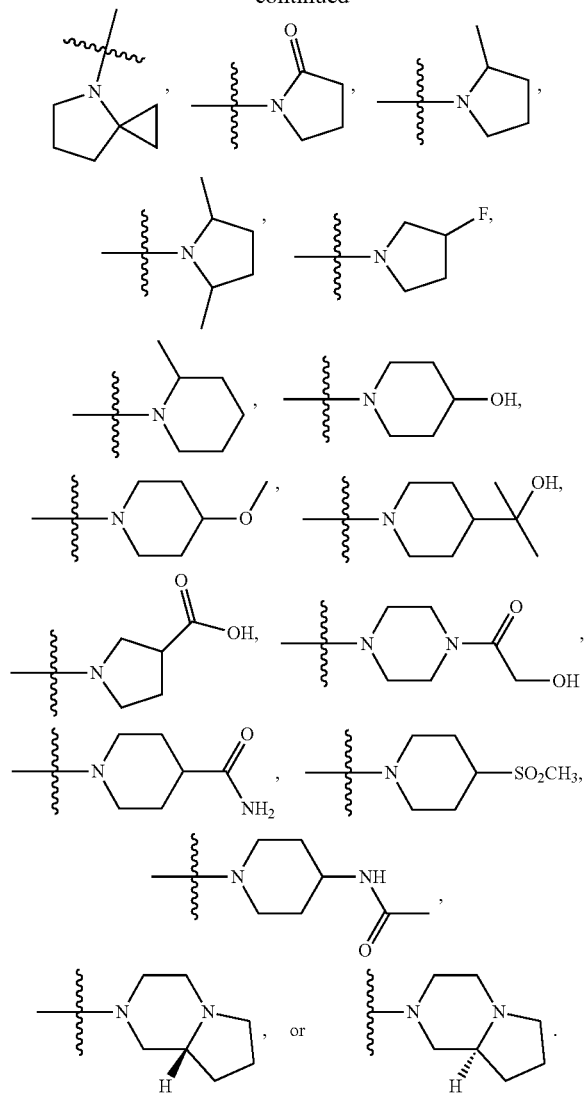

In another embodiment is a compound of Formula (Ii), or a solvate, hydrate, tautomer, N-oxide, stereoisomer, or pharmaceutically acceptable salt thereof, wherein $R^4$ is $C_{1-9}$heteroaryl optionally substituted with 1 or 2 $R^{14}$. In another embodiment is a compound of Formula (Ii), or a solvate, hydrate, tautomer, N-oxide, stereoisomer, or pharmaceutically acceptable salt thereof, wherein $R^4$ is an unsubstituted $C_{1-9}$heteroaryl. In another embodiment is a compound of Formula (Ii), or a solvate, hydrate, tautomer, N-oxide, stereoisomer, or pharmaceutically acceptable salt thereof, wherein $R^4$ is $C_{2-9}$heteroaryl substituted with 1 or 2 $R^{14}$. In another embodiment is a compound of Formula (Ii), or a solvate, hydrate, tautomer, N-oxide, stereoisomer, or pharmaceutically acceptable salt thereof, wherein $R^4$ is $C_{2-9}$heteroaryl optionally substituted with 1 or 2 $R^{14}$, wherein the $C_{2-9}$heteroaryl is selected from pyrrole, furan, thiophene, thiazole, pyrazole, oxazole, oxadiazole, thiadiazole, pyridine, pyrimidine, pyrazine, indole, benzothiophene, benzofuran, and imidazopyridine. In another embodiment is a compound of Formula (Ii), or a solvate, hydrate, tautomer, N-oxide, stereoisomer, or pharmaceutically acceptable salt thereof, wherein $R^4$ is In another embodiment is a compound of Formula (Ii), or a solvate, hydrate, tautomer, N-oxide, stereoisomer, or pharmaceutically acceptable salt thereof, wherein $R^5$ is H, CN, halogen, $C_{1-6}$alkyl, $C_{1-6}$haloalkyl, or $C_{1-6}$haloalkoxy. In another embodiment is a compound of Formula (Ii), or a solvate, hydrate, tautomer, N-oxide, stereoisomer, or pharmaceutically acceptable salt thereof, wherein $R^5$ is H. In another embodiment is a compound of Formula (Ii), or a solvate, hydrate, tautomer, N-oxide, stereoisomer, or pharmaceutically acceptable salt thereof, wherein $R^5$ is —CN. In another embodiment is a compound of Formula (Ii), or a solvate, hydrate, tautomer, N-oxide, stereoisomer, or pharmaceutically acceptable salt thereof, wherein $R^5$ is halogen. In another embodiment is a compound of Formula (Ii), or a solvate, hydrate, tautomer, N-oxide, stereoisomer, or pharmaceutically acceptable salt thereof, wherein $R^5$ is —Cl. In another embodiment is a compound of Formula (Ii), or a solvate, hydrate, tautomer, N-oxide, stereoisomer, or pharmaceutically acceptable salt thereof, wherein $R^5$ is —F. In another embodiment is a compound of Formula (Ii), or a solvate, hydrate, tautomer, N-oxide, stereoisomer, or pharmaceutically acceptable salt thereof, wherein $R^5$ is $C_{1-6}$alkyl. In another embodiment is a compound of Formula (Ii), or a solvate, hydrate, tautomer, N-oxide, stereoisomer, or pharmaceutically acceptable salt thereof, wherein $R^5$ is —CH$_3$. In another embodiment is a compound of Formula (Ii), or a solvate, hydrate, tautomer, N-oxide, stereoisomer, or pharmaceutically acceptable salt thereof, wherein $R^5$ is $C_{1-6}$haloalkyl. In another embodiment is a compound of Formula (Ii), or a solvate, hydrate, tautomer, N-oxide, stereoisomer, or pharmaceutically acceptable salt thereof, wherein $R^5$ is —CF$_3$. In another embodiment is a compound of Formula (Ii), or a solvate, hydrate, tautomer, N-oxide, stereoisomer, or pharmaceutically acceptable salt thereof, wherein $R^5$ is $C_{1-6}$haloalkoxy. In another embodiment is a compound of Formula (Ii), or a solvate, hydrate, tautomer, N-oxide, stereoisomer, or pharmaceutically acceptable salt thereof, wherein $R^5$ is —OCF$_3$. In another embodiment is a compound of Formula (Ii), or a solvate, hydrate, tautomer, N-oxide, stereoisomer, or pharmaceutically acceptable salt thereof, wherein $R^6$ is H. In another embodiment is a compound of Formula (Ii), or a solvate, hydrate, tautomer, N-oxide, stereoisomer, or pharmaceutically acceptable salt thereof, wherein $R^6$ is halogen. In another embodiment is a compound of Formula (Ii), or a solvate, hydrate, tautomer, N-oxide, stereoisomer, or pharmaceutically acceptable salt thereof, wherein $R^6$ is —Cl. In another embodiment is a compound of Formula (Ii), or a solvate, hydrate, tautomer, N-oxide, stereoisomer, or pharmaceutically acceptable salt thereof, wherein $R^6$ is —F. In another embodiment is a compound of Formula (Ii), or a solvate, hydrate, tautomer, N-oxide, stereoisomer, or pharmaceutically acceptable salt thereof, wherein $R^6$ is $C_{1-6}$alkyl. In another embodiment is a compound of Formula (Ii), or a solvate, hydrate, tautomer, N-oxide, stereoisomer, or pharmaceutically acceptable salt thereof, wherein $R^6$ is —$CH_3$.

In another embodiment is a compound of Formula (I) having the structure of Formula (Ij):

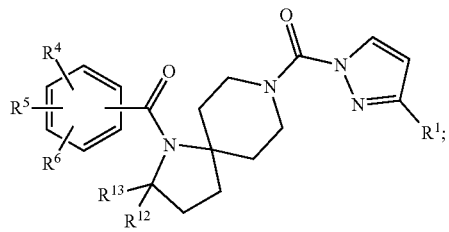

Formula (Ij)

wherein:
$R^1$ is —$N(R^2)C(O)R^{15}$ or —$N(H)SO_2R^{15}$;
$R^2$ is H or $C_{1-6}$alkyl;
$R^4$ is H, halogen, —$OR^7$, $C_{1-6}$alkyl, $C_{1-6}$alkyl-OH, $C_{2-6}$alkenyl, $C_{2-6}$alkynyl, $C_{1-6}$haloalkyl, —O—$C_{3-8}$cycloalkyl, —O—$C_{3-8}$cycloalkyl-OH, —N(H)—$C_{1-6}$alkyl-$CO_2H$, —$SO_2R^{17}$, —$CO_2R^8$, —$C(O)NR^8R^9$, $C_{3-8}$cycloalkyl, $C_{2-9}$heterocycloalkyl, —$C_{1-6}$alkyl-$C_{2-9}$heterocycloalkyl, $C_{6-10}$aryl, $C_{1-9}$heteroaryl, wherein $C_{3-8}$cycloalkyl, $C_{2-9}$heterocycloalkyl, —$C_{1-6}$alkyl-$C_{2-9}$heterocycloalkyl, $C_{6-10}$aryl, $C_{1-9}$heteroaryl are optionally substituted with 1 or 2 $R^{14}$;
$R^5$ is H, —CN, halogen, $C_{1-6}$alkyl, $C_{1-6}$haloalkyl, $C_{1-6}$haloalkoxy, or phenyl;
$R^6$ is H, halogen, or $C_{1-6}$alkyl;
$R^7$ is H, $C_{1-6}$alkyl, $C_{1-6}$haloalkyl, $C_{3-8}$cycloalkyl, $C_{2-9}$heterocycloalkyl, $C_{6-10}$aryl, or $C_{1-9}$heteroaryl, wherein $C_{2-9}$heterocycloalkyl, $C_{6-10}$aryl, or $C_{1-9}$heteroaryl are optionally substituted with 1 or 2 $R^{14}$;
each $R^8$ and each $R^9$ are independently selected from H and $C_{1-6}$alkyl; or $R^8$ and $R^9$ together with the nitrogen to which they are attached are combined to form a heterocycloalkyl ring;
$R^{12}$ is H, halogen, or $C_{1-6}$alkyl;
$R^{13}$ is H or $C_{1-6}$alkyl;
each $R^{14}$ is independently selected from halogen, —OH, oxo, $C_{1-6}$alkyl, $C_{1-6}$haloalkyl, $C_{1-6}$alkoxy, —$C_{1-6}$alkyl-OH, $C_{3-8}$cycloalkyl, —$CO_2R^8$, —$C(O)NR^8R^9$, —C(O)—$C_{1-6}$alkyl, —C(O)—$C_{1-6}$alkyl-OH, —$SO_2$—$C_{1-6}$alkyl, —$N(R^8)SO_2$—$C_{1-6}$alkyl, and —$N(R^8)C(O)$—$C_{1-6}$alkyl;
$R^{15}$ is $C_{1-6}$alkyl or $C_{3-8}$cycloalkyl; and
$R^{17}$ is $C_{1-6}$alkyl or $C_{3-8}$cycloalkyl;
or a solvate, hydrate, tautomer, N-oxide, stereoisomer, or pharmaceutically acceptable salt thereof.

In another embodiment is a compound of Formula (Ij), or a solvate, hydrate, tautomer, N-oxide, stereoisomer, or pharmaceutically acceptable salt thereof, wherein $R^1$ is —$N(R^2)C(O)R^{15}$. In another embodiment is a compound of Formula (Ij), or a solvate, hydrate, tautomer, N-oxide, stereoisomer, or pharmaceutically acceptable salt thereof, wherein $R^1$ is —$N(R^2)C(O)R^{15}$ and $R^2$ is H. In another embodiment is a compound of Formula (Ij), or a solvate, hydrate, tautomer, N-oxide, stereoisomer, or pharmaceutically acceptable salt thereof, wherein $R^1$ is —$N(H)C(O)R^{15}$ and $R^{15}$ is $C_{1-6}$alkyl. In another embodiment is a compound of Formula (Ij), or a solvate, hydrate, tautomer, N-oxide, stereoisomer, or pharmaceutically acceptable salt thereof, wherein $R^1$ is —$N(H)C(O)R^{15}$ and $R^{15}$ is —$CH_3$. In another embodiment is a compound of Formula (Ij), or a solvate, hydrate, tautomer, N-oxide, stereoisomer, or pharmaceutically acceptable salt thereof, wherein $R^1$ is —$N(H)C(O)R^{15}$ and $R^{15}$ is $C_{3-8}$cycloalkyl. In another embodiment is a compound of Formula (Ij), or a solvate, hydrate, tautomer, N-oxide, stereoisomer, or pharmaceutically acceptable salt thereof, wherein $R^1$ is —$N(R^2)C(O)R^{15}$ and $R^2$ is $C_{1-6}$alkyl. In another embodiment is a compound of Formula (Ij), or a solvate, hydrate, tautomer, N-oxide, stereoisomer, or pharmaceutically acceptable salt thereof, wherein $R^1$ is —$N(R^2)C(O)R^{15}$ and $R^2$ is —$CH_3$. In another embodiment is a compound of Formula (Ij), or a solvate, hydrate, tautomer, N-oxide, stereoisomer, or pharmaceutically acceptable salt thereof, wherein $R^1$ is —$N(CH_3)C(O)R^{15}$ and $R^{15}$ is $C_{1-6}$alkyl. In another embodiment is a compound of Formula (Ij), or a solvate, hydrate, tautomer, N-oxide, stereoisomer, or pharmaceutically acceptable salt thereof, wherein $R^1$ is —$N(CH_3)C(O)R^{15}$ and $R^{15}$ is —$CH_3$. In another embodiment is a compound of Formula (Ij), or a solvate, hydrate, tautomer, N-oxide, stereoisomer, or pharmaceutically acceptable salt thereof, wherein $R^1$ is —$N(CH_3)C(O)R^{15}$ and $R^{15}$ is $C_{3-8}$cycloalkyl. In another embodiment is a compound of Formula (Ij), or a solvate, hydrate, tautomer, N-oxide, stereoisomer, or pharmaceutically acceptable salt thereof, wherein $R^1$ is —$N(H)SO_2R^{15}$. In another embodiment is a compound of Formula (Ij), or a solvate, hydrate, tautomer, N-oxide, stereoisomer, or pharmaceutically acceptable salt thereof, wherein $R^1$ is —$N(H)SO_2R^{15}$ and $R^{15}$ is $C_{1-6}$alkyl. In another embodiment is a compound of Formula (Ij), or a solvate, hydrate, tautomer, N-oxide, stereoisomer, or pharmaceutically acceptable salt thereof, wherein $R^1$ is —$N(H)SO_2R^{15}$ and $R^{15}$ is —$CH_3$. In another embodiment is a compound of Formula (Ij), or a solvate, hydrate, tautomer, N-oxide, stereoisomer, or pharmaceutically acceptable salt thereof, wherein $R^1$ is —$N(H)SO_2R^{15}$ and $R^{15}$ is $C_{3-8}$cycloalkyl.

In another embodiment is a compound of Formula (Ij), or a solvate, hydrate, tautomer, N-oxide, stereoisomer, or pharmaceutically acceptable salt thereof, wherein $R^4$ is halogen, —$OR^7$, $C_{1-6}$alkyl-OH, —N(H)—$C_{1-6}$alkyl-$CO_2H$, $C_{2-6}$alkynyl, $C_{1-6}$haloalkyl, —$CO_2R^8$, —$C(O)NR^8R^9$, $C_{3-8}$cycloalkyl, $C_{2-9}$heterocycloalkyl, $C_{6-10}$aryl, or $C_{1-9}$heteroaryl, wherein $C_{3-8}$cycloalkyl, $C_{2-9}$heterocycloalkyl, $C_{6-10}$aryl, or $C_{1-9}$heteroaryl are optionally substituted with 1 or 2 $R^{14}$. In another embodiment is a compound of Formula (Ij), or a solvate, hydrate, tautomer, N-oxide, stereoisomer, or pharmaceutically acceptable salt thereof, wherein $R^4$ is halogen, —$OR^7$, —N(H)—$C_{1-6}$alkyl-$CO_2H$, $C_{1-6}$haloalkyl, —$C(O)NR^8R^9$, $C_{3-8}$cycloalkyl, $C_{2-9}$heterocycloalkyl, or $C_{1-9}$heteroaryl, wherein $C_{2-9}$heterocycloalkyl or $C_{1-9}$heteroaryl are optionally substituted with 1 or 2 $R^{14}$. In another embodiment is a compound of Formula (Ij), or a solvate, hydrate, tautomer, N-oxide, stereoisomer, or pharmaceutically acceptable salt thereof, wherein $R^4$ is halogen. In another embodiment is a compound of Formula (Ij), or a solvate, hydrate, tautomer, N-oxide, stereoisomer, or pharmaceutically acceptable salt thereof, wherein $R^4$ is —Cl. In another embodiment is a compound of Formula (Ij), or a solvate, hydrate, tautomer, N-oxide, stereoisomer, or pharmaceutically acceptable salt thereof, wherein $R^4$ is $C_{1-6}$haloalkyl. In another embodiment is a compound of Formula (Ij), or a solvate, hydrate, tautomer, N-oxide, stereoisomer, or pharmaceutically acceptable salt thereof, wherein $R^4$ is —$CF_3$. In another embodiment is a compound of Formula (Ij), or a solvate, hydrate, tautomer, N-oxide, stereoisomer, or pharmaceutically acceptable salt thereof, wherein $R^4$ is —N(H)—$C_{1-6}$alkyl-$CO_2$H. In another embodiment is a compound of Formula (Ij), or a solvate, hydrate, tautomer, N-oxide, stereoisomer, or pharmaceutically acceptable salt thereof, wherein $R^4$ is —N(H)$CH_2CO_2$H. In another embodiment is a compound of Formula (Ij), or a solvate, hydrate, tautomer, N-oxide, stereoisomer, or pharmaceutically acceptable salt thereof, wherein $R^4$ is —N(H)$CH_2CH_2CO_2$H. In another embodiment is a compound of Formula (Ij), or a solvate, hydrate, tautomer, N-oxide, stereoisomer, or pharmaceutically acceptable salt thereof, wherein $R^4$ is —N(H)$CH_2CH_2CH_2CO_2$H. In another embodiment is a compound of Formula (Ij), or a solvate, hydrate, tautomer, N-oxide, stereoisomer, or pharmaceutically acceptable salt thereof, wherein $R^4$ is —C(O)$NR^8R^9$. In another embodiment is a compound of Formula (Ij), or a solvate, hydrate, tautomer, N-oxide, stereoisomer, or pharmaceutically acceptable salt thereof, wherein $R^4$ is —C(O)$NH_2$. In another embodiment is a compound of Formula (Ij), or a solvate, hydrate, tautomer, N-oxide, stereoisomer, or pharmaceutically acceptable salt thereof, wherein $R^4$ is $C_{3-8}$cycloalkyl. In another embodiment is a compound of Formula (Ij), or a solvate, hydrate, tautomer, N-oxide, stereoisomer, or pharmaceutically acceptable salt thereof, wherein $R^4$ is —$OR^7$. In another embodiment is a compound of Formula (Ij), or a solvate, hydrate, tautomer, N-oxide, stereoisomer, or pharmaceutically acceptable salt thereof, wherein $R^4$ is —$OR^7$ and $R^7$ is unsubstituted $C_{3-8}$cycloalkyl or $C_{6-10}$aryl optionally substituted with halogen. In another embodiment is a compound of Formula (Ij), or a solvate, hydrate, tautomer, N-oxide, stereoisomer, or pharmaceutically acceptable salt thereof, wherein $R^4$ is —$OR^7$ and $R^7$ is unsubstituted $C_{3-8}$cycloalkyl. In another embodiment is a compound of Formula (Ij), or a solvate, hydrate, tautomer, N-oxide, stereoisomer, or pharmaceutically acceptable salt thereof, wherein $R^4$ is —$OR^7$ and $R^7$ is phenyl optionally substituted with halogen. In another embodiment is a compound of Formula (Ij), or a solvate, hydrate, tautomer, N-oxide, stereoisomer, or pharmaceutically acceptable salt thereof, wherein $R^4$ is —$OR^7$ and $R^7$ is phenyl substituted with halogen. In another embodiment is a compound of Formula (Ij), or a solvate, hydrate, tautomer, N-oxide, stereoisomer, or pharmaceutically acceptable salt thereof, wherein $R^4$ is —$OR^7$ and $R^7$ is phenyl substituted with —Cl. In another embodiment is a compound of Formula (Ij), or a solvate, hydrate, tautomer, N-oxide, stereoisomer, or pharmaceutically acceptable salt thereof, wherein $R^4$ is $C_{2-9}$heterocycloalkyl optionally substituted with 1 or 2 $R^{14}$. In another embodiment is a compound of Formula (Ij), or a solvate, hydrate, tautomer, N-oxide, stereoisomer, or pharmaceutically acceptable salt thereof, wherein $R^4$ is an unsubstituted $C_{2-9}$heterocycloalkyl. In another embodiment is a compound of Formula (Ij), or a solvate, hydrate, tautomer, N-oxide, stereoisomer, or pharmaceutically acceptable salt thereof, wherein $R^4$ is $C_{2-9}$heterocycloalkyl substituted with 1 or 2 $R^{14}$. In another embodiment is a compound of Formula (Ij), or a solvate, hydrate, tautomer, N-oxide, stereoisomer, or pharmaceutically acceptable salt thereof, wherein $R^4$ is $C_{4-5}$heterocycloalkyl optionally substituted with 1 or 2 $R^{14}$, wherein the $C_{4-5}$heterocycloalkyl is a monocyclic heterocycloalkyl selected from pyrrolidine, piperidine, piperazine, and morpholine. In another embodiment is a compound of Formula (Ij), or a solvate, hydrate, tautomer, N-oxide, stereoisomer, or pharmaceutically acceptable salt thereof, wherein $R^4$ is $C_{5-9}$heterocycloalkyl optionally substituted with 1 or 2 $R^{14}$, wherein the $C_{5-9}$heterocycloalkyl is a bicyclic heterocycloalkyl. In another embodiment is a compound of Formula (Ij), or a solvate, hydrate, tautomer, N-oxide, stereoisomer, or pharmaceutically acceptable salt thereof, wherein $R^4$ is $C_{5-9}$heterocycloalkyl optionally substituted with 1 or 2 $R^{14}$, wherein the $C_{5-9}$heterocycloalkyl is a spirocyclic heterocycloalkyl. In another embodiment is a compound of Formula (Ij), or a solvate, hydrate, tautomer, N-oxide, stereoisomer, or pharmaceutically acceptable salt thereof, wherein $R^4$ is

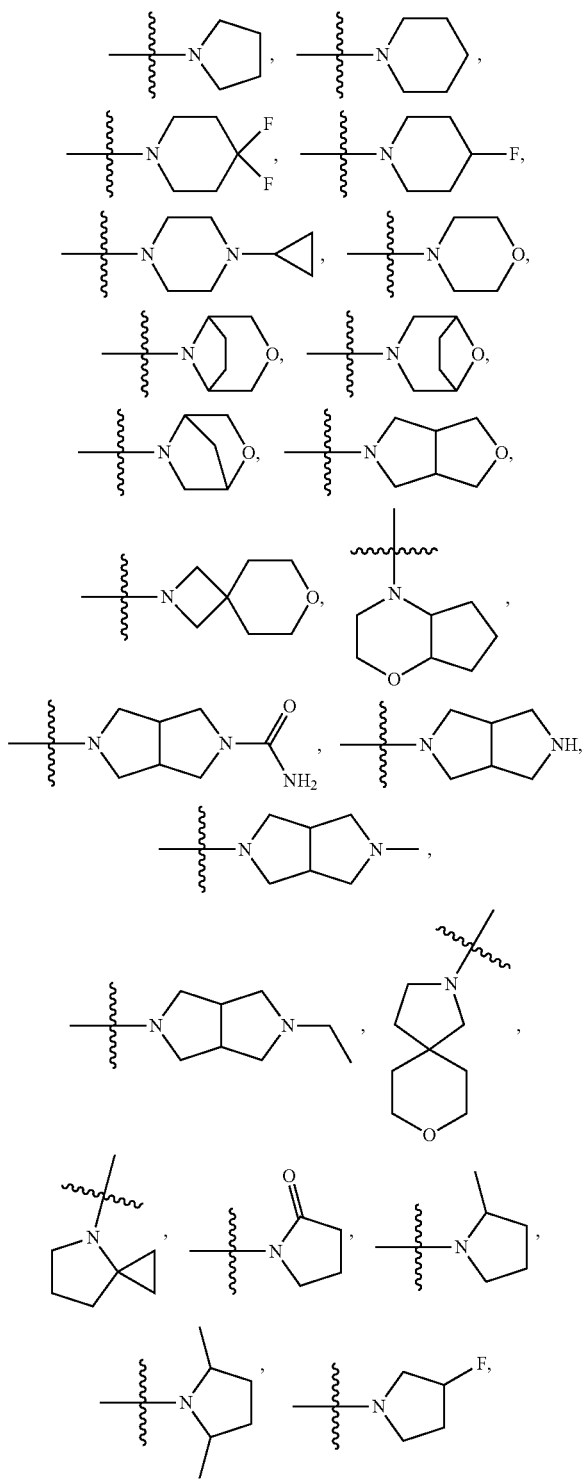

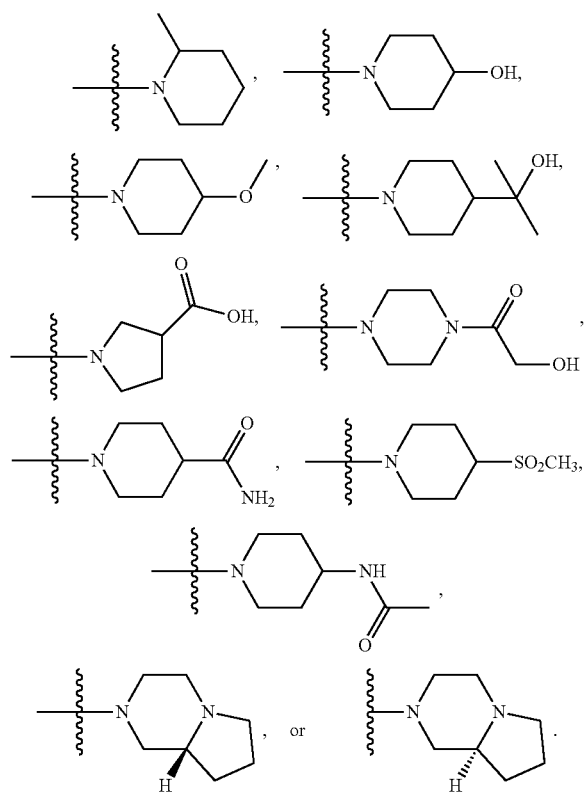

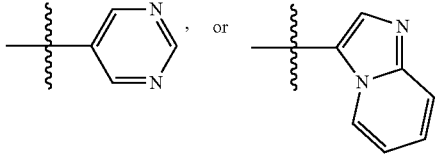

In another embodiment is a compound of Formula (Ij), or a solvate, hydrate, tautomer, N-oxide, stereoisomer, or pharmaceutically acceptable salt thereof, wherein $R^4$ is $C_{1-9}$heteroaryl optionally substituted with 1 or 2 $R^{14}$. In another embodiment is a compound of Formula (Ij), or a solvate, hydrate, tautomer, N-oxide, stereoisomer, or pharmaceutically acceptable salt thereof, wherein $R^4$ is an unsubstituted $C_{1-9}$heteroaryl. In another embodiment is a compound of Formula (Ij), or a solvate, hydrate, tautomer, N-oxide, stereoisomer, or pharmaceutically acceptable salt thereof, wherein $R^4$ is $C_{2-9}$heteroaryl substituted with 1 or 2 $R^{14}$. In another embodiment is a compound of Formula (Ij), or a solvate, hydrate, tautomer, N-oxide, stereoisomer, or pharmaceutically acceptable salt thereof, wherein $R^4$ is $C_{2-9}$heteroaryl optionally substituted with 1 or 2 $R^{14}$, wherein the $C_{2-9}$heteroaryl is selected from pyrrole, furan, thiophene, thiazole, pyrazole, oxazole, oxadiazole, thiadiazole, pyridine, pyrimidine, pyrazine, indole, benzothiophene, benzofuran, and imidazopyridine. In another embodiment is a compound of Formula (Ij), or a solvate, hydrate, tautomer, N-oxide, stereoisomer, or pharmaceutically acceptable salt thereof, wherein $R^4$ is

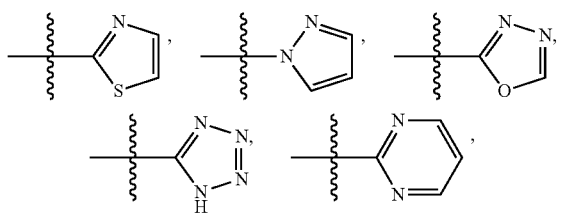

In another embodiment is a compound of Formula (Ij), or a solvate, hydrate, tautomer, N-oxide, stereoisomer, or pharmaceutically acceptable salt thereof, wherein $R^5$ is H, CN, halogen, $C_{1-6}$alkyl, $C_{1-6}$haloalkyl, or $C_{1-6}$haloalkoxy. In another embodiment is a compound of Formula (Ij), or a solvate, hydrate, tautomer, N-oxide, stereoisomer, or pharmaceutically acceptable salt thereof, wherein $R^5$ is H. In another embodiment is a compound of Formula (Ij), or a solvate, hydrate, tautomer, N-oxide, stereoisomer, or pharmaceutically acceptable salt thereof, wherein $R^5$ is —CN. In another embodiment is a compound of Formula (Ij), or a solvate, hydrate, tautomer, N-oxide, stereoisomer, or pharmaceutically acceptable salt thereof, wherein $R^5$ is halogen. In another embodiment is a compound of Formula (Ij), or a solvate, hydrate, tautomer, N-oxide, stereoisomer, or pharmaceutically acceptable salt thereof, wherein $R^5$ is —Cl. In another embodiment is a compound of Formula (Ij), or a solvate, hydrate, tautomer, N-oxide, stereoisomer, or pharmaceutically acceptable salt thereof, wherein $R^5$ is —F. In another embodiment is a compound of Formula (Ij), or a solvate, hydrate, tautomer, N-oxide, stereoisomer, or pharmaceutically acceptable salt thereof, wherein $R^5$ is $C_{1-6}$alkyl. In another embodiment is a compound of Formula (Ij), or a solvate, hydrate, tautomer, N-oxide, stereoisomer, or pharmaceutically acceptable salt thereof, wherein $R^5$ is —$CH_3$. In another embodiment is a compound of Formula (Ij), or a solvate, hydrate, tautomer, N-oxide, stereoisomer, or pharmaceutically acceptable salt thereof, wherein $R^5$ is $C_{1-6}$haloalkyl. In another embodiment is a compound of Formula (Ij), or a solvate, hydrate, tautomer, N-oxide, stereoisomer, or pharmaceutically acceptable salt thereof, wherein $R^5$ is —$CF_3$. In another embodiment is a compound of Formula (Ij), or a solvate, hydrate, tautomer, N-oxide, stereoisomer, or pharmaceutically acceptable salt thereof, wherein $R^5$ is $C_{1-6}$haloalkoxy. In another embodiment is a compound of Formula (Ij), or a solvate, hydrate, tautomer, N-oxide, stereoisomer, or pharmaceutically acceptable salt thereof, wherein $R^5$ is —$OCF_3$. In another embodiment is a compound of Formula (Ij), or a solvate, hydrate, tautomer, N-oxide, stereoisomer, or pharmaceutically acceptable salt thereof, wherein $R^6$ is H. In another embodiment is a compound of Formula (Ij), or a solvate, hydrate, tautomer, N-oxide, stereoisomer, or pharmaceutically acceptable salt thereof, wherein $R^6$ is halogen. In another embodiment is a compound of Formula (Ij), or a solvate, hydrate, tautomer, N-oxide, stereoisomer, or pharmaceutically acceptable salt thereof, wherein $R^6$ is —Cl. In another embodiment is a compound of Formula (Ij), or a solvate, hydrate, tautomer, N-oxide, stereoisomer, or pharmaceutically acceptable salt thereof, wherein $R^6$ is —F. In another embodiment is a compound of Formula (Ij), or a solvate, hydrate, tautomer, N-oxide, stereoisomer, or pharmaceutically acceptable salt thereof, wherein $R^6$ is $C_{1-6}$alkyl. In another embodiment is a compound of Formula (Ij), or a solvate, hydrate, tautomer, N-oxide, stereoisomer, or pharmaceutically acceptable salt thereof, wherein $R^6$ is —$CH_3$.

In another embodiment is a compound of Formula (Ij), or a solvate, hydrate, tautomer, N-oxide, stereoisomer, or pharmaceutically acceptable salt thereof, wherein $R^{12}$ is H. In another embodiment is a compound of Formula (Ij), or a solvate, hydrate, tautomer, N-oxide, stereoisomer, or pharmaceutically acceptable salt thereof, wherein $R^{12}$ is $C_{1-6}$alkyl. In another embodiment is a compound of Formula (Ij), or a solvate, hydrate, tautomer, N-oxide, stereoisomer, or pharmaceutically acceptable salt thereof, wherein $R^{12}$ is —$CH_3$. In another embodiment is a compound of Formula (Ij), or a solvate, hydrate, tautomer, N-oxide, stereoisomer, or pharmaceutically acceptable salt thereof, wherein $R^{13}$ is H. In another embodiment is a compound of Formula (Ij), or a solvate, hydrate, tautomer, N-oxide, stereoisomer, or pharmaceutically acceptable salt thereof, wherein $R^{13}$ is $C_{1-6}$alkyl. In another embodiment is a compound of Formula (Ij), or a solvate, hydrate, tautomer, N-oxide, stereoisomer, or pharmaceutically acceptable salt thereof, wherein $R^{13}$ is —$CH_3$. In another embodiment is a compound of Formula (Ij), or a solvate, hydrate, tautomer, N-oxide, stereoisomer, or pharmaceutically acceptable salt thereof, wherein $R^{12}$ is H and $R^{13}$ is H. In another embodiment is a compound of Formula (Ij), or a solvate, hydrate, tautomer, N-oxide, stereoisomer, or pharmaceutically acceptable salt thereof, wherein $R^{12}$ is H and $R^{13}$ is $C_{1-6}$alkyl. In another embodiment is a compound of Formula (Ij), or a solvate, hydrate, tautomer, N-oxide, stereoisomer, or pharmaceutically acceptable salt thereof, wherein $R^{12}$ is H and $R^{13}$ is —$CH_3$. In another embodiment is a compound of Formula (Ij), or a solvate, hydrate, tautomer, N-oxide, stereoisomer, or pharmaceutically acceptable salt thereof, wherein $R^{12}$ is $C_{1-6}$alkyl and $R^{13}$ is H. In another embodiment is a compound of Formula (Ij), or a solvate, hydrate, tautomer, N-oxide, stereoisomer, or pharmaceutically acceptable salt thereof, wherein $R^{12}$ is —$CH_3$ and $R^{13}$ is H. In another embodiment is a compound of Formula (Ij), or a solvate, hydrate, tautomer, N-oxide, stereoisomer, or pharmaceutically acceptable salt thereof, wherein $R^{12}$ is $C_{1-6}$alkyl and $R^{13}$ is $C_{1-6}$alkyl. In another embodiment is a compound of Formula (Ij), or a solvate, hydrate, tautomer, N-oxide, stereoisomer, or pharmaceutically acceptable salt thereof, wherein $R^{12}$ is —$CH_3$ and $R^{13}$ is —$CH_3$.

In another embodiment is a compound of Formula (I) having the structure of Formula (Ik):

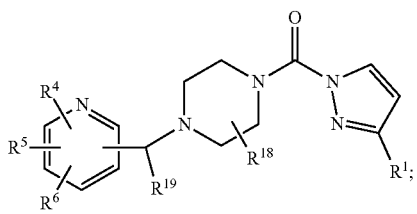

Formula (Ik)

wherein:

$R^1$ is —$N(R^2)C(O)R^{15}$ or —$N(H)SO_2R^{15}$;

$R^2$ is H or $C_{1-6}$alkyl;

$R^4$ is H, halogen, —$OR^7$, $C_{1-6}$alkyl, $C_{1-6}$alkyl-OH, $C_{2-6}$alkenyl, $C_{2-6}$alkynyl, $C_{1-6}$haloalkyl, —O—$C_{3-8}$cycloalkyl, —O—$C_{3-8}$cycloalkyl-OH, —N(H)—$C_{1-6}$alkyl-$CO_2$H, —$SO_2R^{17}$, —$CO_2R^8$, —$C(O)NR^8R^9$, $C_{3-8}$cycloalkyl, $C_{2-9}$heterocycloalkyl, —$C_{1-6}$alkyl-$C_{2-9}$heterocycloalkyl, $C_{6-10}$aryl, $C_{1-9}$heteroaryl, wherein $C_{3-8}$cycloalkyl, $C_{2-9}$heterocycloalkyl, —$C_{1-6}$alkyl-$C_{2-9}$heterocycloalkyl, $C_{6-10}$aryl, $C_{1-9}$heteroaryl are optionally substituted with 1 or 2 $R^{14}$;

$R^5$ is H, —CN, halogen, $C_{1-6}$alkyl, $C_{1-6}$haloalkyl, $C_{1-6}$haloalkoxy, or phenyl;

$R^6$ is H, halogen, or $C_{1-6}$alkyl;

$R^7$ is H, $C_{1-6}$alkyl, $C_{1-6}$haloalkyl, $C_{3-8}$cycloalkyl, $C_{2-9}$heterocycloalkyl, $C_{6-10}$aryl, or $C_{1-9}$heteroaryl, wherein $C_{2-9}$heterocycloalkyl, $C_{6-10}$aryl, or $C_{1-9}$heteroaryl are optionally substituted with 1 or 2 $R^{14}$;

each $R^8$ and each $R^9$ are independently selected from H and $C_{1-6}$alkyl; or $R^8$ and $R^9$ together with the nitrogen to which they are attached are combined to form a heterocycloalkyl ring;

each $R^{14}$ is independently selected from halogen, —OH, oxo, $C_{1-6}$alkyl, $C_{1-6}$haloalkyl, $C_{1-6}$alkoxy, —$C_{1-6}$alkyl-OH, $C_{3-8}$cycloalkyl, —$CO_2R^8$, —$C(O)NR^8R^9$, —C(O)—$C_{1-6}$alkyl, —C(O)—$C_{1-6}$alkyl-OH, —$SO_2$—$C_{1-6}$alkyl, —$N(R^8)SO_2$—$C_{1-6}$alkyl, and —$N(R^8)C(O)$—$C_{1-6}$alkyl;

$R^{15}$ is $C_{1-6}$alkyl or $C_{3-8}$cycloalkyl;

$R^{17}$ is $C_{1-6}$alkyl or $C_{3-8}$cycloalkyl; and $R^{18}$ and $R^{19}$ are independently selected from H and $C_{1-6}$alkyl, wherein $R^{18}$ and $R^{19}$ are not both H;

or a solvate, hydrate, tautomer, N-oxide, stereoisomer, or pharmaceutically acceptable salt thereof.

In another embodiment is a compound of Formula (Ik), or a solvate, hydrate, tautomer, N-oxide, stereoisomer, or pharmaceutically acceptable salt thereof, wherein $R^1$ is —$N(R^2)C(O)R^{15}$. In another embodiment is a compound of Formula (Ik), or a solvate, hydrate, tautomer, N-oxide, stereoisomer, or pharmaceutically acceptable salt thereof, wherein $R^1$ is —$N(R^2)C(O)R^{15}$ and $R^2$ is H. In another embodiment is a compound of Formula (Ik), or a solvate, hydrate, tautomer, N-oxide, stereoisomer, or pharmaceutically acceptable salt thereof, wherein $R^1$ is —$N(H)C(O)R^{15}$ and $R^{15}$ is $C_{1-6}$alkyl. In another embodiment is a compound of Formula (Ik), or a solvate, hydrate, tautomer, N-oxide, stereoisomer, or pharmaceutically acceptable salt thereof, wherein $R^1$ is —$N(H)C(O)R^{15}$ and $R^{15}$ is —$CH_3$. In another embodiment is a compound of Formula (Ik), or a solvate, hydrate, tautomer, N-oxide, stereoisomer, or pharmaceutically acceptable salt thereof, wherein $R^1$ is —$N(H)C(O)R^{15}$ and $R^{15}$ is $C_{3-8}$cycloalkyl. In another embodiment is a compound of Formula (Ik), or a solvate, hydrate, tautomer, N-oxide, stereoisomer, or pharmaceutically acceptable salt thereof, wherein $R^1$ is —$N(R^2)C(O)R^{15}$ and $R^2$ is $C_{1-6}$alkyl. In another embodiment is a compound of Formula (Ik), or a solvate, hydrate, tautomer, N-oxide, stereoisomer, or pharmaceutically acceptable salt thereof, wherein $R^1$ is —$N(R^2)C(O)R^{15}$ and $R^2$ is —$CH_3$. In another embodiment is a compound of Formula (Ik), or a solvate, hydrate, tautomer, N-oxide, stereoisomer, or pharmaceutically acceptable salt thereof, wherein $R^1$ is —$N(CH_3)C(O)R^{15}$ and $R^{15}$ is $C_{1-6}$alkyl. In another embodiment is a compound of Formula (Ik), or a solvate, hydrate, tautomer, N-oxide, stereoisomer, or pharmaceutically acceptable salt thereof, wherein $R^1$ is —$N(CH_3)C(O)R^{15}$ and $R^{15}$ is —$CH_3$. In another embodiment is a compound of Formula (Ik), or a solvate, hydrate, tautomer, N-oxide, stereoisomer, or pharmaceutically acceptable salt thereof, wherein $R^1$ is —$N(CH_3)C(O)R^{15}$ and $R^{15}$ is $C_{3-8}$cycloalkyl. In another embodiment is a compound of Formula (Ik), or a solvate, hydrate, tautomer, N-oxide, stereoisomer, or pharmaceutically acceptable salt thereof, wherein $R^1$ is —$N(H)SO_2R^{15}$. In another embodiment is a compound of Formula (Ik), or a solvate, hydrate, tautomer, N-oxide, stereoisomer, or pharmaceutically acceptable salt thereof, wherein $R^1$ is —$N(H)SO_2R^{15}$ and $R^{15}$ is $C_{1-6}$alkyl. In another embodiment is a compound of Formula (Ik), or a solvate, hydrate, tautomer, N-oxide, stereoisomer, or pharmaceutically acceptable salt thereof, wherein $R^1$ is —N(H)SO$_2$R$^{15}$ and $R^{15}$ is —CH$_3$. In another embodiment is a compound of Formula (Ik), or a solvate, hydrate, tautomer, N-oxide, stereoisomer, or pharmaceutically acceptable salt thereof, wherein $R^1$ is —N(H)SO$_2$R$^{15}$ and $R^{15}$ is C$_{3-8}$cycloalkyl.

In another embodiment is a compound of Formula (Ik), or a solvate, hydrate, tautomer, N-oxide, stereoisomer, or pharmaceutically acceptable salt thereof, wherein $R^4$ is halogen, —OR$^7$, C$_{1-6}$alkyl-OH, —N(H)—C$_{1-6}$alkyl-CO$_2$H, C$_{2-6}$alkynyl, C$_{1-6}$haloalkyl, —CO$_2$R$^8$, —C(O)NR$^8$R$^9$, C$_{3-8}$cycloalkyl, C$_{2-9}$heterocycloalkyl, C$_{6-10}$aryl, or C$_{1-9}$heteroaryl, wherein C$_{3-8}$cycloalkyl, C$_{2-9}$heterocycloalkyl, C$_{6-10}$aryl, or C$_{1-9}$heteroaryl are optionally substituted with 1 or 2 R$^{14}$. In another embodiment is a compound of Formula (Ik), or a solvate, hydrate, tautomer, N-oxide, stereoisomer, or pharmaceutically acceptable salt thereof, wherein $R^4$ is halogen, —OR$^7$, —N(H)—C$_{1-6}$alkyl-CO$_2$H, C$_{1-6}$haloalkyl, —C(O)NR$^8$R$^9$, C$_{3-8}$cycloalkyl, C$_{2-9}$heterocycloalkyl, or C$_{1-9}$heteroaryl, wherein C$_{2-9}$heterocycloalkyl or C$_{1-9}$heteroaryl are optionally substituted with 1 or 2 R$^{14}$. In another embodiment is a compound of Formula (Ik), or a solvate, hydrate, tautomer, N-oxide, stereoisomer, or pharmaceutically acceptable salt thereof, wherein $R^4$ is halogen. In another embodiment is a compound of Formula (Ik), or a solvate, hydrate, tautomer, N-oxide, stereoisomer, or pharmaceutically acceptable salt thereof, wherein $R^4$ is —Cl. In another embodiment is a compound of Formula (Ik), or a solvate, hydrate, tautomer, N-oxide, stereoisomer, or pharmaceutically acceptable salt thereof, wherein $R^4$ is C$_{1-6}$haloalkyl. In another embodiment is a compound of Formula (Ik), or a solvate, hydrate, tautomer, N-oxide, stereoisomer, or pharmaceutically acceptable salt thereof, wherein $R^4$ is —CF$_3$. In another embodiment is a compound of Formula (Ik), or a solvate, hydrate, tautomer, N-oxide, stereoisomer, or pharmaceutically acceptable salt thereof, wherein $R^4$ is —N(H)—C$_{1-6}$alkyl-CO$_2$H. In another embodiment is a compound of Formula (Ik), or a solvate, hydrate, tautomer, N-oxide, stereoisomer, or pharmaceutically acceptable salt thereof, wherein $R^4$ is —N(H)CH$_2$CO$_2$H. In another embodiment is a compound of Formula (Ik), or a solvate, hydrate, tautomer, N-oxide, stereoisomer, or pharmaceutically acceptable salt thereof, wherein $R^4$ is —N(H)CH$_2$CH$_2$CO$_2$H. In another embodiment is a compound of Formula (Ik), or a solvate, hydrate, tautomer, N-oxide, stereoisomer, or pharmaceutically acceptable salt thereof, wherein $R^4$ is —N(H)CH$_2$CH$_2$CH$_2$CO$_2$H. In another embodiment is a compound of Formula (Ik), or a solvate, hydrate, tautomer, N-oxide, stereoisomer, or pharmaceutically acceptable salt thereof, wherein $R^4$ is —C(O)NR$^8$R$^9$. In another embodiment is a compound of Formula (Ik), or a solvate, hydrate, tautomer, N-oxide, stereoisomer, or pharmaceutically acceptable salt thereof, wherein $R^4$ is —C(O)NH$_2$. In another embodiment is a compound of Formula (Ik), or a solvate, hydrate, tautomer, N-oxide, stereoisomer, or pharmaceutically acceptable salt thereof, wherein $R^4$ is C$_{3-8}$cycloalkyl. In another embodiment is a compound of Formula (Ik), or a solvate, hydrate, tautomer, N-oxide, stereoisomer, or pharmaceutically acceptable salt thereof, wherein $R^4$ is —OR$^7$. In another embodiment is a compound of Formula (Ik), or a solvate, hydrate, tautomer, N-oxide, stereoisomer, or pharmaceutically acceptable salt thereof, wherein $R^4$ is —OR$^7$ and $R^7$ is unsubstituted C$_{3-8}$cycloalkyl or C$_{6-10}$aryl optionally substituted with halogen. In another embodiment is a compound of Formula (Ik), or a solvate, hydrate, tautomer, N-oxide, stereoisomer, or pharmaceutically acceptable salt thereof, wherein $R^4$ is —OR$^7$ and $R^7$ is unsubstituted C$_{3-8}$cycloalkyl. In another embodiment is a compound of Formula (Ik), or a solvate, hydrate, tautomer, N-oxide, stereoisomer, or pharmaceutically acceptable salt thereof, wherein $R^4$ is —OR$^7$ and $R^7$ is phenyl optionally substituted with halogen. In another embodiment is a compound of Formula (Ik), or a solvate, hydrate, tautomer, N-oxide, stereoisomer, or pharmaceutically acceptable salt thereof, wherein $R^4$ is —OR$^7$ and $R^7$ is phenyl substituted with halogen. In another embodiment is a compound of Formula (Ik), or a solvate, hydrate, tautomer, N-oxide, stereoisomer, or pharmaceutically acceptable salt thereof, wherein $R^4$ is —OR$^7$ and $R^7$ is phenyl substituted with —Cl. In another embodiment is a compound of Formula (Ik), or a solvate, hydrate, tautomer, N-oxide, stereoisomer, or pharmaceutically acceptable salt thereof, wherein $R^4$ is C$_{2-9}$heterocycloalkyl optionally substituted with 1 or 2 R$^{14}$. In another embodiment is a compound of Formula (Ik), or a solvate, hydrate, tautomer, N-oxide, stereoisomer, or pharmaceutically acceptable salt thereof, wherein $R^4$ is an unsubstituted C$_{2-9}$heterocycloalkyl. In another embodiment is a compound of Formula (Ik), or a solvate, hydrate, tautomer, N-oxide, stereoisomer, or pharmaceutically acceptable salt thereof, wherein $R^4$ is C$_{2-9}$heterocycloalkyl substituted with 1 or 2 R$^{14}$. In another embodiment is a compound of Formula (Ik), or a solvate, hydrate, tautomer, N-oxide, stereoisomer, or pharmaceutically acceptable salt thereof, wherein $R^4$ is C$_{4-5}$heterocycloalkyl optionally substituted with 1 or 2 R$^{14}$, wherein the C$_{4-5}$heterocycloalkyl is a monocyclic heterocycloalkyl selected from pyrrolidine, piperidine, piperazine, and morpholine. In another embodiment is a compound of Formula (Ik), or a solvate, hydrate, tautomer, N-oxide, stereoisomer, or pharmaceutically acceptable salt thereof, wherein $R^4$ is C$_{5-9}$heterocycloalkyl optionally substituted with 1 or 2 R$^{14}$, wherein the C$_{5-9}$heterocycloalkyl is a bicyclic heterocycloalkyl. In another embodiment is a compound of Formula (Ik), or a solvate, hydrate, tautomer, N-oxide, stereoisomer, or pharmaceutically acceptable salt thereof, wherein $R^4$ is C$_{5-9}$heterocycloalkyl optionally substituted with 1 or 2 R$^{14}$, wherein the C$_{5-9}$heterocycloalkyl is a spirocyclic heterocycloalkyl. In another embodiment is a compound of Formula (Ik), or a solvate, hydrate, tautomer, N-oxide, stereoisomer, or pharmaceutically acceptable salt thereof, wherein $R^4$ is

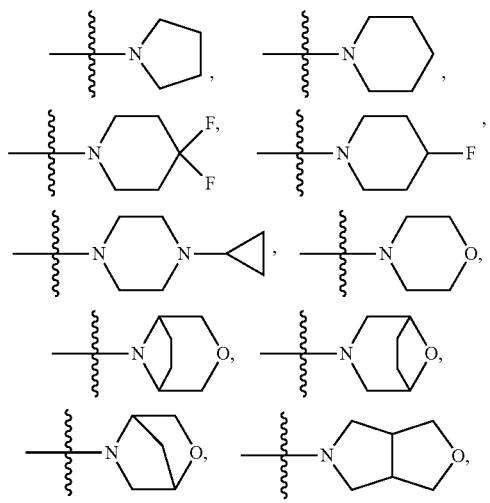

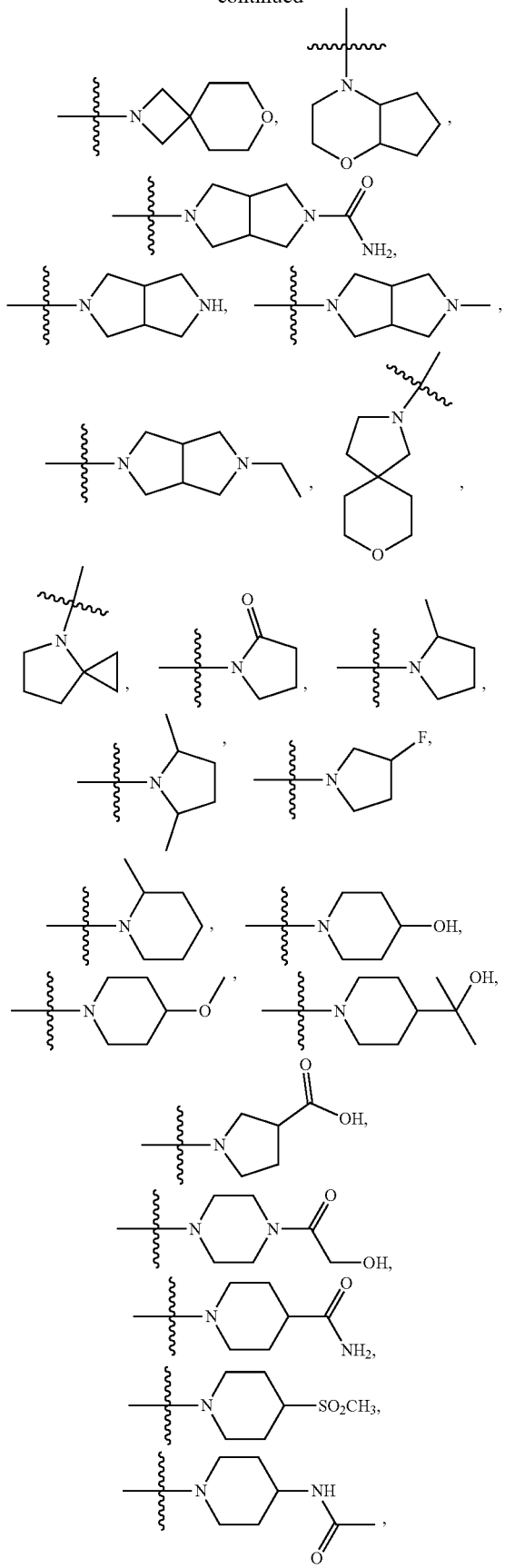

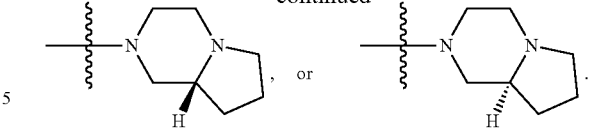

In another embodiment is a compound of Formula (Ik), or a solvate, hydrate, tautomer, N-oxide, stereoisomer, or pharmaceutically acceptable salt thereof, wherein $R^4$ is $C_{1-9}$heteroaryl optionally substituted with 1 or 2 $R^{14}$. In another embodiment is a compound of Formula (Ik), or a solvate, hydrate, tautomer, N-oxide, stereoisomer, or pharmaceutically acceptable salt thereof, wherein $R^4$ is an unsubstituted $C_{1-9}$heteroaryl. In another embodiment is a compound of Formula (Ik), or a solvate, hydrate, tautomer, N-oxide, stereoisomer, or pharmaceutically acceptable salt thereof, wherein $R^4$ is $C_{2-9}$heteroaryl substituted with 1 or 2 $R^{14}$. In another embodiment is a compound of Formula (Ik), or a solvate, hydrate, tautomer, N-oxide, stereoisomer, or pharmaceutically acceptable salt thereof, wherein $R^4$ is $C_{2-9}$heteroaryl optionally substituted with 1 or 2 $R^{14}$, wherein the $C_{2-9}$heteroaryl is selected from pyrrole, furan, thiophene, thiazole, pyrazole, oxazole, oxadiazole, thiadiazole, pyridine, pyrimidine, pyrazine, indole, benzothiophene, benzofuran, and imidazopyridine. In another embodiment is a compound of Formula (Ik), or a solvate, hydrate, tautomer, N-oxide, stereoisomer, or pharmaceutically acceptable salt thereof, wherein $R^4$ is

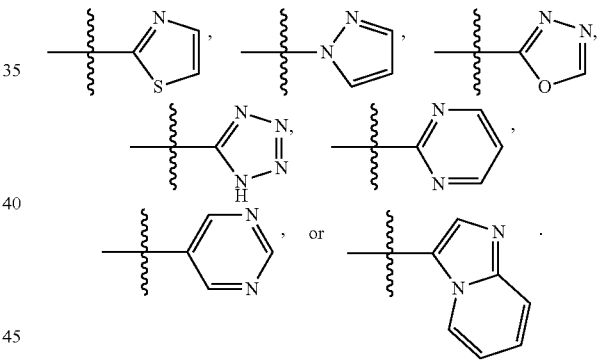

In another embodiment is a compound of Formula (Ik), or a solvate, hydrate, tautomer, N-oxide, stereoisomer, or pharmaceutically acceptable salt thereof, wherein $R^5$ is H, CN, halogen, $C_{1-6}$alkyl, $C_{1-6}$haloalkyl, or $C_{1-6}$haloalkoxy. In another embodiment is a compound of Formula (Ik), or a solvate, hydrate, tautomer, N-oxide, stereoisomer, or pharmaceutically acceptable salt thereof, wherein $R^5$ is H. In another embodiment is a compound of Formula (Ik), or a solvate, hydrate, tautomer, N-oxide, stereoisomer, or pharmaceutically acceptable salt thereof, wherein $R^5$ is —CN. In another embodiment is a compound of Formula (Ik), or a solvate, hydrate, tautomer, N-oxide, stereoisomer, or pharmaceutically acceptable salt thereof, wherein $R^5$ is halogen. In another embodiment is a compound of Formula (Ik), or a solvate, hydrate, tautomer, N-oxide, stereoisomer, or pharmaceutically acceptable salt thereof, wherein $R^5$ is —Cl. In another embodiment is a compound of Formula (Ik), or a solvate, hydrate, tautomer, N-oxide, stereoisomer, or pharmaceutically acceptable salt thereof, wherein $R^5$ is —F. In another embodiment is a compound of Formula (Ik), or a solvate, hydrate, tautomer, N-oxide, stereoisomer, or pharmaceutically acceptable salt thereof, wherein $R^5$ is $C_{1-6}$alkyl. In another embodiment is a compound of Formula (Ik), or a solvate, hydrate, tautomer, N-oxide, stereoisomer, or pharmaceutically acceptable salt thereof, wherein $R^5$ is —$CH_3$. In another embodiment is a compound of Formula (Ik), or a solvate, hydrate, tautomer, N-oxide, stereoisomer, or pharmaceutically acceptable salt thereof, wherein $R^5$ is $C_{1-6}$haloalkyl. In another embodiment is a compound of Formula (Ik), or a solvate, hydrate, tautomer, N-oxide, stereoisomer, or pharmaceutically acceptable salt thereof, wherein $R^5$ is —$CF_3$. In another embodiment is a compound of Formula (Ik), or a solvate, hydrate, tautomer, N-oxide, stereoisomer, or pharmaceutically acceptable salt thereof, wherein $R^5$ is $C_{1-6}$haloalkoxy. In another embodiment is a compound of Formula (Ik), or a solvate, hydrate, tautomer, N-oxide, stereoisomer, or pharmaceutically acceptable salt thereof, wherein $R^5$ is —$OCF_3$. In another embodiment is a compound of Formula (Ik), or a solvate, hydrate, tautomer, N-oxide, stereoisomer, or pharmaceutically acceptable salt thereof, wherein $R^6$ is H. In another embodiment is a compound of Formula (Ik), or a solvate, hydrate, tautomer, N-oxide, stereoisomer, or pharmaceutically acceptable salt thereof, wherein $R^6$ is halogen. In another embodiment is a compound of Formula (Ik), or a solvate, hydrate, tautomer, N-oxide, stereoisomer, or pharmaceutically acceptable salt thereof, wherein $R^6$ is —Cl. In another embodiment is a compound of Formula (Ik), or a solvate, hydrate, tautomer, N-oxide, stereoisomer, or pharmaceutically acceptable salt thereof, wherein $R^6$ is —F. In another embodiment is a compound of Formula (Ik), or a solvate, hydrate, tautomer, N-oxide, stereoisomer, or pharmaceutically acceptable salt thereof, wherein $R^6$ is $C_{1-6}$alkyl. In another embodiment is a compound of Formula (Ik), or a solvate, hydrate, tautomer, N-oxide, stereoisomer, or pharmaceutically acceptable salt thereof, wherein $R^6$ is —$CH_3$.

In another embodiment is a compound of Formula (Ik), or a solvate, hydrate, tautomer, N-oxide, stereoisomer, or pharmaceutically acceptable salt thereof, wherein $R^{18}$ is $C_{1-6}$alkyl. In another embodiment is a compound of Formula (Ik), or a solvate, hydrate, tautomer, N-oxide, stereoisomer, or pharmaceutically acceptable salt thereof, wherein $R^{18}$ is $C_{1-6}$alkyl and $R^{19}$ is H. In another embodiment is a compound of Formula (Ik), or a solvate, hydrate, tautomer, N-oxide, stereoisomer, or pharmaceutically acceptable salt thereof, wherein $R^{18}$ is —$CH_3$ and $R^{19}$ is H. In another embodiment is a compound of Formula (Ik), or a solvate, hydrate, tautomer, N-oxide, stereoisomer, or pharmaceutically acceptable salt thereof, wherein $R^{19}$ is $C_{1-6}$alkyl. In another embodiment is a compound of Formula (Ik), or a solvate, hydrate, tautomer, N-oxide, stereoisomer, or pharmaceutically acceptable salt thereof, wherein $R^{18}$ is H and $R^{19}$ is $C_{1-6}$alkyl. In another embodiment is a compound of Formula (Ik), or a solvate, hydrate, tautomer, N-oxide, stereoisomer, or pharmaceutically acceptable salt thereof, wherein $R^{18}$ is H and $R^{19}$ is —$CH_3$. In another embodiment is a compound of Formula (Ik), or a solvate, hydrate, tautomer, N-oxide, stereoisomer, or pharmaceutically acceptable salt thereof, wherein $R^{18}$ and $R^{19}$ are $C_{1-6}$alkyl. In another embodiment is a compound of Formula (Ik), or a solvate, hydrate, tautomer, N-oxide, stereoisomer, or pharmaceutically acceptable salt thereof, wherein $R^{18}$ and $R^{19}$ are —$CH_3$.

In another embodiment is a compound of Formula (I) having the structure of Formula (Il):

Formula (Il)

wherein:
$R^1$ is —$N(R^2)C(O)R^{15}$ or —$N(H)SO_2R^{15}$;
$R^2$ is H or $C_{1-6}$alkyl;
$R^5$ is H, —CN, halogen, $C_{1-6}$alkyl, $C_{1-6}$haloalkyl, $C_{1-6}$haloalkoxy, or phenyl;
$R^6$ is H, halogen, or $C_{1-6}$alkyl;
$R^{10}$ is —O—$C_{1-6}$haloalkyl, —O—$C_{1-6}$alkyl-$CO_2H$, —O—$C_{3-8}$cycloalkyl, —O—$C_{3-8}$cycloalkyl-$CO_2H$, —N(H)—$C_{1-6}$alkyl-$CO_2H$, or —$SO_2R^{17}$;
$R^{12}$ is H, halogen, or $C_{1-6}$alkyl;
$R^{13}$ is H or $C_{1-6}$alkyl;
$R^{15}$ is $C_{1-6}$alkyl or $C_{3-8}$cycloalkyl; and
$R^{17}$ is $C_{1-6}$alkyl or $C_{3-8}$cycloalkyl;
or a solvate, hydrate, tautomer, N-oxide, stereoisomer, or pharmaceutically acceptable salt thereof.

In another embodiment is a compound of Formula (Il), or a solvate, hydrate, tautomer, N-oxide, stereoisomer, or pharmaceutically acceptable salt thereof, wherein $R^1$ is —$N(R^2)C(O)R^{15}$. In another embodiment is a compound of Formula (Il), or a solvate, hydrate, tautomer, N-oxide, stereoisomer, or pharmaceutically acceptable salt thereof, wherein $R^1$ is —$N(R^2)C(O)R^{15}$ and $R^2$ is H. In another embodiment is a compound of Formula (Il), or a solvate, hydrate, tautomer, N-oxide, stereoisomer, or pharmaceutically acceptable salt thereof, wherein $R^1$ is —$N(H)C(O)R^{15}$ and $R^{15}$ is $C_{1-6}$alkyl. In another embodiment is a compound of Formula (Il), or a solvate, hydrate, tautomer, N-oxide, stereoisomer, or pharmaceutically acceptable salt thereof, wherein $R^1$ is —$N(H)C(O)R^{15}$ and $R^{15}$ is —$CH_3$. In another embodiment is a compound of Formula (Il), or a solvate, hydrate, tautomer, N-oxide, stereoisomer, or pharmaceutically acceptable salt thereof, wherein $R^1$ is —$N(H)C(O)R^{15}$ and $R^{15}$ is $C_{3-8}$cycloalkyl. In another embodiment is a compound of Formula (Il), or a solvate, hydrate, tautomer, N-oxide, stereoisomer, or pharmaceutically acceptable salt thereof, wherein $R^1$ is —$N(R^2)C(O)R^{15}$ and $R^2$ is $C_{1-6}$alkyl. In another embodiment is a compound of Formula (Il), or a solvate, hydrate, tautomer, N-oxide, stereoisomer, or pharmaceutically acceptable salt thereof, wherein $R^1$ is —$N(R^2)C(O)R^{15}$ and $R^2$ is —$CH_3$. In another embodiment is a compound of Formula (Il), or a solvate, hydrate, tautomer, N-oxide, stereoisomer, or pharmaceutically acceptable salt thereof, wherein $R^1$ is —$N(CH_3)C(O)R^{15}$ and $R^{15}$ is $C_{1-6}$alkyl. In another embodiment is a compound of Formula (Il), or a solvate, hydrate, tautomer, N-oxide, stereoisomer, or pharmaceutically acceptable salt thereof, wherein $R^1$ is —$N(CH_3)C(O)R^{15}$ and $R^{15}$ is —$CH_3$. In another embodiment is a compound of Formula (Il), or a solvate, hydrate, tautomer, N-oxide, stereoisomer, or pharmaceutically acceptable salt thereof, wherein $R^1$ is —$N(CH_3)C(O)R^{15}$ and $R^{15}$ is $C_{3-8}$cycloalkyl. In another embodiment is a compound of Formula (Il), or a solvate, hydrate, tautomer, N-oxide, stereoisomer, or pharmaceutically acceptable salt thereof, wherein $R^1$ is —$N(H)SO_2R^{15}$. In another embodiment is a compound of Formula (Il), or a solvate, hydrate, tautomer, N-oxide, stereoisomer, or pharmaceutically acceptable salt thereof, wherein $R^1$ is —N(H)SO$_2$R$^{15}$ and $R^{15}$ is $C_{1-6}$alkyl. In another embodiment is a compound of Formula (Il), or a solvate, hydrate, tautomer, N-oxide, stereoisomer, or pharmaceutically acceptable salt thereof, wherein $R^1$ is —N(H)SO$_2$R$^{15}$ and $R^{15}$ is —CH$_3$. In another embodiment is a compound of Formula (Il), or a solvate, hydrate, tautomer, N-oxide, stereoisomer, or pharmaceutically acceptable salt thereof, wherein $R^1$ is —N(H)SO$_2$R$^{15}$ and $R^{15}$ is $C_{3-8}$cycloalkyl.

In another embodiment is a compound of Formula (Il), or a solvate, hydrate, tautomer, N-oxide, stereoisomer, or pharmaceutically acceptable salt thereof, wherein $R^{10}$ is —O—C$_{1-6}$alkyl-CO$_2$H. In another embodiment is a compound of Formula (Il), or a solvate, hydrate, tautomer, N-oxide, stereoisomer, or pharmaceutically acceptable salt thereof, wherein $R^{10}$ is —OCH$_2$CO$_2$H. In another embodiment is a compound of Formula (Il), or a solvate, hydrate, tautomer, N-oxide, stereoisomer, or pharmaceutically acceptable salt thereof, wherein $R^{10}$ is —OCH$_2$CH$_2$CO$_2$H. In another embodiment is a compound of Formula (Il), or a solvate, hydrate, tautomer, N-oxide, stereoisomer, or pharmaceutically acceptable salt thereof, wherein $R^{10}$ is —OCH$_2$CH$_2$CH$_2$CO$_2$H. In another embodiment is a compound of Formula (Il), or a solvate, hydrate, tautomer, N-oxide, stereoisomer, or pharmaceutically acceptable salt thereof, wherein $R^{10}$ is —N(H)—C$_{1-6}$alkyl-CO$_2$H. In another embodiment is a compound of Formula (Il), or a solvate, hydrate, tautomer, N-oxide, stereoisomer, or pharmaceutically acceptable salt thereof, wherein $R^{10}$ is —N(H)CH$_2$CO$_2$H. In another embodiment is a compound of Formula (Il), or a solvate, hydrate, tautomer, N-oxide, stereoisomer, or pharmaceutically acceptable salt thereof, wherein $R^{10}$ is —N(H)CH$_2$CH$_2$CO$_2$H. In another embodiment is a compound of Formula (Il), or a solvate, hydrate, tautomer, N-oxide, stereoisomer, or pharmaceutically acceptable salt thereof, wherein $R^{10}$ is —N(H)CH$_2$CH$_2$CH$_2$CO$_2$H. In another embodiment is a compound of Formula (Il), or a solvate, hydrate, tautomer, N-oxide, stereoisomer, or pharmaceutically acceptable salt thereof, wherein $R^{10}$ is —O—C$_{1-6}$haloalkyl. In another embodiment is a compound of Formula (Il), or a solvate, hydrate, tautomer, N-oxide, stereoisomer, or pharmaceutically acceptable salt thereof, wherein $R^{10}$ is —OCF$_3$. In another embodiment is a compound of Formula (Il), or a solvate, hydrate, tautomer, N-oxide, stereoisomer, or pharmaceutically acceptable salt thereof, wherein $R^{10}$ is —O—C$_{3-8}$cycloalkyl. In another embodiment is a compound of Formula (Il), or a solvate, hydrate, tautomer, N-oxide, stereoisomer, or pharmaceutically acceptable salt thereof, wherein $R^{10}$ is —O—C$_{3-8}$cycloalkyl-CO$_2$H. In another embodiment is a compound of Formula (Il), or a solvate, hydrate, tautomer, N-oxide, stereoisomer, or pharmaceutically acceptable salt thereof, wherein $R^{10}$ is —SO$_2$R$^{17}$. In another embodiment is a compound of Formula (Il), or a solvate, hydrate, tautomer, N-oxide, stereoisomer, or pharmaceutically acceptable salt thereof, wherein $R^{10}$ is —SO$_2$R$^{17}$ and $R^{17}$ is $C_{1-6}$alkyl. In another embodiment is a compound of Formula (Il), or a solvate, hydrate, tautomer, N-oxide, stereoisomer, or pharmaceutically acceptable salt thereof, wherein $R^{10}$ is —SO$_2$R$^{17}$ and $R^{17}$ is —CH$_3$. In another embodiment is a compound of Formula (Il), or a solvate, hydrate, tautomer, N-oxide, stereoisomer, or pharmaceutically acceptable salt thereof, wherein $R^{10}$ is —SO$_2$R$^{17}$ and $R^{17}$ is $C_{3-8}$cycloalkyl. In another embodiment is a compound of Formula (Il), or a solvate, hydrate, tautomer, N-oxide, stereoisomer, or pharmaceutically acceptable salt thereof, wherein $R^5$ is H, CN, halogen, $C_{1-6}$alkyl, $C_{1-6}$haloalkyl, or $C_{1-6}$haloalkoxy. In another embodiment is a compound of Formula (Il), or a solvate, hydrate, tautomer, N-oxide, stereoisomer, or pharmaceutically acceptable salt thereof, wherein $R^5$ is H. In another embodiment is a compound of Formula (Il), or a solvate, hydrate, tautomer, N-oxide, stereoisomer, or pharmaceutically acceptable salt thereof, wherein $R^5$ is —CN. In another embodiment is a compound of Formula (Il), or a solvate, hydrate, tautomer, N-oxide, stereoisomer, or pharmaceutically acceptable salt thereof, wherein $R^5$ is halogen. In another embodiment is a compound of Formula (Il), or a solvate, hydrate, tautomer, N-oxide, stereoisomer, or pharmaceutically acceptable salt thereof, wherein $R^5$ is —Cl. In another embodiment is a compound of Formula (Il), or a solvate, hydrate, tautomer, N-oxide, stereoisomer, or pharmaceutically acceptable salt thereof, wherein $R^5$ is —F. In another embodiment is a compound of Formula (Il), or a solvate, hydrate, tautomer, N-oxide, stereoisomer, or pharmaceutically acceptable salt thereof, wherein $R^5$ is $C_{1-6}$alkyl. In another embodiment is a compound of Formula (Il), or a solvate, hydrate, tautomer, N-oxide, stereoisomer, or pharmaceutically acceptable salt thereof, wherein $R^5$ is —CH$_3$. In another embodiment is a compound of Formula (Il), or a solvate, hydrate, tautomer, N-oxide, stereoisomer, or pharmaceutically acceptable salt thereof, wherein $R^5$ is $C_{1-6}$haloalkyl. In another embodiment is a compound of Formula (Il), or a solvate, hydrate, tautomer, N-oxide, stereoisomer, or pharmaceutically acceptable salt thereof, wherein $R^5$ is —CF$_3$. In another embodiment is a compound of Formula (Il), or a solvate, hydrate, tautomer, N-oxide, stereoisomer, or pharmaceutically acceptable salt thereof, wherein $R^5$ is $C_{1-6}$haloalkoxy. In another embodiment is a compound of Formula (Il), or a solvate, hydrate, tautomer, N-oxide, stereoisomer, or pharmaceutically acceptable salt thereof, wherein $R^5$ is —OCF$_3$. In another embodiment is a compound of Formula (Il), or a solvate, hydrate, tautomer, N-oxide, stereoisomer, or pharmaceutically acceptable salt thereof, wherein $R^6$ is H. In another embodiment is a compound of Formula (Il), or a solvate, hydrate, tautomer, N-oxide, stereoisomer, or pharmaceutically acceptable salt thereof, wherein $R^6$ is halogen. In another embodiment is a compound of Formula (Il), or a solvate, hydrate, tautomer, N-oxide, stereoisomer, or pharmaceutically acceptable salt thereof, wherein $R^6$ is —Cl. In another embodiment is a compound of Formula (Il), or a solvate, hydrate, tautomer, N-oxide, stereoisomer, or pharmaceutically acceptable salt thereof, wherein $R^6$ is —F. In another embodiment is a compound of Formula (Il), or a solvate, hydrate, tautomer, N-oxide, stereoisomer, or pharmaceutically acceptable salt thereof, wherein $R^6$ is $C_{1-6}$alkyl. In another embodiment is a compound of Formula (Il), or a solvate, hydrate, tautomer, N-oxide, stereoisomer, or pharmaceutically acceptable salt thereof, wherein $R^6$ is —CH$_3$.

In another embodiment is a compound of Formula (Il), or a solvate, hydrate, tautomer, N-oxide, stereoisomer, or pharmaceutically acceptable salt thereof, wherein $R^{12}$ is H. In another embodiment is a compound of Formula (Il), or a solvate, hydrate, tautomer, N-oxide, stereoisomer, or pharmaceutically acceptable salt thereof, wherein $R^{12}$ is $C_{1-6}$alkyl. In another embodiment is a compound of Formula (Il), or a solvate, hydrate, tautomer, N-oxide, stereoisomer, or pharmaceutically acceptable salt thereof, wherein $R^{12}$ is —CH$_3$. In another embodiment is a compound of Formula (Il), or a solvate, hydrate, tautomer, N-oxide, stereoisomer, or pharmaceutically acceptable salt thereof, wherein $R^{13}$ is H. In another embodiment is a compound of Formula (Il), or a solvate, hydrate, tautomer, N-oxide, stereoisomer, or pharmaceutically acceptable salt thereof, wherein $R^{13}$ is $C_{1-6}$alkyl. In another embodiment is a compound of Formula (Il), or a solvate, hydrate, tautomer, N-oxide, stereoisomer, or pharmaceutically acceptable salt thereof, wherein $R^{13}$ is —$CH_3$. In another embodiment is a compound of Formula (Il), or a solvate, hydrate, tautomer, N-oxide, stereoisomer, or pharmaceutically acceptable salt thereof, wherein $R^{12}$ is H and $R^{13}$ is H. In another embodiment is a compound of Formula (Il), or a solvate, hydrate, tautomer, N-oxide, stereoisomer, or pharmaceutically acceptable salt thereof, wherein $R^{12}$ is H and $R^{13}$ is $C_{1-6}$alkyl. In another embodiment is a compound of Formula (Il), or a solvate, hydrate, tautomer, N-oxide, stereoisomer, or pharmaceutically acceptable salt thereof, wherein $R^{12}$ is H and $R^{13}$ is —$CH_3$. In another embodiment is a compound of Formula (Il), or a solvate, hydrate, tautomer, N-oxide, stereoisomer, or pharmaceutically acceptable salt thereof, wherein $R^{12}$ is $C_{1-6}$alkyl and $R^{13}$ is H. In another embodiment is a compound of Formula (Il), or a solvate, hydrate, tautomer, N-oxide, stereoisomer, or pharmaceutically acceptable salt thereof, wherein $R^{12}$ is —$CH_3$ and $R^{13}$ is H. In another embodiment is a compound of Formula (Il), or a solvate, hydrate, tautomer, N-oxide, stereoisomer, or pharmaceutically acceptable salt thereof, wherein $R^{12}$ is $C_{1-6}$alkyl and $R^{13}$ is $C_{1-6}$alkyl. In another embodiment is a compound of Formula (Il), or a solvate, hydrate, tautomer, N-oxide, stereoisomer, or pharmaceutically acceptable salt thereof, wherein $R^{12}$ is —$CH_3$ and $R^{13}$ is —$CH_3$.

In another embodiment is a compound of Formula (I) having the structure of Formula (Im):

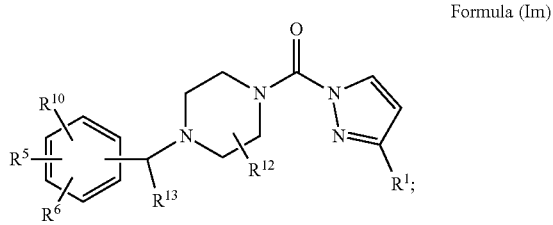

Formula (Im)

wherein:
$R^1$ is —$N(R^2)C(O)R^{15}$ or —$N(H)SO_2R^{15}$;
$R^2$ is H or $C_{1-6}$alkyl;
$R^5$ is H, —CN, halogen, $C_{1-6}$alkyl, $C_{1-6}$haloalkoxy, or phenyl;
$R^6$ is H, halogen, or $C_{1-6}$alkyl;
$R^{10}$ is —O—$C_{1-6}$haloalkyl, —O—$C_{1-6}$alkyl-$CO_2H$, —O—$C_{3-8}$cycloalkyl, —O—$C_{3-8}$cycloalkyl-$CO_2H$, —N(H)—$C_{1-6}$alkyl-$CO_2H$, or —$SO_2R^{17}$;
$R^{12}$ is H, halogen, or $C_{1-6}$alkyl;
$R^{13}$ is H or $C_{1-6}$alkyl;
$R^{15}$ is $C_{1-6}$alkyl or $C_{3-8}$cycloalkyl; and
$R^{17}$ is $C_{1-6}$alkyl or $C_{3-8}$cycloalkyl;
or a solvate, hydrate, tautomer, N-oxide, stereoisomer, or pharmaceutically acceptable salt thereof.

In another embodiment is a compound of Formula (Im), or a solvate, hydrate, tautomer, N-oxide, stereoisomer, or pharmaceutically acceptable salt thereof, wherein $R^1$ is —$N(R^2)C(O)R^{15}$. In another embodiment is a compound of Formula (Im), or a solvate, hydrate, tautomer, N-oxide, stereoisomer, or pharmaceutically acceptable salt thereof, wherein $R^1$ is —$N(R^2)C(O)R^{15}$ and $R^2$ is H. In another embodiment is a compound of Formula (Im), or a solvate, hydrate, tautomer, N-oxide, stereoisomer, or pharmaceutically acceptable salt thereof, wherein $R^1$ is —$N(H)C(O)R^{15}$ and $R^{15}$ is $C_{1-6}$alkyl. In another embodiment is a compound of Formula (Im), or a solvate, hydrate, tautomer, N-oxide, stereoisomer, or pharmaceutically acceptable salt thereof, wherein $R^1$ is —$N(H)C(O)R^{15}$ and $R^{15}$ is —$CH_3$. In another embodiment is a compound of Formula (Im), or a solvate, hydrate, tautomer, N-oxide, stereoisomer, or pharmaceutically acceptable salt thereof, wherein $R^1$ is —$N(H)C(O)R^{15}$ and $R^{15}$ is $C_{3-8}$cycloalkyl. In another embodiment is a compound of Formula (Im), or a solvate, hydrate, tautomer, N-oxide, stereoisomer, or pharmaceutically acceptable salt thereof, wherein $R^1$ is —$N(R^2)C(O)R^{15}$ and $R^2$ is $C_{1-6}$alkyl. In another embodiment is a compound of Formula (Im), or a solvate, hydrate, tautomer, N-oxide, stereoisomer, or pharmaceutically acceptable salt thereof, wherein $R^1$ is —$N(R^2)C(O)R^{15}$ and $R^2$ is —$CH_3$. In another embodiment is a compound of Formula (Im), or a solvate, hydrate, tautomer, N-oxide, stereoisomer, or pharmaceutically acceptable salt thereof, wherein $R^1$ is —$N(CH_3)C(O)R^{15}$ and $R^{15}$ is $C_{1-6}$alkyl. In another embodiment is a compound of Formula (Im), or a solvate, hydrate, tautomer, N-oxide, stereoisomer, or pharmaceutically acceptable salt thereof, wherein $R^1$ is —$N(CH_3)C(O)R^{15}$ and $R^{15}$ is —$CH_3$. In another embodiment is a compound of Formula (Im), or a solvate, hydrate, tautomer, N-oxide, stereoisomer, or pharmaceutically acceptable salt thereof, wherein $R^1$ is —$N(CH_3)C(O)R^{15}$ and $R^{15}$ is $C_{3-8}$cycloalkyl. In another embodiment is a compound of Formula (Im), or a solvate, hydrate, tautomer, N-oxide, stereoisomer, or pharmaceutically acceptable salt thereof, wherein $R^1$ is —$N(H)SO_2R^{15}$. In another embodiment is a compound of Formula (Im), or a solvate, hydrate, tautomer, N-oxide, stereoisomer, or pharmaceutically acceptable salt thereof, wherein $R^1$ is —$N(H)SO_2R^{15}$ and $R^{15}$ is $C_{1-6}$alkyl. In another embodiment is a compound of Formula (Im), or a solvate, hydrate, tautomer, N-oxide, stereoisomer, or pharmaceutically acceptable salt thereof, wherein $R^1$ is —$N(H)SO_2R^{15}$ and $R^{15}$ is —$CH_3$. In another embodiment is a compound of Formula (Im), or a solvate, hydrate, tautomer, N-oxide, stereoisomer, or pharmaceutically acceptable salt thereof, wherein $R^1$ is —$N(H)SO_2R^{15}$ and $R^{15}$ is $C_{3-8}$cycloalkyl.

In another embodiment is a compound of Formula (Im), or a solvate, hydrate, tautomer, N-oxide, stereoisomer, or pharmaceutically acceptable salt thereof, wherein $R^{10}$ is —O—$C_{1-6}$alkyl-$CO_2H$. In another embodiment is a compound of Formula (Im), or a solvate, hydrate, tautomer, N-oxide, stereoisomer, or pharmaceutically acceptable salt thereof, wherein $R^{10}$ is —$OCH_2CO_2H$. In another embodiment is a compound of Formula (Im), or a solvate, hydrate, tautomer, N-oxide, stereoisomer, or pharmaceutically acceptable salt thereof, wherein $R^{10}$ is —$OCH_2CH_2CO_2H$. In another embodiment is a compound of Formula (Im), or a solvate, hydrate, tautomer, N-oxide, stereoisomer, or pharmaceutically acceptable salt thereof, wherein $R^{10}$ is —$OCH_2CH_2CH_2CO_2H$. In another embodiment is a compound of Formula (Im), or a solvate, hydrate, tautomer, N-oxide, stereoisomer, or pharmaceutically acceptable salt thereof, wherein $R^{10}$ is —N(H)—$C_{1-6}$alkyl-$CO_2H$. In another embodiment is a compound of Formula (Im), or a solvate, hydrate, tautomer, N-oxide, stereoisomer, or pharmaceutically acceptable salt thereof, wherein $R^{10}$ is —N(H)$CH_2CO_2H$. In another embodiment is a compound of Formula (Im), or a solvate, hydrate, tautomer, N-oxide, stereoisomer, or pharmaceutically acceptable salt thereof, wherein $R^{10}$ is —N(H)$CH_2CH_2CO_2H$. In another embodiment is a compound of Formula (Im), or a solvate, hydrate, tautomer, N-oxide, stereoisomer, or pharmaceutically acceptable salt thereof, wherein $R^{10}$ is —N(H) $CH_2CH_2CH_2CO_2H$. In another embodiment is a compound of Formula (Im), or a solvate, hydrate, tautomer, N-oxide, stereoisomer, or pharmaceutically acceptable salt thereof, wherein $R^{10}$ is —O—$C_{1-6}$haloalkyl. In another embodiment is a compound of Formula (Im), or a solvate, hydrate, tautomer, N-oxide, stereoisomer, or pharmaceutically acceptable salt thereof, wherein $R^{10}$ is —$OCF_3$. In another embodiment is a compound of Formula (Im), or a solvate, hydrate, tautomer, N-oxide, stereoisomer, or pharmaceutically acceptable salt thereof, wherein $R^{10}$ is —O—$C_{3-8}$cycloalkyl. In another embodiment is a compound of Formula (Im), or a solvate, hydrate, tautomer, N-oxide, stereoisomer, or pharmaceutically acceptable salt thereof, wherein $R^{10}$ is —O—$C_{3-8}$cycloalkyl-$CO_2H$. In another embodiment is a compound of Formula (Im), or a solvate, hydrate, tautomer, N-oxide, stereoisomer, or pharmaceutically acceptable salt thereof, wherein $R^{10}$ is —$SO_2R^{17}$. In another embodiment is a compound of Formula (Im), or a solvate, hydrate, tautomer, N-oxide, stereoisomer, or pharmaceutically acceptable salt thereof, wherein $R^{10}$ is —$SO_2R^{17}$ and $R^{17}$ is $C_{1-6}$alkyl. In another embodiment is a compound of Formula (Im), or a solvate, hydrate, tautomer, N-oxide, stereoisomer, or pharmaceutically acceptable salt thereof, wherein $R^{10}$ is —$SO_2R^{17}$ and $R^{17}$ is —$CH_3$. In another embodiment is a compound of Formula (Im), or a solvate, hydrate, tautomer, N-oxide, stereoisomer, or pharmaceutically acceptable salt thereof, wherein $R^{10}$ is —$SO_2R^{17}$ and $R^{17}$ is $C_{3-8}$cycloalkyl. In another embodiment is a compound of Formula (Im), or a solvate, hydrate, tautomer, N-oxide, stereoisomer, or pharmaceutically acceptable salt thereof, wherein $R^5$ is H, CN, halogen, $C_{1-6}$alkyl, $C_{1-6}$haloalkyl, or $C_{1-6}$haloalkoxy. In another embodiment is a compound of Formula (Im), or a solvate, hydrate, tautomer, N-oxide, stereoisomer, or pharmaceutically acceptable salt thereof, wherein $R^5$ is H. In another embodiment is a compound of Formula (Im), or a solvate, hydrate, tautomer, N-oxide, stereoisomer, or pharmaceutically acceptable salt thereof, wherein $R^5$ is —CN. In another embodiment is a compound of Formula (Im), or a solvate, hydrate, tautomer, N-oxide, stereoisomer, or pharmaceutically acceptable salt thereof, wherein $R^5$ is halogen. In another embodiment is a compound of Formula (Im), or a solvate, hydrate, tautomer, N-oxide, stereoisomer, or pharmaceutically acceptable salt thereof, wherein $R^5$ is —Cl. In another embodiment is a compound of Formula (Im), or a solvate, hydrate, tautomer, N-oxide, stereoisomer, or pharmaceutically acceptable salt thereof, wherein $R^5$ is —F. In another embodiment is a compound of Formula (Im), or a solvate, hydrate, tautomer, N-oxide, stereoisomer, or pharmaceutically acceptable salt thereof, wherein $R^5$ is $C_{1-6}$alkyl. In another embodiment is a compound of Formula (Im), or a solvate, hydrate, tautomer, N-oxide, stereoisomer, or pharmaceutically acceptable salt thereof, wherein $R^5$ is —$CH_3$. In another embodiment is a compound of Formula (Im), or a solvate, hydrate, tautomer, N-oxide, stereoisomer, or pharmaceutically acceptable salt thereof, wherein $R^5$ is $C_{1-6}$haloalkyl. In another embodiment is a compound of Formula (Im), or a solvate, hydrate, tautomer, N-oxide, stereoisomer, or pharmaceutically acceptable salt thereof, wherein $R^5$ is —$CF_3$. In another embodiment is a compound of Formula (Im), or a solvate, hydrate, tautomer, N-oxide, stereoisomer, or pharmaceutically acceptable salt thereof, wherein $R^5$ is $C_{1-6}$haloalkoxy. In another embodiment is a compound of Formula (Im), or a solvate, hydrate, tautomer, N-oxide, stereoisomer, or pharmaceutically acceptable salt thereof, wherein $R^5$ is —$OCF_3$. In another embodiment is a compound of Formula (Im), or a solvate, hydrate, tautomer, N-oxide, stereoisomer, or pharmaceutically acceptable salt thereof, wherein $R^6$ is H. In another embodiment is a compound of Formula (Im), or a solvate, hydrate, tautomer, N-oxide, stereoisomer, or pharmaceutically acceptable salt thereof, wherein $R^6$ is halogen. In another embodiment is a compound of Formula (Im), or a solvate, hydrate, tautomer, N-oxide, stereoisomer, or pharmaceutically acceptable salt thereof, wherein $R^6$ is —Cl. In another embodiment is a compound of Formula (Im), or a solvate, hydrate, tautomer, N-oxide, stereoisomer, or pharmaceutically acceptable salt thereof, wherein $R^6$ is —F. In another embodiment is a compound of Formula (Im), or a solvate, hydrate, tautomer, N-oxide, stereoisomer, or pharmaceutically acceptable salt thereof, wherein $R^6$ is $C_{1-6}$alkyl. In another embodiment is a compound of Formula (Im), or a solvate, hydrate, tautomer, N-oxide, stereoisomer, or pharmaceutically acceptable salt thereof, wherein $R^6$ is —$CH_3$.

In another embodiment is a compound of Formula (Im), or a solvate, hydrate, tautomer, N-oxide, stereoisomer, or pharmaceutically acceptable salt thereof, wherein $R^{12}$ is H. In another embodiment is a compound of Formula (Im), or a solvate, hydrate, tautomer, N-oxide, stereoisomer, or pharmaceutically acceptable salt thereof, wherein $R^{12}$ is $C_{1-6}$alkyl. In another embodiment is a compound of Formula (Im), or a solvate, hydrate, tautomer, N-oxide, stereoisomer, or pharmaceutically acceptable salt thereof, wherein $R^{12}$ is —$CH_3$. In another embodiment is a compound of Formula (Im), or a solvate, hydrate, tautomer, N-oxide, stereoisomer, or pharmaceutically acceptable salt thereof, wherein $R^{13}$ is H. In another embodiment is a compound of Formula (Im), or a solvate, hydrate, tautomer, N-oxide, stereoisomer, or pharmaceutically acceptable salt thereof, wherein $R^{13}$ is $C_{1-6}$alkyl. In another embodiment is a compound of Formula (Im), or a solvate, hydrate, tautomer, N-oxide, stereoisomer, or pharmaceutically acceptable salt thereof, wherein $R^{13}$ is —$CH_3$. In another embodiment is a compound of Formula (Im), or a solvate, hydrate, tautomer, N-oxide, stereoisomer, or pharmaceutically acceptable salt thereof, wherein $R^{12}$ is H and $R^{13}$ is H. In another embodiment is a compound of Formula (Im), or a solvate, hydrate, tautomer, N-oxide, stereoisomer, or pharmaceutically acceptable salt thereof, wherein $R^{12}$ is H and $R^{13}$ is $C_{1-6}$alkyl. In another embodiment is a compound of Formula (Im), or a solvate, hydrate, tautomer, N-oxide, stereoisomer, or pharmaceutically acceptable salt thereof, wherein $R^{12}$ is H and $R^{13}$ is —$CH_3$. In another embodiment is a compound of Formula (Im), or a solvate, hydrate, tautomer, N-oxide, stereoisomer, or pharmaceutically acceptable salt thereof, wherein $R^{12}$ is $C_{1-6}$alkyl and $R^{13}$ is H. In another embodiment is a compound of Formula (Im), or a solvate, hydrate, tautomer, N-oxide, stereoisomer, or pharmaceutically acceptable salt thereof, wherein $R^{12}$ is —$CH_3$ and $R^{13}$ is H. In another embodiment is a compound of Formula (Im), or a solvate, hydrate, tautomer, N-oxide, stereoisomer, or pharmaceutically acceptable salt thereof, wherein $R^{12}$ is $C_{1-6}$alkyl and $R^{13}$ is $C_{1-6}$alkyl. In another embodiment is a compound of Formula (Im), or a solvate, hydrate, tautomer, N-oxide, stereoisomer, or pharmaceutically acceptable salt thereof, wherein $R^{12}$ is —$CH_3$ and $R^{13}$ is —$CH_3$.

Further embodiments provided herein include combinations of one or more of the particular embodiments set forth above.

In some embodiments, the compound disclosed herein is selected from examples 1-224.

In another embodiment is a compound having the structure:

121

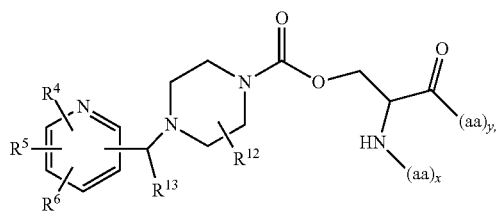

wherein $R^4$, $R^5$, $R^6$, $R^{12}$, and $R^{13}$ are defined as in Formula (Ia) described herein, and x and y are at least one amino acid (aa). In another embodiment is a compound having the structure:

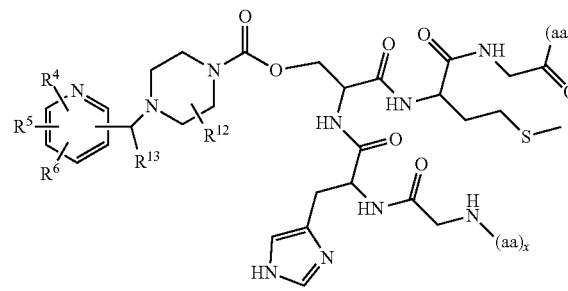

wherein $R^4$, $R^5$, $R^6$, $R^{12}$, and $R^{13}$ are defined as in Formula (Ia) described herein, and x and y are at least one amino acid (aa).

In another embodiment is a compound having the structure:

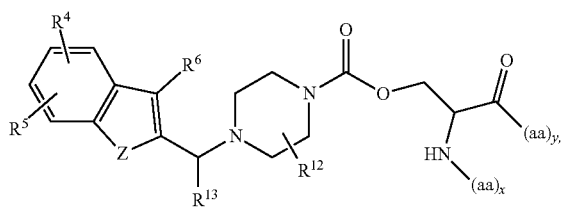

wherein $R^4$, $R^5$, $R^6$, $R^{12}$, $R^{13}$, and Z are defined as in Formula (Ib) described herein, and x and y are at least one amino acid (aa). In another embodiment is a compound having the structure:

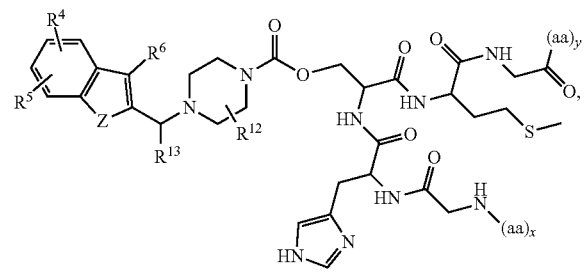

wherein $R^4$, $R^5$, $R^6$, $R^{12}$, $R^{13}$, and Z are defined as in Formula (Ib) described herein, and x and y are at least one amino acid (aa).

In another embodiment is a compound having the structure:

122

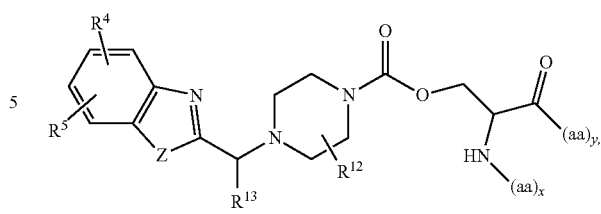

wherein $R^4$, $R^5$, $R^{12}$, $R^{13}$, and Z are defined as in Formula (Ic) described herein, and x and y are at least one amino acid (aa). In another embodiment is a compound having the structure:

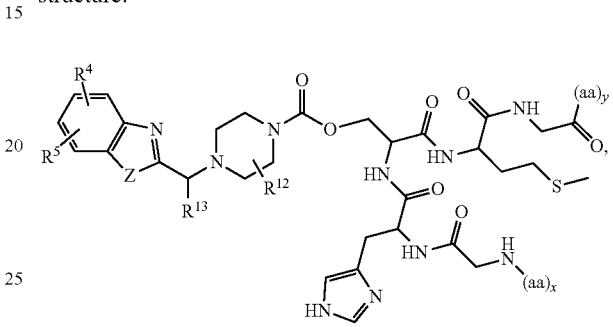

wherein $R^4$, $R^5$, $R^{12}$, $R^{13}$, and Z are defined as in Formula (Ic) described herein, and x and y are at least one amino acid (aa).

In another embodiment is a compound having the structure:

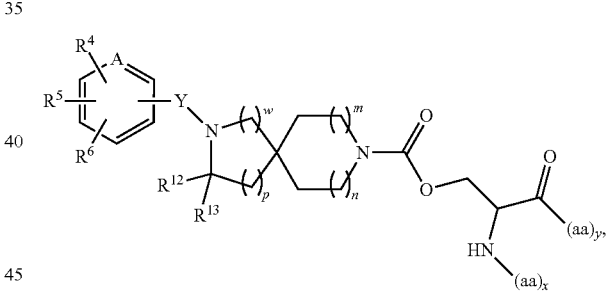

wherein $R^4$, $R^5$, $R^6$, $R^{12}$, $R^{13}$, A, Y, m, n, p, and w are defined as in Formula (Id) described herein, and x and y are at least one amino acid (aa). In another embodiment is a compound having the structure:

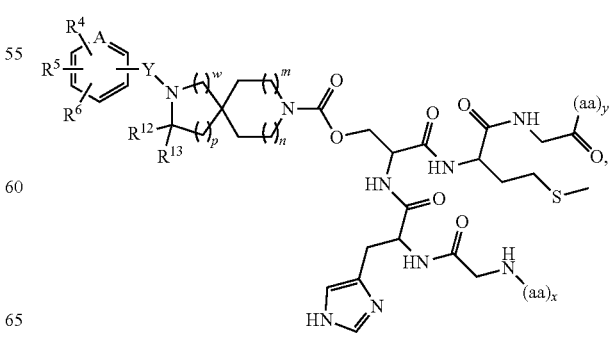

wherein $R^4$, $R^5$, $R^6$, $R^{12}$, $R^{13}$, A, Y, m, n, p, and w are defined as in Formula (Id) described herein, and x and y are at least one amino acid (aa).

In another embodiment is a compound having the structure:

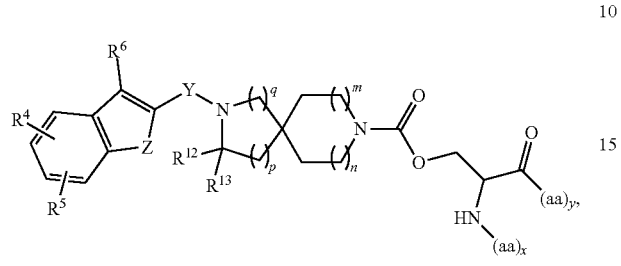

wherein $R^4$, $R^5$, $R^6$, $R^{12}$, $R^{13}$, Y, Z, m, n, p, and q are defined as in Formula (Ie) described herein, and x and y are at least one amino acid (aa). In another embodiment is a compound having the structure:

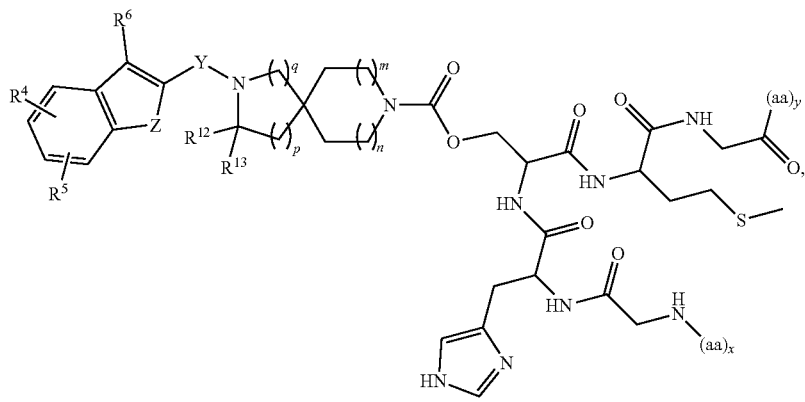

wherein $R^4$, $R^5$, $R^6$, $R^{12}$, $R^{13}$, Y, Z, m, n, p, and q are defined as in Formula (Ie) described herein, and x and y are at least one amino acid (aa).

In another embodiment is a compound having the structure:

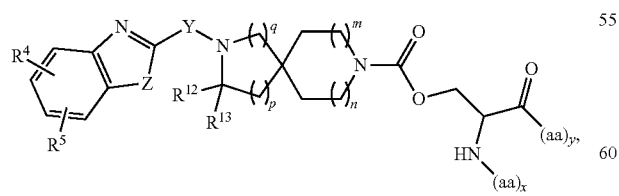

wherein $R^4$, $R^5$, $R^{12}$, $R^{13}$, Y, Z, m, n, p, and q are defined as in Formula (If) described herein, and x and y are at least one amino acid (aa). In another embodiment is a compound having the structure:

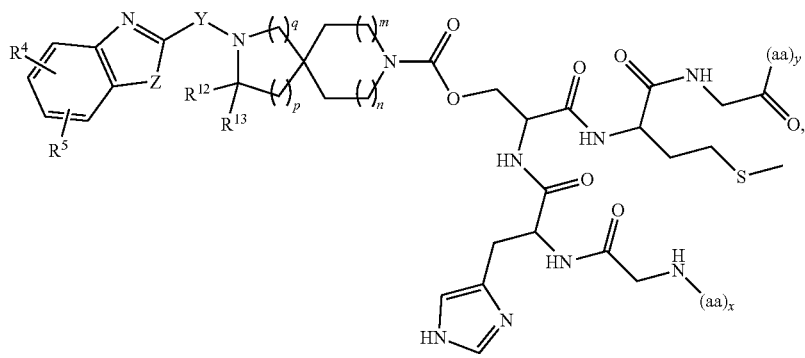

wherein $R^4$, $R^5$, $R^{12}$, $R^{13}$, Y, Z, m, n, p, and q are defined as in Formula (If) described herein, and x and y are at least one amino acid (aa).

In another embodiment is a compound having the structure:

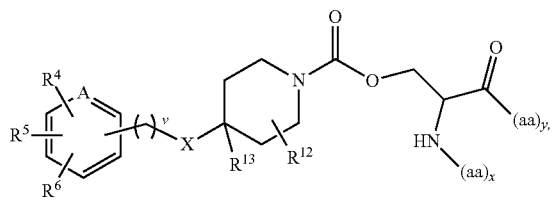

wherein $R^4$, $R^5$, $R^6$, $R^{12}$, $R^{13}$, A, X, and v are defined as in Formula (Ig) described herein, and x and y are at least one amino acid (aa). In another embodiment is a compound having the structure:

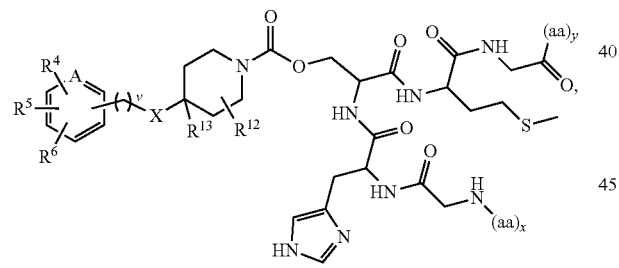

wherein $R^4$, $R^5$, $R^6$, $R^{12}$, $R^{13}$, A, X, and v are defined as in Formula (Ig) described herein, and x and y are at least one amino acid (aa).

In another embodiment is a compound having the structure:

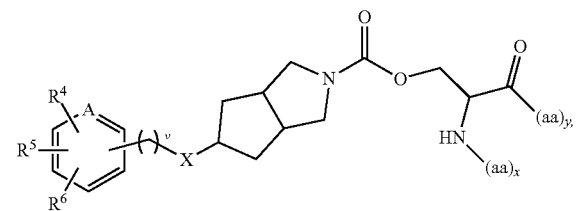

wherein $R^4$, $R^5$, $R^6$, $R^{12}$, $R^{13}$, A, X, and v are defined as in Formula (Ih) described herein, and x and y are at least one amino acid (aa). In another embodiment is a compound having the structure:

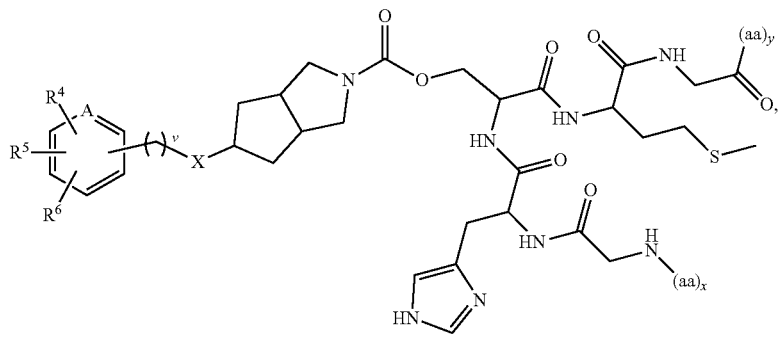

wherein $R^4$, $R^5$, $R^6$, $R^{12}$, $R^{13}$, A, X, and v are defined as in Formula (Ih) described herein, and x and y are at least one amino acid (aa).

In another embodiment is a compound having the structure:

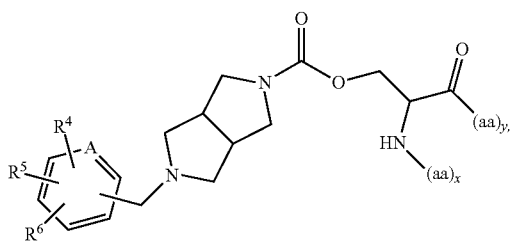

wherein $R^4$, $R^5$, and $R^6$ are defined as in Formula (Ii) described herein, and x and y are at least one amino acid (aa). In another embodiment is a compound having the structure:

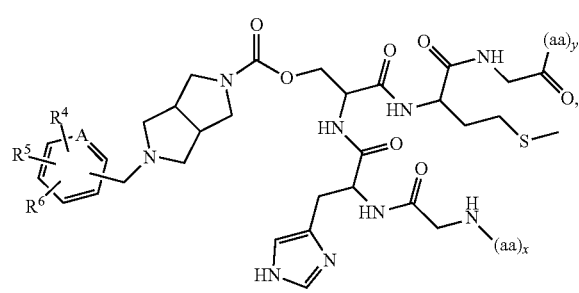

wherein $R^4$, $R^5$, and $R^6$ are defined as in Formula (Ii) described herein, and x and y are at least one amino acid (aa).

In another embodiment is a compound having the structure:

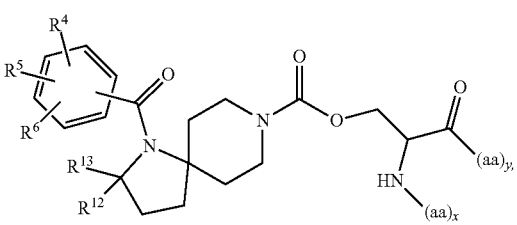

wherein $R^4$, $R^5$, $R^6$, $R^{12}$, and $R^{13}$ are defined as in Formula (Ij) described herein, and x and y are at least one amino acid (aa). In another embodiment is a compound having the structure:

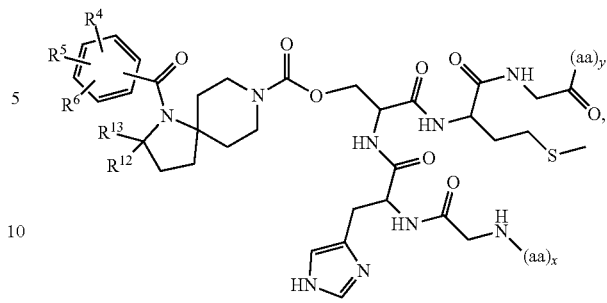

wherein $R^4$, $R^5$, $R^6$, $R^{12}$, and $R^{13}$ are defined as in Formula (Ij) described herein, and x and y are at least one amino acid (aa).

In another embodiment is a compound having the structure:

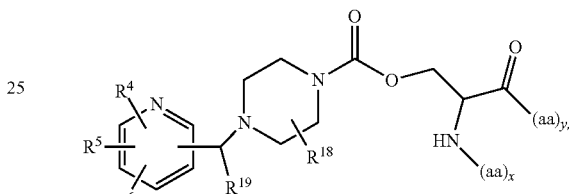

wherein $R^4$, $R^5$, $R^6$, $R^{18}$, and $R^{19}$ are defined as in Formula (Ik) described herein, and x and y are at least one amino acid (aa). In another embodiment is a compound having the structure:

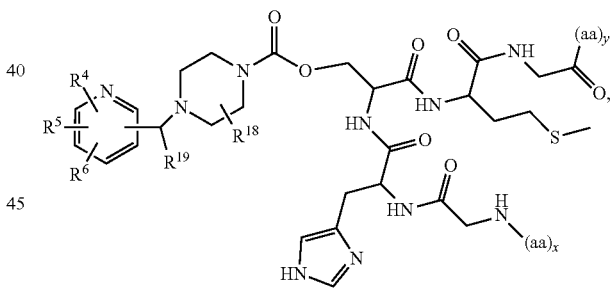

wherein $R^4$, $R^5$, $R^6$, $R^{18}$, and $R^{19}$ are defined as in Formula (Ik) described herein, and x and y are at least one amino acid (aa).

In another embodiment is a compound having the structure:

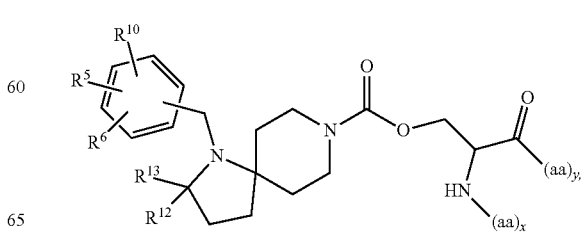

wherein $R^5$, $R^6$, $R^{10}$, $R^{12}$, and $R^{13}$ are defined as in Formula (II) described herein, and x and y are at least one amino acid (aa). In another embodiment is a compound having the structure:

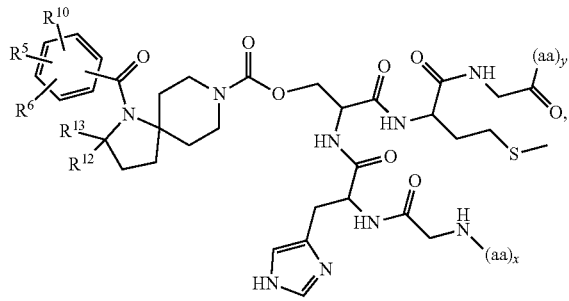

wherein $R^5$, $R^6$, $R^{10}$, $R^{12}$, and $R^{13}$ are defined as in Formula (II) described herein, and x and y are at least one amino acid (aa).

In another embodiment is a compound having the structure:

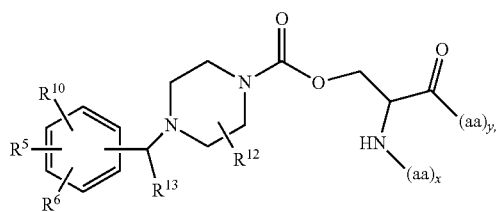

wherein $R^5$, $R^6$, $R^{10}$, $R^{12}$, and $R^{13}$ are defined as in Formula (Im) described herein, and x and y are at least one amino acid (aa). In another embodiment is a compound having the structure:

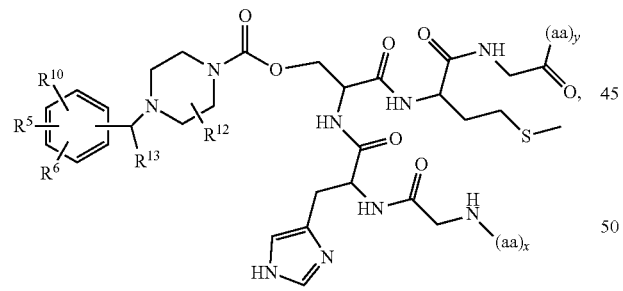

wherein $R^5$, $R^6$, $R^{10}$, $R^{12}$, and $R^{13}$ are defined as in Formula (Im) described herein, and x and y are at least one amino acid (aa).

Described herein are inhibitors of monoacylglycerol lipase (MAGL) having the structure of Formula (I), (Ia), (Ib), (Ic), (Id), (Ie), (If), (Ig), (Ih), (Ii), (Ij), (Ik), (Il), or (Im). In one embodiment, the inhibitors of MAGL are covalent inhibitors of MAGL, that is, the compounds of Formula (I), (Ia), (Ib), (Ic), (Id), (Ie), (If), (Ig), (Ih), (Ii), (Ij), (Ik), (Il), or (Im) react with a serine residue of MAGL to form a modified serine residue, comprising the staying group of Formula (I), (Ia), (Ib), (Ic), (Id), (Ie), (If), (Ig), (Ih), (Ii), (Ij), (Ik), (Il), or (Im); in such an embodiment, the leaving group of Formula (I), (Ia), (Ib), (Ic), (Id), (Ie), (If), (Ig), (Ih), (Ii), (Ij), (Ik), (Il), or (Im) is removed from the compound of Formula (I), (Ia), (Ib), (Ic), (Id), (Ie), (If), (Ig), (Ih), (Ii), (Ij), (Ik), (Il), or (Im). In a further embodiment, the covalent inhibitors of MAGL react irreversibly with a serine residue of MAGL to form the modified serine residue.

The staying group portion of the compounds of Formula (Ia) is

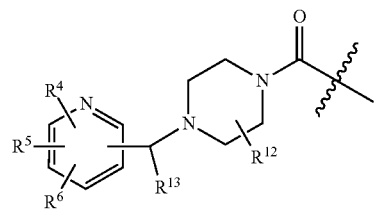

The staying group portion of the compounds of Formula (Ib) is

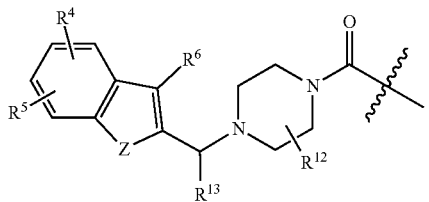

The staying group portion of the compounds of Formula (Ic) is

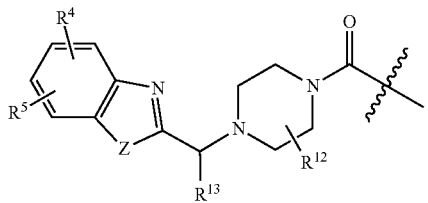

The staying group portion of the compounds of Formula (Id) is

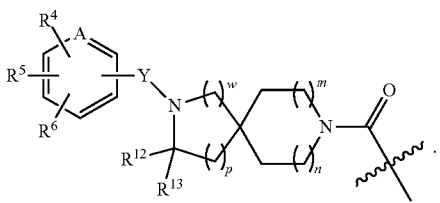

The staying group portion of the compounds of Formula (Ie) is

The staying group portion of the compounds of Formula (If) is

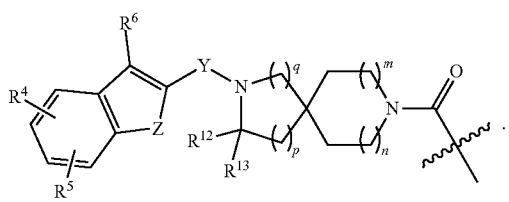

The staying group portion of the compounds of Formula (Ig) is

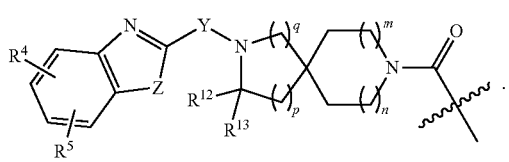

The staying group portion of the compounds of Formula (Ih) is

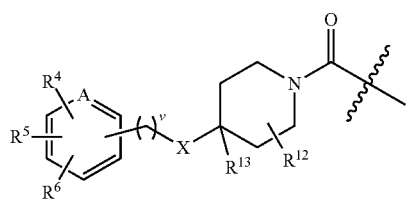

The staying group portion of the compounds of Formula (Ii) is

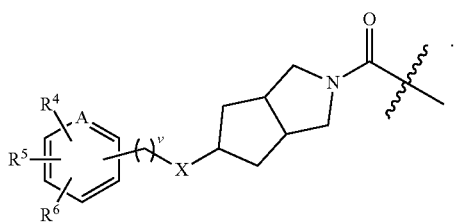

The staying group portion of the compounds of Formula (Ij) is

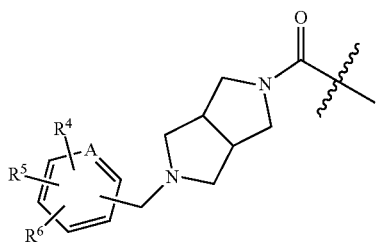

The staying group portion of the compounds of Formula (Ik) is

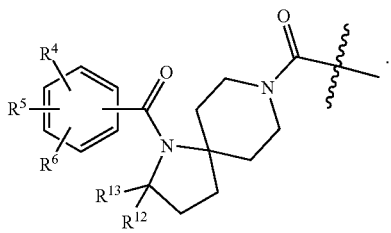

The staying group portion of the compounds of Formula (Il) is

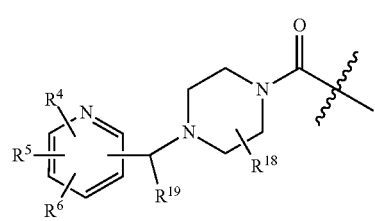

The staying group portion of the compounds of Formula (Im) is

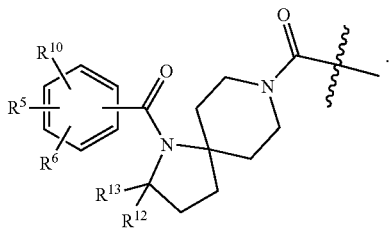

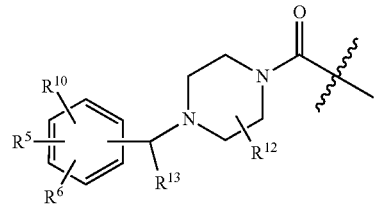

The leaving group portion of the compounds of Formula (I), (Ia), (Ib), (Ic), (Id), (Ie), (If), (Ig), (Ih), (Ii), (Ij), (Ik), (Il), or (Im) is:

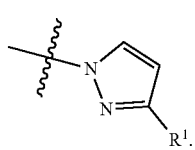

Preparation of Compounds

The compounds used in the reactions described herein are made according to organic synthesis techniques, starting from commercially available chemicals and/or from compounds described in the chemical literature. "Commercially available chemicals" are obtained from standard commercial sources including Acros Organics (Geel, Belgium), Aldrich Chemical (Milwaukee, Wis., including Sigma Chemical and Fluka), Apin Chemicals Ltd. (Milton Park, UK), Ark Pharm, Inc. (Libertyville, Ill.), Avocado Research (Lancashire, U.K.), BDH Inc. (Toronto, Canada), Bionet (Cornwall, U.K.), Chemservice Inc. (West Chester, Pa.), Combi-blocks (San Diego, Calif.), Crescent Chemical Co. (Hauppauge, N.Y.), eMolecules (San Diego, Calif.), Fisher Scientific Co. (Pittsburgh, Pa.), Fisons Chemicals (Leicestershire, UK), Frontier Scientific (Logan, Utah), ICN Biomedicals, Inc. (Costa Mesa, Calif.), Key Organics (Cornwall, U.K.), Lancaster Synthesis (Windham, N.H.), Matrix Scientific, (Columbia, S.C.), Maybridge Chemical Co. Ltd. (Cornwall, U.K.), Parish Chemical Co. (Orem, Utah), Pfaltz & Bauer, Inc. (Waterbury, Conn.), Polyorganix (Houston, Tex.), Pierce Chemical Co. (Rockford, Ill.), Riedel de Haen AG (Hanover, Germany), Ryan Scientific, Inc. (Mount Pleasant, S.C.), Spectrum Chemicals (Gardena, Calif.), Sundia Meditech, (Shanghai, China), TCI America (Portland, Oreg.), Trans World Chemicals, Inc. (Rockville, Md.), and WuXi (Shanghai, China).

Suitable reference books and treatises that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatises that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants are also identified through the indices of known chemicals prepared by the Chemical Abstract Service of the American Chemical Society, which are available in most public and university libraries, as well as through on-line databases (the American Chemical Society, Washington, D.C.). Chemicals that are known but not commercially available in catalogs are optionally prepared by custom chemical synthesis houses, where many of the standard chemical supply houses (e.g., those listed above) provide custom synthesis services. A reference for the preparation and selection of pharmaceutical salts of the compounds described herein is P. H. Stahl & C. G. Wermuth "Handbook of Pharmaceutical Salts", Verlag Helvetica Chimica Acta, Zurich, 2002.

Further Forms of Compounds Disclosed Herein

Isomers

Furthermore, in some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, compounds exist as tautomers. The compounds described herein include all possible tautomers within the formulas described herein. In some situations, the compounds described herein possess one or more chiral centers and each center exists in the R configuration or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion, are useful for the applications described herein. In some embodiments, the compounds described herein are prepared as optically pure enantiomers by chiral chromatographic resolution of the racemic mixture. In some embodiments, the compounds described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, dissociable complexes are preferred (e.g., crystalline diastereomeric salts). In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that does not result in racemization.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that are incorporated into compounds described herein include isotopes of hydrogen, carbon, nitrogen, oxygen, phosphorous, sulfur, fluorine, and chloride, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds described herein, and pharmaceutically acceptable salts, esters, prodrugs, solvate, hydrates or derivatives thereof which contain the aforementioned isotopes and/or other isotopes of other atoms are within the scope of this invention. Certain isotopically-labeled compounds, for example those into which radioactive isotopes such as $^3$H and $^{14}$C are incorporated, are useful in drug and/or substrate tissue distribution assays. Tritiated, i. e., $^3$H and carbon-14, i. e., $^{14}$C, isotopes are particularly preferred for their ease of preparation and detectability. Further, substitution with heavy isotopes such as deuterium, i.e., $^2$H, produces certain therapeutic advantages resulting from greater metabolic stability, for example increased in vivo half-life or reduced dosage requirements. In some embodiments, the isotopically labeled compounds, pharmaceutically acceptable salt, ester, prodrug, solvate, hydrate, or derivative thereof is prepared by any suitable method.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds described herein, or by separately reacting a purified compound in its free form with a suitable acid or base, and isolating the salt thus formed.

Solvates

In some embodiments, the compounds described herein exist as solvates. In some embodiments are methods of treating diseases by administering such solvates. Further described herein are methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein are conveniently prepared or formed during the processes described herein. By way of example only, hydrates of the compounds described herein are conveniently prepared by recrystallization from an aqueous/organic solvent mixture, using organic solvents including, but not limited to, dioxane, tetrahydrofuran or MeOH. In addition, the compounds provided herein exist in unsolvated as well as solvated forms. In general, the solvated forms are considered equivalent to the unsolvated forms for the purposes of the compounds and methods provided herein.

Prodrugs

In some embodiments, the compounds described herein exist in prodrug form. Also described herein are methods of treating diseases by administering such prodrugs. Further described herein are methods of treating diseases by administering such prodrugs as pharmaceutical compositions.

In some embodiments, prodrugs include compounds wherein an amino acid residue, or a polypeptide chain of two or more (e.g., two, three or four) amino acid residues is covalently joined through an amide or ester bond to a free amino, hydroxy, or carboxylic acid group of compounds described herein. The amino acid residues include but are not limited to the 20 naturally occurring amino acids and also includes 4-hydroxyproline, hydroxylysine, demosine, isodemosine, 3-methylhistidine, norvaline, beta-alanine, gamma-aminobutyric acid, cirtulline, homocysteine, homoserine, ornithine, and methionine sulfone. In other embodiments, prodrugs include compounds wherein a nucleic acid residue, or an oligonucleotide of two or more (e.g., two, three or four) nucleic acid residues is covalently joined to a compound described herein.

Pharmaceutically acceptable prodrugs of the compounds described herein also include, but are not limited to, esters, carbonates, thiocarbonates, N-acyl derivatives, N-acyloxyalkyl derivatives, quaternary derivatives of tertiary amines, N-Mannich bases, Schiff bases, amino acid conjugates, phosphate esters, metal salts, and sulfonate esters. In some embodiments, compounds having free amino, amido, hydroxy, or carboxylic groups are converted into prodrugs. For instance, free carboxyl groups are derivatized as amides or alkyl esters. In certain instances, all of these prodrug moieties incorporate groups including but not limited to ether, amine, and carboxylic acid functionalities.

Hydroxy prodrugs include esters, such as though not limited to, acyloxyalkyl (e.g. acyloxymethyl, acyloxyethyl) esters, alkoxycarbonyloxyalkyl esters, alkyl esters, aryl esters, phosphate esters, sulfonate esters, sulfate esters, disulfide containing esters, ethers, amides, carbamates, hemisuccinates, dimethylaminoacetates, and phosphoryloxymethyloxycarbonyls, as outlined in *Advanced Drug Delivery Reviews* 1996, 19, 115.

Amine derived prodrugs include, but are not limited to the following groups and combinations of groups:

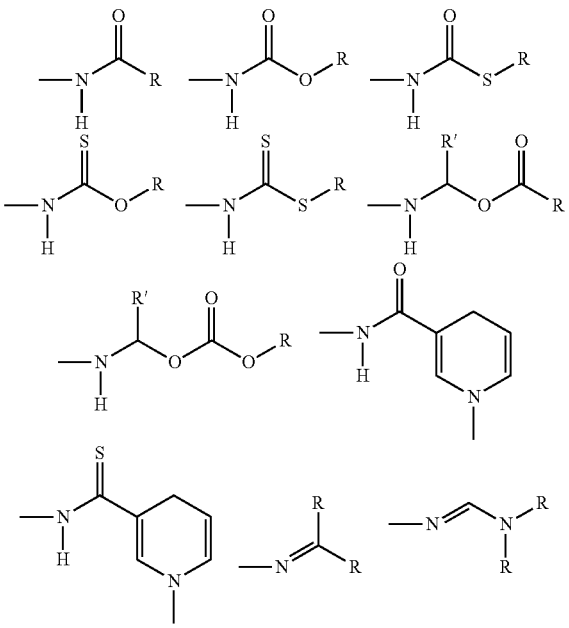

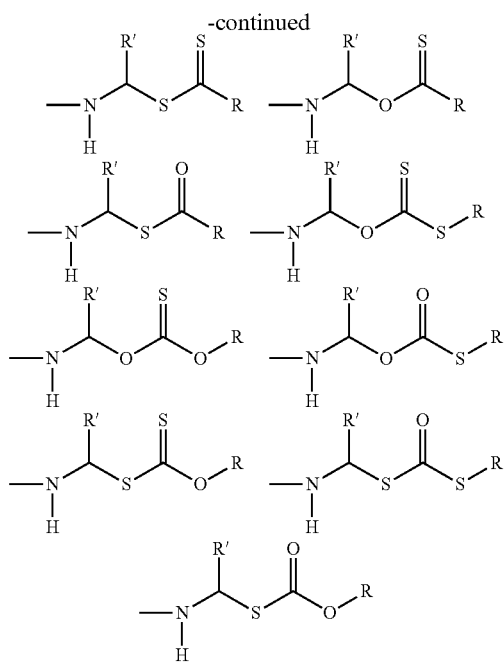

as well as sulfonamides and phosphonamides.

In certain instances, sites on any aromatic ring portions are susceptible to various metabolic reactions, therefore incorporation of appropriate substituents on the aromatic ring structures, reduce, minimize or eliminate this metabolic pathway.

Pharmaceutical Compositions

In certain embodiments, the compound of Formula (I), (Ia), (Ib), (Ic), (Id), (Ie), (If), (Ig), (Ih), (Ii), (Ij), (Ik), (Il), or (Im) as described herein is administered as a pure chemical. In some embodiments, the compound of Formula (I), (Ia), (Ib), (Ic), (Id), (Ie), (If), (Ig), (Ih), (Ii), (Ij), (Ik), (Il), or (Im) described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in *Remington: The Science and Practice of Pharmacy* (Gennaro, 21$^{st}$ Ed. Mack Pub. Co., Easton, Pa. (2005)).

Accordingly, provided herein is a pharmaceutical composition comprising at least one compound of Formula (I), (Ia), (Ib), (Ic), (Id), (Ie), (If), (Ig), (Ih), (Ii), (Ij), (Ik), (Il), or (Im) described herein, or a stereoisomer, pharmaceutically acceptable salt, hydrate, solvate, or N-oxide thereof, together with one or more pharmaceutically acceptable carriers. The carrier(s) (or excipient(s)) is acceptable or suitable if the carrier is compatible with the other ingredients of the composition and not deleterious to the recipient (i.e., the subject) of the composition.

One embodiment provides a pharmaceutical composition comprising a pharmaceutically acceptable excipient and a compound of Formula (I), or a pharmaceutically acceptable salt thereof. Another embodiment provides a pharmaceutical composition comprising a pharmaceutically acceptable excipient and a compound of Formula (Ia), or a pharmaceutically acceptable salt thereof. Another embodiment provides a pharmaceutical composition comprising a pharmaceutically acceptable excipient and a compound of Formula (Ib), or a pharmaceutically acceptable salt thereof. Another embodiment provides a pharmaceutical composition comprising a pharmaceutically acceptable excipient and a compound of Formula (Ic), or a pharmaceutically acceptable salt thereof. Another embodiment provides a pharmaceutical composition comprising a pharmaceutically acceptable excipient and a compound of Formula (Id), or a pharmaceutically acceptable salt thereof. Another embodiment provides a pharmaceutical composition comprising a pharmaceutically acceptable excipient and a compound of Formula (Ie), or a pharmaceutically acceptable salt thereof. Another embodiment provides a pharmaceutical composition comprising a pharmaceutically acceptable excipient and a compound of Formula (If), or a pharmaceutically acceptable salt thereof. Another embodiment provides a pharmaceutical composition comprising a pharmaceutically acceptable excipient and a compound of Formula (Ig), or a pharmaceutically acceptable salt thereof. Another embodiment provides a pharmaceutical composition comprising a pharmaceutically acceptable excipient and a compound of Formula (Ih), or a pharmaceutically acceptable salt thereof. Another embodiment provides a pharmaceutical composition comprising a pharmaceutically acceptable excipient and a compound of Formula (Ii), or a pharmaceutically acceptable salt thereof.

Another embodiment provides a pharmaceutical composition consisting essentially of a pharmaceutically acceptable excipient and a compound of Formula (Ia), or a pharmaceutically acceptable salt thereof. Another embodiment provides a pharmaceutical composition consisting essentially of a pharmaceutically acceptable excipient and a compound of Formula (Ib), or a pharmaceutically acceptable salt thereof. Another embodiment provides a pharmaceutical composition consisting essentially of a pharmaceutically acceptable excipient and a compound of Formula (Ic), or a pharmaceutically acceptable salt thereof. Another embodiment provides a pharmaceutical composition consisting essentially of a pharmaceutically acceptable excipient and a compound of Formula (Id), or a pharmaceutically acceptable salt thereof. Another embodiment provides a pharmaceutical composition consisting essentially of a pharmaceutically acceptable excipient and a compound of Formula (Ie), or a pharmaceutically acceptable salt thereof. Another embodiment provides a pharmaceutical composition consisting essentially of a pharmaceutically acceptable excipient and a compound of Formula (If), or a pharmaceutically acceptable salt thereof. Another embodiment provides a pharmaceutical composition consisting essentially of a pharmaceutically acceptable excipient and a compound of Formula (Ig), or a pharmaceutically acceptable salt thereof. Another embodiment provides a pharmaceutical composition consisting essentially of a pharmaceutically acceptable excipient and a compound of Formula (Ih), or a pharmaceutically acceptable salt thereof. Another embodiment provides a pharmaceutical composition consisting essentially of a pharmaceutically acceptable excipient and a compound of Formula (Ii), or a pharmaceutically acceptable salt thereof.

In certain embodiments, the compound of Formula (I), (Ia), (Ib), (Ic), (Id), (Ie), (If), (Ig), (Ih), (Ii), (Ij), (Ik), (Il), or (Im) as described herein is substantially pure, in that it contains less than about 5%, or less than about 1%, or less than about 0.1%, of other organic small molecules, such as contaminating intermediates or by-products that are created, for example, in one or more of the steps of a synthesis method.

These formulations include those suitable for oral, rectal, topical, buccal, parenteral (e.g., subcutaneous, intramuscular, intradermal, or intravenous), vaginal, ophthalmic, or aerosol administration, although the most suitable form of administration in any given case will depend on the degree and severity of the condition being treated and on the nature of the particular compound being used. For example, disclosed compositions are formulated as a unit dose, and/or are formulated for oral or subcutaneous administration.

Exemplary pharmaceutical compositions are used in the form of a pharmaceutical preparation, for example, in solid, semisolid or liquid form, which includes one or more of a disclosed compound, as an active ingredient, in a mixture with an organic or inorganic carrier or excipient suitable for external, enteral or parenteral applications. In some embodiments, the active ingredient is compounded, for example, with the usual non-toxic, pharmaceutically acceptable carriers for tablets, pellets, capsules, suppositories, solutions, emulsions, suspensions, and any other form suitable for use. The active object compound is included in the pharmaceutical composition in an amount sufficient to produce the desired effect upon the process or condition of the disease.

In some embodiments for preparing solid compositions such as tablets, the principal active ingredient is mixed with a pharmaceutical carrier, e.g., conventional tableting ingredients such as corn starch, lactose, sucrose, sorbitol, talc, stearic acid, magnesium stearate, dicalcium phosphate, or gums, and other pharmaceutical diluents, e.g., water, to form a solid preformulation composition containing a homogeneous mixture of a disclosed compound or a non-toxic pharmaceutically acceptable salt thereof. When referring to these preformulation compositions as homogeneous, it is meant that the active ingredient is dispersed evenly throughout the composition so that the composition is readily subdivided into equally effective unit dosage forms such as tablets, pills and capsules.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, cellulose, microcrystalline cellulose, silicified microcrystalline cellulose, lactose, sucrose, glucose, mannitol, and/or silicic acid; (2) binders, such as, for example, carboxymethylcellulose, hypromellose, alginates, gelatin, polyvinyl pyrrolidone, sucrose and/or acacia; (3) humectants, such as glycerol; (4) disintegrating agents, such as crospovidone, croscarmellose sodium, sodium starch glycolate, agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, docusate sodium, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, in some embodiments, the compositions comprise buffering agents. In some embodiments, solid compositions of a similar type are also employed as fillers in soft and hard-filled gelatin capsules using such excipients as lactose or milk sugars, as well as high molecular weight polyethylene glycols and the like.

In some embodiments, a tablet is made by compression or molding, optionally with one or more accessory ingredients. In some embodiments, compressed tablets are prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. In some embodiments, molded tablets are made by molding in a suitable machine a mixture of the subject composition moistened with an inert liquid diluent. In some embodiments, tablets, and other solid dosage forms, such as dragees, capsules, pills, and granules, are scored or prepared with coatings and shells, such as enteric coatings and other coatings.

Compositions for inhalation or insufflation include solutions and suspensions in pharmaceutically acceptable aqueous or organic solvents, or mixtures thereof, and powders. Liquid dosage forms for oral administration include pharmaceutically acceptable emulsions, microemulsions, solutions, suspensions, syrups and elixirs. In addition to the subject composition, in some embodiments, the liquid dosage forms contain inert diluents, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (optionally, cottonseed, groundnut, corn, germ, olive, castor and sesame oils), glycerol, tetrahydrofuryl alcohol, polyethylene glycols and fatty acid esters of sorbitan, cyclodextrins and mixtures thereof.

In some embodiments, suspensions, in addition to the subject composition, contain suspending agents as, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

In some embodiments, formulations for rectal or vaginal administration are presented as a suppository, which are prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent.

Dosage forms for transdermal administration of a subject composition include powders, sprays, ointments, pastes, creams, lotions, gels, solutions, patches and inhalants. In some embodiments, the active component is mixed under sterile conditions with a pharmaceutically acceptable carrier, and with any preservatives, buffers, or propellants as required.

In some embodiments, the ointments, pastes, creams and gels contain, in addition to a subject composition, excipients, such as animal and vegetable fats, oils, waxes, paraffins, starch, tragacanth, cellulose derivatives, polyethylene glycols, silicones, bentonites, silicic acid, talc, and zinc oxide, or mixtures thereof.

In some embodiments, powders and sprays contain, in addition to a subject composition, excipients such as lactose, talc, silicic acid, aluminum hydroxide, calcium silicates and polyamide powder, or mixtures of these substances. In some embodiments, sprays additionally contain customary propellants, such as chlorofluorohydrocarbons and volatile unsubstituted hydrocarbons, such as butane and propane.

In some embodiments, the compounds described herein are formulated as eye drops for ophthalmic administration.

Compositions and compounds disclosed herein alternatively are administered by aerosol. This is accomplished by preparing an aqueous aerosol, liposomal preparation or solid particles containing the compound. In some embodiments, a non-aqueous (e.g., fluorocarbon propellant) suspension is used. In some embodiments, sonic nebulizers are used because they minimize exposing the agent to shear, which results in degradation of the compounds contained in the subject compositions. Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Pharmaceutical compositions suitable for parenteral administration comprise a subject composition in combination with one or more pharmaceutically-acceptable sterile isotonic aqueous or non-aqueous solutions, dispersions, suspensions or emulsions, or sterile powders which are reconstituted into sterile injectable solutions or dispersions just prior to use, which, in some embodiments, contain antioxidants, buffers, bacteriostats, solutes which render the formulation isotonic with the blood of the intended recipient or suspending or thickening agents.

Examples of suitable aqueous and non-aqueous carriers which are employed in the pharmaceutical compositions include water, ethanol, polyols (such as glycerol, propylene glycol, polyethylene glycol, and the like), and suitable mixtures thereof, vegetable oils such as olive oil, and injectable organic esters such as ethyl oleate and cyclodextrins. Proper fluidity is maintained, for example, by the use of coating materials, such as lecithin, by the maintenance of the required particle size in the case of dispersions, and by the use of surfactants.

Also contemplated are enteral pharmaceutical formulations including a disclosed compound, an enteric material, and a pharmaceutically acceptable carrier or excipient thereof. Enteric materials refer to polymers that are substantially insoluble in the acidic environment of the stomach, and that are predominantly soluble in intestinal fluids at specific pHs. The small intestine is the part of the gastrointestinal tract (gut) between the stomach and the large intestine, and includes the duodenum, jejunum, and ileum. The pH of the duodenum is about 5.5, the pH of the jejunum is about 6.5 and the pH of the distal ileum is about 7.5. Accordingly, enteric materials are not soluble, for example, until a pH of about 5.0, of about 5.2, of about 5.4, of about 5.6, of about 5.8, of about 6.0, of about 6.2, of about 6.4, of about 6.6, of about 6.8, of about 7.0, of about 7.2, of about 7.4, of about 7.6, of about 7.8, of about 8.0, of about 8.2, of about 8.4, of about 8.6, of about 8.8, of about 9.0, of about 9.2, of about 9.4, of about 9.6, of about 9.8, or of about 10.0. Exemplary enteric materials include cellulose acetate phthalate (CAP), hydroxypropyl methylcellulose phthalate (HPMCP), polyvinyl acetate phthalate (PVAP), hydroxypropyl methylcellulose acetate succinate (HPMCAS), cellulose acetate trimellitate, hydroxypropyl methylcellulose succinate, cellulose acetate succinate, cellulose acetate hexahydrophthalate, cellulose propionate phthalate, cellulose acetate maleate, cellulose acetate butyrate, cellulose acetate propionate, copolymer of methylmethacrylic acid and methyl methacrylate, copolymer of methyl acrylate, methylmethacrylate and methacrylic acid, copolymer of methylvinyl ether and maleic anhydride (Gantrez ES series), ethyl methyacrylate-methylmethacrylate-chlorotrimethylammonium ethyl acrylate copolymer, natural resins such as zein, shellac and copal collophorium, and several commercially available enteric dispersion systems (e.g., Eudragit L30D55, Eudragit FS30D, Eudragit L100, Eudragit S100, Kollicoat EMM30D, Estacryl 30D, Coateric, and Aquateric). The solubility of each of the above materials is either known or is readily determinable in vitro.

The dose of the composition comprising at least one compound of Formula (I), (Ia), (Ib), (Ic), (Id), (Ie), (If), (Ig), (Ih), (Ii), (Ij), (Ik), (Il), or (Im) as described herein differs, depending upon the patient's (e.g., human) condition, that is, stage of the disease, general health status, age, and other factors.

Pharmaceutical compositions are administered in a manner appropriate to the disease to be treated (or prevented). An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity. Optimal doses are generally determined using experimental models and/or clinical trials. In some embodiments, the optimal dose depends upon the body mass, weight, or blood volume of the patient.

Oral doses typically range from about 1.0 mg to about 1000 mg, one to four times, or more, per day.

Methods

Disclosed herein are methods of modulating the activity of MAGL. Contemplated methods, for example, comprise exposing said enzyme to a compound described herein. In some embodiments, the compound utilized by one or more of the foregoing methods is one of the generic, subgeneric, or specific compounds described herein, such as a compound of Formula (I), (Ia), (Ib), (Ic), (Id), (Ie), (If), (Ig), (Ih), (Ii), (Ij), (Ik), (Il), or (Im). In some embodiments, provided herein is a compound of Formula (I), (Ia), (Ib), (Ic), (Id), (Ie), (If), (Ig), (Ih), (Ii), (Ij), (Ik), (Il), or (Im) wherein the compound is a MAGL inhibitor. In some embodiments, provided herein is a compound of Formula (I), (Ia), (Ib), (Ic), (Id), (Ie), (If), (Ig), (Ih), (Ii), (Ij), (Ik), (Il), or (Im) wherein the compound is a selective MAGL inhibitor. Another aspect of this disclosure provides methods of treating a disease associated with expression or activity of MAGL in a patient. In some embodiments, provided herein is a compound of Formula (I), (Ia), (Ib), (Ic), (Id), (Ie), (If), (Ig), (Ih), (Ii), (Ij), (Ik), (Il), or (Im) wherein the compound is selective in inhibiting MAGL as compared to inhibition of other serine hydrolases. In some embodiments, provided herein is a compound of Formula (I), (Ia), (Ib), (Ic), (Id), (Ie), (If), (Ig), (Ih), (Ii), (Ij), (Ik), (Il), or (Im) wherein the compound is 10, 100, or 1000 fold selective in inhibiting MAGL as compared to inhibition of other serine hydrolases.

In another embodiment is a method of treating pain in a patient, comprising administering a therapeutically effective amount of a compound of Formula (I), (Ia), (Ib), (Ic), (Id), (Ie), (If), (Ig), (Ih), (Ii), (Ij), (Ik), (Il), or (Im) described herein, or a solvate, hydrate, tautomer, N-oxide, or a pharmaceutically acceptable salt thereof, to a patient in need thereof to treat said pain. In another embodiment is a method of treating neuropathic pain in a patient, comprising administering a therapeutically effective amount of a compound of Formula (I), (Ia), (Ib), (Ic), (Id), (Ie), (If), (Ig), (Ih), (Ii), (Ij), (Ik), (Il), or (Im) described herein, or a solvate, hydrate, tautomer, N-oxide, or a pharmaceutically acceptable salt thereof, to a patient in need thereof to treat said neuropathic pain. In another embodiment is a method of treating inflammatory pain in a patient, comprising administering a therapeutically effective amount of a compound of Formula (I), (Ia), (Ib), (Ic), (Id), (Ie), (If), (Ig), (Ih), (Ii), (Ij), (Ik), (Il), or (Im) described herein, or a solvate, hydrate, tautomer, N-oxide, or a pharmaceutically acceptable salt thereof, to a patient in need thereof to treat said inflammatory pain.

Also contemplated herein in some embodiments are methods of treating and/or preventing in a patient in need thereof a disorder such as one or more of acute or chronic pain, bone cancer pain, rheumatoid arthritis pain, pruritus, vomiting or nausea, Down's syndrome, Parkinson's disease, epilepsy, NSAID-induced ulcers, opioid withdrawal, cannabis withdrawal, nicotine withdrawal, traumatic brain injury, ischemia, renal ischemia, cancers (e.g., solid tumor cancers such as breast, lung, head and neck, ovarian, sarcoma, melanoma, and/or prostate cancer); cancers such as melanoma, metastatic tumors, kidney or bladder cancers, brain, gastrointestinal cancers (e.g., colon cancer), leukemia or blood cancers (e.g., myeloid, lymphoid or monocytic cancers), liver injury, lung injury, skeletal muscle contusions, inflammatory disorders, and/or anxiety disorders. Contemplated methods include administering a pharmaceutically effective amount of a disclosed compound.

In some embodiments, provided herein is a method for treating, ameliorating and/or preventing damage from ischemia, for example, hepatic ischemia or reperfusion in a patient in need thereof, comprising administering a disclosed compound. Methods of treating patients with liver conditions resulting from oxidative stress and/or inflammatory damage are contemplated herein, e.g., contemplated herein are methods of treating liver fibrosis, iron overload, and/or corticosteroid therapy that result in liver damage, in a patient in need thereof.

In some embodiments, provide herein is a method for treating chronic pain such as inflammatory pain, visceral pain, back pain, post operative pain, and pain related to migraine, osteoarthritis, or rheumatoid arthritis.

In some embodiments, provide herein are methods for ameliorating cognitive function in a patient suffering from Down's syndrome or Alzheimer's disease, comprising administering an effective amount of a disclosed compound. Exemplary patients suffering from Down's syndrome are a pediatric patient (e.g., a patient of age 0-11 years, 0-18 years, 0-6 years, or e.g., 12 to 18 years), an adult patient (e.g., 18 years or older), or e.g., an older patient e.g., 18-40 years, 20-50 years). In some embodiments, such patients also suffer from further cognitive impairment and/or dementia, and/or seizures which, in some embodiments are due to production of prostaglandins and/or amyloid beta. For example, such patients also are suffering from, or have one or more of the following symptoms associated with early-mid or late stage cognitive impairment: loss of language, impairment of social skills, progressive loss of activities of daily living, and include psychotic behavior. Provided herein, for example, is a method for treating a patient having Down's syndrome or Alzheimer's disease with cognitive impairment, comprising administering an effective amount of a disclosed compound. Such disclosed methods result in cognitive improvement, for example, measured by IQ or the Arizona Cognitive Test Battery (e.g., measured with a cognitive test battery designed for use in individuals with Down's syndrome). For example, a treated patient using a disclosed method has at least one of: increased memory, improved memory or improved speech. In some embodiments, such disclosed methods result in a patient having an increased quality of life as measured by an adaptive behavior scale after said administration.

In other embodiments, a method for at least partially providing a Down's syndrome patient a neuroprotective (such as a disclosed compounds), that results in delayed onset of neurodegeneration or substantially prevents neurodegeneration, is provided. Administration to a patient is initiated before onset of neurodegeneration and/or onset of neurodegeneration symptoms. Contemplated herein are methods for treating and/or ameliorating cognitive decline, improving sleep duration and/or quality, and/or treating PANDAS (pediatric autoimmune neuropsychiatric disorders associated with streptococcal infections) in a patient in need thereof, comprising administering a disclosed compound.

In another embodiment is a method of treating a disease or disorder in a patient in need thereof, comprising administering to the patient in need thereof a therapeutically effective amount of a compound of Formula (I), (Ia), (Ib), (Ic), (Id), (Ie), (If), (Ig), (Ih), (Ii), (Ij), (Ik), (Il), or (Im) described herein, or a pharmaceutically acceptable salt or solvate thereof, wherein the disease or disorder is selected from the group consisting of migraine, epilepsy/seizure disorder, neuromyelitis optica (NMO), Tourette syndrome, persistent motor tic disorder, persistent vocal tic disorder, and abdominal pain associated with irritable bowel syndrome. In another embodiment is a method of treating migraine in a patient in need thereof, comprising administering to the patient a therapeutically effective amount of a compound of Formula (I), (Ia), (Ib), (Ic), (Id), (Ie), (If), (Ig), (Ih), (Ii), (Ij), (Ik), (Il), or (Im) described herein, or a pharmaceutically acceptable salt or solvate thereof. In another embodiment is a method of treating epilepsy/seizure disorder in a patient in need thereof, comprising administering to the patient a therapeutically effective amount of a compound of Formula (I), (Ia), (Ib), (Ic), (Id), (Ie), (If), (Ig), (Ih), (Ii), (Ij), (Ik), (Il), or (Im) described herein, or a pharmaceutically acceptable salt or solvate thereof. In another embodiment is a method of treating neuromyelitis optica (NMO) in a patient in need thereof, comprising administering to the patient a therapeutically effective amount of a compound of Formula (I), (Ia), (Ib), (Ic), (Id), (Ie), (If), (Ig), (Ih), (Ii), (Ij), (Ik), (Il), or (Im) described herein, or a pharmaceutically acceptable salt or solvate thereof. In another embodiment is a method of treating Tourette syndrome in a patient in need thereof, comprising administering to the patient a therapeutically effective amount of a compound of Formula (I), (Ia), (Ib), (Ic), (Id), (Ie), (If), (Ig), (Ih), (Ii), (Ij), (Ik), (Il), or (Im) described herein, or a pharmaceutically acceptable salt or solvate thereof. In another embodiment is a method of treating persistent motor tic disorder in a patient in need thereof, comprising administering to the patient a therapeutically effective amount of a compound of Formula (I), (Ia), (Ib), (Ic), (Id), (Ie), (If), (Ig), (Ih), (Ii), (Ij), (Ik), (Il), or (Im) described herein, or a pharmaceutically acceptable salt or solvate thereof. In another embodiment is a method of treating persistent vocal tic disorder in a patient in need thereof, comprising administering to the patient a therapeutically effective amount of a compound of Formula (I), (Ia), (Ib), (Ic), (Id), (Ie), (If), (Ig), (Ih), (Ii), (Ij), (Ik), (Il), or (Im) described herein, or a pharmaceutically acceptable salt or solvate thereof. In another embodiment is a method of treating abdominal pain associated with irritable bowel syndrome in a patient in need thereof, comprising administering to the patient a therapeutically effective amount of a compound of Formula (I), (Ia), (Ib), (Ic), (Id), (Ie), (If), (Ig), (Ih), (Ii), (Ij), (Ik), (Il), or (Im) described herein, or a pharmaceutically acceptable salt or solvate thereof.

In another embodiment is a method of treating cancer pain, pain caused by peripheral neuropathy, central pain, fibromyalgia, migraine, vasoocclussive painful crises in sickle cell disease, functional chest pain, rheumatoid arthritis, osteoarthritis, functional dyspepsia, or spasticity, pain, sleep disturbance, or bladder dysfunction associated with multiple sclerosis, in a patient in need thereof, comprising administering to the patient a therapeutically effective amount of a compound of Formula (I), (Ia), (Ib), (Ic), (Id), (Ie), (If), (Ig), (Ih), (Ii), (Ij), (Ik), (Il), or (Im) described herein, or a pharmaceutically acceptable salt or solvate thereof. In another embodiment is a method of treating cancer pain in a patient in need thereof, comprising administering to the patient a therapeutically effective amount of a compound of Formula (I), (Ia), (Ib), (Ic), (Id), (Ie), (If), (Ig), (Ih), (Ii), (Ij), (Ik), (Il), or (Im) described herein, or a pharmaceutically acceptable salt or solvate thereof. In another embodiment is a method of treating pain caused by peripheral neuropathy in a patient in need thereof, comprising administering to the patient a therapeutically effective amount of a compound of Formula (I), (Ia), (Ib), (Ic), (Id), (Ie), (If), (Ig), (Ih), (Ii), (Ij), (Ik), (Il), or (Im) described herein, or a pharmaceutically acceptable salt or solvate thereof. In another embodiment is a method of treating central pain in a patient in need thereof, comprising administering to the patient a therapeutically effective amount of a compound of Formula (I), (Ia), (Ib), (Ic), (Id), (Ie), (If), (Ig), (Ih), (Ii), (Ij), (Ik), (Il), or (Im) described herein, or a pharmaceutically acceptable salt or solvate thereof. In another embodiment is a method of treating fibromyalgia in a patient in need thereof, comprising administering to the patient a therapeutically effective amount of a compound of Formula (I), (Ia), (Ib), (Ic), (Id), (Ie), (If), (Ig), (Ih), (Ii), (Ij), (Ik), (Il), or (Im) described herein, or a pharmaceutically acceptable salt or solvate thereof. In another embodiment is a method of treating migraine in a patient in need thereof, comprising administering to the patient a therapeutically effective amount of a compound of Formula (I), (Ia), (Ib), (Ic), (Id), (Ie), (If), (Ig), (Ih), (Ii), (Ij), (Ik), (Il), or (Im) described herein, or a pharmaceutically acceptable salt or solvate thereof. In another embodiment is a method of treating vasoocclussive painful crises in sickle cell disease in a patient in need thereof, comprising administering to the patient a therapeutically effective amount of a compound of Formula (I), (Ia), (Ib), (Ic), (Id), (Ie), (If), (Ig), (Ih), (Ii), (Ij), (Ik), (Il), or (Im) described herein, or a pharmaceutically acceptable salt or solvate thereof. In another embodiment is a method of treating spasticity, pain, sleep disturbance, or bladder dysfunction associated with multiple sclerosis in a patient in need thereof, comprising administering to the patient a therapeutically effective amount of a compound of Formula (I), (Ia), (Ib), (Ic), (Id), (Ie), (If), (Ig), (Ih), (Ii), (Ij), (Ik), (Il), or (Im) described herein, or a pharmaceutically acceptable salt or solvate thereof. In another embodiment is a method of treating functional chest pain in a patient in need thereof, comprising administering to the patient a therapeutically effective amount of a compound of Formula (I), (Ia), (Ib), (Ic), (Id), (Ie), (If), (Ig), (Ih), (Ii), (Ij), (Ik), (Il), or (Im) described herein, or a pharmaceutically acceptable salt or solvate thereof. In another embodiment is a method of treating rheumatoid arthritis in a patient in need thereof, comprising administering to the patient a therapeutically effective amount of a compound of Formula (I), (Ia), (Ib), (Ic), (Id), (Ie), (If), (Ig), (Ih), (Ii), (Ij), (Ik), (Il), or (Im) described herein, or a pharmaceutically acceptable salt or solvate thereof. In another embodiment is a method of treating osteoarthritis in a patient in need thereof, comprising administering to the patient a therapeutically effective amount of a compound of Formula (I), (Ia), (Ib), (Ic), (Id), (Ie), (If), (Ig), (Ih), (Ii), (Ij), (Ik), (Il), or (Im) described herein, or a pharmaceutically acceptable salt or solvate thereof. In another embodiment is a method of treating functional dyspepsia in a patient in need thereof, comprising administering to the patient a therapeutically effective amount of a compound of Formula (I), (Ia), (Ib), (Ic), (Id), (Ie), (If), (Ig), (Ih), (Ii), (Ij), (Ik), (Il), or (Im) described herein, or a pharmaceutically acceptable salt or solvate thereof.

In another embodiment is a method of lowering intraocular eye pressure (TOP) in a patient in need thereof, comprising administering to the patient a therapeutically effective amount of a compound of Formula (I), (Ia), (Ib), (Ic), (Id), (Ie), (If), (Ig), (Ih), (Ii), (Ij), (Ik), (Il), or (Im) described herein, or a pharmaceutically acceptable salt or solvate thereof. In another embodiment is a method of treating glaucoma in a patient in need thereof, comprising administering to the patient a therapeutically effective amount of a compound of Formula (I), (Ia), (Ib), (Ic), (Id), (Ie), (If), (Ig), (Ih), (Ii), (Ij), (Ik), (Il), or (Im) described herein, or a pharmaceutically acceptable salt or solvate thereof.

In another embodiment is a method of treating atopic dermatitis in a patient in need thereof, comprising administering to the patient a therapeutically effective amount of a compound of Formula (I), (Ia), (Ib), (Ic), (Id), (Ie), (If), (Ig), (Ih), (Ii), (Ij), (Ik), (Il), or (Im) described herein, or a pharmaceutically acceptable salt or solvate thereof.

In another embodiment is a method of treating pruritis in a patient in need thereof, comprising administering to the patient a therapeutically effective amount of a compound of Formula (I), (Ia), (Ib), (Ic), (Id), (Ie), (If), (Ig), (Ih), (Ii), (Ij), (Ik), (Il), or (Im) described herein, or a pharmaceutically acceptable salt or solvate thereof.

In some embodiments, disclosed herein is a method of synergistically potentiating the activity of an opioid analgesic in a patient being treated with an opioid analgesic, comprising administering to the patient a therapeutically effective amount of a compound of Formula (I), (Ia), (Ib), (Ic), (Id), (Ie), (If), (Ig), (Ih), (Ii), (Ij), (Ik), (Il), or (Im) described herein, or a pharmaceutically acceptable salt or solvate thereof. In some embodiments, disclosed herein is a method of reducing the acute side-effects associated with an opioid analgesic in a patient being treated with an opioid analgesic, comprising administering to the patient a therapeutically effective amount of a compound of Formula (I), (Ia), (Ib), (Ic), (Id), (Ie), (If), (Ig), (Ih), (Ii), (Ij), (Ik), (Il), or (Im) described herein, or a pharmaceutically acceptable salt or solvate thereof.

In certain embodiments, a disclosed compound utilized by one or more of the foregoing methods is one of the generic, subgeneric, or specific compounds described herein, such as a compound of Formula (I), (Ia), (Ib), (Ic), (Id), (Ie), (If), (Ig), (Ih), (Ii), (Ij), (Ik), (Il), or (Im).

Disclosed compounds are administered to patients (animals and humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors, with the appropriate dosage ultimately being at the discretion of the attendant physician. For treating clinical conditions and diseases noted above, a contemplated compound disclosed herein is administered orally, subcutaneously, topically, parenterally, by inhalation spray, or rectally in dosage unit formulations containing conventional non-toxic pharmaceutically acceptable carriers, adjuvants and vehicles. Parenteral administration include subcutaneous injections, intravenous, or intramuscular injections or infusion techniques.

Also contemplated herein are combination therapies, for example, co-administering a disclosed compound and an additional active agent, as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually weeks, months or years depending upon the combination selected). Combination therapy is intended to embrace administration of multiple therapeutic agents in a sequential manner, that is, wherein each therapeutic agent is administered at a different time, as well as administration of these therapeutic agents, or at least two of the therapeutic agents, in a substantially simultaneous manner.

Substantially simultaneous administration is accomplished, for example, by administering to the subject a single formulation or composition, (e.g., a tablet or capsule having a fixed ratio of each therapeutic agent or in multiple, single formulations (e.g., capsules) for each of the therapeutic agents. Sequential or substantially simultaneous administration of each therapeutic agent is effected by any appropriate route including, but not limited to, oral routes, intravenous routes, intramuscular routes, and direct absorption through mucous membrane tissues. The therapeutic agents are administered by the same route or by different routes. For example, a first therapeutic agent of the combination selected is administered by intravenous injection while the other therapeutic agents of the combination are administered orally. Alternatively, for example, all therapeutic agents are administered orally or all therapeutic agents are administered by intravenous injection.

Combination therapy also embraces the administration of the therapeutic agents as described above in further combination with other biologically active ingredients and non-drug therapies. Where the combination therapy further comprises a non-drug treatment, the non-drug treatment is conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

The components of the combination are administered to a patient simultaneously or sequentially. It will be appreciated that the components are present in the same pharmaceutically acceptable carrier and, therefore, are administered simultaneously. Alternatively, the active ingredients are present in separate pharmaceutical carriers, such as, conventional oral dosage forms, that are administered either simultaneously or sequentially.

In some embodiments, for contemplated treatment of pain, a disclosed compound is co-administered with another therapeutic for pain such as an opioid, a cannabinoid receptor (CB-1 or CB-2) modulator, a COX-2 inhibitor, acetaminophen, and/or a non-steroidal anti-inflammatory agent. Additional therapeutics e.g., for the treatment of pain that are co-administered include morphine, codeine, hydromorphone, hydrocodone, oxymorphone, fentanyl, tramadol, and levorphanol.

Other contemplated therapeutics for co-administration include aspirin, naproxen, ibuprofen, salsalate, diflunisal, dexibuprofen, fenoprofen, ketoprofen, oxaprozin, loxoprofen, indomethacin, tolmetin, sulindac, etodolac, ketorolac, piroxicam, meloxicam, tenoxicam, droxicam, lornoxicam, celecoxib, parecoxib, rimonabant, and/or etoricoxib.

The following examples are provided merely as illustrative of various embodiments and shall not be construed to limit the invention in any way.

EXAMPLES

List of Abbreviations

As used above, and throughout the description of the invention, the following abbreviations, unless otherwise indicated, shall be understood to have the following meanings:

ACN or MeCN acetonitrile
Bn benzyl
BOC or Boc tert-butyl carbamate
CDI 1,1'-carbonyldiimidazole
Cy cyclohexyl
DCE dichloroethane ($ClCH_2CH_2Cl$)
DCM dichloromethane ($CH_2Cl_2$)
DIPEA or DIEA diisopropylethylamine
DMAP 4-(N,N-dimethylamino)pyridine
DMF dimethylformamide
DMA N,N-dimethylacetamide
DMSO dimethylsulfoxide
equiv equivalent(s)
Et ethyl
EtOH ethanol
EtOAc ethyl acetate
HATU 1-[bis(dimethylamino)methylene]-1H-1,2,3-triazolo[4,5-b]pyridinium 3-oxid hexafluorophosphate
HPLC high performance liquid chromatography
LAH lithium aluminum hydride
Me methyl
MeOH methanol
MS mass spectroscopy
NMM N-methylmorpholine
NMR nuclear magnetic resonance
PMB para-methoxybenzyl
TEA triethylamine
TFA trifluoroacetic acid
THF tetrahydrofuran
TLC thin layer chromatography I. Chemical Synthesis Unless otherwise noted, reagents and solvents were used as received from commercial suppliers. Anhydrous solvents and oven-dried glassware were used for synthetic transformations sensitive to moisture and/or oxygen. Yields were not optimized. Reaction times are approximate and were not optimized. Column chromatography and thin layer chromatography (TLC) were performed on silica gel unless otherwise noted. Spectra are given in ppm (δ) and coupling

149 constants (J) are reported in Hertz. For proton spectra the solvent peak was used as the reference peak.

Example 1: 4-((2-((8-(3-(methylsulfonamido)-1H-pyrazole-1-carbonyl)-1,8-diazaspiro[4.5]decan-1-yl)methyl)-5-(trifluoromethyl)phenyl)amino)butanoic acid

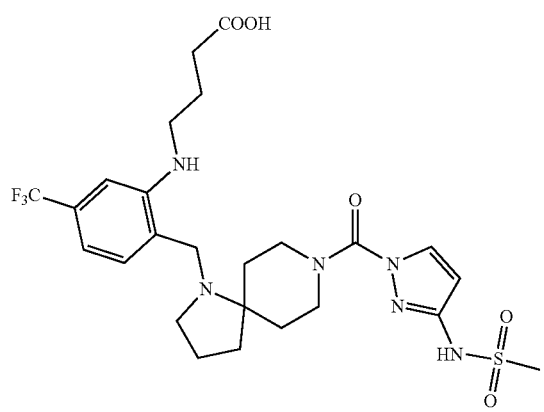 [SMILES: CS(=O)(=O)Nc1ccn(C(=O)N2CCC3(CCCN3Cc3ccc(C(F)(F)F)cc3NCCCC(=O)O)CC2)n1]

Step 1: Preparation of t-butyl 4-((4-methoxybenzyl)amino)butanoate

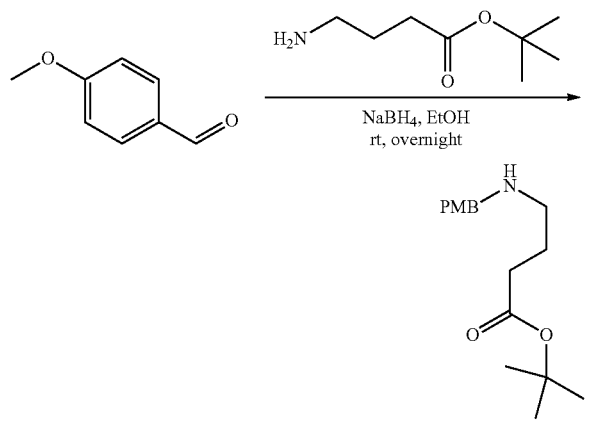

A flask was charged with 4-methoxybenzaldehyde (4.27 g, 31.4 mmol, 1.00 equiv), ethanol (30 mL), and t-butyl 4-aminobutanoate (5.00 g, 31.4 mmol, 1.00 equiv). The resulting solution was stirred 5 h at 70° C. and cooled to room temperature. Sodium borohydride (0.718 g, 18.9 mmol, 0.60 equiv) was added. The resulting solution was stirred overnight at room temperature and concentrated under reduced pressure. The residue was chromatographed to provide 4.55 g (52% yield) of t-butyl 4-((4-methoxybenzyl)amino)butanoate as a yellow oil. LCMS (ESI, m/z): 280 [M+H]⁺.

150

Step 2: Preparation of t-butyl 4-((2-formyl-5-(trifluoromethyl)phenyl)(4-methoxybenzyl)amino)butanoate

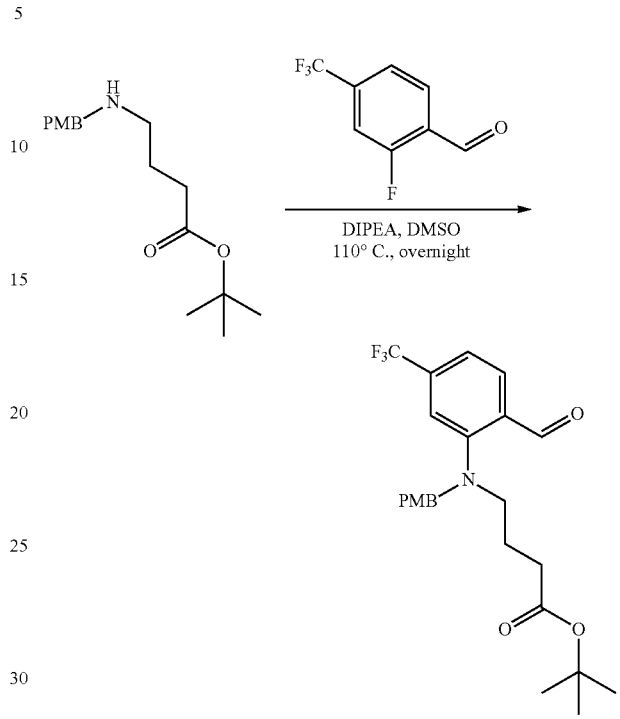

A flask was charged with t-butyl 4-((4-methoxybenzyl)amino)butanoate (3.00 g, 10.7 mmol, 1.00 equiv), DMSO (35 mL), 2-fluoro-4-(trifluoromethyl)benzaldehyde (2.07 g, 10.7 mmol, 1.00 equiv), and DIPEA (4.18 g, 32.3 mmol, 3.00 equiv) under nitrogen. The resulting solution was stirred overnight at 110° C. and quenched with water (50 mL). The resulting solution was extracted with DCM (2×80 mL) and the organic layers were combined, washed with brine (2×50 mL), dried over anhydrous sodium sulfate, filtered and concentrated under reduced pressure. The residue was chromatographed on a silica gel column to provide 2.20 g (45% yield) of t-butyl 4-((2-formyl-5-(trifluoromethyl)phenyl)(4-methoxybenzyl)amino)butanoate as a yellow oil. LCMS (ESI, m/z): 452 [M+H]⁺.

Step 3: Preparation of 4-nitrophenyl 3-(methylsulfonamido)-1H-pyrazole-1-carboxylate

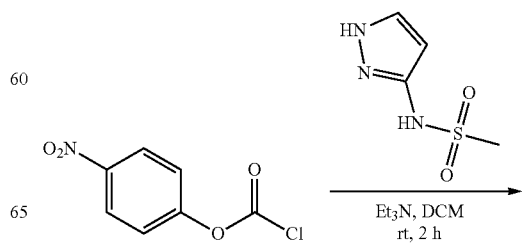

151

-continued

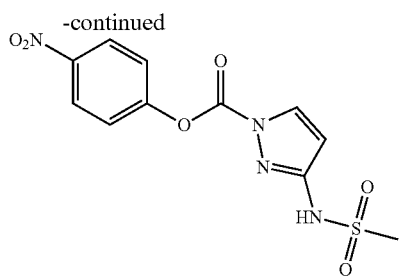

A flask was charged with N-(1H-pyrazol-3-yl)methane-sulfonamide (2.00 g, 12.4 mmol, 1.00 equiv), DCM (40 mL), triethylamine (3.77 g, 37.3 mmol, 3.00 equiv), and 4-nitrophenyl chloroformate (2.49 g, 12.4 mmol, 1.00 equiv). The resulting solution was stirred for 1 h at room temperature and concentrated under reduced pressure to provide 5.00 g (crude) of 4-nitrophenyl 3-methanesulfona-mido-1H-pyrazole-1-carboxylate as a yellow solid. LCMS (ESI, m/z): 327 [M+H]+.

Step 4: Preparation of t-butyl 8-(3-(methylsulfona-mido)-1H-pyrazole-1-carbonyl)-1,8-diazaspiro[4.5]decane-1-carboxylate

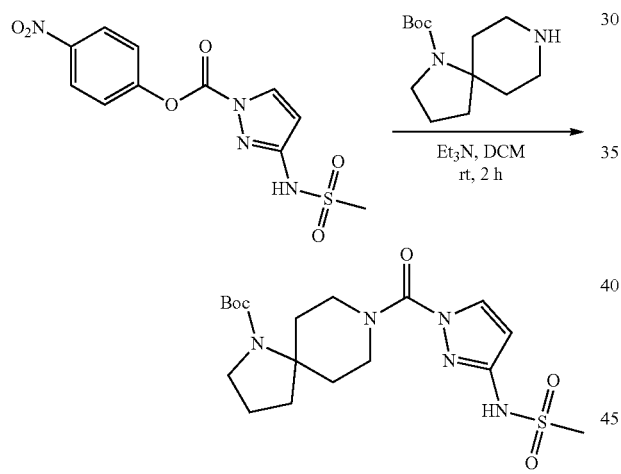

A flask was charged with 4-nitrophenyl 3-methanesulfo-namido-1H-pyrazole-1-carboxylate (3.65 g, 11.2 mmol, 1.00 equiv), DCM (40 mL), t-butyl 1,8-diazaspiro[4.5]decane-1-carboxylate (3.24 g, 13.5 mmol, 1.20 equiv), and triethylamine (3.39 g, 33.6 mmol, 3.00 equiv). The resulting solution was stirred overnight at room temperature and quenched with water (50 mL). The resulting solution was extracted with DCM (2×80 mL) and the organic layers were combined, washed with brine (2×50 mL), dried over anhydrous sodium sulfate, filtered and concentrated under reduced pressure. The residue was chromatographed on a silica gel column to provide 3.46 g (72% yield) of t-butyl 8-(3-(methylsulfonamido)-1H-pyrazole-1-carbonyl)-1,8-diazaspiro[4.5]decane-1-carboxylate as a yellow solid. LCMS (ESI, m/z): 428 [M+H]+.

152

Step 5: Preparation of N-(1-(1,8-diazaspiro[4.5]decane-8-carbonyl)-1H-pyrazol-3-yl)methanesulfo-namide

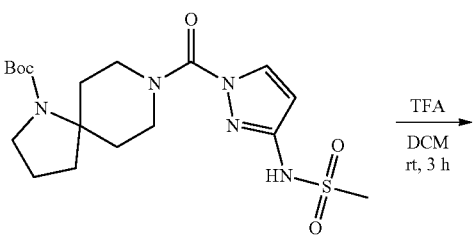

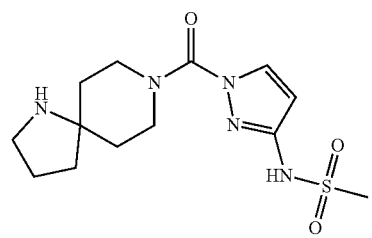

A flask was charged with t-butyl 8-(3-(methylsulfona-mido)-1H-pyrazole-1-carbonyl)-1,8-diazaspiro[4.5]decane-1-carboxylate (200 mg, 0.470 mmol, 1.00 equiv), DCM (10 mL), and TFA (2 mL). The resulting solution was stirred for 3 h at room temperature and concentrated under reduced pressure to provide 250 mg (crude) of N-(1-(1,8-diazaspiro[4.5]decane-8-carbonyl)-1H-pyrazol-3-yl)methanesulfona-mide as a yellow oil. LCMS (ESI, m/z): 328 [M+H]+.

Step 6: Preparation of t-butyl 4-((4-methoxybenzyl)(2-((8-(3-(methylsulfonamido)-1H-pyrazole-1-carbo-nyl)-1,8-diazaspiro[4.5]decan-1-yl)methyl)-5-(trif-luoromethyl)phenyl)amino)butanoate

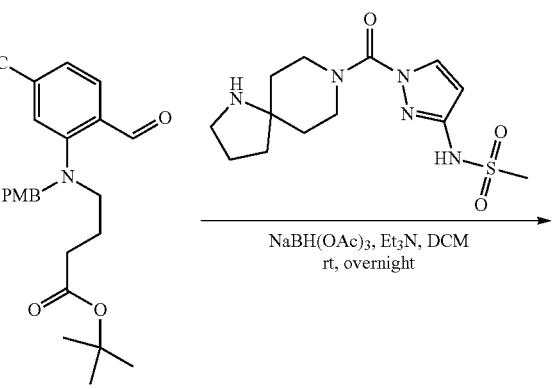

153

-continued

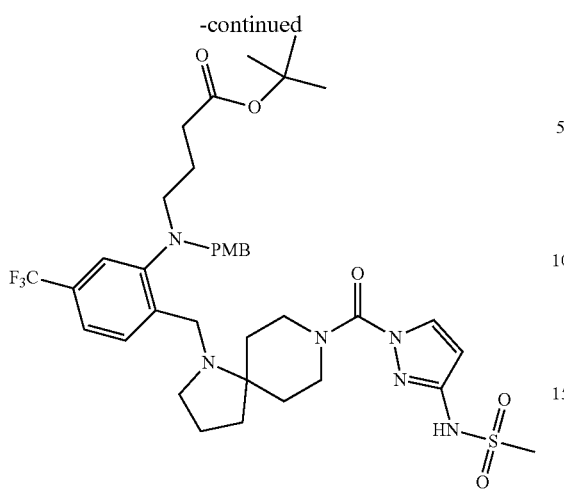

A flask was charged with N-(1-(1,8-diazaspiro[4.5]decane-8-carbonyl)-1H-pyrazol-3-yl)methanesulfonamide (153 mg, 0.470 mmol, 1.20 equiv), DCM (10 mL), triethylamine (118 mg, 1.17 mmol, 3.00 equiv), and t-butyl 4-((2-formyl-5-(trifluoromethyl)phenyl)(4-methoxybenzyl)amino)butanoate (177 mg, 0.390 mmol, 1.00 equiv). Sodium triacetoxyborohydride (248 mg, 1.17 mmol, 3.00 equiv) was added. The resulting solution was stirred overnight at room temperature and quenched with water (30 mL). The resulting solution was extracted with DCM (2×50 mL) and the organic layers were combined, washed with brine (2×30 mL), dried over anhydrous sodium sulfate, filtered and concentrated under reduced pressure. The residue was chromatographed on a silica gel column to provide 220 mg (74% yield) of t-butyl 4-((4-methoxybenzyl)(2-((8-(3-(methylsulfonamido)-1H-pyrazole-1-carbonyl)-1,8-diazaspiro[4.5]decan-1-yl)methyl)-5-(trifluoromethyl)phenyl)amino)butanoate as yellow oil. LCMS (ESI, m/z): 763 [M+H]⁺.

Step 7: Preparation of 4-((2-((8-(3-(methylsulfonamido)-1H-pyrazole-1-carbonyl)-1,8-diazaspiro[4.5]decan-1-yl)methyl)-5-(trifluoromethyl)phenyl)amino)butanoic acid

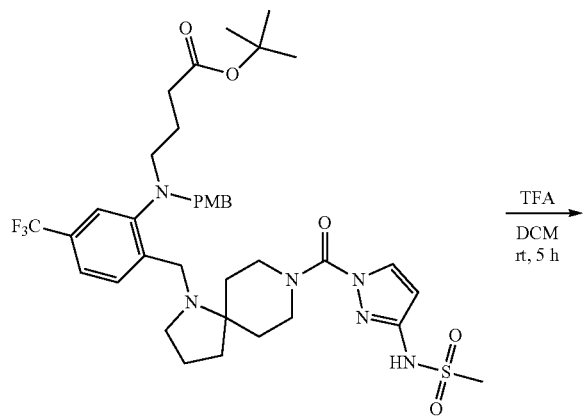

154

-continued

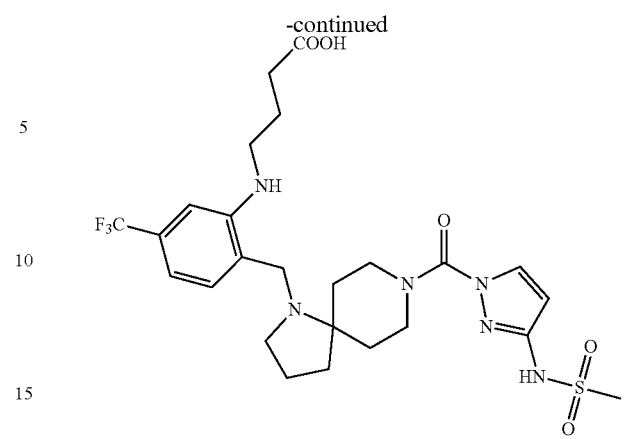

A flask was charged with t-butyl 4-((4-methoxybenzyl)(2-((8-(3-(methylsulfonamido)-1H-pyrazole-1-carbonyl)-1,8-diazaspiro[4.5]decan-1-yl)methyl)-5-(trifluoromethyl)phenyl)amino)butanoate (220 mg, 0.290 mmol, 1.00 equiv), DCM (10 mL), and TFA (2 mL). The resulting solution was stirred for 5 h at room temperature and concentrated under reduced pressure. The crude product (400 mg) was purified by preparative HPLC to provide 23.0 mg (14% yield) of 4-((2-((8-(3-(methylsulfonamido)-1H-pyrazole-1-carbonyl)-1,8-diazaspiro[4.5]decan-1-yl)methyl)-5-(trifluoromethyl)phenyl)amino)butanoic acid as a white solid. ¹H NMR (400 MHz, Methanol-$d_4$) 8.04 (d, J=2.8 Hz, 1H), 7.16 (d, J=7.6 Hz, 1H), 6.83-6.89 (m, 1H), 6.76 (s, 1H), 6.25 (d, J=2.8 Hz, 1H), 4.57-4.59 (m, 2H), 3.78 (s, 2H), 3.11-3.18 (m, 7H), 2.63 (t, J=7.0 Hz, 2H), 2.41 (t, J=7.4 Hz, 2H), 2.01-2.12 (m, 2H), 1.90-1.99 (m, 4H), 1.77-1.85 (m, 2H), 1.51-1.59 (m, 2H). LCMS (ESI, m/z): 587 [M+H]⁺.

Example 2: N-(1-(4-((3-(4-fluoropiperidin-1-yl)-4-(trifluoromethyl)benzyl)(methyl)amino)-4-methylpiperidine-1-carbonyl)-1H-pyrazol-3-yl)methanesulfonamide

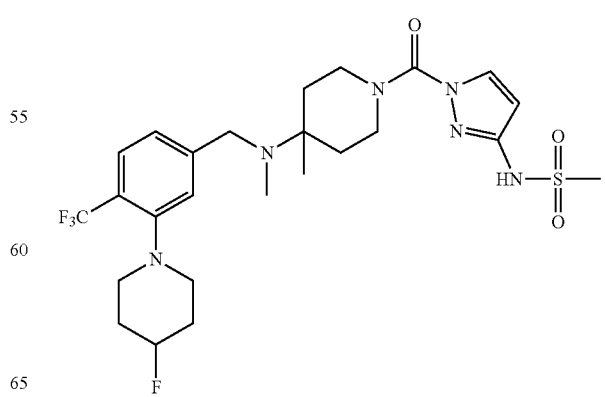

Step 1: Preparation of t-butyl 4-((3-bromo-4-(trifluoromethyl)benzyl)amino)-4-methylpiperidine-1-carboxylate

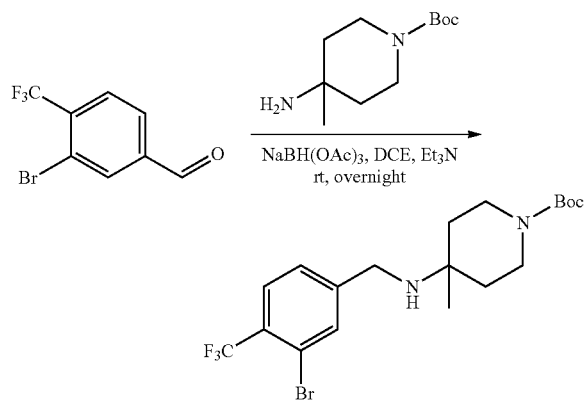

A vial was charged with DCE (10 mL), 3-bromo-4-(trifluoromethyl)benzaldehyde (252 mg, 1.00 mmol, 1.00 equiv), t-butyl 4-amino-4-methylpiperidine-1-carboxylate (214 mg, 1.00 mmol, 1.00 equiv), and triethylamine (303 mg, 2.99 mmol, 3.00 equiv). The resulting solution was stirred for 1 h at room temperature, then sodium triacetoxyborohydride (636 mg, 3.00 mmol, 3.00 equiv) was added. The mixture was stirred overnight at room temperature and quenched with water (10 mL), as described in Example 1, Step 6. The residue was chromatographed on a silica gel column to provide 300 mg (67% yield) of t-butyl 4-((3-bromo-4-(trifluoromethyl)benzyl)amino)-4-methylpiperidine-1-carboxylate as a yellow oil. LCMS (ESI, m/z): 451 [M+H]⁺.

Step 2: Preparation of t-butyl 4-((3-bromo-4-(trifluoromethyl)benzyl)(methyl)amino)-4-methylpiperidine-1-carboxylate

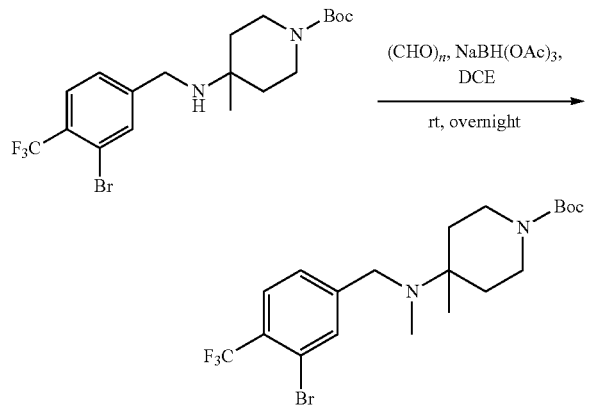

A vial was charged with DCE (10 mL), t-butyl 4-((3-bromo-4-(trifluoromethyl)benzyl)amino)-4-methylpiperidine-1-carboxylate (300 mg, 0.660 mmol, 1.00 equiv), and paraformaldehyde (200 mg, 6.67 mmol, 10.00 equiv). The resulting solution was stirred for 1 h at room temperature, then sodium triacetoxyborohydride (424 mg, 2.00 mmol, 3.00 equiv) was added. The resulting solution was stirred overnight at room temperature and then quenched with water (10 mL), as described in Example 1, Step 6. The residue was chromatographed on a silica gel column to provide 220 mg (71% yield) of t-butyl 4-((3-bromo-4-(trifluoromethyl)benzyl)(methyl)amino)-4-methylpiperidine-1-carboxylate as yellow oil. LCMS (ESI, m/z): 465 [M+H]⁺.

Step 3: Preparation of t-butyl 4-((3-(4-fluoropiperidin-1-yl)-4-(trifluoromethyl)benzyl)(methyl)amino)-4-methylpiperidine-1-carboxylate

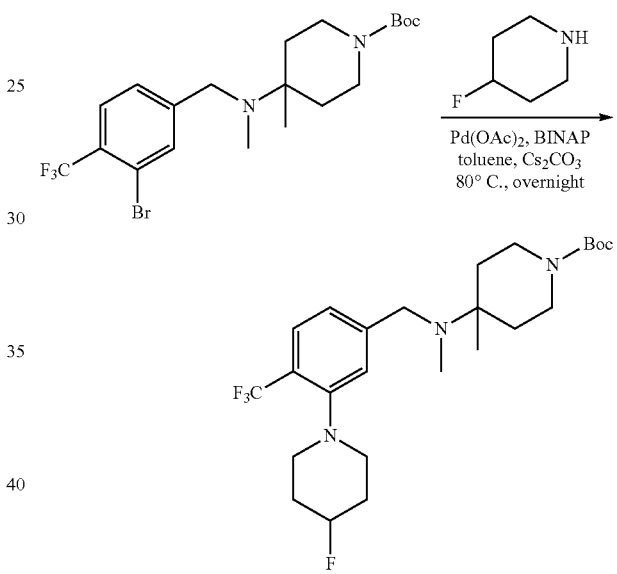

A vial was charged with toluene (10 mL), t-butyl 4-((3-bromo-4-(trifluoromethyl)benzyl)(methyl)amino)-4-methylpiperidine-1-carboxylate (220 mg, 0.470 mmol, 1.00 equiv), 4-fluoropiperidine (49.0 mg, 0.480 mmol, 1.00 equiv), cesium carbonate (464 mg, 1.42 mmol, 3.00 equiv), palladium acetate (21.0 mg, 0.0900 mmol, 0.20 equiv), and 2,2'-bis(diphenylphosphino)-1,1'-binaphthyl (59.0 mg, 0.0900 mmol, 0.20 equiv) under nitrogen. The resulting solution was stirred overnight at 80° C. and then quenched with water (10 ml). The mixture was extracted with EtOAc (3×10 mL) and the organic layers were combined, washed with brine (1×10 mL), dried over anhydrous sodium sulfate, filtered and concentrated under reduced pressure. The residue was chromatographed on a silica gel column to provide 135 mg (59% yield) of t-butyl 4-([[3-(4-fluoropiperidin-1-yl)-4-(trifluoromethyl)phenyl]methyl](methyl)amino)-4-methylpiperidine-1-carboxylate as a yellow oil. LCMS (ESI, m/z): 488 [M+H]⁺.

Step 4: Preparation of N-(3-(4-fluoropiperidin-1-yl)-4-(trifluoromethyl)benzyl)-N,4-dimethylpiperidin-4-amine

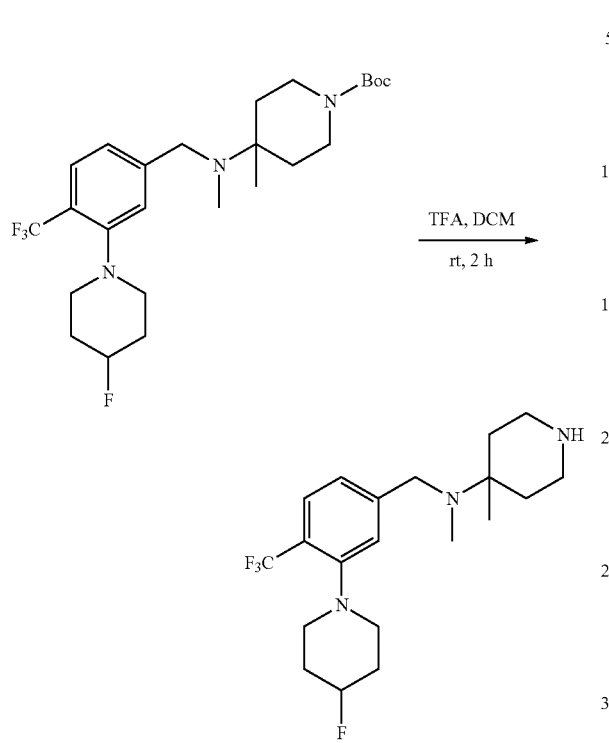

A vial was charged with t-butyl 4-([[3-(4-fluoropiperidin-1-yl)-4-(trifluoromethyl)phenyl]methyl](methyl)amino)-4-methylpiperidine-1-carboxylate (135 mg, 0.280 mmol, 1.00 equiv), DCM (10 ml) and TFA (4 ml). The resulting solution was stirred for 2 h at room temperature and concentrated under reduced pressure. The mixture was diluted with water (10 mL) and the pH value of the solution was adjusted to 9 with sodium hydroxide solution (1 mol/L aq). The mixture was extracted with DCM (3×10 mL) and the organic layers were combined, washed with brine (2×20 mL), dried over anhydrous sodium sulfate, filtered and concentrated under reduced pressure as described in Example 1, Step 3 to provide 100 mg (crude) of N-(3-(4-fluoropiperidin-1-yl)-4-(trifluoromethyl)benzyl)-N,4-dimethylpiperidin-4-amine as a yellow oil. LCMS (ESI, m/z): 388 [M+H]$^+$.

Step 5: Preparation of 4-((3-(4-fluoropiperidin-1-yl)-4-(trifluoromethyl)benzyl)(methyl)amino)-4-methylpiperidine-1-carbonyl chloride

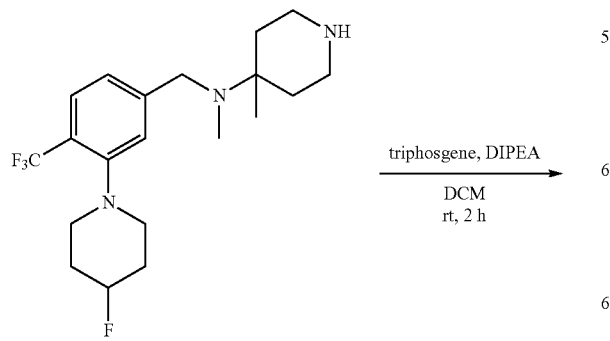

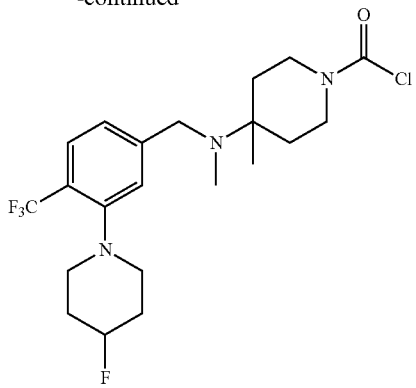

A vial was charged with N-(3-(4-fluoropiperidin-1-yl)-4-(trifluoromethyl)benzyl)-N,4-dimethylpiperidin-4-amine (100 mg, 0.260 mmol, 1.00 equiv), DCM (10 mL) and triphosgene (38.0 mg, 0.130 mmol, 0.50 equiv). DIPEA (100 mg, 0.780 mmol, 3.00 equiv) was added dropwise at 0° C. The resulting solution was stirred for 2 h at room temperature and quenched by water (10 mL). The mixture was extracted with DCM (3×10 mL) and the organic layers were combined, washed with brine (2×10 mL), dried over anhydrous sodium sulfate, filtered and concentrated under reduced pressure to provide 100 mg (crude) of 4-((3-(4-fluoropiperidin-1-yl)-4-(trifluoromethyl)benzyl)(methyl)amino)-4-methylpiperidine-1-carbonyl chloride as a yellow oil.

Step 6: Preparation of N-(1-(4-((3-(4-fluoropiperidin-1-yl)-4-(trifluoromethyl)benzyl)(methyl)amino)-4-methylpiperidine-1-carbonyl)-1H-pyrazol-3-yl)methanesulfonamide

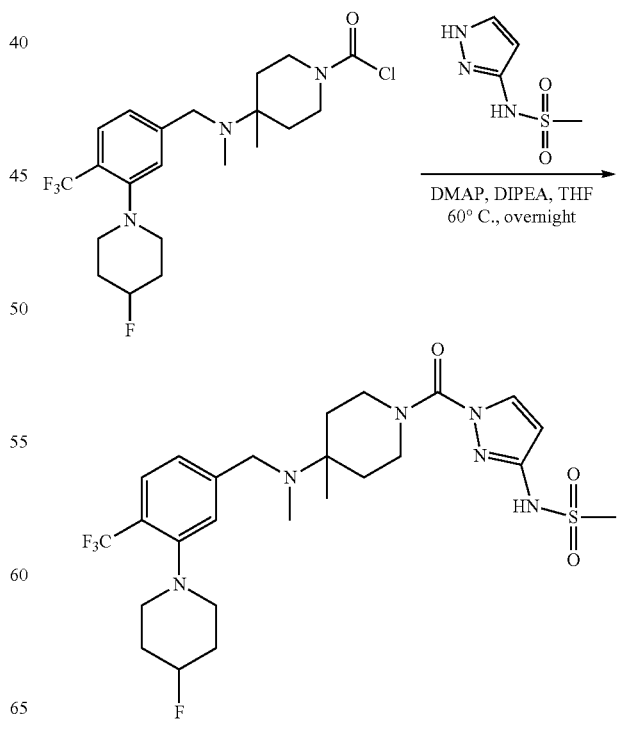

A vial was charged with THF (10 mL), 4-((3-(4-fluoropiperidin-1-yl)-4-(trifluoromethyl)benzyl)(methyl)amino)-4-methylpiperidine-1-carbonyl chloride (100 mg, 0.220 mmol, 1.00 equiv), N-(1H-pyrazol-3-yl)methanesulfonamide (36.0 mg, 0.220 mmol, 1.00 equiv), 4-dimethylaminopyridine (5.00 mg, 0.0400 mmol, 0.20 equiv), and DIPEA (86.0 mg, 0.670 mmol, 3.00 equiv). The resulting solution was stirred overnight at 60° C. and diluted with water (10 mL). The mixture was extracted with EtOAc (3×10 mL) and the organic layers were combined, washed with brine (1×10 mL), dried over anhydrous sodium sulfate, filtered and concentrated under reduced pressure. The crude product (150 mg) was purified by preparative HPLC to provide 6.2 mg (5% yield) of N-(1-(4-((3-(4-fluoropiperidin-1-yl)-4-(trifluoromethyl)benzyl)(methyl)amino)-4-methylpiperidine-1-carbonyl)-1H-pyrazol-3-yl)methanesulfonamide as colorless oil. $^1$H NMR (400 MHz, Chloroform-d) δ 8.04 (s, 1H), 7.56 (d, J=8.1 Hz, 1H), 7.31 (s, 1H), 7.22 (d, J=8.1 Hz, 1H), 6.33 (s, 1H), 4.72-4.96 (m, 1H), 3.87-4.08 (m, 2H), 3.66-3.86 (m, 2H), 3.58 (s, 2H), 3.13 (s, 3H), 3.03-3.12 (m, 2H), 2.79-2.88 (m, 2H), 2.11 (s, 3H), 1.93-2.08 (m, 6H), 1.48-1.70 (m, 3H), 1.07 (s, 3H). LCMS (ESI, m/z): 575 [M+H]$^+$.

Example 3: 2-(2-((4-(3-acetamido-1H-pyrazole-1-carbonyl)piperazin-1-yl)methyl)-5-chlorophenoxy) acetic acid

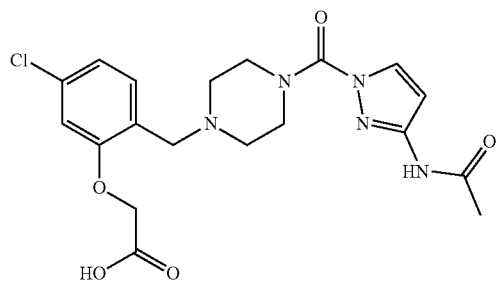 [SMILES: CC(=O)Nc1ccn(C(=O)N2CCN(Cc3ccc(Cl)cc3OCC(=O)O)CC2)n1]

Step 1: Preparation of t-butyl 4-(3-acetamido-1H-pyrazole-1-carbonyl)piperazine-1-carboxylate

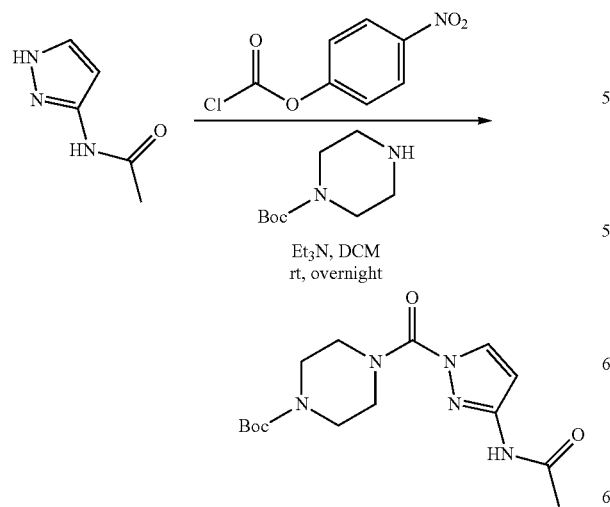

A flask was charged with N-(1H-pyrazol-3-yl)acetamide (5.00 g, 40.0 mmol, 1.00 equiv), triethylamine (16.2 g, 160 mmol, 4.00 equiv) and DCM (40 mL). Then 4-nitrophenyl chloroformate (8.89 g, 44.1 mmol, 1.10 equiv) was added at 0° C. The resulting solution was stirred for 2 h at room temperature and then t-butyl piperazine-1-carboxylate (7.44 g, 40.0 mmol, 1.00 equiv) was added, as described in Example 1, Step 1. The residue was chromatographed on a silica gel column to provide 9.00 g (67% yield) t-butyl 4-(3-acetamido-1H-pyrazole-1-carbonyl)piperazine-1-carboxylate as a yellow solid. LCMS (ESI, m/z): 338 [M+H]$^+$.

Step 2: Preparation of N-(1-(piperazine-1-carbonyl)-1H-pyrazol-3-yl)acetamide

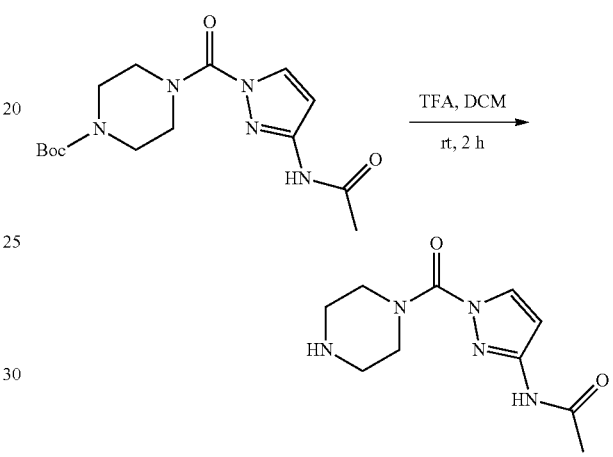

A vial was charged with t-butyl 4-[(3-acetamido-1H-pyrazol-1-yl)carbonyl]piperazine-1-carboxylate (240 mg, 0.720 mmol, 1.00 equiv), TFA (4 mL) and DCM (30 mL), as described in Example 1, Step 3, providing 168 mg (quantitative) of N-(1-(piperazine-1-carbonyl)-1H-pyrazol-3-yl)acetamide as a yellow solid. LCMS (ESI, m/z): 238 [M+H]$^+$.

Step 3: Preparation of t-butyl 2-(5-chloro-2-formylphenoxy)acetate

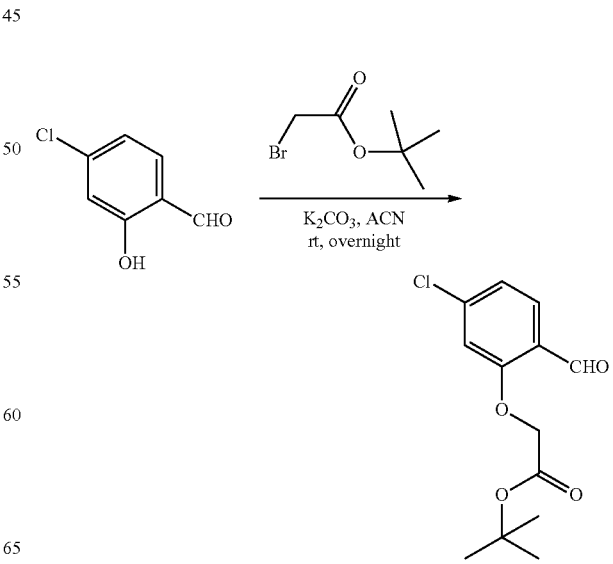

A vial was charged with 4-chloro-2-hydroxybenzaldehyde (1.00 g, 6.39 mmol, 1.00 equiv), t-butyl 2-bromoacetate (1.38 g, 7.07 mmol, 1.10 equiv), potassium carbonate (1.77 g, 12.8 mmol, 2.00 equiv) and ACN (20 mL). The resulting solution was stirred overnight at room temperature and quenched by water (20 mL). The mixture was extracted with DCM (3×30 mL) and the organic layers were combined, washed with water (3×10 mL), dried over anhydrous sodium sulfate, filtered and concentrated under reduced pressure. The residue was chromatographed on a silica gel column to provide 420 mg (24% yield) of t-butyl 2-(5-chloro-2-formylphenoxy)acetate as a white solid. LCMS (ESI, m/z): 271 [M+H]$^+$.

Step 4: Preparation of t-butyl 2-(2-((4-(3-acetamido-1H-pyrazole-1-carbonyl)piperazin-1-yl)methyl)-5-chlorophenoxy)acetate

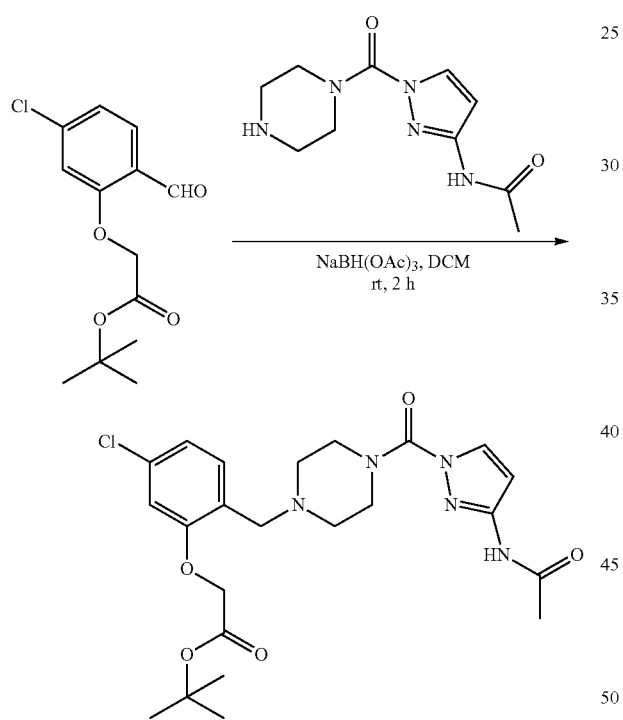

A vial was charged with N-[1-[(piperazin-1-yl)carbonyl]-1H-pyrazol-3-yl]acetamide (143 mg, 0.600 mmol, 1.00 equiv), t-butyl 2-(5-chloro-2-formylphenoxy)acetate (178 mg, 0.660 mmol, 1.10 equiv) and DCM (15 mL). The resulting solution was stirred for 1 h at room temperature and then sodium triacetoxyborohydride (255 mg, 1.20 mmol, 2.00 equiv) was added, as described in Example 1, Step 6. The residue was chromatographed on a silica gel column to provide 200 mg (67% yield) of t-butyl 2-(2-((4-(3-acetamido-1H-pyrazole-1-carbonyl)piperazin-1-yl)methyl)-5-chlorophenoxy)acetate as a white solid. LCMS (ESI, m/z): 492 [M+H]$^+$.

Step 5: Preparation of 2-(2-((4-(3-acetamido-1H-pyrazole-1-carbonyl)piperazin-1-yl)methyl)-5-chlorophenoxy)acetic acid

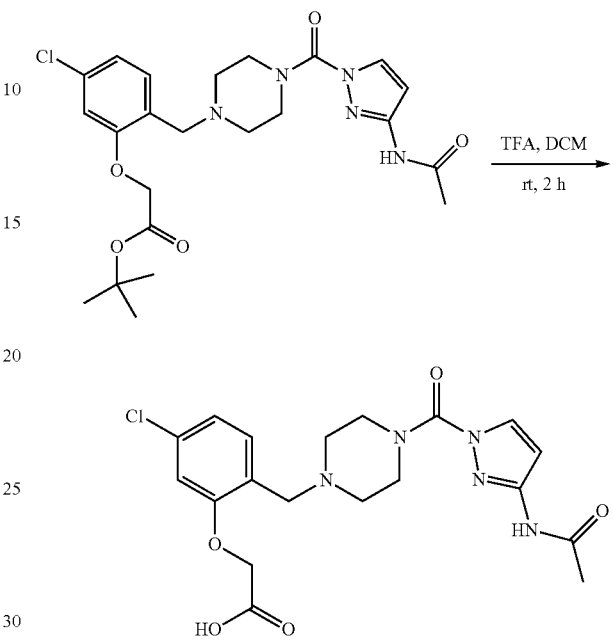

A vial was charged with t-butyl 2-[5-chloro-2-([4-[(3-acetamido-1H-pyrazol-1-yl)carbonyl]piperazin-1-yl]methyl)phenoxy]acetate (200 mg, 0.410 mmol, 1.00 equiv), TFA (2 mL) and DCM (15 mL), as described in Example 1, Step 1. The crude product was purified by preparative HPLC to provide 22.6 mg (13% yield) of 2-(2-((4-(3-acetamido-1H-pyrazole-1-carbonyl)piperazin-1-yl)methyl)-5-chlorophenoxy)acetic acid as a white solid. $^1$H NMR: (300 MHz, Methanol-d$_4$) δ 8.10 (s, 1H), 7.19-7.41 (m, 2H), 7.01-7.12 (m, 1H), 6.80 (m, 1H), 4.68 (s, 2H), 4.01-4.21 (m, 6H), 3.15-3.28 (m, 4H), 2.10 (s, 3H). LCMS (ESI, m/z): 436 [M+H]$^+$.

Example 4: 1-(2-((4-(3-acetamido-1H-pyrazole-1-carbonyl)piperazin-1-yl)methyl)-5-chlorophenoxy)cyclopropane-1-carboxylic acid

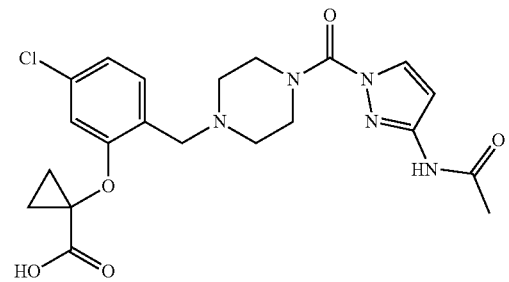 [SMILES: CC(=O)Nc1ccn(C(=O)N2CCN(Cc3ccc(Cl)cc3OC3(C(=O)O)CC3)CC2)n1]

Step 1: Preparation of methyl 1-(5-chloro-2-formylphenoxy)cyclopropane-1-carboxylate

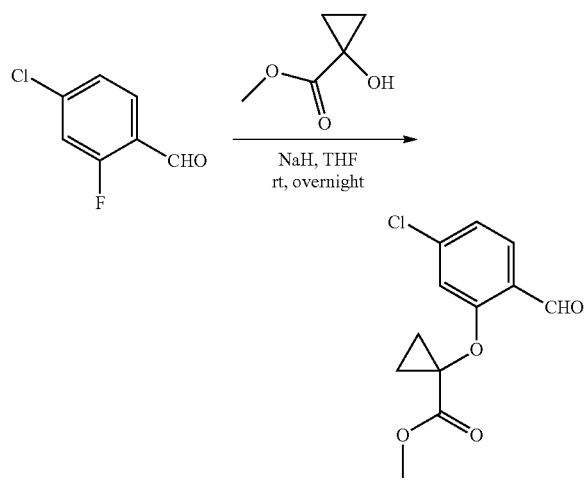

A vial was charged with methyl 1-hydroxycyclopropane-1-carboxylate (1.28 g, 11.0 mmol, 1.10 equiv) and THF (20 mL). Sodium hydride (60% in oil, 600 mg, 15.0 mmol, 1.50 equiv) was added dropwise at 0° C. The resulting solution was stirred for 0.5 h at room temperature. Then 4-chloro-2-fluorobenzaldehyde (1.59 g, 10.0 mmol, 1.00 equiv) was added. The resulting solution was stirred overnight at room temperature and quenched by water (20 mL). The mixture was extracted with DCM (3×30 mL) and the organic layers were combined, washed with water (3×10 mL), dried over anhydrous sodium sulfate, filtered and concentrated under reduced pressure. The residue was chromatographed on a silica gel column to provide 500 mg (20% yield) of methyl 1-(5-chloro-2-formylphenoxy)cyclopropane-1-carboxylate as a white solid. LCMS (ESI, m/z): 255 [M+H]⁺.

Step 2: Preparation of t-butyl 4-(4-chloro-2-(1-(methoxycarbonyl)cyclopropoxy)benzyl)piperazine-1-carboxylate

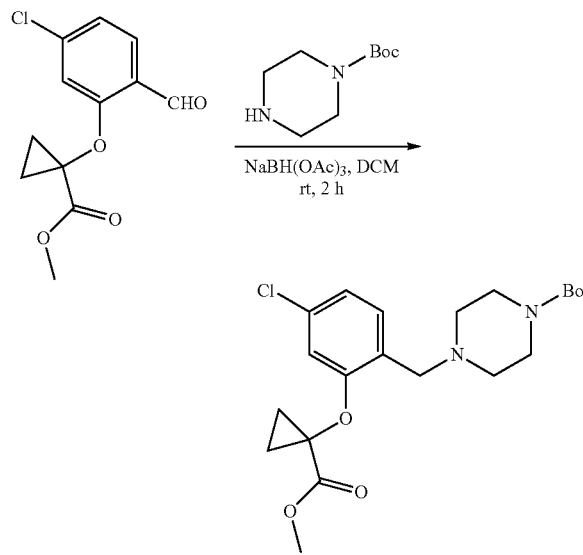

A vial was charged with t-butyl piperazine-1-carboxylate (186 mg, 1.00 mmol, 1.00 equiv), methyl 1-(5-chloro-2-formylphenoxy) cyclopropane-1-carboxylate (280 mg, 1.10 mmol, 1.10 equiv) and DCM (15 mL). The resulting solution was stirred for 1 h at room temperature and then sodium triacetoxyborohydride (424 mg, 2.00 mmol, 2.00 equiv) was added. The resulting solution was stirred for 1 h at room temperature and quenched by water (10 mL), as described in Example 1, Step 6. The residue was chromatographed on a silica gel column to provide 320 mg (75% yield) of t-butyl 4-(4-chloro-2-(1-(methoxycarbonyl)cyclopropoxy)benzyl)piperazine-1-carboxylate as a white solid. LCMS (ESI, m/z): 425 [M+H]⁺.

Step 3: Preparation of 1-(2-((4-(t-butoxycarbonyl)piperazin-1-yl)methyl)-5-chlorophenoxy)cyclopropane-1-carboxylic acid

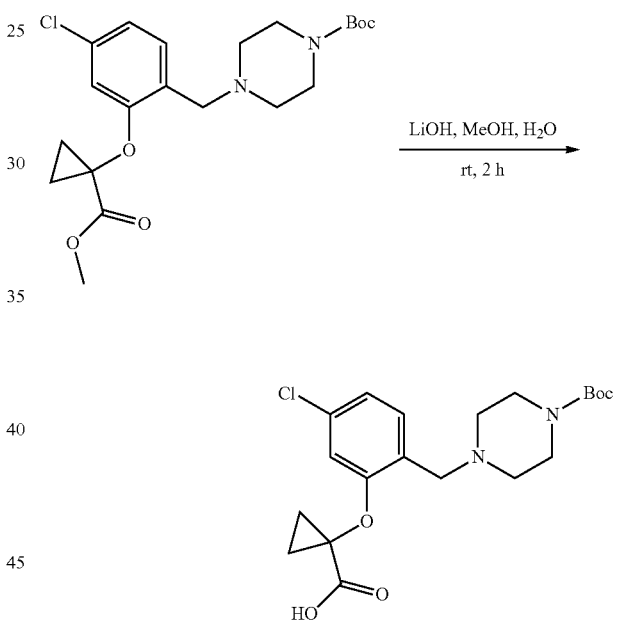

A 40-mL vial was charged with t-butyl 4-(4-chloro-2-(1-(methoxycarbonyl)cyclopropoxy)benzyl)piperazine-1-carboxylate (320 mg, 0.750 mmol, 1.00 equiv), lithium hydroxide (54.0 mg, 2.25 mmol, 3.00 equiv), MeOH (20 mL) and water (5 mL). The resulting solution was stirred for 2 h at room temperature and concentrated under reduced pressure. The resulting solution was quenched by water (20 mL). The pH value of the solution was adjusted to 5~6 with hydrochloric acid (1M). The mixture was extracted with DCM (3×20 mL), washed with water (3×10 mL), dried over anhydrous sodium sulfate, filtered and concentrated under reduced pressure, resulting in 280 mg (90% yield) of 1-(2-((4-(t-butoxycarbonyl)piperazin-1-yl)methyl)-5-chlorophenoxy)cyclopropane-1-carboxylic acid as a white solid. LCMS (ESI, m/z): 411 [M+H]⁺.

Step 4: Preparation of 1-(5-chloro-2-(piperazin-1-ylmethyl)phenoxy)cyclopropane-1-carboxylic acid

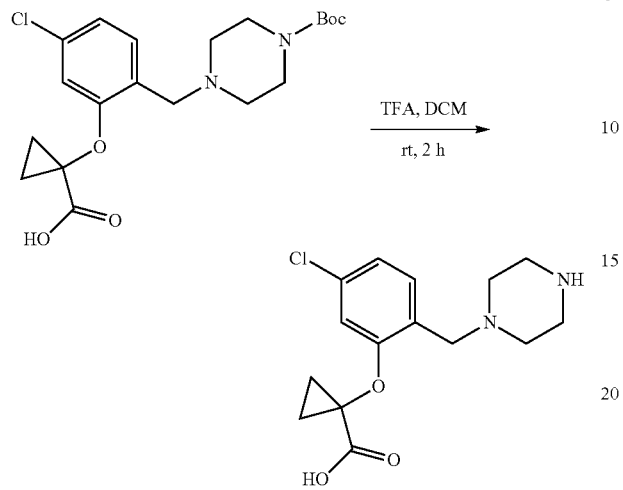

A vial was charged with 1-(2-((4-(t-butoxycarbonyl)piperazin-1-yl)methyl)-5-chlorophenoxy)cyclopropane-1-carboxylic acid (280 mg, 0.680 mmol, 1.00 equiv), TFA (2 mL) and DCM (15 mL), as described in Example 1, Step 3, resulting in 211 mg (quantitative) of 1-(5-chloro-2-(piperazin-1-ylmethyl)phenoxy)cyclopropane-1-carboxylic acid as a white solid. LCMS (ESI, m/z): 311 [M+H]$^+$.

Step 5: Preparation of 1-(2-((4-(3-acetamido-1H-pyrazole-1-carbonyl)piperazin-1-yl)methyl)-5-chlorophenoxy)cyclopropane-1-carboxylic acid

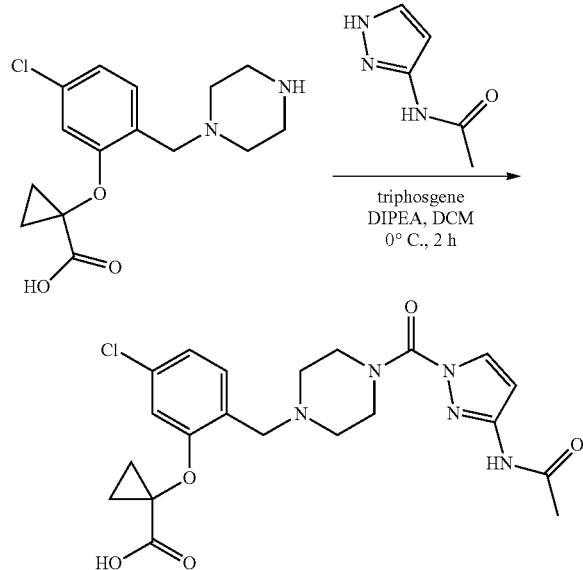

A vial was charged with N-(1H-pyrazol-3-yl)acetamide (85.0 mg, 0.680 mmol, 1.00 equiv), triphosgene (101 mg, 0.340 mmol, 0.50 equiv) and DCM (15 mL). Then DIPEA (529 mg, 4.10 mmol, 6.00 equiv) was added at 0° C. The resulting solution was stirred for 2 h at room temperature. Then 1-(5-chloro-2-(piperazin-1-ylmethyl)phenoxy)cyclopropane-1-carboxylic acid (211 mg, 0.680 mmol, 1.00 equiv) was added, as described in Example 2, Step 5. The crude product was purified by preparative HPLC to provide 56.0 mg (18% yield) of 1-(2-((4-(3-acetamido-1H-pyrazole-1-carbonyl)piperazin-1-yl)methyl)-5-chlorophenoxy)cyclopropane-1-carboxylic acid as a white solid. $^1$H NMR: (300 MHz, Methanol-d$_4$) δ 8.08 (s, 1H), 7.27-7.41 (m, 2H), 6.98-7.12 (m, 1H), 6.79 (s, 1H), 4.05 (br, 6H), 3.12 (br, 4H), 2.11 (s, 3H), 1.41-1.51 (m, 2H), 1.21-1.32 (m, 2H). LCMS (ESI, m/z): 462 [M+H]$^+$.

Example 5: N-(1-(4-(3-(1,3,4-Oxadiazol-2-yl)-4-(trifluoromethyl)phenoxy)piperidine-1-carbonyl)-1H-pyrazol-3-yl)methanesulfonamide

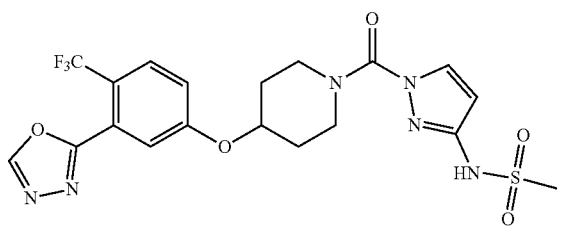 [SMILES: CS(=O)(=O)Nc1ccn(C(=O)N2CCC(Oc3ccc(C(F)(F)F)c(-c4nnco4)c3)CC2)n1]

Step 1: Synthesis of tert-butyl 4-(3-(methoxycarbonyl)-4-(trifluoromethyl)phenoxy)piperidine-1-carboxylate

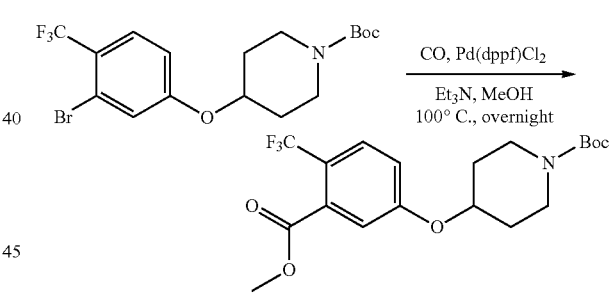

A 30-mL pressure tank reactor was charged with tert-butyl 4-[3-bromo-4-(trifluoromethyl)phenoxy]piperidine-1-carboxylate (1.00 g, 2.36 mmol, 1.00 equiv), [1,1-is (diphenylphosphino)ferrocene]dichloropalladium(II) (173 mg, 0.236 mmol, 0.10 equiv), methanol (10 mL), and triethylamine (715 mg, 7.08 mmol, 3.00 equiv). Carbon monoxide was introduced, and the reaction mixture was stirred overnight at 100° C. before quenching with water (20 mL). The resulting solution was extracted with ethyl acetate (3×20 mL) and the organic layers were combined, washed with brine (2×20 mL), dried over anhydrous sodium sulfate, filtered and concentrated under reduced pressure. The residue was chromatographed on a silica gel column to provide 0.750 g (79% yield) of tert-butyl 4-(3-(methoxycarbonyl)-4-(trifluoromethyl)phenoxy)piperidine-1-carboxylate. LCMS (ESI, m/z): 404 [M+H]$^+$.

Step 2: Synthesis of tert-butyl 4-(3-(hydrazinecarbonyl)-4-(trifluoromethyl)phenoxy)piperidine-1-carboxylate

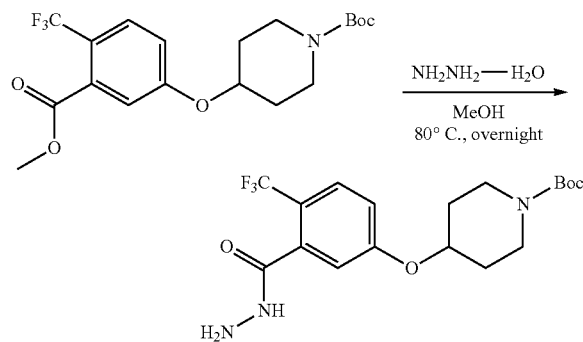

A flask was charged with tert-butyl 4-(3-(methoxycarbonyl)-4-(trifluoromethyl)phenoxy)piperidine-1-carboxylate (750 mg, 1.86 mmol, 1.00 equiv), methanol (30 mL), and hydrazine hydrate (465 mg, 9.29 mmol, 5.00 equiv). The reaction mixture was stirred overnight at 80° C. and quenched with water (20 mL). The resulting solution was extracted with ethyl acetate (3×20 mL) and the organic layers were combined, washed with brine (2×20 mL), dried over anhydrous sodium sulfate, filtered and concentrated under reduced pressure. The residue was chromatographed on a silica gel to provide 573 mg (76% yield) of tert-butyl 4-(3-(hydrazinecarbonyl)-4-(trifluoromethyl)phenoxy)piperidine-1-carboxylate. LCMS (ESI, m/z): 404 [M+H]+.

Step 3: Synthesis of tert-butyl 4-(3-(1,3,4-oxadiazol-2-yl)-4-(trifluoromethyl)phenoxy)piperidine-1-carboxylate

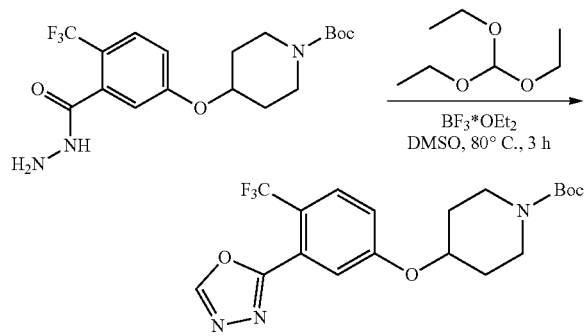

A flask was charged with tert-butyl 4-(3-(hydrazinecarbonyl)-4-(trifluoromethyl)phenoxy)piperidine-1-carboxylate (130 mg, 0.320 mmol, 1.00 equiv), dimethyl sulfoxide (10 mL), and (diethoxymethoxy)ethane (191 mg, 1.29 mmol, 4.00 equiv). The resulting solution was stirred for 1 h at room temperature prior to addition of boron trifluoride diethylether (55.0 mg, 0.390 mmol, 1.20 equiv). The reaction mixture was stirred for 3 h at 80° C. and quenched with water (20 mL). The resulting solution was extracted with ethyl acetate (3×20 mL) and the organic layers were combined, washed with brine (2×20 mL), dried over anhydrous sodium sulfate, filtered and concentrated under reduced pressure. The residue was chromatographed on a silica gel column to provide 40.0 mg (30% yield) of tert-butyl 4-(3-(1,3,4-oxadiazol-2-yl)-4-(trifluoromethyl)phenoxy)piperidine-1-carboxylate. LCMS (ESI, m/z): 414 [M+H]+.

Step 4: Synthesis of 2-(5-(piperidin-4-yloxy)-2-(trifluoromethyl)phenyl)-1,3,4-oxadiazole

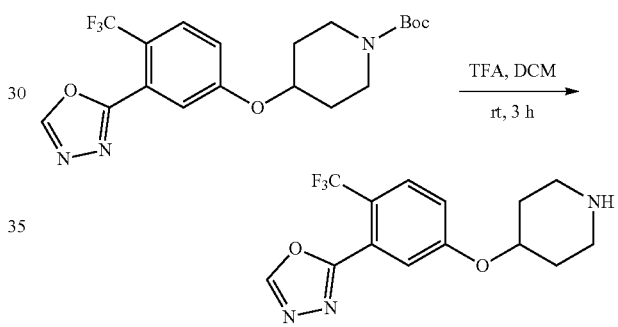

A flask was charged with tert-butyl 4-(3-(1,3,4-oxadiazol-2-yl)-4-(trifluoromethyl)phenoxy)piperidine-1-carboxylate (80.0 mg, 0.190 mmol, 1.00 equiv), dichloromethane (4 mL), and trifluoroacetic acid (1 mL). The resulting solution was stirred for 3 h at room temperature and concentrated under reduced pressure to provide 100 mg (crude) of 2-(5-(piperidin-4-yloxy)-2-(trifluoromethyl)phenyl)-1,3,4-oxadiazole. LCMS (ESI, m/z): 314 [M+H]+.

Step 5: Synthesis of N-(1-(4-(3-(1,3,4-oxadiazol-2-yl)-4-(trifluoromethyl)phenoxy)piperidine-1-carbonyl)-1H-pyrazol-3-yl)methanesulfonamide

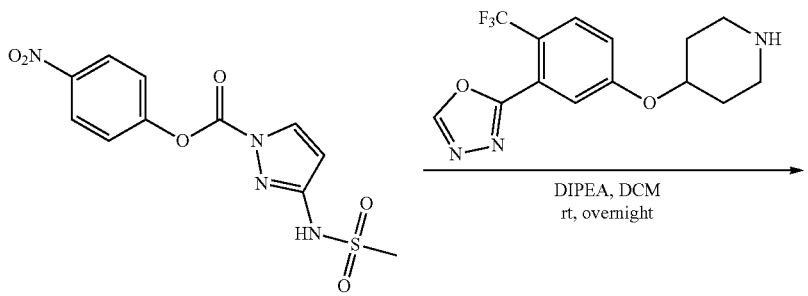

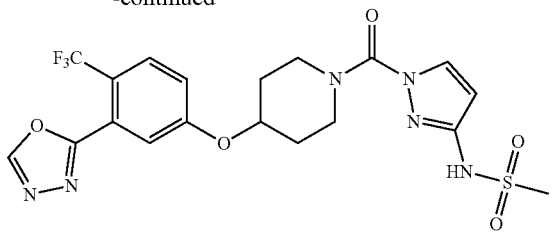

A vial was charged with 4-nitrophenyl 3-methanesulfonamido-1H-pyrazole-1-carboxylate (104 mg, 0.320 mmol, 2.00 equiv), dichloromethane (10 mL), and 2-(5-(piperidin-4-yloxy)-2-(trifluoromethyl)phenyl)-1,3,4-oxadiazole (48.6 mg, 0.160 mmol, 1.00 equiv) under nitrogen. N,N-Diisopropylethylamine (60.0 mg, 0.470 mmol, 3.00 equiv) was added dropwise at 0° C., and the resulting solution was stirred overnight at room temperature and quenched with water (10 mL). The mixture was extracted with dichloromethane (3×10 mL) and the organic layers were combined, washed with brine (2×10 mL), dried over anhydrous sodium sulfate, filtered and concentrated under reduced pressure. The crude product (160 mg) was purified by preparative HPLC to afford 25.8 mg (33% yield) of N-(1-(4-(3-(1,3,4-oxadiazol-2-yl)-4-(trifluoromethyl)phenoxy)piperidine-1-carbonyl)-1H-pyrazol-3-yl)methanesulfonamide. $^1$H NMR (400 MHz, Chloroform-d) δ 8.61 (s, 1H), 8.08 (d, J=2.8 Hz, 1H), 7.81 (d, J=8.8 Hz, 1H), 7.60 (d, J=2.8 Hz, 1H), 7.32 (s, 1H), 7.19-7.22 (m, 1H), 6.34 (d, J=2.8 Hz, 1H), 4.77-4.82 (m, 1H), 3.93-3.99 (m, 4H), 3.18 (s, 3H), 2.10-2.17 (m, 2H), 1.97-2.03 (m, 2H). LCMS (ESI, m/z): 501 [M+H]$^+$.

Example 6: N-(1-(4-(4-chloro-3-(cyclopentyloxy)phenoxy)piperidine-1-carbonyl)-1H-pyrazol-3-yl)methanesulfonamide

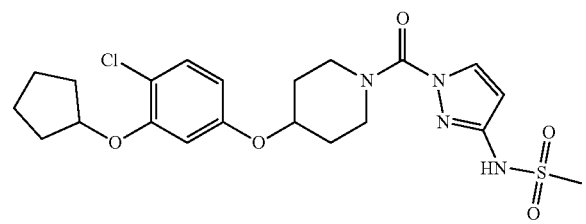 [SMILES: CS(=O)(=O)Nc1ccn(C(=O)N2CCC(Oc3ccc(Cl)c(OC4CCCC4)c3)CC2)n1]

Step 1: Preparation of 4-nitrophenyl 3-(methylsulfonamido)-1H-pyrazole-1-carboxylate

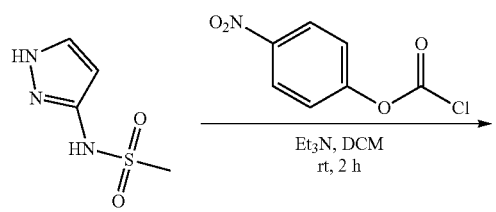

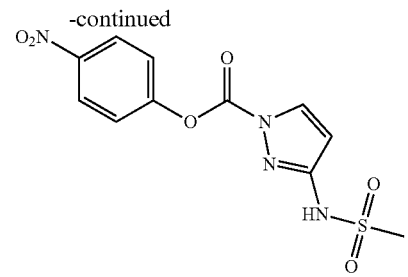

A vial was charged with N-(1H-pyrazol-3-yl)methanesulfonamide (172 mg, 1.07 mmol, 1.00 equiv) in DCM (10 mL) and 4-nitrophenyl chloroformate (237 mg, 1.18 mmol, 1.10 equiv). Triethylamine (324 mg, 3.21 mmol, 3.00 equiv) was added, as described in Example 1, Step 1. The resulting solution was stirred for 2 h at room temperature and concentrated under reduced pressure to provide 360 mg (crude) of 4-nitrophenyl 3-methanesulfonamido-1H-pyrazole-1-carboxylate as a yellow oil. LCMS (ESI, m/z): 327 [M+H]$^+$.

Step 2: Preparation of t-butyl 4-(3-bromo-4-chlorophenoxy)piperidine-1-carboxylate

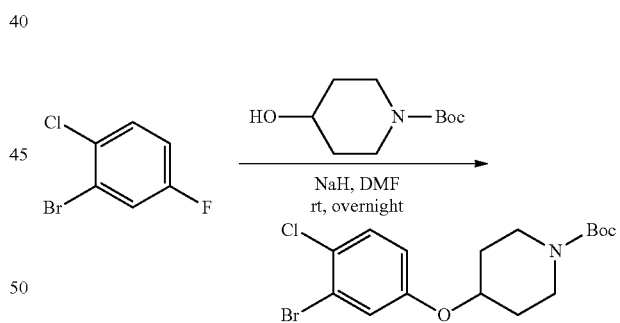

A flask was charged with t-butyl 4-hydroxypiperidine-1-carboxylate (2.88 g, 14.3 mmol, 1.50 equiv), N,N-dimethylformamide (20 mL), and sodium hydride (574 mg, 14.3 mmol, 1.50 equiv, 60% in mineral oil). The resulting solution was stirred for 0.5 h at 0° C. 2-Bromo-1-chloro-4-fluorobenzene (2.00 g, 9.55 mmol, 1.00 equiv) was added. The resulting solution was stirred overnight at room temperature and quenched with water (20 mL), as described in Example 1, Step 4. The residue was chromatographed on a silica gel column to provide 2.62 g (70% yield) of t-butyl 4-(3-bromo-4-chlorophenoxy)piperidine-1-carboxylate as yellow oil. LCMS (ESI, m/z): 390 [M+H]$^+$.

Step 3: Preparation of t-butyl 4-(4-chloro-3-hydroxyphenoxy)piperidine-1-carboxylate

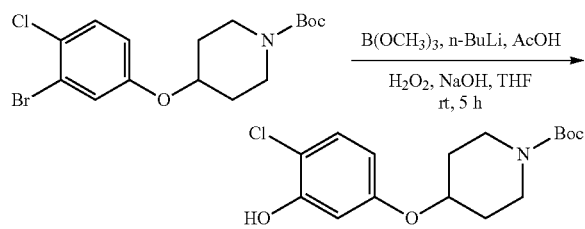

A flask was charged with t-butyl 4-(3-bromo-4-chlorophenoxy)piperidine-1-carboxylate (585 mg, 1.50 mmol, 1.00 equiv), trimethyl borate (203 mg, 1.95 mmol, 1.30 equiv), and THF (10 mL) under nitrogen. The mixture was cooled to −78° C. n-Butyllithium (0.78 mL, 1.95 mmol, 1.30 equiv, 2.5 M in hexane) was added dropwise at −78° C. over 0.5 h. Acetic acid (180 mg, 3.00 mmol, 2.00 equiv) was added at −20° C. Hydrogen peroxide (855 mg, 7.50 mmol, 5.00 equiv, 30% in water) was added dropwise at −10° C. over 5 min. The resulting solution was stirred for 5 h at room temperature and quenched with saturated sodium thiosulfate solution (20 mL). The resulting mixture was concentrated under reduced pressure. The residue was chromatographed on a silica gel column to provide 300 mg (61% yield) of t-butyl 4-(4-chloro-3-hydroxyphenoxy)piperidine-1-carboxylate as a yellow oil. LCMS (ESI, m/z): 328 [M+H]$^+$.

Step 4: Preparation of t-butyl 4-(4-chloro-3-(cyclopentyloxy)phenoxy)piperidine-1-carboxylate

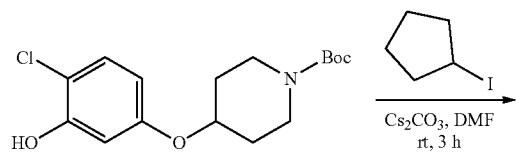

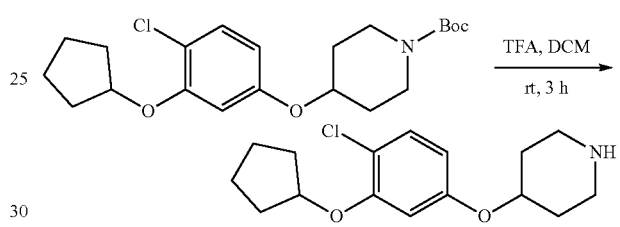

A flask was charged with t-butyl 4-(4-chloro-3-hydroxyphenoxy) piperidine-1-carboxylate (300 mg, 0.920 mmol, 1.00 equiv), N,N-dimethylformamide (5 mL), iodocyclopentane (359 mg, 1.83 mmol, 2.00 equiv), and cesium carbonate (897 mg, 2.75 mmol, 3.00 equiv). The resulting solution was stirred for 3 h at room temperature and quenched with water (10 mL), as described in Example 3, Step 3. The residue was chromatographed on a silica gel column to provide 260 mg (72% yield) of t-butyl 4-(4-chloro-3-(cyclopentyloxy)phenoxy)piperidine-1-carboxylate as a yellow oil. LCMS (ESI, m/z): 396 [M+H]$^+$.

Step 5: Preparation of 4-(4-chloro-3-(cyclopentyloxy)phenoxy)piperidine

A flask was charged with t-butyl 4-(4-chloro-3-(cyclopentyloxy)phenoxy)piperidine-1-carboxylate (260 mg, 0.660 mmol, 1.00 equiv), DCM (10 mL), and TFA (2 mL), as described in Example 1, Step 3, to provide 294 mg (crude) of 4-(4-chloro-3-(cyclopentyloxy)phenoxy)piperidine as a yellow oil. LCMS (ESI, m/z): 296 [M+H]$^+$.

Step 6: Preparation of N-(1-(4-(4-chloro-3-(cyclopentyloxy)phenoxy)piperidine-1-carbonyl)-1H-pyrazol-3-yl)methanesulfonamide

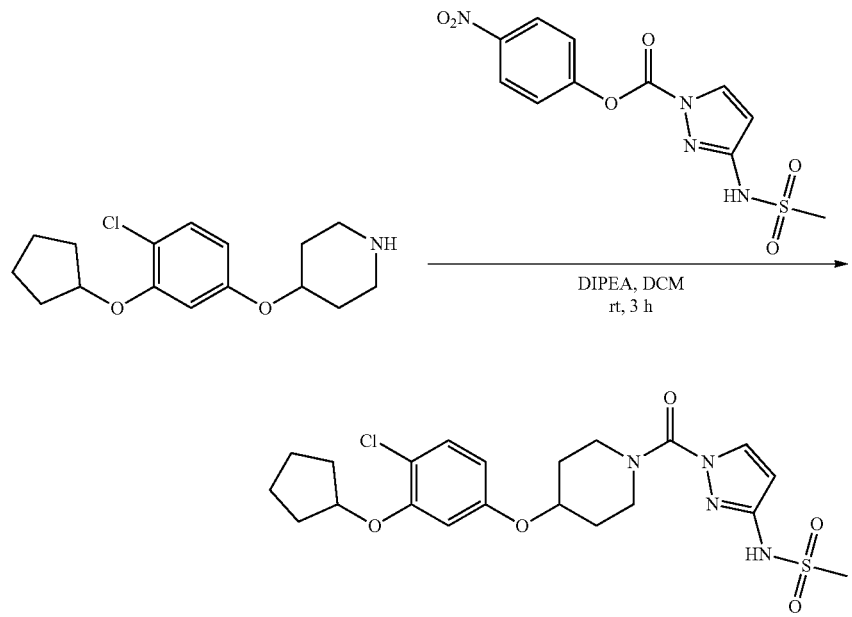

A vial was charged with 4-nitrophenyl 3-methanesulfonamido-1H-pyrazole-1-carboxylate (430 mg, 1.32 mmol, 2.00 equiv), 4-(4-chloro-3-(cyclopentyloxy)phenoxy)piperidine (194 mg, 0.658 mmol, 1.00 equiv), and DCM (10 mL) under nitrogen. DIPEA (255 mg, 1.98 mmol, 3.00 equiv) was added dropwise at 0° C. The resulting solution was stirred for 3 h at room temperature and quenched with water (10 mL). The mixture was extracted with DCM (3×10 mL) and the organic layers were combined, washed with brine (2×10 mL), dried over anhydrous sodium sulfate, filtered and concentrated under reduced pressure. The crude product (250 mg) was purified by preparative HPLC to provide 88.2 mg (28% yield) of N-(1-(4-(4-chloro-3-(cyclopentyloxy)phenoxy)piperidine-1-carbonyl)-1H-pyrazol-3-yl)methanesulfonamide as a white solid. $^1$H NMR (400 MHz, Chloroform-d) δ 8.08 (d, J=2.8 Hz, 1H), 7.25 (d, J=8.8 Hz, 1H), 7.16 (s, 1H), 6.54 (d, J=2.4 Hz, 1H), 6.43-6.46 (m, 1H), 6.34 (d, J=2.8 Hz, 1H), 4.77-4.80 (m, 1H), 4.56-4.59 (m, 1H), 3.85-3.97 (m, 4H), 3.17 (s, 3H), 2.02-2.10 (m, 2H), 1.85-1.99 (m, 8H), 1.64-1.67 (m, 2H). LCMS (ESI, m/z): 505 [M+Na]$^+$.

Example 7: N-(1-(4-(2-(1,3,4-oxadiazol-2-yl)-3-(trifluoromethyl)phenoxy)piperidine-1-carbonyl)-1H-pyrazol-3-yl)methanesulfonamide

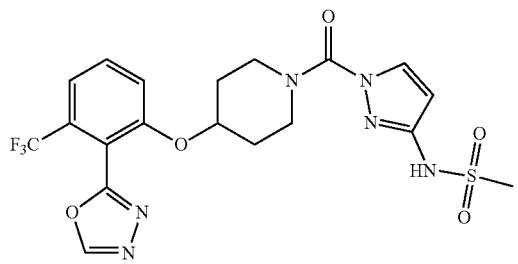 [SMILES: CS(=O)(=O)Nc1ccn(C(=O)N2CCC(Oc3cccc(C(F)(F)F)c3-c3nnco3)CC2)n1]

Step 1: Preparation of 4-nitrophenyl 3-(methylsulfonamido)-1H-pyrazole-1-carboxylate

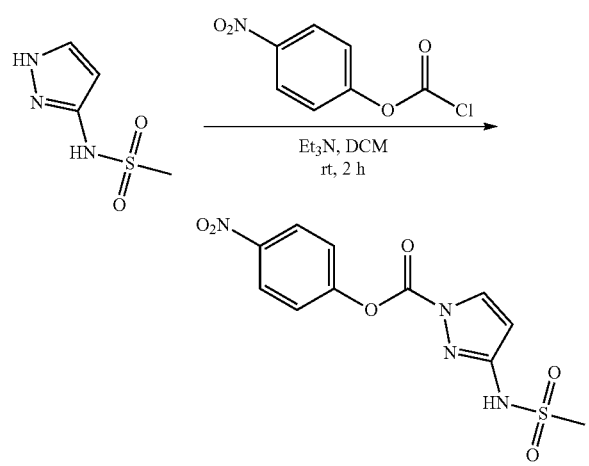

A vial was charged with N-(1H-pyrazol-3-yl)methanesulfonamide (172 mg, 1.07 mmol, 1.00 equiv) in DCM (10 mL) and 4-nitrophenyl chloroformate (237 mg, 1.18 mmol, 1.10 equiv). Triethylamine (324 mg, 3.21 mmol, 3.00 equiv) was added, as described in Example 1, Step 1 to provide 360 mg (crude) of 4-nitrophenyl 3-(methylsulfonamido)-1H-pyrazole-1-carboxylate as a yellow oil. LCMS (ESI, m/z): 327 [M+H]$^+$.

Step 2: Preparation of t-butyl 4-(2-bromo-3-(trifluoromethyl)phenoxy)piperidine-1-carboxylate

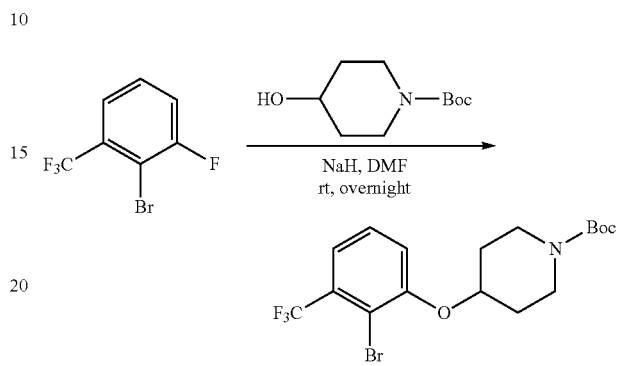

A flask was charged with t-butyl 4-hydroxypiperidine-1-carboxylate (1.24 g, 6.16 mmol, 1.50 equiv) and N,N-dimethylformamide (20 mL). The resulting solution was stirred for 0.5 h at 0° C. Sodium hydride (247 mg, 6.16 mmol, 1.50 equiv, 60% in mineral oil) was added. The resulting solution was stirred for 0.5 h at 0° C. 2-Bromo-1-fluoro-3-(trifluoromethyl)benzene (1.00 g, 4.12 mmol, 1.00 equiv) was added, as described in Example 4, Step 1. The residue was chromatographed on a silica gel column to provide 1.30 g (74% yield) of t-butyl 4-(2-bromo-3-(trifluoromethyl)phenoxy)piperidine-1-carboxylate as a yellow oil. LCMS (ESI, m/z): 424 [M+H]$^+$.

Step 3: Preparation of t-butyl 4-(2-(methoxycarbonyl)-3-(trifluoromethyl)phenoxy)piperidine-1-carboxylate

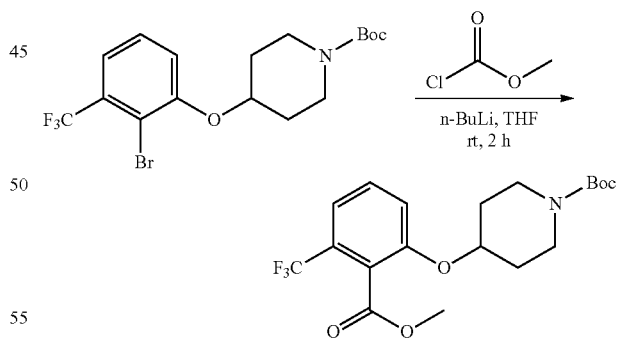

A flask was charged with t-butyl 4-(2-bromo-3-(trifluoromethyl)phenoxy)piperidine-1-carboxylate (1.80 g, 4.18 mmol, 1.00 equiv) under nitrogen. THF (10 mL) was added. n-Butyllithium (2 mL, 5.02 mmol, 1.20 equiv, 2.5 M in n-hexane) was added dropwise at −78° C. The mixture was stirred for 15 min at −78° C. Chloro(methoxy)methanone (1.19 g, 12.6 mmol, 3.00 equiv) was added. The resulting solution was stirred for 2 h at room temperature and quenched with water (10 mL). The resulting solution was extracted with EtOAc (3×20 mL) and the organic layers were combined, washed with brine (2×20 mL), dried over anhydrous sodium sulfate, filtered and concentrated under reduced pressure. The residue was chromatographed on a silica gel column to provide 0.180 g (11% yield) of t-butyl 4-(2-(methoxycarbonyl)-3-(trifluoromethyl)phenoxy)piperidine-1-carboxylate as a yellow oil. LCMS (ESI, m/z): 404 [M+H]+.

Step 4: Preparation of t-butyl 4-(2-(hydrazinecarbonyl)-3-(trifluoromethyl)phenoxy)piperidine-1-carboxylate

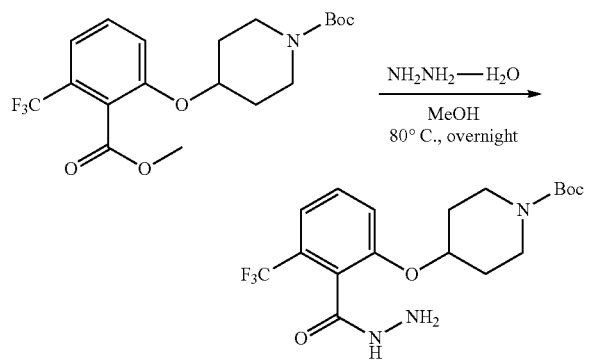

A flask was charged with t-butyl 4-(2-(methoxycarbonyl)-3-(trifluoromethyl)phenoxy)piperidine-1-carboxylate (300 mg, 0.740 mmol, 1.00 equiv), hydrazine hydrate (247 mg, 3.70 mmol, 5.00 equiv, 80% in water), and MeOH (40 mL). The resulting solution was stirred overnight at 80° C. and quenched with water (10 mL), as described in Example 5, Step 4. The residue was chromatographed on a silica gel column to provide 199 mg (66% yield) of t-butyl 4-(2-(hydrazinecarbonyl)-3-(trifluoromethyl)phenoxy)piperidine-1-carboxylate as a yellow oil. LCMS (ESI, m/z): 404 [M+H]+.

Step 5: Preparation of t-butyl 4-(2-(1,3,4-oxadiazol-2-yl)-3-(trifluoromethyl)phenoxy)piperidine-1-carboxylate

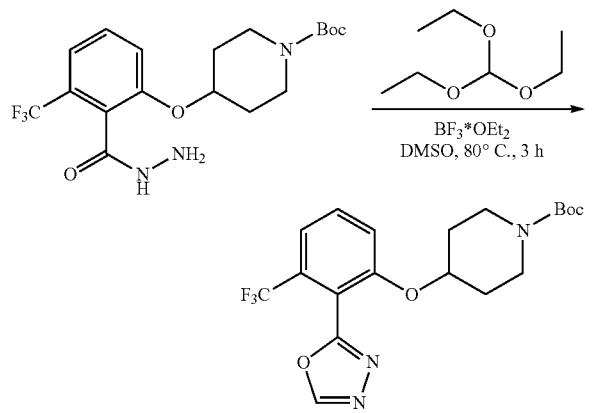

A flask was charged with t-butyl 4-(2-(hydrazinecarbonyl)-3-(trifluoromethyl)phenoxy)piperidine-1-carboxylate (199 mg, 0.490 mmol, 1.00 equiv), DMSO (10 mL), and (diethoxymethoxy)ethane (293 mg, 1.98 mmol, 4.00 equiv). The resulting solution was stirred 1 h at room temperature. Boron trifluoride etherate (84.2 mg, 0.588 mmol, 1.20 equiv) was added. The resulting solution was stirred for 3 h at 80° C. and quenched with water (10 mL), as described in Example 5, Step 5. The residue was chromatographed on a silica gel column to provide 33.0 mg (16% yield) of t-butyl 4-(2-(1,3,4-oxadiazol-2-yl)-3-(trifluoromethyl)phenoxy)piperidine-1-carboxylate as a yellow oil. LCMS (ESI, m/z): 414 [M+H]+.

Step 6: Preparation of 2-(2-(piperidin-4-yloxy)-6-(trifluoromethyl)phenyl)-1,3,4-oxadiazole

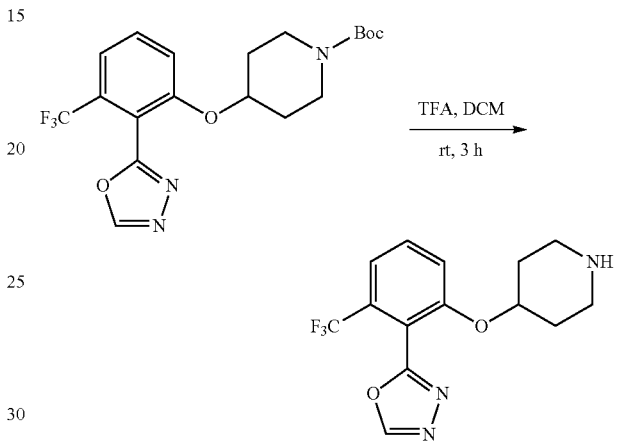

A flask was charged with t-butyl 4-(2-(1,3,4-oxadiazol-2-yl)-3-(trifluoromethyl)phenoxy)piperidine-1-carboxylate (33.0 mg, 0.0800 mmol, 1.00 equiv), DCM (4 mL), and TFA (1 mL), as described in Example 1, Step 3 to provide 30.0 mg (crude) of 2-(2-(piperidin-4-yloxy)-6-(trifluoromethyl)phenyl)-1,3,4-oxadiazole as a red oil. LCMS (ESI, m/z): 314 [M+H]+.

Step 7: Preparation of N-(1-(4-(2-(1,3,4-oxadiazol-2-yl)-3-(trifluoromethyl)phenoxy)piperidine-1-carbonyl)-1H-pyrazol-3-yl)methanesulfonamide

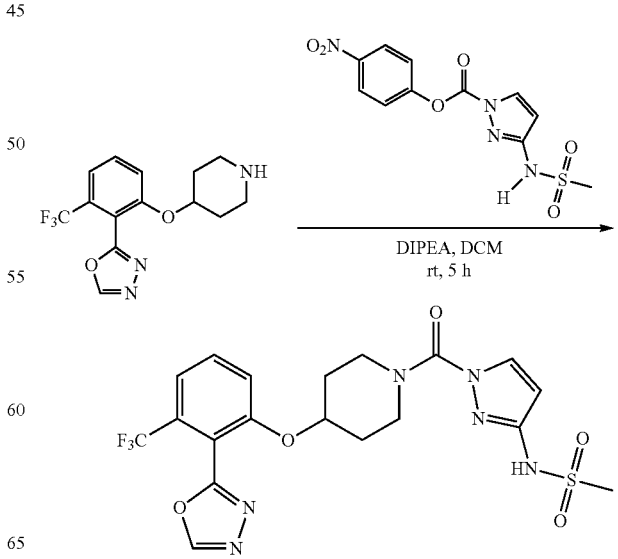

A vial was charged with 2-(2-(piperidin-4-yloxy)-6-(trifluoromethyl)phenyl)-1,3,4-oxadiazole (20.0 mg, 0.0639 mmol, 1.00 equiv), 4-nitrophenyl 3-(methylsulfonamido)-1H-pyrazole-1-carboxylate (52.2 mg, 0.160 mmol, 2.50 equiv), and DCM (5 mL) under nitrogen. DIPEA (24.8 mg, 0.192 mmol, 3.00 equiv) was added dropwise at 0° C. The resulting solution was stirred for 5 h at room temperature and quenched with water (5 mL), as described in Example 2, Step 6. The crude product (200 mg) was purified by preparative HPLC to provide 10.5 mg (33% yield) of N-(1-(4-(2-(1,3,4-oxadiazol-2-yl)-3-(trifluoromethyl)phenoxy)piperidine-1-carbonyl)-1H-pyrazol-3-yl)methanesulfonamide as a white solid. $^1$H NMR (400 MHz, Chloroform-d) δ 8.60 (s, 1H), 8.14 (d, J=8.0 Hz, 1H), 8.08 (d, J=2.4 Hz, 1H), 7.40 (d, J=8.4 Hz, 1H), 7.31 (s, 1H), 6.36 (d, J=2.4 Hz, 1H), 4.97 (br, 1H) 4.10-4.13 (m, 2H), 3.91-3.93 (m, 2H), 3.16 (s, 3H), 2.03-2.16 (m, 4H). LCMS (ESI, m/z): 501 [M+H]$^+$.

Example 8: N-(1-(4-(4-chloro-3-(7-oxa-2-azaspiro[3.5]nonan-2-yl)benzyl)piperazine-1-carbonyl)-1H-pyrazol-3-yl)methanesulfonamide

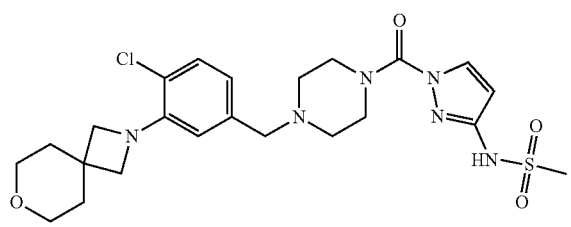 [SMILES: CS(=O)(=O)Nc1ccn(C(=O)N2CCN(Cc3ccc(Cl)c(N4CC5(CCOCC5)C4)c3)CC2)n1]

Step 1: Preparation of t-butyl 4-(3-bromo-4-chlorobenzyl)piperazine-1-carboxylate

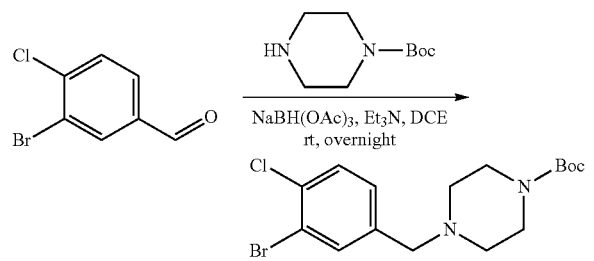

A flask was charged with 3-bromo-4-chlorobenzaldehyde (1.00 g, 4.56 mmol, 1.00 equiv), t-butyl piperazine-1-carboxylate (1.02 g, 5.48 mmol, 1.20 equiv), triethylamine (1.38 g, 13.7 mmol, 3.00 equiv), and DCE (10 mL). The mixture was stirred for 30 min at room temperature. Sodium triacetoxyborohydride (2.90 g, 13.7 mmol, 3.00 equiv) was added. The resulting solution was stirred overnight at room temperature and quenched with water (10 mL), as described in Example 1, Step 6. The residue was chromatographed on a silica gel column to provide 1.50 g (84% yield) of t-butyl 4-(3-bromo-4-chlorobenzyl)piperazine-1-carboxylate as a white oil. LCMS (ESI, m/z): 389 [M+H]$^+$.

Step 2: Preparation of t-butyl 4-(4-chloro-3-(7-oxa-2-azaspiro[3.5]nonan-2-yl)benzyl)piperazine-1-carboxylate

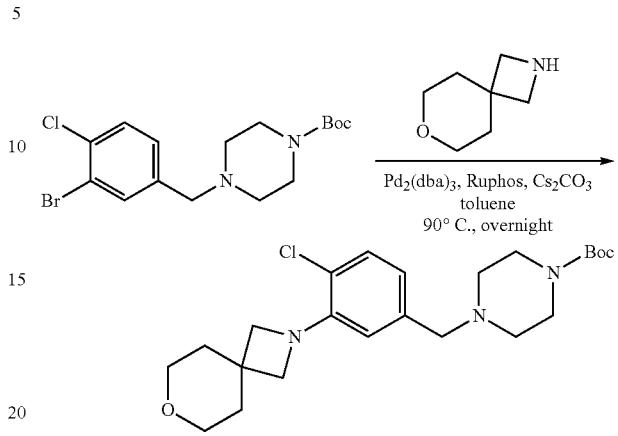

A flask was charged with t-butyl 4-(3-bromo-4-chlorobenzyl)piperazine-1-carboxylate (200 mg, 0.513 mmol, 1.00 equiv), 7-oxa-2-azaspiro[3.5]nonane (78.2 mg, 0.616 mmol, 1.20 equiv), tris(dibenzylideneacetone)dipalladium (23.5 mg, 0.0256 mmol, 0.05 equiv), dicyclohexyl(2',6'-diisopropoxybiphenyl-2-yl)phosphine (47.9 mg, 0.102 mmol, 0.20 equiv), cesium carbonate (502 mg, 1.54 mmol, 3.00 equiv), and toluene (5 mL). The resulting solution was stirred overnight at 90° C. and quenched with water (5 mL). The resulting solution was extracted with DCM (3×20 mL) and the organic layers were combined, washed with brine (2×5 mL), dried over anhydrous sodium sulfate, filtered and concentrated under reduced pressure. The residue was chromatographed on a silica gel column to provide 105 mg (47% yield) of t-butyl 4-(4-chloro-3-(7-oxa-2-azaspiro[3.5]nonan-2-yl)benzyl)piperazine-1-carboxylate as a yellow oil. LCMS (ESI, m/z): 436 [M+H]$^+$.

Step 3: Preparation of 2-(2-chloro-5-(piperazin-1-ylmethyl)phenyl)-7-oxa-2-azaspiro[3.5]nonane

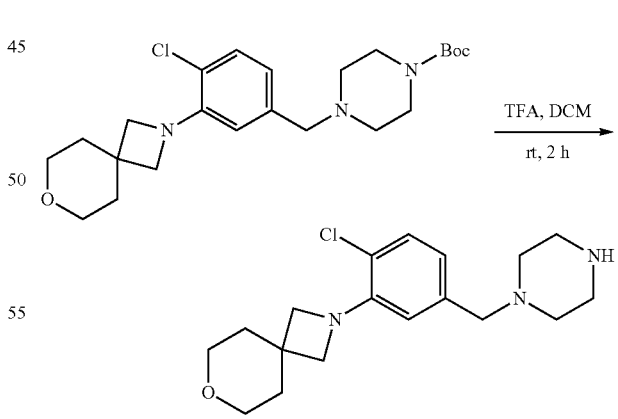

A flask was charged with t-butyl 4-(4-chloro-3-(7-oxa-2-azaspiro[3.5]nonan-2-yl)benzyl)piperazine-1-carboxylate (105 mg, 0.241 mmol, 1.00 equiv), DCM (4 mL), and TFA (1 mL), as described in Example 1, Step 3 to provide 100 mg (crude) of 2-(2-chloro-5-(piperazin-1-ylmethyl)phenyl)-7-oxa-2-azaspiro[3.5]nonane as a yellow oil. LCMS (ESI, m/z): 336 [M+H]$^+$.

Step 4: Preparation of N-(1-(4-(4-chloro-3-(7-oxa-2-azaspiro[3.5]nonan-2-yl)benzyl)piperazine-1-carbonyl)-1H-pyrazol-3-yl)methanesulfonamide

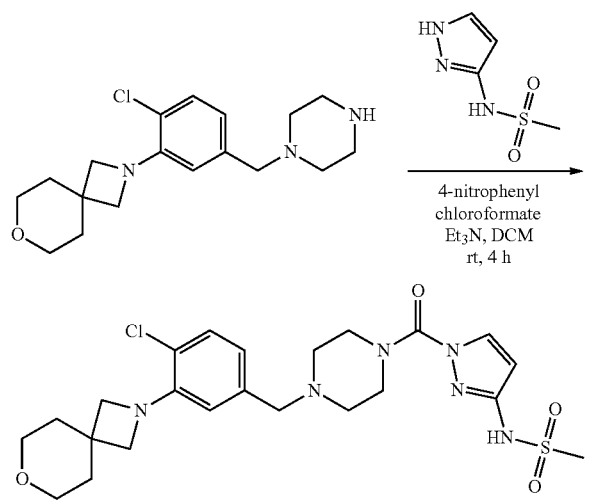

A flask was charged with 4-nitrophenylchloroformate (114 mg, 0.564 mmol, 2.10 equiv), DCM (5 mL), and N-(1H-pyrazol-3-yl)methanesulfonamide (86.2 mg, 0.535 mmol, 2.00 equiv). Triethylamine (108 mg, 1.07 mmol, 4.00 equiv) was added dropwise at 0° C. The mixture was stirred for 2 h at room temperature. 2-(2-Chloro-5-(piperazin-1-ylmethyl)phenyl)-7-oxa-2-azaspiro[3.5]nonane (90.0 mg, 0.268 mmol, 1.00 equiv) was added. The resulting solution was stirred for 2 h at room temperature and quenched with water (5 mL), as described in Example 1, Step 1. The crude product (140 mg) was purified by preparative HPLC to provide 56.0 mg (40% yield) of N-(1-(4-(4-chloro-3-(7-oxa-2-azaspiro[3.5]nonan-2-yl)b enzyl)piperazine-1-carbonyl)-1H-pyrazol-3-yl)methanesulfonamide as a white solid. $^1$H NMR (300 MHz, Chloroform-d) δ 8.04 (d, J=3.0 Hz, 1H), 7.15 (d, J=8.1 Hz, 1H), 6.65-6.68 (m, 1H), 6.50 (br, 1H), 6.31 (d, J=3.0 Hz, 1H), 3.86-3.89 (m, 8H), 3.66-3.70 (m, 4H), 3.50 (br, 2H), 3.13 (s, 3H), 2.56 (br, 4H), 1.83-1.86 (m, 4H). LCMS (ESI, m/z): 523 [M+H]$^+$.

Example 9: 5-(2-Chloro-5-((4-(3-(methylsulfonamido)-1H-pyrazole-1-carbonyl)piperazin-1-yl)methyl)phenyl)hexahydropyrrolo[3,4-c]pyrrole-2(1H)-carboxamide

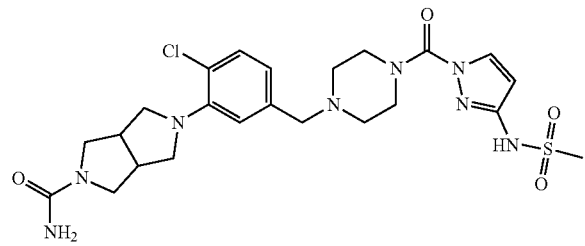 [SMILES: CS(=O)(=O)Nc1ccn(C(=O)N2CCN(Cc3ccc(Cl)c(N4CC5CN(C(N)=O)CC5C4)c3)CC2)n1]

Step 1: Preparation of t-butyl 5-(2-chloro-5-formylphenyl)hexahydropyrrolo[3,4-c]pyrrole-2(1H)-carboxylate

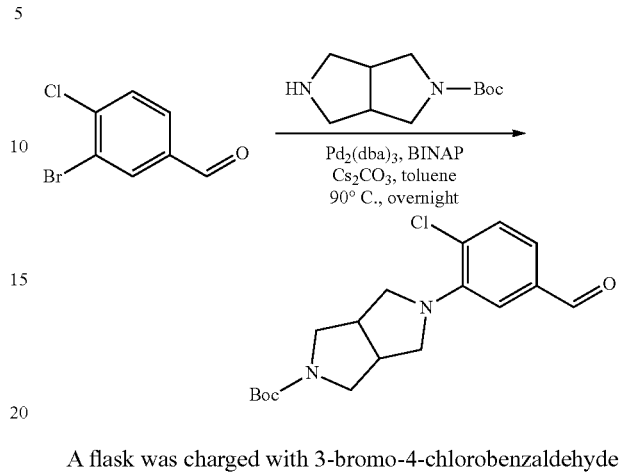

A flask was charged with 3-bromo-4-chlorobenzaldehyde (4.00 g, 18.2 mmol, 1.00 equiv), t-butyl octahydropyrrolo[3,4-c]pyrrole-2-carboxylate (5.83 g, 27.5 mmol, 1.50 equiv), tris(dibenzylideneacetone)dipalladium (838 mg, 0.920 mmol, 0.05 equiv), 2,2'-bis(diphenylphosphino)-1,1'-binaphthyl (1.71 g, 2.75 mmol, 0.15 equiv), cesium carbonate (17.9 g, 54.9 mmol, 3.00 equiv), and toluene (50 mL). The resulting solution was stirred overnight at 90° C. and quenched with water (100 mL). The resulting solution was extracted with EtOAc (3×100 mL) and the organic layers were combined, washed with brine (2×100 mL), dried over anhydrous sodium sulfate, filtered and concentrated under reduced pressure. The residue was chromatographed on a silica gel column to provide 5.00 g (78% yield) of t-butyl 5-(2-chloro-5-formylphenyl)hexahydropyrrolo[3,4-c]pyrrole-2(1H)-carboxylate as a yellow oil. LCMS (ESI, m/z): 351 [M+H]$^+$.

Step 2: Preparation of t-butyl 5-(2-chloro-5-((4-(3-(methylsulfonamido)-1H-pyrazole-1-carbonyl)piperazin-1-yl)methyl)phenyl)hexahydropyrrolo[3,4-c]pyrrole-2(1H)-carboxylate

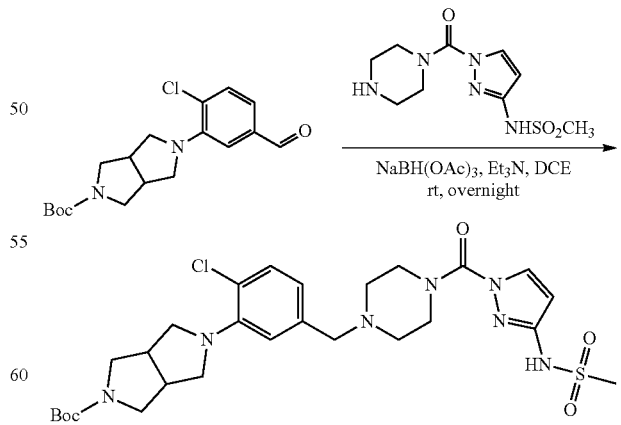

A flask was charged with t-butyl 5-(2-chloro-5-formylphenyl)hexahydropyrrolo[3,4-c]pyrrole-2(1H)-carboxylate (1.40 g, 3.99 mmol, 1.00 equiv), DCE (20 mL), N-[1-[(piperazin-1-yl)carbonyl]-1H-pyrazol-3-yl]

methanesulfonamide (1.42 g, 5.20 mmol, 1.30 equiv), and triethylamine (1.21 g, 11.9 mmol, 3.00 equiv). The resulting solution was stirred for 1 h at room temperature. Sodium triacetoxyborohydride (2.54 g, 12.0 mmol, 3.00 equiv) was added. The resulting solution was stirred overnight at room temperature and quenched with water (20 mL), as described in Example 1, Step 6. The residue was chromatographed on a silica gel column to provide 1.73 g (71% yield) of t-butyl 5-(2-chloro-5-((4-(3-(methylsulfonamido)-1H-pyrazole-1-carbonyl)piperazin-1-yl)methyl)phenyl)hexahydropyrrolo[3,4-c]pyrrole-2(1H)-carboxylate as a yellow oil. LCMS (ESI, m/z): 608 [M+H]⁺.

Step 3: Preparation of N-(1-(4-(4-chloro-3-(hexahydropyrrolo[3,4-c]pyrrol-2(1H)-yl)benzyl)piperazine-1-carbonyl)-1H-pyrazol-3-yl)methanesulfonamide

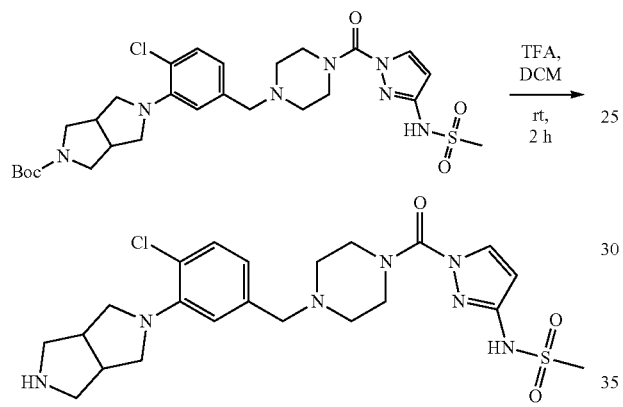

A flask was charged with t-butyl 5-(2-chloro-5-((4-(3-(methylsulfonamido)-1H-pyrazole-1-carbonyl)piperazin-1-yl)methyl)phenyl)hexahydropyrrolo[3,4-c]pyrrole-2(1H)-carboxylate (250 mg, 0.410 mmol, 1.00 equiv), DCM (5 mL), and TFA (1 mL). The resulting solution was stirred for 2 h at room temperature and concentrated under reduced pressure. The mixture was dissolved in saturated NaHCO₃ solution (10 mL), as described in Example 1, Step 3. The crude product (200 mg) was purified by preparative HPLC to provide 57.0 mg (27% yield) of N-(1-(4-(4-chloro-3-(hexahydropyrrolo[3,4-c]pyrrol-2(1H)-yl)benzyl)piperazine-1-carbonyl)-1H-pyrazol-3-yl)methanesulfonamide as a white solid. LCMS (ESI, m/z): 508 [M+H]⁺.

Step 4: Preparation of 5-(2-chloro-5-((4-(3-(methylsulfonamido)-1H-pyrazole-1-carbonyl)piperazin-1-yl)methyl)phenyl)hexahydropyrrolo[3,4-c]pyrrole-2(1H)-carboxamide

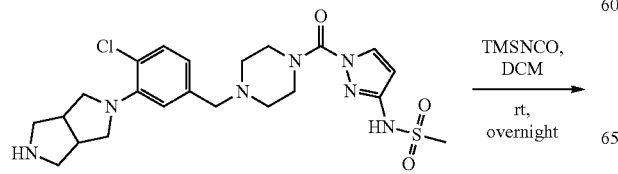

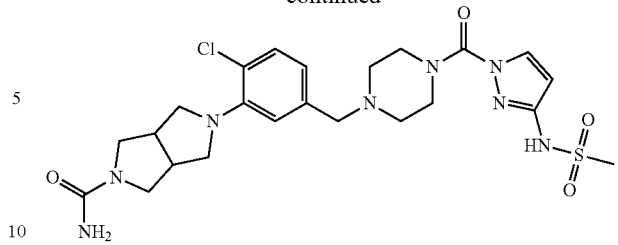

A 50-mL round-bottom flask was charged with N-(1-(4-(4-chloro-3-(hexahydropyrrolo[3,4-c]pyrrol-2(1H)-yl)benzyl)piperazine-1-carbonyl)-1H-pyrazol-3-yl)methanesulfonamide (167 mg, 0.329 mmol, 1.00 equiv), DCM (5 mL), and isocyanatotrimethylsilane (75.7 mg, 0.658 mmol, 2.00 equiv). The resulting solution was stirred overnight at room temperature and concentrated under reduced pressure. The crude product (200 mg) was purified by preparative HPLC to provide 36.0 mg (20% yield) of 5-(2-chloro-5-((4-(3-(methylsulfonamido)-1H-pyrazole-1-carbonyl)piperazin-1-yl)methyl)phenyl)hexahydropyrrolo[3,4-c]pyrrole-2(1H)-carboxamide as a white solid. ¹H NMR (300 MHz, Methanol-d₄) δ 8.25 (br, 1H), 8.02 (d, J=2.7 Hz, 1H), 7.25 (s, 1H), 6.91 (br, 1H), 6.80-6.83 (m, 1H), 6.33 (d, J=2.7 Hz, 1H), 4.54 (br, 2H), 3.84 (br, 4H), 3.51-3.70 (m, 6H), 3.36-3.41 (m, 2H), 3.25-3.28 (m, 2H), 3.12 (s, 3H), 3.04 (br, 2H), 2.54 (br, 4H). LCMS (ESI, m/z): 551 [M+H]⁺.

Example 10: 4-((4-(3-(methylsulfonamido)-1H-pyrazole-1-carbonyl)piperazin-1-yl)methyl)-2-(trifluoromethyl)benzamide

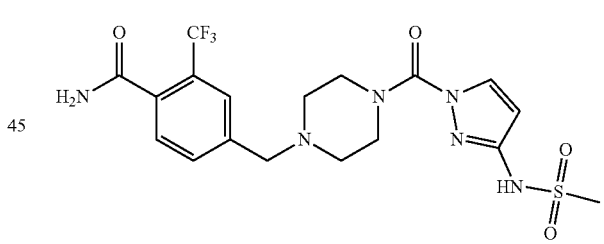

Step 1: Preparation of 4-nitrophenyl 3-(methylsulfonamido)-1H-pyrazole-1-carboxylate

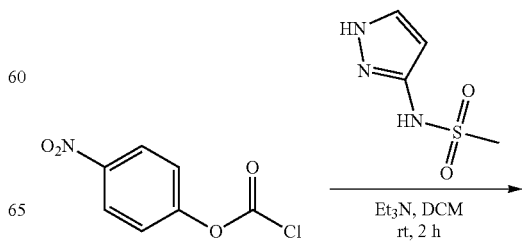

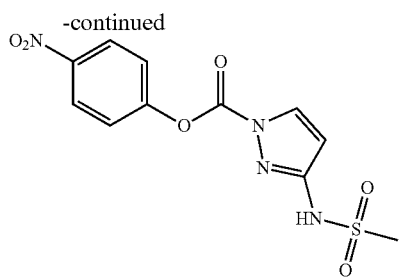

A flask was charged with N-(1H-pyrazol-3-yl)methanesulfonamide (161 mg, 1.00 mmol, 1.00 equiv), DCM (10 mL), triethylamine (404 mg, 3.99 mmol, 4.00 equiv), and 4-nitrophenyl chloroformate (241 mg, 1.20 mmol, 1.20 equiv), as described in Example 1, Step 1 to provide 326 mg (crude) of 4-nitrophenyl 3-(methylsulfonamido)-1H-pyrazole-1-carboxylate as a yellow powder. LCMS (ESI, m/z): 327 [M+H]⁺.

Step 2: Preparation of methyl 4-formyl-2-(trifluoromethyl)benzoate

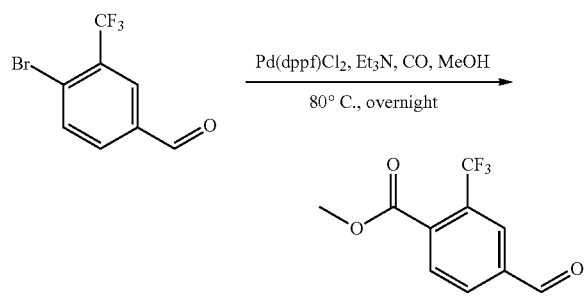

A flask was charged with 4-bromo-3-(trifluoromethyl) benzaldehyde (1.61 g, 6.36 mmol, 1.00 equiv), 1,1'-bis(diphenylphosphino)ferrocenepalladium dichloride (0.466 g, 0.636 mmol, 0.10 equiv), triethylamine (1.93 g, 19.1 mmol, 3.00 equiv), and MeOH (15 mL). Carbon monoxide (10 atm) was introduced in. The resulting solution was stirred overnight at 80° C. and then quenched with water (30 mL), as described in Example 5, Step 3. The residue was chromatographed on a silica gel column to provide 1.00 g (68% yield) of methyl 4-formyl-2-(trifluoromethyl)benzoate as a yellow oil. ¹H NMR (400 MHz, Chloroform-d) δ10.4 (s, 1H), 8.28 (s, 1H), 8.15 (d, J=8.0 Hz, 1H), 7.96 (d, J=8.0 Hz, 1H), 4.00 (s, 3H).

Step 3: Preparation of t-butyl 4-(4-(methoxycarbonyl)-3-(trifluoromethyl)benzyl)piperazine-1-carboxylate

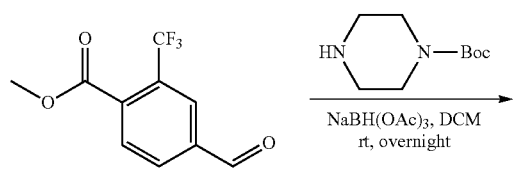

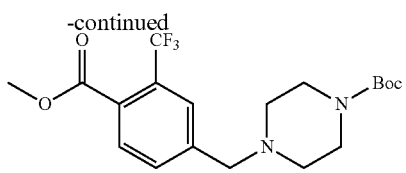

A flask was charged with methyl 4-formyl-2-(trifluoromethyl)benzoate (0.800 g, 3.45 mmol, 1.00 equiv), t-butyl piperazine-1-carboxylate (0.962 g, 5.17 mmol, 1.50 equiv), and DCM (15 mL). The mixture was stirred for 2 h at room temperature. Sodium triacetoxyborohydride (2.93 g, 13.8 mmol, 4.00 equiv) was added. The resulting solution was stirred overnight at room temperature and then quenched with water (30 mL), as described in Example 1, Step 6. The residue was chromatographed on a silica gel column to provide 1.26 g (91% yield) of t-butyl 4-(4-(methoxycarbonyl)-3-(trifluoromethyl)benzyl)piperazine-1-carboxylate as yellow oil. LCMS (ESI, m/z): 403 [M+H]⁺.

Step 4: Preparation of 4-((4-(t-butoxycarbonyl)piperazin-1-yl)methyl)-2-(trifluoromethyl)benzoic acid

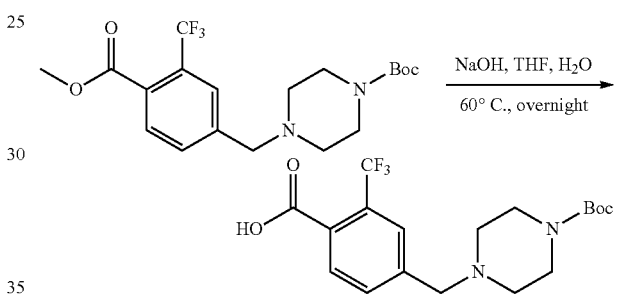

A flask was charged with t-butyl 4-(4-(methoxycarbonyl)-3-(trifluoromethyl)benzyl)piperazine-1-carboxylate (1.21 g, 3.01 mmol, 1.00 equiv), THF (10 mL), water (2 mL), and sodium hydroxide (2.41 g, 60.2 mmol, 20.00 equiv). The resulting solution was stirred overnight at 60° C. The pH of the solution was adjusted to 6 with hydrochloric acid (1M). The resulting solution was extracted with DCM (3×80 mL) and the organic layers were combined, washed with brine (100 mL), dried over anhydrous sodium sulfate, filtered and concentrated under reduced pressure to provide 1.40 g (crude) of 4-((4-(t-butoxycarbonyl)piperazin-1-yl)methyl)-2-(trifluoromethyl)benzoic acid as a white solid. LCMS (ESI, m/z): 389 [M+H]⁺.

Step 5: Preparation of t-butyl 4-(4-carbamoyl-3-(trifluoromethyl)benzyl)piperazine-1-carboxylate

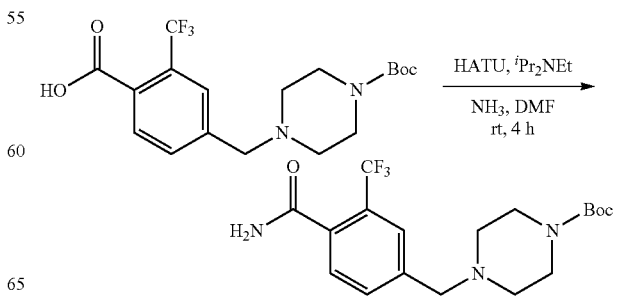

A flask was charged with 4-((4-(t-butoxycarbonyl)piper-azin-1-yl)methyl)-2-(trifluoromethyl)benzoic acid (1.24 g, 3.19 mmol, 1.00 equiv), HATU (2.43 g, 6.39 mmol, 2.00 equiv), DIPEA (1.24 g, 12.8 mmol, 4.00 equiv), N,N-dimethylformamide (10 mL), and ammonia (0.5 M in 1,4-dioxane solution, 63.8 ml, 31.9 mmol, 10.00 equiv). The resulting solution was stirred overnight at room temperature and then concentrated under reduced pressure. The residue was chromatographed on a silica gel column to provide 1.00 g (81% yield) of t-butyl 4-(4-carbamoyl-3-(trifluoromethyl) benzyl)piperazine-1-carboxylate as a white solid. LCMS (ESI, m/z): 388 [M+H]⁺.

Step 6: Preparation of 4-(piperazin-1-ylmethyl)-2-(trifluoromethyl)benzamide

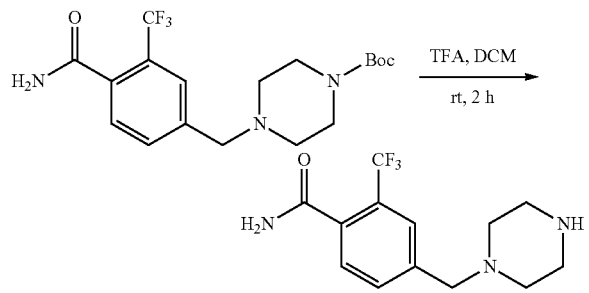

A flask was charged with t-butyl 4-[[4-carbamoyl-3-(trifluoromethyl)phenyl]methyl]piperazine-1-carboxylate (520 mg, 1.34 mmol, 1.00 equiv), DCM (10 mL), and TFA (3 mL), as described in Example 1, Step 3. The resulting solution was stirred for 2 h at room temperature and concentrated under reduced pressure to provide 550 mg (crude) of 4-(piperazin-1-ylmethyl)-2-(trifluoromethyl)benzamide as a yellow oil. LCMS (ESI, m/z): 288 [M+H]⁺.

Step 7: Preparation of 4-((4-(3-(methylsulfona-mido)-1H-pyrazole-1-carbonyl)piperazin-1-yl)methyl)-2-(trifluoromethyl)benzamide

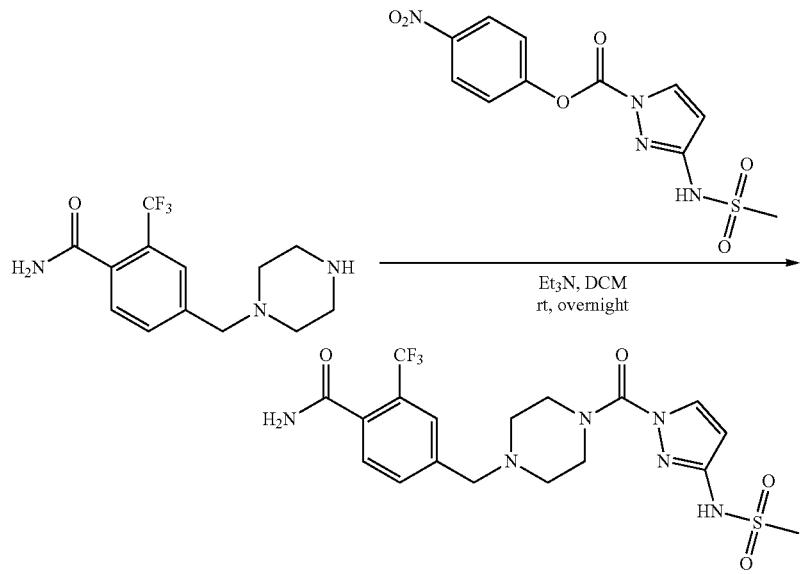

A flask was charged with 4-(piperazin-1-ylmethyl)-2-(trifluoromethyl)benzamide (185 mg, 0.645 mmol, 1.00 equiv), 4-nitrophenyl 3-(methylsulfonamido)-1H-pyrazole-1-carboxylate (316 mg, 0.968 mmol, 1.50 equiv), DCM (10 mL), and triethylamine (261 mg, 2.58 mmol, 4.00 equiv), as described in Example 1, Step 1. The crude product (280 mg) was purified by preparative HPLC to provide 86.9 mg (28% yield) of 4-((4-(3-(methylsulfonamido)-1H-pyrazole-1-carbonyl)piperazin-1-yl)methyl)-2-(trifluoromethyl)benzamide as a white solid. ¹H NMR (300 MHz, Chloroform-d) δ 8.04 (d, J=2.8 Hz, 1H), 7.70 (s, 1H), 7.59-7.61 (m, 2H), 7.17 (br, 1H), 6.31 (d, J=2.8 Hz, 1H), 5.94 (br, 1H), 5.83 (br, 1H), 3.86 (br, 4H), 3.62 (s, 2H), 3.14 (s, 3H), 2.52-2.56 (m, 4H). LCMS (ESI, m/z): 475 [M+H]⁺.

Example 11: (S)—N-(1-(4-(1-(4-chloro-3-(4-fluo-ropiperidin-1-yl)phenyl)ethyl)piperazine-1-carbo-nyl)-1H-pyrazol-3-yl)methanesulfonamide

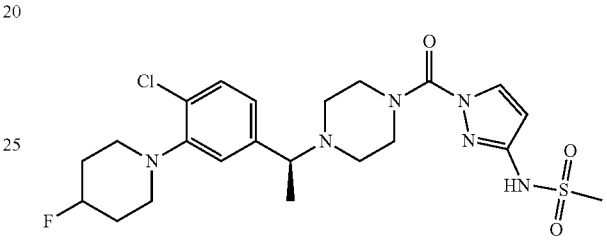

Step 1: Preparation of 1-(3-bromo-4-chlorophenyl)ethan-1-ol

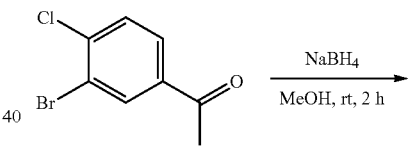

-continued

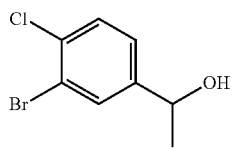

A vial was charged with 1-(3-bromo-4-chlorophenyl)ethan-1-one (1.00 g, 4.28 mmol, 1.00 equiv) and MeOH (20 mL). Sodium borohydride (0.325 g, 8.56 mmol, 2.00 equiv) was added at 0° C. The resulting solution was stirred for 2 h at room temperature and quenched by water (10 mL), as described in Example 1, Step 4 to provide 0.930 g (quantitative) of 1-(3-bromo-4-chlorophenyl)ethan-1-ol as a yellow oil. LCMS (ESI, m/z): 235 [M+H]⁺.

Step 2: Preparation of 2-bromo-4-(1-bromoethyl)-1-chlorobenzene

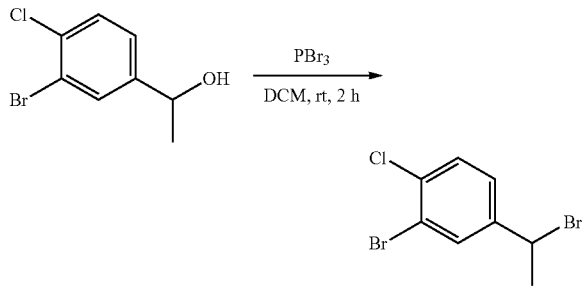

A flask was charged with 1-(3-bromo-4-chlorophenyl)ethan-1-ol (0.900 g, 3.81 mmol, 1.00 equiv) and DCM (20 mL). Tribromophosphane (10.3 g, 38.1 mmol, 10.0 equiv) was added dropwise at 0° C. under nitrogen atmosphere. The resulting solution was stirred for 2 h at room temperature and quenched by saturated NaHCO₃ solution (50 mL). The mixture was extracted with EtOAc (3×50 mL) and the organic layers were combined, dried over anhydrous sodium sulfate, filtered and concentrated under reduced pressure. The residue was chromatographed on a silica gel column to provide 0.827 g (72% yield) of 2-bromo-4-(1-bromoethyl)-1-chlorobenzene as a yellow oil.

Step 3: Preparation of t-butyl 4-(1-(3-bromo-4-chlorophenyl)ethyl)piperazine-1-carboxylate

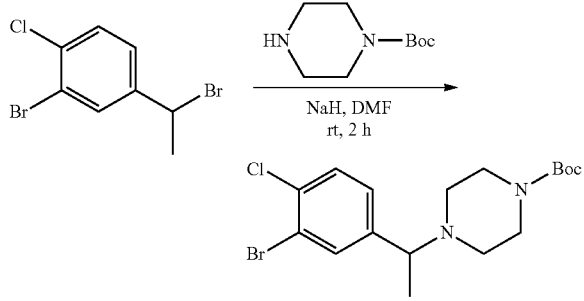

A 40-mL vial was charged with 2-bromo-4-(1-bromoethyl)-1-chlorobenzene (0.827 g, 2.77 mmol, 1.00 equiv) and N,N-dimethylformamide (20 mL). Then sodium hydride (60% in oil, 0.556 g, 13.9 mmol, 3.00 equiv) was added at 0° C. and stirred for 0.5 h at room temperature. Then t-butyl piperazine-1-carboxylate (1.03 g, 5.53 mmol, 2.00 equiv) was added. The resulting solution was stirred overnight at room temperature and quenched by water (10 mL), as described in Example 4, Step 1. The residue was chromatographed on a silica gel column to provide 0.950 g (85% yield) of t-butyl 4-(1-(3-bromo-4-chlorophenyl)ethyl)piperazine-1-carboxylate as a yellow oil. LCMS (ESI, m/z): 403 [M+H]⁺.

Step 4: Preparation of t-butyl 4-(1-(4-chloro-3-(4-fluoropiperidin-1-yl)phenyl)ethyl)piperazine-1-carboxylate

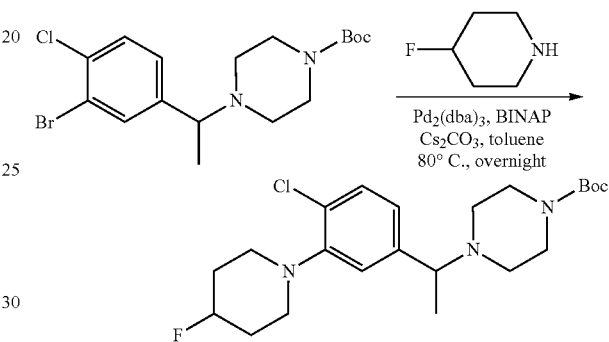

A 40-mL vial was charged with t-butyl 4-[1-(3-bromo-4-chlorophenyl)ethyl]piperazine-1-carboxylate (590 mg, 1.46 mmol, 1.00 equiv), 4-fluoropiperidine (304 mg, 2.19 mmol, 1.50 equiv), cesium carbonate (1430 mg, 4.38 mmol, 3.00 equiv) and toluene (20 mL). Tris(dibenylideneacetone)dipalladium (75.6 mg, 0.0730 mmol, 0.05 equiv) and racemic-2,2'-bis(diphenylphosphino)-1,1'-binaphthyl (684 mg, 1.10 mmol, 0.75 equiv) were added under nitrogen atmosphere. The resulting solution was stirred overnight at 80° C. and quenched by water (10 mL), as described in Example 9, Step 1. The residue was chromatographed on a silica gel column to provide 453 mg (73% yield) of t-butyl 4-(1-(4-chloro-3-(4-fluoropiperidin-1-yl)phenyl)ethyl)piperazine-1-carboxylate as a yellow oil. LCMS (ESI, m/z): 426 [M+H]⁺.

Step 5: Preparation of 1-(1-(4-chloro-3-(4-fluoropiperidin-1-yl)phenyl)ethyl)piperazine

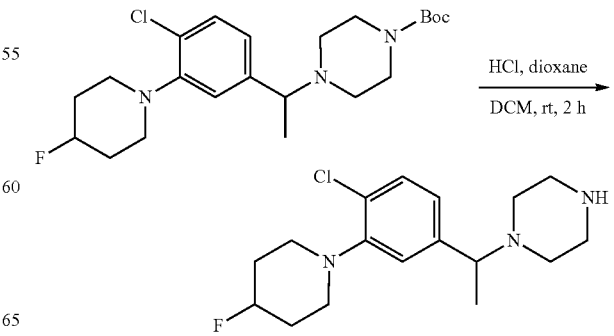

A flask was charged with t-butyl 4-(1-(4-chloro-3-(4-fluoropiperidin-1-yl)phenyl)ethyl)piperazine-1-carboxylate (453 mg, 1.06 mmol, 1.00 equiv), concentrated HCl (2 mL) and DCM (10 mL). The resulting solution was stirred for 2 h at room temperature and concentrated under reduced pressure to provide 345 mg (quantitative) of 1-(1-(4-chloro-3-(4-fluoropiperidin-1-yl)phenyl)ethyl)piperazine as a white solid. LCMS (ESI, m/z): 326[M+H]$^+$.

Step 6: Preparation of 4-nitrophenyl 3-(methylsulfonamido)-1H-pyrazole-1-carboxylate

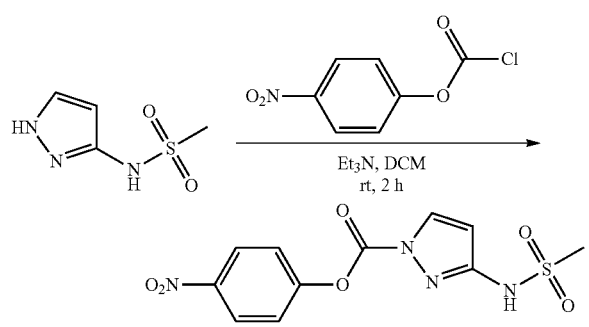

A 40-mL vial was charged with N-(1H-pyrazol-3-yl)methanesulfonamide (273 mg, 1.69 mmol, 1.00 equiv), triethylamine (428 mg, 4.23 mmol, 3.00 equiv) and DCM (15 mL). 4-Nitrophenyl chloroformate (279 mg, 1.38 mmol, 1.00 equiv) was added dropwise at 0° C., as described in Example 1, Step 1 to provide 450 mg (quantitative) of 4-nitrophenyl 3-(methylsulfonamido)-1H-pyrazole-1-carboxylate as a yellow solid. LCMS (ESI, m/z): 327[M+H]$^+$.

Step 7: Preparation of N-(1-(4-(1-(4-chloro-3-(4-fluoropiperidin-1-yl)phenyl)ethyl)piperazine-1-carbonyl)-1H-pyrazol-3-yl)methanesulfonamide

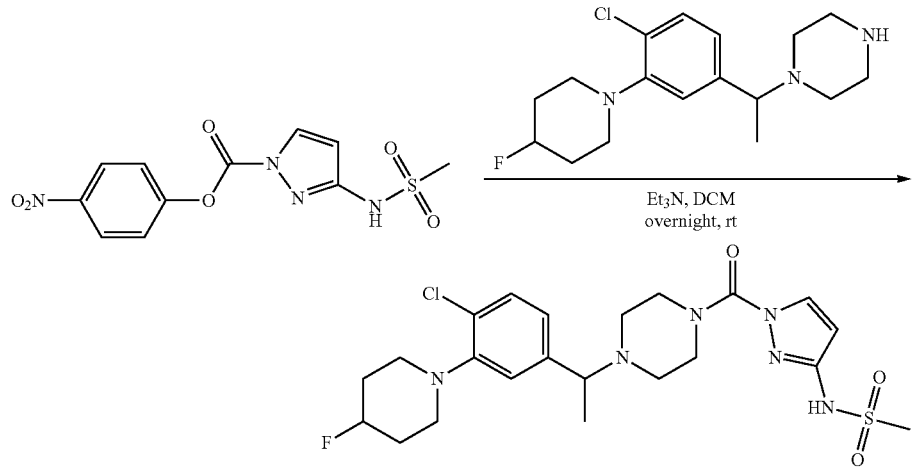

A flask was charged with 1-(1-(4-chloro-3-(4-fluoropiperidin-1-yl)phenyl)ethyl)piperazine (345 mg, 1.06 mmol, 1.00 equiv), 4-nitrophenyl 3-(methylsulfonamido)-1H-pyrazole-1-carboxylate (450 mg, 1.38 mmol, 1.30 equiv), triethylamine (535 mg, 5.29 mmol, 5.00 equiv) and DCM (15 mL). The resulting solution was stirred overnight at room temperature and quenched by water (10 mL), as described in Example 1, Step 1. The residue was chromatographed on a silica gel column to provide crude product. The crude product was purified by preparative HPLC to provide 195 mg (36% yield) of N-(1-(4-(1-(4-chloro-3-(4-fluoropiperidin-1-yl)phenyl)ethyl)piperazine-1-carbonyl)-1H-pyrazol-3-yl)methanesulfonamide as a white solid. LCMS (ESI, m/z): 513 [M+H]$^+$.

Step 8: Preparation of (S)—N-(1-(4-(1-(4-chloro-3-(4-fluoropiperidin-1-yl)phenyl)ethyl)piperazine-1-carbonyl)-1H-pyrazol-3-yl)methanesulfonamide

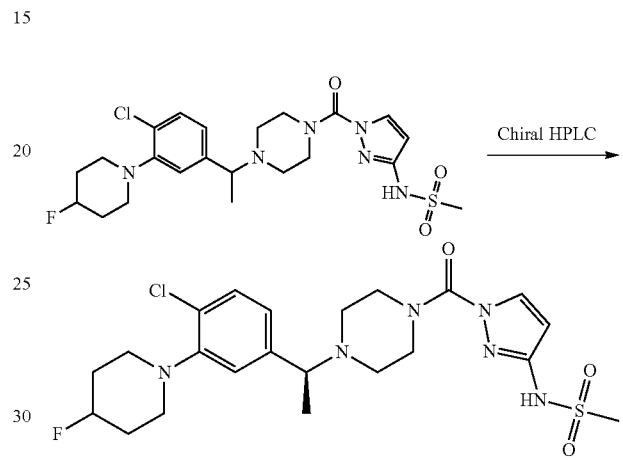

N-(1-(4-(1-(4-chloro-3-(4-fluoropiperidin-1-yl)phenyl)ethyl)piperazine-1-carbonyl)-1H-pyrazol-3-yl)methanesulfonamide (195 mg, 0.380 mmol, 1.00 equiv) was separated by chiral HPLC. Chiral HPLC separation resulted in 53.8 mg (55% yield) of (S)—N-(1-(4-(1-(4-chloro-3-(4-fluoropiperidin-1-yl)phenyl)ethyl)piperazine-1-carbonyl)-1H-pyrazol-3-yl)methanesulfonamide as a white solid. $^1$H NMR (300 MHz, Methanol-d$_4$) δ 7.97-8.09 (d, J=2.7 Hz, 1H), 7.27-7.39 (d, J=8.1 Hz, 1H), 7.08-7.18 (d, J=1.8 Hz, 1H), 6.92-7.05 (d, J=8.1 Hz, 1H), 6.17-6.31 (d, J=2.7 Hz, 1H), 4.67-4.95 (m, 1H), 3.70-3.90 (br, 4H), 3.43-3.57 (m, 1H), 3.05-3.23 (m, 5H), 2.92-3.03 (m, 2H), 2.58-2.72 (m, 2H), 2.41-2.58 (m, 2H), 1.89-2.20 (m, 4H), 1.33-1.48 (d, J=6.9 Hz, 3H). LCMS (ESI, m/z): 513 [M+H]+.

Example 12: N-(1-(4-(4-chloro-3-(4-azaspiro[2.4]heptan-4-yl)benzyl)piperazine-1-carbonyl)-1H-pyrazol-3-yl)methanesulfonamide

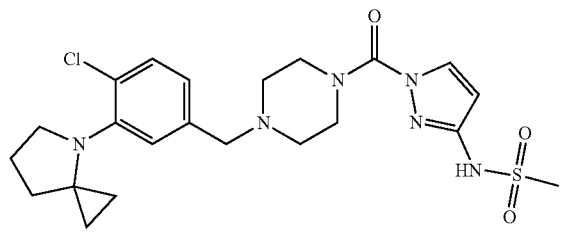 [SMILES: CS(=O)(=O)Nc1ccn(C(=O)N2CCN(Cc3ccc(Cl)c(N4CCCC45CC5)c3)CC2)n1]

Step 1: Preparation of 4-nitrophenyl 3-(methylsulfonamido)-1H-pyrazole-1-carboxylate

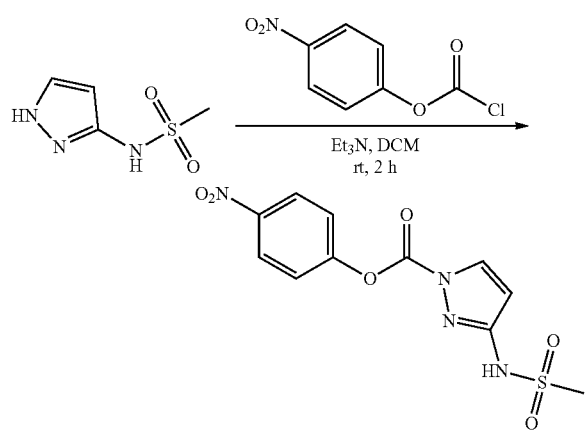

A flask was charged with N-(1H-pyrazol-3-yl)methanesulfonamide (322 mg, 2.00 mmol, 1.00 equiv), DCM (10 mL) and triethylamine (606 mg, 5.99 mmol, 3.00 equiv). 4-Nitrophenyl chloroformate (485 mg, 2.41 mmol, 1.20 equiv) was added at 0° C., as described in Example 1, Step 1 to provide 635 mg (crude) of 4-nitrophenyl 3-methanesulfonamido-1H-pyrazole-1-carboxylate as a yellow solid. LCMS (ESI, m/z): 327 [M+H]+.

Step 2: Preparation of t-butyl 4-(3-bromo-4-chlorobenzyl)piperazine-1-carboxylate

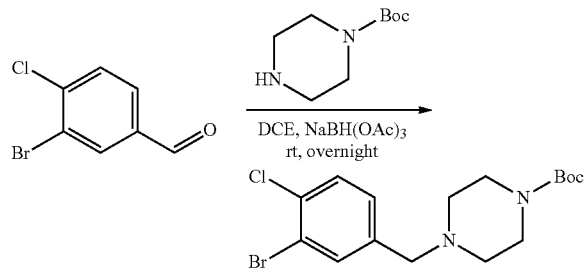

A flask was charged with 3-bromo-4-chlorobenzaldehyde (4.38 g, 20.0 mmol, 1.00 equiv), t-butyl piperazine-1-carboxylate (4.09 g, 22.0 mmol, 1.10 equiv) and DCE (15 mL). After stirring at room temperature for 1 h, sodium triacetoxyborohydride (8.48 g, 40.01 mmol, 2.00 equiv) was added. The resulting solution was stirred overnight at room temperature and quenched by water (10 mL), as described in Example 1, Step 6. The residue was chromatographed on a silica gel column to provide 3.9 g (50% yield) of t-butyl 4-(3-bromo-4-chlorobenzyl)piperazine-1-carboxylate as a white solid. LCMS (ESI, m/z): 389 [M+H]+.

Step 3: Preparation of t-butyl 4-(4-chloro-3-(2-oxopyrrolidin-1-yl)benzyl)piperazine-1-carboxylate

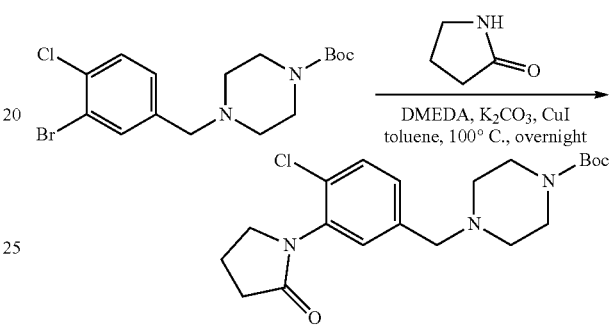

A 50-mL round-bottom flask was charged with t-butyl 4-[(3-bromo-4-chlorophenyl)methyl]piperazine-1-carboxylate (500 mg, 1.28 mmol, 1.00 equiv), pyrrolidin-2-one (163 mg, 1.92 mmol, 1.50 equiv), toluene (10 mL), potassium carbonate (530 mg, 3.83 mmol, 3.00 equiv), cuprous iodide (24.3 mg, 0.130 mmol, 0.10 equiv) and N,N'-dimethylethanediamine (22.5 mg, 0.262 mmol, 0.20 equiv). The resulting solution was stirred overnight at 100° C. under nitrogen atmosphere and quenched by water (30 mL). The mixture was extracted with EtOAc (3×50 mL) and the organic layers were combined, washed with water (3×20 mL), dried over anhydrous sodium sulfate, filtered and concentrated under reduced pressure. The residue was chromatographed on a silica gel column to provide 333 mg (66% yield) of t-butyl 4-(4-chloro-3-(2-oxopyrrolidin-1-yl)benzyl)piperazine-1-carboxylate as a yellow oil. LCMS (ESI, m/z): 394 [M+H]+.

Step 4: Preparation of t-butyl 4-(4-chloro-3-(4-azaspiro[2.4]heptan-4-yl)benzyl)piperazine-1-carboxylate

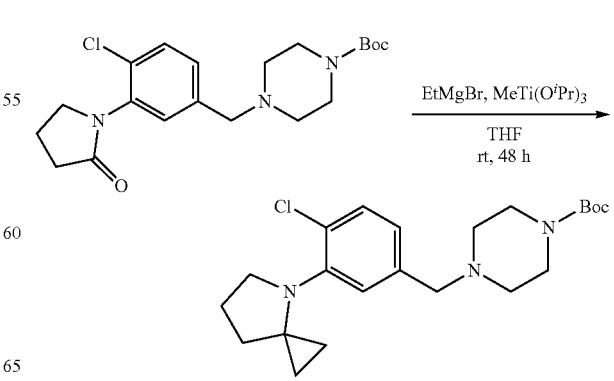

A flask was charged with t-butyl 4-(4-chloro-3-(2-oxopyrrolidin-1-yl)benzyl)piperazine-1-carboxylate (333 mg, 0.852 mmol, 1.00 equiv) and THF (5 mL). Ethylmagnesium bromide (3.0 mol/L in ether, 0.56 mL, 1.70 mmol, 2.00 equiv) and methyltitanium triisopropoxide (1.0 mol/L in THF, 1.27 mL, 1.27 mmol, 1.50 equiv) was added. The resulting solution was stirred for 48 h at room temperature under nitrogen atmosphere and quenched by water (30 mL). The mixture was extracted with EtOAc (3×50 mL) and the organic layers were combined, washed with water (3×20 mL), dried over anhydrous sodium sulfate, filtered and concentrated under reduced pressure. The residue was chromatographed on a silica gel column to provide 175 mg (51% yield) of t-butyl 4-(4-chloro-3-(4-azaspiro[2.4]heptan-4-yl)benzyl)piperazine-1-carboxylate as a yellow oil. LCMS (ESI, m/z): 406 [M+H]⁺.

Step 5: Preparation of 4-(2-chloro-5-(piperazin-1-ylmethyl)phenyl)-4-azaspiro[2.4]heptane

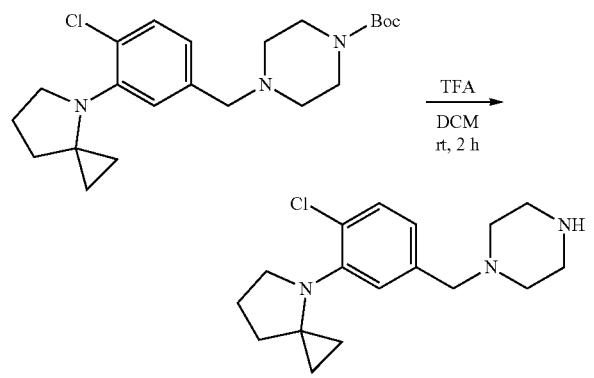

A flask was charged with t-butyl 4-(4-chloro-3-(4-azaspiro[2.4]heptan-4-yl)benzyl)piperazine-1-carboxylate (175 mg, 0.431 mmol, 1.00 equiv), DCM (10 mL) and TFA (1 mL), as described in Example 1, Step 3 to provide 130 mg (quantitative) of 4-(2-chloro-5-(piperazin-1-ylmethyl)phenyl)-4-azaspiro[2.4]heptane as a yellow oil. LCMS (ESI, m/z): 306 [M+H]⁺.

Step 6: Preparation of N-(1-(4-(4-chloro-3-(4-azaspiro[2.4]heptan-4-yl)benzyl)piperazine-1-carbonyl)-1H-pyrazol-3-yl)methanesulfonamide

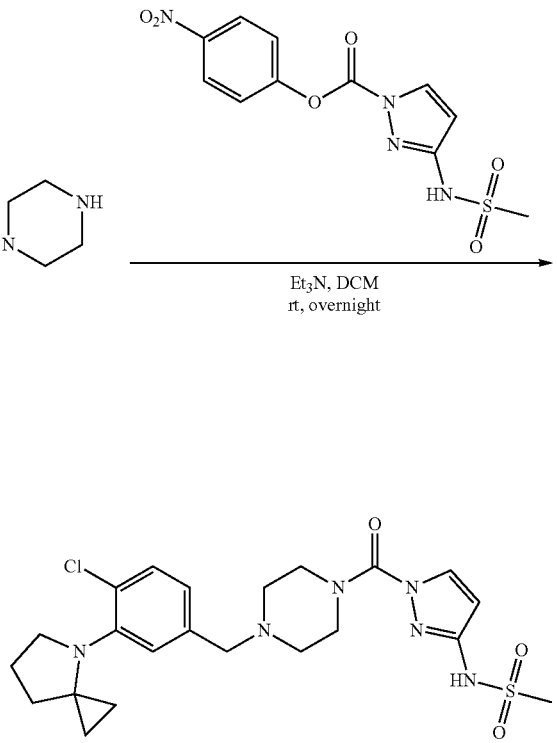

A 50-mL round-bottom flask was charged with 4-(2-chloro-5-(piperazin-1-ylmethyl)phenyl)-4-azaspiro[2.4]heptane (130 mg, 0.425 mmol, 1.00 equiv), DCM (20 mL), 4-nitrophenyl 3-methanesulfonamido-1H-pyrazole-1-carboxylate (163 mg, 0.510 mmol, 1.20 equiv) and triethylamine (85.9 mg, 0.850 mmol, 2.00 equiv). The resulting solution was stirred overnight at room temperature and quenched by water (10 mL), as described in Example 1, Step 1. The crude product was purified by preparative HPLC to provide 35.9 mg (17% yield) of N-(1-(4-(4-chloro-3-(4-azaspiro[2.4]heptan-4-yl)benzyl)piperazine-1-carbonyl)-1H-pyrazol-3-yl)methanesulfonamide as a light yellow solid. ¹H NMR: (400 MHz, Methanol-$d_4$) δ 8.00-8.10 (s, 1H), 7.30-7.39 (d, J=1.7 Hz, 1H), 7.20-7.30 (m, 1H), 6.85-6.96 (d, J=2.8 Hz, 1H), 6.20-6.30 (m, 1H), 3.78-4.00 (m, 4H), 3.55 (m, 2H), 3.40-3.49 (m, 2H), 3.13 (s, 3H), 2.48-2.68 (m, 4H), 1.84-2.08 (m, 4H), 0.77-0.87 (m, 2H), 0.68-0.77 (m, 2H). LCMS (ESI, m/z): 493 [M+H]⁺.

Example 13: N-(1-(1-((5,7-dichloro-1H-indol-2-yl)methyl)-1,8-diazaspiro[4.5]decane-8-carbonyl)-1H-pyrazol-3-yl)acetamide

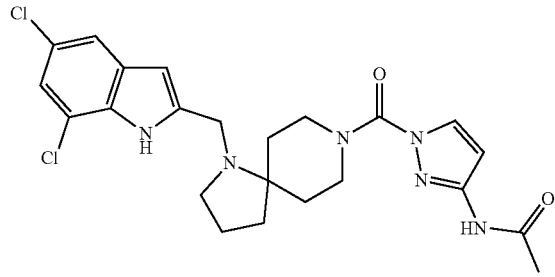 [SMILES: CC(=O)Nc1ccn(C(=O)N2CCC3(CCCN3Cc3cc4cc(Cl)cc(Cl)c4[nH]3)CC2)n1]

Step 1: Preparation of t-butyl 8-(3-acetamido-1H-pyrazole-1-carbonyl)-1,8-diazaspiro[4.5]decane-1-carboxylate

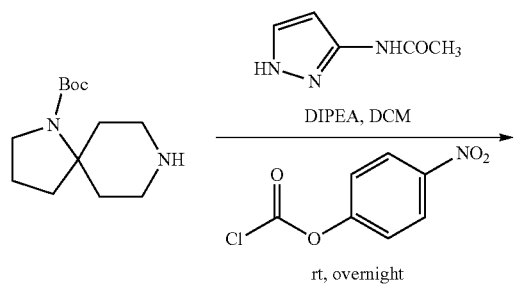

A flask was charged with N-(1H-pyrazol-3-yl)acetamide (1.00 g, 7.99 mmol, 1.00 equiv), DCM (15 mL) and DIPEA (2.06 g, 15.9 mmol, 1.99 equiv). 4-Nitrophenyl chloroformate (1.78 g, 8.83 mmol, 1.11 equiv) in DCM (5 mL) was added dropwise at 0° C. The mixture was stirred for 2 h at room temperature. Then t-butyl 1,8-diazaspiro[4.5]decane-1-carboxylate (1.92 g, 7.99 mmol, 1.00 equiv) was added. The resulting solution was stirred overnight at room temperature and quenched by water (20 mL), as described in Example 2, Step 6. The residue was chromatographed on a silica gel column to provide 2.23 g (71% yield) of t-butyl 8-(3-acetamido-1H-pyrazole-1-carbonyl)-1,8-diazaspiro[4.5]decane-1-carboxylate as an off-white solid. LCMS (ESI, m/z): 392 [M+H]+.

Step 2: Preparation of N-(1-(1,8-diazaspiro[4.5]decane-8-carbonyl)-1H-pyrazol-3-yl)acetamide

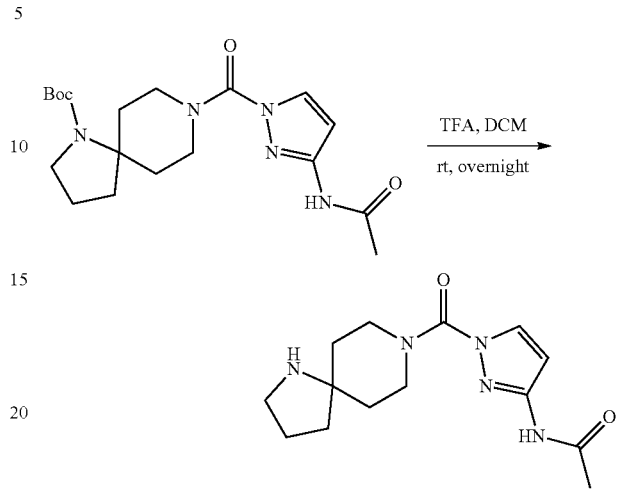

A flask was charged with of t-butyl 8-(3-acetamido-1H-pyrazole-1-carbonyl)-1,8-diazaspiro[4.5]decane-1-carboxylate (2.23 g, 5.70 mmol, 1.00 equiv), DCM (20 mL) and TFA (10 mL), as described in Example 1, Step 3. The resulting solution was stirred overnight at room temperature and concentrated under reduced pressure to provide 1.58 g (crude) of N-(1-(1,8-diazaspiro[4.5]decane-8-carbonyl)-1H-pyrazol-3-yl)acetamide as a light yellow oil. LCMS (ESI, m/z): 292 [M+H]+.

Step 3: Preparation of ethyl (E)-2-(2-(2,4-dichlorophenyl)hydrazineylidene)propanoate

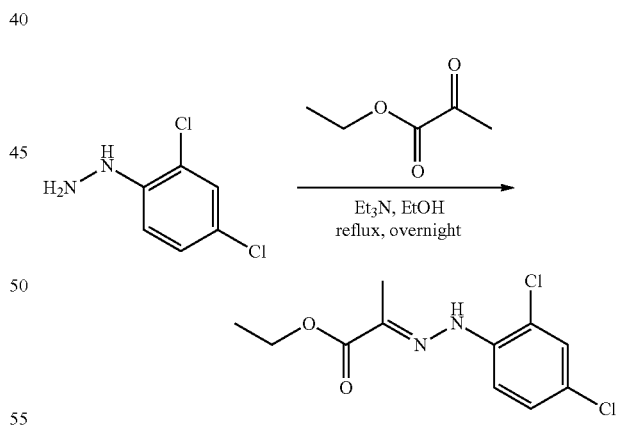

A 250-mL round-bottom flask was charged with (2,4-dichlorophenyl)hydrazine (10.0 g, 56.8 mmol, 1.00 equiv), ethanol (50 mL), ethyl 2-oxopropanoate (6.59 g, 56.8 mmol, 1.00 equiv) and triethylamine (5.74 g, 56.8 mmol, 1.50 equiv). The resulting solution was refluxed overnight and concentrated under reduced pressure. The residue was chromatographed on a silica gel column to provide 3.15 g (31% yield) of ethyl (E)-2-(2-(2,4-dichlorophenyl)hydraziney-lidene)propanoate as a light yellow solid. LCMS (ESI, m/z): 275 [M+H]+.

Step 4: Preparation of ethyl 5,7-dichloro-1H-indole-2-carboxylate

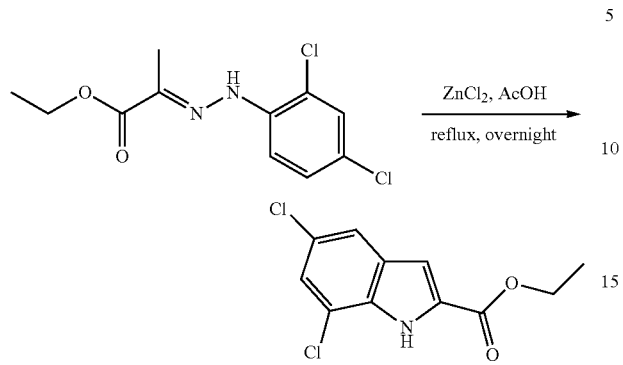

A flask was charged with ethyl (2E)-2-[2-(2,4-dichlorophenyl)hydrazin-1-ylidene]propanoate (3.00 g, 10.9 mmol, 1.00 equiv), acetic acid (50 mL) and zinc chloride (27.2 g, 200 mmol, 18.3 equiv). The resulting solution was refluxed for overnight, cooled to room temperature and poured into water (200 mL). The solid was collected by filtration, washed with water (3×10 mL), and dried to provide 2.30 g (82% yield) of ethyl 5,7-dichloro-1H-indole-2-carboxylate as a brown solid. LCMS (ESI, m/z): 258 [M+H]$^+$.

Step 5: Preparation of (5,7-dichloro-1H-indol-2-yl)methanol

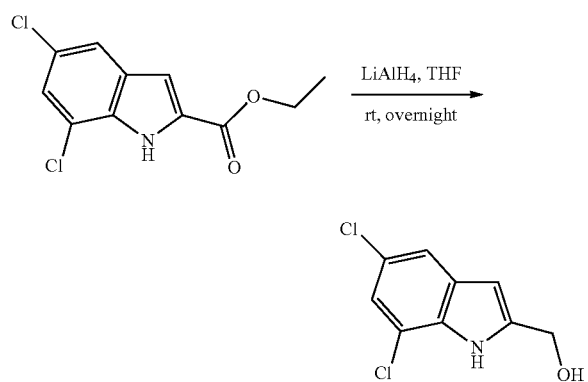

A vial was charged with ethyl 5,7-dichloro-1H-indole-2-carboxylate (500 mg, 1.94 mmol, 1.00 equiv), THF (10 mL) and lithium aluminum hydride (111 mg, 2.92 mmol, 1.51 equiv). The resulting solution was stirred overnight at room temperature under nitrogen. Then water (111 ml), 15% sodium hydroxide solution (111 mg) and water (333 mL) were added in sequence at 0° C. The solids were filtered out and washed with THF (3×10 mL). The filtrate was concentrated under reduced pressure to provide 339 mg (81% yield) of (5,7-dichloro-1H-indol-2-yl)methanol as a brown oil. LCMS (ESI, m/z): 216 [M+H]$^+$.

Step 6: Preparation of 5,7-dichloro-1H-indole-2-carbaldehyde

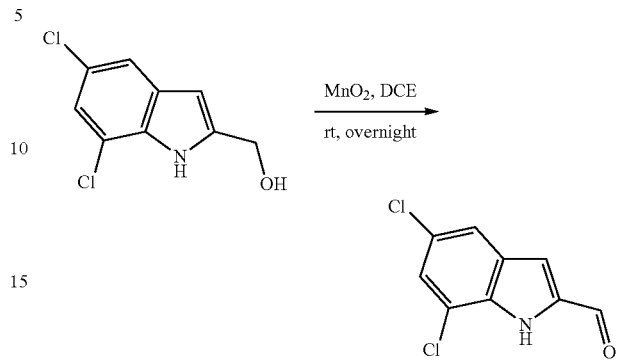

A vial was charged with (5,7-dichloro-1H-indol-2-yl)methanol (0.339 g, 1.57 mmol, 1.00 equiv), DCE (10 mL) and manganese dioxide (1.37 g, 15.8 mmol, 10.0 equiv). The resulting solution was stirred overnight at room temperature. The solids were filtered out and washed with DCE (3×10 mL). The filtrate was concentrated under reduced pressure. The residue was chromatographed on a silica gel column to provide 0.203 g (60% yield) of 5,7-dichloro-1H-indole-2-carbaldehyde as a brown oil. LCMS (ESI, m/z): 214 [M+H]$^+$.

Step 7: Preparation of N-(1-(1-((5,7-dichloro-1H-indol-2-yl)methyl)-1,8-diazaspiro[4.5]decane-8-carbonyl)-1H-pyrazol-3-yl)acetamide

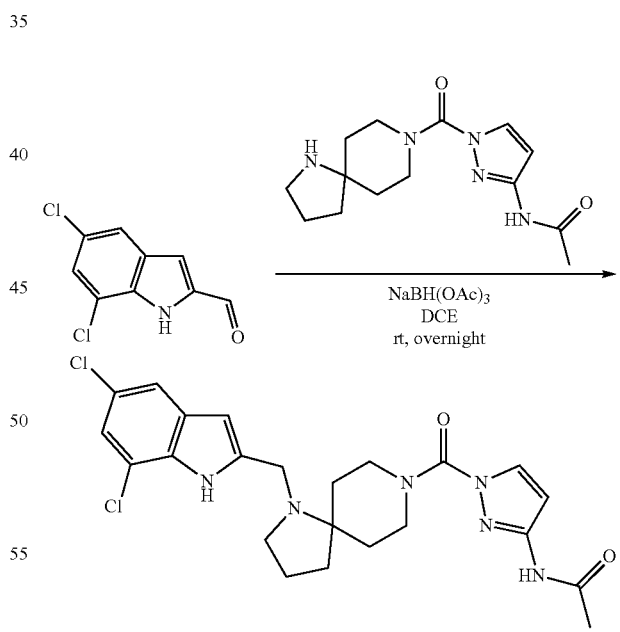

A vial was charged with 5,7-dichloro-1H-indole-2-carbaldehyde (102 mg, 0.477 mmol, 1.00 equiv), DCE (10 mL) and N-(1-[1,8-diazaspiro[4.5]decan-8-ylmethyl]-1H-pyrazol-3-yl)acetamide (132 mg, 0.477 mmol, 1.00 equiv). The mixture was stirred for 2 h at room temperature. Then sodium triacetoxyborohydride (253 mg, 1.19 mmol, 2.51 equiv) was added. The resulting solution was stirred overnight at room temperature and quenched by water (10 mL), as described in Example 1, Step 6. The crude product was purified by preparative HPLC to provide 59.7 mg (26% yield) of N-(1-(1-((5,7-dichloro-1H-indol-2-yl)methyl)-1,8-diazaspiro[4.5]decane-8-carbonyl)-1H-pyrazol-3-yl)acetamide as a light yellow oil. ¹H NMR (400 MHz, Chloroform-d) δ 8.72 (br, 1H), 7.90-8.15 (m, 2H), 7.35-7.50 (m, 1H), 7.12-7.15 (m, 1H), 6.80-7.02 (m, 1H), 6.30 (d, J=2.7 Hz, 1H), 4.48-4.72 (m, 2H), 3.79 (s, 2H), 3.02 (m, 2H), 2.62-2.85 (m, 2H), 2.18 (s, 3H), 1.80-1.98 (m, 6H), 1.45-1.59 (m, 2H). LCMS (ESI, m/z): 489 [M+H]⁺.

Example 14: 2-((8-(3-acetamido-1H-pyrazole-1-carbonyl)-1,8-diazaspiro[4.5]decan-1-yl)methyl)-1H-indole-5-carboxamide

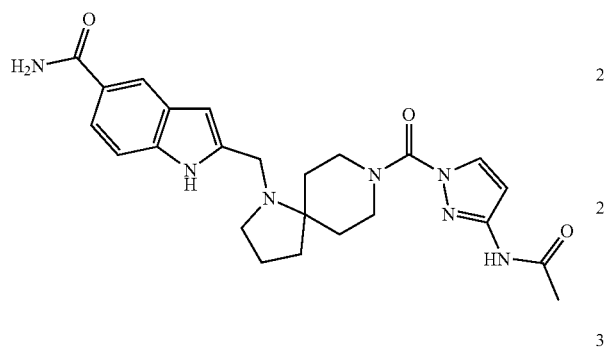

Step 1: Synthesis of t-butyl 8-(3-acetamido-1H-pyrazole-1-carbonyl)-1,8-diazaspiro[4.5]decane-1-carboxylate

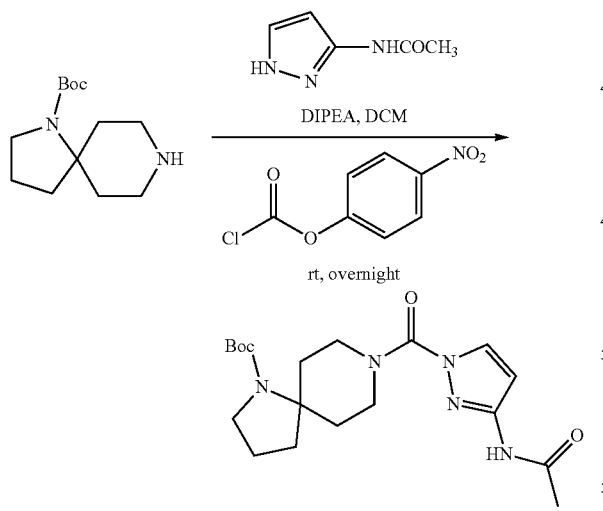

A flask was charged with N-(1H-pyrazol-4-yl)acetamide (1.00 g, 7.99 mmol, 1.00 equiv), DCM (15 mL) and DIPEA (2.06 g, 15.9 mmol, 2.00 equiv). 4-Nitrophenyl chloroformate (1.78 g, 8.83 mmol, 1.11 equiv) in DCM (5 mL) was added dropwise at 0° C. The mixture was stirred for 2 h at room temperature, then t-butyl 1,8-diazaspiro[4.5]decane-1-carboxylate (1.92 g, 7.99 mmol, 1.00 equiv) was added. The resulting solution was stirred overnight at room temperature and quenched by water (20 mL). The mixture was extracted with DCM (3×20 mL) and the organic layers were combined, washed with water (3×20 mL), dried over anhydrous sodium sulfate, filtered and concentrated under reduced pressure. The residue was chromatographed to provide 2.23 g (71% yield) of t-butyl 8-(3-acetamido-1H-pyrazole-1-carbonyl)-1,8-diazaspiro[4.5]decane-1-carboxylate as an off-white solid. LCMS (ESI, m/z): 392 [M+H]⁺.

Step 2: Synthesis of N-(1-(1,8-diazaspiro[4.5]decane-8-carbonyl)-1H-pyrazol-3-yl)acetamide

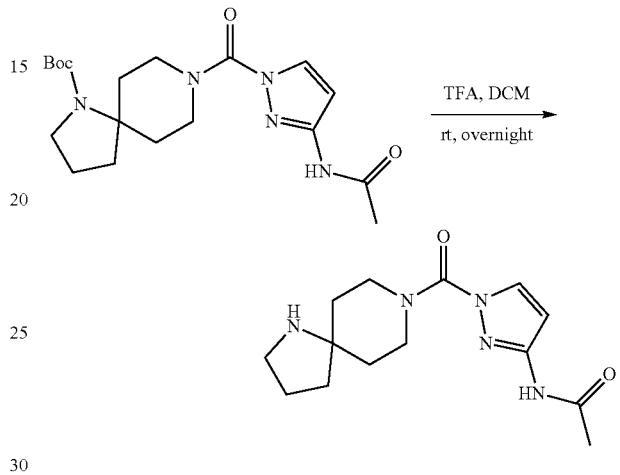

A round-bottom flask was charged with t-butyl 8-(3-acetamido-1H-pyrazole-1-carbonyl)-1,8-diazaspiro[4.5]decane-1-carboxylate (2.23 g, 5.70 mmol, 1.00 equiv), DCM (10 mL) and TFA (3 mL), as described in Example 1, Step 3. The resulting solution was stirred overnight at room temperature and concentrated under reduced pressure to provide 1.58 g (crude) of N-(1-(1,8-diazaspiro[4.5]decane-8-carbonyl)-1H-pyrazol-3-yl)acetamide as a light yellow oil. LCMS (ESI, m/z): 292 [M+H]⁺.

Step 3: Preparation of methyl 4-amino-3-iodobenzoate

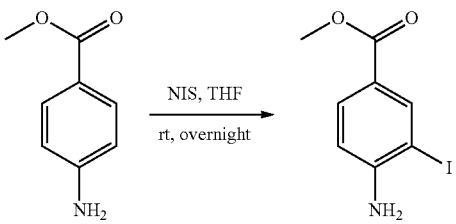

A flask was charged with methyl 4-aminobenzoate (9.00 g, 59.5 mmol, 1.00 equiv), THF (100 mL) and 1-iodo-5-pyrrolidinedione (16.2 g, 72.0 mmol, 1.20 equiv). The resulting solution was stirred overnight at room temperature and concentrated under reduced pressure. The residue was diluted with water (50 mL) and extracted with DCM (3×50 mL), the organic layers were combined, washed with water (3×50 mL), dried over anhydrous sodium sulfate, filtered and concentrated under reduced pressure. The residue was chromatographed on a silica gel column to provide 7.60 g (46% yield) of methyl 4-amino-3-iodobenzoate as a yellow solid. LCMS (ESI, m/z): 278 [M+H]⁺.

Step 4: Preparation of methyl 3-iodo-4-(2,2,2-trifluoroacetamido)benzoate

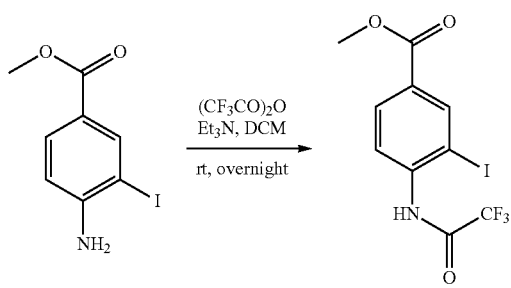 [SMILES: COC(=O)c1ccc(N)c(I)c1 ; COC(=O)c1ccc(NC(=O)C(F)(F)F)c(I)c1]

A round-bottom flask was charged with methyl 4-amino-3-iodobenzoate (7.50 g, 27.1 mmol, 1.00 equiv), DCM (50 mL), triethylamine (7.20 g, 71.3 mmol, 2.63 equiv) and trifluoroacetic anhydride (8.90 g, 42.4 mmol, 1.57 equiv). The resulting solution was stirred overnight at room temperature and washed with water (3×50 mL). The organic layer was dried over anhydrous sodium sulfate, filtered and concentrated under reduced pressure, as described in Example 1, Step 1. The residue was chromatographed on a silica gel column to provide 8.00 g (79% yield) of methyl 3-iodo-4-(2,2,2-trifluoroacetamido)benzoate as a yellow solid.

Step 5: Preparation of methyl 2-(hydroxymethyl)-1H-indole-5-carboxylate

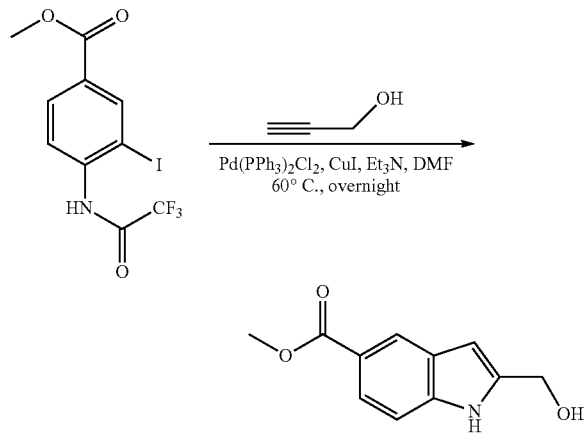

A three-necked round-bottom flask was charged with methyl 3-iodo-4-(2,2,2-trifluoroacetamido)benzoate (3.73 g, 10.0 mmol, 1.00 equiv), N,N-dimethylformamide (50 mL), prop-2-yn-1-ol (0.840 g, 15.0 mmol, 1.50 equiv), triethylamine (5.05 g, 50.0 mmol, 5.00 equiv), cuprous iodide (0.190 g, 1.00 mmol, 0.10 equiv) and bis(triphenylphosphine)palladium(II) chloride (0.350 g, 0.500 mmol, 0.05 equiv) under nitrogen. The resulting solution was stirred overnight at 60° C. and diluted with water (500 mL). The mixture was extracted with EtOAc (3×500 mL) and the organic layers were combined, washed with water (3×100 mL), dried over anhydrous sodium sulfate, filtered and concentrated under reduced pressure. The residue was chromatographed on a silica gel column to provide 1.80 g (85% yield) of methyl 2-(hydroxymethyl)-1H-indole-5-carboxylate as a brown oil. LCMS (ESI, m/z): 206 [M+H]$^+$.

Step 6: Preparation of 2-(hydroxymethyl)-1H-indole-5-carboxylic acid

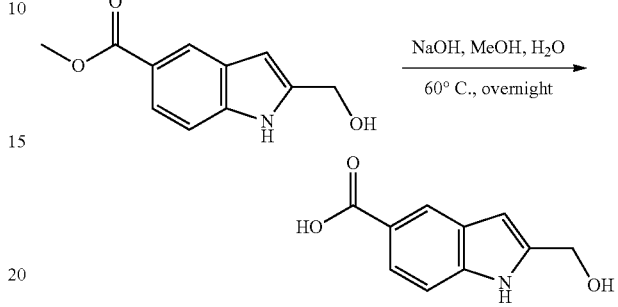

A vial was charged with methyl 2-(hydroxymethyl)-1H-indole-5-carboxylate (800 mg, 3.90 mmol, 1.00 equiv), methanol (5 mL), water (5 mL) and sodium hydroxide (234 mg, 5.85 mmol, 1.50 equiv). The resulting solution was stirred overnight at 60° C. and concentrated under reduced pressure. The residue was diluted with water (25 mL) and the pH value was adjusted to 4~5 with 1 N hydrochloric acid solution, as described in Example 4, Step 3. The solid was collected by filtration, washed with water (3×10 mL) and dried to provide 620 mg (83% yield) of 2-(hydroxymethyl)-1H-indole-5-carboxylic acid as a light brown solid. LCMS (ESI, m/z): 192 [M+H]$^+$.

Step 7: Preparation of 2-formyl-1H-indole-5-carboxylic acid

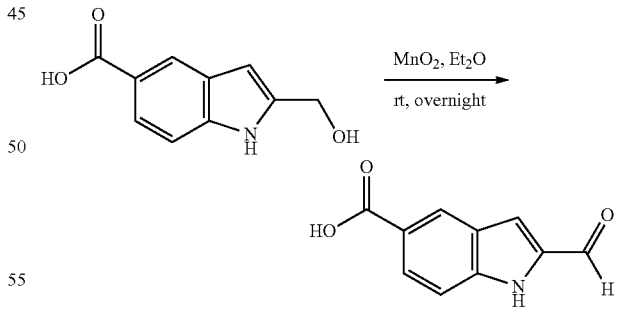

A vial was charged with 2-(hydroxymethyl)-1H-indole-5-carboxylic acid (0.300 g, 1.57 mmol, 1.00 equiv), ether (10 mL) and manganese dioxide (1.37 g, 15.7 mmol, 10.0 equiv). The resulting solution was stirred overnight at room temperature. The solid was filtered out and washed with acetonitrile (3×10 mL), as described in Example 13, Step 6 to provide 0.189 g (64% yield) of 2-formyl-1H-indole-5-carboxylic acid as a yellow oil. LCMS (ESI, m/z): 190 [M+H]$^+$.

Step 8: Preparation of 2-((8-(3-acetamido-1H-pyrazole-1-carbonyl)-1,8-diazaspiro[4.5]decan-1-yl)methyl)-1H-indole-5-carboxylic acid

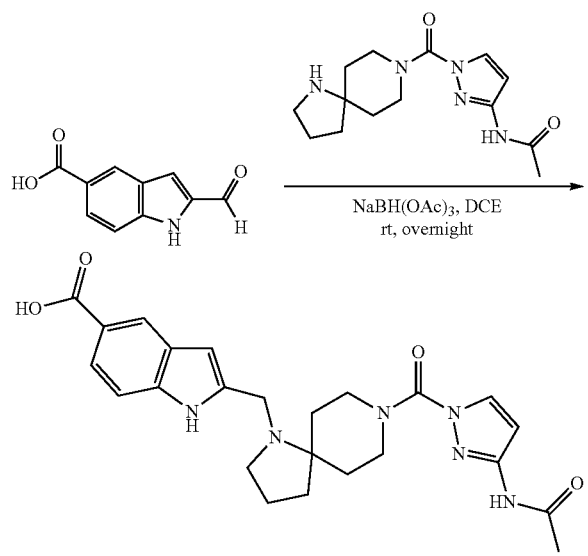

A vial was charged with 2-formyl-1H-indole-5-carboxylic acid (137 mg, 0.725 mmol, 1.00 equiv), DCE (10 mL) and N-(1-(1,8-diazaspiro[4.5]decane-8-carbonyl)-1H-pyrazol-3-yl)acetamide (211 mg, 0.725 mmol, 1.00 equiv) and sodium triacetoxyborohydride (385 mg, 1.82 mmol, 2.50 equiv). The resulting solution was stirred overnight at room temperature and quenched by water (10 mL), as described in Example 1, Step 6. The residue was chromatographed on a silica gel column to provide 75.0 mg (22% yield) of 2-((8-(3-acetamido-1H-pyrazole-1-carbonyl)-1,8-diazaspiro[4.5]decan-1-yl)methyl)-1H-indole-5-carboxylic acid as a yellow oil. LCMS (ESI, m/z): 465 [M+H]$^+$.

Step 9: Preparation of 2-((8-(3-acetamido-1H-pyrazole-1-carbonyl)-1,8-diazaspiro[4.5]decan-1-yl)methyl)-1H-indole-5-carboxamide

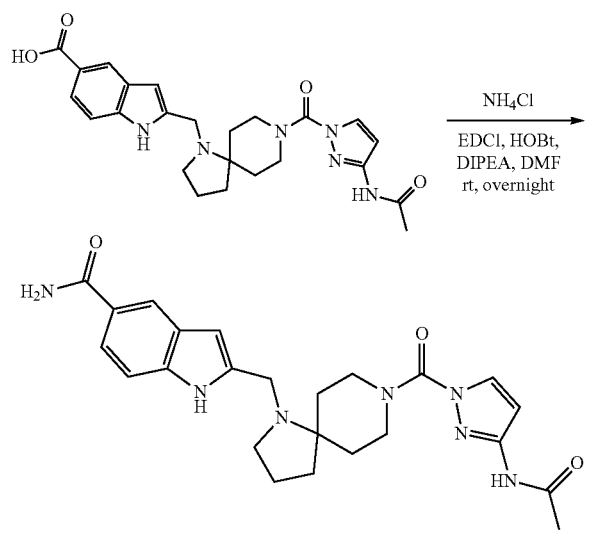

A vial was charged with 2-((8-(3-acetamido-1H-pyrazole-1-carbonyl)-1,8-diazaspiro[4.5]decan-1-yl)methyl)-1H-indole-5-carboxylic acid (75.0 mg, 0.161 mmol, 1.00 equiv), N,N-dimethylformamide (5 mL), DIPEA (41.5 mg, 0.322 mmol, 2.00 equiv), N-(3-dimethylaminopropyl)-N'-ethylcarbodiimide hydrochloride (34.0 mg, 0.177 mmol, 1.10 equiv) and 1-hydroxybenzotrizole (23.9 mg, 0.177 mmol, 1.10 equiv). The mixture was stirred for 2 hours at room temperature. Then ammonium chloride (12.8 mg, 0.242 mmol, 1.50 equiv) was added. The resulting solution was stirred overnight at room temperature and quenched by water (50 mL). The mixture was extracted with EtOAc (3×50 mL) and the organic layers were combined, washed with water (3×50 mL), dried over anhydrous sodium sulfate, filtered and concentrated under reduced pressure. The crude product was purified by preparative HPLC to provide 14.9 mg (20% yield) of 2-((8-(3-acetamido-1H-pyrazole-1-carbonyl)-1,8-diazaspiro[4.5]decan-1-yl)methyl)-1H-indole-5-carboxamide as a light yellow solid. $^1$H NMR (300 MHz, Methanol-$d_4$) δ 7.99-8.17 (m, 2H), 7.58-7.80 (m, 1H), 7.30-7.48 (m, 1H), 6.72-6.89 (m, 1H), 6.31 (s, 1H), 4.50-4.70 (m, 2H), 3.85 (s, 2H), 3.08-3.26 (m, 2H), 2.78-2.90 (m, 2H), 2.14 (s, 3H), 1.78-2.05 (m, 6H), 1.53-1.65 (m, 2H). LCMS (ESI, m/z): 464 [M+H]$^+$.

Example 15: N-(1-(4-(2-(thiazol-2-yl)-4-(trifluoromethyl)phenoxy)piperidine-1-carbonyl)-1H-pyrazol-3-yl)methanesulfonamide

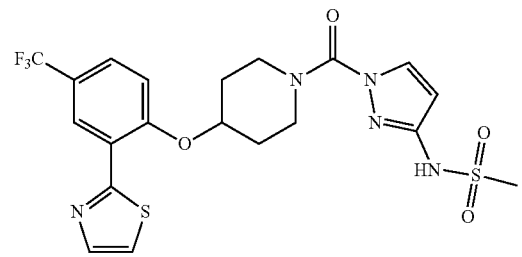 [SMILES: CS(=O)(=O)Nc1ccn(C(=O)N2CCC(Oc3ccc(C(F)(F)F)cc3-c3nccs3)CC2)n1]

Step 1: Preparation of t-butyl 4-(2-bromo-4-(trifluoromethyl)phenoxy)piperidine-1-carboxylate

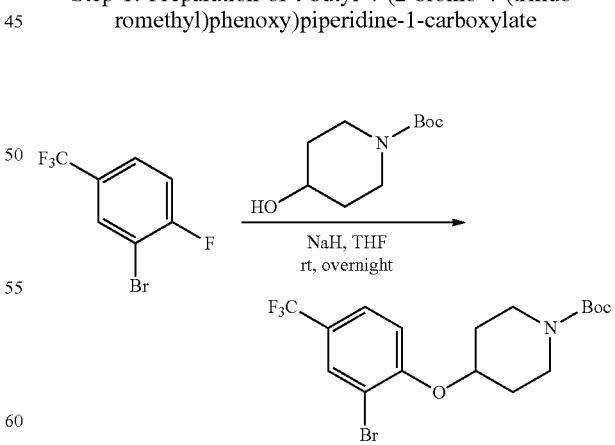

A flask was charged with t-butyl 4-hydroxypiperidine-1-carboxylate (2.0 g, 9.94 mmol, 1.00 equiv) and THF (40 mL). Then sodium hydride (60% in oil, 0.800 g, 20.0 mmol, 2.00 equiv) was added at 0° C. The resulting solution was stirred for 1 hour at room temperature and 2-bromo-1- fluoro-4-(trifluoromethyl)benzene (3.20 g, 13.2 mmol, 1.30 equiv) was added. The resulting solution was stirred overnight at room temperature and quenched by water (20 mL), as described in Example 4, Step 1. The residue was chromatographed on a silica gel column to provide 3.40 g (81% yield) t-butyl 4-(2-bromo-4-(trifluoromethyl)phenoxy)piperidine-1-carboxylate as a white solid. LCMS (ESI, m/z): 424 [M+H]⁺.

Step 2: Preparation of t-butyl 4-(2-(thiazol-2-yl)-4-(trifluoromethyl)phenoxy)piperidine-1-carboxylate

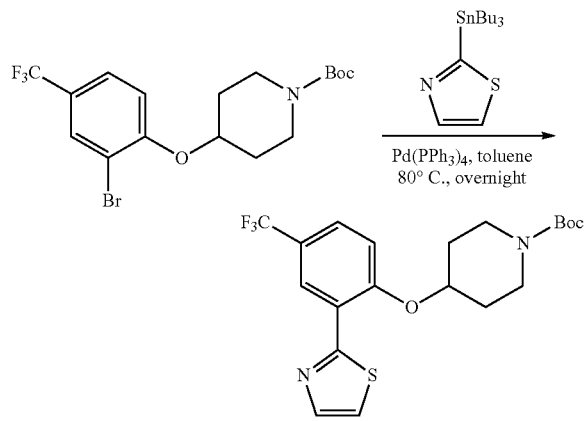

A flask was charged with t-butyl 4-[2-bromo-4-(trifluoromethyl)phenoxy]piperidine-1-carboxylate (424 mg, 1.00 mmol, 1.00 equiv), tetrakis(triphenylphosphane) palladium (104 mg, 0.100 mmol, 0.10 equiv), 2-(tributylstannyl)-1,3-thiazole (450 mg, 1.20 mmol, 1.20 equiv) and toluene (20 mL). The resulting solution was stirred overnight at 80° C. under nitrogen and quenched by water (20 mL). The mixture was extracted with DCM (3×30 mL) and the organic layers were combined, washed with water (3×10 mL), dried over anhydrous sodium sulfate, filtered and concentrated under reduced pressure. The residue was chromatographed on a silica gel column to provide 259 mg (60% yield) of t-butyl 4-(2-(thiazol-2-yl)-4-(trifluoromethyl)phenoxy)piperidine-1-carboxylate as a yellow solid. LCMS (ESI, m/z): 429 [M+H]⁺.

Step 3: Preparation of 2-(2-(piperidin-4-yloxy)-5-(trifluoromethyl)phenyl)thiazole

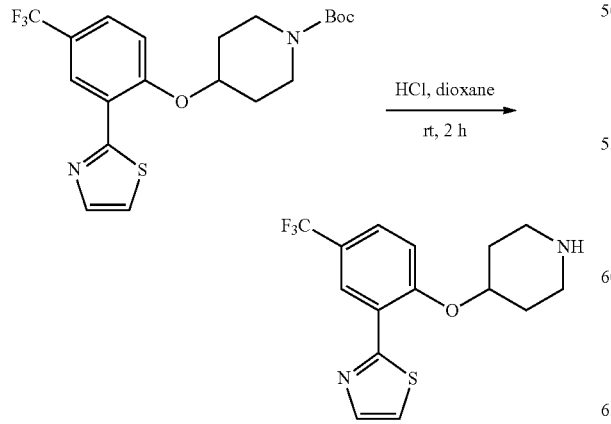

A flask was charged with t-butyl 4-[2-(1,3-thiazol-2-yl)-4-(trifluoromethyl)phenoxy]piperidine-1-carboxylate (259 mg, 0.60 mmol, 1.00 equiv), 1,4-dioxane (20 mL) and hydrochloric acid (4 mL), as described in Example 11, Step 5. The resulting solution was stirred for 2 h at room temperature and concentrated under reduced pressure to provide 195 mg (crude) of 2-(2-(piperidin-4-yloxy)-5-(trifluoromethyl)phenyl)thiazole as a white solid. LCMS (ESI, m/z): 329 [M+H]⁺.

Step 4: Preparation of 4-(2-(thiazol-2-yl)-4-(trifluoromethyl)phenoxy)piperidine-1-carbonyl chloride

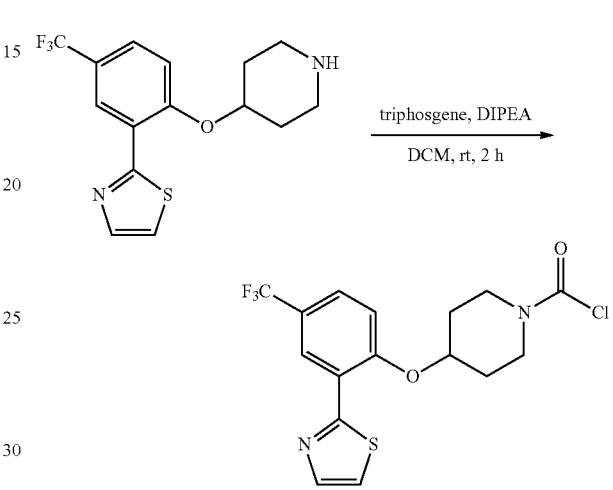

A flask was charged with 2-(2-(piperidin-4-yloxy)-5-(trifluoromethyl)phenyl)thiazole (195 mg, 0.590 mmol, 1.00 equiv), triphosgene (89.0 mg, 0.300 mmol, 0.50 equiv) and DCM (20 mL). Then DIPEA (307 mg, 2.38 mmol, 4.00 equiv) was added at 0° C. The resulting solution was stirred for 2 h at room temperature and quenched by water (10 mL), as described in Example 2, Step 5 to provide 230 mg (crude) of 4-[2-(1,3-thiazol-2-yl)-4-(trifluoromethyl)phenoxy]piperidine-1-carbonyl chloride as a white solid.

Step 5: Preparation of N-(1-(4-(2-(thiazol-2-yl)-4-(trifluoromethyl)phenoxy)piperidine-1-carbonyl)-1H-pyrazol-3-yl)methanesulfonamide

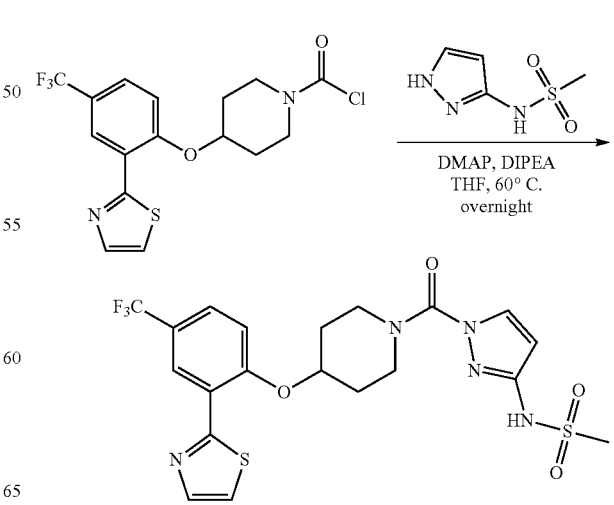

A flask was charged with 4-[2-(1,3-thiazol-2-yl)-4-(trifluoromethyl)phenoxy]piperidine-1-carbonyl chloride (232 mg, 0.590 mmol, 1.00 equiv), 4-dimethylaminopyridine (14.5 mg, 0.118 mmol, 0.200 equiv), DIPEA (153 mg, 1.18 mmol, 2.00 equiv), N-(1H-pyrazol-3-yl)methanesulfonamide (118 mg, 0.730 mmol, 1.00 equiv) and THF (20 mL). The resulting solution was stirred overnight at 60° C. and quenched by water (10 mL), as described in Example 2, Step 6. The crude product was purified by preparative HPLC to provide 64.0 mg (21% yield) of N-(1-(4-(2-(thiazol-2-yl)-4-(trifluoromethyl)phenoxy)piperidine-1-carbonyl)-1H-pyrazol-3-yl)methanesulfonamide as a white solid. $^1$H NMR (300 MHz, Chloroform-d) δ 8.75-8.80 (m, 1H), 8.05-8.15 (m, 1H), 7.91-8.02 (m, 1H), 7.55-7.68 (m, 1H), 7.40-7.50 (m, 1H), 7.01-7.20 (m, 1H), 6.30 (s, 1H), 5.00 (s, 1H), 3.81-4.25 (m, 4H), 3.11 (s, 3H), 2.05-2.31 (m, 4H). LCMS (ESI, m/z): 516 [M+H]$^+$.

Example 16: N-(1-(5-(3-chloro-5-(2-hydroxypropan-2-yl)benzyl)octahydropyrrolo[3,4-c]pyrrole-2-carbonyl)-1H-pyrazol-3-yl)acetamide

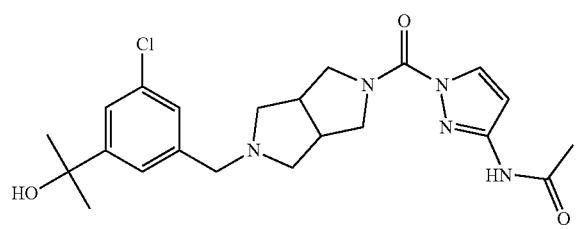 [SMILES: CC(=O)Nc1ccn(C(=O)N2CC3CN(Cc4cc(Cl)cc(C(C)(C)O)c4)CC3C2)n1]

Step 1: Synthesis of 2-(3-bromo-5-chlorophenyl)propan-2-ol

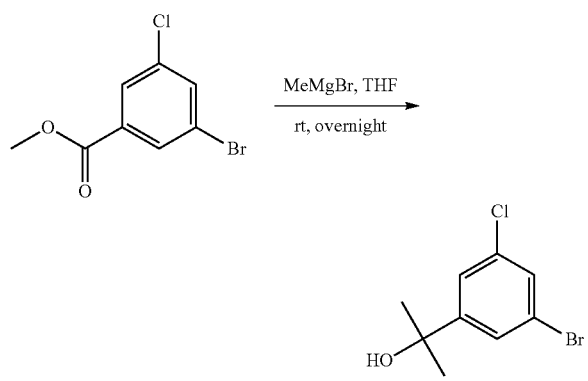

A flask was charged with methyl 3-bromo-5-chlorobenzoate (1.50 g, 6.05 mmol, 1.00 equiv), THF (10 mL) under nitrogen. The mixture was cooled to −78° C. Methylmagnesium bromide (6.05 mL, 18.2 mmol, 3.00 equiv, 3 M in ethyl ether) was added dropwise at −78° C. The resulting solution was stirred overnight at room temperature and quenched with saturated NH$_4$Cl solution (30 mL). The resulting solution was extracted with DCM (2×50 mL) and the organic layers were combined, washed with brine (2×30 mL), dried over anhydrous sodium sulfate, filtered and concentrated under reduced pressure. The residue was chromatographed on a silica gel column to provide 1.40 g (93% yield) of 2-(3-bromo-5-chlorophenyl)propan-2-ol as an off-white solid.

Step 2: Preparation of 3-chloro-5-(2-hydroxypropan-2-yl)benzaldehyde

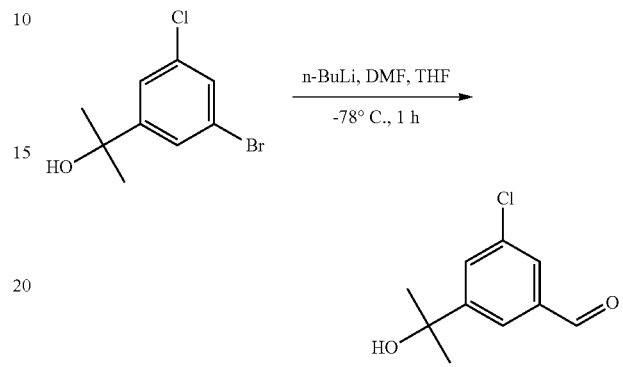

A flask was charged with 2-(3-bromo-5-chlorophenyl)propan-2-ol (1.40 g, 5.65 mmol, 1.00 equiv) and THF (10 mL) under nitrogen. The mixture was cooled to −78° C. n-Butyllithium (4.52 mL, 11.3 mmol, 2.00 equiv, 2.5 M in hexane) was added dropwise at −78° C. The mixture was stirred for 30 min at −78° C. and N,N-dimethylformamide (1.24 g, 17.0 mmol, 3.00 equiv) was added. The resulting solution was stirred for 1 h at −78° C. and quenched with saturated NH$_4$Cl solution (30 mL), as described in Example 7, Step 3. The residue was chromatographed on a silica gel column to provide 360 mg (32% yield) of 3-chloro-5-(2-hydroxypropan-2-yl)benzaldehyde as a off-white solid. $^1$H NMR (300 MHz, Chloroform-d) δ 10.01 (s, 1H), 7.89 (s, 1H), 7.84-7.72 (m, 2H), 1.64 (s, 6H).

Step 3: Preparation of t-butyl 5-(3-acetamido-1H-pyrazole-1-carbonyl)hexahydropyrrolo[3,4-c]pyrrole-2(1H)-carboxylate

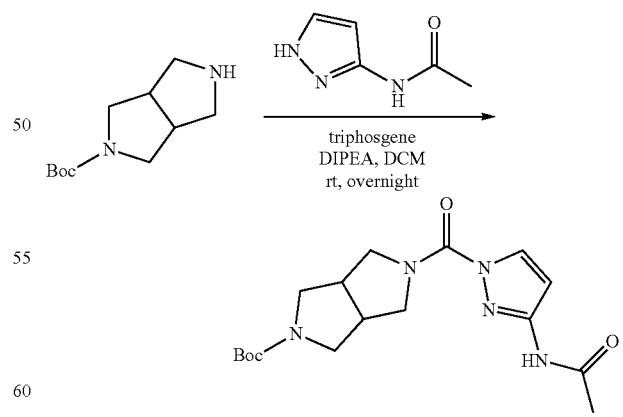

A flask was charged with triphosgene (0.980 g, 3.30 mmol, 0.70 equiv) and DCM (25 mL). N-(1H-pyrazol-3-yl)acetamide (1.06 g, 8.50 mmol, 1.80 equiv) was added at 0° C. DIPEA (2.44 g, 18.9 mmol, 4.00 equiv) was added at 0° C. and the mixture was stirred for 2 h at room temperature.

t-Butyl octahydropyrrolo[3,4-c]pyrrole-2-carboxylate (1.00 g, 4.72 mmol, 1.00 equiv) was added. The resulting solution was stirred overnight at room temperature and then quenched with water (10 mL), as described in Example 2, Step 5. The residue was chromatographed on a silica gel column to provide 1.10 g (38% yield) of t-butyl 5-(3-acetamido-1H-pyrazole-1-carbonyl)hexahydropyrrolo[3,4-c]pyrrole-2(1H)-carboxylate as a yellow oil. LCMS (ESI, m/z): 364 [M+H]⁺.

Step 4: Preparation of N-(1-(octahydropyrrolo[3,4-c]pyrrole-2-carbonyl)-1H-pyrazol-3-yl)acetamide

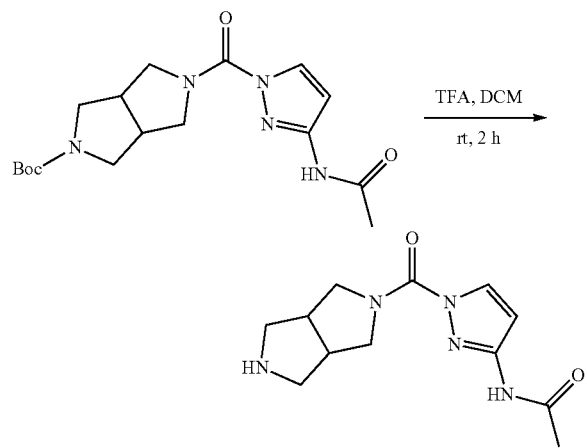

A flask was charged with t-butyl 5-(3-acetamido-1H-pyrazole-1-carbonyl)hexahydropyrrolo[3,4-c]pyrrole-2(1H)-carboxylate (400 mg, 1.10 mmol, 1.00 equiv), DCM (10 mL), and TFA (2 mL). The resulting solution was stirred for 2 h at room temperature and concentrated under reduced pressure as described in Example 1, Step 3 to provide 420 mg (crude) of N-(1-(octahydropyrrolo[3,4-c]pyrrole-2-carbonyl)-1H-pyrazol-3-yl)acetamide as a yellow oil. LCMS (ESI, m/z): 264 [M+H]⁺.

Step 5: Preparation of N-(1-(5-(3-chloro-5-(2-hydroxypropan-2-yl)benzyl)octahydropyrrolo[3,4-c]pyrrole-2-carbonyl)-1H-pyrazol-3-yl)acetamide

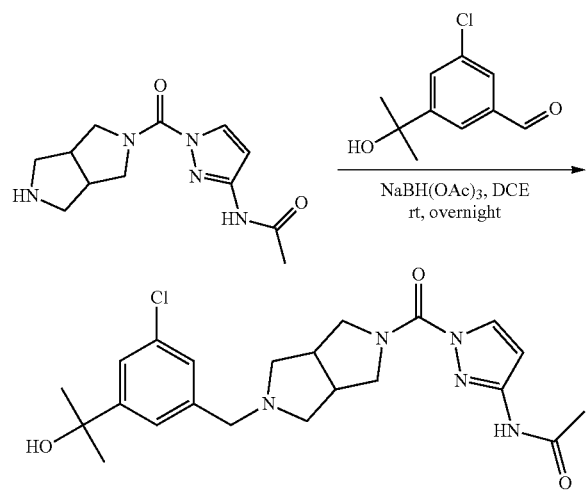

A flask was charged with N-(1-(octahydropyrrolo[3,4-c]pyrrole-2-carbonyl)-1H-pyrazol-3-yl)acetamide (192 mg, 0.730 mmol, 1.20 equiv), 3-chloro-5-(2-hydroxypropan-2-yl)benzaldehyde (120 mg, 0.610 mmol, 1.00 equiv), and DCE (15 mL). The mixture was stirred for 1 h at room temperature. Sodium triacetoxyborohydride (517 mg, 2.44 mmol, 4.00 equiv) was added. The resulting solution was stirred overnight at room temperature and then quenched with water (10 mL), as described in Example 1, Step 6. The crude product (120 mg) was purified by preparative HPLC to provide 32.3 mg (12% yield) of N-(1-(5-(3-chloro-5-(2-hydroxypropan-2-yl)benzyl)octahydropyrrolo[3,4-c]pyrrole-2-carbonyl)-1H-pyrazol-3-yl)acetamide as a white solid. ¹H NMR (300 MHz, Chloroform-d) δ 8.11-8.12 (m, 2H), 7.44 (s, 1H), 7.31 (s, 1H), 7.16 (s, 1H), 6.87 (d, J=2.7 Hz, 1H), 3.91 (br, 4H), 3.59 (s, 2H), 2.88 (br, 2H), 2.61-2.64 (m, 4H), 2.19 (s, 4H), 1.57 (s, 6H). LCMS (ESI, m/z): 446 [M+H]⁺.

Example 17: N-(1-(4-(3-chloro-5-(4-chlorophenoxy)benzyl)piperazine-1-carbonyl)-1H-pyrazol-3-yl)acetamide

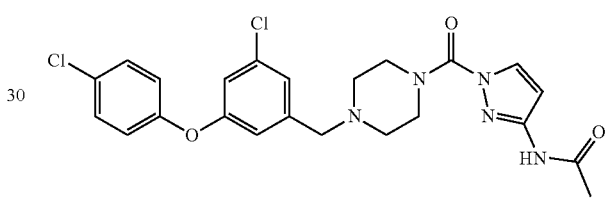

Step 1: Preparation of bis(4-chlorophenyl)iodonium tetrafluoroborate

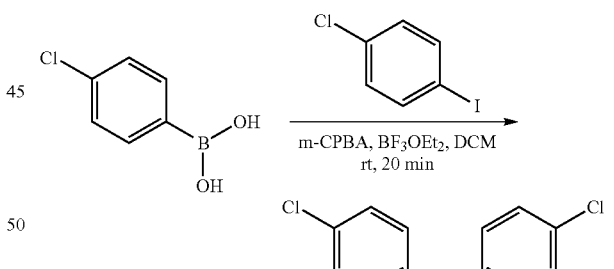

A flask was charged with meta-chloroperoxybenzoic acid (1.60 g, 9.27 mmol, 1.10 equiv), DCM (10 mL), boron trifluoride diethyl ether complex (3.58 g, 25.2 mmol, 3.00 equiv) and 1-chloro-4-iodobenzene (2.00 g, 8.39 mmol, 1.00 equiv). The resulting solution was stirred for 0.5 h at room temperature. Then (4-chlorophenyl)boronic acid (1.44 g, 9.22 mmol, 1.10 equiv) was added at 0° C. The resulting solution was stirred for 20 min at room temperature and concentrated under reduced pressure. The crude product was triturated to provide 3.00 g (78% yield) of bis(4-chlorophenyl)iodonium tetrafluoroborate as a white solid. LCMS (ESI, m/z): 349 [M−BF₄⁻]⁺.

Step 2: Preparation of 4-nitrophenyl 3-acetamido-1H-pyrazole-1-carboxylate

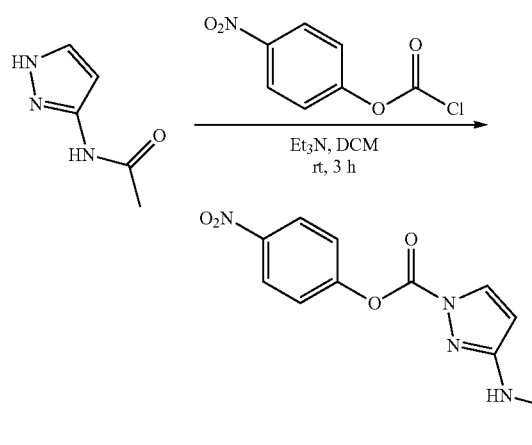

A flask was charged with N-(1H-pyrazol-3-yl)acetamide (120 mg, 0.960 mmol, 1.00 equiv), DCM (10 mL), 4-nitrophenyl chloroformate (203 mg, 1.01 mmol, 1.05 equiv), and triethylamine (291 mg, 2.88 mmol, 3.00 equiv), as described in Example 1, Step 1. The resulting solution was stirred for 3 h at room temperature and concentrated under reduced pressure to provide 280 mg (crude) of 4-nitrophenyl 3-acetamido-1H-pyrazole-1-carboxylate as a yellow oil. LCMS (ESI, m/z): 291 [M+H]$^+$.

Step 3: Preparation of t-butyl 4-(3-chloro-5-hydroxybenzyl)piperazine-1-carboxylate

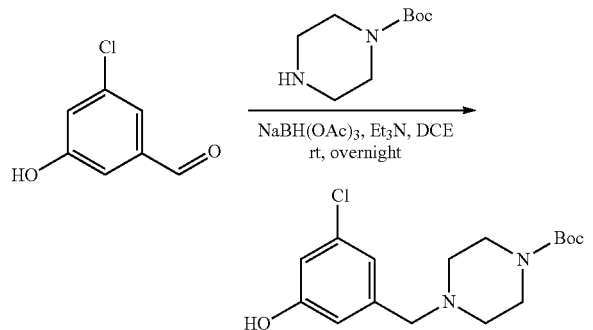

A flask was charged with 3-chloro-5-hydroxybenzaldehyde (300 mg, 1.92 mmol, 1.00 equiv), DCE (10 mL), t-butyl piperazine-1-carboxylate (536 mg, 2.88 mmol, 1.50 equiv), and triethylamine (582 mg, 5.76 mmol, 3.00 equiv). The resulting solution was stirred for 1 h at room temperature. Sodium triacetoxyborohydride (1.21 g, 5.76 mmol, 3.00 equiv) was added. The resulting solution was stirred overnight at room temperature and quenched with water (20 mL), as described in Example 1, Step 6. The residue was chromatographed on a silica gel column to provide 460 mg (73% yield) of t-butyl 4-(3-chloro-5-hydroxybenzyl)piperazine-1-carboxylate as a white solid. LCMS (ESI, m/z): 327 [M+H]$^+$.

Step 4: Preparation of t-butyl 4-(3-chloro-5-(4-chlorophenoxy)benzyl)piperazine-1-carboxylate

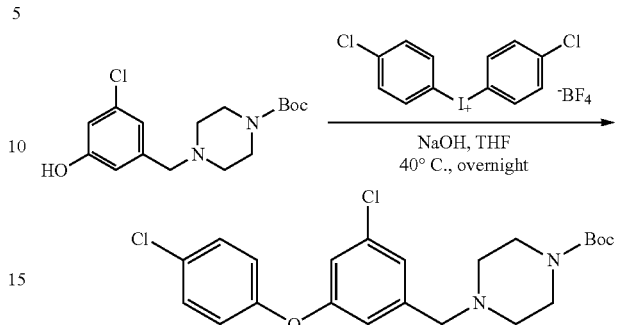

A flask was charged with t-butyl 4-(3-chloro-5-hydroxybenzyl)piperazine-1-carboxylate (160 mg, 0.491 mmol, 1.00 equiv), THF (10 mL), sodium hydroxide (21.6 mg, 0.540 mmol, 1.10 equiv). The resulting solution was stirred for 15 min at 0° C. Then bis(4-chlorophenyl)iodanium tetrafluoroborate (235 mg, 0.540 mmol, 1.10 equiv) was added. The resulting solution was stirred overnight at 40° C. and quenched with water (10 mL), as described in Example 4, Step 3. The residue was chromatographed on a silica gel column to provide 60.0 mg (28% yield) of t-butyl 4-(3-chloro-5-(4-chlorophenoxy)benzyl)piperazine-1-carboxylate as a colorless oil. LCMS (ESI, m/z): 437 [M+H]$^+$.

Step 5: Preparation of 1-(3-chloro-5-(4-chlorophenoxy)benzyl)piperazine

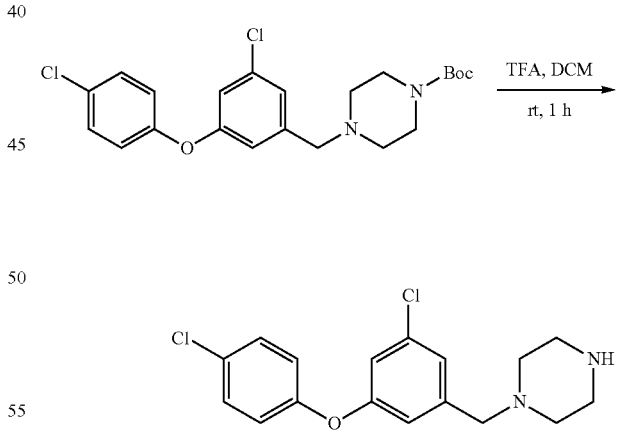

A flask was charged with t-butyl 4-(3-chloro-5-(4-chlorophenoxy)benzyl)piperazine-1-carboxylate (60.0 mg, 0.138 mmol, 1.00 equiv), DCM (5 mL), and TFA (1 mL), as described in Example 1, Step 3. The resulting solution was stirred for 1 h at room temperature and concentrated under reduced pressure to provide 60.0 mg (crude) of 1-(3-chloro-5-(4-chlorophenoxy)benzyl)piperazine as a yellow oil. LCMS (ESI, m/z): 337 [M+H]$^+$.-

Part 6: Preparation of N-(1-(4-(3-chloro-5-(4-chlorophenoxy)benzyl)piperazine-1-carbonyl)-1H-pyrazol-3-yl)acetamide

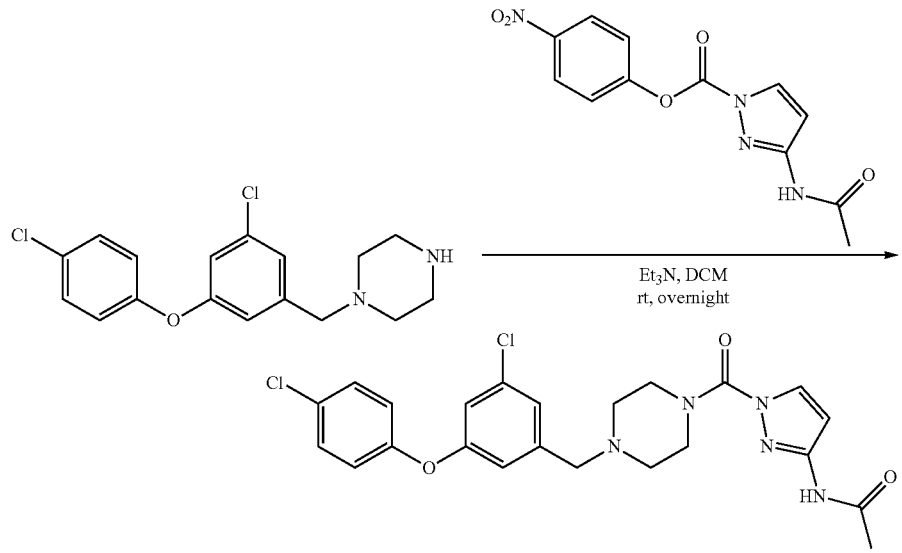

A flask was charged with 1-(3-chloro-5-(4-chlorophenoxy)benzyl)piperazine (60.0 mg, 0.179 mmol, 1.00 equiv), DCM (10 mL), 4-nitrophenyl 3-acetamido-1H-pyrazole-1-carboxylate (104 mg, 0.360 mmol, 2.00 equiv), and triethylamine (54.2 mg, 0.537 mmol, 3.00 equiv). The resulting solution was stirred overnight at room temperature and quenched with water (10 mL, as described in Example 1, Step 1. The crude product (200 mg) was purified by preparative HPLC to provide 7.10 mg (8% yield) of N-(1-(4-(3-chloro-5-(4-chlorophenoxy)benzyl)piperazine-1-carbonyl)-1H-pyrazol-3-yl)acetamide as a white solid. $^{1}$H NMR (300 MHz, Chloroform-d) δ 8.02 (d, J=2.7 Hz, 1H), 7.72 (br, 1H), 7.30-7.37 (m, 2H), 7.11 (s, 1H), 6.94-7.00 (m, 2H), 6.88-6.91 (m, 3H), 3.88 (br, 4H), 3.53 (br, 2H), 2.56 (br, 4H), 2.19 (s, 3H). LCMS (ESI, m/z): 488 [M+H]$^{+}$.

Example 18: N-(1-(5-(3-(2-chlorophenoxy)benzyl) octahydropyrrolo[3,4-c]pyrrole-2-carbonyl)-1H-pyrazol-3-yl)acetamide

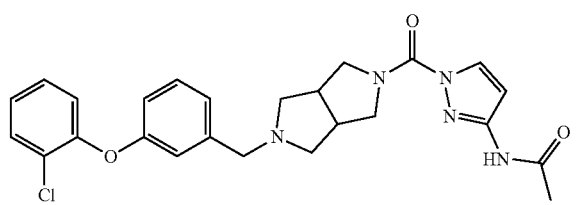 [SMILES: CC(=O)Nc1ccn(C(=O)N2CC3CN(Cc4cccc(Oc5ccccc5Cl)c4)CC3C2)n1]

Step 1: Preparation of t-butyl 5-(chlorocarbonyl) hexahydropyrrolo[3,4-c]pyrrole-2(1H)-carboxylate

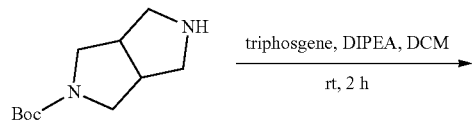

-continued

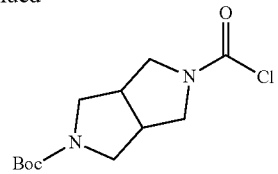

A flask was charged with triphosgene (1.78 g, 5.99 mmol, 0.60 equiv), and DCM (50 mL). t-Butyl hexahydropyrrolo[3,4-c]pyrrole-2(1H)-carboxylate (2.12 g, 9.99 mmol, 1.00 equiv) and DIPEA (3.87 g, 29.9 mmol, 3.00 equiv) were added at 0° C. The resulting solution was stirred for 2 h at room temperature and quenched with water (30 mL), as described in Example 2, Step 5 to provide 2.75 g (crude) of t-butyl 5-(chlorocarbonyl)hexahydropyrrolo[3,4-c]pyrrole-2 (1H)-carboxylate as a yellow oil. LCMS (ESI, m/z): 275 [M+H]$^{+}$.

Step 2: Preparation of t-butyl 5-(3-acetamido-1H-pyrazole-1-carbonyl)hexahydropyrrolo[3,4-c]pyrrole-2(1H)-carboxylate

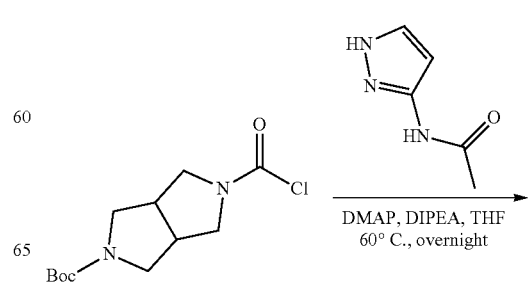

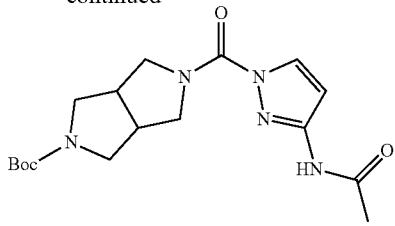

A flask was charged with t-butyl 5-(chlorocarbonyl)hexahydropyrrolo[3,4-c]pyrrole-2(1H)-carboxylate (5.50 g, 20.0 mmol, 1.00 equiv), N-(1H-pyrazol-3-yl)acetamide (2.75 g, 22.0 mmol, 1.10 equiv), 4-dimethylaminopyridine (246 mg, 2.01 mmol, 0.10 equiv), THF (100 mL), and DIPEA (7.74 g, 59.9 mmol, 3.00 equiv). The resulting solution was stirred overnight at 60° C. and quenched with water (100 mL), as described in Example 2, Step 6. The residue was chromatographed on a silica gel column to provide 3.738 g (51% yield) of t-butyl 5-(3-acetamido-1H-pyrazole-1-carbonyl) hexahydropyrrolo[3,4-c]pyrrole-2(1H)-carboxylate as a light yellow solid. LCMS (ESI, m/z): 364 [M+H]+.

Step 3: Preparation of N-(1-(octahydropyrrolo[3,4-c]pyrrole-2-carbonyl)-1H-pyrazol-3-yl)acetamide

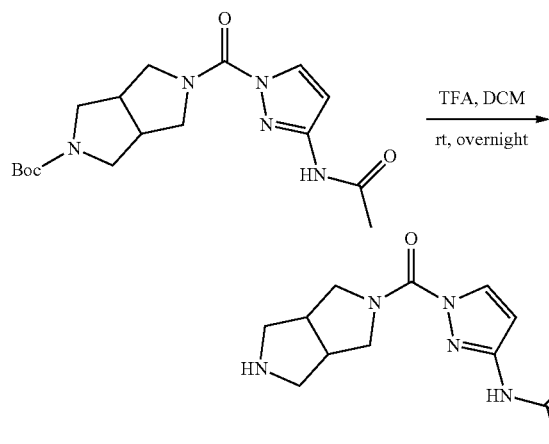

A flask was charged with t-butyl 5-(3-acetamido-1H-pyrazole-1-carbonyl)hexahydropyrrolo[3,4-c]pyrrole-2(1H)-carboxylate (1.70 g, 4.68 mmol, 1.00 equiv), DCM (25 mL), and TFA (5 mL), as described in Example 1, Step 3 to provide 1.23 g (crude) N-(1-(octahydropyrrolo[3,4-c]pyrrole-2-carbonyl)-1H-pyrazol-3-yl)acetamide as a yellow oil. LCMS (ESI, m/z): 264 [M+H]+.

Step 4: Preparation of 3-(2-chlorophenoxy)benzaldehyde

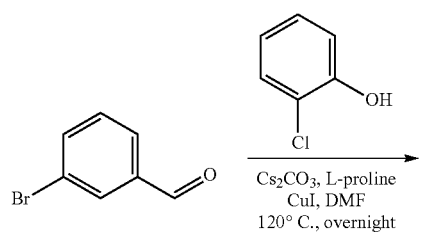

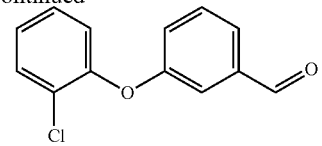

A flask was charged with 2-chlorophenol (5.12 g, 39.8 mmol, 2.00 equiv), 3-bromobenzaldehyde (3.70 g, 20.0 mmol, 1.00 equiv), cesium carbonate (19.6 g, 60.1 mmol, 3.00 equiv), L-proline (123 mg, 1.06 mmol, 0.05 equiv), copper(I)iodide (382 mg, 2.01 mmol, 0.10 equiv), and N,N-dimethylformamide (150 mL) under nitrogen. The resulting solution was stirred overnight at 120° C. and quenched with water (50 mL). The mixture was extracted with EtOAc (3×50 mL) and the organic layers were combined, washed with brine (3×50 mL), dried over anhydrous sodium sulfate, filtered and concentrated under reduced pressure. The residue was chromatographed on a silica gel column to provide 0.610 g (13% yield) of 3-(2-chlorophenoxy)benzaldehyde as a yellow oil. LCMS (ESI, m/z): 233 [M+H]+.

Step 5: Preparation of N-(1-(5-(3-(2-chlorophenoxy)benzyl)octahydropyrrolo[3,4-c]pyrrole-2-carbonyl)-1H-pyrazol-3-yl)acetamide

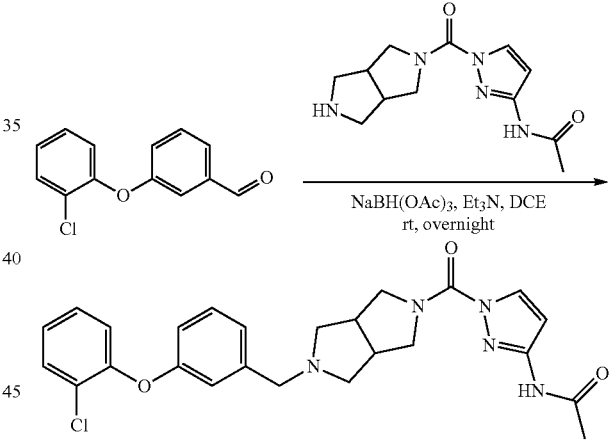

A flask was charged with 3-(2-chlorophenoxy)benzaldehyde (116 mg, 0.501 mmol, 1.00 equiv), N-(1-(octahydropyrrolo[3,4-c]pyrrole-2-carbonyl)-1H-pyrazol-3-yl)acetamide (131 mg, 0.501 mmol, 1.00 equiv), DCE (5 mL), and triethylamine (151 mg, 1.49 mmol, 3.00 equiv). The resulting solution was stirred for 2 h at room temperature. Sodium triacetoxyborohydride (318 mg, 1.50 mmol, 3.00 equiv) was added. The resulting solution was stirred overnight at room temperature and quenched with water (20 mL), as described in Example 1, Step 6. The crude product (269 mg) was purified by preparative HPLC to provide 107.7 mg (45% yield) of N-(1-(5-(3-(2-chlorophenoxy)benzyl)octahydropyrrolo[3,4-c]pyrrole-2-carbonyl)-1H-pyrazol-3-yl)acetamide as a white solid. $^1$H NMR (400 MHz, Chloroform-d) δ 8.13 (d, J=2.8 Hz, 1H), 7.84 (br, 1H), 7.43-7.45 (m, 1H), 7.24-7.28 (m, 1H), 7.18-7.23 (m, 1H), 7.03-7.08 (m, 2H), 6.93-7.01 (m, 2H), 6.81-6.90 (m, 2H), 4.04 (br, 2H), 3.73 (br, 2H), 3.58 (s, 2H), 2.86 (br, 2H), 2.50-2.70 (m, 4H), 2.17 (s, 3H). LCMS (ESI, m/z): 480 [M+H]+.

Example 19: N-(1-(4-(methyl(2-(pyrrolidin-1-yl)-4-(trifluoromethyl)phenyl)amino)piperidine-1-carbonyl)-1H-pyrazol-3-yl)methanesulfonamide

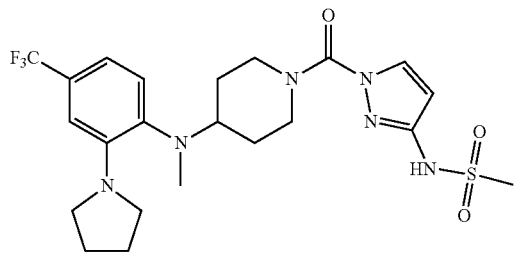 [SMILES: CN(c1ccc(C(F)(F)F)cc1N1CCCC1)C1CCN(C(=O)n2ccc(NS(C)(=O)=O)n2)CC1]

Step 1: Synthesis of 4-nitrophenyl 3-(methylsulfonamido)-1H-pyrazole-1-carboxylate

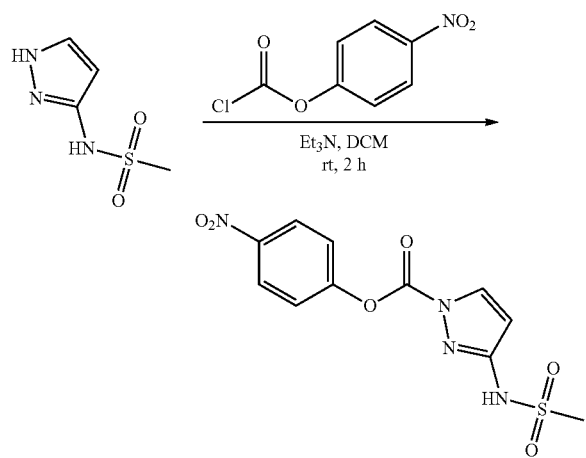

A flask was charged with N-(1H-pyrazol-3-yl)methanesulfonamide (4.50 g, 27.9 mmol, 1.00 equiv), 4-nitrophenyl chloroformate (5.90 g, 29.3 mmol, 1.05 equiv), DCM (50 mL), and triethylamine (8.50 g, 84.0 mmol, 3.00 equiv). The resulting solution was stirred for 2 h at room temperature and concentrated under reduced pressure, as described in Example 1, Step 1 to provide 10.0 g (crude) of 4-nitrophenyl 3-methanesulfonamido-1H-pyrazole-1-carboxylate as a yellow solid. LCMS (ESI, m/z): 327 [M+H]$^+$.

Step 2: Preparation of t-butyl 4-((2-bromo-4-(trifluoromethyl)phenyl)amino)piperidine-1-carboxylate

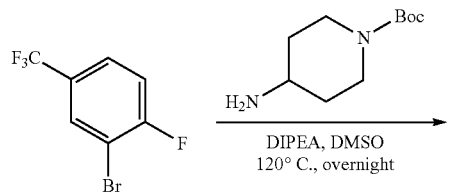

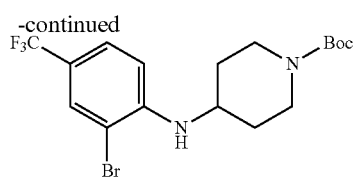

A flask was charged with t-butyl 4-aminopiperidine-1-carboxylate (416 mg, 2.06 mmol, 2.00 equiv), 2-bromo-1-fluoro-4-(trifluoromethyl)benzene (250 mg, 1.03 mmol, 1.00 equiv), DIPEA (403 mg, 3.09 mmol, 3.00 equiv), and dimethyl sulfoxide (10 mL), as described in Example 1, Step 5. The residue was chromatographed on a silica gel column to provide 420 mg (96% yield) of t-butyl 4-((2-bromo-4-(trifluoromethyl)phenyl)amino)piperidine-1-carboxylate as a yellow oil. LCMS (ESI, m/z): 423 [M+H]$^+$.

Step 3: Preparation of t-butyl 4-((2-bromo-4-(trifluoromethyl)phenyl)(methyl)amino)piperidine-1-carboxylate

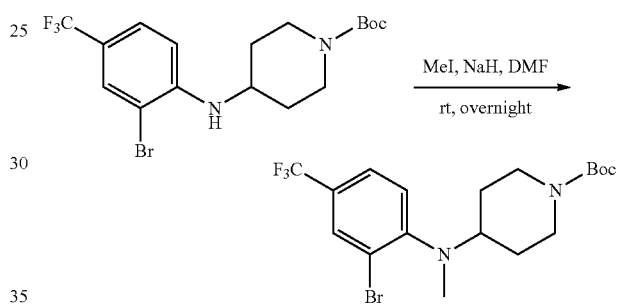

A flask was charged with t-butyl 4-((2-bromo-4-(trifluoromethyl)phenyl)amino)piperidine-1-carboxylate (350 mg, 0.830 mmol, 1.00 equiv), N,N-dimethylformamide (10 mL), and sodium hydride (49.8 mg, 1.25 mmol, 1.50 equiv, 60% in mineral oil). The resulting solution was stirred for 1 h at 0° C. Methyl iodide (176 mg, 1.24 mmol, 1.50 equiv) was added. The resulting solution was stirred overnight at room temperature and quenched with water (10 mL). The resulting solution was extracted with EtOAc (3×10 mL) and the organic layers were combined, washed with brine (2×10 mL), dried over anhydrous sodium sulfate, filtered and concentrated under reduced pressure. The residue was chromatographed on a silica gel column to provide 290 mg (98% yield) of t-butyl 4-((2-bromo-4-(trifluoromethyl)phenyl)(methyl)amino)piperidine-1-carboxylate as a yellow oil. LCMS (ESI, m/z): 437 [M+H]$^+$.

Step 4: Preparation of t-butyl 4-(methyl(2-(pyrrolidin-1-yl)-4-(trifluoromethyl)phenyl)amino)piperidine-1-carboxylate

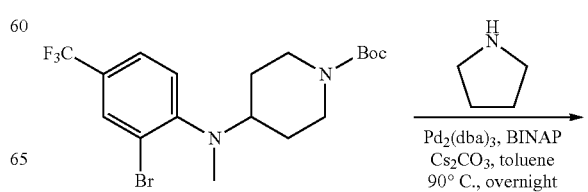

-continued

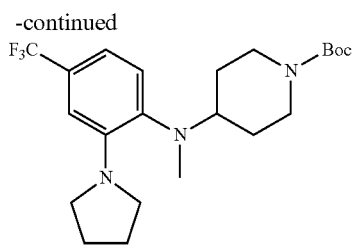

A flask was charged with t-butyl 4-((2-bromo-4-(trifluoromethyl)phenyl)(methyl)amino)piperidine-1-carboxylate (380 mg, 0.870 mmol, 1.00 equiv), pyrrolidine (124 mg, 1.74 mmol, 2.00 equiv), tris(dibenzylideneacetone)dipalladium (39.8 mg, 0.0435 mmol, 0.05 equiv), 2,2'-bis(diphenylphosphino)-1,1'-binaphthyl (81.3 mg, 0.130 mmol, 0.15 equiv), cesium carbonate (851 mg, 2.61 mmol, 3.00 equiv), and toluene (10 mL) under nitrogen. The resulting solution was stirred overnight at 90° C. and quenched with water (10 mL), as described in Example 9, Step 1. The residue was chromatographed on a silica gel column to provide 130 mg (35% yield) of t-butyl 4-(methyl(2-(pyrrolidin-1-yl)-4-(trifluoromethyl)phenyl)amino)piperidine-1-carboxylate as a yellow oil. LCMS (ESI, m/z): 428 [M+H]$^+$.

Step 5: Preparation of N-methyl-N-(2-(pyrrolidin-1-yl)-4-(trifluoromethyl)phenyl)piperidin-4-amine

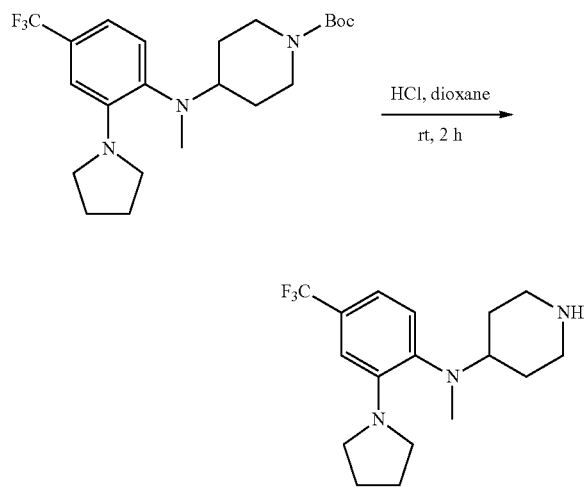

A flask was charged with t-butyl 4-(methyl(2-(pyrrolidin-1-yl)-4-(trifluoromethyl)phenyl)amino)piperidine-1-carboxylate (130 mg, 0.304 mmol, 1.00 equiv), 1,4-dioxane (5 mL), and concentrated hydrochloric acid (1 mL), as described in Example 11, Step 5 to provide 150 mg (crude) of N-methyl-N-(2-(pyrrolidin-1-yl)-4-(trifluoromethyl)phenyl)piperidin-4-amine as a yellow oil. LCMS (ESI, m/z): 328 [M+H]$^+$.

Step 6: Preparation of N-(1-(4-(methyl(2-(pyrrolidin-1-yl)-4-(trifluoromethyl)phenyl)amino)piperidine-1-carbonyl)-1H-pyrazol-3-yl)methanesulfonamide

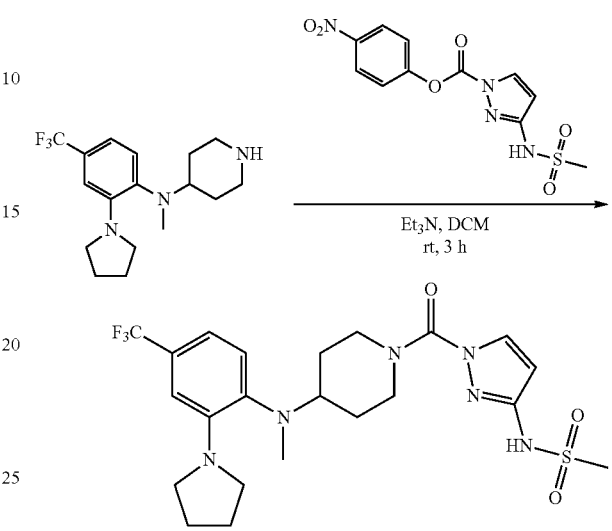

A flask was charged with N-methyl-N-(2-(pyrrolidin-1-yl)-4-(trifluoromethyl)phenyl)piperidin-4-amine (101 mg, 0.310 mmol, 1.00 equiv), 4-nitrophenyl 3-methanesulfonamido-1H-pyrazole-1-carboxylate (202 mg, 0.620 mmol, 2.00 equiv), DCM (10 mL), triethylamine (93.9 mg, 0.930 mmol, 3.00 equiv). The resulting solution was stirred for 3 h at room temperature and quenched with water (10 mL), as described in Example 1, Step 1. The crude product (200 mg) was purified by preparative HPLC to provide 65.1 mg (41% yield) of N-(1-(4-(methyl(2-(pyrrolidin-1-yl)-4-(trifluoromethyl)phenyl)amino)piperidine-1-carbonyl)-1H-pyrazol-3-yl)methanesulfonamide as a white solid. $^1$H NMR (400 MHz, Chloroform-d) δ 8.02 (d, J=2.7 Hz, 1H), 7.00-7.12 (m, 4H), 6.32 (d, J=2.7 Hz, 1H), 4.49-4.52 (m, 2H), 3.44-3.52 (m, 1H), 3.26-3.29 (m, 4H), 3.13 (s, 3H), 2.98-3.03 (m, 2H), 2.67 (s, 3H), 1.90-1.94 (m, 4H), 1.66-1.79 (m, 4H). LCMS (ESI, m/z): 515 [M+H]$^+$.

Example 20: N-(1-(1-(4-chloro-3-cyclopropylbenzoyl)-1,8-diazaspiro[4.5]decane-8-carbonyl)-1H-pyrazol-3-yl)acetamide

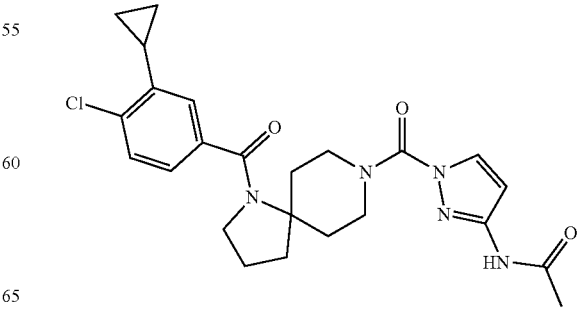

Step 1: Synthesis of t-butyl 1-(3-bromo-4-chlorobenzoyl)-1,8-diazaspiro[4.5]decane-8-carboxylate

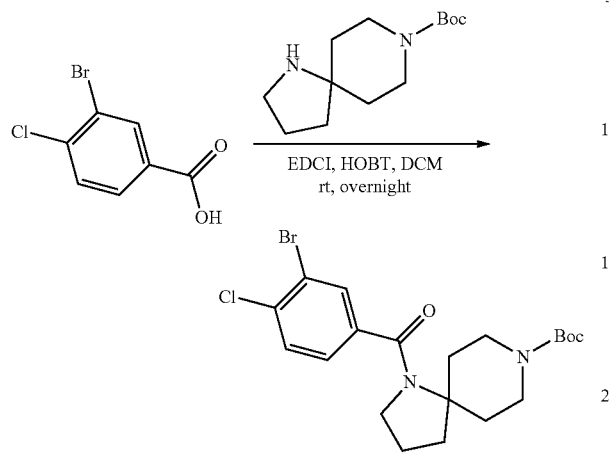

A flask was charged with 3-bromo-4-chlorobenzoic acid (400 mg, 1.71 mmol, 1.00 equiv), DCM (10 mL), N-(3-dimethylaminopropyl)-N'-ethylcarbodiimide hydrochloride (493 mg, 2.57 mmol, 1.50 equiv), and 1-hydroxybenzotrizole (347 mg, 2.57 mmol, 1.50 equiv). The mixture was stirred for 30 min at room temperature. t-Butyl 1,8-diazaspiro[4.5]decane-8-carboxylate (616 mg, 2.57 mmol, 1.50 equiv) was added. The resulting solution was stirred overnight at room temperature and quenched with water (30 mL), as described in Example 14, Step 8. The residue was chromatographed on a silica gel column to provide 650 mg (84% yield) of t-butyl 1-(3-bromo-4-chlorobenzoyl)-1,8-diazaspiro[4.5]decane-8-carboxylate as a yellow oil. LCMS (ESI, m/z): 457 [M+H]$^+$.

Step 2: Prepartion of t-butyl 1-(4-chloro-3-cyclopropylbenzoyl)-1,8-diazaspiro[4.5]decane-8-carboxylate

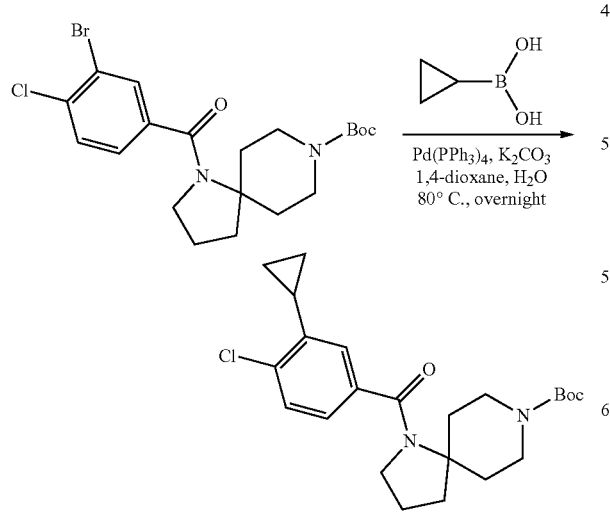

A 50-mL round-bottom flask was charged with t-butyl 1-(3-bromo-4-chlorobenzoyl)-1,8-diazaspiro[4.5]decane-8-carboxylate (400 mg, 0.877 mmol, 1.00 equiv), 1,4-dioxane (10 mL), water (2 mL), cyclopropylboronic acid (112 mg, 1.32 mmol, 1.50 equiv), tetrakis(triphenylphosphine)palladium (48.0 mg, 0.0400 mmol, 0.05 equiv), and potassium carbonate (360 mg, 2.60 mmol, 3.00 equiv) under nitrogen. The resulting solution was stirred overnight at 80° C. and quenched with water (30 mL). The resulting solution was extracted with DCM (2×50 mL) and the organic layers were combined, washed with brine (2×30 mL), dried over anhydrous sodium sulfate, filtered and concentrated under reduced pressure. The residue was chromatographed on a silica gel column to provide 280 mg (76% yield) of t-butyl 1-(4-chloro-3-cyclopropylbenzoyl)-1,8-diazaspiro[4.5]decane-8-carboxylate as a light yellow oil. LCMS (ESI, m/z): 419 [M+H]$^+$.

Step 3: Preparation of (4-chloro-3-cyclopropylphenyl)(1,8-diazaspiro[4.5]decan-1-yl)methanone

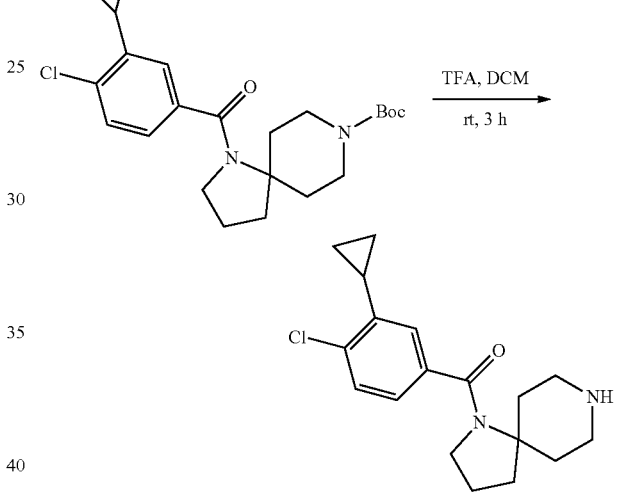

A flask was charged with t-butyl 1-(4-chloro-3-cyclopropylbenzoyl)-1,8-diazaspiro[4.5]decane-8-carboxylate (200 mg, 0.480 mmol, 1.00 equiv), DCM (10 mL), and TFA (2 mL), as described in Example 1, Step 3 to provide 210 mg (crude) of (4-chloro-3-cyclopropylphenyl)(1,8-diazaspiro[4.5]decan-1-yl)methanone as a light yellow oil. LCMS (ESI, m/z): 319 [M+H]$^+$.

Step 4: Preparation of 1-(4-chloro-3-cyclopropylbenzoyl)-1,8-diazaspiro[4.5]decane-8-carbonyl chloride

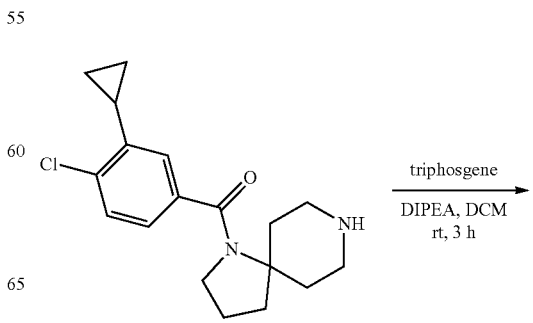

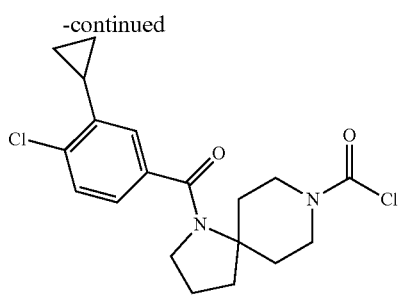

A flask was charged with triphosgene (70.0 mg, 0.240 mmol, 0.50 equiv), DCM (10 mL), and (4-chloro-3-cyclopropylphenyl)(1,8-diazaspiro[4.5]decan-1-yl)methanone (152 mg, 0.480 mmol, 1.00 equiv). DIPEA (185 mg, 1.44 mmol, 3.00 equiv) was added at 0° C. The resulting solution was stirred for 3 h at room temperature and quenched with water (30 mL), as described in Example 2, Step 5 to provide 180 mg (crude) of 1-[(4-chloro-3-cyclopropylphenyl)carbonyl]-1,8-diazaspiro[4.5]decane-8-carbonyl chloride as a yellow oil. LCMS (ESI, m/z): 381 [M+H]+.

Step 5: Preparation of N-(1-(1-(4-chloro-3-cyclopropylbenzoyl)-1,8-diazaspiro[4.5]decane-8-carbonyl)-1H-pyrazol-3-yl)acetamide

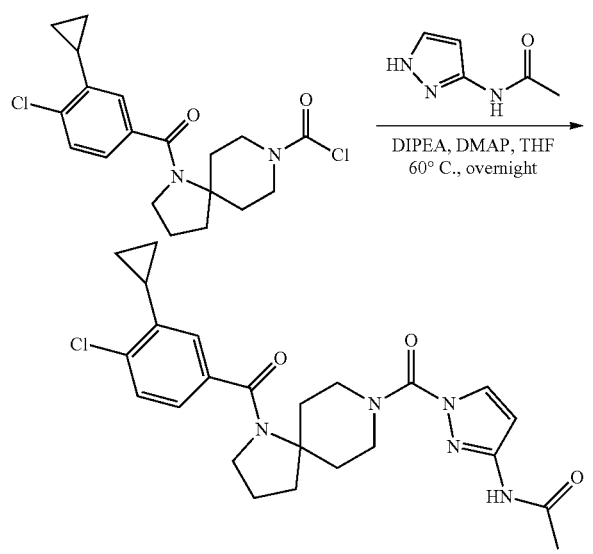

A 50-mL round-bottom flask was charged 1-[(4-chloro-3-cyclopropylphenyl)carbonyl]-1,8-diazaspiro[4.5]decane-8-carbonyl chloride (175 mg, 0.460 mmol, 1.00 equiv), THF (10 mL), N-(1H-pyrazol-3-yl)acetamide (69.0 mg, 0.552 mmol, 1.20 equiv), DIPEA (184 mg, 1.43 mmol, 3.00 equiv), and 4-dimethylaminopyridine (12.0 mg, 0.092 mmol, 0.20 equiv). The resulting solution was stirred overnight at 60° C. and quenched with water (30 mL), as described in Example 2, Step 6. The crude product (300 mg) was purified by preparative HPLC to provide 27.7 mg (13% yield) of N-[1-([1-[(4-chloro-3-cyclopropylphenyl)carbonyl]-1,8-diazaspiro[4.5]decan-8-yl]carbonyl)-1H-pyrazol-3-yl]acetamide as a white solid. $^1$H NMR (300 MHz, Chloroform-d) δ 8.13 (br, 1H), 7.99 (d, J=2.7 Hz, 1H), 7.35 (d, J=8.1 Hz, 1H), 7.12-7.15 (m, 1H), 6.99 (s, 1H), 6.72 (d, J=2.7 Hz, 1H), 4.52-4.56 (m, 2H), 3.40 (t, J=6.8 Hz, 2H), 3.20-3.28 (m, 2H), 3.02-3.10 (m, 2H), 2.14-2.18 (m, 4H), 2.08 (t, J=6.8 Hz, 2H), 1.78-1.87 (m, 2H), 1.51-1.87 (m, 2H), 1.01-1.06 (m, 2H), 0.67-0.72 (m, 2H). LCMS (ESI, m/z): 470 [M+H]+.

Example 21: N-(1-(4-(4-chloro-3-cyclopentylphenoxy)piperidine-1-carbonyl)-1H-pyrazol-3-yl)methanesulfonamide

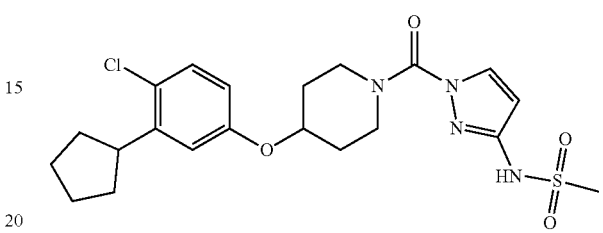

Step 1: Preparation of 4-nitrophenyl 3-(methylsulfonamido)-1H-pyrazole-1-carboxylate

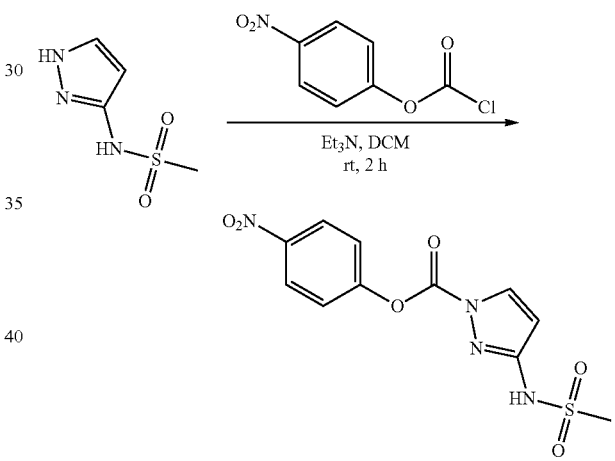

A vial was charged with N-(1H-pyrazol-3-yl)methanesulfonamide (172 mg, 1.07 mmol, 1.00 equiv) in DCM (10 mL), and 4-nitrophenyl chloroformate (237 mg, 1.18 mmol, 1.10 equiv). Triethylamine (324 mg, 3.21 mmol, 3.00 equiv) was added. The resulting solution was stirred for 2 h at room temperature and concentrated under reduced pressure, as described in Example 1, Step 1 to provide 360 mg (crude) of 4-nitrophenyl 3-(methylsulfonamido)-1H-pyrazole-1-carboxylate as a yellow oil. LCMS (ESI, m/z): 327 [M+H]+.

Step 2: Preparation of t-butyl 4-(3-bromo-4-chlorophenoxy)piperidine-1-carboxylate

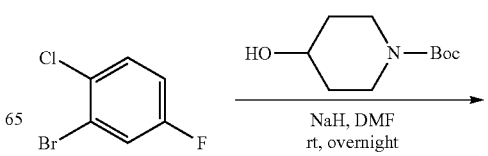

-continued

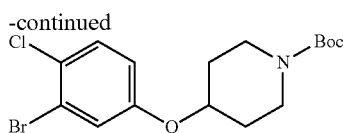

A 100-mL round-bottom flask was charged with t-butyl 4-hydroxypiperidine-1-carboxylate (2.88 g, 14.3 mmol, 1.50 equiv) and N,N-dimethylformamide (20 mL). The resulting solution was stirred for 0.5 h at 0° C. Sodium hydride (574 mg, 14.3 mmol, 1.50 equiv, 60% in mineral oil) was added. The resulting solution was stirred for 0.5 h at 0° C. 2-Bromo-1-chloro-4-fluorobenzene (2.00 g, 9.55 mmol, 1.00 equiv) was added. The resulting solution was stirred overnight at room temperature and quenched with water (20 mL), as described in Example 19, Step 3. The residue was chromatographed on a silica gel column to provide 2.62 g (70% yield) of t-butyl 4-(3-bromo-4-chlorophenoxy)piperidine-1-carboxylate as a yellow oil. LCMS (ESI, m/z): 390 [M+H]$^+$.

Step 3: Preparation of t-butyl 4-(4-chloro-3-cyclopentylphenoxy)piperidine-1-carboxylate

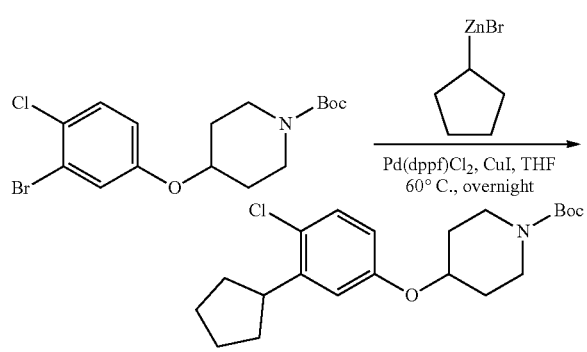

A 40-mL vial was charged with t-butyl 4-(3-bromo-4-chlorophenoxy)piperidine-1-carboxylate (500 mg, 1.28 mmol, 1.00 equiv), bromo(cyclopentyl)zinc (0.77 mL, 3.83 mmol, 3.00 equiv, 0.5 M in THF), 1,1'-bis(diphenylphosphino)ferrocene]dichloropalladium(II) (187 mg, 0.260 mmol, 0.20 equiv), copper (I) iodide (48.6 mg, 0.260 mmol, 0.20 equiv), and THF (10 mL) under nitrogen. The resulting solution was stirred overnight at 60° C. and quenched with water (10 mL). The resulting solution was extracted with EtOAc (3×15 mL) and the organic layers were combined, washed with brine (2×15 mL), dried over anhydrous sodium sulfate, filtered and concentrated under reduced pressure. The residue was chromatographed on a silica gel column to provide 205 mg (42% yield) of t-butyl 4-(4-chloro-3-cyclopentylphenoxy)piperidine-1-carboxylate as a yellow oil. LCMS (ESI, m/z): 380 [M+H]$^+$.

Step 4: Preparation of 4-(4-chloro-3-cyclopentylphenoxy)piperidine

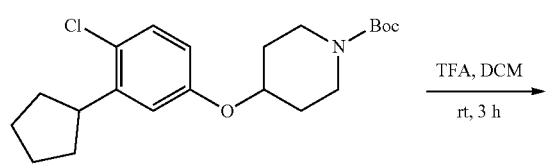

-continued

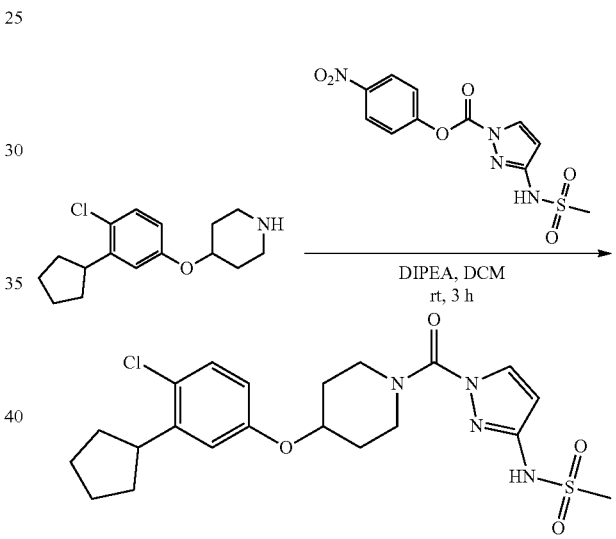

A flask was charged with t-butyl 4-(4-chloro-3-cyclopentylphenoxy)piperidine-1-carboxylate (205 mg, 0.540 mmol, 1.00 equiv), DCM (10 mL), and TFA (2 mL). The resulting solution was stirred for 3 h at room temperature and concentrated under reduced pressure, as described in Example 1, Step 3 to provide 250 mg (crude) of 4-(4-chloro-3-cyclopentylphenoxy)piperidine as a yellow oil. LCMS (ESI, m/z): 280 [M+H]$^+$.

Step 5: Preparation of N-(1-(4-(4-chloro-3-cyclopentylphenoxy)piperidine-1-carbonyl)-1H-pyrazol-3-yl)methanesulfonamide

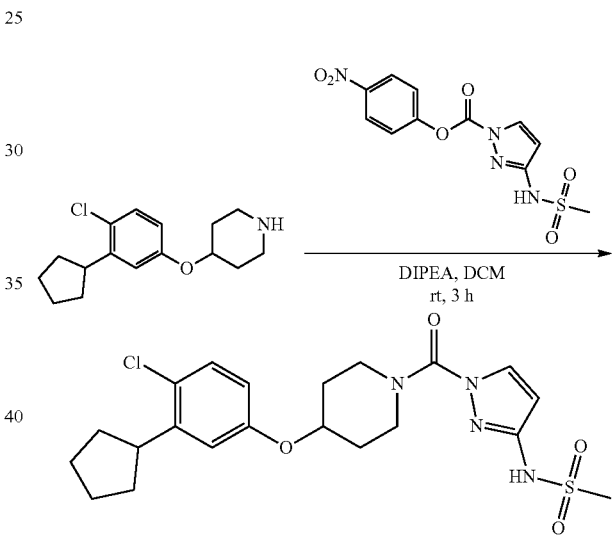

A flask was charged with 4-(4-chloro-3-cyclopentylphenoxy)piperidine (150 mg, 0.540 mmol, 1.00 equiv) in DCM (10 mL) and 4-nitrophenyl 3-(methylsulfonamido)-1H-pyrazole-1-carboxylate (350 mg, 1.07 mmol, 2.00 equiv). DIPEA (209 mg, 1.62 mmol, 3.00 equiv) was added dropwise at 0° C. The resulting solution was stirred 3 h at room temperature and quenched with water (10 mL), as described in Example 2, Step 6. The crude product (300 mg) was purified by preparative HPLC to provide 74.7 mg (30% yield) of N-(1-(4-(4-chloro-3-cyclopentylphenoxy)piperidine-1-carbonyl)-1H-pyrazol-3-yl)methanesulfonamide as a yellow solid. $^1$H NMR (300 MHz, Chloroform-d) δ 8.03 (d, J=2.7 Hz, 1H), 7.22-7.25 (m, 1H), 6.86 (d, J=3.0 Hz, 1H), 6.65-6.69 (m, 1H), 6.30 (d, J=2.7 Hz, 1H) 4.55-4.56 (m, 1H), 3.86-3.91 (m, 4H), 3.36-3.38 (m, 1H), 3.15 (s, 3H), 1.84-2.11 (m, 6H), 1.70-1.84 (m, 4H), 1.51-1.56 (m, 2H). LCMS (ESI, m/z): 489 [M+Na]$^+$.

Example 22: N-(1-(4-(4-(tetrahydro-1H-furo[3,4-c]pyrrol-5(3H)-yl)-2-(trifluoromethyl)benzyl)piperazine-1-carbonyl)-1H-pyrazol-3-yl)acetamide

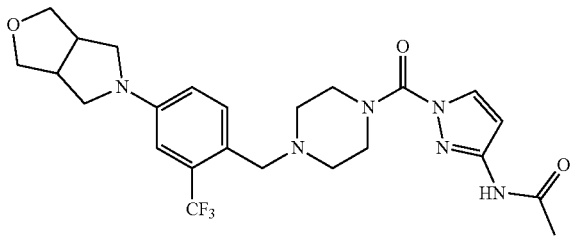 [SMILES: CC(=O)Nc1ccn(C(=O)N2CCN(Cc3ccc(N4CC5COCC5C4)cc3C(F)(F)F)CC2)n1]

Step 1: Preparation of 4-(tetrahydro-1H-furo[3,4-c]pyrrol-5(3H)-yl)-2-(trifluoromethyl)benzaldehyde

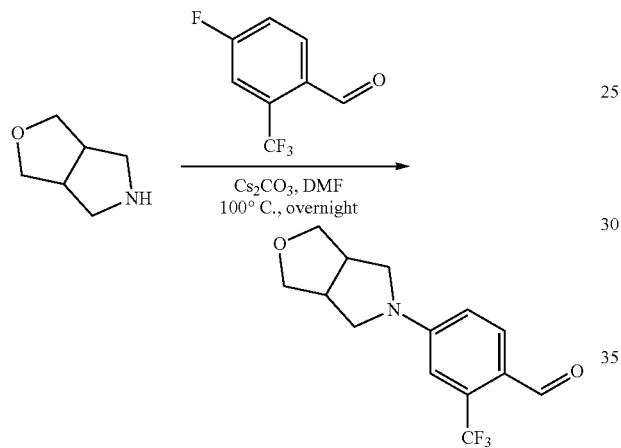

A round-bottom flask was charged with hexahydro-1H-furo[3,4-c]pyrrole (1.18 g, 10.4 mmol, 2.00 equiv), 4-fluoro-2-(trifluoromethyl)benzaldehyde (1.00 g, 5.21 mmol, 1.00 equiv), cesium carbonate (3.40 g, 10.4 mmol, 2.00 equiv), and DMF (10 mL). The reaction mixture was stirred overnight at 100° C. and quenched with water (20 mL). The resulting solution was extracted with EtOAc (3×50 mL) and the organic layers were combined, washed with brine (1×50 mL), dried over Na$_2$SO$_4$, filtered and concentrated under reduced pressure. The residue was chromatographed on a silica gel to provide 0.800 g (54% yield) of 4-(tetrahydro-1H-furo[3,4-c]pyrrol-5(3H)-yl)-2-(trifluoromethyl)benzaldehyde as a yellow oil. LCMS (ESI, m/z): 286 [M+H]$^+$.

Step 2: Preparation of t-Butyl 4-(3-acetamido-1H-pyrazole-1-carbonyl)piperazine-1-carboxylate

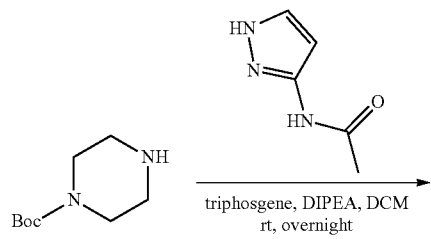

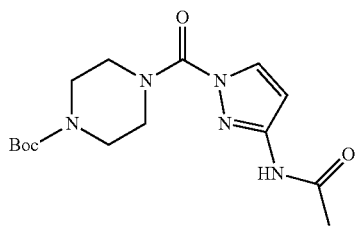

A round-bottom flask was charged with triphosgene (334 mg, 1.12 mmol, 0.70 equiv) and DCM (10 mL). N-(1H-pyrazol-3-yl)acetamide (302 mg, 2.41 mmol, 1.50 equiv) was added at 0° C., followed by DIPEA (830 mg, 6.42 mmol, 4.00 equiv). The mixture was stirred for 2 h at 0° C. prior to addition of t-butyl piperazine-1-carboxylate (300 mg, 1.61 mmol, 1.00 equiv). The reaction mixture was stirred overnight at room temperature and quenched with water (20 mL). The resulting solution was extracted with DCM (3×20 mL) and the organic layers were combined, washed with brine (1×20 mL), dried over anhydrous Na$_2$SO$_4$, filtered and concentrated under reduced pressure. The residue was chromatographed on a silica gel column to provide 420 mg (77% yield) of t-butyl 4-(3-acetamido-1H-pyrazole-1-carbonyl)piperazine-1-carboxylate as a yellow solid. LCMS (ESI, m/z): 338 [M+H]$^+$.

Step 3: Preparation of N-(1-(Piperazine-1-carbonyl)-1H-pyrazol-3-yl)acetamide

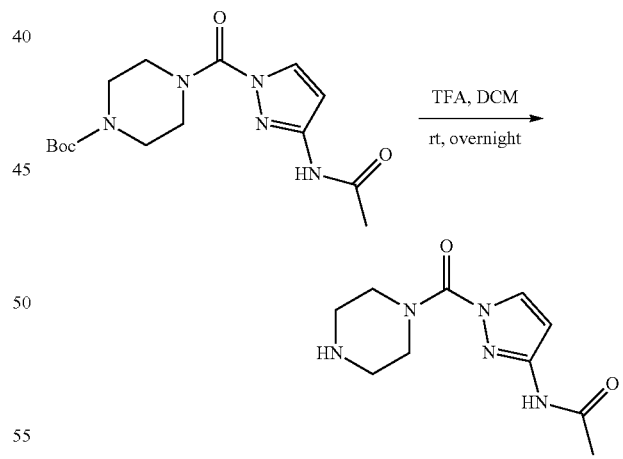

A round-bottom flask was charged with t-butyl 4-(3-acetamido-1H-pyrazole-1-carbonyl)piperazine-1-carboxylate (200 mg, 0.590 mmol, 1.00 equiv), DCM (8 mL), and TFA (2 mL). The resulting solution was stirred overnight at room temperature and concentrated under reduced pressure to provide 141 mg (quantitative) of N-(1-(piperazine-1-carbonyl)-1H-pyrazol-3-yl)acetamide as a white oil. LCMS (ESI, m/z): 238 [M+H]$^+$.

Step 4: Preparation of N-(1-(4-(4-(tetrahydro-1H-furo[3,4-c]pyrrol-5(3H)-yl)-2-(trifluoromethyl)benzyl)piperazine-1-carbonyl)-1H-pyrazol-3-yl)acetamide

Example 23: N-(1-(2-(4-(pyrrolidin-1-yl)-2-(trifluoromethyl)benzyl)-2,8-diazaspiro[4.5]decane-8-carbonyl)-1H-pyrazol-3-yl)acetamide

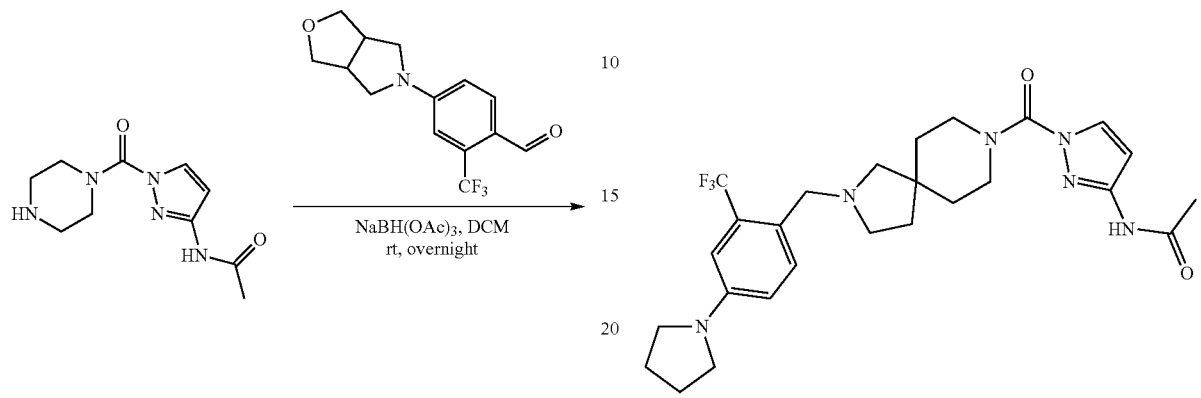

A round-bottom flask was charged with N-(1-(piperazine-1-carbonyl)-1H-pyrazol-3-yl)acetamide (141 mg, 0.590 mmol, 1.20 equiv), 4-(tetrahydro-1H-furo[3,4-c]pyrrol-5(3H)-yl)-2-(trifluoromethyl)benzaldehyde (141 mg, 0.490 mmol, 1.00 equiv), and DCM (10 mL). The mixture was stirred for 2 h at room temperature prior to addition of sodium triacetoxyborohydride (416 mg, 1.96 mmol, 4.00 equiv). The reaction mixture was stirred overnight at room temperature and quenched with water (10 mL). The resulting solution was extracted with DCM (3×15 mL) and the organic layers were combined, washed with brine (1×50 mL), dried over anhydrous $Na_2SO_4$, filtered and concentrated under reduced pressure. The crude product (260 mg) was purified by preparative HPLC to afford 39.7 mg (16% yield) of N-[1-([4-[(4-[hexahydro-1H-furo[3,4-c]pyrrol-5-yl]-2-(trifluoromethyl)phenyl)methyl]piperazin-1-yl]carbonyl)-1H-pyrazol-3-yl]acetamide as a white solid. $^1$H NMR (300 MHz, Chloroform-d) δ 8.01 (d, J=2.7 Hz, 1H), 7.71 (br, 1H), 7.53-7.51 (m, 1H), 6.91-6.83 (m, 2H), 6.76-6.73 (m, 1H), 4.03-3.96 (m, 2H), 3.81 (br, 4H), 3.70-3.66 (m, 2H), 3.60 (br, 2H), 3.51-3.46 (m, 2H), 3.29-3.25 (m, 2H), 3.08-3.02 (m, 2H), 2.53 (br, 4H), 2.18 (s, 3H). LCMS (ESI, m/z): 507 [M+H]$^+$.

Step 1: Preparation of 4-(pyrrolidin-1-yl)-2-(trifluoromethyl)benzaldehyde

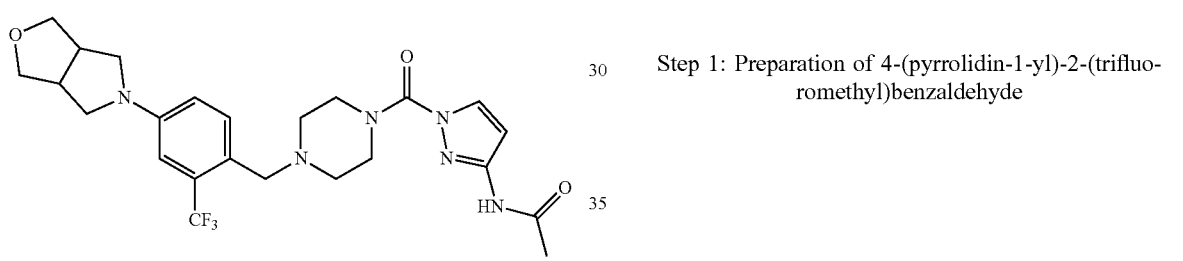

A round-bottom flask was charged with 4-fluoro-2-(trifluoromethyl)benzaldehyde (8.00 g, 41.6 mmol, 1.00 equiv), pyrrolidine (5.92 g, 83.2 mmol, 2.00 equiv), $K_2CO_3$ (17.2 g, 124 mmol, 3.00 equiv), and DMSO (80 mL) under nitrogen. The reaction mixture was stirred overnight at 90° C. and quenched with water (100 mL). The resulting solution was extracted with EtOAc (3×150 mL) and the organic layers were combined, washed with brine (1×200 mL), dried over anhydrous $Na_2SO_4$, filtered and concentrated under reduced pressure. The residue was chromatographed on a silica gel column to provide 6.00 g (59% yield) of 4-(pyrrolidin-1-yl)-2-(trifluoromethyl)benzaldehyde as a yellow solid. LCMS (ESI, m/z): 244 [M+H]$^+$.

Step 2: Preparation of N-(1-(2-(4-(pyrrolidin-1-yl)-2-(trifluoromethyl)benzyl)-2,8-diazaspiro[4.5]decane-8-carbonyl)-1H-pyrazol-3-yl)acetamide

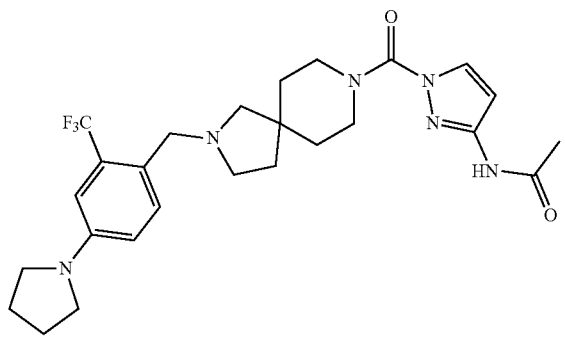 [SMILES: CC(=O)Nc1ccn(C(=O)N2CCC3(CCN(Cc4ccc(N5CCCC5)cc4C(F)(F)F)C3)CC2)n1]

The title compound was prepared as described in Example 22, Steps 2-4, using t-butyl 2,8-diazaspiro[4.5]decane-2-carboxylate and N-(1H-pyrazol-3-yl)acetamide in Step 2; t-butyl 8-(3-acetamido-1H-pyrazole-1-carbonyl)-2,8-diazaspiro[4.5]decane-2-carboxylate in Step 3; and N-(1-(2,8-diazaspiro[4.5]decane-8-carbonyl)-1H-pyrazol-3-yl)acetamide in Step 4 to provide 90.3 mg (40% yield) of N-[1-[(2-[[4-(pyrrolidin-1-yl)-2-(trifluoromethyl)phenyl]methyl]-2,8-diazaspiro[4.5]decan-8-yl)carbonyl]-1H-pyrazol-3-yl]acetamide as a white solid. $^1$H NMR (300 MHz, Chloroform-d) δ 7.97 (d, J=2.7 Hz, 1H), 7.73 (br, 1H), 7.49 (br, 1H), 6.86 (d, J=2.7 Hz, 1H), 6.76 (d, J=2.4 Hz, 1H), 6.66 (d, J=8.7 Hz, 1H), 3.71-3.63 (m, 6H), 3.30 (t, J=6.6 Hz, 4H), 2.64 (br, 2H), 2.44 (br, 2H), 2.18 (s, 3H), 2.06-2.00 (m, 4H), 1.68 (br, 6H). LCMS (ESI, m/z): 519 [M+H]$^+$.

Example 24: N-(1-(5-(4-Chloro-3-(1-hydroxycyclopentyl)benzyl)octahydropyrrolo[3,4-c]pyrrole-2-carbonyl)-1H-pyrazol-3-yl)acetamide

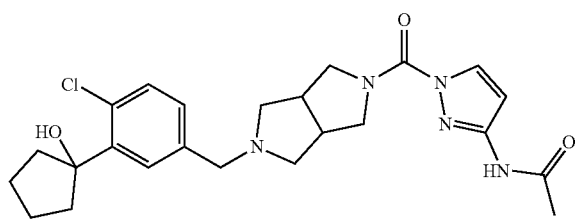 [SMILES: CC(=O)Nc1ccn(C(=O)N2CC3CN(Cc4ccc(Cl)c(C5(O)CCCC5)c4)CC3C2)n1]

Step 1: Preparation of 1-(5-bromo-2-chlorophenyl)cyclopentan-1-ol

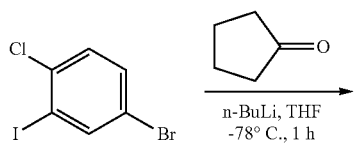

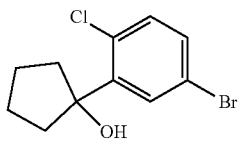

A round-bottom flask was charged with 4-bromo-1-chloro-2-iodobenzene (800 mg, 2.52 mmol, 1.00 equiv) and THF (10 mL) under nitrogen. n-Butyllithium (1.01 mL, 2.52 mmol, 1.00 equiv, 2.5 M in hexane) was added dropwise at −78° C. The mixture was stirred for 1 h at −78° C. prior to drop-wise addition of cyclopentanone (212 mg, 2.52 mmol, 1.00 equiv) over 10 min at −78° C. The reaction mixture was stirred for 1 h at −78° C. and quenched with saturated NH$_4$Cl solution (30 mL). The resulting solution was extracted with EtOAc (3×50 mL) and the organic layers were combined, washed with brine (2×30 mL), dried over anhydrous Na$_2$SO$_4$, filtered and concentrated under reduced pressure. The residue was chromatographed on a silica gel column to provide 400 mg (58% yield) of 1-(5-bromo-2-chlorophenyl)cyclopentan-1-ol as a yellow solid. LCMS (ESI, m/z): 257 [M−OH]$^+$.

Step 2: Preparation of 4-chloro-3-(1-hydroxycyclopentyl)benzaldehyde

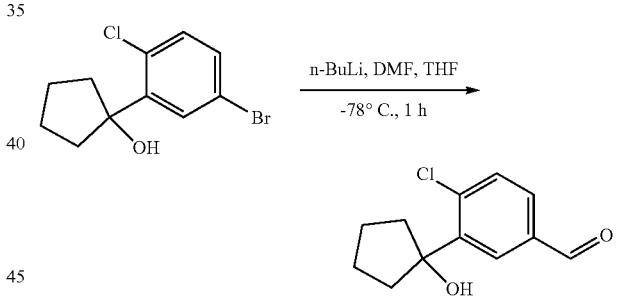

A round-bottom flask was charged with 1-(5-bromo-2-chlorophenyl)cyclopentan-1-ol (400 mg, 1.45 mmol, 1.00 equiv) and THF (10 mL) under nitrogen. The mixture was cooled to −78° C. prior to drop-wise addition of n-butyllithium (1.18 mL, 2.90 mmol, 2.00 equiv, 2.5 M in hexane) at −78° C. The mixture was stirred for 30 min at −78° C. and DMF (318 mg, 4.35 mmol, 3.00 equiv) was added. The reaction mixture was stirred for 1 h at −78° C. and quenched with saturated NH$_4$Cl solution (30 mL). The resulting solution was extracted with EtOAc (2×50 mL), the organic layers were combined, washed with brine (2×30 mL), dried over anhydrous Na$_2$SO$_4$, filtered and concentrated under reduced pressure. The residue was chromatographed on a silica gel column to provide 180 mg (55% yield) of 4-chloro-3-(1-hydroxycyclopentyl)benzaldehyde as a yellow oil. LCMS (ESI, m/z): 207 [M−OH]$^+$.

Step 3: Preparation of 4-nitrophenyl 3-acetamido-1H-pyrazole-1-carboxylate

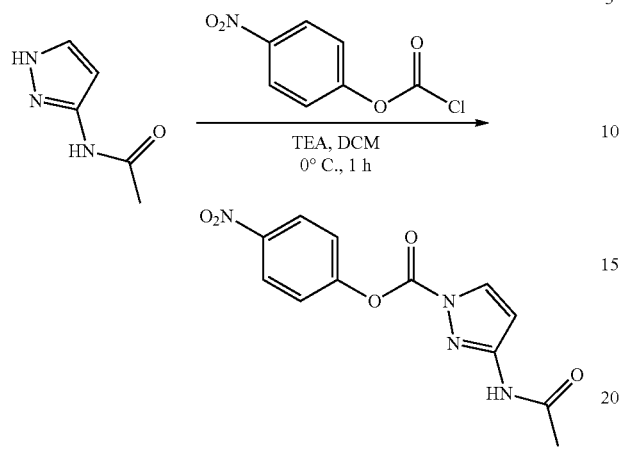

A round-bottom flask was charged with N-(1H-pyrazol-3-yl)acetamide (0.688 g, 5.50 mmol, 1.00 equiv), DCM (25 mL), and TEA (1.67 g, 16.5 mmol, 3.00 equiv). 4-Nitrophenyl chloroformate (1.22 g, 6.05 mmol, 1.10 equiv) was added at 0° C. The resulting solution was stirred for 1 h at 0° C. and concentrated under reduced pressure to provide 1.60 g (crude) of 4-nitrophenyl 3-acetamido-1H-pyrazole-1-carboxylate as yellow oil. LCMS (ESI, m/z): 291 [M+H]$^+$.

Step 4: Preparation of t-butyl 5-(3-acetamido-1H-pyrazole-1-carbonyl)hexahydropyrrolo[3,4-c]pyrrole-2(1H)-carboxylate

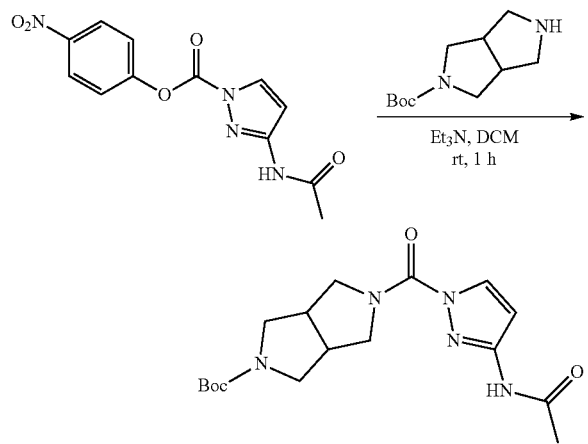

A round-bottom flask was charged with t-butyl octahydropyrrolo[3,4-c]pyrrole-2-carboxylate (1.06 g, 4.99 mmol, 1.00 equiv), 4-nitrophenyl 3-acetamido-1H-pyrazole-1-carboxylate (1.60 g, 5.51 mmol, 1.10 equiv), TEA (1.52 g, 15.0 mmol, 3.00 equiv), and DCM (20 mL). The reaction mixture was stirred for 1 h at room temperature and then quenched with water (25 mL). The resulting mixture was extracted with DCM (3×25 mL) and the organic layers were combined, washed with brine (1×25 mL), dried over anhydrous Na$_2$SO$_4$, filtered and concentrated under reduced pressure. The residue was chromatographed on a silica gel column to provide 670 mg (37% yield) of t-butyl 5-(3-acetamido-1H-pyrazole-1-carbonyl)hexahydropyrrolo[3,4-c]pyrrole-2(1H)-carboxylate as a white solid. LCMS (ESI, m/z): 364 [M+H]$^+$.

Step 5: Preparation of N-(1-(octahydropyrrolo[3,4-c]pyrrole-2-carbonyl)-1H-pyrazol-3-yl)acetamide

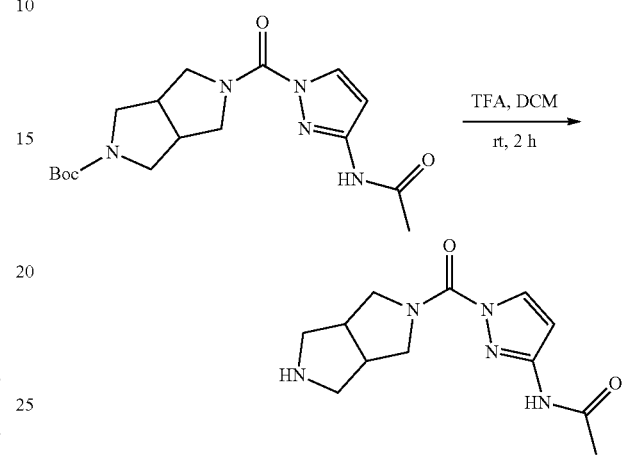

round-bottom flask was charged with t-butyl 5-(3-acetamido-1H-pyrazole-1-carbonyl)hexahydropyrrolo[3,4-c]pyrrole-2(1H)-carboxylate (157 mg, 0.430 mmol, 1.00 equiv), DCM (10 mL), and TFA (2 mL). The resulting solution was stirred for 2 h at room temperature and concentrated under reduced pressure to provide 113 mg (quantitative) of N-(1-(octahydropyrrolo[3,4-c]pyrrole-2-carbonyl)-1H-pyrazol-3-yl)acetamide as a yellow oil. LCMS (ESI, m/z): 264 [M+H]$^+$.

Step 6: Preparation of N-(1-(5-(4-chloro-3-(1-hydroxycyclopentyl)benzyl)octahydropyrrolo[3,4-c]pyrrole-2-carbonyl)-1H-pyrazol-3-yl)acetamide

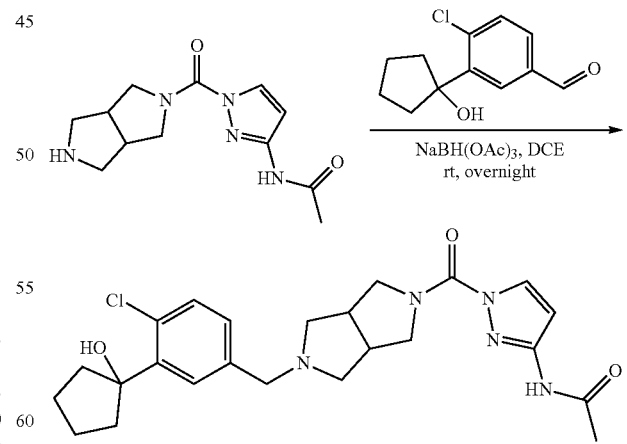

A round-bottom flask was charged with N-(1-(octahydropyrrolo[3,4-c]pyrrole-2-carbonyl)-1H-pyrazol-3-yl)acetamide (113 mg, 0.430 mmol, 1.20 equiv), 4-chloro-3-(1-hydroxycyclopentyl)benzaldehyde (80.0 mg, 0.360 mmol, 1.00 equiv), and DCE (15 mL). The mixture was stirred for 1 h at room temperature prior to addition of sodium triacetoxyborohydride (305 mg, 1.44 mmol, 4.00 equiv). The reaction mixture was stirred overnight at room temperature and quenched with water (10 mL). The resulting solution was extracted with DCM (3×15 mL) and the organic layers were combined, washed with brine (1×20 mL), dried over anhydrous Na$_2$SO$_4$, filtered and concentrated under reduced pressure. The crude product (200 mg) was purified by preparative HPLC to afford 83.2 mg (50% yield) of N-(1-(5-(4-chloro-3-(1-hydroxycyclopentyl)benzyl)octahydropyrrolo[3,4-c]pyrrole-2-carbonyl)-1H-pyrazol-3-yl)acetamide as a white solid. $^1$H NMR (300 MHz, Chloroform-d) δ 8.11 (d, J=2.7 Hz, 1H), 8.06 (br, 1H), 7.61 (s, 1H), 7.31-7.29 (m, 1H), 7.14-7.11 (m, 1H), 6.87 (d, J=2.7 Hz, 1H), 3.98-3.92 (m, 2H), 3.85-3.81 (m, 2H), 3.58 (s, 2H), 2.87 (br, 2H), 2.77 (br, 1H), 2.59 (br, 4H), 2.33-2.23 (m, 2H), 2.18 (s, 3H), 2.12-2.06 (m, 2H), 1.99-1.92 (m, 2H), 1.90-1.84 (m, 2H). LCMS (ESI, m/z): 472 [M+H]$^+$.

Example 25: 1-(3-((8-(3-Acetamido-1H-pyrazole-1-carbonyl)-2,8-diazaspiro[4.5]decan-2-yl)methyl)-5-(trifluoromethyl)phenyl)cyclopentane-1-carboxylic acid

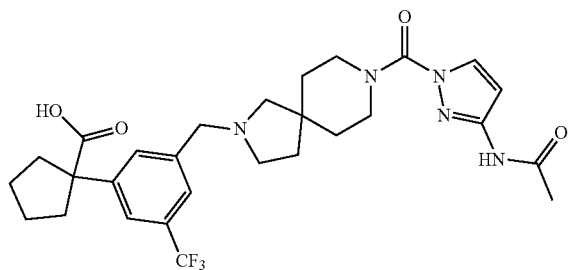 [SMILES: CC(=O)Nc1ccn(C(=O)N2CCC3(CCN(Cc4cc(C(F)(F)F)cc(C5(C(=O)O)CCCC5)c4)C3)CC2)n1]

Step 1: Preparation of t-butyl 2-(3-bromo-5-(trifluoromethyl)phenyl)acetate

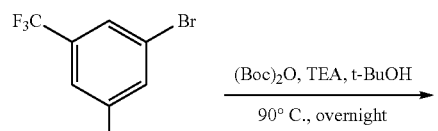

A round-bottom flask was charged with 2-(3-bromo-5-(trifluoromethyl)phenyl)acetic acid (12.0 g, 42.4 mmol, 1.00 equiv), di-t-butyl dicarbonate (18.6 g, 85.2 mmol, 2.00 equiv), TEA (12.9 g, 127 mmol, 3.00 equiv), and t-BuOH (100 mL). The reaction mixture was stirred overnight at 90° C. and quenched with water (100 mL). The resulting solution was extracted with EtOAc (3×150 mL) and the organic layers were combined, washed with brine (2×100 mL), dried over anhydrous Na$_2$SO$_4$, filtered and concentrated under reduced pressure. The residue was chromatographed on a silica gel column to provide 14.0 g (97% yield) of tert-butyl 2-(3-bromo-5-(trifluoromethyl)phenyl)acetate as a colorless liquid. $^1$H NMR (400 MHz, Chloroform-d) δ 7.69 (s, 1H), 7.65 (s, 1H), 7.50 (s, 1H), 3.59 (s, 2H), 1.47 (s, 9H).

Step 2: Preparation of t-butyl 1-(3-bromo-5-(trifluoromethyl)phenyl)cyclopentane-1-carboxylate

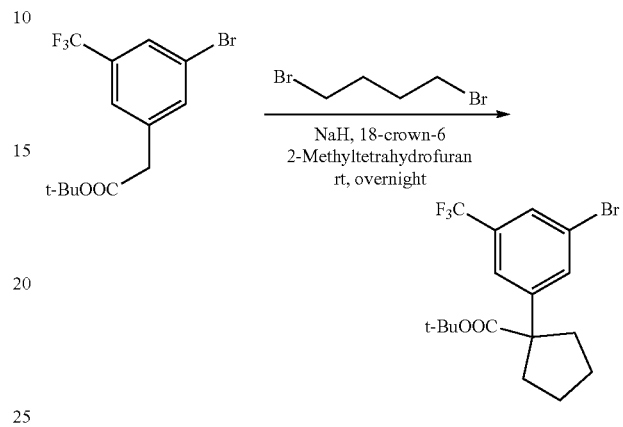

A round-bottom flask was charged with t-butyl 2-(3-bromo-5-(trifluoromethyl)phenyl)acetate (7.00 g, 20.6 mmol, 1.00 equiv), 18-crown-6 (0.273 g, 1.03 mmol, 0.05 equiv), and 2-methyltetrahydrofuran (70 mL). Sodium hydride (2.07 g, 60% in mineral oil, 51.7 mmol, 2.50 equiv) was added at 0° C. The mixture was stirred for 20 min at 0° C. prior to addition of 1,4-dibromobutane (6.65 g, 30.8 mmol, 1.50 equiv). The reaction mixture was stirred overnight at room temperature and quenched with water (70 mL). The resulting solution was extracted with EtOAc (3×100 mL) and the organic layers were combined, washed with brine (1×100 mL), dried over anhydrous Na$_2$SO$_4$, filtered and concentrated under reduced pressure. The residue was chromatographed on a silica gel column to provide 6.20 g (76% yield) of t-butyl 1-(3-bromo-5-(trifluoromethyl)phenyl)cyclopentane-1-carboxylate as colorless oil. $^1$H NMR (300 MHz, Chloroform-d) δ 7.70 (s, 1H), 7.65 (s, 1H), 7.56 (s, 1H), 2.65-2.61 (m, 2H), 1.90-1.75 (m, 6H), 1.37 (s, 9H).

Step 3: Preparation of t-butyl 1-(3-formyl-5-(trifluoromethyl)phenyl)cyclopentane-1-carboxylate

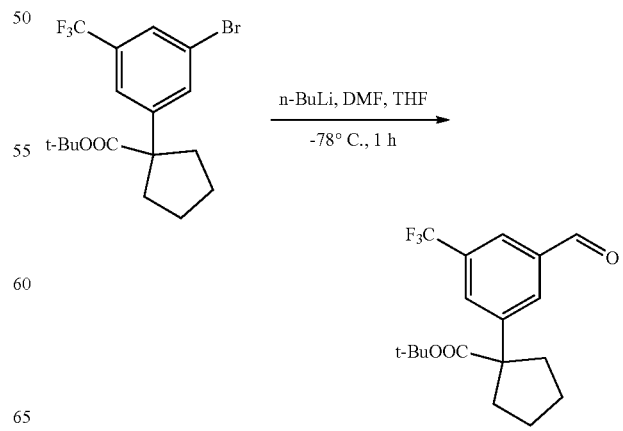

A round-bottom flask was charged with t-butyl 1-(3-bromo-5-(trifluoromethyl)phenyl)cyclopentane-1-carboxylate (6.20 g, 15.8 mmol, 1.00 equiv), and THF (50 mL) under nitrogen. n-Butyllithium (8.22 mL, 2.5M in hexane, 20.6 mmol, 1.30 equiv) was added dropwise at −78° C. The resulting solution was stirred for 30 min at −78° C. prior to addition of DMF (5.77 g, 78.9 mmol, 5.00 equiv). The reaction mixture was stirred for 1 h at −78° C. and quenched with saturated NH₄Cl solution (50 mL). The resulting solution was extracted with EtOAc (3×100 mL) and the organic layers were combined, washed with brine (1×100 mL), dried over anhydrous Na₂SO₄, filtered and concentrated under reduced pressure. The residue was chromatographed on a silica gel column to provide 3.50 g (65% yield) of t-butyl 1-(3-formyl-5-(trifluoromethyl)phenyl)cyclopentane-1-carboxylate as a colorless oil. ¹H NMR (300 MHz, Chloroform-d) δ 10.1 (s, 1H), 8.08 (s, 1H), 8.03 (s, 1H), 7.90 (s, 1H), 2.75-2.69 (m, 2H), 1.93-1.78 (m, 6H), 1.37 (s, 9H).

Step 4: Preparation of t-butyl 1-(3-((8-(3-acetamido-1H-pyrazole-1-carbonyl)-2,8-diazaspiro[4.5]decan-2-yl)methyl)-5-(trifluoromethyl)phenyl)cyclopentane-1-carboxylate

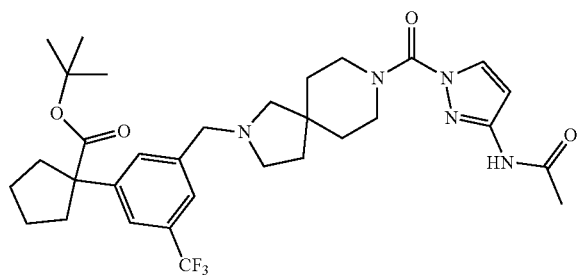 [SMILES: CC(=O)Nc1ccn(C(=O)N2CCC3(CCN(Cc4cc(C(F)(F)F)cc(C5(C(=O)OC(C)(C)C)CCCC5)c4)C3)CC2)n1]

The title compound was prepared as described in Example 22, Steps 2-4, using tert-butyl 2,8-diazaspiro[4.5]decane-2-carboxylate and N-(1H-pyrazol-3-yl)acetamide in Step 2; tert-butyl 8-(3-acetamido-1H-pyrazole-1-carbonyl)-2,8-diazaspiro[4.5]decane-2-carboxylate in Step 3; and N-(1-(2,8-diazaspiro[4.5]decane-8-carbonyl)-1H-pyrazol-3-yl)acetamide and tert-butyl 1-(3-formyl-5-(trifluoromethyl)phenyl)cyclopentane-1-carboxylate in Step 4 to provide 180 mg (67% yield) of tert-butyl 1-[3-([8-[(3-acetamido-1H-pyrazol-1-yl)carbonyl]-2,8-diazaspiro[4.5]decan-2-yl]methyl)-5-(trifluoromethyl)phenyl]cyclopentane-1-carboxylate as yellow oil. LCMS (ESI, m/z): 618 [M+H]⁺.

Step 5: Preparation of 1-(3-((8-(3-acetamido-1H-pyrazole-1-carbonyl)-2,8-diazaspiro[4.5]decan-2-yl)methyl)-5-(trifluoromethyl)phenyl)cyclopentane-1-carboxylic acid

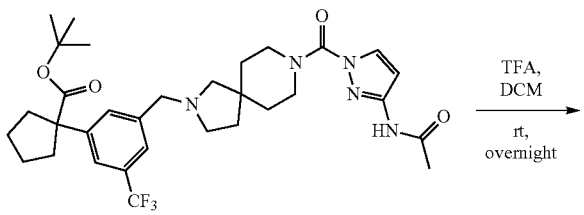

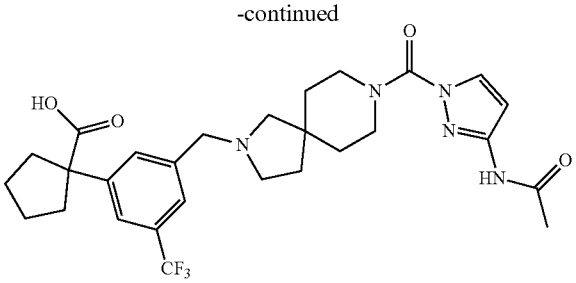

A round-bottom flask was charged with t-butyl 1-(3-((8-(3-acetamido-1H-pyrazole-1-carbonyl)-2,8-diazaspiro[4.5]decan-2-yl)methyl)-5-(trifluoromethyl)phenyl)cyclopentane-1-carboxylate (180 mg, 0.290 mmol, 1.00 equiv), DCM (12 mL), trifluoroacetic acid (3 mL). The resulting solution was stirred overnight at room temperature and concentrated under reduced pressure. The crude product was dissolved in DCM (15 mL) and the pH value of the solution was adjusted to 8 with saturated NaHCO₃ solution. The mixture was extracted with DCM (3×20 mL) and the organic layers were combined, washed with brine (2×15 mL), dried over anhydrous Na₂SO₄, filtered and concentrated under reduced pressure. The crude product (200 mg) was purified by preparative HPLC to afford 85.0 mg (52% yield) of 1-(3-((8-(3-acetamido-1H-pyrazole-1-carbonyl)-2,8-diazaspiro[4.5]decan-2-yl)methyl)-5-(trifluoromethyl)phenyl)cyclopentane-1-carboxylic acid as a white solid. ¹H NMR (400 MHz, Methanol-d₄) δ 8.00 (d, J=2.8 Hz, 1H), 7.72 (s, 1H), 7.65 (s, 1H), 7.55 (s, 1H), 6.78 (d, J=2.8 Hz, 1H), 3.98 (br, 2H), 3.91-3.81 (m, 2H), 3.78-3.71 (m, 2H), 2.97 (br, 2H), 2.79 (br, 2H), 2.75-2.68 (m, 2H), 2.11 (s, 3H), 1.89-1.86 (m, 3H), 1.84-1.77 (m, 3H), 1.75-1.70 (m, 6H). LCMS (ESI, m/z): 562 [M+H]⁺.

Example 26: N-(1-(4-((4-Chloro-3-(tetrahydro-1H-furo[3,4-c]pyrrol-5(3H)-yl)benzyl)(methyl)amino)-4-methylpiperidine-1-carbonyl)-1H-pyrazol-3-yl)methanesulfonamide

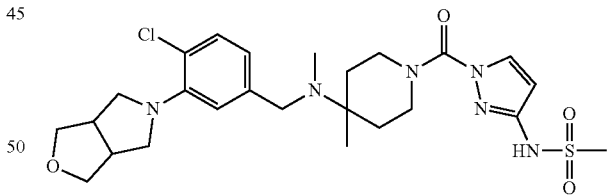

Step 1: Preparation of 4-nitrophenyl 3-(methylsulfonamido)-1H-pyrazole-1-carboxylate

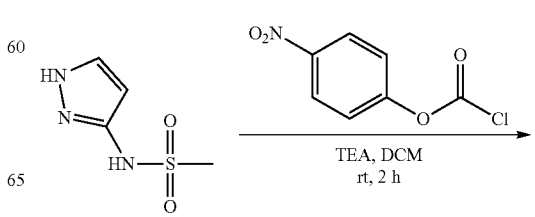

239

-continued

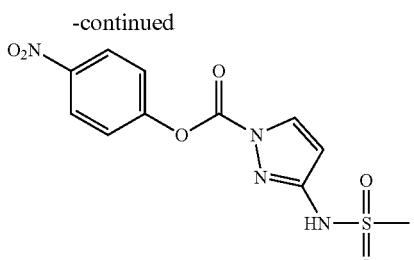

A round-bottom flask was charged with N-(1H-pyrazol-3-yl)methanesulfonamide (131 mg, 0.810 mmol, 1.00 equiv), TEA (246 mg, 2.43 mmol, 3.00 equiv), and DCM (10 mL). 4-Nitrophenyl chloroformate (180 mg, 0.890 mmol, 1.10 equiv) was added at 0° C. The resulting solution was stirred for 2 h at room temperature and concentrated under reduced pressure to provide 264 mg (crude) of 4-nitrophenyl 3-methanesulfonamido-1H-pyrazole-1-carboxylate as a yellow oil. LCMS (ESI, m/z): 327 [M+H]$^+$.

Step 2: Preparation of 4-chloro-3-(tetrahydro-1H-furo[3,4-c]pyrrol-5(3H)-yl)benzaldehyde

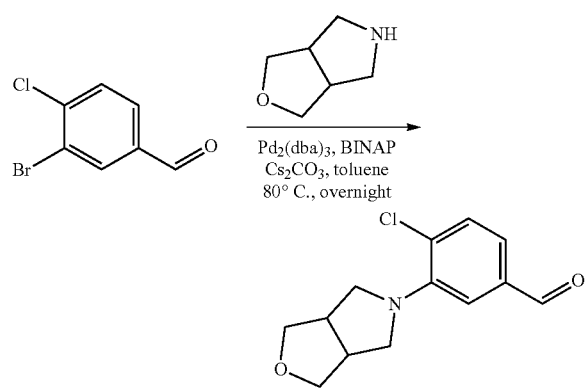

A round-bottom flask was charged with 3-bromo-4-chlorobenzaldehyde (0.800 g, 3.65 mmol, 1.00 equiv), hexahydro-1H-furo[3,4-c]pyrrole (0.498 g, 4.40 mmol, 1.20 equiv), tris(dibenzylideneacetone)dipalladium (0.168 g, 0.180 mmol, 0.05 equiv), 2,2'-bis(diphenylphosphino)-1,1'-binaphthyl (0.342 g, 0.550 mmol, 0.15 equiv), cesium carbonate (3.59 g, 11.0 mmol, 3.00 equiv), and toluene (20 mL) under nitrogen. The reaction mixture was stirred overnight at 80° C. and quenched with water (30 mL). The resulting solution was extracted with EtOAc (3×50 mL) and the organic layers were combined, washed with brine (1×80 mL), dried over anhydrous Na$_2$SO$_4$, filtered and concentrated under reduced pressure. The residue was chromatographed on a silica gel column to provide 0.770 g (84% yield) of 4-chloro-3-(tetrahydro-1H-furo[3,4-c]pyrrol-5(3H)-yl)benzaldehyde as a yellow oil. LCMS (ESI, m/z): 252 [M+H]$^+$.

240

Step 3: Preparation of t-butyl 4-((4-chloro-3-(tetrahydro-1H-furo[3,4-c]pyrrol-5(3H)-yl)benzyl)amino)-4-methylpiperidine-1-carboxylate

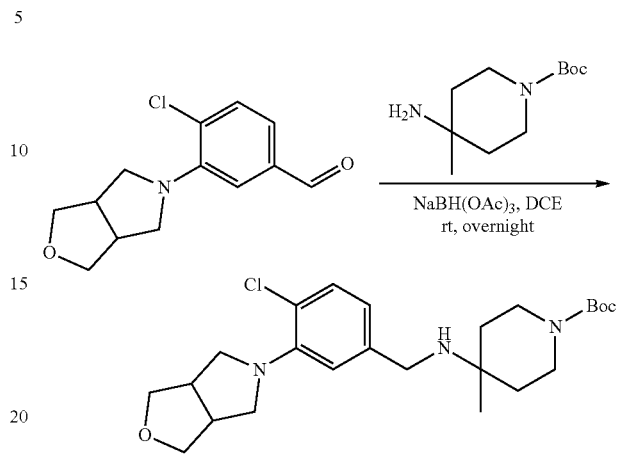

A round-bottom flask was charged with 4-chloro-3-(tetrahydro-1H-furo[3,4-c]pyrrol-5(3H)-yl)benzaldehyde (0.400 g, 1.59 mmol, 1.00 equiv), tert-butyl 4-amino-4-methylpiperidine-1-carboxylate (0.409 g, 1.91 mmol, 1.20 equiv), and DCE (15 mL). The mixture was stirred for 1 h at room temperature prior to addition of sodium triacetoxyborohydride (1.01 g, 4.76 mmol, 3.00 equiv). The reaction mixture was stirred overnight at room temperature and quenched with water (15 mL). The resulting solution was extracted with DCM (3×20 mL) and the organic layers were combined, washed with brine (1×50 mL), dried over anhydrous Na$_2$SO$_4$, filtered and concentrated under reduced pressure. The residue was chromatographed on a silica gel column to provide 0.620 g (87% yield) of t-butyl 4-((4-chloro-3-(tetrahydro-1H-furo[3,4-c]pyrrol-5(3H)-yl)benzyl)amino)-4-methylpiperidine-1-carboxylate as a yellow oil. LCMS (ESI, m/z): 450 [M+H]$^+$.

Step 4: Preparation of t-butyl 4-((4-chloro-3-(tetrahydro-1H-furo[3,4-c]pyrrol-5(3H)-yl)benzyl)(methyl)amino)-4-methylpiperidine-1-carboxylate

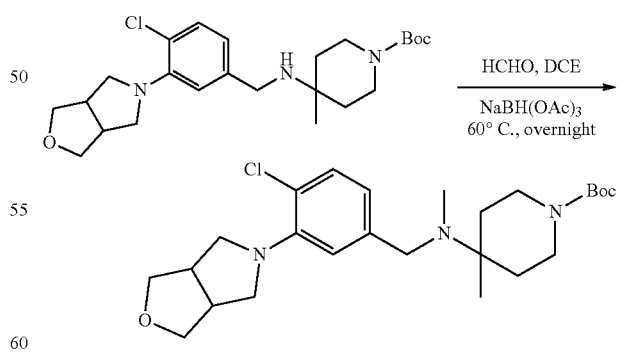

A round-bottom flask was charged with t-butyl 4-((4-chloro-3-(tetrahydro-1H-furo[3,4-c]pyrrol-5(3H)-yl)benzyl)amino)-4-methylpiperidine-1-carboxylate (620 mg, 1.38 mmol, 1.00 equiv), paraformaldehyde (621 mg, 20.7 mmol, 15.00 equiv), and DCE (15 mL). The mixture was stirred for 1 h at room temperature prior to addition of sodium triacetoxyborohydride (878 mg, 4.14 mmol, 3.00 equiv). The reaction mixture was stirred overnight at 60° C. and quenched with water (20 mL). The resulting solution was extracted with DCM (3×30 mL) and the organic layers were combined, washed with brine (1×50 mL), dried over anhydrous $Na_2SO_4$, filtered and concentrated under reduced pressure. The residue was chromatographed on a silica gel column to provide 495 mg (77% yield) of t-butyl 4-((4-chloro-3-(tetrahydro-1H-furo[3,4-c]pyrrol-5(3H)-yl)benzyl)(methyl)amino)-4-methylpiperidine-1-carboxylate as a yellow oil. LCMS (ESI, m/z): 464 [M+H]+.

Step 5: Preparation of N-(4-chloro-3-(tetrahydro-1H-furo[3,4-c]pyrrol-5(3H)-yl)benzyl)-N,4-dimethylpiperidin-4-amine

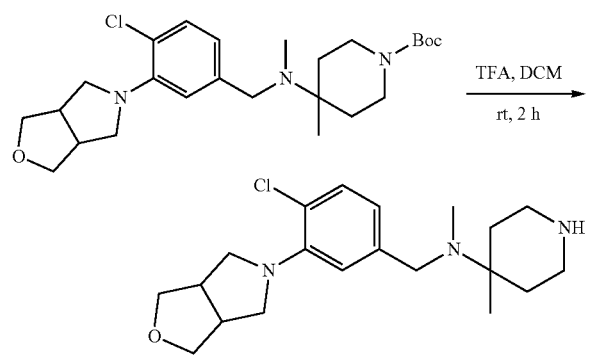

A round-bottom flask was charged with t-butyl 4-((4-chloro-3-(tetrahydro-1H-furo[3,4-c]pyrrol-5(3H)-yl)benzyl)(methyl)amino)-4-methylpiperidine-1-carboxylate (250 mg, 0.540 mmol, 1.00 equiv), DCM (10 mL), and TFA (2 mL). The resulting solution was stirred for 2 h at room temperature and concentrated under reduced pressure to provide 196 mg (quantitative) of N-(4-chloro-3-(tetrahydro-1H-furo[3,4-c]pyrrol-5(3H)-yl)benzyl)-N,4-dimethylpiperidin-4-amine as a yellow oil. LCMS (ESI, m/z): 364 [M+H]+.

Step 6: Preparation of N-(1-(4-((4-chloro-3-(tetrahydro-1H-furo[3,4-c]pyrrol-5(3H)-yl)benzyl)(methyl)amino)-4-methylpiperidine-1-carbonyl)-1H-pyrazol-3-yl)methanesulfonamide A round-bottom flask was charged with N-(4-chloro-3-(tetrahydro-1H-furo[3,4-c]pyrrol-5(3H)-yl)benzyl)-N,4-dimethylpiperidin-4-amine (196 mg, 0.540 mmol, 1.00 equiv), 4-nitrophenyl 3-(methylsulfonamido)-1H-pyrazole-1-carboxylate (264 mg, 0.810 mmol, 1.50 equiv), TEA (164 mg, 1.62 mmol, 3.00 equiv), and DCM (10 mL). The reaction mixture was stirred for 2 h at room temperature and quenched with water (15 mL). The resulting solution was extracted with DCM (3×20 mL) and the organic layers were combined, washed with brine (1×50 mL), dried over anhydrous $Na_2SO_4$, filtered and concentrated under reduced pressure. The crude product (400 mg) was purified by preparative HPLC to provide 150.8 mg (51% yield) of N-(1-(4-((4-chloro-3-(tetrahydro-1H-furo[3,4-c]pyrrol-5(3H)-yl)benzyl)(methyl)amino)-4-methylpiperidine-1-carbonyl)-1H-pyrazol-3-yl)methanesulfonamide as a white solid. $^1$H NMR (400 MHz, Chloroform-d) δ 8.01 (d, J=2.8 Hz, 1H), 7.27-7.25 (m, 1H), 7.00 (br, 1H), 6.91-6.89 (m, 1H), 6.33 (d, J=2.8 Hz, 1H), 3.97-3.93 (m, 4H), 3.72-3.69 (m, 4H), 3.50 (s, 2H), 3.38-3.34 (m, 2H), 3.11 (s, 5H), 2.97-2.94 (m, 2H), 2.10 (s, 3H), 2.06-1.99 (m, 2H), 1.61-1.55 (m, 2H), 1.04 (s, 3H). LCMS (ESI, m/z): 551 [M+H]+.

Example 27: N-(1-((2R,4R)-4-((4-chloro-3-(tetrahydro-1H-furo[3,4-c]pyrrol-5(3H)-yl)benzyl)(methyl)amino)-2-methylpiperidine-1-carbonyl)-1H-pyrazol-3-yl)methanesulfonamide

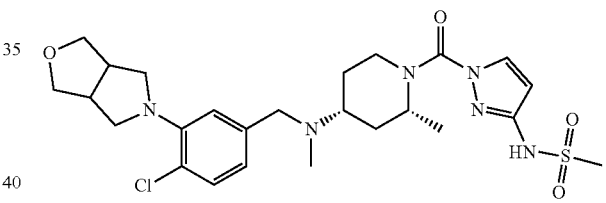

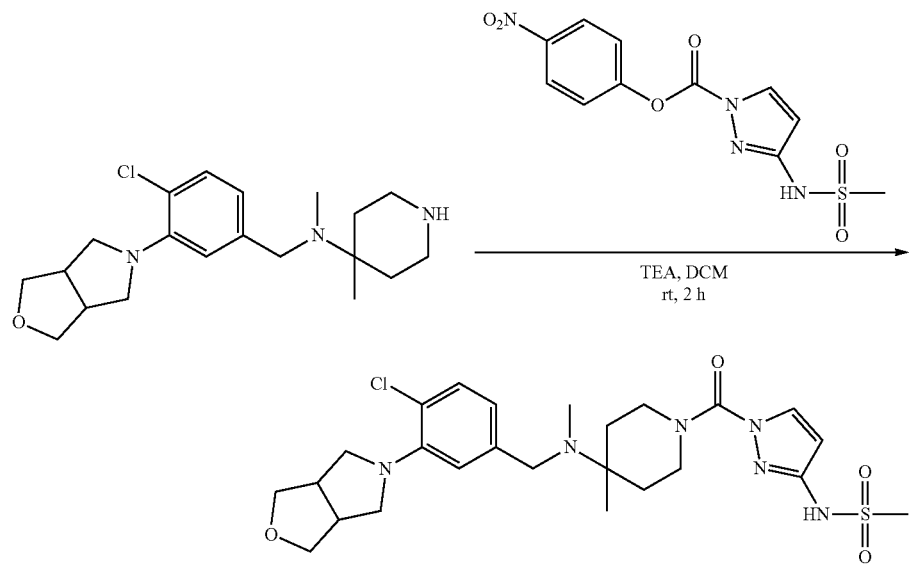

Step 1: Preparation of t-butyl (2R,4S)-4-hydroxy-2-methylpiperidine-1-carboxylate

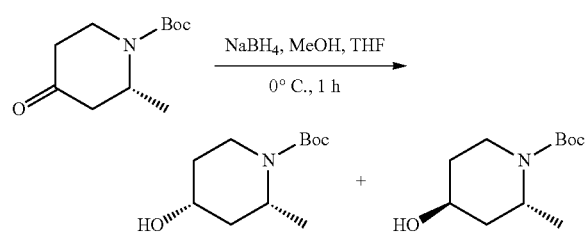

A round-bottom flask was charged with t-butyl (2R)-2-methyl-4-oxopiperidine-1-carboxylate (10.0 g, 46.9 mmol, 1.00 equiv) and THF (36 mL). Sodium borohydride (1.07 g, 28.2 mmol, 0.60 equiv) was added at 0° C., followed by dropwise addition of MeOH (12 mL). The reaction mixture was stirred for 1 h at 0° C. and quenched with water (50 mL). The resulting solution was extracted with DCM (3×80 mL) and the organic layers were combined, washed with brine (2×100 mL), dried over anhydrous $Na_2SO_4$, filtered and concentrated under reduced pressure. The crude product (11.0 g) was purified by preparative HPLC to provide 4.90 g (49% yield) of -butyl (2R,4S)-4-hydroxy-2-methylpiperidine-1-carboxylate as a yellow oil. LCMS (ESI, m/z): 216 $[M+H]^+$, and 4.10 g (41% yield) of t-butyl (2R,4R)-4-hydroxy-2-methylpiperidine-1-carboxylate as a white solid. LCMS (ESI, m/z): 216 $[M+H]^+$.

Step 2: Preparation of t-butyl (2R,4S)-2-methyl-4-((methylsulfonyl)oxy)piperidine-1-carboxylate

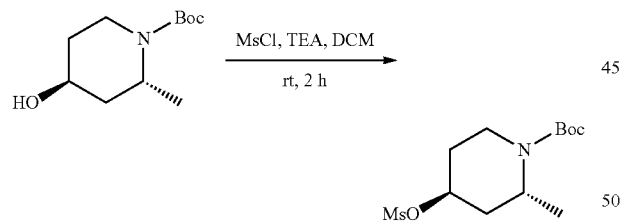

A round-bottom flask was charged with t-butyl (2R,4S)-4-hydroxy-2-methylpiperidine-1-carboxylate (300 mg, 1.39 mmol, 1.00 equiv), DCM (10 mL), and TEA (423 mg, 4.18 mmol, 3.00 equiv). Methanesulfonyl chloride (239 mg, 2.10 mmol, 1.50 equiv) was added at 0° C., and the reaction mixture was stirred for 2 h at room temperature and quenched with saturated $NH_4Cl$ solution (20 mL). The resulting solution was extracted with DCM (3×30 mL) and the organic layers were combined, washed with brine (1×50 mL), dried over anhydrous $Na_2SO_4$, filtered and concentrated under reduced pressure to provide 286 mg (70% yield) of t-butyl (2R,4S)-2-methyl-4-((methylsulfonyl)oxy)piperidine-1-carboxylate as a colorless oil. LCMS (ESI, m/z): 294 $[M+H]^+$.

Step 3: Preparation of t-butyl (2R,4R)-2-methyl-4-(methylamino)piperidine-1-carboxylate

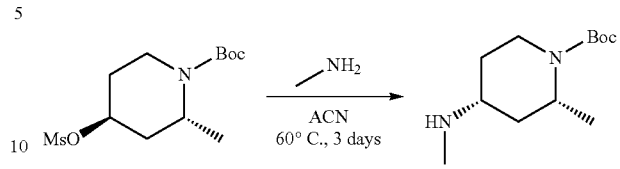

A round-bottom flask was charged with t-butyl (2R,4S)-2-methyl-4-((methylsulfonyl)oxy)piperidine-1-carboxylate (286 mg, 0.970 mmol, 1.00 equiv), ACN (8 mL), and methanamine (8 mL). The reaction mixture was stirred for 3 days at 60° C. and quenched with water (15 mL). The resulting solution was extracted with DCM (3×20 mL) and the organic layers were combined, washed with brine (1×50 mL), dried over anhydrous $Na_2SO_4$, filtered and concentrated under reduced pressure. The residue was chromatographed on a silica gel column to provide 140 mg (63% yield) of t-butyl (2R,4R)-2-methyl-4-(methylamino)piperidine-1-carboxylate as a yellow oil. LCMS (ESI, m/z): 229 $[M+H]^+$.

Step 4: Preparation of t-butyl (2R,4R)-4-((4-chloro-3-(tetrahydro-1H-furo[3,4-c]pyrrol-5(3H)-yl)benzyl)(methyl)amino)-2-methylpiperidine-1-carboxylate

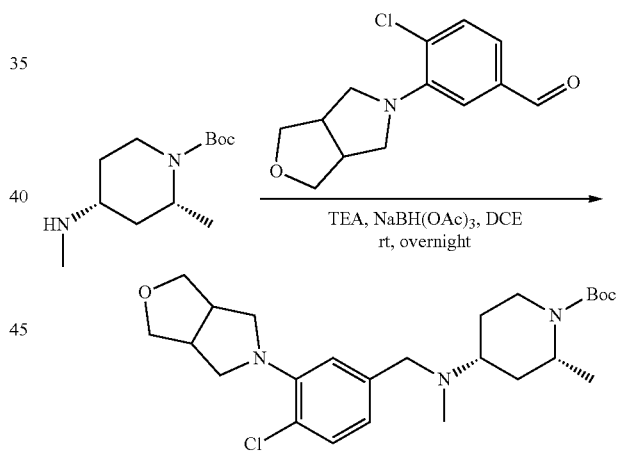

A round-bottom flask was charged with 4-chloro-3-(tetrahydro-1H-furo[3,4-c]pyrrol-5(3H)-yl)benzaldehyde (prepared as described in Example 26, Step 2, 154 mg, 0.610 mmol, 1.00 equiv), t-butyl (2R,4R)-2-methyl-4-(methylamino)piperidine-1-carboxylate (140 mg, 0.610 mmol, 1.00 equiv), TEA (186 mg, 1.84 mmol, 3.00 equiv), and DCE (10 mL). The mixture was stirred for 1 h at room temperature prior to addition of sodium triacetoxyborohydride (390 mg, 1.84 mmol, 3.00 equiv). The reaction mixture was stirred overnight at room temperature and quenched with water (20 mL). The resulting solution was extracted with DCM (3×30 mL) and the organic layers were combined, washed with brine (1×50 mL), dried over anhydrous $Na_2SO_4$, filtered and concentrated under reduced pressure. The residue was chromatographed on a silica gel column to provide 210 mg (74% yield) of t-butyl (2R,4R)-4-((4-chloro-3-(tetrahydro-1H- furo[3,4-c]pyrrol-5(3H)-yl)benzyl)(methyl)amino)-2-methylpiperidine-1-carboxylate as yellow oil. LCMS (ESI, m/z): 464 [M+H]⁺.

Step 5: Preparation of (2R,4R)—N-(4-chloro-3-(tetrahydro-1H-furo[3,4-c]pyrrol-5(3H)-yl)benzyl)-N,2-dimethylpiperidin-4-amine

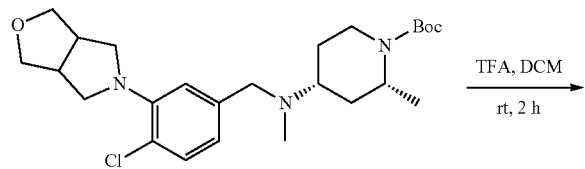

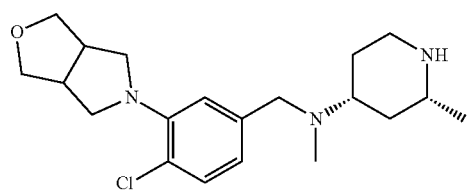

A round-bottom flask was charged with t-butyl (2R,4R)-4-((4-chloro-3-(tetrahydro-1H-furo[3,4-c]pyrrol-5(3H)-yl) benzyl)(methyl)amino)-2-methylpiperidine-1-carboxylate (210 mg, 0.450 mmol, 1.00 equiv), DCM (10 mL), and TFA (2 mL). The resulting solution was stirred for 2 h at room temperature and concentrated under reduced pressure to provide 164 mg (quantitative) of (2R,4R)—N-(4-chloro-3-(tetrahydro-1H-furo[3,4-c]pyrrol-5(3H)-yl)benzyl)-N,2-dimethylpiperidin-4-amine as a yellow oil. LCMS (ESI, m/z): 364 [M+H]⁺.

Step 6: Preparation of N-(1-((2R,4R)-4-((4-chloro-3-(tetrahydro-1H-furo[3,4-c]pyrrol-5(3H)-yl)benzyl) (methyl)amino)-2-methylpiperidine-1-carbonyl)-1H-pyrazol-3-yl)methanesulfonamide A round-bottom flask was charged with (2R,4R)—N-(4-chloro-3-(tetrahydro-1H-furo[3,4-c]pyrrol-5(3H)-yl)benzyl)-N,2-dimethylpiperidin-4-amine (164 mg, 0.450 mmol, 1.00 equiv), 4-nitrophenyl 3-(methylsulfonamido)-1H-pyrazole-1-carboxylate (prepared as described in Example 26, Stet 1, 221 mg, 0.680 mmol, 1.50 equiv), TEA (137 mg, 1.35 mmol, 3.00 equiv), and DCM (10 mL). The reaction mixture was stirred for 2 h at room temperature and quenched with water (15 mL). The resulting solution was extracted with DCM (3×20 mL) and the organic layers were combined, washed with brine (1×50 mL), dried over anhydrous Na₂SO₄, filtered and concentrated under reduced pressure. The crude product (400 mg) was purified by preparative HPLC to provide 23.7 mg (10% yield) of N-(1-((2R,4R)-4-((4-chloro-3-(tetrahydro-1H-furo[3,4-c]pyrrol-5(3H)-yl) benzyl)(methyl)amino)-2-methylpiperidine-1-carbonyl)-1H-pyrazol-3-yl)methanesulfonamide as a white solid. ¹H NMR (400 MHz, MeOH-d₄) δ 8.05 (d, J=2.8 Hz, 1H), 7.30 (d, J=8.4 Hz, 1H), 7.10 (s, 1H), 6.98-6.95 (m, 1H), 6.25 (d, J=2.8 Hz, 1H), 4.25-4.21 (m, 2H), 4.02-3.99 (m, 2H), 3.67-3.61 (m, 4H), 3.47-3.32 (m, 1H), 3.21-3.19 (m, 4H), 3.15 (s, 3H), 3.00-2.92 (m, 2H), 2.86-2.80 (m, 1H), 2.35-2.30 (m, 4H), 2.11-2.05 (m, 1H), 1.80-1.73 (m, 2H), 1.43 (d, J=6.4 Hz, 3H). LCMS (ESI, m/z): 551 [M+H]⁺.

Example 28: N-(14(3aR,5s,6aS)-5-((3-(Trifluoromethyl)benzyl)oxy)octahydrocyclopenta[c]pyrrole-2-carbonyl)-1H-pyrazol-3-yl)methanesulfonamide

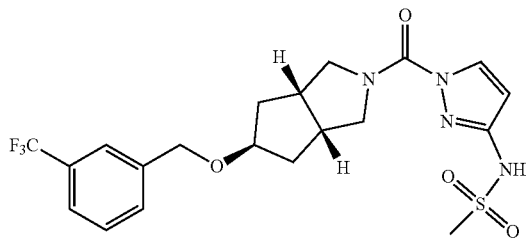 [SMILES: CS(=O)(=O)Nc1ccn(C(=O)N2C[C@H]3C[C@H](OCc4cccc(C(F)(F)F)c4)C[C@H]3C2)n1]

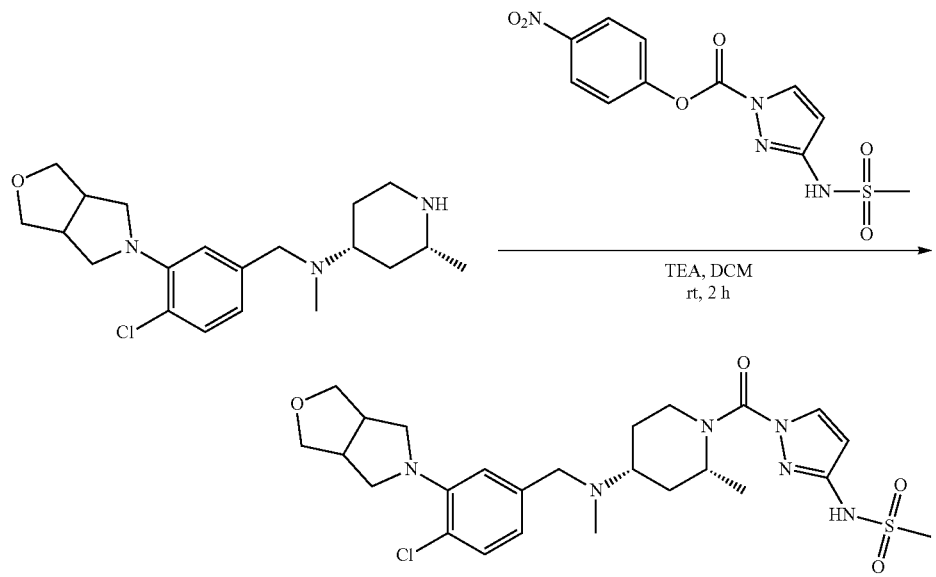

Step 1: Preparation of t-butyl (3aR,5s,6aS)-5-((4-nitrobenzoyl)oxy)hexahydrocyclopenta[c]pyrrole-2(1H)-carboxylate

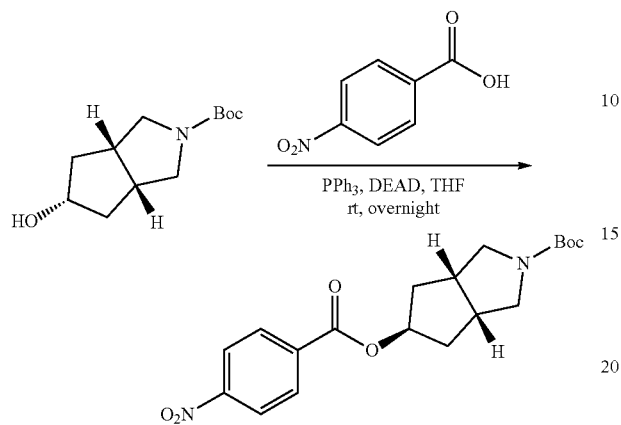

A round-bottom flask was charged with t-butyl (3aR,5r,6aS)-5-hydroxyhexahydrocyclopenta[c]pyrrole-2(1H)-carboxylate (prepared as described in Example 27, Step 1, using t-butyl (3aR,6aS)-5-oxohexahydrocyclopenta[c]pyrrole-2(1H)-carboxylate; 2.27 g, 9.99 mmol, 1.00 equiv), 4-nitrobenzoic acid (6.68 g, 40.0 mmol, 4.00 equiv), triphenylphosphine (10.5 g, 40.0 mmol, 4.00 equiv) and THF (30 mL). Diethyl azodicarboxylate (6.96 g, 40.0 mmol, 4.00 equiv) was added dropwise at 0° C., and the reaction mixture was stirred overnight at room temperature under nitrogen atmosphere and quenched by water (50 mL). The resulting solution was extracted with EtOAc (3×50 mL) and the organic layers were combined, washed with water (3×20 mL), dried over anhydrous Na$_2$SO$_4$, filtered and concentrated under reduced pressure. The residue was chromatographed on a silica gel column to provide 2.36 g (62% yield) of t-butyl (3aR,5s,6aS)-5-((4-nitrobenzoyl)oxy)hexahydrocyclopenta[c]pyrrole-2(1H)-carboxylate as a white solid. LCMS (ESI, m/z): 377 [M+H]$^+$.

Step 2: Preparation of t-butyl (3aR,5s,6aS)-5-hydroxyhexahydrocyclopenta[c]pyrrole-2(1H)-carboxylate

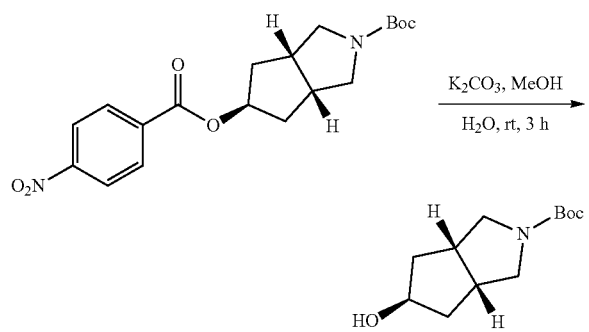

A round-bottom flask was charged with t-butyl (3aR,5s,6aS)-5-((4-nitrobenzoyl)oxy)hexahydrocyclopenta[c]pyrrole-2(1H)-carboxylate (2.36 g, 6.27 mmol, 1.00 equiv), MeOH (30 mL), K$_2$CO$_3$ (2.60 g, 18.8 mmol, 3.00 equiv) and water (5 mL). The reaction mixture was stirred for 3 h at room temperature and concentrated under reduced pressure. The resulting solution was diluted with water (30 mL), extracted with EtOAc (3×50 mL) and the organic layers were combined, washed with water (3×20 mL), dried over anhydrous Na$_2$SO$_4$, filtered and concentrated under reduced pressure to provide 1.31 g (crude) of t-butyl (3aR,5s,6aS)-5-hydroxyhexahydrocyclopenta[c]pyrrole-2(1H)-carboxylate as a white solid. LCMS (ESI, m/z): 228 [M+H]$^+$.

Step 3: Preparation of t-butyl (3aR,5s,6aS)-5-((3-(trifluoromethyl)benzyl)oxy)hexahydrocyclopenta[c]pyrrole-2(1H)-carboxylate

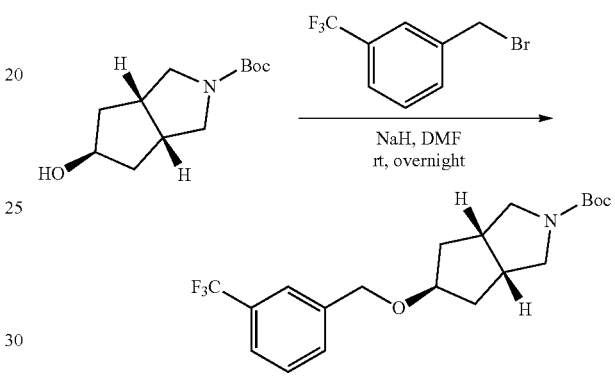

A round-bottom flask was charged with t-butyl (3aR,5s,6aS)-5-hydroxyhexahydrocyclopenta[c]pyrrole-2(1H)-carboxylate (681 mg, 3.00 mmol, 1.00 equiv) and DMF (15 mL). Sodium hydride (60% in oil, 400 mg, 10.0 mmol, 2.00 equiv) was added at 0° C., and the reaction mixture was stirred for 0.5 h at room temperature prior to addition of 1-(bromomethyl)-3-(trifluoromethyl)benzene (714 mg, 3.00 mmol, 1.00 equiv). The resulting solution was stirred overnight at room temperature and quenched with water (20 mL). The mixture was extracted with EtOAc (3×20 mL) and the organic layers were combined, washed with water (3×20 mL), dried over anhydrous Na$_2$SO$_4$, filtered and concentrated under reduced pressure. The residue was chromatographed on a silica gel column to provide 680 mg (59% yield) of t-butyl (3aR,5s,6aS)-5-((3-(trifluoromethyl)benzyl)oxy)hexahydrocyclopenta[c]pyrrole-2(1H)-carboxylate as a yellow oil. LCMS (ESI, m/z): 386 [M+H]$^+$.

Step 4: Preparation of (3aR,5s,6aS)-5-((3-(trifluoromethyl)benzyl)oxy)octahydrocyclopenta[c]pyrrole

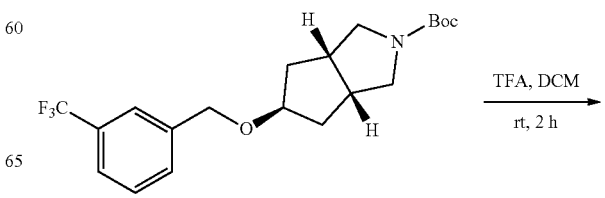

-continued

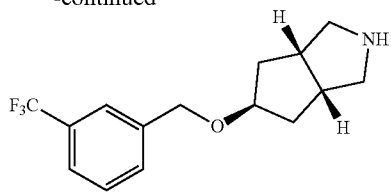

A round-bottom flask was charged with t-butyl (3aR,5s,6aS)-5-((3-(trifluoromethyl)benzyl)oxy)hexahydrocyclopenta[c]pyrrole-2(1H)-carboxylate (116 mg, 0.300 mmol, 1.00 equiv), TFA (2 mL) and DCM (5 mL). The resulting solution was stirred for 2 h at room temperature and concentrated under reduced pressure to afford 148 mg (quantitative) of (3aR,5s,6aS)-5-((3-(trifluoromethyl)benzyl)oxy)octahydrocyclopenta[c]pyrrole as a yellow oil. LCMS (ESI, m/z): 286 [M+H]$^+$.

Step 5: Preparation of N-(1-((3aR,5s,6aS)-5-((3-(trifluoromethyl)benzyl)oxy)octahydrocyclopenta[c]pyrrole-2-carbonyl)-1H-pyrazol-3-yl)methanesulfonamide

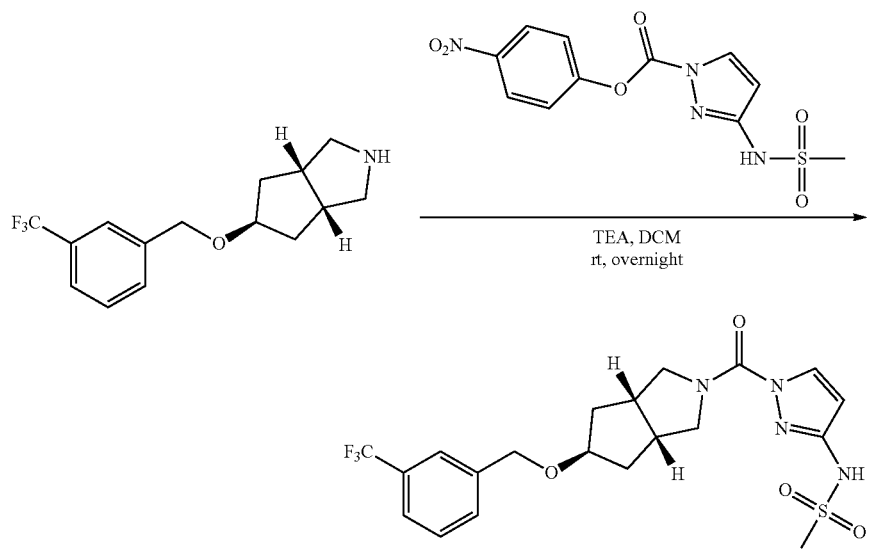

A vial was charged with (3aR,5s,6aS)-5-((3-(trifluoromethyl)benzyl)oxy)octahydrocyclopenta[c]pyrrole (85.8 mg, 0.300 mmol, 1.00 equiv), TEA (182 mg, 1.80 mmol, 6.00 equiv), 4-nitrophenyl 3-(methylsulfonamido)-1H-pyrazole-1-carboxylate (Example 26, Step 1; 147 mg, 0.450 mmol, 1.50 equiv) and DCM (15 mL). The reaction mixture was stirred overnight at room temperature. The resulting solution was quenched with water (10 mL), extracted with DCM (3×20 mL) and the organic layers were combined, washed with brine (2×20 mL), dried over anhydrous Na$_2$SO$_4$, filtered and concentrated under reduced pressure. The residue was chromatographed on a silica gel column. The crude product was purified by preparative HPLC to afford 56.4 mg (40% yield) of N-(1-((3aR,5s,6aS)-5-((3-(trifluoromethyl)benzypoxy)octahydrocyclopenta[c]pyrrole-2-carbonyl)-1H-pyrazol-3-yl)methanesulfonamide as a white solid. $^1$H NMR: (300 MHz, MeOH-d$_4$) δ 8.14 (d, J=2.7 Hz, 1H), 7.69-7.48 (m, 4H), 6.24 (d, J=3.0 Hz, 1H), 4.55 (s, 2H), 4.29-4.19 (m, 1H), 4.05-3.68 (m, 4H), 3.12 (s, 3H), 2.99-2.85 (m, 2H), 2.21-2.09 (m, 2H), 1.82-1.71 (m, 2H). LCMS (ESI, m/z): 473 [M+H]$^+$.

Example 29: N-(4-methyl-1-(3-(methylsulfonamido)-1H-pyrazole-1-carbonyl)piperidin-4-yl)-N-(2-(pyrrolidin-1-yl)-4-(trifluoromethyl)benzyl)glycine

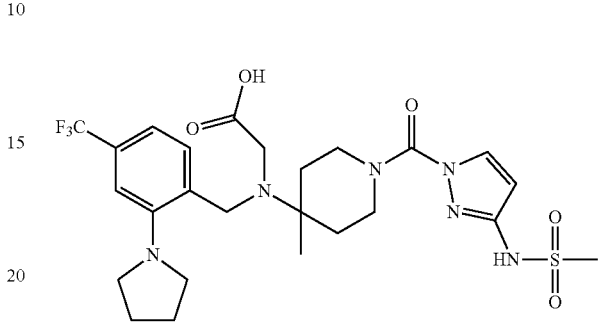

Step 1: Preparation of 2-(pyrrolidin-1-yl)-4-(trifluoromethyl)benzaldehyde

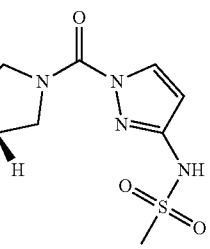

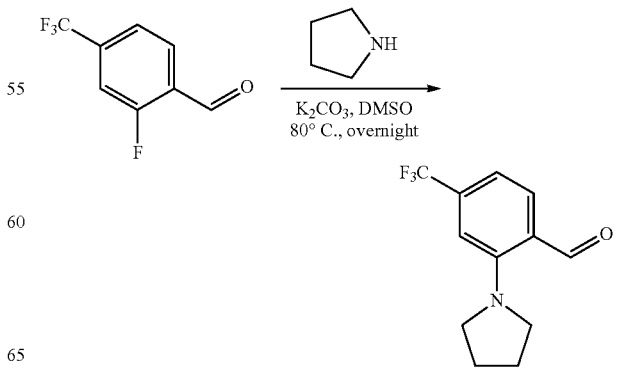

A round-bottom flask was charged with 2-fluoro-4-(trifluoromethyl)benzaldehyde (4.80 g, 25.0 mmol, 1.00 equiv), pyrrolidine (5.33 g, 75.0 mmol, 3.00 equiv), DMSO (30 mL), and K₂CO₃ (10.4 g, 75.0 mmol, 3.00 equiv). The reaction mixture was stirred overnight at 80° C. and quenched with water (30 mL). The resulting solution was extracted with EtOAc (3×50 mL) and the organic layers were combined, washed with brine (2×50 mL), dried over anhydrous Na₂SO₄, filtered and concentrated under reduced pressure. The residue was chromatographed on a silica gel column to provide 3.60 g (59% yield) of 2-(pyrrolidin-1-yl)-4-(trifluoromethyl)benzaldehyde as a brown oil. LCMS (ESI, m/z): 244 [M+H]⁺.

Step 2: Preparation of t-butyl 4-methyl-4-((2-(pyrrolidin-1-yl)-4-(trifluoromethyl)benzyl)amino)piperidine-1-carboxylate

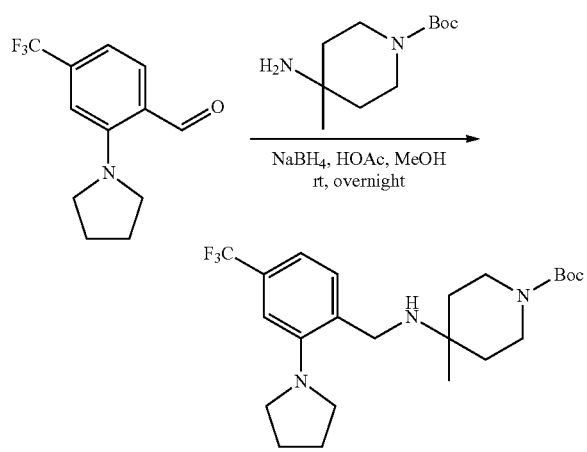

A round-bottom flask was charged with 2-(pyrrolidin-1-yl)-4-(trifluoromethyl)benzaldehyde (243 mg, 1.00 mmol, 1.00 equiv), t-butyl 4-amino-4-methylpiperidine-1-carboxylate (257 mg, 1.20 mmol, 1.20 equiv), MeOH (10 mL), and acetic acid (180 mg, 3.00 mmol, 3.00 equiv). The mixture was stirred for 1 h at 60° C. prior to addition of sodium borohydride (152 mg, 4.00 mmol, 4.00 equiv). The reaction mixture was stirred overnight at room temperature and quenched with water (20 mL). The resulting solution was extracted with DCM (3×30 mL) and the organic layers were combined, washed with brine (30 mL), dried over anhydrous Na₂SO₄, filtered and concentrated under reduced pressure. The residue was chromatographed on a silica gel column to provide 200 mg (45% yield) of t-butyl 4-methyl-4-((2-(pyrrolidin-1-yl)-4-(trifluoromethyl)benzyl)amino)piperidine-1-carboxylate as a yellow oil. LCMS (ESI, m/z): 442 [M+H]⁺.

Step 3: Preparation of t-butyl 4-((2-(tert-butoxy)-2-oxoethyl)(2-(pyrrolidin-1-yl)-4-(trifluoromethyl)benzyl)amino)-4-methylpiperidine-1-carboxylate

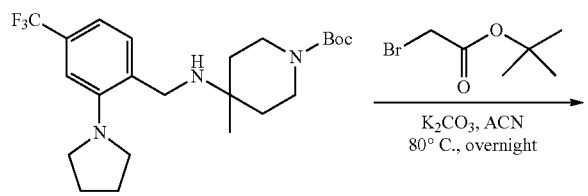

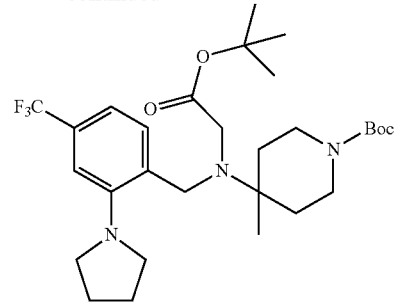

A round-bottom flask was charged with t-butyl 4-methyl-4-((2-(pyrrolidin-1-yl)-4-(trifluoromethyl)benzyl)amino)piperidine-1-carboxylate (220 mg, 0.500 mmol, 1.00 equiv), t-butyl 2-bromoacetate (116 mg, 0.600 mmol, 1.20 equiv), ACN (20 mL), and K₂CO₃ (207 mg, 1.50 mmol, 3.00 equiv). The reaction mixture was stirred overnight at 80° C. and quenched with water (20 mL). The resulting solution was extracted with DCM (3×30 mL) and the organic layers were combined, washed with brine (30 mL), dried over anhydrous Na₂SO₄, filtered and concentrated under reduced pressure. The residue was chromatographed on a silica gel column to provide 130 mg (47% yield) of t-butyl 4-((2-(t-butoxy)-2-oxoethyl)(2-(pyrrolidin-1-yl)-4-(trifluoromethyl)benzyl)amino)-4-methylpiperidine-1-carboxylate as yellow oil. LCMS (ESI, m/z): 556 [M+H]⁺.

Step 4: Preparation of N-(4-methylpiperidin-4-yl)-N-(2-(pyrrolidin-1-yl)-4-(trifluoromethyl)benzyl)glycine

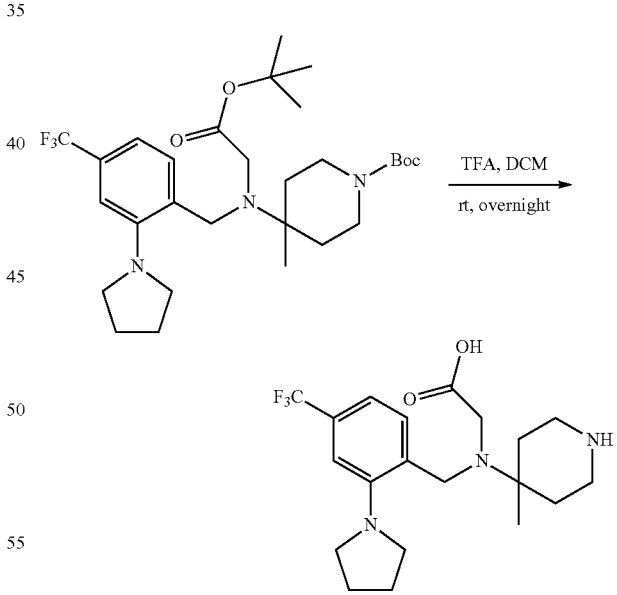

A 50-mL round-bottom flask was charged with t-butyl 4-((2-(t-butoxy)-2-oxoethyl)(2-(pyrrolidin-1-yl)-4-(trifluoromethyl)benzyl)amino)-4-methylpiperidine-1-carboxylate (130 mg, 0.230 mmol, 1.00 equiv), DCM (10 mL), and TFA (3 mL). The resulting solution was stirred overnight at room temperature and concentrated under reduced pressure to provide 93.4 mg (quantitative) of N-(4-methylpiperidin-4-yl)-N-(2-(pyrrolidin-1-yl)-4-(trifluoromethyl)benzyl)glycine as a yellow oil. LCMS (ESI, m/z): 400 [M+H]⁺.

Step 5: Preparation of N-(4-methyl-1-(3-(methyl-sulfonamido)-1H-pyrazole-1-carbonyl)piperidin-4-yl)-N-(2-(pyrrolidin-1-yl)-4-(trifluoromethyl)benzyl)glycine

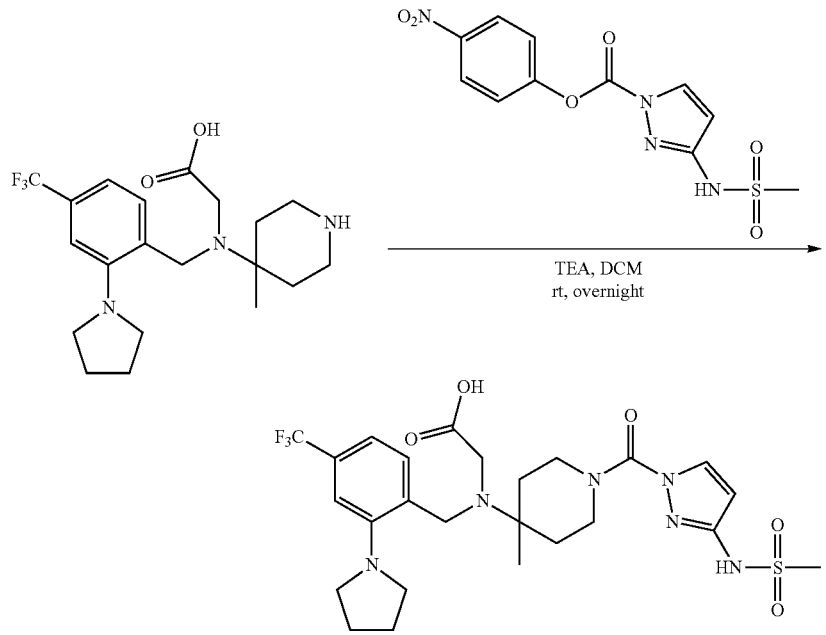

A round-bottom flask was charged with N-(4-methylpiperidin-4-yl)-N-(2-(pyrrolidin-1-yl)-4-(trifluoromethyl)benzyl)glycine (93.4 mg, 0.230 mmol, 1.00 equiv), 4-nitrophenyl 3-(methylsulfonamido)-1H-pyrazole-1-carboxylate (Example 26, Step 1, 114 mg, 0.350 mmol, 1.50 equiv), DCM (10 mL), and TEA (70.9 mg, 0.700 mmol, 3.00 equiv). The reaction mixture was stirred overnight at room temperature and then quenched with saturated NaHCO$_3$ solution (10 mL). The resulting solution was extracted with DCM (3×30 mL) and the organic layers were combined, washed with brine (30 mL), dried over anhydrous Na$_2$SO$_4$, filtered and concentrated under reduced pressure. The crude product (200 mg) was purified by preparative HPLC to afford 10.9 mg (8%) of N-(4-methyl-1-(3-(methylsulfonamido)-1H-pyrazole-1-carbonyl)piperidin-4-yl)-N-(2-(pyrrolidin-1-yl)-4-(trifluoromethyl)benzyl)glycine as a white solid. $^1$H NMR (300 MHz, Methanol-d$_4$) δ 8.09 (d, J=3.0 Hz, 1H), 7.70 (br, 1H), 7.58 (s, 1H), 7.47 (d, J=8.1 Hz, 1H), 6.28 (d, J=3.0 Hz, 1H), 4.71-4.63 (m, 2H), 4.51 (br, 2H), 3.56 (s, 2H), 3.29-3.21 (m, 2H), 3.14 (br, 4H), 3.09 (s, 3H), 2.19 (br, 4H), 2.10 (br, 4H), 1.66 (s, 3H). LCMS (ESI, m/z): 587 [M+H]$^-$.

Example 30: N-(1-(4-((3-chloro-4-(4-fluoropiperidin-1-yl)benzyl)oxy)piperidine-1-carbonyl)-1H-pyrazol-3-yl)methanesulfonamide

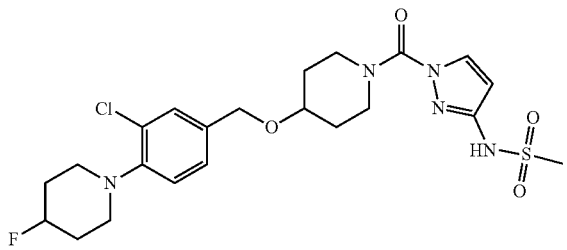 [SMILES: CS(=O)(=O)Nc1ccn(C(=O)N2CCC(OCc3ccc(N4CCC(F)CC4)c(Cl)c3)CC2)n1]

Step 1: Preparation of t-butyl 4-((4-bromo-3-chlorobenzyl)oxy)piperidine-1-carboxylate

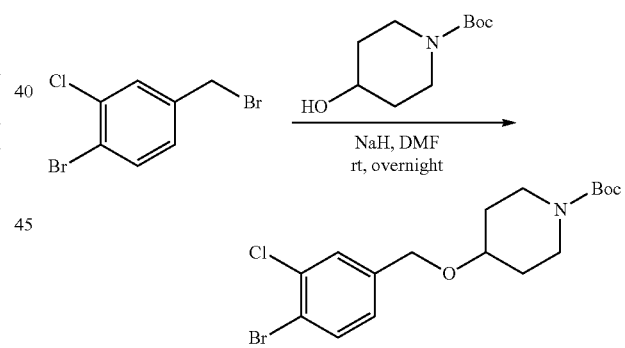

A round-bottom flask was charged with t-butyl 4-hydroxypiperidine-1-carboxylate (804 mg, 3.99 mmol, 2.00 equiv) and DMF (10 mL). Sodium hydride (240 mg, 6.00 mmol, 3.00 equiv, 60% in mineral oil) was added at 0° C., and the mixture was stirred for 1 h at 0° C. prior to addition of 1-bromo-4-(bromomethyl)-2-chlorobenzene (564 mg, 2.00 mmol, 1.00 equiv). The reaction mixture was stirred overnight at room temperature and quenched with water (10 mL). The resulting solution was extracted with EtOAc (3×15 mL) and the organic layers were combined, washed with brine (1×20 mL), dried over anhydrous Na$_2$SO$_4$, filtered and concentrated under reduced pressure. The residue was chromatographed on a silica gel column to provide 403 mg (50% yield) of t-butyl 4-((4-bromo-3-chlorobenzyl)oxy)piperidine-1-carboxylate as a yellow oil. LCMS (ESI, m/z): 404 [M+H]$^+$.

Step 2: Preparation of t-butyl 4-((3-chloro-4-(4-fluoropiperidin-1-yl)benzyl)oxy)piperidine-1-carboxylate

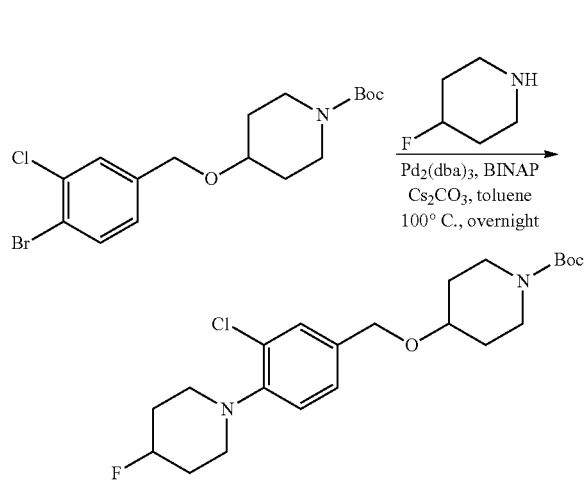

A round-bottom flask was charged with t-butyl 4-((4-bromo-3-chlorobenzyl)oxy)piperidine-1-carboxylate (403 mg, 1.00 mmol, 1.00 equiv), 4-fluoropiperidine (206 mg, 2.00 mmol, 2.00 equiv), tris(dibenzylideneacetone)dipalladium (46.0 mg, 0.0500 mmol, 0.05 equiv), 2,2'-bis(diphenylphosphino)-1,1'-binaphthyl (93.0 mg, 0.150 mmol, 0.15 equiv), Cs$_2$CO$_3$ (978 mg, 3.00 mmol, 3.00 equiv), and toluene (10 mL) under nitrogen. The reaction mixture was stirred overnight at 100° C. and quenched with water (10 mL). The resulting solution was extracted with DCM (3×15 mL) and the organic layers were combined, washed with brine (1×20 mL), dried over anhydrous Na$_2$SO$_4$, filtered and concentrated under reduced pressure. The residue was chromatographed on a silica gel column to provide 170 mg (40% yield) of t-butyl 4-((3-chloro-4-(4-fluoropiperidin-1-yl)benzyl)oxy)piperidine-1-carboxylate as a yellow oil. LCMS (ESI, m/z): 427 [M+H]$^+$.

Step 3: Preparation of 1-(2-chloro-4-((piperidin-4-yloxy)methyl)phenyl)-4-fluoropiperidine

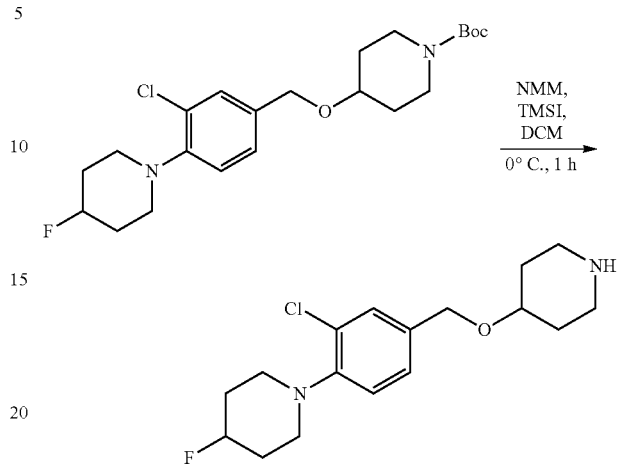

A round-bottom flask was charged with t-butyl 4-((3-chloro-4-(4-fluoropiperidin-1-yl)benzyl)oxy)piperidine-1-carboxylate (169 mg, 0.397 mmol, 1.00 equiv), DCM (10 mL). N-Methylmorpholine (200 mg, 1.98 mmol, 5.00 equiv) was added at 0° C. followed by trimethyiodosilane (318 mg, 1.59 mmol, 4.00 equiv). The reaction mixture was stirred for 1 h at 0° C. and quenched with saturated NaHSO$_3$ solution (10 mL). The resulting solution was extracted with EtOAc (3×20 mL) and the organic layers were combined, washed with brine (3×10 mL), dried over anhydrous Na$_2$SO$_4$, filtered and concentrated under reduced pressure to provide 120 mg (crude) of 1-(2-chloro-4-((piperidin-4-yloxy)methyl)phenyl)-4-fluoropiperidine as a yellow oil. LCMS (ESI, m/z): 327 [M+H]$^+$.

Step 4: Preparation of N-(1-(4-((3-chloro-4-(4-fluoropiperidin-1-yl)benzyl)oxy)piperidine-1-carbonyl)-1H-pyrazol-3-yl)methanesulfonamide

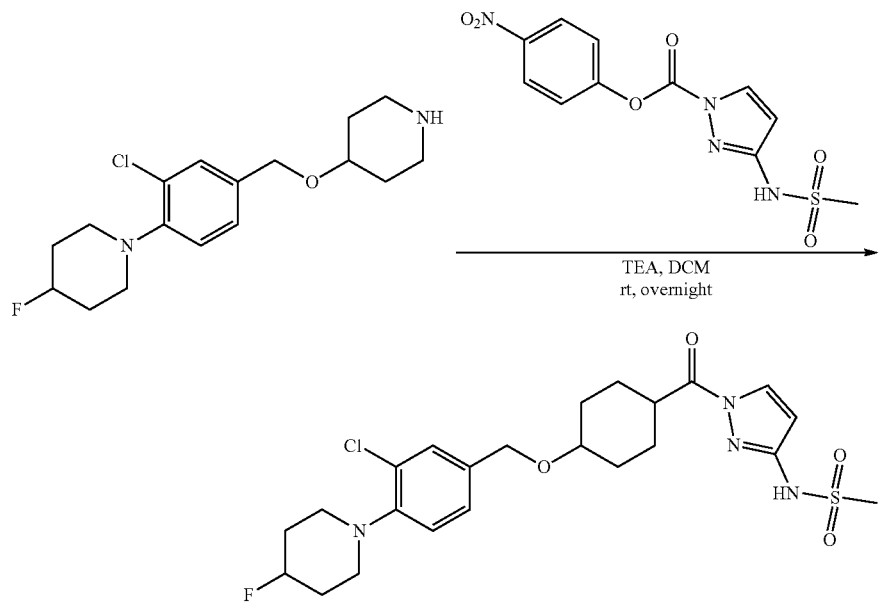

A round-bottom flask was charged with 1-(2-chloro-4-((piperidin-4-yloxy)methyl)phenyl)-4-fluoropiperidine (120 mg, 0.368 mmol, 1.00 equiv), 4-nitrophenyl 3-(methylsulfonamido)-1H-pyrazole-1-carboxylate (Example 26, Step 1, 180 mg, 0.552 mmol, 1.50 equiv), triethylamine (112 mg, 1.11 mmol, 3.00 equiv), and DCM (10 mL). The resulting solution was stirred overnight at room temperature and then quenched with water (20 mL). The mixture was extracted with DCM (3×20 mL) and the organic layers were combined, washed with brine (20 mL), dried over anhydrous Na$_2$SO$_4$, filtered and concentrated under reduced pressure. The crude product (200 mg) was purified by preparative HPLC to provide 32.6 mg (17% yield) of N-(1-(4-((3-chloro-4-(4-fluoropiperidin-1-yl)benzyl)oxy)piperidine-1-carbonyl)-1H-pyrazol-3-yl)methanesulfonamide as an off-white solid. $^1$H NMR (400 MHz, Chloroform-d) δ 8.05 (d, J=2.4 Hz, 1H), 7.38 (s, 1H), 7.28-7.21 (m, 1H), 7.06-7.04 (m, 1H), 6.90 (br, 1H), 6.33 (d, J=2.4 Hz, 1H), 4.92-4.80 (m, 1H), 4.50 (s, 2H), 4.06-4.02 (m, 2H), 3.74-3.71 (m, 1H), 3.65-3.61 (m, 2H), 3.20-3.14 (m, 5H), 3.04-2.99 (m, 2H), 2.14-1.96 (m, 6H), 1.84-1.77 (m, 2H). LCMS (ESI, m/z): 514 [M+H]$^+$.

Example 31: (S)—N-(1-(4-((6-chloro-5-(4-fluoropiperidin-1-yl)pyridin-3-yl)methyl)-3-methylpiperazine-1-carbonyl)-1H-pyrazol-3-yl)methanesulfonamide

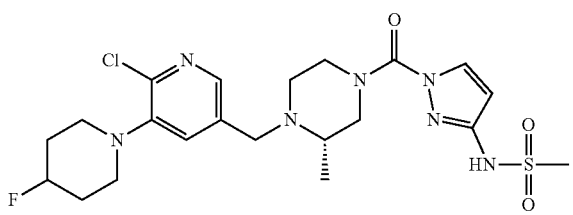 [SMILES: C[C@H]1CN(C(=O)n2ccc(NS(C)(=O)=O)n2)CCN1Cc1cnc(Cl)c(N2CCC(F)CC2)c1]

Step 1: Preparation of t-butyl (S)-4-(5-bromo-6-chloronicotinoyl)-3-methylpiperazine-1-carboxylate

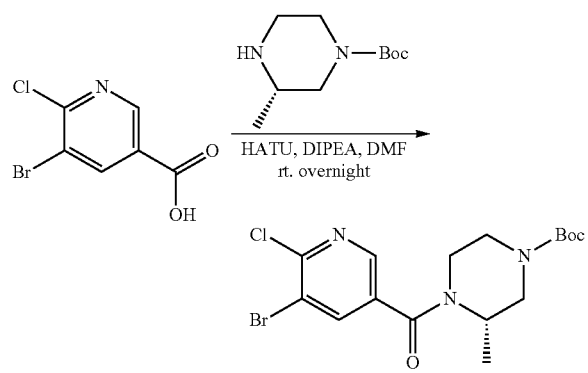

A round-bottom flask was charged with 5-bromo-6-chloropyridine-3-carboxylic acid (2.00 g, 8.47 mmol, 1.00 equiv), (S)-t-butyl 3-methylpiperazine-1-carboxylate (1.69 g, 8.47 mmol, 1.00 equiv), DIPEA (4.37 g, 33.9 mmol, 4.00 equiv), o-(7-Azabenzotriazol-1-yl)-N,N,N',N'-tetramethyluronium hexafluorophosphate (4.83 g, 12.7 mmol, 1.50 equiv) and DMF (20 mL). The resulting solution was stirred overnight at room temperature and quenched with water (15 mL). The mixture was extracted with EtOAc (3×30 mL) and the organic layers were combined, washed with brine (2×30 mL), dried over anhydrous Na$_2$SO$_4$, filtered and concentrated under reduced pressure. The residue was chromatographed on a silica gel column with EtOAc/petroleum ether (⅓) to provide 3.36 g (95% yield) of t-butyl (S)-4-(5-bromo-6-chloronicotinoyl)-3-methylpiperazine-1-carboxylate as a yellow oil. LCMS (ESI, m/z): 418 [M+H]$^+$.

Step 2: Preparation of t-butyl (S)-4-((5-bromo-6-chloropyridin-3-yl)methyl)-3-methylpiperazine-1-carboxylate

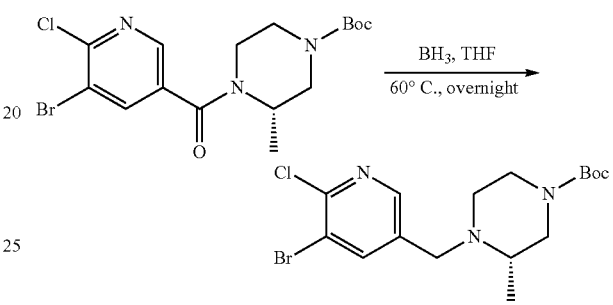

A vial was charged with t-butyl (S)-4-(5-bromo-6-chloronicotinoyl)-3-methylpiperazine-1-carboxylate (1.00 g, 2.39 mmol, 1.00 equiv), borane (1 M in THF, 12.0 mL, 11.9 mmol, 5.00 equiv) and THF (15 mL). The resulting solution was stirred overnight at 60° C. and quenched with MeOH (10 mL). The resulting solution was stirred for 2 hours at 60° C. and concentrated under reduced pressure. The residue was chromatographed on a silica gel column to provide 0.453 g (47% yield) of t-butyl (S)-4-((5-bromo-6-chloropyridin-3-yl)methyl)-3-methylpiperazine-1-carboxylate as a yellow oil. LCMS (ESI, m/z): 404 [M+H]$^+$.

Step 3: Preparation of t-butyl (S)-4-((6-chloro-5-(4-fluoropiperidin-1-yl)pyridin-3-yl)methyl)-3-methylpiperazine-1-carboxylate

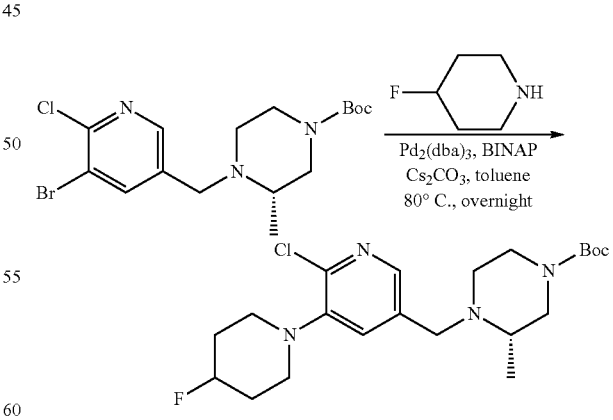

A vial was charged with t-butyl (S)-4-((5-bromo-6-chloropyridin-3-yl)methyl)-3-methylpiperazine-1-carboxylate (400 mg, 0.988 mmol, 1.00 equiv), 4-fluoropiperidine (206 mg, 1.48 mmol, 1.50 equiv), Cs$_2$CO$_3$ (966 mg, 2.96 mmol, 3.00 equiv), racemic-2,2'-bis(diphenylphosphino)-1,1'-binaphthyl (154 mg, 0.247 mmol 0.25 equiv) and toluene (15 mL). Tris(dibenylideneacetone)dipalladium-chloroform (102 mg, 0.0988 mmol, 0.10 equiv) was added under nitrogen atmosphere, and the resulting solution was stirred overnight at 80° C. under nitrogen atmosphere and concentrated under reduced pressure. The crude product was quenched with water (10 mL). The mixture was extracted with EtOAc (3×20 mL) and the organic layers were combined, washed with brine (2×20 mL), dried over anhydrous Na$_2$SO$_4$, filtered and concentrated under reduced pressure. The residue was chromatographed on a silica gel column to provide 70 mg (17% yield) of t-butyl (S)-4-((6-chloro-5-(4-fluoropiperidin-1-yl)pyridin-3-yl)methyl)-3-methylpiperazine-1-carboxylate as a yellow oil. LCMS (ESI, m/z): 427 [M+H]$^-$.

Step 4: Preparation of (S)-1-((6-chloro-5-(4-fluoropiperidin-1-yl)pyridin-3-yl)methyl)-2-methylpiperazine

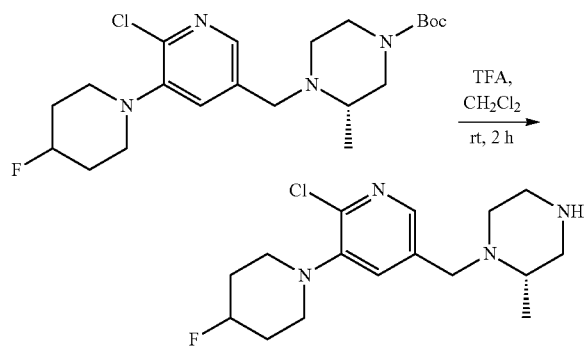

A vial was charged with t-butyl (S)-4-((6-chloro-5-(4-fluoropiperidin-1-yl)pyridin-3-yl)methyl)-3-methylpiperazine-1-carboxylate (70.0 mg, 0.164 mmol, 1.00 equiv), TFA (2 mL) and DCM (10 mL). The resulting solution was stirred for 2 h at room temperature and concentrated under reduced pressure to provide 53.6 mg (quantitative) of (S)-1-((6-chloro-5-(4-fluoropiperidin-1-yl)pyridin-3-yl)methyl)-2-methylpiperazine as a yellow oil. LCMS (ESI, m/z): 327 [M+H]$^+$.

Step 5: Preparation of 4-nitrophenyl 3-(methylsulfonamido)-1H-pyrazole-1-carboxylate

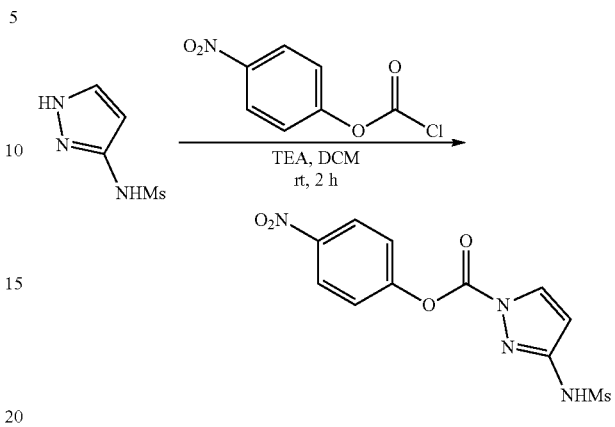

A round-bottom flask was charged with N-(1H-pyrazol-3-yl)methanesulfonamide (300 mg, 1.86 mmol, 1.00 equiv), DCM (10 mL) and 4-nitrophenyl chloroformate (452 mg, 2.24 mmol, 1.20 equiv). Triethylamine (563 mg, 5.56 mmol, 3.00 equiv) was added dropwise at 0° C., and the resulting solution was stirred for 2 h at room temperature. The mixture was concentrated under reduced pressure to provide 540 mg (crude) of 4-nitrophenyl 3-(methylsulfonamido)-1H-pyrazole-1-carboxylate as a yellow oil. LCMS (ESI, m/z): 327 [M+H]$^-$.

Step 6: Preparation of (S)—N-(1-(4-((6-chloro-5-(4-fluoropiperidin-1-yl)pyridin-3-yl)methyl)-3-methylpiperazine-1-carbonyl)-1H-pyrazol-3-yl)methanesulfonamide

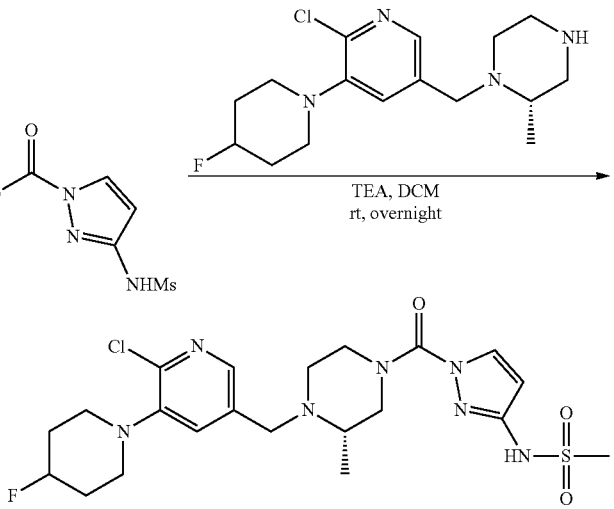

A vial was charged with (S)-1-((6-chloro-5-(4-fluoropiperidin-1-yl)pyridin-3-yl)methyl)-2-methylpiperazine (53.6 mg, 0.164 mmol, 1.00 equiv), 4-nitrophenyl 3-(methylsulfonamido)-1H-pyrazole-1-carboxylate (80.2 mg, 0.246 mmol, 1.50 equiv), TEA (66.3 mg, 0.656 mmol, 4.00 equiv) and DCM (15 mL). The reaction mixture was stirred overnight at room temperature and quenched with water (10 mL). The resulting solution was extracted with DCM (3×20 mL) and the organic layers were combined, washed with brine (2×20 mL), dried over anhydrous Na$_2$SO$_4$, filtered and concentrated under reduced pressure. The crude product was purified by preparative HPLC to afford 27.2 mg (32% yield) of (S)—N-(1-(4-(((6-chloro-5-(4-fluoropiperidin-1-yl)pyridin-3-yl)methyl)-3-methylpiperazine-1-carbonyl)-1H-pyrazol-3-yl)methanesulfonamide as a white solid. $^1$H NMR (300 MHz, Methanol-d$_4$) δ 8.03 (d, J=2.8 Hz, 1H), 7.97 (d, J=1.9 Hz, 1H), 7.56 (d, J=2.0 Hz, 1H), 6.21 (d, J=2.7 Hz, 1H), 4.95-4.70 (m, 1H), 4.37-4.09 (m, 2H), 4.08-3.98 (m, 1H), 3.50-3.34 (m, 2H), 3.29-3.15 (m, 3H), 3.12 (s, 3H), 3.10-2.99 (m, 2H), 2.83-2.71 (m, 1H), 2.71-2.58 (m, 1H), 2.38-2.24 (m, 1H), 2.20-1.92 (m, 4H), 1.19 (d, J=6.3 Hz, 3H). LCMS (ESI, m/z): 514 [M+H]$^+$.

Example 32: (S)—N-(1-(4-(4-chloro-3-(4-isopropoxypiperidin-1-yl)benzyl)-3-methylpiperazine-1-carbonyl)-1H-pyrazol-3-yl)methanesulfonamide

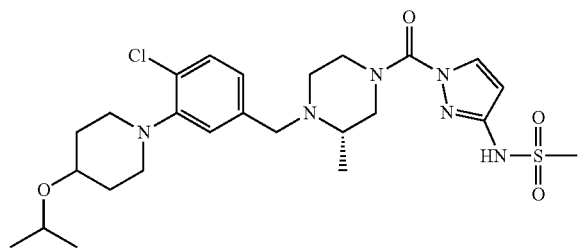 [SMILES: CC(C)OC1CCN(c2cc(CN3CCN(C(=O)n4ccc(NS(C)(=O)=O)n4)C[C@@H]3C)ccc2Cl)CC1]

Step 1: Preparation of t-butyl (S)-4-(3-bromo-4-chlorobenzyl)-3-methylpiperazine-1-carboxylate

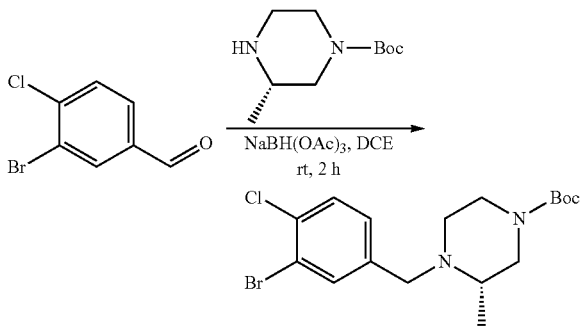

A round-bottom flask was charged with 3-bromo-4-chlorobenzaldehyde (10.0 g, 45.7 mmol, 1.00 equiv), (S)-t-butyl 3-methylpiperazine-1-carboxylate (9.13 g, 45.7 mmol, 1.00 equiv) and DCE (50 mL). The resulting solution was stirred for 1 h at room temperature prior to addition of sodium triacetoxyborohydride (19.4 g, 91.4 mmol, 2.00 equiv). The reaction mixture was stirred for 2 h at room temperature and quenched with water (20 mL). The resulting solution was extracted with DCM (3×50 mL) and the organic layers were combined, washed with brine (2×50 mL), dried over anhydrous Na$_2$SO$_4$, filtered and concentrated under reduced pressure. The residue was chromatographed on a silica gel column to provide 9.04 g (49% yield) of t-butyl (S)-4-(3-bromo-4-chlorobenzyl)-3-methylpiperazine-1-carboxylate as a yellow oil. LCMS (ESI, m/z): 403 [M+H]$^+$.

Step 2: Preparation of t-butyl (S)-4-(4-chloro-3-(4-hydroxypiperidin-1-yl)benzyl)-3-methylpiperazine-1-carboxylate

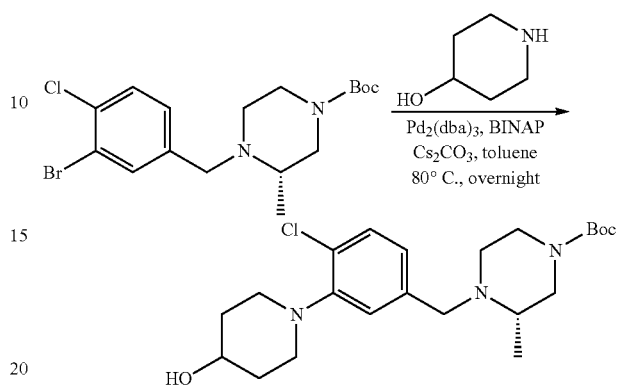

A vial was charged with t-butyl (S)-4-(3-bromo-4-chlorobenzyl)-3-methylpiperazine-1-carboxylate (0.500 g, 1.24 mmol, 1.00 equiv), piperidin-4-ol (0.188 g, 1.86 mmol, 1.50 equiv), Cs$_2$CO$_3$ (1.21 g, 3.72 mmol, 3.00 equiv), racemic-2,2'-bis(diphenylphosphino)-1,1'-binaphthyl (0.193 g, 0.310 mmol, 0.25 equiv) and toluene (15 mL). Tris(dibenylideneacetone)dipalladium-chloroform (0.128 g, 0.124 mmol, 0.10 equiv) was added under nitrogen atmosphere and the resulting solution was stirred overnight at 80° C. before concentrating under reduced pressure. The crude product was quenched with water (10 mL). The mixture was extracted with EtOAc (3×20 mL) and the organic layers were combined, washed with brine (2×20 mL), dried over anhydrous Na$_2$SO$_4$, filtered and concentrated under reduced pressure. The residue was chromatographed on a silica gel column to provide 0.575 g (crude) of t-butyl (S)-4-(4-chloro-3-(4-hydroxypiperidin-1-yl)benzyl)-3-methylpiperazine-1-carboxylate as a yellow oil. LCMS (ESI, m/z): 424 [M+H]$^+$.

Step 3: Preparation of t-butyl (S)-4-(4-chloro-3-(4-isopropoxypiperidin-1-yl)benzyl)-3-methylpiperazine-1-carboxylate

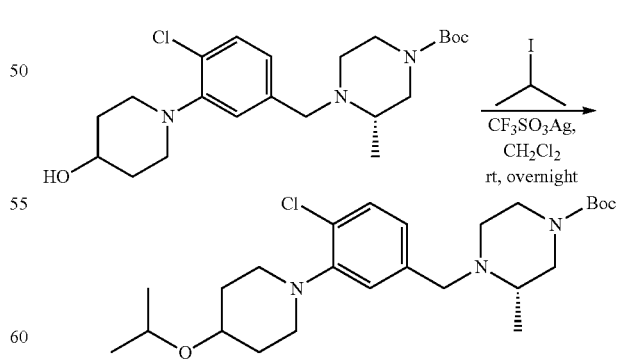

A vial was charged with t-butyl (S)-4-(4-chloro-3-(4-hydroxypiperidin-1-yl)benzyl)-3-methylpiperazine-1-carboxylate (243 mg, 0.573 mmol, 1.00 equiv), 2-iodopropane (244 mg, 1.43 mmol, 2.50 equiv), silver trifluoromethanesulfonate (368 mg, 1.43 mmol, 2.50 equiv) and DCM (10 mL). The resulting solution was stirred overnight at room temperature and quenched with water (10 mL). The mixture was extracted with DCM (3×20 mL) and the organic layers were combined, washed with brine (2×20 mL), dried over anhydrous Na₂SO₄, filtered and concentrated under reduced pressure. The residue was chromatographed on a silica gel column to provide 121 mg (45% yield) of t-butyl (S)-4-(4-chloro-3-(4-isopropoxypiperidin-1-yl)benzyl)-3-methylpiperazine-1-carboxylate as a yellow oil. LCMS (ESI, m/z): 466 [M+H]⁺.

Step 4: Preparation of (S)—N-(1-(4-(4-chloro-3-(4-isopropoxypiperidin-1-yl)benzyl)-3-methylpiperazine-1-carbonyl)-1H-pyrazol-3-yl)methanesulfonamide

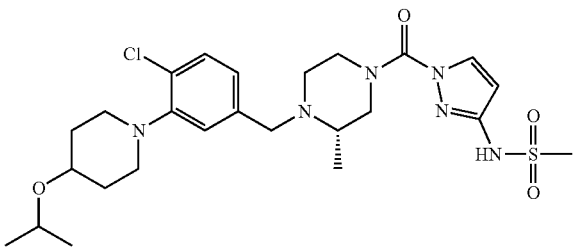 [SMILES: CC(C)OC1CCN(c2cc(CN3CCN(C(=O)n4ccc(NS(C)(=O)=O)n4)C[C@@H]3C)ccc2Cl)CC1]

The title compound was prepared as described in Example 31, Steps 4-6, using t-butyl (S)-4-(4-chloro-3-(4-isopropoxypiperidin-1-yl)benzyl)-3-methylpiperazine-1-carboxylate in Step 4 to provide (S)—N-(1-(4-(4-chloro-3-(4-isopropoxypiperidin-1-yl)benzyl)-3-methylpiperazine-1-carbonyl)-1H-pyrazol-3-yl)methanesulfonamide as a white solid. ¹H NMR (300 MHz, MeOH-d₄) δ 8.04 (d, J=2.9 Hz, 1H), 7.33-7.25 (m, 1H), 7.15-7.08 (m, 1H), 7.01-6.94 (m, 1H), 6.22 (d, J=2.8 Hz, 1H), 4.38-4.07 (m, 2H), 4.07-3.92 (m, 1H), 3.92-3.74 (m, 1H), 3.70-3.51 (m, 1H), 3.51-3.34 (m, 1H), 3.30-3.17 (m, 4H), 3.12 (s, 3H), 2.87-2.72 (m, 3H), 2.68-2.55 (m, 1H), 2.32-2.20 (m, 1H), 2.08-1.92 (m, 2H), 1.79-1.62 (m, 2H), 1.24-1.10 (m, 9H). LCMS (ESI, m/z): 553 [M+H]⁺.

Example 33: (S)—N-(1-(4-((5-(4-fluoropiperidin-1-yl)-6-(trifluoromethyl)pyridin-3-yl)methyl)-3-methylpiperazine-1-carbonyl)-1H-pyrazol-3-yl)methanesulfonamide

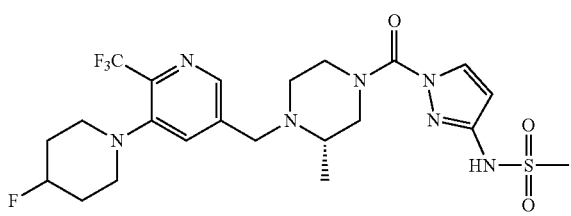 [SMILES: C[C@H]1CN(C(=O)n2ccc(NS(C)(=O)=O)n2)CCN1Cc1cnc(C(F)(F)F)c(N2CCC(F)CC2)c1]

Step 1: Preparation of potassium (S)-((4-(t-butoxycarbonyl)-2-methylpiperazin-1-yl)methyl)trifluoroborate

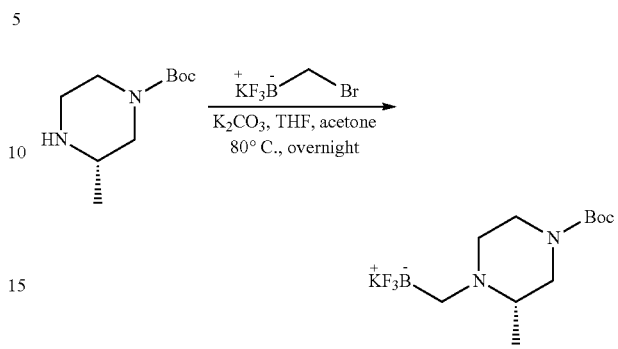

A round-bottom flask was charged with t-butyl (3S)-3-methylpiperazine-1-carboxylate (2.00 g, 10.0 mmol, 1.00 equiv), potassium (bromomethyl) trifluoroboranuide (2.01 g, 10.0 mmol, 1.00 equiv), and THF (20 mL). The resulting solution was stirred overnight at 80° C. and concentrated under reduced pressure. Potassium carbonate (1.38 g, 10.0 mmol, 1.00 equiv) and acetone (15 mL) were added, and the resulting solution was stirred for 2 h at room temperature. The mixture was dissolved in acetone (2×100 mL) and filtered. The filtered liquors were combined and concentrated under reduced pressure to provide 2.90 g (91% yield) of potassium (S)-((4-(tert-butoxycarbonyl)-2-methylpiperazin-1-yl)methyl)trifluoroborate as a yellow solid. LCMS (ESI, m/z): 281 [M−K]⁻.

Step 2: Preparation of 5-bromo-3-(4-fluoropiperidin-1-yl)-2-(trifluoromethyl)pyridine

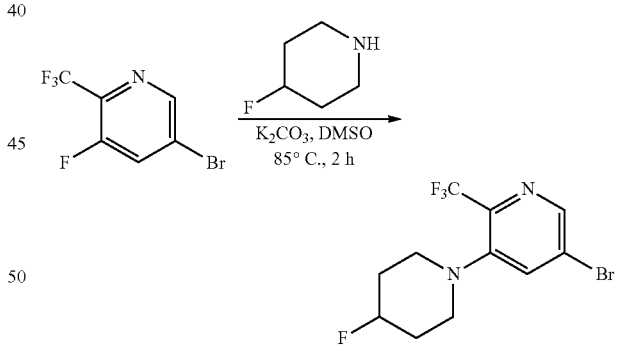

A vial was charged with 5-bromo-3-fluoro-2-(trifluoromethyl)pyridine (400 mg, 1.66 mmol, 1.00 equiv), 4-fluoropiperidine (203 mg, 1.98 mmol, 1.20 equiv), K₂CO₃ (681 mg, 4.94 mmol, 3.00 equiv), and DMSO (10 mL). The reaction mixture was stirred for 2 h at 85° C. and quenched with water (10 mL). The resulting solution was extracted with DCM (3×20 mL) and the organic layers were combined, washed with brine (2×10 mL), dried over anhydrous Na₂SO₄, filtered and concentrated under reduced pressure. The residue was chromatographed on a silica gel column to provide 140 mg (26% yield) of 5-bromo-3-(4-fluoropiperidin-1-yl)-2-(trifluoromethyl)pyridine as a yellow solid. LCMS (ESI, m/z): 327 [M+H]⁺.

Step 3: Preparation of t-butyl (S)-4-((5-(4-fluoropi-peridin-1-yl)-6-(trifluoromethyl)pyridin-3-yl)methyl)-3-methylpiperazine-1-carboxylate

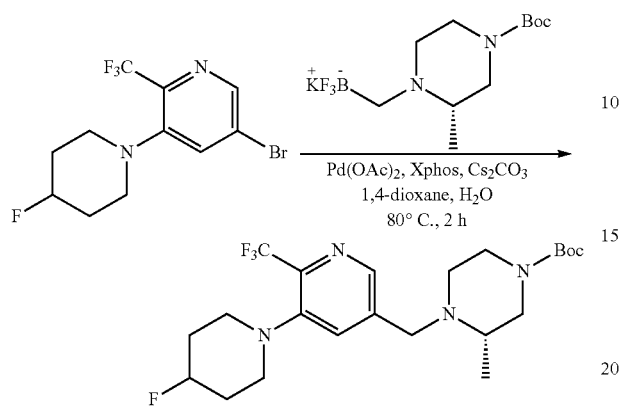

A vial was charged with 5-bromo-3-(4-fluoropiperidin-1-yl)-2-(trifluoromethyl)pyridine (140 mg, 0.429 mmol, 1.00 equiv), potassium (S)-((4-(t-butoxycarbonyl)-2-methylpip-erazin-1-yl)methyl)trifluoroborate (206 mg, 0.644 mmol, 1.50 equiv), 2-(dicyclohexylphosphino)-2',4',6'-triisopropy-lbiphenyl (82.0 mg, 0.172 mmol, 0.40 equiv), Cs$_2$CO$_3$ (420 mg, 1.29 mmol, 3.00 equiv), palladium acetate (19.0 mg, 0.0860 mmol, 0.20 equiv), 1,4-dioxane (10 mL), and water (2 mL) under nitrogen. The reaction mixture was stirred for 2 h at 80° C. and quenched with water (10 mL). The resulting solution was extracted with EtOAc (3×20 mL) and the organic layers were combined, washed with brine (2×10 mL), dried over anhydrous Na$_2$SO$_4$, filtered and concentrated under reduced pressure. The residue was chromatographed on a silica gel column to provide 130 mg (66% yield) of t-butyl (S)-4-((5-(4-fluoropiperidin-1-yl)-6-(trif-luoromethyl)pyridin-3-yl)methyl)-3-methylpiperazine-1-carboxylate as a yellow oil. LCMS (ESI, m/z): 461 [M+H]$^+$.

Step 4: Preparation of (S)-1-((5-(4-fluoropiperidin-1-yl)-6-(trifluoromethyl)pyridin-3-yl)methyl)-2-methylpiperazine

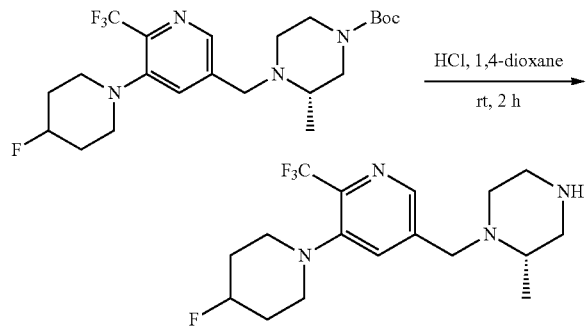

A round-bottom flask was charged with t-butyl (S)-4-((5-(4-fluoropiperidin-1-yl)-6-(trifluoromethyl)pyridin-3-yl)methyl)-3-methylpiperazine-1-carboxylate (130 mg, 0.283 mmol, 1.00 equiv), concentrated hydrochloric acid (1 mL) and 1,4-dioxane (3 mL). The resulting solution was stirred for 2 h at room temperature and concentrated under reduced pressure to provide 102 mg (quantitative) of (S)-1-((5-(4-fluoropiperidin-1-yl)-6-(trifluoromethyl)pyridin-3-yl)methyl)-2-methylpiperazine as a yellow solid. LCMS (ESI, m/z): 361 [M+H]$^+$.

Step 5: Preparation of (S)—N-(1-(4-((5-(4-fluoropi-peridin-1-yl)-6-(trifluoromethyl)pyridin-3-yl)methyl)-3-methylpiperazine-1-carbonyl)-1H-pyra-zol-3-yl)methanesulfonamide

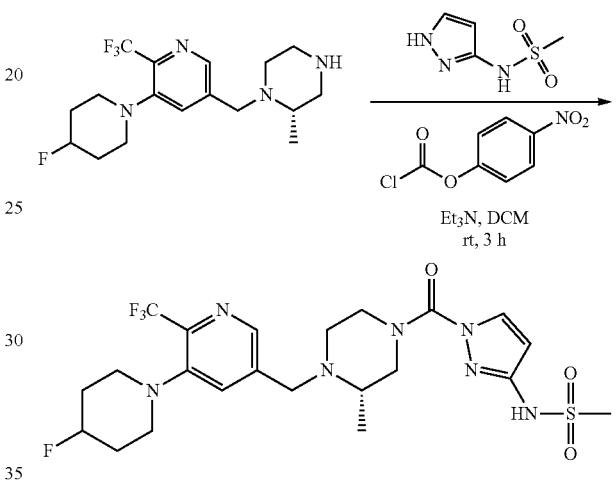

A round-bottom flask was charged with N-(1H-pyrazol-3-yl)methanesulfonamide (68.0 mg, 0.425 mmol, 1.50 equiv), TEA (86.0 mg, 0.849 mmol, 3.00 equiv) and DCM (20 mL). 4-Nitrophenyl carbonochloridate (63.0 mg, 0.311 mmol, 1.10 equiv) was added at 0° C. and the resulting solution was stirred for 2 h at room temperature prior to addition of (S)-1-((5-(4-fluoropiperidin-1-yl)-6-(trifluorom-ethyl)pyridin-3-yl)methyl)-2-methylpiperazine (102 mg, 0.283 mmol, 1.00 equiv). The resulting solution was stirred 1 h at room temperature and quenched with water (20 mL). The mixture was extracted with DCM (3×30 mL) and the organic layers were combined, washed with brine (2×20 mL), dried over anhydrous Na$_2$SO$_4$, filtered and concentrated under reduced pressure. The crude product was purified by preparative HPLC to afford 59.0 mg (38% yield) of (S)—N-(1-(4-((5-(4-fluoropiperidin-1-yl)-6-(trifluorom-ethyl)pyridin-3-yl)methyl)-3-methylpiperazine-1-carbo-nyl)-1H-pyrazol-3-yl)methanesulfonamide as a white solid. $^1$H NMR (400 MHz, Chloroform-d) δ 8.39 (s, 1H), 8.07 (d, J=2.8 Hz, 1H), 7.68 (s, 1H), 7.00 (s, 1H), 6.32 (d, J=2.8 Hz, 1H), 5.00-4.92 (m, 0.5H), 4.84-4.82 (m, 0.5H), 4.22-4.19 (m, 2H), 4.07-4.03 (m, 1H), 3.50-3.44 (m, 1H), 3.35-3.26 (m, 2H), 3.16-3.13 (m, 5H), 2.94-2.91 (m, 2H), 2.75-2.66 (m, 2H), 2.33-2.28 (m, 1H), 2.14-2.00 (m, 4H), 1.19 (d, J=6.4 Hz, 3H). LCMS (ESI, m/z): 548 [M+H]$^+$.

Example 34: N-(1-(4-(2-Chloro-3-(2-hydroxy-2-methylpropoxy)benzyl)piperazine-1-carbonyl)-1H-pyrazol-3-yl)methanesulfonamide

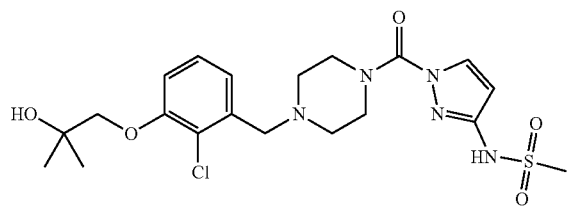 [SMILES: CC(C)(O)COc1cccc(CN2CCN(C(=O)n3ccc(NS(C)(=O)=O)n3)CC2)c1Cl]

Step 1: Preparation of 2-chloro-3-(2-hydroxy-2-methylpropoxy)benzaldehyde

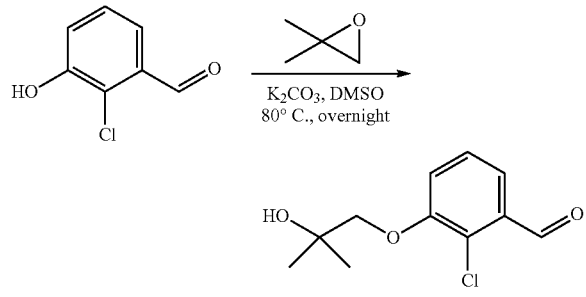

A round-bottom flask was charged with 2-chloro-3-hydroxybenzaldehyde (0.624 g, 4.00 mmol, 1.00 equiv), 2,2-dimethyloxirane (0.576 g, 8.00 mol, 2.00 equiv), potassium carbonate (1.66 g, 12.0 mmol, 3.00 equiv), and DMSO (10 mL). The reaction mixture was stirred overnight at 80° C. and quenched with water (30 mL). The resulting solution was extracted with EtOAc (3×40 mL) and the organic layers were combined, washed with brine (30 mL), dried over anhydrous $Na_2SO_4$, filtered and concentrated under reduced pressure. The residue was chromatographed on a silica gel column to provide 550 mg (60% yield) of 2-chloro-3-(2-hydroxy-2-methylpropoxy)benzaldehyde as a colorless oil. LCMS (ESI, m/z): 229 $[M+H]^+$.

Step 2: Preparation of 4-nitrophenyl 3-(methylsulfonamido)-1H-pyrazole-1-carboxylate

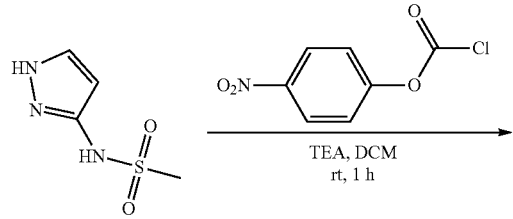

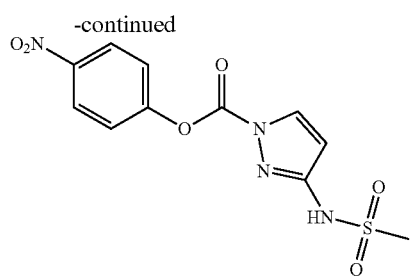

A round-bottom flask was charged with N-(1H-pyrazol-3-yl)methanesulfonamide (1.00 g, 6.20 mmol, 1.00 equiv), 4-nitrophenyl chloroformate (1.50 g, 7.44 mmol, 1.20 equiv), DCM (20 mL), and TEA (1.88 g, 18.6 mmol, 3.00 equiv). The resulting solution was stirred for 1 h at room temperature and concentrated under reduced pressure to provide 2.02 g (crude) of 4-nitrophenyl 3-(methylsulfonamido)-1H-pyrazole-1-carboxylate as a yellow oil. LCMS (ESI, m/z): 327 $[M+H]^+$.

Step 3: Preparation of t-butyl 4-(3-(methylsulfonamido)-1H-pyrazole-1-carbonyl)piperazine-1-carboxylate

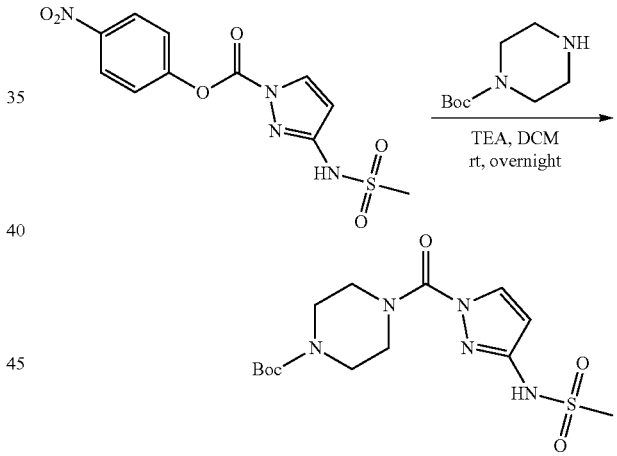

A round-bottom flask was charged with 4-nitrophenyl 3-(methylsulfonamido)-1H-pyrazole-1-carboxylate (2.02 g, 6.19 mmol, 1.00 equiv), t-butyl piperazine-1-carboxylate (1.27 g, 6.82 mmol, 1.10 equiv), DCM (20 mL), and TEA (1.88 g, 18.6 mmol, 3.00 equiv). The reaction mixture was stirred overnight at room temperature and quenched with water (20 mL). The resulting solution was extracted with DCM (3×40 mL) and the organic layers were combined, washed with brine (1×30 mL), dried over anhydrous $Na_2SO_4$, filtered and concentrated under reduced pressure. The residue was chromatographed on a silica gel column to provide 1 g (43% yield) of t-butyl 4-(3-(methylsulfonamido)-1H-pyrazole-1-carbonyl)piperazine-1-carboxylate as a yellow oil. LCMS (ESI, m/z): 374 $[M+H]^+$.

Step 4: Preparation of N-(1-(piperazine-1-carbonyl)-1H-pyrazol-3-yl)methanesulfonamide

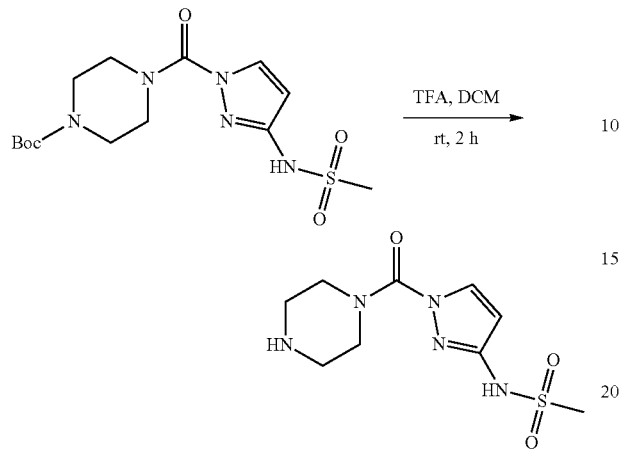

A round-bottom flask was charged with t-butyl 4-(3-(methylsulfonamido)-1H-pyrazole-1-carbonyl)piperazine-1-carboxylate (160 mg, 0.430 mmol, 1.00 equiv), DCM (10 mL), and TFA (2 mL). The resulting solution was stirred for 2 h at room temperature and concentrated under reduced pressure to provide 117 mg (quantitative) of N-(1-(piperazine-1-carbonyl)-1H-pyrazol-3-yl)methanesulfonamide as a yellow oil. LCMS (ESI, m/z): 274 [M+H]$^+$.

Step 5: Preparation of N-(1-(4-(2-chloro-3-(2-hydroxy-2-methylpropoxy)benzyl)piperazine-1-carbonyl)-1H-pyrazol-3-yl)methanesulfonamide

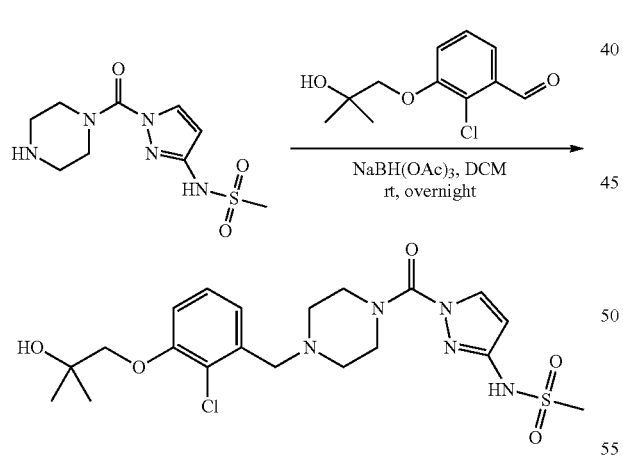

A round-bottom flask was charged with N-(1-(piperazine-1-carbonyl)-1H-pyrazol-3-yl)methanesulfonamide (117 mg, 0.430 mmol, 1.10 equiv), 2-chloro-3-(2-hydroxy-2-methylpropoxy)benzaldehyde (88.7 mg, 0.390 mmol, 1.00 equiv), and DCM (15 mL). The mixture was stirred for 2 h at room temperature prior to addition of sodium triacetoxyborohydride (331 mg, 1.56 mmol, 4.00 equiv). The reaction mixture was stirred overnight at room temperature and quenched with saturated NaHCO$_3$ solution (20 mL). The resulting solution was extracted with DCM (3×30 mL) and the organic layers were combined, washed with brine (30 mL), dried over anhydrous Na$_2$SO$_4$, filtered and concentrated under reduced pressure. The crude product (200 mg) was purified by preparative HPLC to provide 20.9 mg (11% yield) of N-(1-(4-(2-chloro-3-(2-hydroxy-2-methylpropoxy)benzyl)piperazine-1-carbonyl)-1H-pyrazol-3-yl)methanesulfonamide as a colorless oil. $^1$H NMR (300 MHz, Chloroform-d) δ 8.02 (d, J=2.7 Hz, 1H), 7.20 (t, J=7.5 Hz, 1H), 7.09 (d, J=7.5 Hz, 1H), 6.85 (d, J=7.5 Hz, 1H), 6.30 (d, J=2.7 Hz, 1H), 3.85 (br, 6H), 3.68 (s, 2H), 3.13 (s, 3H), 2.62-2.59 (m, 4H), 1.39 (s, 6H). LCMS (ESI, m/z): 486 [M+H]$^+$.

Example 35: N-(1-(4-(cyclopropyl(2-(pyrrolidin-1-yl)-4-(trifluoromethyl)benzyl)amino)piperidine-1-carbonyl)-1H-pyrazol-3-yl)methanesulfonamide

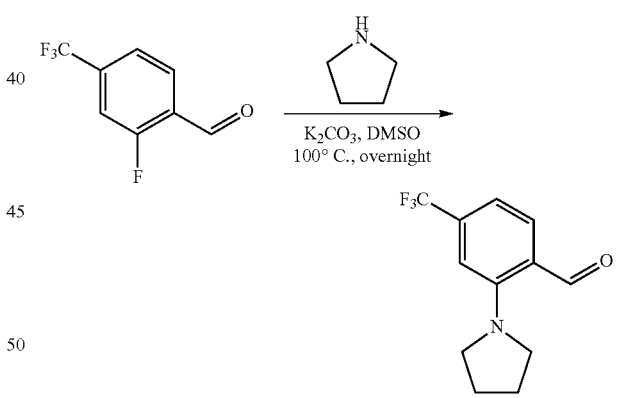

Step 1: Preparation of 2-(pyrrolidin-1-yl)-4-(trifluoromethyl)benzaldehyde

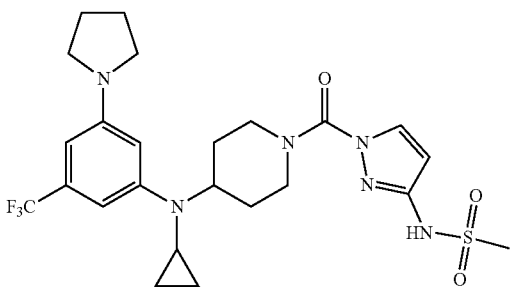 [SMILES: CS(=O)(=O)Nc1ccn(C(=O)N2CCC(N(c3cc(N4CCCC4)cc(C(F)(F)F)c3)C3CC3)CC2)n1]

A round-bottom flask was charged with 2-fluoro-4-(trifluoromethyl)benzaldehyde (10.0 g, 52.0 mmol, 1.00 equiv), pyrrolidine (7.40 g, 104 mmol, 2.00 equiv), K$_2$CO$_3$ (21.7 g, 157 mmol, 3.00 equiv), and DMSO (100 mL) under nitrogen. The reaction mixture was stirred overnight at 100° C. and quenched with water (50 mL). The resulting solution was extracted with EtOAc (3×50 mL) and the organic layers were combined, washed with brine (100 mL), dried over anhydrous Na$_2$SO$_4$, filtered and concentrated under reduced pressure. The residue was chromatographed on a silica gel column to provide 6.00 g (47% yield) of 2-(pyrrolidin-1-yl)-4-(trifluoromethyl)benzaldehyde as a yellow oil. LCMS (ESI, m/z): 244 [M+H]$^+$.

Step 2: Preparation of t-butyl 4-((2-(pyrrolidin-1-yl)-4-(trifluoromethyl)benzyl)amino)piperidine-1-carboxylate

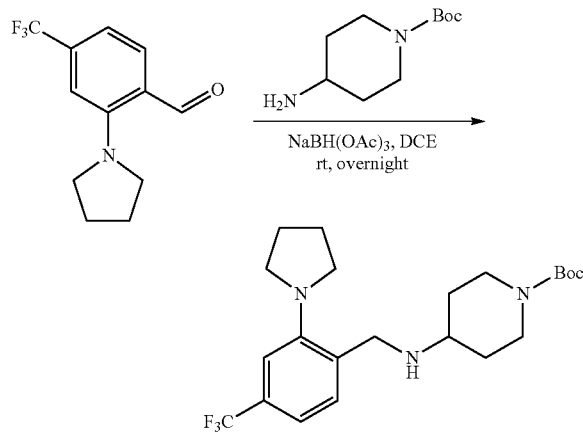

A round-bottom flask was charged with 2-(pyrrolidin-1-yl)-4-(trifluoromethyl)benzaldehyde (1.12 g, 4.61 mmol, 1.00 equiv), t-butyl 4-aminopiperidine-1-carboxylate (1.11 g, 5.53 mmol, 1.20 equiv), and DCE (50 mL). The mixture was stirred for 1 h at room temperature prior to addition of sodium triacetoxyborohydride (2.93 g, 13.8 mmol, 3.00 equiv). The reaction mixture was stirred overnight at room temperature and quenched with water (50 mL). The resulting solution was extracted with DCM (3×80 mL) and the organic layers were combined, washed with brine (2×50 mL), dried over anhydrous Na$_2$SO$_4$, filtered and concentrated under reduced pressure. The residue was chromatographed on a silica gel column to provide 1.20 g (61% yield) of t-butyl 4-((2-(pyrrolidin-1-yl)-4-(trifluoromethyl)b enzyl)amino)piperidine-1-carboxylate as a colorless oil. LCMS (ESI, m/z): 428 [M+H]$^+$.

Step 3: Preparation of t-butyl 4-(cyclopropyl(2-(pyrrolidin-1-yl)-4-(trifluoromethyl)benzyl)amino) piperidine-1-carboxylate

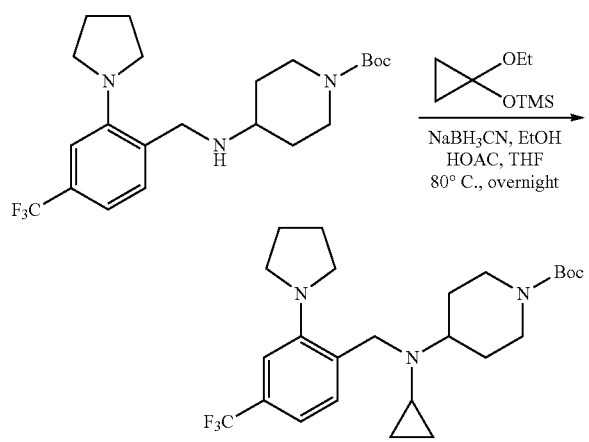

A round-bottom flask was charged with t-butyl 4-((2-(pyrrolidin-1-yl)-4-(trifluoromethyl)benzyl)amino)piperidine-1-carboxylate (2.00 g, 4.68 mmol, 1.00 equiv), (1-ethoxycyclopropoxy)trimethylsilane (2.85 g, 16.4 mmol, 3.50 equiv), sodium cyanoborohydride (885 mg, 14.1 mmol, 3.00 equiv), acetic acid (2.81 g, 46.8 mmol, 10.00 equiv), THF (60 mL), and EtOH (30 mL). The reaction mixture was stirred overnight at 80° C. and quenched with water (50 mL). The resulting solution was extracted with EtOAc (3×80 mL) and the organic layers were combined, washed with brine (2×50 mL), dried over anhydrous Na$_2$SO$_4$, filtered and concentrated under reduced pressure. The residue was chromatographed on a silica gel column to provide 880 mg (40% yield) of t-butyl 4-(cyclopropyl(2-(pyrrolidin-1-yl)-4-(trifluoromethyl)benzypamino)piperidine-1-carboxylate as a yellow oil. LCMS (ESI, m/z): 468 [M+H]$^+$.

Step 4: Preparation of N-cyclopropyl-N-(2-(pyrrolidin-1-yl)-4-(trifluoromethyl)benzyl)piperidin-4-amine

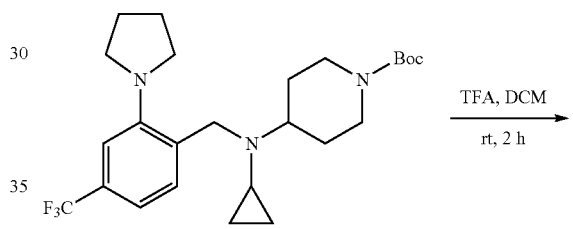

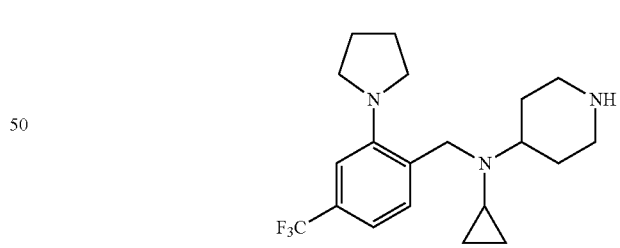

A round-bottom flask was charged with t-butyl 4-(cyclopropyl(2-(pyrrolidin-1-yl)-4-(trifluoromethyl)benzyl)amino)piperidine-1-carboxylate (400 mg, 0.857 mmol, 1.00 equiv), DCM (10 mL), and TFA (2 mL). The resulting solution was stirred for 2 h at room temperature and concentrated under reduced pressure to provide 314 mg (quantitative) of N-cyclopropyl-N-(2-(pyrrolidin-1-yl)-4-(trifluoromethyl)benzyl)piperidin-4-amine as a yellow oil. LCMS (ESI, m/z): 368 [M+H]$^+$.

Step 5: Preparation of N-(1-(4-(cyclopropyl(2-(pyr-rolidin-1-yl)-4-(trifluoromethyl)benzyl)amino)piperidine-1-carbonyl)-1H-pyrazol-3-yl)methanesulfonamide

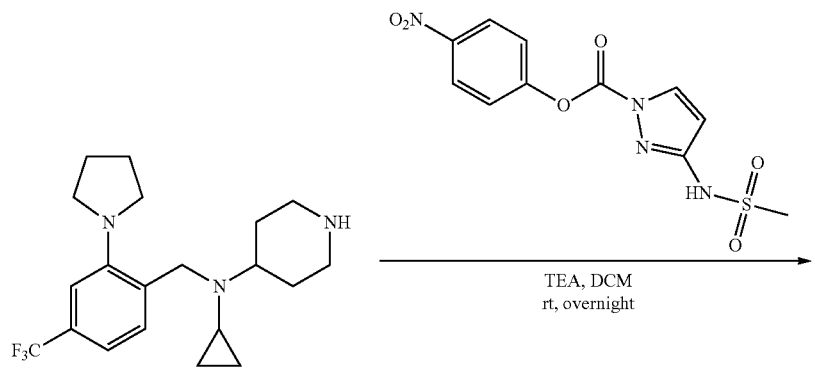

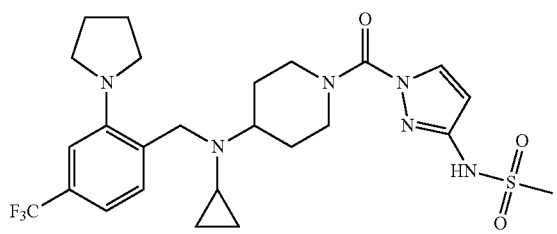

A round-bottom flask was charged with N-cyclopropyl-N-(2-(pyrrolidin-1-yl)-4-(trifluoromethyl)benzyl)piperidin-4-amine (314 mg, 0.856 mmol, 1.00 equiv), 4-nitrophenyl 3-methanesulfonamido-1H-pyrazole-1-carboxylate (Example 34, Step 2; 335 mg, 1.03 mmol, 1.20 equiv), TEA (260 mg, 2.57 mmol, 3.00 equiv), and DCM (10 mL). The reaction mixture was stirred overnight at room temperature and then quenched with water (20 mL). The resulting solution was extracted with DCM (3×30 mL) and the organic layers were combined, washed with brine (20 mL), dried over anhydrous Na₂SO₄, filtered and concentrated under reduced pressure. The crude product (200 mg) was purified by preparative HPLC to afford 219.6 mg (46% yield) of N-(1-(4-(cyclopropyl(2-(pyrrolidin-1-yl)-4-(trifluoromethyl)benzyl)amino)piperidine-1-carbonyl)-1H-pyrazol-3-yl)methanesulfonamide as an off-white solid. ¹H NMR (400 MHz, Chloroform-d) δ 8.01 (d, J=2.8 Hz, 1H), 7.60 (d, J=8.8 Hz, 1H), 7.26-7.11 (m, 2H), 6.30 (d, J=2.8 Hz, 1H), 4.54-4.51 (m, 2H), 3.88 (s, 2H), 3.17-3.12 (m, 7H), 2.90-2.84 (m, 2H), 2.72-2.65 (m, 1H), 2.15-2.10 (m, 1H), 2.09-1.92 (m, 4H), 1.87-1.84 (m, 2H), 1.78-1.67 (m, 2H), 0.53-0.41 (m, 4H). LCMS (ESI, m/z): 555 [M+H]⁺.

Examples 36-226

Examples 36-226 were prepared by similar procedures as described in Examples 1-35.

| Ex | Name | Structure | NMR (¹H NMR, 300 MHz or 400 MHz, chloroform-d) | MS [M + H]⁺ |
|---|---|---|---|---|
| 36 | N-(1-((3aR,5s,6aS)-5-((2-Chlorobenzyl)(methyl)amino)octahydrocyclopenta[c]pyrrole-2-carbonyl)-1H-pyrazol-3-yl)acetamide | 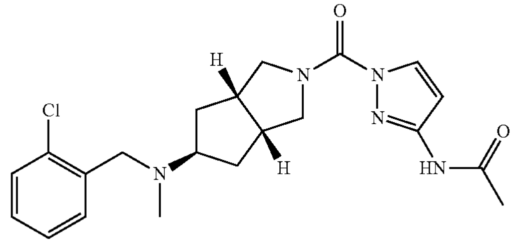 [SMILES: CC(=O)Nc1ccn(C(=O)N2C[C@H]3C[C@H](N(C)Cc4ccccc4Cl)C[C@H]3C2)n1] | δ 8.11 (d, J = 2.4 Hz, 1H), 7.75 (br, 1H), 7.47 (br, 1H), 7.30-7.33 (m, 1H), 7.14-7.26 (m, 2H), 6.85 (d, J = 2.4 Hz, 1H), 3.95 (br, 2H), 3.61-3.74 (m, 4H), 3.18 (br, 1H), 2.82 (br, 2H), 2.16 (s, 6H), 1.85-1.98 (m, 4H) | 416.2 |

| Ex | Name | Structure | NMR (¹H NMR, 300 MHz or 400 MHz, chloroform-d) | MS [M + H]⁺ |
|---|---|---|---|---|
| 37 | N-(1-((3aR, 5r,6aS)-5-((2-Chlorobenzyl)(methyl)amino) octahydro cyclopenta[c] pyrrole-2-carbonyl)-1H-pyrazol-3-yl)acetamide | 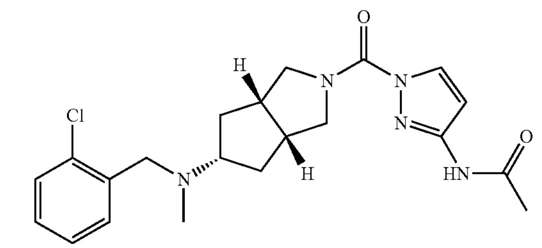 [SMILES: CC(=O)Nc1ccn(C(=O)N2C[C@H]3C[C@@H](N(C)Cc4ccccc4Cl)C[C@H]3C2)n1] | δ 8.11 (d, J = 2.4 Hz, 1H), 7.84 (s, 1H), 7.44-7.45 (m, 1H), 7.24-7.30 (m, 1H), 7.13-7.22 (m, 2H), 6.84 (d, J = 2.4 Hz, 1H), 3.79-3.91 (m, 4H), 3.63 (s, 2H), 2.96-2.99 (m, 1H), 2.58-2.69 (m, 2H), 2.13-2.22 (m, 8H), 1.50-1.60 (m, 2H) | 416.2 |
| 38 | N-(1-(1-((5-Chloro-1H-indol-2-yl)methyl)-1,8-diazaspiro[4.5]decane-8-carbonyl)-1H-pyrazol-3-yl)acetamide | 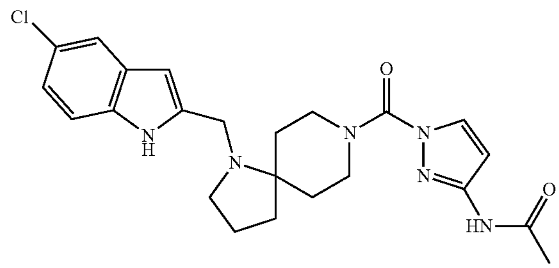 [SMILES: CC(=O)Nc1ccn(C(=O)N2CCC3(CCCN3Cc3cc4cc(Cl)ccc4[nH]3)CC2)n1] | δ 8.65 (br, 1H), 8.05 (d, J = 2.7 Hz, 1H), 7.80-8.00 (m, 1H), 7.48 (m, 1H), 7.20-7.25 (m, 1H), 7.00-7.18 (m, 1H), 6.89 (d, J = 2.7 Hz, 1H), 6.25 (s, 1H), 4.42-4.88 (m, 2H), 3.79 (s, 2H), 3.02 (t, J = 2.3 Hz, 2H), 2.51-2.95 (m, 2H), 2.19 (s, 3H), 1.69-2.02 (m, 6H), 1.41-1.60 (m, 2H) | 455.3 |
| 39 | N-(1-(1-((5-Chlorobenzo[b]thiophen-2-yl)methyl)-1,8-diazaspiro[4.5]decane-8-carbonyl)-1H-pyrazol-3-yl)acetamide | 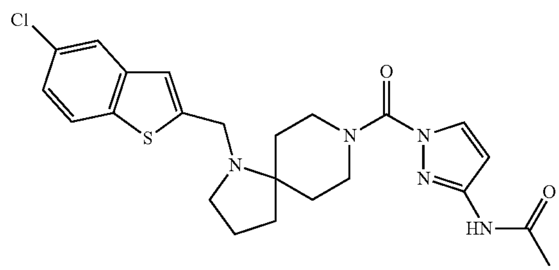 [SMILES: CC(=O)Nc1ccn(C(=O)N2CCC3(CCCN3Cc3cc4cc(Cl)ccc4s3)CC2)n1] | δ 8.00 (d, J = 2.7 Hz, 1H), 7.82 (m, 1H), 7.65 (m, 1H), 7.20-7.25 (m, 1H), 7.00-7.20 (m, 1H), 6.89 (d, J = 2.7 Hz, 1H), 4.50-4.70 (m, 2H), 3.82 (s, 2H), 3.05 (t, J = 2.3 Hz, 2H), 2.76-2.95 (m, 2H), 2.19 (s, 3H), 1.80-2.05 (m, 6H), 1.48-1.60 (m, 2H) | 472.2 |
| 40 | N-(1-(5-(4-(4-Chlorophenoxy)benzyl)octahydropyrrolo[3,4-c]pyrrole-2-carbonyl)-1H-pyrazol-3-yl)methanesulfonamide | 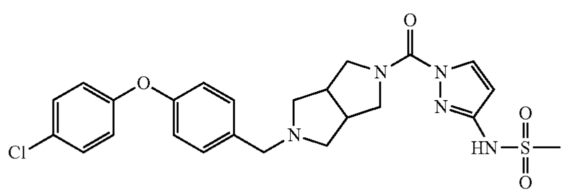 [SMILES: CS(=O)(=O)Nc1ccn(C(=O)N2CC3CN(Cc4ccc(Oc5ccc(Cl)cc5)cc4)CC3C2)n1] | δ 8.16 (d, J = 2.7 Hz, 1H), 7.27-7.30 (m, 3H), 7.25-7.27 (m, 1H), 6.91-6.94 (m, 4H), 6.30 (d, J = 2.7 Hz, 1H), 4.04 (br, 2H), 3.75-3.79 (m, 2H), 3.57 (s, 3H), 3.13 (s, 3H), 2.89 (br, 2H), 2.62-2.67 (m, 2H), 2.52-2.54 (m, 2H) | 516.0 |
| 41 | N-(1-(5-(3-(4-Chlorophenoxy)benzyl)octahydropyrrolo[3,4-c]pyrrole-2-carbonyl)-1H-pyrazol-3-yl)methanesulfonamide | 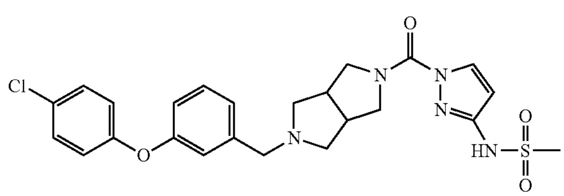 [SMILES: CS(=O)(=O)Nc1ccn(C(=O)N2CC3CN(Cc4cccc(Oc5ccc(Cl)cc5)c4)CC3C2)n1] | δ 8.14 (d, J = 3.0 Hz, 1H), 7.26-7.30 (m, 3H), 7.05-7.08 (m, 1H), 6.99 (s, 1H), 6.84-6.91 (m, 3H), 6.29 (d, J = 3.0 Hz, 1H), 4.03 (br, 2H), 3.77 (br, 2H), 3.59 (s, 2H), 3.12 (s, 3H), 2.88 (br, 2H), 2.54-2.67 (m, 4H) | 516.2 |

| Ex | Name | Structure | NMR (¹H NMR, 300 MHz or 400 MHz, chloroform-d) | MS [M + H]⁺ |
|---|---|---|---|---|
| 42 | (S)-N-(1-(4-(4-Chloro-3-(pyrrolidin-1-yl)benzyl)-3-methyl-piperazine-1-carbonyl)-1H-pyrazol-3-yl)methane-sulfonamide | 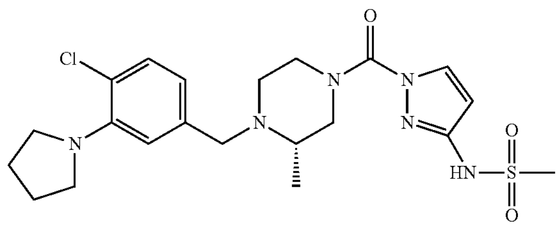 | δ 8.06 (d, J = 2.4 Hz, 1H), 7.25 (d, J = 8.0 Hz, 1H), 7.10 (br, 1H) 6.85 (s, 1H), 6.76 (d, J = 8.0 Hz, 1H), 6.31 (d, J = 2.4 Hz, 1H), 4.27-4.08 (m, 2H), 4.06-3.94 (m, 1H), 3.43-3.39 (m, 5H), 3.30-3.13 (m, 5H), 2.86-2.74 (m, 1H), 2.68-2.54 (m, 1H), 2.32-2.16 (m, 1H), 2.03-1.92 (m, 4H), 1.20-1.19 (m, 3H) | 481.1 |
| 43 | N-(1-(1-((5,6-Dichloro-1H-indol-2-yl)methyl)-1,8-diazaspiro[4.5]decane-8-carbonyl)-1H-pyrazol-3-yl)acetamide | 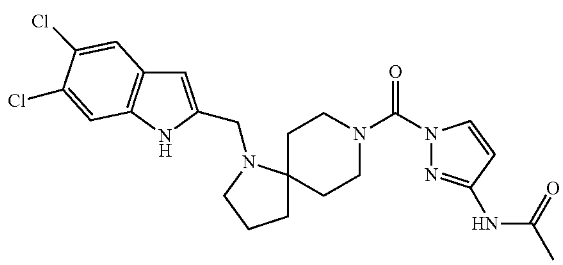 [SMILES: CC(=O)Nc1ccn(C(=O)N2CCC3(CCCN3Cc3cc4cc(Cl)c(Cl)cc4[nH]3)CC2)n1] | δ 8.03 (d, J = 2.7 Hz, 1H), 7.62-7.78 (m, 1H), 7.60 (s, 1H), 7.33-7.50 (m, 1H), 6.89 (d, J = 2.7 Hz, 1H), 6.25 (s, 1H), 4.55-4.72 (m, 2H), 3.68-3.98 (m, 2H), 3.00-3.15 (m, 2H), 2.65-2.93 (m, 2H), 2.18 (s, 3H), 1.85-2.03 (m, 6H), 1.58-1.72 (m, 2H) | 511.1 [M + Na]⁺ |
| 44 | N-(1-(5-(4-(4-Chlorophenoxy)benzyl)octahydropyrrolo[3,4-c]pyrrole-2-carbonyl)-1H-pyrazol-3-yl)acetamide | 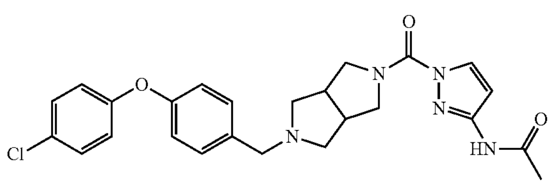 [SMILES: CC(=O)Nc1ccn(C(=O)N2CC3CN(Cc4ccc(Oc5ccc(Cl)cc5)cc4)CC3C2)n1] | δ 8.14 (d, J = 2.4 Hz, 1H), 7.69 (br, 1H), 7.26-7.30 (m, 3H), 6.88-6.95 (m, 5H), 3.60-4.00 (m, 7H), 2.93 (br, 2H), 2.72 (br, 1H), 2.55-2.57 (m, 2H), 2.18 (s, 3H) | 480.0 |
| 45 | N-(1-(5-(5-Chloro-2-(trifluoromethyl)benzyl)octahydropyrrolo[3,4-c]pyrrole-2-carbonyl)-1H-pyrazol-3-yl)methane-sulfonamide | 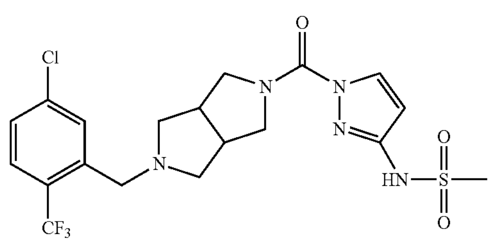 [SMILES: CS(=O)(=O)Nc1ccn(C(=O)N2CC3CN(Cc4cc(Cl)ccc4C(F)(F)F)CC3C2)n1] | δ 11.3 (br, 1H), 7.70 (s, 2H), 7.52-7.55 (m, 1H), 7.30-7.32 (m, 1H), 6.44 (d, J = 2.4 Hz, 1H), 3.71 (br, 4H), 3.82 (s, 5H), 2.83 (br, 2H), 2.58 (br, 2H), 2.47 (br, 2H) | 491.9 |
| 46 | N-(1-(2-(5-Chloro-2-(trifluoromethyl)benzyl)-2,8-diazaspiro[4.5]decane-8-carbonyl)-1H-pyrazol-3-yl)methane-sulfonamide | 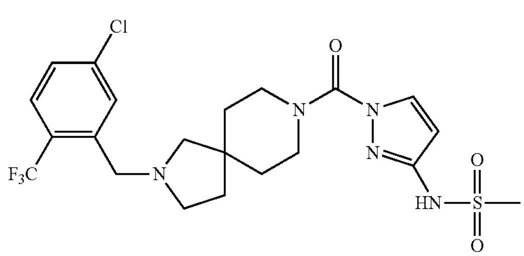 [SMILES: CS(=O)(=O)Nc1ccn(C(=O)N2CCC3(CCN(Cc4cc(Cl)ccc4C(F)(F)F)C3)CC2)n1] | δ 11.1 (br, 1H), 7.74 (br, 1H), 7.67 (d, J = 2.4 Hz, 1H), 7.53-7.56 (m, 1H), 7.29-7.32 (m, 1H), 6.42 (d, J = 2.4 Hz, 1H), 3.72 (br, 2H), 3.39-3.59 (m, 4H), 3.26 (s, 3H), 2.63 (br, 2H), 2.40 (br, 2H), 1.66 (br, 2H), 1.51 (br, 4H) | 520.0 |

| Ex | Name | Structure | NMR (¹H NMR, 300 MHz or 400 MHz, chloroform-d) | MS [M + H]⁺ |
|---|---|---|---|---|
| 47 | N-(1-(5-(4-(Pyrrolidin-1-yl)-2-(trifluoromethyl)benzyl)octahydropyrrolo[3,4-c]pyrrole-2-carbonyl)-1H-pyrazol-3-yl)methanesulfonamide | 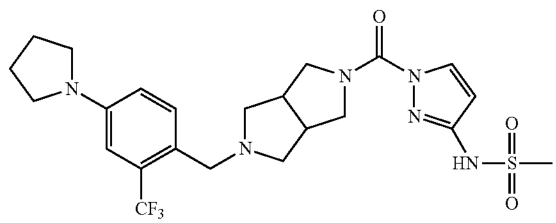 [SMILES: CS(=O)(=O)Nc1ccn(C(=O)N2CC3CN(Cc4ccc(N5CCCC5)cc4C(F)(F)F)CC3C2)n1] | δ 11.1 (br, 1H), 7.64 (d, J = 2.7 Hz, 1H), 7.44 (d, J = 8.7 Hz, 1H), 6.72 (s, 1H), 6.64-6.67 (m, 1H), 6.42 (d, J = 2.7 Hz, 1H), 3.63 (br, 4H), 3.24-3.31 (m, 9H), 2.78 (br, 2H), 2.53 (br, 2H), 2.44 (br, 2H), 1.95-2.06 (m, 4H) | 527.0 |
| 48 | N-(1-(2-(4-(Pyrrolidin-1-yl)-2-(trifluoromethyl)benzyl)-2,8-diazaspiro[4.5]decane-8-carbonyl)-1H-pyrazol-3-yl)methanesulfonamide | 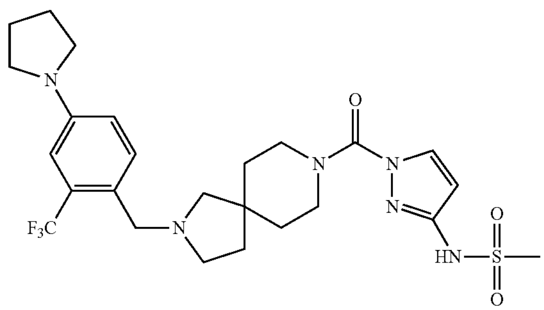 [SMILES: CS(=O)(=O)Nc1ccn(C(=O)N2CCC3(CCN(Cc4ccc(N5CCCC5)cc4C(F)(F)F)C3)CC2)n1] | δ 11.6 (br, 1H), 7.69 (d, J = 2.4 Hz, 1H), 7.45 (d, J = 8.4 Hz, 1H), 6.72 (s, 1H), 6.61-6.65 (m, 1H), 6.40 (d, J = 2.4 Hz, 1H), 3.66 (br, 2H), 3.38-3.51 (m, 4H), 3.23-3.30 (m, 7H), 2.64 (br, 2H), 2.38 (br, 2H), 1.90-2.05 (m, 4H), 1.60 (t, J = 11.7 Hz, 2H), 1.45 (br, 4H) | 555.1 |
| 49 | 2-((8-(3-Acetamido-1H-pyrazole-1-carbonyl)-1,8-diazaspiro[4.5]decan-1-yl)methyl)-1H-indole-5-carboxylic acid | 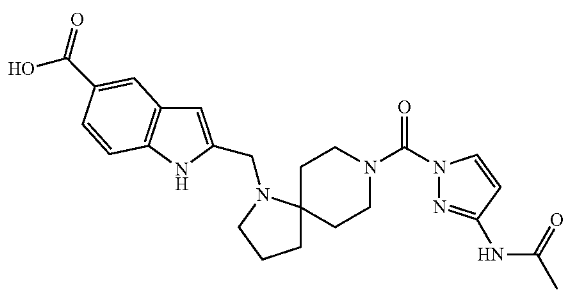 [SMILES: CC(=O)Nc1ccn(C(=O)N2CCC3(CCCN3Cc3cc4cc(C(=O)O)ccc4[nH]3)CC2)n1] | δ 8.24 (s, 1H), 7.90-8.12 (m, 1H), 7.67-7.89 (m, 1H), 7.20-7.43 (m, 1H), 6.66-6.87 (m, 1H), 6.40 (s, 1H), 4.52-4.68 (m, 2H), 3.86 (s, 2H), 3.08-3.24 (m, 2H), 2.80-2.91 (m, 2H), 2.14 (s, 3H), 1.82-2.07 (m, 6H), 1.52-1.68 (m, 2H) | 487.2 [M + Na]⁺ |
| 50 | N-(1-((3aR,5r,6aS)-5-(Methyl(4-(pyrrolidin-1-yl)-2-(trifluoromethyl)benzyl)amino)octahydrocyclopenta[c]pyrrole-2-carbonyl)-1H-pyrazol-3-yl)methanesulfonamide | 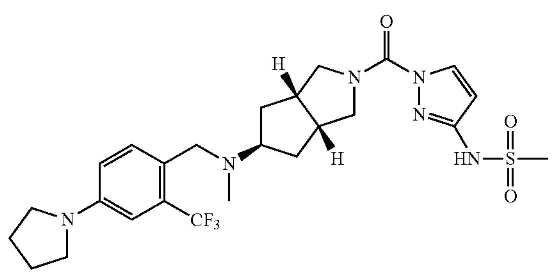 [SMILES: CN(Cc1ccc(N2CCCC2)cc1C(F)(F)F)[C@H]1C[C@@H]2CN(C(=O)n3ccc(NS(C)(=O)=O)n3)C[C@@H]2C1] | δ 8.16 (d, J = 2.7 Hz, 1H), 7.57 (br, 1H), 6.74 (d, J = 2.4 Hz, 1H), 6.66-6.68 (m, 1H), 6.32 (d, J = 2.7 Hz, 1H), 3.99 (br, 2H), 3.60 (br, 4H), 3.23-3.32 (m, 4H), 3.19 (s, 4H), 2.86 (br, 2H), 2.14 (br, 3H), 1.85-2.06 (m, 8H) | 555.1 |
| 51 | N-(1-((3aR,5r,6aS)-5-((5-Chloro-2-(trifluoromethyl)benzyl)(methyl)amino)octahydrocyclopenta[c]pyrrole-2-carbonyl)-1H-pyrazol-3-yl)methanesulfonamide | 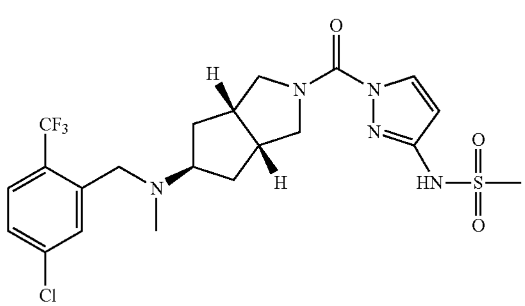 [SMILES: CN(Cc1cc(Cl)ccc1C(F)(F)F)[C@H]1C[C@@H]2CN(C(=O)n3ccc(NS(C)(=O)=O)n3)C[C@@H]2C1] | δ 8.17 (d, J = 2.7 Hz, 1H), 7.86 (br, 1H), 7.53-7.60 (m, 1H), 7.28-7.31 (m, 1H), 6.86 (br, 1H), 6.32 (d, J = 2.7 Hz, 1H), 4.01 (br, 2H), 3.63-3.88 (m, 4H), 3.14 (s, 4H), 2.87 (br, 2H), 2.15 (s, 3H), 1.86 (br, 4H) | 520.1 |

| Ex | Name | Structure | NMR (¹H NMR, 300 MHz or 400 MHz, chloroform-d) | MS [M + H]+ |
|---|---|---|---|---|
| 52 | N-(1-(4-((6-(Trifluoromethyl)benzo[b]thiophen-2-yl)methyl)piperazine-1-carbonyl)-1H-pyrazol-3-yl)methanesulfonamide | 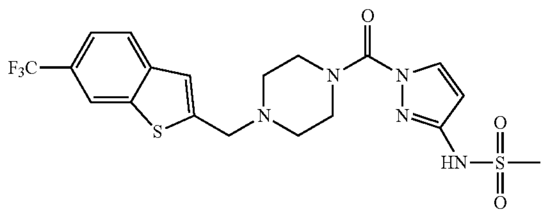 [SMILES: CS(=O)(=O)Nc1ccn(C(=O)N2CCN(Cc3cc4ccc(C(F)(F)F)cc4s3)CC2)n1] | δ 8.06 (m, 2H), 7.78 (d, J = 8.4 Hz, 1H), 7.56 (d, J = 8.4 Hz, 1H), 7.24-7.26 (m, 2H), 6.31 (d, J = 2.4 Hz, 1H), 3.89 (br, 6H), 3.15 (s, 3H), 2.66 (br, 4H) | 488.1 |
| 53 | N-(1-(1-((6-(Trifluoromethyl)benzo[b]thiophen-2-yl)methyl)-1,8-diazaspiro[4.5]decane-8-carbonyl)-1H-pyrazol-3-yl)methanesulfonamide | 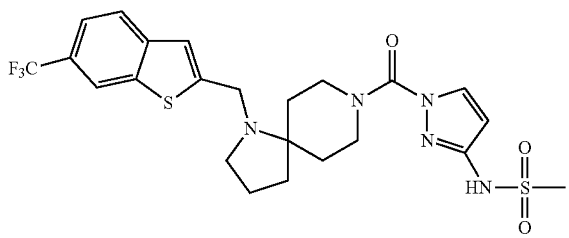 [SMILES: CS(=O)(=O)Nc1ccn(C(=O)N2CCC3(CCCN3Cc3cc4ccc(C(F)(F)F)cc4s3)CC2)n1] | δ 8.03 (s, 2H), 7.75 (d, J = 8.4 Hz, 1H), 7.53 (d, J = 8.4 Hz, 1H), 7.06-7.21 (m, 2H), 6.33 (d, J = 2.4 Hz, 1H), 4.59-4.61 (m, 2H), 3.96 (s, 2H), 3.04-3.13 (m, 5H), 2.85 (s, 2H), 1.87-2.01 (m, 6H), 1.59 (br, 2H) | 542.0 |
| 54 | N-(1-(4-(Benzo[b]thiophen-2-ylmethyl)piperazine-1-carbonyl)-1H-pyrazol-3-yl)methanesulfonamide | 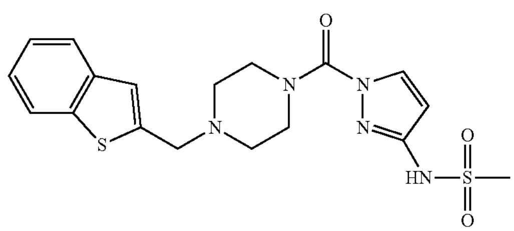 [SMILES: CS(=O)(=O)Nc1ccn(C(=O)N2CCN(Cc3cc4ccccc4s3)CC2)n1] | δ 8.08-7.97 (m, 1H), 7.87-7.75 (m, 1H), 7.75-7.65 (m, 1H), 7.42-7.23 (m, 2H), 7.17 (s, 1H), 6.30 (s, 1H), 3.97-3.72 (m, 6H), 3.13 (s, 3H), 2.69-2.46 (m, 4H), 2.02 (d, J = 1.2 Hz, 1H) | 420.0 |
| 55 | N-(1-(4-((1H-Indol-2-yl)methyl)piperazine-1-carbonyl)-1H-pyrazol-3-yl)methanesulfonamide | 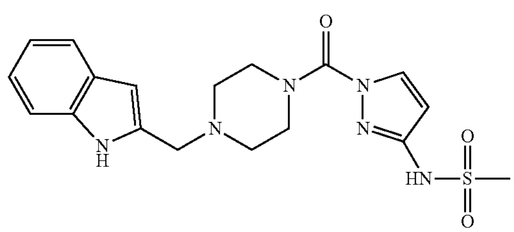 [SMILES: CS(=O)(=O)Nc1ccn(C(=O)N2CCN(Cc3cc4ccccc4[nH]3)CC2)n1] | δ 8.60 (s, 1H), 8.02 (s, 1H), 7.65-7.48 (m, 1H), 7.41-7.32 (m, 1H), 7.22-7.05 (m, 2H), 6.44-6.23 (m, 2H), 3.91-3.77 (m, 4H), 3.71 (s, 2H), 3.12 (s, 3H), 2.64-2.48 (m, 4H), 2.03 (s, 1H) | 403.1 |
| 56 | N-(1-(4-(Benzo[d]thiazol-2-ylmethyl)piperazine-1-carbonyl)-1H-pyrazol-3-yl)methanesulfonamide | 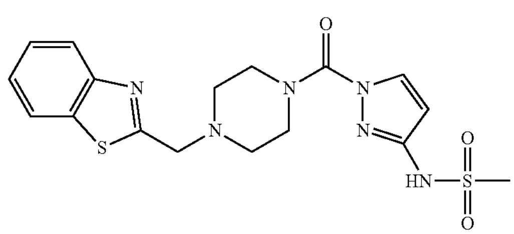 [SMILES: CS(=O)(=O)Nc1ccn(C(=O)N2CCN(Cc3nc4ccccc4s3)CC2)n1] | δ 8.07-7.95 (m, 2H), 7.92-7.84 (m, 1H), 7.53-7.44 (m, 1H), 7.44-7.35 (m, 1H), 6.30 (s, 1H), 4.02 (s, 2H), 3.95-3.79 (m, 4H), 3.14 (s, 3H), 2.78-2.62 (m, 4H), 2.02 (s, 1H) | 421.0 |
| 57 | N-(1-(4-((3-Methylbenzo[b]thiophen-2-yl)methyl)piperazine-1-carbonyl)-1H-pyrazol-3-yl)methanesulfonamide | 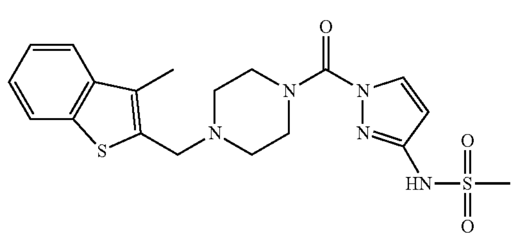 [SMILES: Cc1c(CN2CCN(C(=O)n3ccc(NS(C)(=O)=O)n3)CC2)sc2ccccc12] | δ 8.04 (s, 1H), 7.86-7.75 (m, 1H), 7.69-7.59 (m, 1H), 7.42-7.30 (m, 2H), 6.31 (s, 1H), 3.90-3.84 (m, 4H), 3.83 (s, 2H), 3.14 (s, 3H), 2.70-2.56 (m, 4H), 2.38 (s, 3H), 2.03 (d, J = 0.7 Hz, 1H) | 434.1 |

-continued

| Ex | Name | Structure | NMR (¹H NMR, 300 MHz or 400 MHz, chloroform-d) | MS [M + H]⁺ |
|---|---|---|---|---|
| 58 | N-(1-(2-(2-(Pyrrolidin-1-yl)-4-(trifluoromethyl)benzyl)-2,8-diazaspiro[4.5]decane-8-carbonyl)-1H-pyrazol-3-yl)methanesulfonamide | 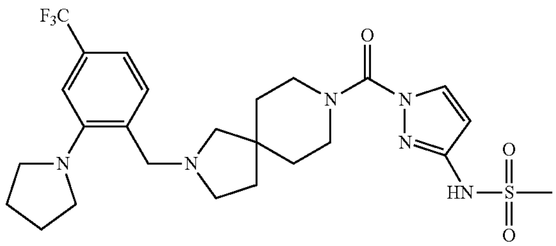 [SMILES: CS(=O)(=O)Nc1ccn(C(=O)N2CCC3(CCN(Cc4ccc(C(F)(F)F)cc4N4CCCC4)C3)CC2)n1] | δ 8.01 (d, J = 3.0 Hz, 1H), 7.53 (br, 1H), 7.09 (br, 2H), 6.31 (d, J = 3.0 Hz, 1H), 3.61-3.79 (m, 6H), 3.22-3.24 (m, 4H), 3.13 (s, 3H), 2.68 (br, 2H), 2.50 (br, 2H), 1.93-2.01 (m, 4H), 1.90 (br, 6H) | 555.1 |
| 59 | N-(1-(2-(3-Morpholino-5-(trifluoromethyl)benzyl)-2,8-diazaspiro[4.5]decane-8-carbonyl)-1H-pyrazol-3-yl)methanesulfonamide | 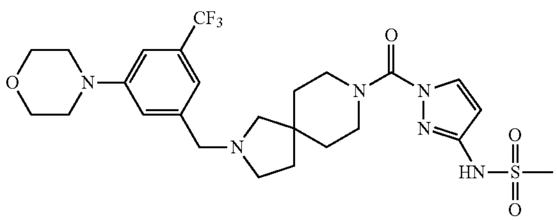 [SMILES: CS(=O)(=O)Nc1ccn(C(=O)N2CCC3(CCN(Cc4cc(N5CCOCC5)cc(C(F)(F)F)c4)C3)CC2)n1] | δ 8.00 (d, J = 3.0 Hz, 1H), 6.98-7.03 (m, 3H), 6.30 (d, J = 3.0 Hz, 1H), 3.85-3.88 (m, 4H), 3.61-3.78 (m, 6H), 3.19-3.22 (m, 4H), 3.11 (s, 3H), 2.66 (br, 2H), 2.45 (br, 2H), 1.69 (br, 6H) | 571.1 |
| 60 | N-(1-(8-(2-(4-Fluoropiperidin-1-yl)-4-(trifluoromethyl)benzyl)-2,8-diazaspiro[4.5]decane-2-carbonyl)-1H-pyrazol-3-yl)methanesulfonamide | 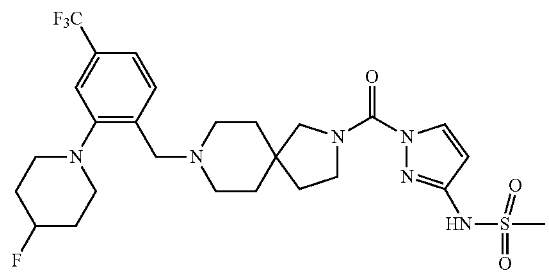 [SMILES: CS(=O)(=O)Nc1ccn(C(=O)N2CCC3(CCN(Cc4ccc(C(F)(F)F)cc4N4CCC(F)CC4)CC3)C2)n1] | δ 8.18 (d, J = 2.7 Hz, 1H), 7.57-7.60 (m, 1H), 7.30-7.32 (m, 2H), 6.30 (d, J = 2.7 Hz, 1H), 4.72-7.90 (m, 1H), 3.74-3.99 (m, 3H), 3.57 (br, 3H), 3.11-3.15 (m, 5H), 2.83-2.90 (m, 2H), 2.40-2.53 (m, 4H), 1.99-2.14 (m, 4H), 1.82-1.84 (m, 2H), 1.62 (br, 4H) | 587.4 |
| 61 | N-(1-(4-((6-Chloro-2-methyl-pyridin-3-yl)methyl)piperazine-1-carbonyl)-1H-pyrazol-3-yl)methanesulfonamide | 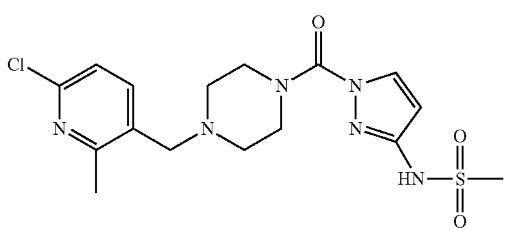 [SMILES: Cc1nc(Cl)ccc1CN1CCN(C(=O)n2ccc(NS(C)(=O)=O)n2)CC1] | δ 8.00 (d, J = 2.8 Hz, 1H), 7.56 (d, J = 8.0 Hz, 1H), 7.16 (d, J = 8.0 Hz, 1H), 6.29 (d, J = 2.8 Hz, 1H), 4.46 (s, 1H), 3.82 (t, J = 4.9 Hz, 4H), 3.49 (s, 2H), 3.14 (s, 3H), 2.57 (s, 3H), 2.53 (t, J = 5.0 Hz, 4H) | 413.1 |
| 62 | N-(1-(2-(2-Morpholino-4-(trifluoromethyl)benzyl)-2,8-diazaspiro[4.5]decane-8-carbonyl)-1H-pyrazol-3-yl)methanesulfonamide | 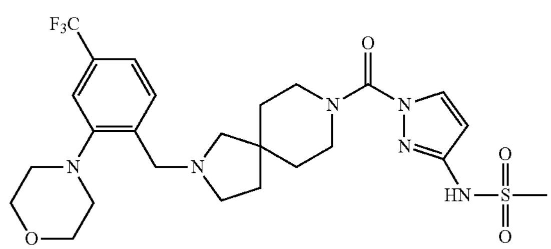 [SMILES: CS(=O)(=O)Nc1ccn(C(=O)N2CCC3(CCN(Cc4ccc(C(F)(F)F)cc4N4CCOCC4)C3)CC2)n1] | δ 8.01 (d, J = 2.7 Hz, 1H), 7.56-7.61 (m, 1H), 7.29-7.34 (m, 2H), 6.31 (d, J = 2.7 Hz, 1H), 3.60-3.88 (m, 10H), 3.13 (s, 3H), 3.01 (br, 4H), 2.67 (br, 2H), 2.48 (br, 2H), 1.68 (br, 6H) | 571.1 |
| 63 | N-(1-(2-(4-Chloro-2-(pyrrolidin-1-yl)benzyl)-2,8-diazaspiro[4.5]decane-8-carbonyl)-1H-pyrazol-3-yl)methanesulfonamide | 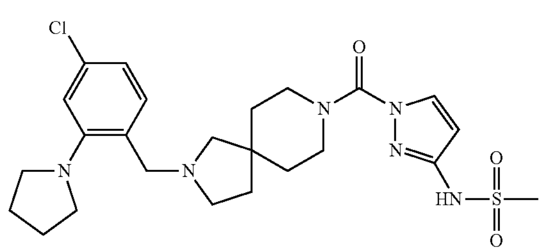 | δ 8.00 (d, J = 2.7 Hz, 1H), 7.30-7.32 (m, 1H), 6.80-6.84 (m, 2H), 6.31 (d, J = 2.7 Hz, 1H), 3.60-3.79 (m, 6H), 3.20-3.24 (m, 4H), 3.15 (s, 3H), 2.66 (br, 2H), 2.45 (br, 2H), 1.90-1.96 (m, 4H), 1.68 (br, 6H) | 521.1 |

| Ex | Name | NMR (¹H NMR, 300 MHz or 400 MHz, chloroform-d) | MS [M + H]⁺ |
|---|---|---|---|
| 64 | N-(1-(2-(3-(Pyrrolidin-1-yl)-5-(trifluoromethyl)benzyl)-2,8-diazaspiro[4.5]decane-8-carbonyl)-1H-pyrazol-3-yl)methanesulfonamide | δ 8.00 (d, J = 3.0 Hz, 1H), 6.84 (s, 1H), 6.63-6.68 (m, 2H), 6.30 (d, J = 3.0 Hz, 1H), 3.60-3.78 (m, 6H), 3.28-3.35 (m, 4H), 3.10 (s, 3H), 2.69 (br, 2H), 2.46 (br, 2H), 2.00-2.06 (m, 4H), 1.66-1.74 (m, 6H) | 555.1 |
| 65 | N-(1-(4-((7-Chloro-3-methyl-1H-indol-2-yl)methyl)piperazine-1-carbonyl)-1H-pyrazol-3-yl)methanesulfonamide | δ 8.56 (s, 1H), 8.04 (s, 1H), 7.47-7.37 (m, 1H), 7.20-7.13 (m, 1H), 7.08-6.99 (m, 1H), 6.37-6.28 (m, 1H), 4.39 (s, 1H), 3.92-3.79 (m, 4H), 3.69 (s, 2H), 3.13 (s, 3H), 2.68-2.48 (m, 4H), 2.26 (s, 3H) | 451.1 |
| 66 | N-(1-(4-((5-Chlorobenzo[b]thiophen-2-yl)methyl)piperazine-1-carbonyl)-1H-pyrazol-3-yl)methanesulfonamide | δ 7.85 (s, 1H), 7.57-7.43 (m, 2H), 7.13 (s, 1H), 7.17-6.98 (m, 1H), 6.96-6.87 (m, 1H), 6.13 (s, 1H), 3.75-3.58 (m, 6H), 2.95 (s, 3H), 2.44 (t, J = 5.0 Hz, 4H) | 454.0 |
| 67 | N-(1-(4-((4-Chlorobenzo[b]thiophen-2-yl)methyl)piperazine-1-carbonyl)-1H-pyrazol-3-yl)methanesulfonamide | δ 7.95 (s, 1H), 7.68-7.51 (m, 1H), 7.26-7.23 (m, 2H), 7.18 (s, 1H), 7.17-7.11 (m, 1H), 6.29-6.12 (m, 1H), 3.86-3.68 (m, 6H), 3.04 (s, 3H), 2.55 (t, J = 5.0 Hz, 4H) | 454.1 |
| 68 | N-(1-(2-(3-Chloro-5-(pyrrolidin-1-yl)benzyl)-2,8-diazaspiro[4.5]decane-8-carbonyl)-1H-pyrazol-3-yl)methanesulfonamide | (Methanol-d₄) δ 8.02 (d, J = 2.7 Hz, 1H), 6.65 (s, 1H), 6.49-6.54 (m, 2H), 6.23 (d, J = 2.7 Hz, 1H), 3.65-3.87 (m, 6H), 3.26-3.37 (m, 4H), 3.13 (s, 3H), 2.90-2.94 (m, 2H), 2.74 (s, 2H), 2.01-2.08 (m, 4H), 1.89 (t, J = 6.9 Hz, 2H), 1.67-1.75 (m, 4H) | 521.2 |

| Ex | Name | Structure | NMR (1H NMR, 300 MHz or 400 MHz, chloroform-d) | MS [M + H]+ |
|----|------|-----------|------------------------------------------------|-------------|
| 69 | N-(1-(4-(4-Ethynylbenzyl)piperazine-1-carbonyl)-1H-pyrazol-3-yl)methanesulfonamide | 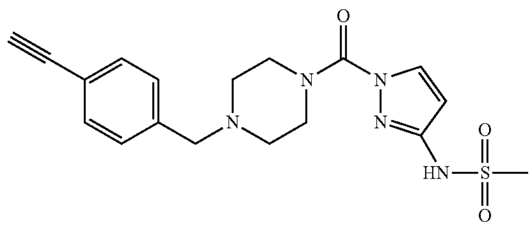 [SMILES: C#Cc1ccc(CN2CCN(C(=O)n3ccc(NS(C)(=O)=O)n3)CC2)cc1] | δ 8.03 (d, J = 2.6 Hz, 1H), 7.44-7.47 (m, 2H), 7.27-7.30 (m, 2H), 6.30 (d, J = 2.6 Hz, 1H), 3.83 (br, 4H), 3.54 (br, 2H), 2.99-3.12 (m, 4H), 2.52 (br, 4H) | 387.9 |
| 70 | N-(1-(4-((3-Chlorobenzo[b]thiophen-2-yl)methyl)piperazine-1-carbonyl)-1H-pyrazol-3-yl)methanesulfonamide | 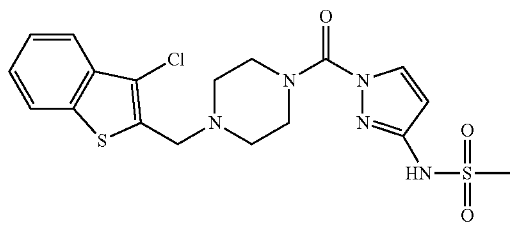 | δ 7.84 (d, J = 2.8 Hz, 1H), 7.65-7.56 (m, 2H), 7.33-7.17 (m, 2H), 6.12 (s, 1H), 4.12-3.73 (m, 3H), 3.74-3.64 (m, 4H), 2.95 (s, 3H), 2.55-2.42 (m, 4H) | 454.0 |
| 71 | N-(1-(4-((2-(Pyrrolidin-1-yl)-6-(trifluoromethyl)pyridin-3-yl)methyl)piperazine-1-carbonyl)-1H-pyrazol-3-yl)methanesulfonamide | 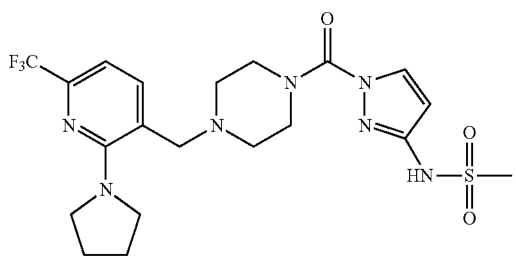 | δ 8.06 (d, J = 2.7 Hz, 1H), 7.54-7.56 (m, 1H), 7.17 (br, 1H), 6.91-6.93 (m, 1H), 6.33 (d, J = 2.7 Hz, 1H), 3.84 (br, 4H), 3.68-3.71 (m, 4H), 3.58 (s, 2H), 3.16 (s, 3H) 2.52-2.54 (m, 4H), 1.93-2.03 (m, 4H) | 502.4 |
| 72 | N-(1-(2-(4-(Pyrrolidin-1-yl)-3-(trifluoromethyl)benzyl)-2,8-diazaspiro[4.5]decane-8-carbonyl)-1H-pyrazol-3-yl)methanesulfonamide | 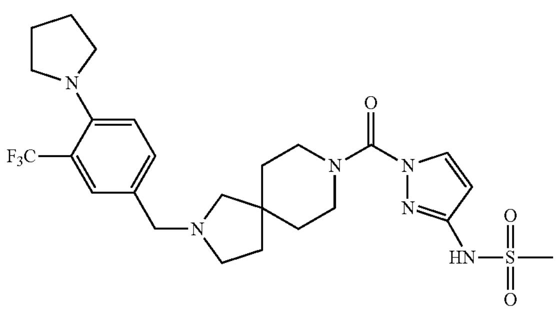 [SMILES: CS(=O)(=O)Nc1ccn(C(=O)N2CCC3(CCN(Cc4ccc(N5CCCC5)c(C(F)(F)F)c4)C3)CC2)n1] | δ 7.99 (d, J = 2.7 Hz, 1H), 7.50 (s, 1H), 7.34-7.36 (m, 1H), 6.90-6.93 (m, 1H), 6.30 (d, J = 2.7 Hz, 1H), 3.61-3.76 (m, 6H), 3.30-3.34 (m, 4H), 3.10 (s, 3H), 2.70-2.74 (m, 2H), 2.50 (br, 2H), 1.90-1.99 (m, 4H), 1.62-1.76 (m, 6H) | 555.5 |
| 73 | N-(1-(2-(3-(Pyrrolidin-1-yl)-4-(trifluoromethyl)benzyl)-2,8-diazaspiro[4.5]decane-8-carbonyl)-1H-pyrazol-3-yl)methanesulfonamide | 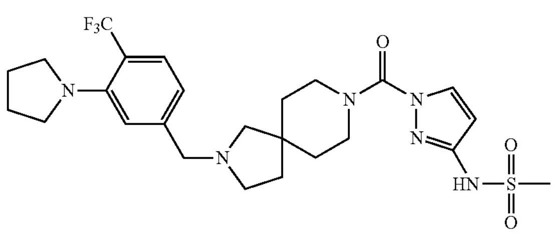 [SMILES: CS(=O)(=O)Nc1ccn(C(=O)N2CCC3(CCN(Cc4ccc(C(F)(F)F)c(N5CCCC5)c4)C3)CC2)n1] | δ 8.00 (d, J = 2.7 Hz, 1H), 7.51-7.53 (m, 1H), 6.97-7.12 (m, 1H), 6.77-6.79 (m, 1H), 6.31 (d, J = 2.7 Hz, 1H), 3.67-3.91 (m, 6H), 3.36 (br, 5H), 3.13 (s, 3H), 2.54-2.98 (m, 3H), 2.09-2.14 (m, 5H), 1.73-1.97 (m, 5H) | 555.1 |

-continued

| Ex | Name | Structure | NMR (¹H NMR, 300 MHz or 400 MHz, chloroform-d) | MS [M + H]⁺ |
|---|---|---|---|---|
| 74 | N-(1-(2-(2-(3-Oxa-8-azabicyclo[3.2.1]octan-8-yl)-4-(trifluoromethyl)benzyl)-2,8-diazaspiro[4.5]decane-8-carbonyl)-1H-pyrazol-3-yl)methanesulfonamide | 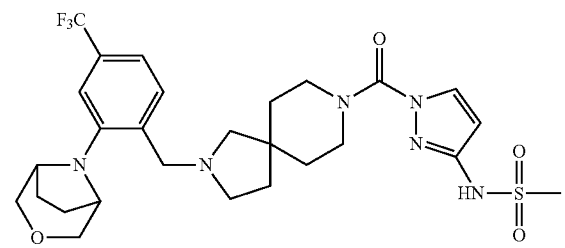 [SMILES: CS(=O)(=O)Nc1ccn(C(=O)N2CCC3(CCN(Cc4ccc(C(F)(F)F)cc4N4C5CCC4COC5)C3)CC2)n1] | δ 8.00 (d, J = 2.7 Hz, 1H), 7.61 (br, 1H), 7.12-7.22 (m, 1H), 7.06 (s, 1H), 6.32 (d, J = 2.7 Hz, 1H), 3.91-3.94 (m, 2H), 3.61-3.83 (m, 10H), 3.20 (s, 3H), 2.76-2.97 (m, 2H), 2.55-2.70 (m, 2H), 1.94-2.07 (m, 4H), 1.70-1.90 (m, 6H) | 597.1 |
| 75 | N-(1-(4-Methyl-4-(methyl(2-(pyrrolidin-1-yl)-4-(trifluoromethyl)benzyl)amino)piperidine-1-carbonyl)-1H-pyrazol-3-yl)methanesulfonamide | 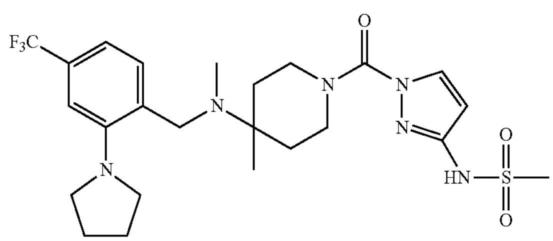 [SMILES: CN(Cc1ccc(C(F)(F)F)cc1N1CCCC1)C1(C)CCN(C(=O)n2ccc(NS(C)(=O)=O)n2)CC1] | δ 8.02 (d, J = 2.7 Hz, 1H), 7.80-7.83 (m, 1H), 7.14-7.20 (m, 2H), 6.32 (d, J = 2.7 Hz, 1H), 3.99-4.03 (m, 2H), 3.68-3.75 (m, 2H), 3.58 (s, 2H), 3.12-3.18 (m, 7H), 2.09 (s, 3H), 1.94-2.03 (m, 6H), 1.56-1.63 (m, 2H), 1.25 (s, 3H) | 565.2 [M + Na]⁺ |
| 76 | 4-((2-((4-(3-Acetamido-1H-pyrazole-1-carbonyl)piperazin-1-yl)methyl)-5-(trifluoromethyl)phenyl)amino)butanoic acid | 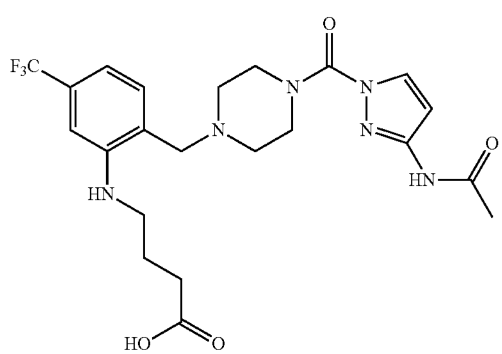 [SMILES: CC(=O)Nc1ccn(C(=O)N2CCN(Cc3ccc(C(F)(F)F)cc3NCCCC(=O)O)CC2)n1] | (Methanol-d₄) δ 8.03 (d, J = 3.2 Hz, 1H), 7.13-7.15 (m, 1H), 6.79-6.84 (m, 3H), 3.86 (s, 4H), 3.59 (s, 2H), 3.22 (t, J = 6.8 Hz, 2H), 2.52 (s, 4H), 2.45 (t, J = 7.2 Hz, 2H), 2.11 (s, 3H), 1.96-2.02 (m, 2H) | 497.1 |
| 77 | 3-((2-((4-(3-(Methylsulfonamido)-1H-pyrazole-1-carbonyl)piperazin-1-yl)methyl)-5-(trifluoromethyl)phenyl)amino)propanoic acid | 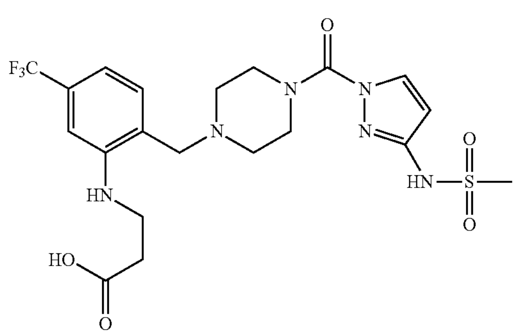 [SMILES: CS(=O)(=O)Nc1ccn(C(=O)N2CCN(Cc3ccc(C(F)(F)F)cc3NCCC(=O)O)CC2)n1] | (Methanol-d₄) δ 8.03 (d, J = 2.8 Hz, 1H), 7.12 (d, J = 8.0 Hz, 1H), 6.82-6.87 (m, 2H), 6.24 (d, J = 2.8 Hz, 1H), 3.88 (s, 4H), 3.56 (s, 2H), 3.42 (t, J = 6.2 Hz, 2H), 3.11 (s, 3H), 2.59 (t, J = 6.2 Hz, 2H), 2.47-2.49 (m, 4H) | 519.0 |

| Ex | Name | Structure | NMR (¹H NMR, 300 MHz or 400 MHz, chloroform-d) | MS [M + H]⁺ |
|---|---|---|---|---|
| 78 | 4-((2-((5-(3-(Methyl-sulfonamido)-1H-pyrazole-1-carbonyl)hexahydro pyrrolo[3,4-c]pyrrol-2(1H)-yl)methyl)-5-(trifluoromethyl)phenyl)amino)butanoic acid | 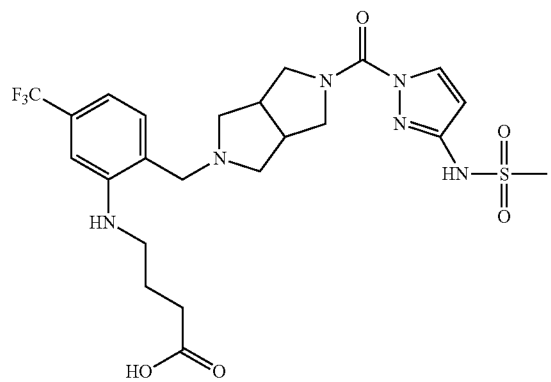 [SMILES: CS(=O)(=O)Nc1ccn(C(=O)N2CC3CN(Cc4ccc(C(F)(F)F)cc4NCCCC(=O)O)CC3C2)n1] | (Methanol-d₄) δ 8.17 (d, J = 2.7 Hz, 1H), 7.16-7.18 (m, 1H), 6.81-6.85 (m, 2H), 6.28 (d, J = 2.7 Hz, 1H), 4.02 (br, 4H), 3.70 (s, 2H), 3.12-3.17 (m, 5H), 3.00 (br, 2H), 2.68-2.71 (m, 2H), 2.58-2.63 (m, 2H), 2.32 (t, J = 7.0 Hz, 2H), 1.84-1.88 (m, 2H) | 559.0 |
| 79 | 4-((2-((8-(3-Acetamido-1H-pyrazole-1-carbonyl)-1,8-diazaspiro[4.5]decan-1-yl)methyl)-5-(trifluoromethyl)phenyl)amino)butanoic acid | 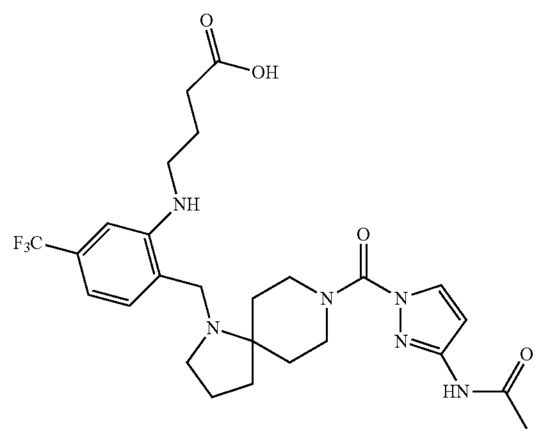 [SMILES: CC(=O)Nc1ccn(C(=O)N2CCC3(CCCN3Cc3ccc(C(F)(F)F)cc3NCCCC(=O)O)CC2)n1] | (Methanol-d₄) δ 8.05 (d, J = 3.0 Hz, 1H), 7.17-7.20 (m, 1H), 6.79-6.86 (m, 3H), 4.60-4.64 (m, 2H), 3.81 (s, 2H), 3.11-3.22 (m, 4H), 2.66 (t, J = 6.9 Hz, 2H), 2.46 (t, J = 7.4 Hz, 2H), 2.15 (s, 3H), 2.05-2.12 (m, 6H), 1.82-2.02 (m, 2H), 1.55-1.60 (m, 2H) | 551.0 |
| 80 | N-(1-(4-(2-(Pyrrolidin-1-yl)-4-(trifluoromethyl)phenoxy)piperidine-1-carbonyl)-1H-pyrazol-3-yl)methane-sulfonamide | 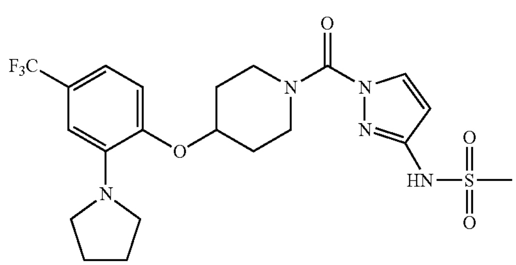 | δ 8.05 (d, J = 2.7 Hz, 1H), 7.01-7.05 (m, 2H), 6.94 (br, 1H), 6.86-6.88 (m, 1H), 6.33 (d, J = 2.7 Hz, 1H), 4.63-4.68 (m, 1H), 3.98-4.02 (m, 2H), 3.79-3.81 (m, 2H), 3.36-3.40 (m, 4H), 3.14 (s, 3H), 2.07-2.14 (m, 2H), 1.92-1.99 (m, 6H) | 502.2 |
| 81 | N-(1-(4-((2-(Pyrrolidin-1-yl)pyridin-3-yl)methyl)piperazine-1-carbonyl)-1H-pyrazol-3-yl)methane-sulfonamide | 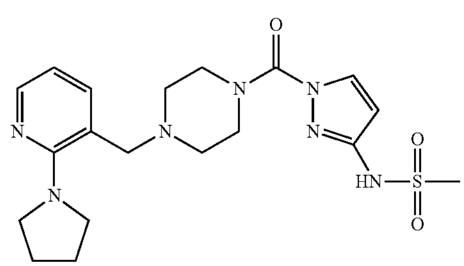 [SMILES: CS(=O)(=O)Nc1ccn(C(=O)N2CCN(Cc3cccnc3N3CCCC3)CC2)n1] | δ 8.02-8.10 (m, 2H), 7.43-7.46 (m, 1H), 6.58-6.62 (m, 1H), 6.28 (d, J = 2.7 Hz, 1H), 3.81 (br, 4H), 3.55-3.61 (m, 4H), 3.52 (s, 2H), 3.13 (s, 3H), 2.50 (t, J = 4.8 Hz, 4H), 1.90-1.96 (m, 4H) | 434.4 |

| Ex | Name | Structure | NMR (¹H NMR, 300 MHz or 400 MHz, chloroform-d) | MS [M + H]⁺ |
|----|------|-----------|----|----|
| 82 | N-(1-(4-((3-(Pyrrolidin-1-yl)pyridin-4-yl)methyl)piperazine-1-carbonyl)-1H-pyrazol-3-yl)methanesulfonamide | 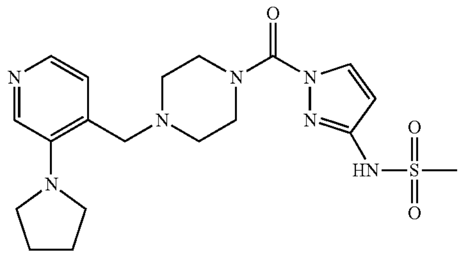 [SMILES: CS(=O)(=O)Nc1ccn(C(=O)N2CCN(Cc3ccncc3N3CCCC3)CC2)n1] | δ 8.26 (s, 1H), 8.16 (d, J = 5.1 Hz, 1H), 8.06 (d, J = 2.8 Hz, 1H), 7.40 (d, J = 5.1 Hz, 1H), 6.38 (d, J = 2.8 Hz, 1H), 3.91 (br, 4H), 3.58 (s, 2H), 3.31 (t, J = 6.6 Hz, 4H), 3.10 (s, 3H), 2.56 (br, 4H), 1.96-2.02 (m, 4H) | 434.4 |
| 83 | N-(1-(1-(4-Chloro-3-methylbenzyl)-1,8-diazaspiro[4.5]decane-8-carbonyl)-1H-pyrazol-3-yl)cyclopropanecarboxamide | 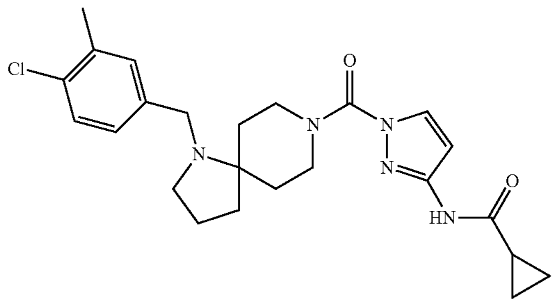 [SMILES: Cc1cc(CN2CCCC23CCN(C(=O)n2ccc(NC(=O)C4CC4)n2)CC3)ccc1Cl] | δ 8.07 (br, 1H), 7.99 (d, J = 3.0 Hz, 1H), 7.24-7.26 (m, 1H), 7.10-7.18 (m, 2H), 6.85 (d, J = 3.0 Hz, 1H), 4.58-4.62 (m, 2H), 3.56 (br, 2H), 3.01-3.10 (m, 2H), 3.56 (br, 2H), 2.35 (s, 3H), 1.83-1.88 (m, 6H), 1.53-1.61 (m, 3H), 1.08-1.14 (m, 2H), 0.87-0.92 (m, 2H) | 456.1 |
| 84 | N-(1-(1-(4-Chloro-3-methylbenzoyl)-1,8-diazaspiro[4.5]decane-8-carbonyl)-1H-pyrazol-3-yl)acetamide | 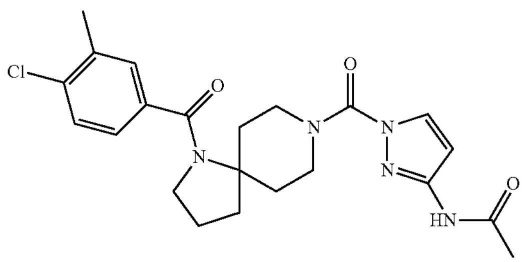 [SMILES: CC(=O)Nc1ccn(C(=O)N2CCC3(CCCN3C(=O)c3ccc(Cl)c(C)c3)CC2)n1] | δ 8.22 (br, 1H), 7.99 (d, J = 2.7 Hz, 1H), 7.33-7.35 (m, 1H), 7.27-7.28 (m, 1H), 7.15-7.18 (m, 1H), 6.86 (d, J = 3.0 Hz, 1H), 4.52-4.57 (m, 2H), 3.43 (t, J = 6.6 Hz, 2H), 3.19-3.29 (m, 2H), 3.02-3.10 (m, 2H), 2.38 (s, 3H), 2.19 (s, 3H), 2.07 (t, J = 6.8 Hz, 2H), 1.78-1.87 (m, 2H), 1.46-1.50 (m, 2H) | 444.0 |
| 85 | N-(1-(1-(4-Cyano-3-methylbenzoyl)-1,8-diazaspiro[4.5]decane-8-carbonyl)-1H-pyrazol-3-yl)acetamide | 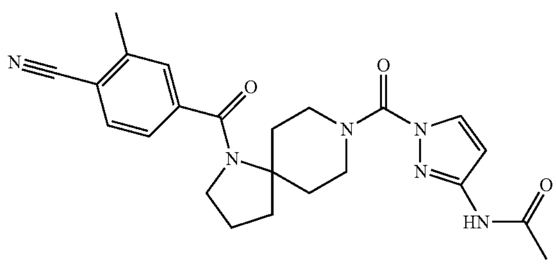 [SMILES: CC(=O)Nc1ccn(C(=O)N2CCC3(CCCN3C(=O)c3ccc(C#N)c(C)c3)CC2)n1] | δ 8.00 (d, J = 2.7 Hz, 2H), 7.63 (d, J = 7.8 Hz, 1H), 7.27-7.35 (m, 2H), 6.87 (d, J = 2.7 Hz, 1H), 4.56-4.60 (m, 2H), 3.34 (t, J = 6.8 Hz, 2H), 3.18-3.26 (m, 2H), 3.03-3.11 (m, 2H), 2.57 (s, 3H), 2.19 (s, 3H), 2.08-2.12 (m, 2H), 1.81-1.90 (m, 2H), 1.48-1.52 (m, 2H) | 435.1 |
| 86 | N-(1-(4-((3-(Pyrrolidin-1-yl)pyridin-2-yl)methyl)piperazine-1-carbonyl)-1H-pyrazol-3-yl)methanesulfonamide | 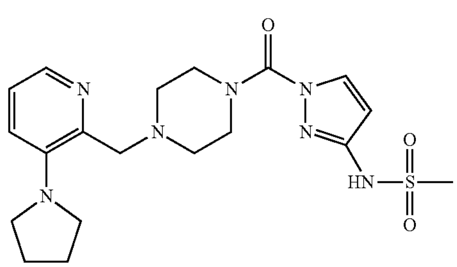 [SMILES: CS(=O)(=O)Nc1ccn(C(=O)N2CCN(Cc3ncccc3N3CCCC3)CC2)n1] | δ 8.09-8.10 (m, 1H), 8.04 (d, J = 2.8 Hz, 1H), 7.15-7.17 (m, 1H), 7.09-7.12 (m, 1H), 6.33 (d, J = 2.8 Hz, 1H), 3.85 (br, 4H), 3.78 (s, 2H), 3.31 (t, J = 6.8 Hz, 4H), 3.13 (s, 3H), 2.61 (t, J = 4.8 Hz, 4H), 1.93-2.01 (m, 4H) | 434.2 |

| Ex | Name | Structure | NMR (¹H NMR, 300 MHz or 400 MHz, chloroform-d) | MS [M + H]⁺ |
|---|---|---|---|---|
| 87 | N-(1-(1-(4-Cyano-3-cyclopropyl-benzoyl)-1,8-diazaspiro[4.5]decane-8-carbonyl)-1H-pyrazol-3-yl)acetamide | 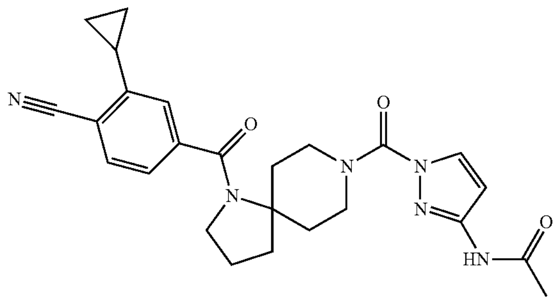 [SMILES: CC(=O)Nc1ccn(C(=O)N2CCC3(CCCN3C(=O)c3ccc(C#N)c(C4CC4)c3)CC2)n1] | δ 8.15 (br, 1H), 7.99 (d, J = 2.7 Hz, 1H), 7.60-7.63 (m, 1H), 7.22-7.27 (m, 1H), 6.96 (s, 1H), 6.86 (d, J = 2.7 Hz, 1H), 4.54-4.59 (m, 2H), 3.34 (t, J = 6.6 Hz, 2H), 3.21-3.25 (m, 2H), 3.02-3.06 (m, 2H), 2.27-2.33 (m, 1H), 2.19 (s, 3H), 2.07 (t, J = 6.8 Hz, 2H), 1.87-1.89 (m, 1H), 1.83-1.84 (m, 1H), 1.48-1.52 (m, 2H), 1.15-1.21 (m, 2H), 0.80-0.85 (m, 2H) | 461.2 |
| 88 | N-(1-(3-Methyl-4-(2-(pyrrolidin-1-yl)-4-(trifluoromethyl)benzyl)piperazine-1-carbonyl)-1H-pyrazol-3-yl)methane-sulfonamide | 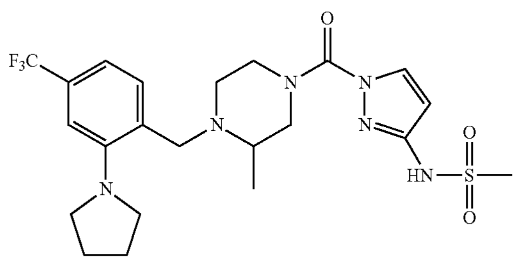 [SMILES: CC1CN(C(=O)n2ccc(NS(C)(=O)=O)n2)CCN1Cc1ccc(C(F)(F)F)cc1N1CCCC1] | δ 8.04 (d, J = 2.7 Hz, 1H), 7.65-7.67 (m, 1H), 7.13-7.16 (m, 3H), 6.31 (d, J = 2.7 Hz, 1H), 3.94-4.16 (m, 3H), 3.34-3.37 (m, 1H), 3.23-3.28 (m, 4H), 312-3.21 (m, 5H), 2.70 (br, 2H), 2.27 (br, 1H), 1.89-2.01 (m, 4H), 1.14-1.15 (m, 3H) | 515.0 |
| 89 | N-(1-(4-(2-(Cyclopropyl-sulfonyl)-4-(trifluoromethyl)benzyl)piperazine-1-carbonyl)-1H-pyrazol-3-yl)methane-sulfonamide | 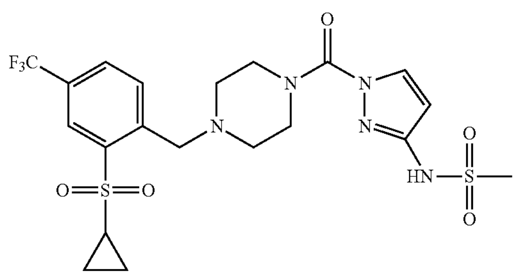 [SMILES: CS(=O)(=O)Nc1ccn(C(=O)N2CCN(Cc3ccc(C(F)(F)F)cc3S(=O)(=O)C3CC3)CC2)n1] | δ 8.20 (d, J = 2.7 Hz, 1H), 8.05 (br, 1H), 7.77-7.86 (m, 2H), 7.02 (br, 1H), 6.33 (br, 1H), 4.10 (s, 2H), 3.83 (br, 4H), 3.23 (br, 1H), 3.14 (s, 3H), 2.66 (br, 4H), 1.34-1.40 (m, 2H), 1.02-1.07 (m, 2H) | 536.4 |
| 90 | N-(1-(4-((6-Chloro-2-(pyrrolidin-1-yl)pyridin-3-yl)methyl)piperazine-1-carbonyl)-1H-pyrazol-3-yl)methane-sulfonamide | 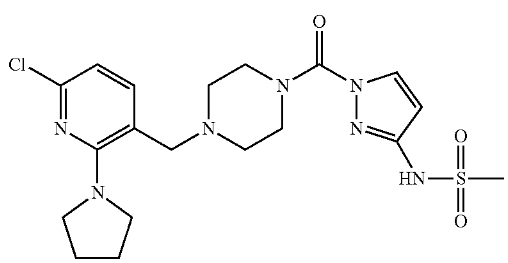 [SMILES: CS(=O)(=O)Nc1ccn(C(=O)N2CCN(Cc3ccc(Cl)nc3N3CCCC3)CC2)n1] | δ 8.04 (d, J = 2.7 Hz, 1H), 7.32-7.34 (m, 1H), 6.55 (d, J = 7.5 Hz, 1H), 6.31 (d, J = 2.7 Hz, 1H), 3.82 (br, 4H), 3.64 (br, 4H), 3.50 (br, 2H), 3.14 (s, 3H), 2.50 (br, 4H), 1.90-1.94 (m, 4H) | 468.0 |
| 91 | N-(1-(4-Methyl-4-(methyl((2-(pyrrolidin-1-yl)-6-(trifluoromethyl)pyridin-3-yl)methyl)amino)piperidine-1-carbonyl)-1H-pyrazol-3-yl)methane-sulfonamide | 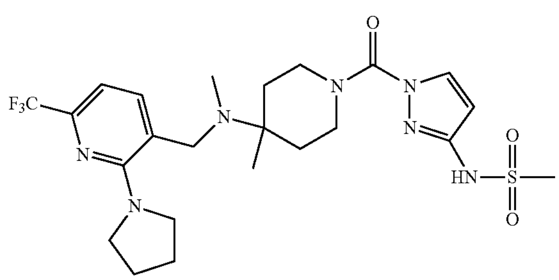 [SMILES: CN(Cc1ccc(C(F)(F)F)nc1N1CCCC1)C1(C)CCN(C(=O)n2ccc(NS(C)(=O)=O)n2)CC1] | δ 8.02-8.05 (m, 2H), 7.08-7.09 (m, 1H), 7.02 (br, 1H), 6.34 (d, J = 2.7 Hz, 1H), 3.99-4.02 (m, 2H), 3.69-3.74 (m, 2H), 3.62 (s, 2H), 3.54 (br, 4H), 3.15 (s, 3H), 2.11 (s, 3H), 1.94-2.05 (m, 6H), 1.63-1.65 (m, 2H), 1.12 (s, 3H) | 544.5 |

| Ex | Name | Structure | NMR (¹H NMR, 300 MHz or 400 MHz, chloroform-d) | MS [M + H]⁺ |
|---|---|---|---|---|
| 92 | N-(1-(4-(2-(3-Oxa-8-azabicyclo[3.2.1]octan-8-yl)-4-(trifluoromethyl)phenoxy)piperidine-1-carbonyl)-1H-pyrazol-3-yl)methanesulfonamide | 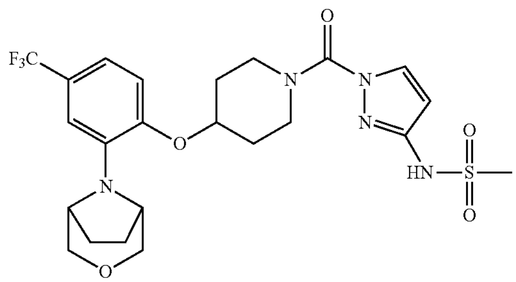 [SMILES: CS(=O)(=O)Nc1ccn(C(=O)N2CCC(Oc3ccc(C(F)(F)F)cc3N3C4CCC3COC4)CC2)n1] | δ 8.05-8.09 (m, 1H), 7.05-7.20 (m, 1H), 6.85-6.95 (m, 2H), 7.01 (s, 1H), 6.86-6.97 (m, 1H), 6.35-6.38 (m, 1H), 4.75 (s, 1H), 3.85-4.10 (m, 8H), 3.60-3.73 (m, 2H), 3.10 (s, 3H), 1.87-2.21 (m, 8H) | 544.0 |
| 93 | N-(5-Chloro-2-(trifluoromethyl)benzyl)-N-((3aR,5r,6aS)-2-(3-(methyl-sulfonamido)-1H-pyrazole-1-carbonyl)octahydro-cyclopenta[c]pyrrol-5-yl)glycine | 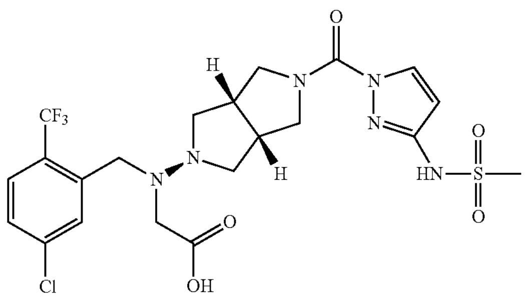 | (Methanol-d₄) δ 8.11-8.14 (m, 2H), 7.63-7.66 (m, 1H), 7.42-7.45 (m, 1H), 6.25 (d, J = 2.7 Hz, 1H), 3.98-4.18 (m, 4H), 3.55-3.88 (m, 3H), 3.42-3.51 (m, 2H), 3.09 (s, 3H), 2.88 (br, 2H), 1.91-2.05 (m, 4H) | 564.1 |
| 94 | N-(1-(4-Methyl-4-(methyl(2-morpholino-4-(trifluoromethyl)benzyl)amino)piperidine-1-carbonyl)-1H-pyrazol-3-yl)methanesulfonamide | 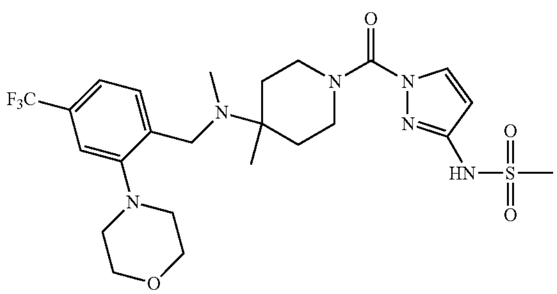 [SMILES: CN(Cc1ccc(C(F)(F)F)cc1N1CCOCC1)C1(C)CCN(C(=O)n2ccc(NS(C)(=O)=O)n2)CC1] | δ 8.02 (d, J = 3.0 Hz, 1H), 7.78-7.80 (m, 1H), 7.36-7.38 (m, 1H), 7.26-7.30 (m, 1H), 7.01 (br, 1H), 6.32 (d, J = 3.0 Hz, 1H), 3.86-3.92 (m, 6H), 3.65-3.77 (m, 4H), 3.14 (s, 3H), 2.88-2.91 (m, 4H), 2.01-2.12 (m, 3H), 1.97-2.01 (m, 2H), 1.62-1.65 (m, 2H), 1.11 (br, 3H) | 559.6 |
| 95 | N-(1-(4-((2-(Pyrrolidin-1-yl)-6-(trifluoromethyl)pyridin-3-yl)oxy)piperidine-1-carbonyl)-1H-pyrazol-3-yl)methanesulfonamide | 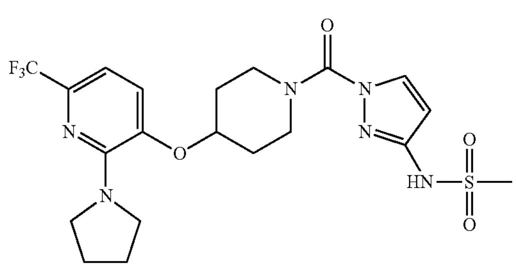 [SMILES: CS(=O)(=O)Nc1ccn(C(=O)N2CCC(Oc3ccc(C(F)(F)F)nc3N3CCCC3)CC2)n1] | δ 8.03-8.08 (m, 1H), 7.10-7.30 (m, 1H), 6.85-6.95 (m, 2H), 6.32 (s, 1H), 4.54-4.66 (m, 1H), 3.78-4.13 (m, 4H), 3.61-3.76 (m, 4H), 3.11 (s, 3H), 2.02-2.17 (m, 2H), 1.85-2.01 (m, 6H) | 503.1 |
| 96 | N-(1-(4-(2-(1,3,4-Oxadiazol-2-yl)-4-(trifluoromethyl)phenoxy)piperidine-1-carbonyl)-1H-pyrazol-3-yl)methanesulfonamide | 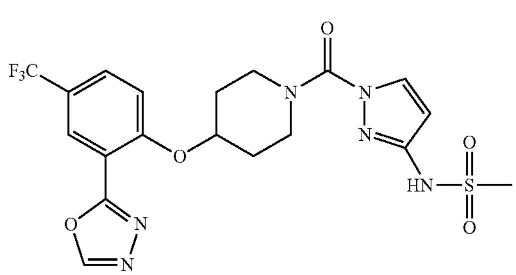 [SMILES: CS(=O)(=O)Nc1ccn(C(=O)N2CCC(Oc3ccc(C(F)(F)F)cc3-c3nnco3)CC2)n1] | δ 8.65 (s, 1H), 8.25-8.30 (m, 1H), 8.12-8.15 (m, 1H), 7.71-7.80 (m, 1H), 7.15-7.20 (m, 2H), 6.30-6.34 (m, 1H), 4.95-5.05 (m, 1H), 4.05-4.25 (m, 2H), 3.80-3.95 (m, 2H), 3.05-3.35 (s, 3H), 1.88-2.35 (m, 4H) | 523.1 [M + Na]⁺ |

| Ex | Name | Structure | NMR (¹H NMR, 300 MHz or 400 MHz, chloroform-d) | MS [M + H]+ |
|---|---|---|---|---|
| 97 | 1-(2-((Methyl (4-methyl-1-(3-(methyl-sulfonamido)-1H-pyrazole-1-carbonyl) piperidin-4-yl)amino) methyl)-5-(trifluoromethyl) phenyl) pyrrolidine-3-carboxylic acid | 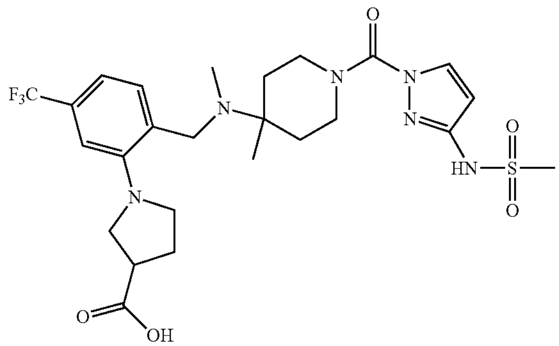 [SMILES: CN(Cc1ccc(C(F)(F)F)cc1N1CCC(C(=O)O)C1)C1(C)CCN(C(=O)n2ccc(NS(C)(=O)=O)n2)CC1] | (Methanol-$d_4$) δ 8.05 (d, J = 2.7 Hz, 1H), 7.76-7.79 (m, 1H), 7.32-7.36 (m, 2H), 6.25 (d, J = 2.7 Hz, 1H), 3.98-4.15 (m, 4H), 3.74 (br, 2H), 3.45-3.47 (m, 1H), 3.24-3.29 (m, 2H), 3.10-3.14 (m, 5H), 2.26-2.29 (m, 5H), 2.10 (br, 2H), 1.79-1.89 (m, 2H), 1.33 (s, 3H) | 587.2 |
| 98 | N-(1-(4-(2-(1H-Pyrazol-1-yl)-4-(trifluoromethyl) phenoxy) piperidine-1-carbonyl)-1H-pyrazol-3-yl) methane-sulfonamide | 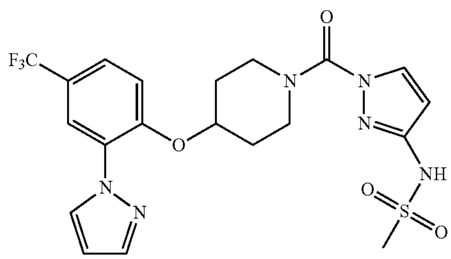 [SMILES: CS(=O)(=O)Nc1ccn(C(=O)N2CCC(Oc3ccc(C(F)(F)F)cc3-n3cccn3)CC2)n1] | δ 8.02-8.05 (m, 3H), 7.74 (d, J = 1.5 Hz, 1H), 7.55-7.58 (m, 1H), 7.09-7.17 (m, 2H), 6.47 (t, J = 2.1 Hz, 1H), 6.30 (d, J = 2.7 Hz, 1H), 4.76-4.77 (m, 1H), 3.87-3.91 (m, 2H), 3.63-3.70 (m, 2H), 3.12 (s, 3H), 2.01-2.11 (m, 2H), 1.89-1.98 (m, 2H) | 499.1 |
| 99 | (2-((1-(3-(Methyl-sulfonamido)-1H-pyrazole-1-carbonyl) piperidin-4-yl)oxy)-5-(trifluoromethyl) phenyl)glycine | 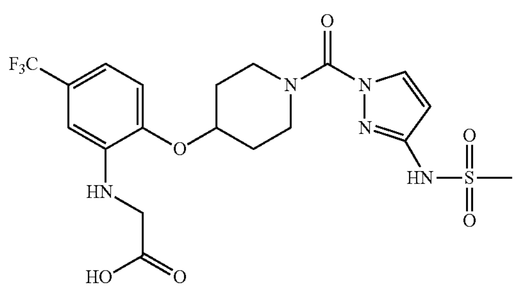 [SMILES: CS(=O)(=O)Nc1ccn(C(=O)N2CCC(Oc3ccc(C(F)(F)F)cc3NCC(=O)O)CC2)n1] | δ 8.05-8.08 (m, 1H), 6.98-7.05 (m, 1H), 6.90-6.95 (m, 1H), 6.68-6.72 (m, 1H), 6.25 (s, 1H), 4.80-4.86 (m, 1H), 3.71-4.11 (m, 6H), 3.11 (s, 3H), 1.86-2.18 (m, 4H) | 506.2 |
| 100 | N-(1-(4-(2-(2-Oxopyrrolidin-1-yl)-4-(trifluoromethyl) phenoxy) piperidine-1-carbonyl)-1H-pyrazol-3-yl) methane-sulfonamide | 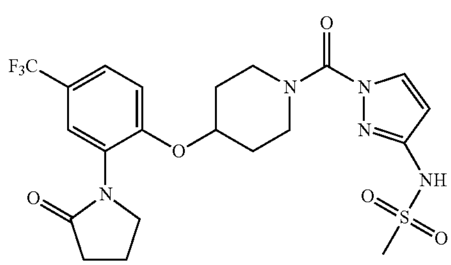 [SMILES: CS(=O)(=O)Nc1ccn(C(=O)N2CCC(Oc3ccc(C(F)(F)F)cc3N3CCCC3=O)CC2)n1] | (Dimethyl sulfoxide-$d_6$) δ 8.10 (d, J = 2.7 Hz, 1H), 7.63-7.66 (m, 2H), 7.40 (d, J = 9.3 Hz, 1H), 6.16 (d, J = 2.7 Hz, 1H), 4.90 (br, 1H), 3.76-3.85 (m, 3H), 3.69-3.73 (m, 3H), 3.14 (s, 3H), 2.38-2.43 (m, 2H), 2.02-2.15 (m, 4H), 1.76-1.81 (m, 2H) | 516.2 |
| 101 | N-(1-(4-(2-(Pyrrolidine-1-carbonyl)-4-(trifluoromethyl) phenoxy) piperidine-1-carbonyl)-1H-pyrazol-3-yl) methane-sulfonamide | 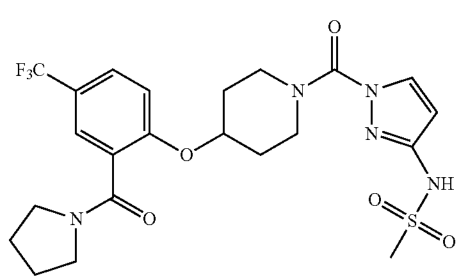 [SMILES: CS(=O)(=O)Nc1ccn(C(=O)N2CCC(Oc3ccc(C(F)(F)F)cc3C(=O)N3CCCC3)CC2)n1] | δ 8.03 (d, J = 3.0 Hz, 1H), 7.58-7.61 (m, 2H), 7.34 (s, 1H), 7.04 (d, J = 8.4 Hz, 1H), 6.30 (d, J = 3.0 Hz, 1H), 4.75 (br, 1H), 3.92-3.97 (m, 2H), 3.76-3.83 (m, 2H), 3.63-3.67 (m, 2H), 3.23-3.28 (m, 2H), 3.12 (s, 3H), 1.85-2.08 (m, 8H) | 552.1 [M + Na]+ |

| Ex | Name | Structure | NMR (¹H NMR, 300 MHz or 400 MHz, chloroform-d) | MS [M + H]⁺ |
|---|---|---|---|---|
| 102 | (2-((Methyl(4-methyl-1-(3-(methyl-sulfonamido)-1H-pyrazole-1-carbonyl)piperidin-4-yl)amino)methyl)-5-(trifluoromethyl)phenyl)glycine | 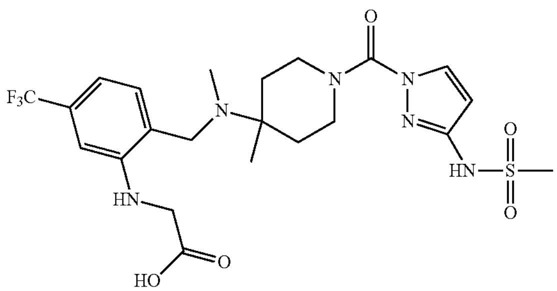 [SMILES: CN(Cc1ccc(C(F)(F)F)cc1NCC(=O)O)C1(C)CCN(C(=O)n2ccc(NS(C)(=O)=O)n2)CC1] | (Methanol-d₄) δ 8.05 (d, J = 2.7 Hz, 1H), 7.30-7.32 (m, 1H), 6.91-6.93 (m, 1H), 6.83 (s, 1H), 6.24 (d, J = 2.7 Hz, 1H), 4.28 (br, 2H), 3.98 (br, 2H), 3.82 (s, 2H), 3.48-3.52 (m, 2H), 3.13 (s, 3H), 2.27 (s, 3H), 2.10-2.15 (m, 2H), 1.87-1.92 (m, 2H), 1.33 (s, 3H) | 547.2 |
| 103 | N-(4-Methyl-1-(3-(methyl-sulfonamido)-1H-pyrazole-1-carbonyl)piperidin-4-yl)-N-(2-(pyrrolidin-1-yl)-4-(trifluoromethyl)benzyl)acetamide | 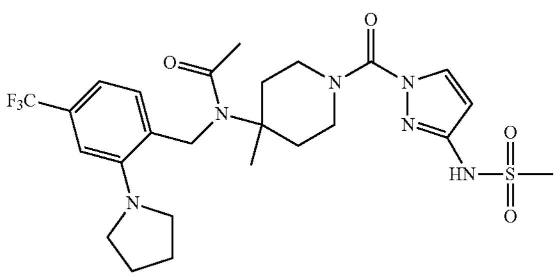 [SMILES: CC(=O)N(Cc1ccc(C(F)(F)F)cc1N1CCCC1)C1(C)CCN(C(=O)n2ccc(NS(C)(=O)=O)n2)CC1] | δ 7.98 (d, J = 2.7 Hz, 1H), 7.35-7.38 (m, 1H), 7.23-7.25 (m, 2H), 7.17 (br, 1H), 6.27 (d, J = 2.7 Hz, 1H), 4.53 (s, 2H), 4.20-4.24 (m, 2H), 3.15-3.30 (m, 6H), 3.07 (s, 3H), 2.00-2.19 (m, 11H), 1.54 (s, 3H) | 593.3 [M + Na]⁺ |
| 104 | N-(1-(4-((2-(4-(2-Hydroxyacetyl)piperazin-1-yl)-4-(trifluoromethyl)benzyl)(methyl)amino)-4-methyl-piperidine-1-carbonyl)-1H-pyrazol-3-yl)methane-sulfonamide | 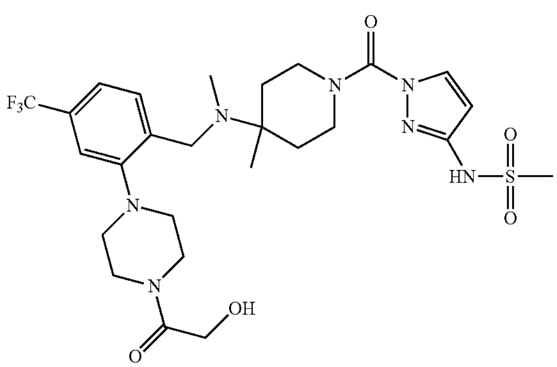 [SMILES: CN(Cc1ccc(C(F)(F)F)cc1N1CCN(C(=O)CO)CC1)C1(C)CCN(C(=O)n2ccc(NS(C)(=O)=O)n2)CC1] | δ 8.02 (d, J = 2.7 Hz, 1H), 7.78-7.81 (m, 1H), 7.27-7.42 (m, 2H), 6.32 (d, J = 2.7 Hz, 1H), 4.24 (s, 2H), 3.76-3.90 (m, 6H), 3.68 (br, 2H), 3.45 (br, 2H), 3.13 (s, 3H), 2.94 (br, 4H), 2.11 (s, 3H), 1.97-2.01 (m, 2H), 1.63-1.67 (m, 2H), 1.12 (s, 3H) | 616.6 |
| 105 | 4-(2-((8-(3-Acetamido-1H-pyrazole-1-carbonyl)-1,8-diazaspiro[4.5]decan-1-yl)methyl)-5-chlorophenoxy)butanoic acid | 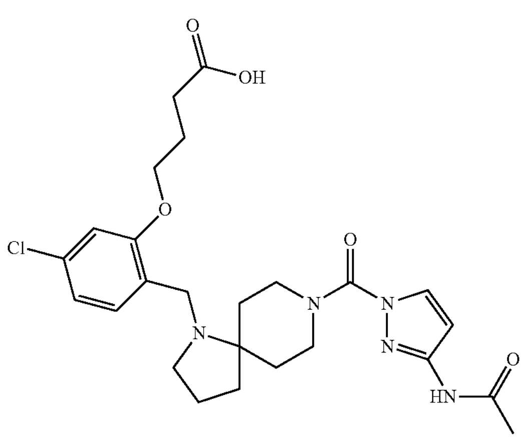 [SMILES: CC(=O)Nc1ccn(C(=O)N2CCC3(CCCN3Cc3ccc(Cl)cc3OCCCC(=O)O)CC2)n1] | (Methanol-d₄) δ 8.05 (s, 1H), 7.35 (d, J = 8.1 Hz, 1H), 7.10 (s, 1H), 6.97-7.00 (m, 1H), 6.81 (s, 1H), 4.73-4.76 (m, 2H), 4.11-4.15 (m, 4H), 3.07-3.30 (m, 4H), 2.38-2.43 (m, 2H), 2.22-2.27 (m, 4H), 2.02-2.18 (m, 7H), 1.80-1.87 (m, 2H) | 518.5 |

-continued

| Ex | Name | Structure | NMR (¹H NMR, 300 MHz or 400 MHz, chloroform-d) | MS [M + H]⁺ |
|---|---|---|---|---|
| 106 | 4-(2-((4-(3-Acetamido-1H-pyrazole-1-carbonyl)piperazin-1-yl)methyl)-5-chlorophenoxy)butanoic acid | 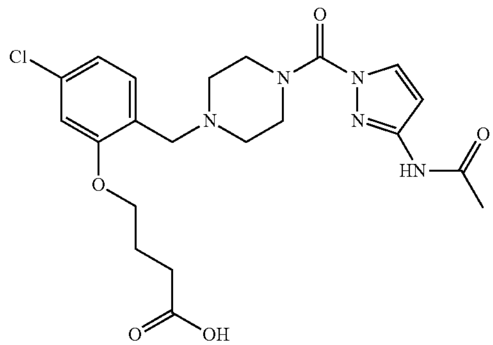 [SMILES: CC(=O)Nc1ccn(C(=O)N2CCN(Cc3ccc(Cl)cc3OCCCC(=O)O)CC2)n1] | (Methanol-d₄) δ 8.03-8.04 (m, 1H), 7.29 (d, J = 8.1 Hz, 1H), 6.93-7.02 (m, 2H), 6.79 (s, 1H), 3.93-4.08 (m, 2H), 3.76 (br, 4H), 3.68-3.76 (m, 2H), 2.77-2.78 (m, 4H), 2.41-2.46 (m, 2H), 2.12 (br, 5H) | 464.4 |
| 107 | N-(1-(4-((5-Fluoro-1H-indol-2-yl)methyl)piperazine-1-carbonyl)-1H-pyrazol-3-yl)methanesulfonamide | 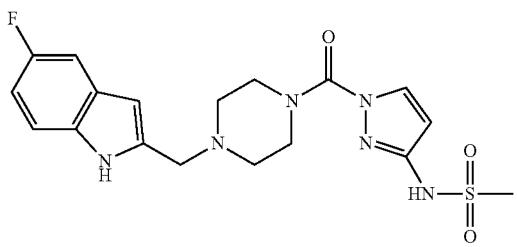 [SMILES: CS(=O)(=O)Nc1ccn(C(=O)N2CCN(Cc3cc4cc(F)ccc4[nH]3)CC2)n1] | δ 8.54 (s, 1H), 8.06 (s, 1H), 7.27 (s, 1H), 7.23-7.18 (m, 1H), 6.97-6.86 (m, 1H), 6.35 (s, 2H), 3.87 (s, 4H), 3.72 (s, 2H), 3.14 (s, 3H), 2.65-2.51 (m, 4H) | 421.2 |
| 108 | (2-((4-(3-Acetamido-1H-pyrazole-1-carbonyl)piperazin-1-yl)methyl)-5-chlorophenyl)glycine | 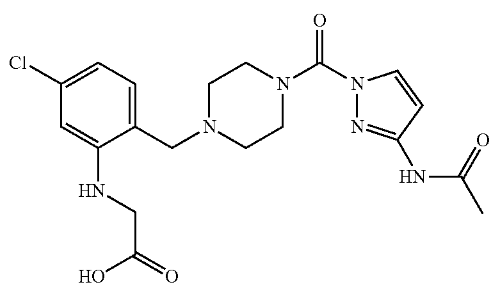 [SMILES: CC(=O)Nc1ccn(C(=O)N2CCN(Cc3ccc(Cl)cc3NCC(=O)O)CC2)n1] | (Methanol-d₄) δ 8.09 (s, 1H), 6.92-7.01 (m, 1H), 6.76-6.88 (m, 1H), 6.48-6.68 (m, 2H), 3.82-4.01 (m, 6H), 3.64 (s, 2H), 2.52 (bs, 4H), 2.11 (s, 3H) | 457.3 [M + Na]⁺ |
| 109 | N-(1-(4-(3-(4-Fluoropiperidin-1-yl)-4-(trifluoromethyl)phenoxy)piperidine-1-carbonyl)-1H-pyrazol-3-yl)methanesulfonamide | 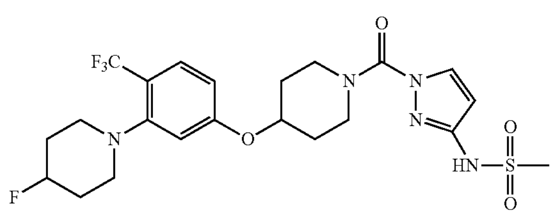 [SMILES: CS(=O)(=O)Nc1ccn(C(=O)N2CCC(Oc3ccc(C(F)(F)F)c(N4CCC(F)CC4)c3)CC2)n1] | δ 8.08 (d, J = 2.8 Hz, 1H), 7.56 (d, J = 8.8 Hz, 1H), 6.72-6.87 (m, 3H), 6.34 (d, J = 2.8 Hz, 1H), 4.74-4.95 (m, 1H), 4.65-4.72 (m, 1H), 3.93 (br, 4H), 3.48 (s, 3H), 3.12-3.06 (m, 2H), 2.83-2.89 (m, 2H), 1.90-2.18 (m, 8H) | 556.3 [M + Na]⁺ |
| 110 | N-(1-(4-(3-(Cyclopentyloxy)-4-(trifluoromethyl)phenoxy)piperidine-1-carbonyl)-1H-pyrazol-3-yl)methanesulfonamide | 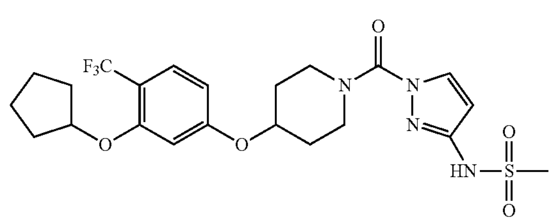 [SMILES: CS(=O)(=O)Nc1ccn(C(=O)N2CCC(Oc3ccc(C(F)(F)F)c(OC4CCCC4)c3)CC2)n1] | δ 8.07 (d, J = 2.8 Hz, 1H), 7.47 (d, J = 8.8 Hz, 1H), 7.15 (s, 1H), 6.53 (s, 1H), 6.46-6.49 (m, 1H), 6.34 (d, J = 2.8 Hz, 1H) 4.82-4.85 (m, 1H), 4.65-4.69 (m, 1H), 3.89-3.97 (m, 4H), 3.17 (s, 3H), 2.05-2.17 (m, 2H), 1.82-2.01 (m, 8H), 1.64-1.70 (m, 2H) | 539.2 [M + Na]⁺ |

| Ex | Name | Structure | NMR (¹H NMR, 300 MHz or 400 MHz, chloroform-d) | MS [M + H]⁺ |
|---|---|---|---|---|
| 111 | N-(1-(4-(4-Chloro-3-(cyclopentyl-oxy)benzyl)piperazine-1-carbonyl)-1H-pyrazol-3-yl)methane-sulfonamide | 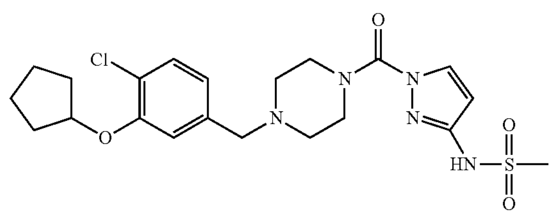 [SMILES: CS(=O)(=O)Nc1ccn(C(=O)N2CCN(Cc3ccc(Cl)c(OC4CCCC4)c3)CC2)n1] | δ 8.04 (d, J = 2.7 Hz, 1H), 7.29 (s, 1H), 6.94-6.96 (m, 2H), 6.80 (d, J = 8.1 Hz, 1H), 6.32 (d, J = 2.7 Hz, 1H), 4.82-4.83 (m, 1H), 3.84 (br, 4H), 3.50 (br, 2H), 3.13 (s, 3H), 2.52 (br, 4H), 1.80-1.89 (m, 6H), 1.63-1.65 (m, 2H) | 482.2 |
| 112 | N-(1-(5-(3-(Trifluoro-methyl)benzyl)octahydropyrrolo[3,4-c]pyrrole-2-carbonyl)-1H-pyrazol-3-yl)acetamide | 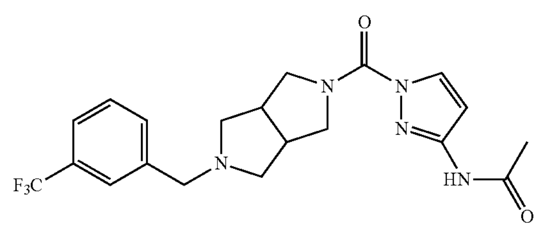 [SMILES: CC(=O)Nc1ccn(C(=O)N2CC3CN(Cc4cccc(C(F)(F)F)c4)CC3C2)n1] | δ 8.14 (d, J = 2.7 Hz, 1H), 7.79 (br, 1H), 7.40-7.57 (m, 4H), 6.88 (d, J = 2.7 Hz, 1H), 4.00-4.03 (m, 2H), 3.76-3.80 (m, 2H), 3.65 (s, 2H), 2.88 (br, 2H), 2.52-2.67 (m, 4H), 2.18 (s, 3H) | 422.2 |
| 113 | N-(1-(5-(3-(Trifluoro-methoxy)benzyl)octahydropyrrolo[3,4-c]pyrrole-2-carbonyl)-1H-pyrazol-3-yl)acetamide | 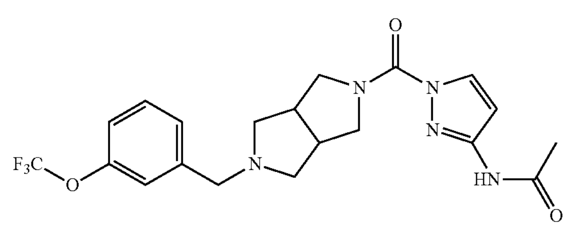 [SMILES: CC(=O)Nc1ccn(C(=O)N2CC3CN(Cc4cccc(OC(F)(F)F)c4)CC3C2)n1] | δ 8.14 (d, J = 2.7 Hz, 1H), 7.90 (br, 1H), 7.32 (t, J = 7.8 Hz, 1H), 7.19-7.25 (m, 2H), 7.10 (d, J = 8.1 Hz, 1H), 6.88 (d, J = 2.7 Hz, 1H), 4.02-4.04 (m, 2H), 3.75-3.78 (m, 2H), 3.61 (s, 2H), 2.87 (br, 2H), 2.52-2.64 (m, 4H), 2.18 (s, 3H) | 438.4 |
| 114 | N-(1-(5-(3-(Trifluoro-methyl)benzyl)octahydropyrrolo[3,4-c]pyrrole-2-carbonyl)-1H-pyrazol-3-yl)methane-sulfonamide | 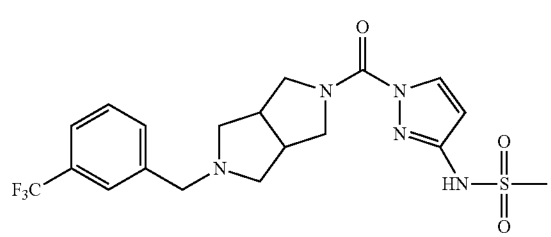 [SMILES: CS(=O)(=O)Nc1ccn(C(=O)N2CC3CN(Cc4cccc(C(F)(F)F)c4)CC3C2)n1] | δ 8.16 (d, J = 2.7 Hz, 1H), 7.49-7.56 (m, 3H), 7.42 (t, J = 7.5 Hz, 1H), 6.31 (d, J = 2.7 Hz, 1H), 4.04 (br, 2H), 3.75-3.79 (m, 2H), 3.65 (s, 2H), 3.13 (s, 3H), 2.90 (br, 2H), 2.54-2.66 (m, 4H) | 458.2 |
| 115 | N-(1-(5-(3-(Trifluoro-methoxy)benzyl)octahydropyrrolo[3,4-c]pyrrole-2-carbonyl)-1H-pyrazol-3-yl)methane-sulfonamide | 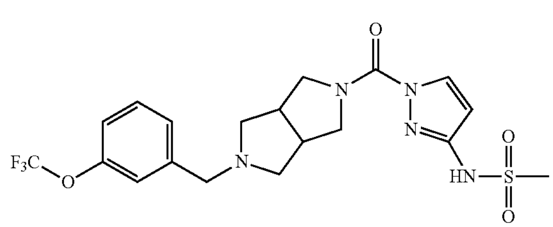 [SMILES: CS(=O)(=O)Nc1ccn(C(=O)N2CC3CN(Cc4cccc(OC(F)(F)F)c4)CC3C2)n1] | δ 8.15-8.16 (m, 1H), 7.31 (t, J = 7.8 Hz, 1H), 7.18-7.24 (m, 2H), 7.09 (d, J = 8.1 Hz, 1H), 6.28-6.29 (m, 1H), 4.03 (br, 2H), 3.75-3.79 (m, 2H), 3.62 (s, 2H), 3.13 (s, 3H), 2.89 (br, 2H), 2.53-2.66 (m, 4H) | 474.1 |

| Ex | Name | Structure | NMR (¹H NMR, 300 MHz or 400 MHz, chloroform-d) | MS [M + H]⁺ |
|---|---|---|---|---|
| 116 | N-(1-(4-(3-(1,3,4-Oxadiazol-2-yl)-4-(trifluoromethyl)benzyl)piperazine-1-carbonyl)-1H-pyrazol-3-yl)methanesulfonamide | 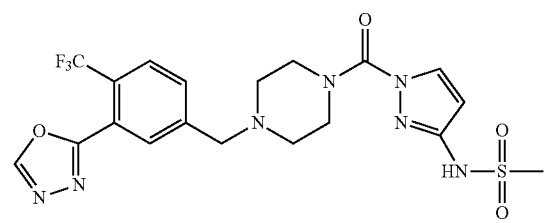 [SMILES: CS(=O)(=O)Nc1ccn(C(=O)N2CCN(Cc3ccc(C(F)(F)F)c(-c4nnco4)c3)CC2)n1] | δ 8.62 (s, 1H), 8.05-8.07 (m, 2H), 7.86 (d, J = 8.0 Hz, 1H), 7.71 (d, J = 8.0 Hz, 1H), 7.43 (br, 1H), 6.32 (d, J = 2.8 Hz, 1H), 3.87 (br, 4H), 3.68 (s, 2H), 3.16 (s, 3H), 2.58 (t, J = 4.8 Hz, 4H) | 522.2 [M + Na]⁺ |
| 117 | (S)-N-(1-(4-(4-Chloro-3-(3-fluoropyrrolidin-1-yl)benzyl)piperazine-1-carbonyl)-1H-pyrazol-3-yl)methanesulfonamide | 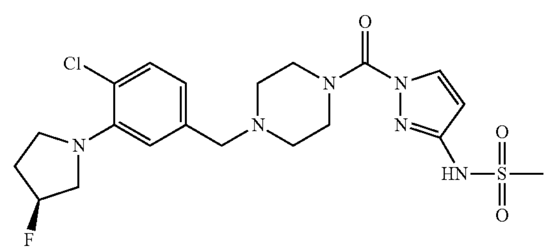 [SMILES: CS(=O)(=O)Nc1ccn(C(=O)N2CCN(Cc3ccc(Cl)c(N4CC[C@H](F)C4)c3)CC2)n1] | δ 8.05 (d, J = 2.8 Hz, 1H), 7.27-7.28 (m, 1H), 6.91 (br, 1H), 6.79-6.81 (m, 1H), 6.32 (d, J = 2.8 Hz, 1H), 5.26-5.42 (m, 1H), 3.87-4.06 (m, 5H), 3.64-3.70 (m, 1H), 3.45-3.55 (m, 3H), 3.32-3.37 (m, 1H), 3.14 (s, 3H), 2.56 (br, 4H), 2.10-2.32 (m, 2H) | 485.4 |
| 118 | 4-(((3R,4S)-1-(3-Acetamido-1H-pyrazole-1-carbonyl)-3-fluoropiperidin-4-yl)oxy)-2-(trifluoromethyl)benzamide | 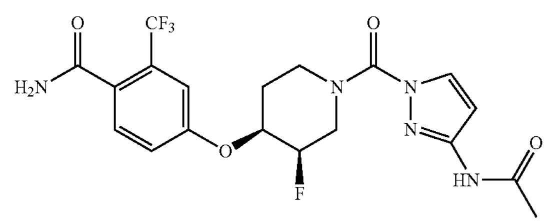 [SMILES: CC(=O)Nc1ccn(C(=O)N2CC[C@H](Oc3ccc(C(N)=O)c(C(F)(F)F)c3)[C@H](F)C2)n1] | δ 8.05 (d, J = 2.8 Hz, 1H), 7.84 (br, 1H), 7.60 (d, J = 8.4 Hz, 1H), 7.30 (s, 1H), 7.15-7.19 (m, 1H), 6.92 (d, J = 2.8 Hz, 1H), 5.83 (br, 2H), 4.72-4.98 (m, 2H), 4.25-4.34 (m, 1H), 3.95-4.17 (m, 2H), 3.79-3.83 (m, 1H), 2.20-2.27 (m, 4H), 1.97-2.05 (m, 1H) | 458.4 |
| 119 | (S)-N-(1-(4-(3-(3-Fluoropyrrolidin-1-yl)-4-(trifluoromethyl)benzyl)piperazine-1-carbonyl)-1H-pyrazol-3-yl)methanesulfonamide | 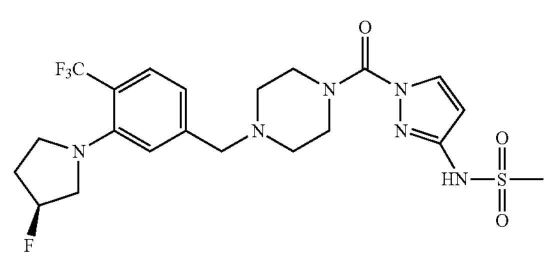 | δ 8.04 (d, J = 3.0 Hz, 1H), 7.54 (d, J = 8.1 Hz, 1H), 7.02 (s, 1H), 6.90 (d, J = 8.1 Hz, 1H), 6.31 (d, J = 3.0 Hz, 1H), 5.22-5.42 (m, 1H), 3.81-3.85 (m, 4H), 3.31-3.74 (m, 6H), 3.13 (s, 3H), 2.54 (br, 4H), 2.05-2.33 (m, 2H) | 519.2 |
| 120 | (R)-N-(1-(4-(3-(3-Fluoropyrrolidin-1-yl)-4-(trifluoromethyl)benzyl)piperazine-1-carbonyl)-1H-pyrazol-3-yl)methanesulfonamide | 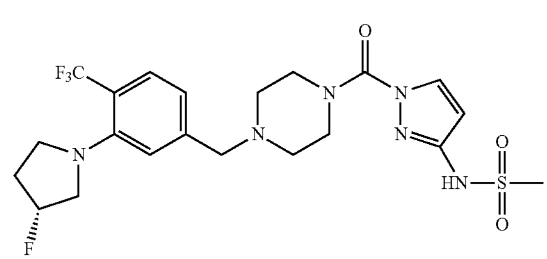 [SMILES: CS(=O)(=O)Nc1ccn(C(=O)N2CCN(Cc3ccc(C(F)(F)F)c(N4CC[C@@H](F)C4)c3)CC2)n1] | δ 8.04 (d, J = 2.7 Hz, 1H), 7.53-7.56 (m, 1H), 7.03 (br, 1H), 6.89-6.91 (m, 1H), 6.32 (d, J = 2.7 Hz, 1H), 5.22-5.42 (m, 1H), 3.82-3.87 (m, 4H), 3.31-3.74 (m, 6H), 3.13 (s, 3H), 2.56 (br, 4H), 2.05-2.33 (m, 2H) | 519.5 |

| Ex | Name | Structure | NMR (¹H NMR, 300 MHz or 400 MHz, chloroform-d) | MS [M + H]⁺ |
|---|---|---|---|---|
| 121 | N-(1-(5-(4-(Pyrrolidin-1-yl)-2-(trifluoromethyl)benzyl)octahydropyrrolo[3,4-c]pyrrole-2-carbonyl)-1H-pyrazol-3-yl)acetamide | 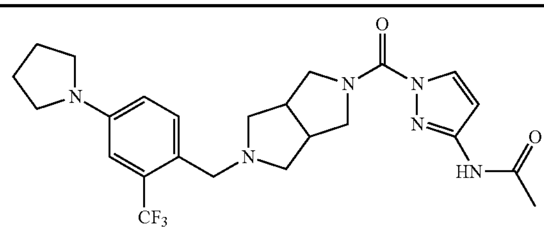 | δ 8.16 (d, J = 2.8 Hz, 1H), 7.84 (br, 1H), 7.46-7.49 (m, 1H), 6.89 (s, 1H), 6.76 (s, d, J = 2.8 Hz, 1H), 6.64-6.67 (m, 1H), 4.11 (br, 2H), 3.72-3.74 (m, 2H), 3.67 (s, 2H), 3.29-3.33 (m, 4H), 2.87 (br, 2H), 2.57-2.64 (m, 4H), 2.20 (s, 3H), 2.01-2.07 (m, 4H) | 491.5 |
| 122 | (R)-N-(1-(4-(4-Chloro-3-(3-fluoropyrrolidin-1-yl)benzyl)piperazine-1-carbonyl)-1H-pyrazol-3-yl)methanesulfonamide | 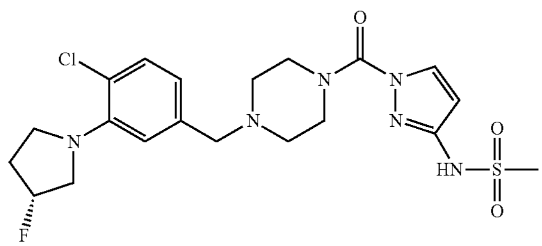 [SMILES: CS(=O)(=O)Nc1ccn(C(=O)N2CCN(Cc3ccc(Cl)c(N4CC[C@@H](F)C4)c3)CC2)n1] | δ 8.04 (d, J = 2.7 Hz, 1H), 7.24-7.26 (m, 1H), 6.89 (br, 1H), 6.76-6.80 (m, 1H), 6.32 (d, J = 2.7 Hz, 1H), 5.22-5.41 (m, 1H), 4.01-4.07 (m, 1H), 3.70-3.95 (m, 4H), 3.61-3.68 (m, 1H), 3.42-3.55 (m, 3H), 3.30-3.36 (m, 1H), 3.13 (s, 3H), 2.54 (br, 4H), 2.01-2.31 (m, 2H) | 485.4 |
| 123 | 4-((4-(3-Acetamido-1H-pyrazole-1-carbonyl)piperazin-1-yl)methyl)-2-(trifluoromethyl)benzamide | 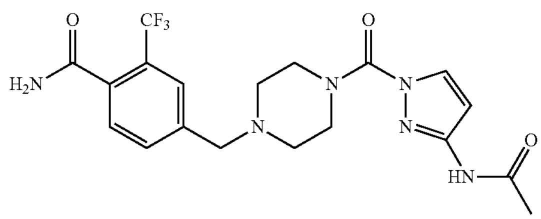 [SMILES: CC(=O)Nc1ccn(C(=O)N2CCN(Cc3ccc(C(N)=O)c(C(F)(F)F)c3)CC2)n1] | (Methanol-d₄) δ 8.05 (d, J = 2.8 Hz, 1H), 7.79 (s, 1H), 7.70 (d, J = 7.6 Hz, 1H), 7.57 (d, J = 8.0 Hz, 1H), 6.81 (d, J = 2.8 Hz, 1H), 3.89 (s, 4H), 3.70 (s, 2H), 2.57-2.59 (m, 4H), 2.13 (s, 3H) | 439.4 |
| 124 | 4-((5-(3-Acetamido-1H-pyrazole-1-carbonyl)hexahydropyrrolo[3,4-c]pyrrol-2(1H)-yl)methyl)-2-(trifluoromethyl)benzamide | 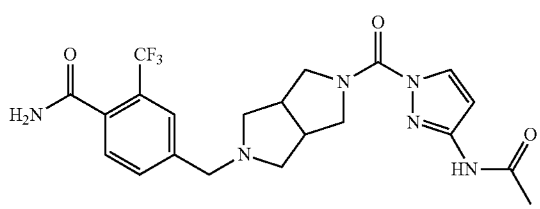 [SMILES: CC(=O)Nc1ccn(C(=O)N2CC3CN(Cc4ccc(C(N)=O)c(C(F)(F)F)c4)CC3C2)n1] | (Methanol-d₄) δ 8.14 (d, J = 2.8 Hz, 1H), 7.73 (s, 1H), 7.66 (d, J = 8.0 Hz, 1H), 7.54 (d, J = 7.6 Hz, 1H), 6.82 (d, J = 2.8 Hz, 1H), 3.91-3.99 (m, 4H), 3.72 (s, 2H), 2.94-2.95 (m, 2H), 2.69-2.71 (m, 2H), 2.55-2.57 (m, 2H), 2.14 (s, 3H) | 465.5 |
| 125 | 4-((8-(3-Acetamido-1H-pyrazole-1-carbonyl)-2,8-diazaspiro[4.5]decan-2-yl)methyl)-2-(trifluoromethyl)benzamide | 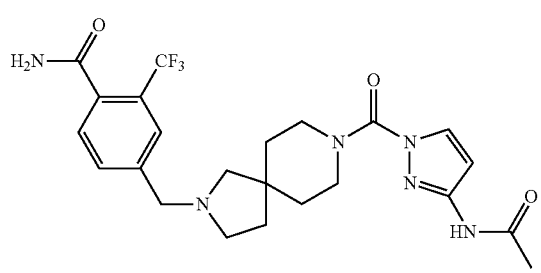 [SMILES: CC(=O)Nc1ccn(C(=O)N2CCC3(CCN(Cc4ccc(C(N)=O)c(C(F)(F)F)c4)C3)CC2)n1] | (Methanol-d₄) δ 8.02 (d, J = 2.8 Hz, 1H), 7.77 (s, 1H), 7.68 (d, J = 8.0 Hz, 1H), 7.56 (d, J = 8.0 Hz, 1H), 6.80 (d, J = 2.8 Hz, 1H), 3.80-3.84 (m, 2H), 3.69-3.71 (m, 4H), 2.67-2.71 (m, 2H), 2.52 (s, 2H), 2.14 (s, 3H), 1.76-1.80 (m, 2H), 1.68-1.73 (m, 4H) | 493.5 |

-continued

| Ex | Name | Structure | NMR (¹H NMR, 300 MHz or 400 MHz, chloroform-d) | MS [M + H]⁺ |
|---|---|---|---|---|
| 126 | 4-((7-(3-Acetamido-1H-pyrazole-1-carbonyl)-2,7-diazaspiro[3.5]nonan-2-yl)methyl)-2-(trifluoromethyl)benzamide | 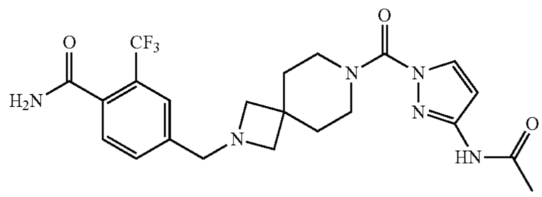 [SMILES: CC(=O)Nc1ccn(C(=O)N2CCC3(CC2)CN(Cc2ccc(C(N)=O)c(C(F)(F)F)c2)C3)n1] | (Methanol-d₄) δ 8.01 (d, J = 3.0 Hz, 1H), 7.73 (s, 1H) 7.64 (d, J = 7.8 Hz, 1H), 7.56 (d, J = 7.8 Hz, 1H), 6.80 (d, J = 2.7 Hz, 1H), 3.72-3.81 (m, 6H), 3.20 (s, 4H), 2.14 (s, 3H), 1.89-1.92 (m, 4H) | 479.5 |
| 127 | N-(1-(4-(3-(Trifluoromethyl)benzyl)piperazine-1-carbonyl)-1H-pyrazol-3-yl)acetamide | 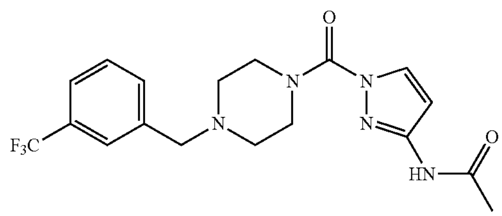 [SMILES: CC(=O)Nc1ccn(C(=O)N2CCN(Cc3cccc(C(F)(F)F)c3)CC2)n1] | δ 8.01 (d, J = 2.7 Hz, 1H), 7.72 (br, 1H), 7.60 (s, 1H), 7.52-7.54 (m, 2H), 7.42-7.47 (m, 1H), 6.87 (d, J = 2.7 Hz, 1H), 3.85 (br, 4H), 3.59 (s, 2H), 2.51-2.54 (m, 4H), 2.17 (s, 3H) | 396.5 |
| 128 | N-(1-(4-(3-(Trifluoromethoxy)benzyl)piperazine-1-carbonyl)-1H-pyrazol-3-yl)acetamide | 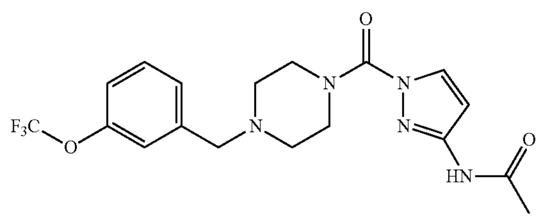 [SMILES: CC(=O)Nc1ccn(C(=O)N2CCN(Cc3cccc(OC(F)(F)F)c3)CC2)n1] | δ 8.01 (d, J = 2.7 Hz, 1H), 7.77 (br, 1H), 7.32-7.38 (m, 1H), 7.23-7.24 (m, 1H), 7.11-7.14 (m, 1H), 6.87 (d, J = 2.7 Hz, 1H), 3.86 (br, 4H), 3.56 (s, 2H), 2.51-2.54 (m, 4H), 2.17 (s, 3H) | 412.5 |
| 129 | N-(1-(4-(2-Methyl-3-(trifluoromethyl)benzyl)piperazine-1-carbonyl)-1H-pyrazol-3-yl)acetamide | 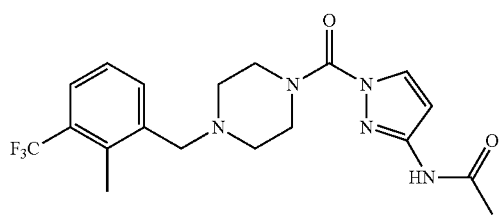 [SMILES: CC(=O)Nc1ccn(C(=O)N2CCN(Cc3cccc(C(F)(F)F)c3C)CC2)n1] | δ 8.01 (d, J = 2.7 Hz, 1H), 7.70 (br, 1H), 7.56-7.61 (m, 1H), 7.43-7.45 (m, 1H), 7.21-7.24 (m, 1H), 6.88 (d, J = 2.7 Hz, 1H), 3.82 (br, 4H), 3.55 (br, 2H), 2.49-2.53 (m, 7H), 2.18 (s, 3H) | 410.5 |
| 130 | 4-(((1-(3-Acetamido-1H-pyrazole-1-carbonyl)-4-methylpiperidin-4-yl)(methyl)amino)methyl)-2-(trifluoromethyl)benzamide | 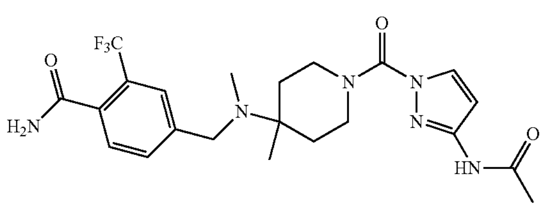 [SMILES: CC(=O)Nc1ccn(C(=O)N2CCC(C)(N(C)Cc3ccc(C(N)=O)c(C(F)(F)F)c3)CC2)n1] | (Methanol-d₄) δ 8.02 (d, J = 2.8 Hz, 1H), 7.74 (s, 1H), 7.70 (d, J = 8.0 Hz, 1H), 7.54 (d, J = 8.0 Hz, 1H), 6.79 (d, J = 2.8 Hz, 1H), 3.85-3.91 (m, 2H), 3.79-3.82 (m, 2H), 3.72 (s, 2H), 2.11-2.12 (m, 6H), 2.01-2.05 (m, 2H), 1.63-1.70 (m, 2H), 1.12 (s, 3H) | 481.5 |
| 131 | N-(1-(4-((3-Methyl-[1,1'-biphenyl]-4-yl)methyl)piperazine-1-carbonyl)-1H-pyrazol-3-yl)acetamide | 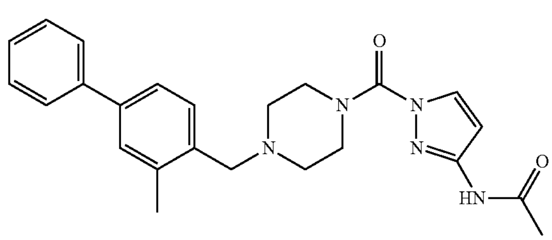 [SMILES: CC(=O)Nc1ccn(C(=O)N2CCN(Cc3ccc(-c4ccccc4)cc3C)CC2)n1] | δ 8.02 (d, J = 2.7 Hz, 1H), 7.74 (br, 1H), 7.57-7.60 (m, 2H), 7.41-7.46 (m, 3H), 7.26-7.38 (m, 3H), 6.89 (d, J = 2.7 Hz, 1H), 3.84 (br, 4H), 3.57 (br, 2H), 2.58 (br, 4H), 2.44 (s, 3H), 2.18 (s, 3H) | 418.5 |

| Ex | Name | Structure | NMR (¹H NMR, 300 MHz or 400 MHz, chloroform-d) | MS [M + H]⁺ |
|---|---|---|---|---|
| 132 | 1-(3-(((1-(3-Acetamido-1H-pyrazole-1-carbonyl)-4-methyl-piperidin-4-yl)(methyl)amino)methyl)-5-(trifluoromethyl)phenyl)cyclopentane-1-carboxylic acid | 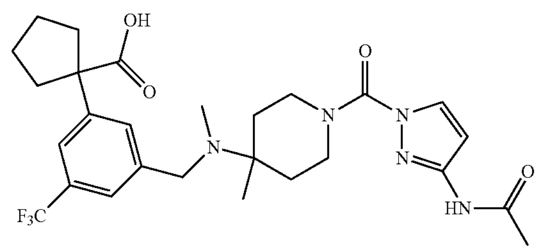 [SMILES: CC(=O)Nc1ccn(C(=O)N2CCC(C)(N(C)Cc3cc(C(F)(F)F)cc(C4(C(=O)O)CCCC4)c3)CC2)n1] | (Methanol-d₄) δ 8.02 (d, J = 2.7 Hz, 1H), 7.71 (s, 1H), 7.56 (s, 1H), 7.52 (s, 1H), 6.79 (d, J = 2.7 Hz, 1H), 3.83-3.92 (m, 4H), 3.78 (s, 2H), 2.66-2.70 (m, 2H), 2.20 (s, 3H), 2.12 (s, 3H), 2.02-2.07 (m, 2H), 1.83-1.89 (m, 2H), 1.68-1.76 (m, 6H), 1.18 (s, 3H) | 572.2 [M + Na]⁺ |
| 133 | N-(1-((3R)-4-(4-Chloro-3-(tetrahydro-1H-furo[3,4-c]pyrrol-5(3H)-yl)benzyl)-3-methyl-piperazine-1-carbonyl)-1H-pyrazol-3-yl)methanesulfonamide | 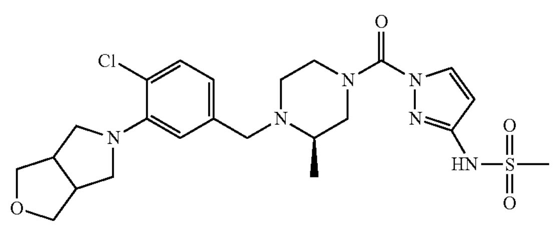 [SMILES: C[C@@H]1CN(C(=O)n2ccc(NS(C)(=O)=O)n2)CCN1Cc1ccc(Cl)c(N2CC3COCC3C2)c1] | δ 8.05 (d, J = 2.8 Hz, 1H), 7.12-7.29 (m, 1H), 7.03 (br, 1H), 6.90-6.95 (m, 2H), 6.32 (d, J = 2.8 Hz, 1H), 4.17 (br, 2H), 3.96-4.02 (m, 3H), 3.68-3.71 (m, 2H), 3.42 (br, 1H), 3.31-3.35 (m, 2H), 3.15-3.20 (m, 7H), 2.98-3.03 (m, 2H), 2.74-2.77 (m, 1H), 2.61 (br, 1H), 2.21-2.25 (m, 1H), 1.19 (d, J = 5.2 Hz, 3H) | 523.5 |
| 134 | N-(1-((3R,4S)-3-Fluoro-4-(3-(4-fluoropiperidin-1-yl)-4-(trifluoromethyl)phenoxy)piperidine-1-carbonyl)-1H-pyrazol-3-yl)methanesulfonamide | 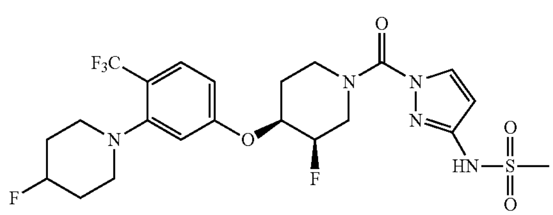 [SMILES: CS(=O)(=O)Nc1ccn(C(=O)N2CC[C@H](Oc3ccc(C(F)(F)F)c(N4CCC(F)CC4)c3)[C@H](F)C2)n1] | δ 8.07 (d, J = 2.8 Hz, 1H), 7.55 (d, J = 8.9 Hz, 1H), 7.03 (br, 1H), 6.88-6.95 (m, 1H), 6.70-6.81 (m, 1H), 6.33 (d, J = 2.8 Hz, 1H), 4.86-5.05 (m, 1H), 4.60-4.86 (m, 2H), 4.30-4.50 (m, 1H), 3.87-4.16 (m, 2H), 3.62-3.79 (m, 1H), 3.17 (s, 3H), 3.00-3.13 (m, 2H), 2.77-2.90 (m, 2H), 2.15-2.32 (m, 1H), 1.89-2.15 (m, 5H) | 551.9 |
| 135 | N-(1-((2S)-4-(4-Chloro-3-(tetrahydro-1H-furo[3,4-c]pyrrol-5(3H)-yl)benzyl)-2-methyl-piperazine-1-carbonyl)-1H-pyrazol-3-yl)methanesulfonamide | 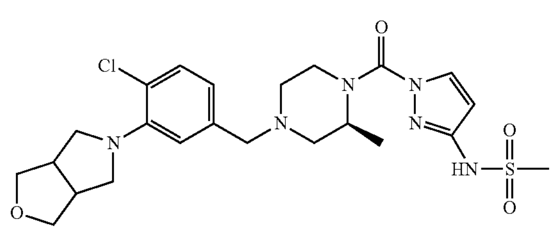 [SMILES: C[C@H]1CN(Cc2ccc(Cl)c(N3CC4COCC4C3)c2)CCN1C(=O)n1ccc(NS(C)(=O)=O)n1] | δ 8.05 (d, J = 2.8 Hz, 1H), 7.28 (s, 1H), 6.89-7.01 (m, 3H), 6.32 (d, J = 2.8 Hz, 1H), 4.71 (br, 1H), 4.35-4.38 (m, 1H), 4.01-4.04 (m, 2H), 3.69-3.71 (m, 2H), 3.28-3.55 (m, 5H), 3.15-3.27 (m, 5H), 2.88-2.99 (m, 3H), 2.70 (br, 1H), 2.25 (br, 2H), 1.47 (d, J = 5.2 Hz, 3H) | 523.5 |

| Ex | Name | Structure | NMR (¹H NMR, 300 MHz or 400 MHz, chloroform-d) | MS [M + H]⁺ |
|---|---|---|---|---|
| 136 | (S)-N-(1-(4-(4-Chloro-3-(4-fluoro-piperidin-1-yl)benzyl)-2-methyl-piperazine-1-carbonyl)-1H-pyrazol-3-yl)methane-sulfonamide | 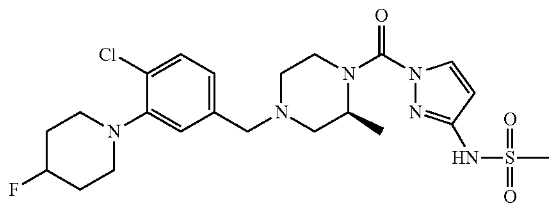 [SMILES: C[C@H]1CN(Cc2ccc(Cl)c(N3CCC(F)CC3)c2)CCN1C(=O)n1ccc(NS(C)(=O)=O)n1] | δ 8.03 (d, J = 2.7 Hz, 1H), 7.30 (d, J = 8.1 Hz, 1H), 7.07 (s, 1H), 6.93 (d, J = 8.1 Hz, 1H), 6.86 (br, 1H), 6.30 (d, J = 2.7 Hz, 1H), 4.90-4.94 (m, 1H), 4.67-4.78 (m, 1H), 4.31-4.36 (m, 1H), 3.32-3.56 (m, 3H), 3.12-3.17 (m, 5H), 2.98-3.04 (m, 2H), 2.83-2.90 (m, 1H), 2.62-2.66 (m, 1H), 2.05-2.25 (m, 6H), 1.49 (d, J = 6.9 Hz, 3H) | 513.4 |
| 137 | N-(1-((2R)-4-(4-Chloro-3-(tetrahydro-1H-furo[3,4-c]pyrrol-5(3H)-yl)benzyl)-2-methyl-piperazine-1-carbonyl)-1H-pyrazol-3-yl)methane-sulfonamide | 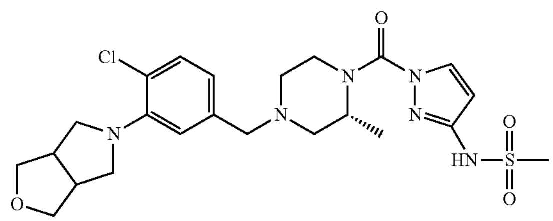 [SMILES: C[C@@H]1CN(Cc2ccc(Cl)c(N3CC4COCC4C3)c2)CCN1C(=O)n1ccc(NS(C)(=O)=O)n1] | δ 8.05 (d, J = 2.8 Hz, 1H), 7.30 (s, 1H), 7.01 (s, 1H), 6.91-6.92 (m, 1H), 6.83 (br, 1H), 6.32 (d, J = 2.8 Hz, 1H), 4.69 (br, 1H), 4.34-4.37 (m, 1H), 4.00-4.04 (m, 2H), 3.68-3.71 (m, 2H), 3.54-3.57 (m, 1H), 3.39-3.50 (m, 1H), 3.28-3.37 (m, 3H), 3.14-3.26 (m, 5H), 2.99 (br, 2H), 2.86-2.88 (m, 1H), 2.66-2.69 (m, 1H), 2.22-2.27 (m, 2H), 1.47 (d, J = 6 Hz, 3H) | 523.5 |
| 138 | (R)-N-(1-(4-(4-Chloro-3-(4-fluoro-piperidin-1-yl)benzyl)-3-methyl-piperazine-1-carbonyl)-1H-pyrazol-3-yl)methane-sulfonamide | 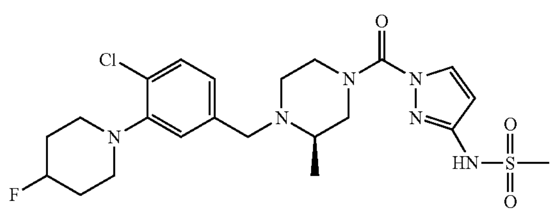 [SMILES: C[C@@H]1CN(C(=O)n2ccc(NS(C)(=O)=O)n2)CCN1Cc1ccc(Cl)c(N2CCC(F)CC2)c1] | δ 8.04 (d, J = 2.7 Hz, 1H), 7.30 (d, J = 7.8 Hz, 1H), 6.92-7.02 (m, 3H), 6.30 (d, J = 2.7 Hz, 1H), 4.75-4.94 (m, 1H), 4.15-4.18 (m, 2H), 3.94-3.98 (m, 1H), 3.37-3.44 (m, 1H), 3.13-3.25 (m, 7H), 2.98-3.04 (m, 2H), 2.72-2.75 (m, 1H), 2.59 (br, 1H), 2.01-2.25 (m, 5H), 1.18 (d, J = 6.3 Hz, 3H) | 513.0 |
| 139 | (R)-N-(1-(1-(4-Chloro-3-(4-fluoro-piperidin-1-yl)phenyl)ethyl)piperazine-1-carbonyl)-1H-pyrazol-3-yl)methane-sulfonamide | 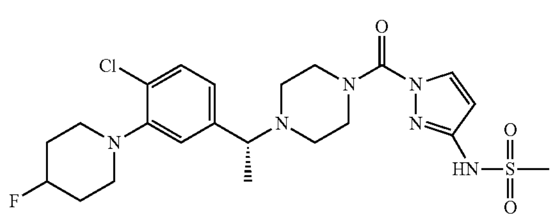 [SMILES: C[C@H](c1ccc(Cl)c(N2CCC(F)CC2)c1)N1CCN(C(=O)n2ccc(NS(C)(=O)=O)n2)CC1] | (Methanol-d₄) δ 7.97-8.09 (d, J = 2.7 Hz, 1H), 7.27-7.39 (d, J = 8.1 Hz, 1H), 7.08-7.18 (d, J = 1.8 Hz, 1H), 6.92-7.05 (d, J = 8.1 Hz, 1H), 6.17-6.31 (d, J = 2.7 Hz, 1H), 4.67-4.95 (m, 1H), 3.70-3.90 (br, 4H), 3.43-3.57 (m, 1H), 3.05-3.23 (m, 5H), 2.92-3.03 (m, 2H), 2.58-2.72 (m, 2H), 2.41-2.58 (m, | 512.9 |

| Ex | Name | Structure | NMR (¹H NMR, 300 MHz or 400 MHz, chloroform-d) | MS [M + H]⁺ |
|---|---|---|---|---|
| | | | 2H), 1.89-2.20 (m, 4H), 1.33-1.48 (d, J = 6.9 Hz, 3H) | |
| 140 | N-(1-(5-(4-chloro-3-(Tetrahydro-1H-furo[3,4-c]pyrrol-5(3H)-yl)benzyl) octahydro pyrrolo[3,4-c]pyrrole-2-carbonyl)-1H-pyrazol-3-yl) methane-sulfonamide | 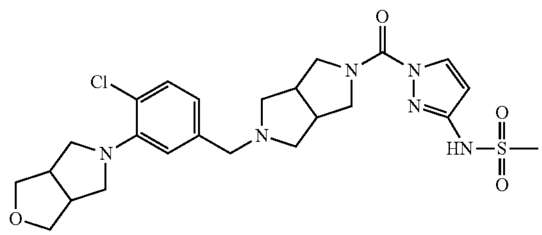 [SMILES: CS(=O)(=O)Nc1ccn(C(=O)N2CC3CN(Cc4ccc(Cl)c(N5CC6COCC6C5)c4)CC3C2)n1] | δ 8.17 (d, J = 2.8 Hz, 1H), 7.25 (s, 1H), 7.04 (br, 1H), 6.84-6.88 (m, 1H), 6.36 (d, J = 2.8 Hz, 1H), 4.11 (br, 2H), 3.93-3.96 (m, 2H), 3.71-3.74 (m, 4H), 3.57 (br, 2H), 3.41 (br, 2H), 3.13 (s, 3H), 2.82-3.07 (m, 6H), 2.56-2.61 (m, 4H) | 535.5 |
| 141 | N-(1-(4-(3-(4-Fluoro-piperidin-1-yl)-4-(trifluoromethyl) benzyl)-3-methyl-piperazine-1-carbonyl)-1H-pyrazol-3-yl) methane-sulfonamide | 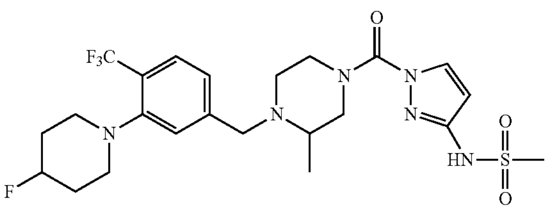 | δ 8.04 (s, 1H), 7.56 (d, J = 8.1 Hz, 1H), 7.33 (s, 1H), 7.18 (d, J = 8.1 Hz, 1H), 6.99 (br, 1H), 6.30 (s, 1H), 4.68-5.00 (m, 1H), 4.08-4.35 (m, 2H), 4.02 (m, 1H), 3.35-3.55 (m, 1H), 3.19-3.34 (m, 2H), 3.14 (s, 3H), 3.00-3.12 (m, 2H), 2.78-2.93 (m, 2H), 2.68-2.78 (m, 1H), 2.62 (m, 1H), 2.16-2.35 (m, 1H), 1.90-2.16 (m, 4H), 1.08-1.27 (m, 3H) | 547.0 |
| 142 | (R)-N-(1-(4-(4-Chloro-3-(4-fluoro-piperidin-1-yl)benzyl)-2-methyl-piperazine-1-carbonyl)-1H-pyrazol-3-yl) methane-sulfonamide | 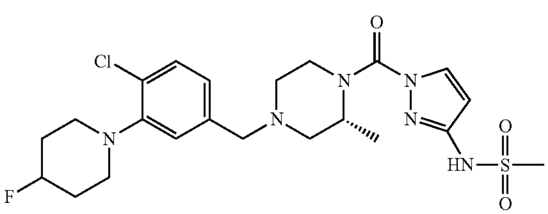 [SMILES: C[C@@H]1CN(Cc2ccc(Cl)c(N3CCC(F)CC3)c2)CCN1C(=O)n1ccc(NS(C)(=O)=O)n1] | δ 8.05 (d, J = 2.7 Hz, 1H), 7.32 (d, J = 7.8 Hz, 1H), 7.09 (s, 1H), 6.95 (d, J = 6.6 Hz, 2H), 6.32 (d, J = 2.7 Hz, 1H), 4.76-4.96 (m, 1H), 4.70 (br, 1H), 4.34-4.38 (m, 1H), 3.35-3.59 (m, 3H), 3.16-3.21 (m, 5H), 2.98-3.08 (m, 2H), 2.85-2.89 (m, 1H), 2.65-2.68 (m, 1H), 2.02-2.27 (m, 6H), 1.46 (d, J = 6.6 Hz, 3H) | 513.4 |
| 143 | N-(1-((3S)-4-(4-Chloro-3-(tetrahydro-1H-furo[3,4-c]pyrrol-5(3H)-yl)benzyl)-3-methyl-piperazine-1-carbonyl)-1H-pyrazol-3-yl) methane-sulfonamide | 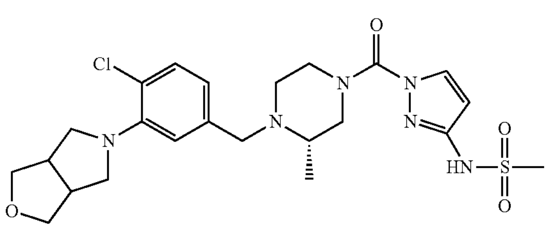 [SMILES: C[C@H]1CN(C(=O)n2ccc(NS(C)(=O)=O)n2)CCN1Cc1ccc(Cl)c(N2CC3COCC3C2)c1] | δ 8.04 (d, J = 2.7 Hz, 1H), 7.26-7.28 (m, 1H), 7.06 (br, 1H), 6.87-6.94 (m, 2H), 6.30 (d, J = 2.7 Hz, 1H), 4.15 (br, 2H), 3.96-3.99 (m, 3H), 3.65-3.69 (m, 2H), 3.42 (br, 1H), 3.14-3.36 (m, 9H), 2.96 (br, 2H), 2.74 (br, 1H), 2.61 (br, 1H), 2.23 (br, 1H), 1.19 (br, 3H) | 523.3 |

| Ex | Name | Structure | NMR (¹H NMR, 300 MHz or 400 MHz, chloroform-d) | MS [M + H]⁺ |
|---|---|---|---|---|
| 144 | N-(1-(4-(3,5-Dichlorobenzyl)piperazine-1-carbonyl)-1H-pyrazol-3-yl)acetamide | 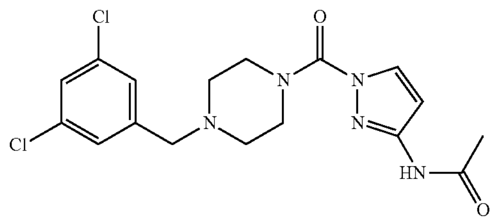 [SMILES: CC(=O)Nc1ccn(C(=O)N2CCN(Cc3cc(Cl)cc(Cl)c3)CC2)n1] | δ 8.02 (d, J = 2.7 Hz, 1H), 7.68-7.73 (m, 1H), 7.38-7.40 (m, 2H), 6.88 (d, J = 2.7 Hz, 1H), 3.87-4.00 (m, 4H), 3.39-3.64 (m, 2H), 2.40-2.71 (m, 4H), 2.18 (s, 3H) | 396.1 |
| 145 | N-(1-(5-(3-Chloro-5-fluorobenzyl)octahydropyrrolo[3,4-c]pyrrole-2-carbonyl)-1H-pyrazol-3-yl)acetamide | 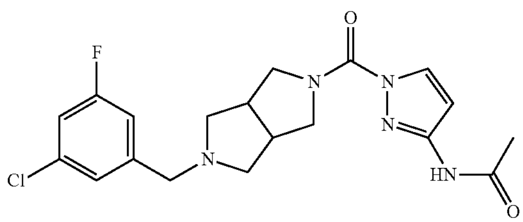 [SMILES: CC(=O)Nc1ccn(C(=O)N2CC3CN(Cc4cc(F)cc(Cl)c4)CC3C2)n1] | δ 8.14 (d, J = 2.7 Hz, 1H), 7.71 (br, 1H), 7.10 (s, 1H), 6.91-6.99 (m, 2H), 6.87 (d, J = 2.7 Hz, 1H), 4.03 (br, 2H), 3.77-3.81 (m, 2H), 3.55 (s, 2H), 2.88 (br, 2H), 2.54-2.63 (m, 4H), 2.18 (s, 3H) | 406.1 |
| 146 | N-(1-(5-(3-Chloro-5-(trifluoromethyl)benzyl)octahydropyrrolo[3,4-c]pyrrole-2-carbonyl)-1H-pyrazol-3-yl)acetamide | 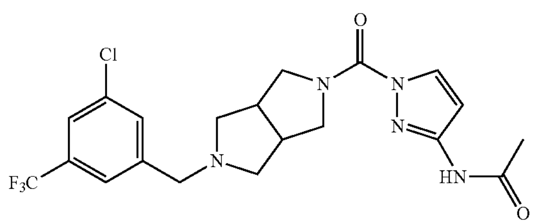 [SMILES: CC(=O)Nc1ccn(C(=O)N2CC3CN(Cc4cc(Cl)cc(C(F)(F)F)c4)CC3C2)n1] | δ 8.14 (d, J = 2.7 Hz, 1H), 7.71 (br, 1H), 7.47-7.53 (m, 3H), 6.88 (d, J = 2.7 Hz, 1H), 4.02 (br, 2H), 3.79-3.83 (m, 2H), 3.64 (s, 2H), 2.91 (br, 2H), 2.65 (br, 2H), 2.54-2.56 (m, 2H), 2.18 (s, 3H) | 456.1 |
| 147 | N-(1-(4-(4-Chloro-3-(4,4-difluoropiperidin-1-yl)benzyl)piperazine-1-carbonyl)-1H-pyrazol-3-yl)methanesulfonamide | 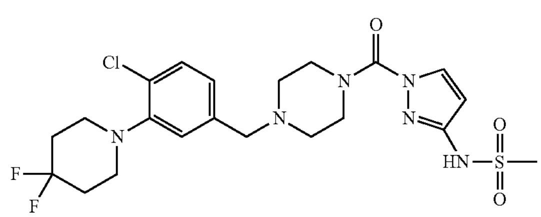 | (Methanol-d₄) δ 7.87-8.02 (m, 1H), 7.31-7.37 (m, 1H), 7.11-7.21 (m, 1H), 6.98-7.08 (m, 1H), 6.15-6.21 (m, 1H), 3.77-3.95 (m, 4H), 3.49-3.61 (m, 2H), 3.01-3.22 (m, 7H), 2.46-2.68 (m, 4H), 1.99-2.24 (m, 4H) | 517.2 |
| 148 | (S)-N-(1-(4-(4-Chloro-3-(4-fluoropiperidin-1-yl)benzyl)-3-methylpiperazine-1-carbonyl)-1H-pyrazol-3-yl)methanesulfonamide | 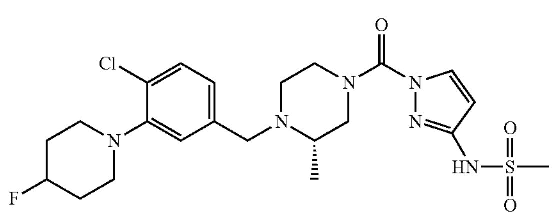 | δ 8.04 (d, J = 2.7 Hz, 1H), 7.30 (d, J = 8.1 Hz, 1H), 6.92-7.01 (m, 3H), 6.30 (d, J = 2.7 Hz, 1H), 4.75-4.95 (m, 1H), 4.15-4.18 (m, 2H), 3.94-3.98 (m, 1H), 3.36-3.44 (m, 1H), 3.13-3.25 (m, 7H), 2.98-3.04 (m, 2H), 2.71-2.75 (m, 1H), 2.57-2.61 (m, 1H), 1.99-2.24 (m, 5H), 1.15 (d, J = 6.3 Hz, 3H) | 535.2 [M + Na]⁺ |
| 149 | N-(1-(4-(3-(4-Chlorophenoxy)benzyl)piperazine-1-carbonyl)-1H-pyrazol-3-yl)methanesulfonamide | 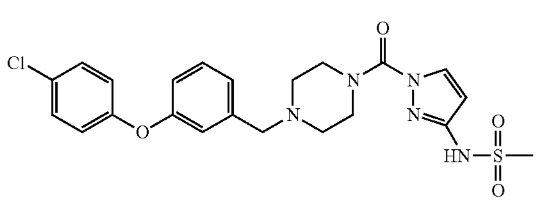 [SMILES: CS(=O)(=O)Nc1ccn(C(=O)N2CCN(Cc3cccc(Oc4ccc(Cl)cc4)c3)CC2)n1] | δ 8.04 (d, J = 2.7 Hz, 1H), 7.26-7.32 (m, 3H), 7.06-7.09 (m, 1H), 6.95-7.01 (m, 1H), 6.87-6.94 (m, 3H), 6.31 (d, J = 2.7 Hz, 1H), 3.83 (br, 4H), 3.53 (s, 2H), 3.13 (s, | 490.2 |

| Ex | Name | Structure | NMR (¹H NMR, 300 MHz or 400 MHz, chloroform-d) | MS [M + H]⁺ |
|---|---|---|---|---|
| | | | 3H), 2.51-2.54 (m, 4H) | |
| 150 | N-(1-(5-(4-Chloro-3-(2-hydroxypropan-2-yl)benzyl) octahydro pyrrolo[3,4-c] pyrrole-2-carbonyl)-1H-pyrazol-3-yl)acetamide | 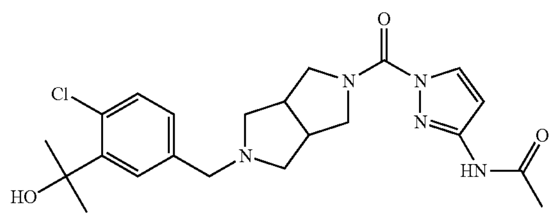 [SMILES: CC(=O)Nc1ccn(C(=O)N2CC3CN(Cc4ccc(Cl)c(C(C)(C)O)c4)CC3C2)n1] | δ 8.13 (d, J = 2.7 Hz, 1H), 8.03 (br, 1H), 7.68 (s, 1H), 7.27-7.30 (m, 1H), 7.09-7.12 (m, 1H), 6.88 (d, J = 2.7 Hz, 1H), 3.87-3.94 (m, 4H), 3.58 (s, 2H), 2.86-2.92 (m, 3H), 2.59-2.62 (m, 4H), 2.19 (s, 3H), 1.74 (s, 6H) | 446.2 |
| 151 | (S)-N-(1-(4-(3-(2-Methyl-pyrrolidin-1-yl)-4-(trifluoromethyl) benzyl) piperazine-1-carbonyl)-1H-pyrazol-3-yl)methane-sulfonamide | 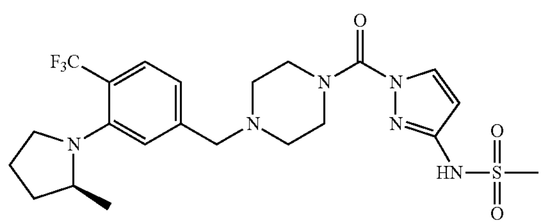 [SMILES: C[C@H]1CCCN1c1cc(CN2CCN(C(=O)n3ccc(NS(C)(=O)=O)n3)CC2)ccc1C(F)(F)F] | (Methanol-d₄) δ 7.96-8.09 (m, 1H), 7.26-7.61 (m, 2H), 7.05-7.16 (m, 1H), 6.12-6.26 (m, 1H), 3.44-3.97 (m, 8H), 3.08-3.17 (m, 3H), 2.81-2.96 (m, 1H), 2.46-2.64 (m, 4H), 2.07-2.25 (m, 1H), 1.75-2.02 (m, 2H), 1.48-1.65 (m, 1H), 0.94-1.05 (m, 3H) | 515.0 |
| 152 | N-(1-(4-(4-Chloro-3-(hexahydro-pyrrolo [3,4-c]pyrrol-2(1H)-yl) benzyl) piperazine-1-carbonyl)-1H-pyrazol-3-yl)methane-sulfonamide | 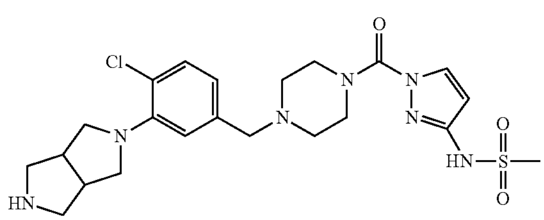 [SMILES: CS(=O)(=O)Nc1ccn(C(=O)N2CCN(Cc3ccc(Cl)c(N4CC5CNCC5C4)c3)CC2)n1] | (Pyridine-d₅) δ 8.40 (d, J = 2.8 Hz, 1H), 7.40-7.46 (m, 1H), 7.08 (s, 1H), 6.91-6.98 (m, 1H), 6.61 (d, J = 2.8 Hz, 1H), 3.94 (br, 4H), 3.42 (s, 2H), 3.34 (s, 3H), 3.10-3.18 (m, 4H), 2.99-3.01 (m, 2H), 2.80-2.85 (m, 2H), 2.63 (br, 2H), 2.44-2.47 (m, 4H) | 508.2 |
| 153 | N-(1-(4-(4-Chloro-3-(5-ethyl-hexahydro-pyrrolo [3,4-c]pyrrol-2(1H)-yl) benzyl) piperazine-1-carbonyl)-1H-pyrazol-3-yl)methane-sulfonamide | 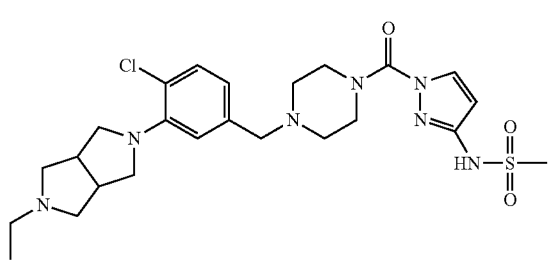 [SMILES: CCN1CC2CN(c3cc(CN4CCN(C(=O)n5ccc(NS(C)(=O)=O)n5)CC4)ccc3Cl)CC2C1] | (Methanol-d₄) δ 7.99 (d, J = 2.7 Hz, 1H), 7.28-7.31 (m, 1H), 7.10 (s, 1H), 6.95-6.98 (m, 1H), 6.18 (d, J = 2.7 Hz, 1H), 3.85 (br, 4H), 3.53 (s, 2H), 3.32-3.40 (m, 4H), 3.07 (s, 3H), 2.95-3.02 (m, 4H), 2.71-2.74 (m, 2H), 2.52-2.55 (m, 6H), 1.20 (t, J = 7.2 Hz, 3H) | 546.3 |

-continued

| Ex | Name | Structure | NMR (¹H NMR, 300 MHz or 400 MHz, chloroform-d) | MS [M + H]⁺ |
|---|---|---|---|---|
| 154 | N-(1-(2-(6-(Trifluoro-methyl)benzo[b]thiophene-2-carbonyl)-2,8-diazaspiro[4.5]decane-8-carbonyl)-1H-pyrazol-3-yl)acetamide | 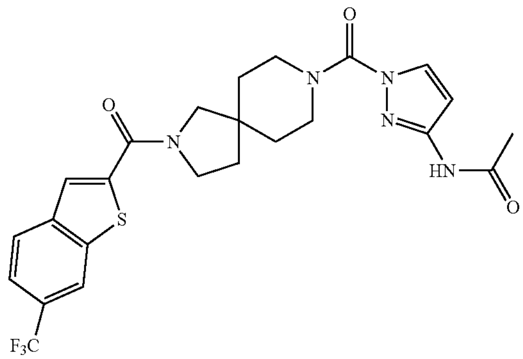 [SMILES: CC(=O)Nc1ccn(C(=O)N2CCC3(CCN(C(=O)c4cc5ccc(C(F)(F)F)cc5s4)C3)CC2)n1] | δ 8.16 (s, 1H), 7.93-8.02 (m, 2H), 7.61-7.77 (m, 3H), 6.88 (br, 1H), 3.94-4.03 (m, 2H), 3.62-3.83 (m, 5H), 2.19 (s, 3H), 1.98-2.02 (m, 2H), 1.74 (br, 5H) | 520.2 |
| 155 | N-(1-(1-(6-(Trifluoro-methyl)benzo[b]thiophene-2-carbonyl)-1,8-diazaspiro[4.5]decane-8-carbonyl)-1H-pyrazol-3-yl)acetamide | 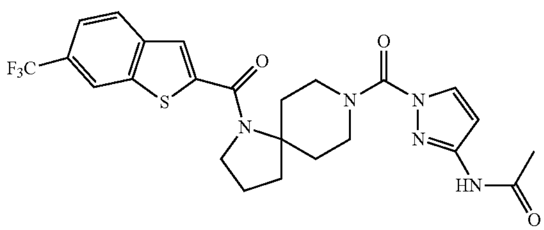 [SMILES: CC(=O)Nc1ccn(C(=O)N2CCC3(CCCN3C(=O)c3cc4ccc(C(F)(F)F)cc4s3)CC2)n1] | δ 8.15 (s, 1H), 7.98-8.01 (m, 2H), 7.90 (d, J = 8.4 Hz, 1H), 7.59-7.65 (m, 2H), 6.87 (d, J = 2.7 Hz, 1H), 4.57-4.60 (m, 2H), 3.91 (t, J = 6.6 Hz, 2H), 3.25-3.30 (m, 2H), 3.20-3.24 (m, 2H), 2.19 (s, 3H), 2.10-2.15 (m, 2H), 1.93-2.02 (m, 2H), 2.47-2.50 (m, 2H) | 520.2 |
| 156 | (R)-N-(1-(4-(3-(2-Methyl-pyrrolidin-1-yl)-4-(trifluoromethyl)benzyl)piperazine-1-carbonyl)-1H-pyrazol-3-yl)methane-sulfonamide | 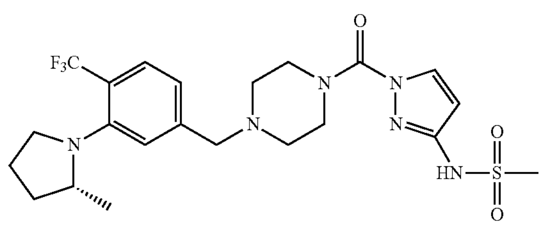 [SMILES: C[C@@H]1CCCN1c1cc(CN2CCN(C(=O)n3ccc(NS(C)(=O)=O)n3)CC2)ccc1C(F)(F)F] | (Methanol-d₄) δ 7.93-8.21 (m, 1H), 7.28-7.71 (m, 2H), 6.98-7.21 (m, 1H), 6.12-6.38 (m, 1H), 3.25-4.08 (m, 11H), 2.81-2.99 (m, 1H), 2.46-2.64 (m, 4H), 1.41-2.25 (m, 4H), 0.88-1.12 (m, 3H) | 515.0 |
| 157 | N-(1-(4-(3-((1R,4R)-2-Oxa-5-azabicyclo[2.2.1]heptan-5-yl)-4-chlorobenzyl)piperazine-1-carbonyl)-1H-pyrazol-3-yl)methane-sulfonamide | 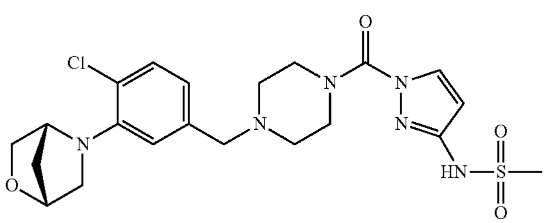 [SMILES: CS(=O)(=O)Nc1ccn(C(=O)N2CCN(Cc3ccc(Cl)c(N4C[C@H]5C[C@@H]4CO5)c3)CC2)n1] | δ 8.04 (d, J = 2.7 Hz, 1H), 7.24 (s, 1H), 6.72-6.91 (m, 2H), 6.32 (d, J = 2.7 Hz, 1H), 4.61 (s, 1H), 4.43 (s, 1H), 4.09-4.12 (m, 1H), 3.74-3.90 (m, 6H), 3.50 (br, 2H), 3.30-3.33 (m, 1H), 3.12 (s, 3H), 2.54 (br, 4H), 2.01-2.04 (m, 1H), 1.93-1.96 (m, 1H) | 517.1 [M + Na]⁺ |
| 158 | N-(1-(4-(4-Chloro-3-((4aS,7aR)-hexahydro-cyclopenta[b][1,4]oxazin-4(4aH)-yl)benzyl)piperazine-1-carbonyl)-1H-pyrazol-3-yl)methane-sulfonamide | 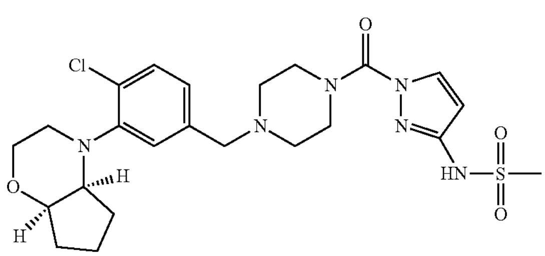 [SMILES: CS(=O)(=O)Nc1ccn(C(=O)N2CCN(Cc3ccc(Cl)c(N4CCO[C@@H]5CCC[C@@H]54)c3)CC2)n1] | δ 8.04 (d, J = 2.7 Hz, 1H), 7.28-7.30 (m, 1H), 7.02 (s, 1H), 6.90-6.93 (m, 1H), 6.32 (d, J = 2.7 Hz, 1H), 4.04 (br, 1H), 3.90-3.93 (m, 1H), 3.78-3.89 (m, 6H), 3.44-3.50 (m, 3H), 3.13 (s, 3H), 2.72-2.76 (m, 1H), 2.49-2.52 (m, 4H), 1.74-1.94 (m, 4H), 1.50-1.57 (m, | 544.8 [M + Na]⁺ |

| Ex | Name | Structure | NMR (¹H NMR, 300 MHz or 400 MHz, chloroform-d) | MS [M + H]⁺ |
|---|---|---|---|---|
| | | | 1H), 1.24-1.30 (m, 1H) | |
| 159 | N-(1-(4-(4-Chloro-3-(8-oxa-2-azaspiro[4.5]decan-2-yl)benzyl)piperazine-1-carbonyl)-1H-pyrazol-3-yl)methane-sulfonamide | 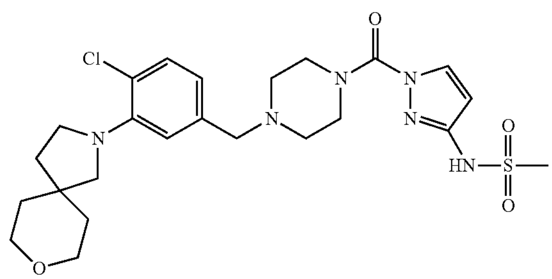 [SMILES: CS(=O)(=O)Nc1ccn(C(=O)N2CCN(Cc3ccc(Cl)c(N4CCC5(CCOCC5)C4)c3)CC2)n1] | δ 8.04 (d, J = 2.7 Hz, 1H), 7.22 (s, 1H), 6.72-6.91 (m, 3H), 6.32 (d, J = 2.7 Hz, 1H), 3.84 (br, 3H), 3.64-3.78 (m, 5H), 3.50 (t, J = 6.9 Hz, 4H), 3.29 (s, 2H), 3.13 (s, 3H), 2.55 (br, 4H), 1.86 (t, J = 6.9 Hz, 2H), 1.66-1.74 (m, 4H) | 537.3 |
| 160 | N-(1-(2-(3-Chloro-4-(tetrahydro-1H-furo[3,4-c]pyrrol-5(3H)-yl)benzyl)-2,8-diazaspiro[4.5]decane-8-carbonyl)-1H-pyrazol-3-yl)methane-sulfonamide | 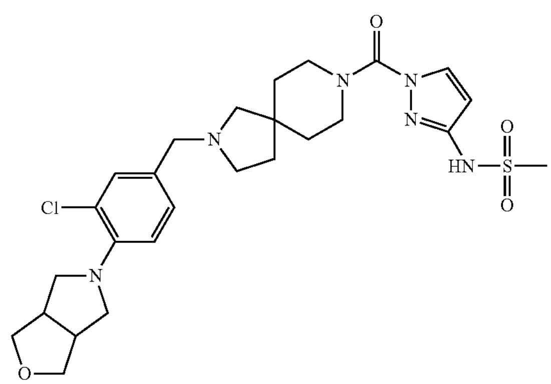 [SMILES: CS(=O)(=O)Nc1ccn(C(=O)N2CCC3(CCN(Cc4ccc(N5CC6COCC6C5)c(Cl)c4)C3)CC2)n1] | δ 8.00 (d, J = 2.7 Hz, 1H), 7.31 (s, 1H), 7.15-7.17 (m, 1H), 6.92 (d, J = 8.1 Hz, 1H), 6.31 (d, J = 2.7 Hz, 1H), 3.97-4.02 (m, 2H), 3.57-3.78 (m, 8H), 3.23-3.28 (m, 2H), 3.13-3.18 (m, 5H), 2.89-3.01 (m, 2H), 2.67 (br, 2H), 2.47 (br, 2H), 1.69-1.73 (m, 6H) | 563.3 |
| 161 | N-(1-(4-(2-(Pyrrolidin-1-yl)-4-(trifluoromethyl)benzyl)piperazine-1-carbonyl)-1H-pyrazol-3-yl)iso-butyramide | 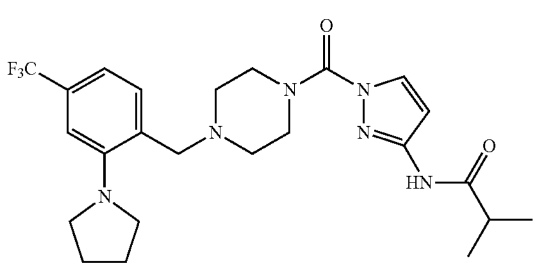 [SMILES: CC(C)C(=O)Nc1ccn(C(=O)N2CCN(Cc3ccc(C(F)(F)F)cc3N3CCCC3)CC2)n1] | δ 8.01 (d, J = 3.0 Hz, 1H), 7.75 (br, 1H), 7.52-7.55 (m, 1H), 7.09-7.11 (m, 2H), 6.90 (d, J = 3.0 Hz, 1H), 3.84 (br, 4H), 3.59 (br, 2H), 3.22-3.26 (m, 4H), 2.48-2.54 (m, 5H), 1.91-1.99 (m, 4H), 1.25 (d, J = 6.9 Hz, 6H) | 515.4 [M + Na]⁺ |
| 162 | N-(1-(2-(2-Chlorobenzyl)-2,8-diazaspiro[4.5]decane-8-carbonyl)-1H-pyrazol-3-yl)methane-sulfonamide | 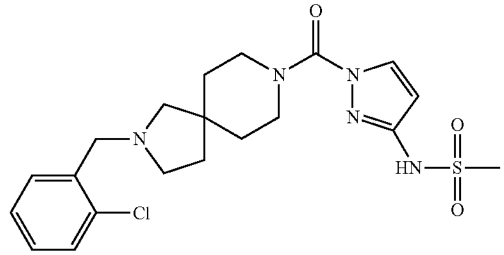 [SMILES: CS(=O)(=O)Nc1ccn(C(=O)N2CCC3(CCN(Cc4ccccc4Cl)C3)CC2)n1] | δ 8.00-8.01 (m, 1H), 7.46-7.48 (m, 1H), 7.33-7.36 (m, 1H), 7.16-7.24 (m, 2H), 6.31-6.32 (m, 1H), 3.62-3.80 (m, 6H), 3.13 (s, 3H), 2.71 (t, J = 6.8 Hz, 2H), 2.52 (s, 2H), 1.65-1.74 (m, 6H) | 452.2 |

-continued

| Ex | Name | Structure | NMR (¹H NMR, 300 MHz or 400 MHz, chloroform-d) | MS [M + H]⁺ |
|---|---|---|---|---|
| 163 | N-(1-(2-(3-Chlorobenzyl)-2,8-diazaspiro[4.5]decane-8-carbonyl)-1H-pyrazol-3-yl)methanesulfonamide | 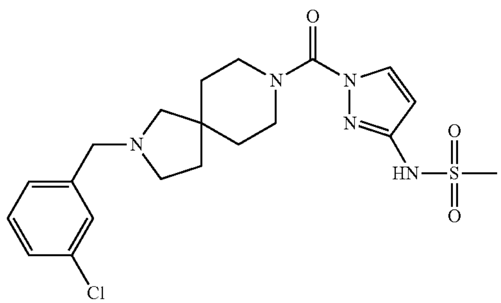 [SMILES: CS(=O)(=O)Nc1ccn(C(=O)N2CCC3(CCN(Cc4cccc(Cl)c4)C3)CC2)n1] | δ 8.00-8.01 (m, 1H), 7.34 (s, 1H), 7.24 (br, 3H), 6.31-6.32 (m, 1H), 3.61-3.79 (m, 6H), 3.13 (s, 3H), 2.64 (br, 2H), 2.45 (br, 2H), 1.69 (br, 6H) | 452.1 |
| 164 | N-(1-(2-(4-Chlorobenzyl)-2,8-diazaspiro[4.5]decane-8-carbonyl)-1H-pyrazol-3-yl)methanesulfonamide | 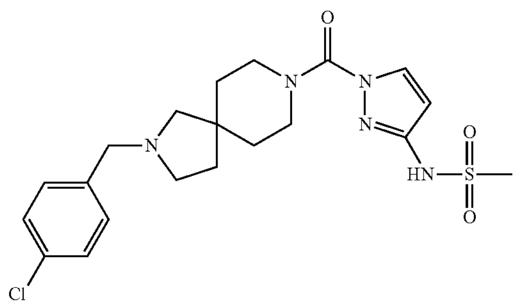 [SMILES: CS(=O)(=O)Nc1ccn(C(=O)N2CCC3(CCN(Cc4ccc(Cl)cc4)C3)CC2)n1] | δ 8.00-8.01 (m, 1H), 7.29 (br, 4H), 6.30-6.32 (m, 1H), 3.61-3.78 (m, 6H), 3.18 (s, 3H), 2.64 (br, 2H), 2.43 (br, 2H), 1.69 (br, 6H) | 452.0 |
| 165 | N-(1-(2-Benzyl-2,8-diazaspiro[4.5]decane-8-carbonyl)-1H-pyrazol-3-yl)methanesulfonamide | 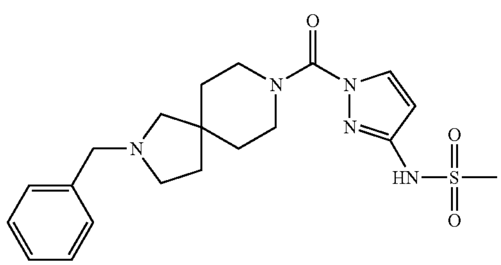 [SMILES: CS(=O)(=O)Nc1ccn(C(=O)N2CCC3(CCN(Cc4ccccc4)C3)CC2)n1] | δ 7.99-8.00 (m, 1H), 7.26-7.35 (m, 5H), 6.30-6.31 (m, 1H), 3.61-3.78 (m, 6H), 3.12 (s, 3H), 2.69 (t, J = 6.4 Hz, 2H), 2.48 (br, 2H), 1.64-1.75 (m, 6H) | 418.1 |
| 166 | N-(1-(5-(3-Morpholino-5-(trifluoromethyl)benzyl)octahydropyrrolo[3,4-c]pyrrole-2-carbonyl)-1H-pyrazol-3-yl)acetamide | 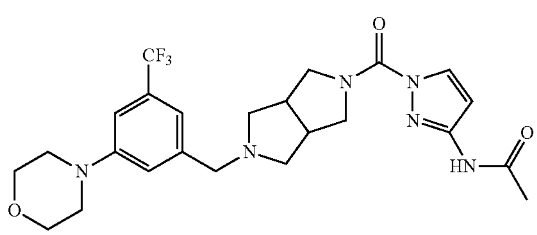 [SMILES: CC(=O)Nc1ccn(C(=O)N2CC3CN(Cc4cc(N5CCOCC5)cc(C(F)(F)F)c4)CC3C2)n1] | δ 8.15 (d, J = 2.8 Hz, 1H), 7.75 (br, 1H), 7.02-7.10 (m, 3H), 6.60 (d, J = 2.8 Hz, 1H), 4.02 (br, 2H), 3.87-3.93 (m, 6H), 3.63 (br, 2H), 3.30-3.33 (m, 4H), 2.92 (br, 2H), 2.60 (br, 4H), 2.21 (s, 3H) | 507.2 |
| 167 | N-(1-(5-(3-Chloro-5-morpholinobenzyl)octahydropyrrolo[3,4-c]pyrrole-2-carbonyl)-1H-pyrazol-3-yl)acetamide | 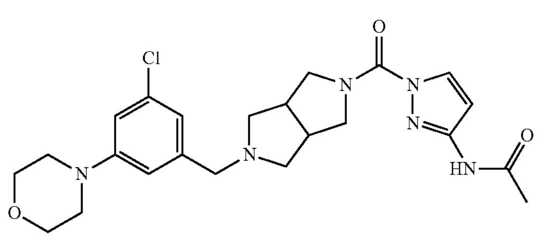 [SMILES: CC(=O)Nc1ccn(C(=O)N2CC3CN(Cc4cc(Cl)cc(N5CCOCC5)c4)CC3C2)n1] | δ 8.15 (d, J = 2.8 Hz, 1H), 7.79-7.82 (m, 1H), 6.90 (d, J = 2.8 Hz, 1H), 6.77-6.82 (m, 3H), 4.03 (br, 2H), 3.84-3.90 (m, 6H), 3.53 (s, 2H), 3.15-3.18 (m, 4H), 3.89 (br, 2H), 2.63 (br, 2H), 2.54-2.56 (m, 2H), 2.20 (s, 3H) | 473.3 |

| Ex | Name | Structure | NMR (¹H NMR, 300 MHz or 400 MHz, chloroform-d) | MS [M + H]⁺ |
|---|---|---|---|---|
| 168 | N-(1-(5-(3-(Pyrrolidin-1-yl)-5-(trifluoromethyl)benzyl)octahydropyrrolo[3,4-c]pyrrole-2-carbonyl)-1H-pyrazol-3-yl)acetamide | 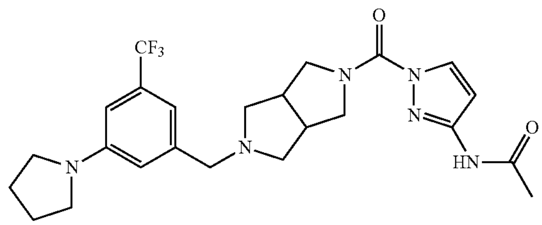 [SMILES: CC(=O)Nc1ccn(C(=O)N2CC3CN(Cc4cc(N5CCCC5)cc(C(F)(F)F)c4)CC3C2)n1] | δ 8.15 (d, J = 2.8 Hz, 1H), 7.78 (br, 1H), 6.90 (d, J = 2.8 Hz, 1H), 6.83 (s, 1H), 6.64-6.70 (m, 2H), 4.02 (br, 2H), 3.86 (br, 2H), 3.60 (br, 2H), 3.30 (t, J = 6.4 Hz, 4H), 2.91 (br, 2H), 2.66 (br, 2H), 2.57-2.59 (m, 2H), 2.20 (s, 3H), 1.99-2.06 (m, 4H) | 491.3 |
| 169 | N-(1-(5-(2-Chloro-4-(pyrrolidin-1-yl)benzyl)octahydropyrrolo[3,4-c]pyrrole-2-carbonyl)-1H-pyrazol-3-yl)acetamide | 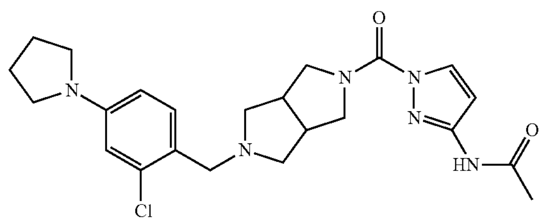 [SMILES: CC(=O)Nc1ccn(C(=O)N2CC3CN(Cc4ccc(N5CCCC5)cc4Cl)CC3C2)n1] | δ 8.14 (d, J = 2.8 Hz, 1H), 7.90-7.94 (m, 1H), 7.20-7.23 (m, 1H), 6.89 (d, J = 2.8 Hz, 1H), 6.54 (s, 1H), 6.41-6.45 (m, 1H), 4.04 (br, 2H), 3.70-3.79 (m, 4H), 3.27 (t, J = 6.4 Hz, 4H), 2.89 (br, 2H), 2.75 (br, 2H), 2.59-2.61 (m, 2H), 2.20 (s, 3H), 1.99-2.05 (m, 4H) | 457.1 |
| 170 | N-(1-(5-(4-Chlorobenzyl)octahydro-pyrrolo[3,4-c]pyrrole-2-carbonyl)-1H-pyrazol-3-yl)acetamide | 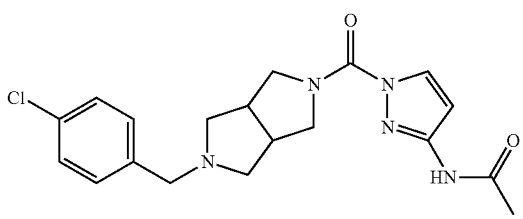 [SMILES: CC(=O)Nc1ccn(C(=O)N2CC3CN(Cc4ccc(Cl)cc4)CC3C2)n1] | δ 8.13 (s, 1H), 7.77 (br, 1H), 7.21-7.36 (m, 3H), 6.87 (s, 1H), 4.02 (br, 2H), 3.78 (br, 2H), 3.58 (s, 2H), 2.88 (br, 2H), 2.64 (br, 2H), 2.46-2.58 (m, 2H), 2.18 (s, 3H) | 388.1 |
| 171 | N-(1-(5-(4-Morpholino-3-(trifluoromethyl)benzyl)octahydropyrrolo[3,4-c]pyrrole-2-carbonyl)-1H-pyrazol-3-yl)acetamide | 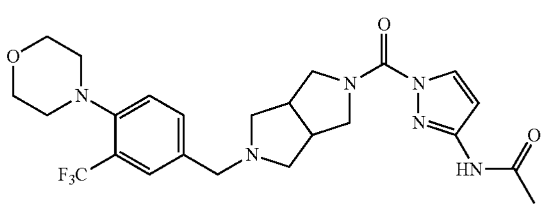 [SMILES: CC(=O)Nc1ccn(C(=O)N2CC3CN(Cc4ccc(N5CCOCC5)c(C(F)(F)F)c4)CC3C2)n1] | δ 8.16 (d, J = 2.8 Hz, 1H), 7.73 (br, 1H), 7.58 (s, 1H), 7.49-7.51 (m, 1H), 7.31-7.40 (m, 1H), 6.90 (d, J = 2.8 Hz, 1H), 4.05 (br, 2H), 3.84-3.86 (m, 6H), 3.62 (s, 2H), 2.92-2.94 (m, 6H), 2.65 (br, 2H), 2.54-2.56 (m, 2H), 2.21 (s, 3H) | 507.2 |
| 172 | N-(1-(5-(3-Chloro-5-(pyrrolidin-1-yl)benzyl)octahydropyrrolo[3,4-c]pyrrole-2-carbonyl)-1H-pyrazol-3-yl)acetamide | 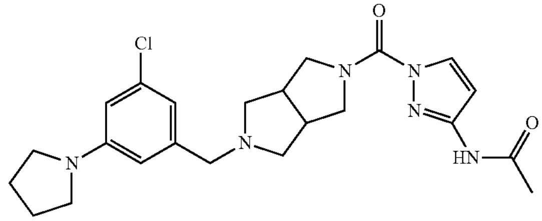 | δ 8.13 (d, J = 2.7 Hz, 1H), 7.80 (br, 1H), 6.87 (d, J = 2.7 Hz, 1H), 6.57 (s, 1H), 6.42 (s, 2H), 3.70-4.12 (m, 4H), 3.55 (br, 2H), 3.17-3.31 (m, 4H), 2.91 (br, 2H), 2.46-2.82 (m, 4H), 2.19 (s, 3H), 1.93-2.04 (m, 4H) | 457.2 |

| Ex | Name | Structure | NMR (¹H NMR, 300 MHz or 400 MHz, chloroform-d) | MS [M + H]⁺ |
|---|---|---|---|---|
| 173 | N-(1-(5-(3-Phenoxybenzyl)octahydropyrrolo[3,4-c]pyrrole-2-carbonyl)-1H-pyrazol-3-yl)acetamide | 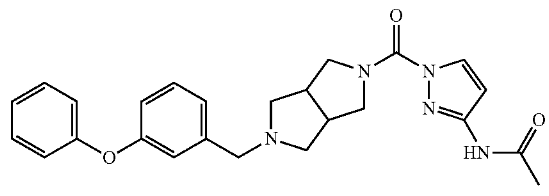 [SMILES: CC(=O)Nc1ccn(C(=O)N2CC3CN(Cc4cccc(Oc5ccccc5)c4)CC3C2)n1] | δ 8.12 (s, 1H), 7.80 (br, 1H), 7.28-7.39 (m, 3H), 7.04-7.14 (m, 2H), 6.96-7.04 (m, 3H), 6.84-6.95 (m, 2H), 4.02 (br, 2H), 3.49-3.88 (m, 4H), 2.45-3.02 (m, 6H), 2.18 (s, 3H) | 446.2 |
| 174 | N-(1-(5-(2,4-Dichlorobenzyl)octahydropyrrolo[3,4-c]pyrrole-2-carbonyl)-1H-pyrazol-3-yl)acetamide | 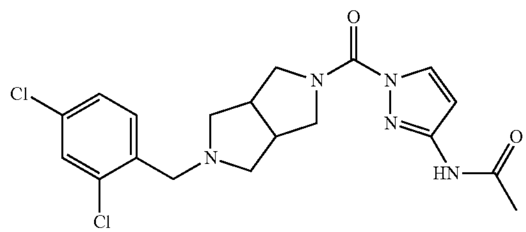 [SMILES: CC(=O)Nc1ccn(C(=O)N2CC3CN(Cc4ccc(Cl)cc4Cl)CC3C2)n1] | δ 8.13 (s, 1H), 7.97 (br, 1H), 7.32-7.45 (m, 2H), 7.16-7.26 (m, 1H), 6.88 (s, 1H), 4.05 (br, 2H), 3.60-3.89 (m, 4H), 2.89 (br, 2H), 2.52-2.79 (m, 4H), 2.18 (s, 3H) | 422.0 |
| 175 | N-(1-(2-(3-(Trifluoromethyl)benzyl)-2,8-diazaspiro[4.5]decane-8-carbonyl)-1H-pyrazol-3-yl)acetamide | 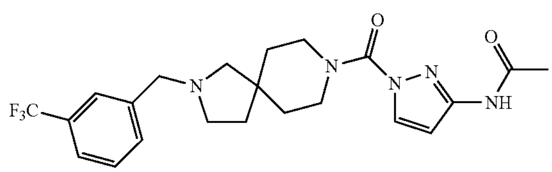 [SMILES: CC(=O)Nc1ccn(C(=O)N2CCC3(CCN(Cc4cccc(C(F)(F)F)c4)C3)CC2)n1] | δ 7.97 (d, J = 2.7 Hz, 1H), 7.79 (br, 1H), 7.59 (s, 1H), 7.53-7.50 (m, 2H), 7.45-7.40 (m, 1H), 6.86 (d, J = 2.7 Hz, 1H), 3.80-3.60 (m, 6H), 2.65 (t, J = 6.6 Hz, 2H), 2.44 (br, 2H), 2.18 (s, 3H), 1.75-1.63 (m, 6H) | 450.2 |
| 176 | N-(1-(2-(3-Chloro-5-fluorobenzyl)-2,8-diazaspiro[4.5]decane-8-carbonyl)-1H-pyrazol-3-yl)acetamide | 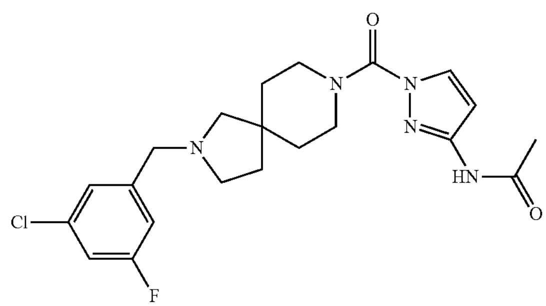 [SMILES: CC(=O)Nc1ccn(C(=O)N2CCC3(CCN(Cc4cc(F)cc(Cl)c4)C3)CC2)n1] | δ 7.98 (d, J = 2.7 Hz, 1H), 7.72 (br, 1H), 7.14 (br, 1H), 7.00-6.98 (m, 2H), 6.87 (d, J = 2.7 Hz, 1H), 3.81-3.77 (m, 2H), 3.68-3.60 (m, 2H), 2.44 (br, 2H), 2.65 (br, 2H), 2.45 (br, 2H), 2.18 (s, 3H), 1.70 (s, 6H) | 434.2 |
| 177 | N-(1-(4-((4-Chloro-3-(tetrahydro-1H-furo[3,4-c]pyrrol-5(3H)-yl)benzyl)(methyl)amino)piperidine-1-carbonyl)-1H-pyrazol-3-yl)methanesulfonamide | 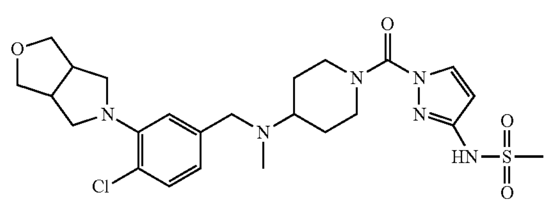 [SMILES: CN(Cc1ccc(Cl)c(N2CC3COCC3C2)c1)C1CCN(C(=O)n2ccc(NS(C)(=O)=O)n2)CC1] | δ 8.04 (d, J = 2.8 Hz, 1H), 7.29-7.27 (m, 1H), 6.98 (s, 1H), 6.91-6.88 (m, 1H), 6.34 (d, J = 2.8 Hz, 1H), 4.60-4.57 (m, 2H), 4.02-4.00 (m, 2H), 3.71-3.68 (m, 2H), 3.56 (s, 2H), 3.34-3.30 (m, 2H), 3.19-3.16 (m, 5H), 3.04-2.98 (m, 4H), 2.76-2.70 (m, 1H), 2.23 (s, 3H), 1.93-1.90 (m, 2H), 1.76-1.66 (m, 2H) | 537.3 |

| Ex | Name | Structure | NMR (¹H NMR, 300 MHz or 400 MHz, chloroform-d) | MS [M + H]⁺ |
|---|---|---|---|---|
| 178 | N-(1-((2S)-2-Methyl-4-(3-(tetrahydro-1H-furo[3,4-c]pyrrol-5(3H)-yl)-4-(trifluoromethyl)benzyl)piperazine-1-carbonyl)-1H-pyrazol-3-yl)methanesulfonamide | 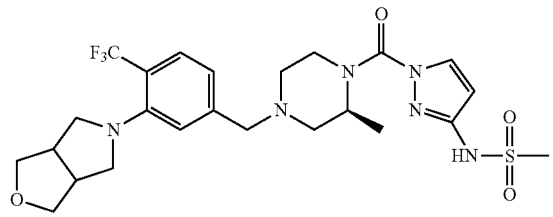 [SMILES: C[C@H]1CN(Cc2ccc(C(F)(F)F)c(N3CC4COCC4C3)c2)CCN1C(=O)n1ccc(NS(C)(=O)=O)n1] | δ 8.03 (d, J = 2.8 Hz, 1H), 7.55 (d, J = 8.0 Hz, 1H), 7.28 (s, 1H), 7.09 (d, J = 8.0 Hz, 1H), 6.29 (d, J = 2.8 Hz, 1H), 4.69 (br, 1H), 4.38-4.34 (m, 1H), 4.06-4.02 (m, 2H), 3.61-3.57 (m, 3H), 3.48-3.39 (m, 2H), 3.20-3.16 (m, 2H), 3.14 (s, 3H), 3.04-2.99 (m, 2H), 2.93-2.90 (m, 2H), 2.87-2.84 (m, 1H), 2.66-2.63 (m, 1H), 2.28-2.21 (m, 2H), 1.45 (d, J = 6.8 Hz, 3H) | 557.2 |
| 179 | N-(1-((3S)-3-Methyl-4-(3-(tetrahydro-1H-furo[3,4-c]pyrrol-5(3H)-yl)-4-(trifluoromethyl)benzyl)piperazine-1-carbonyl)-1H-pyrazol-3-yl)methanesulfonamide | 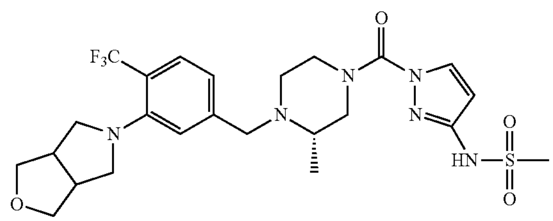 | δ 8.04 (d, J = 2.8 Hz, 1H), 7.55 (d, J = 8.0 Hz, 1H), 7.24 (br, 1H), 7.09 (d, J = 8.0 Hz, 1H), 6.30 (d, J = 2.8 Hz, 1H), 4.17 (br, 2H), 4.04-4.00 (m, 3H), 3.61-3.58 (m, 2H), 3.44 (br, 1H), 3.31-3.17 (m, 4H), 3.13 (s, 3H), 3.03-3.01 (m, 2H), 2.95-2.91 (m, 2H), 2.76-2.74 (m, 1H), 2.63 (br, 1H), 2.26 (br, 1H), 1.18 (br, 3H) | 557.1 |
| 180 | N-(1-((2R)-2-Methyl-4-(3-(tetrahydro-1H-furo[3,4-c]pyrrol-5(3H)-yl)-4-(trifluoromethyl)benzyl)piperazine-1-carbonyl)-1H-pyrazol-3-yl)methanesulfonamide | 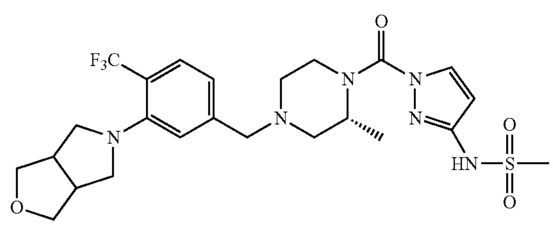 | δ 8.03 (d, J = 2.8 Hz, 1H), 7.55 (d, J = 8.0 Hz, 1H), 7.29 (s, 1H), 7.20-6.90 (m, 2H), 6.29 (d, J = 2.8 Hz, 1H), 4.70 (br, 1H), 4.39-4.36 (m, 1H), 4.06-4.02 (m, 2H), 3.65-3.57 (m, 3H), 3.50-3.42 (m, 2H), 3.20-3.14 (m, 5H), 3.04-2.99 (m, 2H), 2.93-2.88 (m, 3H), 2.70-2.66 (m, 1H), 2.32-2.20 (m, 2H), 1.45 (d, J = 6.8 Hz, 3H) | 557.1 |
| 181 | N-(1-(4-(3-(Tetrahydro-1H-furo[3,4-c]pyrrol-5(3H)-yl)-4-(trifluoromethyl)benzyl)piperazine-1-carbonyl)-1H-pyrazol-3-yl)methanesulfonamide | 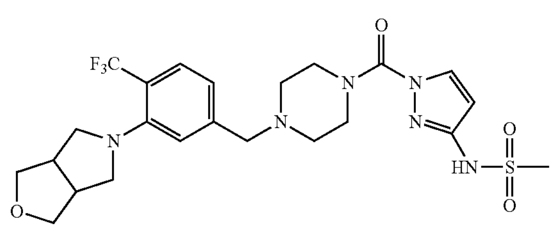 [SMILES: CS(=O)(=O)Nc1ccn(C(=O)N2CCN(Cc3ccc(C(F)(F)F)c(N4CC5COCC5C4)c3)CC2)n1] | δ 8.04 (d, J = 2.8 Hz, 1H), 7.55 (d, J = 8.4 Hz, 1H), 7.24 (s, 1H), 7.08 (d, J = 8.0 Hz, 1H), 6.30 (d, J = 2.8 Hz, 1H), 4.04-4.00 (m, 2H), 3.86 (br, 4H), 3.62-3.57 (m, 4H), 3.21-3.15 (m, 2H), 3.13 (s, 3H), 3.03-3.00 (m, 2H), 2.93 (br, 2H), 2.56 (br, 4H) | 543.2 |

| Ex | Name | Structure | NMR (¹H NMR, 300 MHz or 400 MHz, chloroform-d) | MS [M + H]⁺ |
|---|---|---|---|---|
| 182 | N-(1-((3R)-3-Methyl-4-(3-(tetrahydro-1H-furo[3,4-c]pyrrol-5(3H)-yl)-4-(trifluoromethyl)benzyl)piperazine-1-carbonyl)-1H-pyrazol-3-yl)methanesulfonamide | 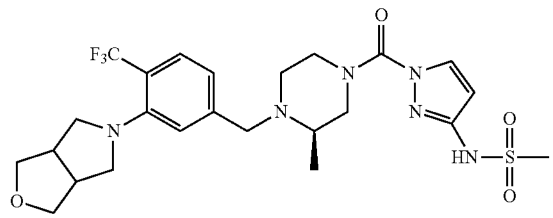 | δ 8.04 (d, J = 2.8 Hz, 1H), 7.56 (d, J = 8.0 Hz, 1H), 7.10-7.04 (m, 2H), 6.30 (d, J = 2.8 Hz, 1H), 4.18 (br, 2H), 4.06-4.00 (m, 3H), 3.61-3.58 (m, 2H), 3.48 (br, 1H), 3.35-3.19 (m, 4H), 3.13 (s, 3H), 3.04-3.02 (m, 2H), 2.97-2.91 (m, 2H), 2.78-2.68 (m, 2H), 2.29 (br, 1H), 1.21 (br, 3H) | 557.3 |
| 183 | N-(1-(4-((4-Chloro-3-(pyrrolidin-1-yl)benzyl)(methyl)amino)-4-methyl-piperidine-1-carbonyl)-1H-pyrazol-3-yl)methanesulfonamide | 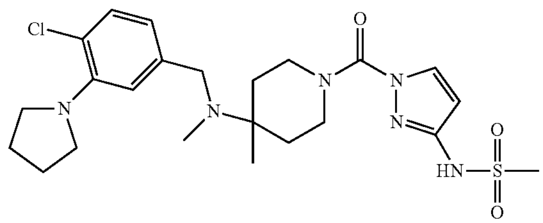 [SMILES: CN(Cc1ccc(Cl)c(N2CCCC2)c1)C1(C)CCN(C(=O)n2ccc(NS(C)(=O)=O)n2)CC1] | δ 8.05 (d, J = 2.8 Hz, 1H), 7.25 (d, J = 8.0 Hz, 1H), 6.88 (s, 1H), 6.80 (d, J = 8.4 Hz, 1H), 6.34 (d, J = 2.8 Hz, 1H), 4.04-4.01 (m, 2H), 3.78-3.72 (m, 2H), 3.51 (s, 2H), 3.46-3.32 (m, 4H), 3.15 (s, 3H), 2.12 (s, 3H), 2.04-2.01 (m, 2H), 1.98-1.95 (m, 4H), 1.63-1.58 (m, 2H), 1.06 (s, 3H) | 509.2 |
| 184 | N-(1-(4-(((5-Chloro-2-(trifluoromethyl)benzyl)(methyl)amino)methyl)piperidine-1-carbonyl)-1H-pyrazol-3-yl)methanesulfonamide | 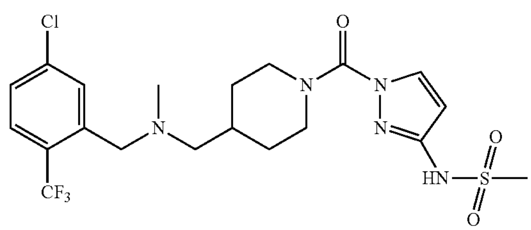 [SMILES: CN(Cc1cc(Cl)ccc1C(F)(F)F)CC1CCN(C(=O)n2ccc(NS(C)(=O)=O)n2)CC1] | δ 8.01 (d, J = 2.7 Hz, 1H), 7.81 (s, 1H), 7.55 (d, J = 8.1 Hz, 1H), 7.31 (d, J = 8.1 Hz, 1H), 6.87 (br, 1H), 6.32 (d, J = 2.7 Hz, 1H), 4.51-4.47 (m, 2H), 3.61 (s, 2H), 3.14 (s, 3H), 3.05¬-2.96 (m, 2H), 2.30-2.28 (m, 2H), 2.22 (s, 3H), 1.94-1.89 (m, 2H), 1.82 (br, 1H), 1.32-1.20 (m, 2H) | 508.0 |
| 185 | (S)-N-(1-(3-Methyl-4-(4-(trifluoromethyl)-3-(4-(trifluoromethyl)piperidin-1-yl)benzyl)piperazine-1-carbonyl)-1H-pyrazol-3-yl)methanesulfonamide | 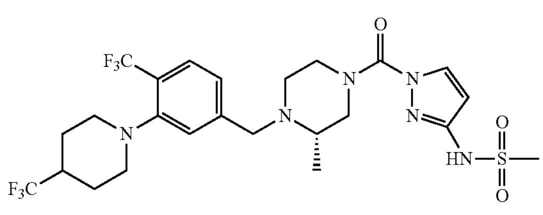 [SMILES: C[C@H]1CN(C(=O)n2ccc(NS(C)(=O)=O)n2)CCN1Cc1ccc(C(F)(F)F)c(N2CCC(C(F)(F)F)CC2)c1] | (Methanol-d4) δ 8.02 (d, J = 2.9 Hz, 1H), 7.62-7.55 (m, 1H), 7.52-7.41 (br, 1H), 7.34-7.23 (m, 1H), 6.20 (d, J = 2.9 Hz, 1H), 4.34-4.20 (m, 1H), 4.20-4.10 (m, 1H), 4.10-4.00 (m, 1H), 3.54-3.39 (m, 1H), 3.39-3.31 (m, 1H), 3.30-3.18 (m, 1H), 3.15-3.03 (m, 5H), 2.89-2.70 (m, 3H), 2.70-2.57 (m, 1H), 2.38-2.21 (m, 2H), 2.00-1.84 (m, 2H), 1.80-1.62 (m, 2H), 1.22-1.12 (m, 3H) | 597.1 |

| Ex | Name | Structure | NMR (¹H NMR, 300 MHz or 400 MHz, chloroform-d) | MS [M + H]+ |
|---|---|---|---|---|
| 186 | (S)-N-(1-(4-(4-Chloro-3-(4,4-difluoro-piperidin-1-yl)benzyl)-3-methyl-piperazine-1-carbonyl)-1H-pyrazol-3-yl)methane-sulfonamide | 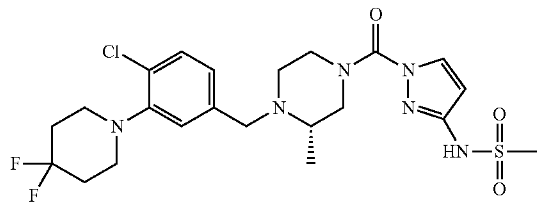 [SMILES: C[C@H]1CN(C(=O)n2ccc(NS(C)(=O)=O)n2)CCN1Cc1ccc(Cl)c(N2CCC(F)(F)CC2)c1] | (Methanol-d4) δ 8.02 (d, J = 2.9 Hz, 1H), 7.39-7.28 (m, 1H), 7.19-7.12 (m, 1H), 7.10-7.00 (m, 1H), 6.20 (d, J = 2.9 Hz, 1H), 4.36-4.06 (m, 2H), 4.05-3.94 (m, 1H), 3.48-3.37 (m, 1H), 3.29-3.18 (m, 2H), 3.18-3.04 (m, 7H), 2.85-2.73 (m, 1H), 2.68-2.52 (m, 1H), 2.32-2.01 (m, 5H), 1.19 (d, J = 6.2 Hz, 3H) | 531.1 |
| 187 | (S)-N-(1-(4-(3-(4-Fluoro-piperidin-1-yl)-4-(trifluoromethyl)benzyl)-3-methyl-piperazine-1-carbonyl)-1H-pyrazol-3-yl)methane-sulfonamide | 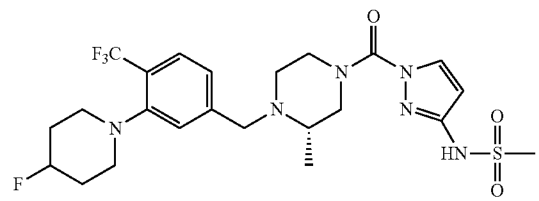 [SMILES: C[C@H]1CN(C(=O)n2ccc(NS(C)(=O)=O)n2)CCN1Cc1ccc(C(F)(F)F)c(N2CCC(F)CC2)c1] | (Methanol-d4) δ 8.04 (d, J = 2.9 Hz, 1H), 7.63-7.53 (m, 1H), 7.51-7.43 (br, 1H), 7.33-7.24 (m, 1H), 6.22 (d, J = 2.8 Hz, 1H), 4.85-4.65 (m, 1H), 4.40-3.97 (m, 3H), 3.52-3.40 (m, 1H), 3.40-3.33 (m, 1H), 3.29-3.19 (m, 1H), 3.13 (s, 3H), 3.12-3.00 (m, 2H), 2.92-2.71 (m, 3H), 2.71-2.58 (m, 1H), 2.38-2.22 (m, 1H), 2.55-1.80 (m, 4H), 1.19 (d, J = 6.3 Hz, 3H) | 547.1 |
| 188 | (S)-N-(1-(4-(4-Chloro-3-(4-(trifluoromethyl)piperidin-1-yl)benzyl)-3-methyl-piperazine-1-carbonyl)-1H-pyrazol-3-yl)methane-sulfonamide | 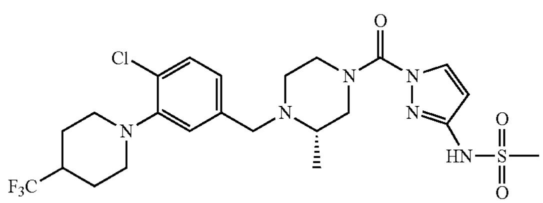 [SMILES: C[C@H]1CN(C(=O)n2ccc(NS(C)(=O)=O)n2)CCN1Cc1ccc(Cl)c(N2CCC(C(F)(F)F)CC2)c1] | (Methanol-d4) δ 8.04 (d, J = 2.8 Hz, 1H), 7.39-7.28 (m, 1H), 7.09-7.20 (m, 1H), 7.08-6.95 (m, 1H), 6.22 (d, J = 2.9 Hz, 1H), 4.37-4.08 (m, 2H), 4.08-3.96 (m, 1H), 3.55-3.36 (m, 3H), 3.30-3.19 (m, 2H), 3.13 (s, 3H), 2.87-2.58 (m, 4H), 2.40-2.23 (m, 2H), 2.08-1.89 (m, 2H), 1.89-1.68 (m, 2H), 1.20 (d, J = 2.9 Hz, 3H) | 563.1 |
| 189 | N-(1-((S)-4-(4-Chloro-3-((S)-3-fluoro-pyrrolidin-1-yl)benzyl)-3-methyl-piperazine-1-carbonyl)-1H-pyrazol-3-yl)methane-sulfonamide | 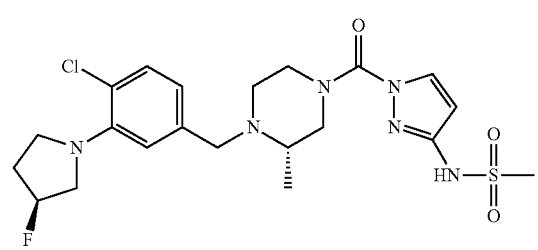 | (Methanol-d4) δ 8.03 (d, J = 2.8 Hz, 1H), 7.29-7.18 (m, 1H), 7.04-6.95 (m, 1H), 6.88-6.77 (m, 1H), 6.21 (d, J = 2.9 Hz, 1H), 5.44-5.15 (m, 1H), 4.31-4.08 (m, 2H), 4.03-3.96 (m, 1H), 3.96-3.76 (m, 1H), 3.72-3.58 (m, 1H), 3.51-3.34 (m, 2H), 3.29-3.15 (m, 3H), 3.12 (s, 3H), 2.85-2.75 (m, 1H), 2.70-2.53 (m, 1H), | 499.1 |

| Ex | Name | Structure | NMR (¹H NMR, 300 MHz or 400 MHz, chloroform-d) | MS [M + H]⁺ |
|---|---|---|---|---|
| | | | 2.32-2.20 (m, 2H), 2.20-2.03 (m, 1H), 1.19 (d, J = 6.3 Hz, 1H) | |
| 190 | (S)-N-(1-(4-(4-Chloro-3-(4-isopropyl-3-oxo-piperazin-1-yl)benzyl)-3-methyl-piperazine-1-carbonyl)-1H-pyrazol-3-yl)methane-sulfonamide | 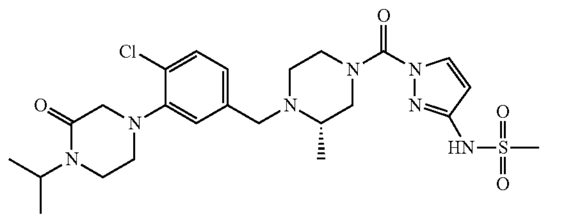 [SMILES: CC(C)N1CCN(c2cc(CN3CCN(C(=O)n4ccc(NS(C)(=O)=O)n4)C[C@@H]3C)ccc2Cl)CC1=O] | (Methanol-d4) δ 8.02 (d, J = 2.8 Hz, 1H), 7.38-7.31 (m, 1H), 7.11-7.18 (m, 1H), 7.11-7.03 (m, 1H), 6.20 (d, J = 2.9 Hz, 1H), 4.84-4.76 (m, 1H), 4.31-4.07 (m, 2H), 4.07-3.95 (m, 1H), 3.74 (s, 2H), 3.49-3.34 (m, 5H), 3.30-3.18 (m, 2H), 3.11 (s, 3H), 2.84-2.71 (m, 1H), 2.69-2.53 (m, 1H), 2.32-2.19 (m, 1H), 1.24-1.13 (m, 9H) | 552.2 |
| 191 | 1-(3-((5-(3-Acetamido-1H-pyrazole-1-carbonyl)hexahydro pyrrolo[3,4-c]pyrrol-2(1H)-yl)methyl)-5-(trifluoromethyl)phenyl)cyclopentane-1-carboxylic acid | 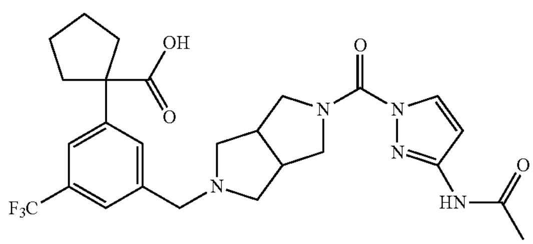 [SMILES: CC(=O)Nc1ccn(C(=O)N2CC3CN(Cc4cc(C(F)(F)F)cc(C5(C(=O)O)CCCC5)c4)CC3C2)n1] | (Methanol-d4) δ 8.12 (d, J = 2.7 Hz, 1H), 7.68 (s, 1H), 7.57 (s, 1H), 7.48 (s, 1H), 6.80 (d, J = 2.7 Hz, 1H), 3.94 (br, 4H), 3.78 (s, 2H), 2.95 (br, 2H), 2.86-2.78 (m, 2H), 2.68-2.62 (m, 4H), 2.11 (s, 3H), 1.86-1.72 (m, 6H) | 534.2 |
| 192 | N-(1-((S)-4-(3-((S)-3-Fluoro-pyrrolidin-1-yl)-4-(trifluoromethyl)benzyl)-3-methyl-piperazine-1-carbonyl)-1H-pyrazol-3-yl)methane-sulfonamide | 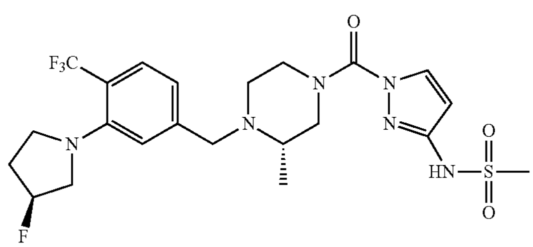 [SMILES: C[C@H]1CN(C(=O)n2ccc(NS(C)(=O)=O)n2)CCN1Cc1ccc(C(F)(F)F)c(N2CC[C@H](F)C2)c1] | (Methanol-d4) δ 8.04 (d, J = 2.8 Hz, 1H), 7.59-7.48 (m, 1H), 7.23-7.12 (br, 1H), 7.04-6.95 (m, 1H), 6.22 (d, J = 2.9 Hz, 1H), 5.47-5.15 (m, 1H), 4.35-4.09 (m, 2H), 4.09-3.98 (m, 1H), 3.83-3.53 (m, 2H), 3.50-3.32 (m, 3H), 3.29-3.18 (m, 2H), 3.12 (s, 3H), 2.85-2.74 (m, 1H), 2.69-2.59 (m, 1H), 2.35-2.05 (m, 3H), 1.19 (d, J = 6.3 Hz, 3H) | 533.3 |
| 193 | 1-(3-(((1-(3-Acetamido-1H-pyrazole-1-carbonyl)piperidin-4-yl)(methyl)amino)methyl)-5-(trifluoro-methyl)phenyl)cyclopentane-1-carboxylic acid | 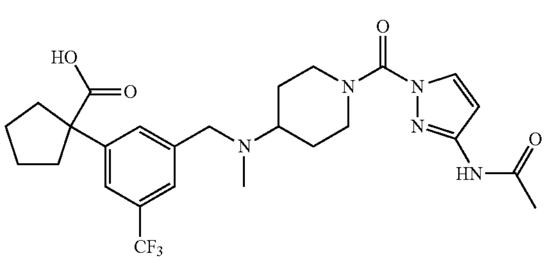 [SMILES: CC(=O)Nc1ccn(C(=O)N2CCC(N(C)Cc3cc(C(F)(F)F)cc(C4(C(=O)O)CCCC4)c3)CC2)n1] | (Methanol-d4) δ 8.05 (d, J = 2.7 Hz, 1H), 7.71 (s, 1H), 7.63 (s, 1H), 7.58 (s, 1H), 6.81 (d, J = 2.7 Hz, 1H), 4.68-4.64 (m, 2H), 3.92 (s, 2H), 3.10-2.97 (m, 3H), 2.73-2.70 (m, 2H), 2.41 (s, 3H), 2.15 (s, 3H), 2.05-2.01 (m, 2H), 1.98-1.75 (m, 8H) | 536.3 |

| Ex | Name | Structure | NMR (¹H NMR, 300 MHz or 400 MHz, chloroform-d) | MS [M + H]⁺ |
|---|---|---|---|---|
| 194 | N-(1-((2S,4S)-4-((4-chloro-3-(Tetrahydro-1H-furo[3,4-c]pyrrol-5(3H)-yl)benzyl)(methyl)amino)-2-methyl-piperidine-1-carbonyl)-1H-pyrazol-3-yl)methanesulfonamide | 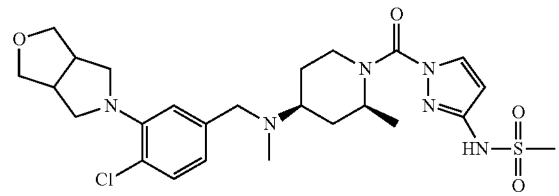 [SMILES: C[C@H]1C[C@@H](N(C)Cc2ccc(Cl)c(N3CC4COCC4C3)c2)CCN1C(=O)n1ccc(NS(C)(=O)=O)n1] | (Methanol-d4) δ 8.04 (d, J = 2.8 Hz, 1H), 7.29 (d, J = 8.0 Hz, 1H), 7.09 (s, 1H), 6.96-6.94 (m, 1H), 6.24 (d, J = 2.8 Hz, 1H), 4.25-4.20 (m, 2H), 4.03-3.99 (m, 2H), 3.64-3.60 (m, 4H), 3.47-3.40 (m, 1H), 3.19-3.16 (m, 4H), 3.14 (s, 3H), 2.99-2.95 (m, 2H), 2.78-2.76 (m, 1H), 2.30-2.24 (m, 4H), 2.07-2.04 (m, 1H), 1.78-1.71 (m, 2H), 1.43 (d, J = 6.4 Hz, 3H) | 551.2 |
| 195 | N-(1-(1-(4-Chloro-3-(pyrrolidin-1-yl)benzyl)-1,8-diazaspiro[4.5]decane-8-carbonyl)-1H-pyrazol-3-yl)methanesulfonamide | 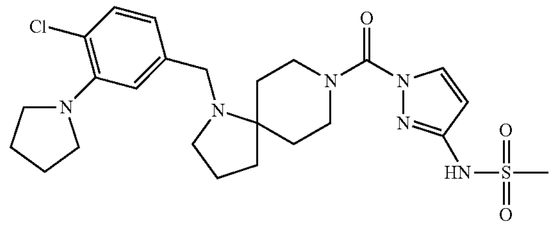 [SMILES: CS(=O)(=O)Nc1ccn(C(=O)N2CCC3(CCCN3Cc3ccc(Cl)c(N4CCCC4)c3)CC2)n1] | (Methanol-d4) δ 8.05 (d, J = 2.8 Hz, 1H), 7.24 (d, J = 8.0 Hz, 1H), 6.98 (d, J = 2.0 Hz, 1H), 6.86-6.79 (m, 1H), 6.25 (d, J = 2.8 Hz, 1H), 4.70-4.51 (m, 2H), 3.63 (s, 2H), 3.39-3.34 (m, 4H), 3.21-3.08 (m, 5H), 2.82-2.72 (m, 2H), 2.03-1.90 (m, 8H), 1.90-1.79 (m, 2H), 1.61-1.50 (m, 2H) | 521.2 |
| 196 | N-(1-(4-((4-Chloro-2-(4-fluoro-piperidin-1-yl)benzyl)(methyl)amino)-4-methyl-piperidine-1-carbonyl)-1H-pyrazol-3-yl)methanesulfonamide | 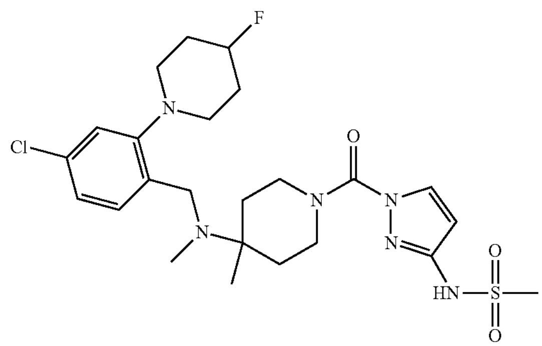 [SMILES: CN(Cc1ccc(Cl)cc1N1CCC(F)CC1)C1(C)CCN(C(=O)n2ccc(NS(C)(=O)=O)n2)CC1] | (Methanol-d4) δ 8.05 (d, J = 2.8 Hz, 1H), 7.70-7.60 (m, 1H), 7.18-7.05 (m, 2H), 6.25 (d, J = 2.8 Hz, 1H), 4.90-4.68 (m, 1H), 4.00-3.88 (m, 2H), 3.88-3.75 (m, 2H), 3.68 (s, 2H), 3.14 (s, 3H), 3.08-2.97 (m, 2H), 2.88-2.75 (m, 2H), 2.15 (s, 3H), 2.10-2.00 (m, 4H), 2.00-1.90 (m, 2H), 1.72-1.60 (m, 2H), 1.16 (s, 3H) | 541.3 |
| 197 | N-(1-(4-((4-Chloro-2-(tetrahydro-1H-furo[3,4-c]pyrrol-5(3H)-yl)benzyl)(methyl)amino)-4-methyl-piperidine-1-carbonyl)-1H-pyrazol-3-yl)methanesulfonamide | 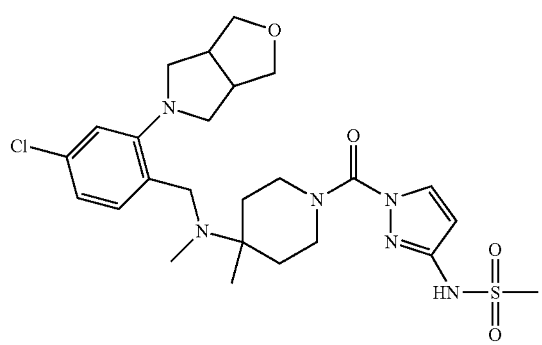 [SMILES: CN(Cc1ccc(Cl)cc1N1CC2COCC2C1)C1(C)CCN(C(=O)n2ccc(NS(C)(=O)=O)n2)CC1] | (Methanol-d4) δ 8.05 (d, J = 2.8 Hz, 1H), 7.70-7.60 (m, 1H), 7.12-7.00 (m, 2H), 6.25 (d, J = 2.8 Hz, 1H), 4.10-4.00 (m, 2H), 4.00-3.88 (m, 2H), 3.88-3.72 (m, 2H), 3.72-3.58 (m, 4H), 3.13 (s, 3H), 3.12-3.02 (m, 2H), 3.02-2.87 (m, 4H), 2.13 (s, 3H), 2.10-1.98 (m, 2H), 1.74-1.57 (m, 2H), 1.15 (s, 3H) | 551.2 |

| Ex | Name | Structure | NMR (¹H NMR, 300 MHz or 400 MHz, chloroform-d) | MS [M + H]⁺ |
|---|---|---|---|---|
| 198 | N-(1-(4-((4-Chloro-2-morpholino-benzyl)(methyl)amino)-4-methyl-piperidine-1-carbonyl)-1H-pyrazol-3-yl)methane-sulfonamide | 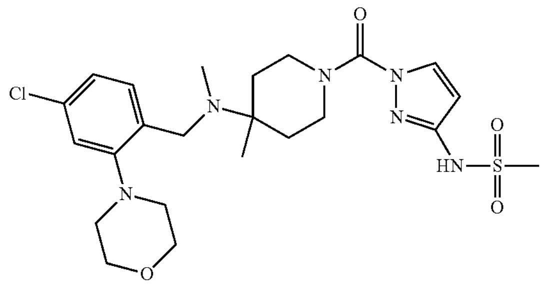 [SMILES: CN(Cc1ccc(Cl)cc1N1CCOCC1)C1(C)CCN(C(=O)n2ccc(NS(C)(=O)=O)n2)CC1] | (Methanol-d4) δ 8.05 (d, J = 2.8 Hz, 1H), 7.70-7.60 (m, 1H), 7.18-7.08 (m, 2H), 6.25 (d, J = 2.8 Hz, 1H), 4.05-3.88 (m, 2H), 3.88-3.73 (m, 6H), 3.69 (s, 2H), 3.14 (s, 3H), 2.95-2.80 (m, 4H), 2.14 (s, 3H), 2.10-2.00 (m, 2H), 1.73-1.59 (m, 2H), 1.16 (s, 3H) | 525.2 |
| 199 | N-(1-((S)-4-(4-Chloro-3-((R)-2-methyl-pyrrolidin-1-yl)benzyl)-3-methyl-piperazine-1-carbonyl)-1H-pyrazol-3-yl)methane-sulfonamide | 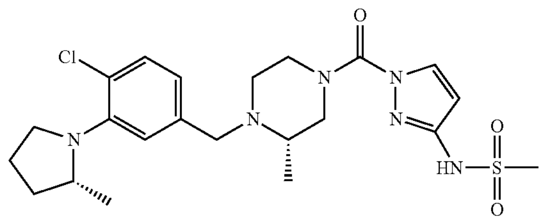 [SMILES: C[C@@H]1CCCN1c1cc(CN2CCN(C(=O)n3ccc(NS(C)(=O)=O)n3)C[C@@H]2C)ccc1Cl] | δ 8.05 (d, J = 2.8 Hz, 1H), 7.26 (d, J = 8.0 Hz, 1H), 7.06-6.86 (m, 2H), 6.80 (d, J = 8.0 Hz, 1H), 6.32 (d, J = 2.8 Hz, 1H), 4.28-4.09 (m, 2H), 4.08-3.94 (m, 2H), 3.93-3.83 (m, 1H), 3.47-3.34 (m, 1H), 3.28-3.10 (m, 5H), 3.06-2.92 (m, 1H), 2.85-2.72 (m, 1H), 2.68-2.53 (m, 1H), 2.29-2.16 (m, 2H), 2.04-1.91 (m, 1H), 1.89-1.72 (m, 1H), 1.70-1.56 (m, 1H), 1.19 (d, J = 6.1 Hz, 3H), 1.06 (d, J = 6.0 Hz, 3H) | 495.3 |
| 200 | N-(1-((R)-4-(4-Chloro-3-((R)-2-methyl-pyrrolidin-1-yl)benzyl)-3-methyl-piperazine-1-carbonyl)-1H-pyrazol-3-yl)methane-sulfonamide | 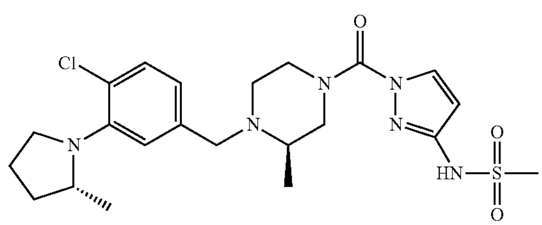 [SMILES: C[C@@H]1CN(C(=O)n2ccc(NS(C)(=O)=O)n2)CCN1Cc1ccc(Cl)c(N2CCC[C@H]2C)c1] | δ 8.05 (d, J = 2.8 Hz, 1H), 7.26 (d, J = 8.0 Hz, 1H), 6.90 (s, 1H), 6.81 (d, J = 8.0 Hz, 1H), 6.32 (d, J = 2.8 Hz, 1H), 4.25-4.05 (m, 2H), 4.03-3.91 (m, 2H), 3.90-3.82 (m, 1H), 3.54-3.37 (m, 1H), 3.33-3.18 (m, 2H), 3.15 (s, 3H), 3.05-2.93 (m, 1H), 2.84-2.73 (m, 1H), 2.68-2.55 (m, 1H), 2.33-2.14 (m, 2H), 2.03-1.91 (m, 1H), 1.89-1.74 (m, 1H), 1.69-1.54 (m, 1H), 1.19 (d, J = 6.1 Hz, 3H), 1.06 (d, J = 6.0 Hz, 3H) | 495.3 |
| 201 | (R)-N-(1-(4-(4-Chloro-3-(4,4-difluoro-piperidin-1-yl)benzyl)-3-methyl-piperazine-1-carbonyl)-1H-pyrazol-3-yl)methane-sulfonamide | 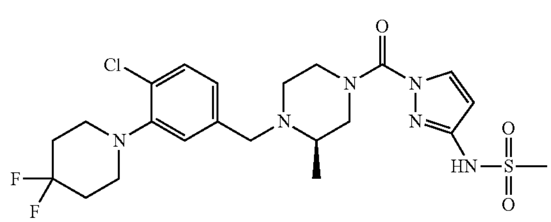 [SMILES: C[C@@H]1CN(C(=O)n2ccc(NS(C)(=O)=O)n2)CCN1Cc1ccc(Cl)c(N2CCC(F)(F)CC2)c1] | (Methanol-d4) δ 8.15-8.02 (m, 1H), 7.35 (d, J = 8.0 Hz, 1H), 7.17 (s, 1H), 7.05 (d, J = 8.1 Hz, 1H), 6.29-6.20 (m, 1H), 4.40-4.09 (m, 2H), 4.03 (d, J = 13.3 Hz, 1H), 3.52-3.37 (m, 1H), 3.30-3.20 (m, 2H), 3.20-3.05 | 531.2 |

| Ex | Name | Structure | NMR (¹H NMR, 300 MHz or 400 MHz, chloroform-d) | MS [M + H]⁺ |
|---|---|---|---|---|
| | | | (m, 7H), 2.83-2.75 (m, 1H), 2.68-2.58 (m, 1H), 2.27 (t, J = 11.5 Hz, 1H), 2.20-2.09 (m, 4H), 1.21 (d, J = 6.0 Hz, 3H) | |
| 202 | (R)-N-(1-(4-(4-Chloro-3-(4-(trifluoromethyl)piperidin-1-yl)benzyl)-3-methyl-piperazine-1-carbonyl)-1H-pyrazol-3-yl)methanesulfonamide | 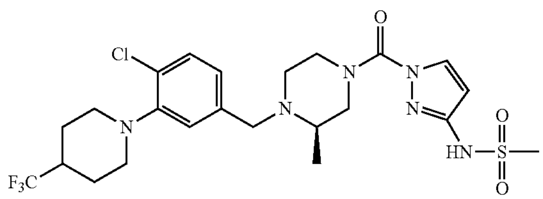 [SMILES: C[C@@H]1CN(C(=O)n2ccc(NS(C)(=O)=O)n2)CCN1Cc1ccc(Cl)c(N2CCC(C(F)(F)F)CC2)c1] | δ 8.06 (d, J = 2.8 Hz, 1H), 7.35-7.30 (m, 1H), 7.03-6.94 (m, 2H), 6.32 (d, J = 2.8 Hz, 1H), 4.26-4.06 (m, 2H), 4.05-3.93 (m, 1H), 3.55-3.35 (m, 3H), 3.31-3.17 (m, 2H), 3.16 (s, 3H), 2.81-2.55 (m, 4H), 2.31-2.10 (m, 2H), 2.04-1.95 (m, 2H), 1.94-1.79 (m, 2H), 1.19 (d, J = 6.2 Hz, 3H) | 563.3 |
| 203 | N-(1-((R)-4-(4-Chloro-3-((S)-3-fluoro-pyrrolidin-1-yl)benzyl)-3-methyl-piperazine-1-carbonyl)-1H-pyrazol-3-yl)methanesulfonamide | 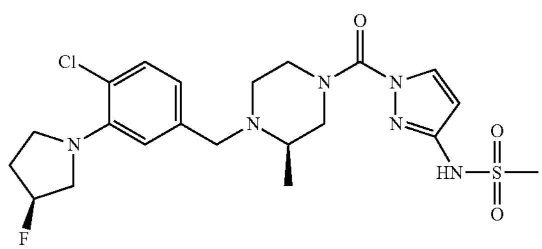 [SMILES: C[C@@H]1CN(C(=O)n2ccc(NS(C)(=O)=O)n2)CCN1Cc1ccc(Cl)c(N2CC[C@H](F)C2)c1] | δ 8.06 (d, J = 2.8 Hz, 1H), 7.28-7.24 (m, 1H), 6.89 (s, 1H), 6.84-6.79 (m, 1H), 6.32 (d, J = 2.8 Hz, 1H), 5.44-5.25 (m, 1H), 4.28-4.10 (m, 2H), 4.08-3.91 (m, 2H), 3.71-3.61 (m, 1H), 3.58-3.40 (m, 2H), 3.39-3.30 (m, 1H), 3.29-3.19 (m, 2H), 3.15 (s, 3H), 2.82-2.73 (m, 1H), 2.69-2.55 (m, 1H), 2.40-2.05 (m, 3H), 1.19 (d, J = 5.6 Hz, 3H) | 499.2 |
| 204 | N-(1-(1-(4-Chloro-2-(4-fluoro-piperidin-1-yl)benzyl)-1,8-diazaspiro[4.5]decane-8-carbonyl)-1H-pyrazol-3-yl)methanesulfonamide | 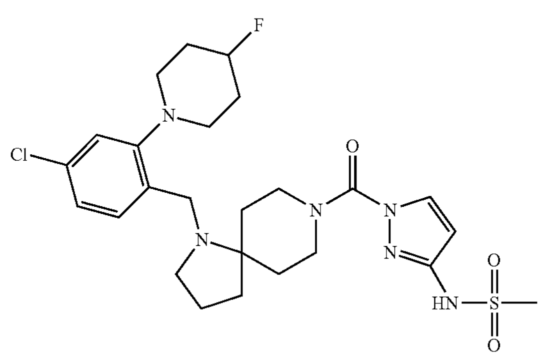 [SMILES: CS(=O)(=O)Nc1ccn(C(=O)N2CCC3(CCCN3Cc3ccc(Cl)cc3N3CCC(F)CC3)CC2)n1] | (Methanol-d4) δ 8.06 (d, J = 2.8 Hz, 1H), 7.47 (d, J = 8.4 Hz, 1H), 7.13 (d, J = 2.0 Hz, 1H), 7.09-7.02 (m, 1H), 6.25 (d, J = 2.8 Hz, 1H), 4.90-4.70 (m, 1H), 4.69-4.55 (m, 2H), 3.75 (s, 2H), 3.21-3.10 (m, 5H), 3.09-3.00 (m, 2H), 2.88-2.75 (m, 4H), 2.14-1.90 (m, 8H), 1.90-1.78 (m, 2H), 1.61-1.51 (m, 2H) | 553.2 |

| Ex | Name | NMR (¹H NMR, 300 MHz or 400 MHz, chloroform-d) | MS [M + H]⁺ |
|---|---|---|---|
| 205 | N-(1-(1-(4-Chloro-2-(tetrahydro-1H-furo[3,4-c]pyrrol-5(3H)-yl)benzyl)-1,8-diazaspiro[4.5]decane-8-carbonyl)-1H-pyrazol-3-yl)methanesulfonamide | (Methanol-d4) δ 8.06 (d, J = 2.8 Hz, 1H), 7.53 (d, J = 8.4 Hz, 1H), 7.10 (d, J = 2.0 Hz, 1H), 7.08-7.00 (m, 1H), 6.26 (d, J = 2.8 Hz, 1H), 4.70-4.55 (m, 2H), 4.02-3.91 (m, 2H), 3.76 (s, 2H), 3.71-3.61 (m, 2H), 3.21-3.05 (m, 7H), 3.01-2.89 (m, 4H), 2.81-2.71 (m, 2H), 2.03-1.90 (m, 4H), 1.90-1.79 (m, 2H), 1.62-1.50 (m, 2H) | 563.3 |
| 206 | N-(1-(4-((4-Chloro-3-(4-fluoropiperidin-1-yl)benzyl)(methyl)amino)piperidine-1-carbonyl)-1H-pyrazol-3-yl)methanesulfonamide | (Methanol-d4) δ 8.04 (d, J = 2.5 Hz, 1H), 7.33 (d, J = 8.0 Hz, 1H), 7.16 (s, 1H), 7.00 (d, J = 8.1 Hz, 1H), 6.24 (d, J = 2.6 Hz, 1H), 4.90-4.70 (m, 1H), 4.70-4.47 (m, 2H), 3.63 (s, 2H), 3.25-3.10 (m, 5H), 3.10-2.90 (m, 4H), 2.84-2.74 (m, 1H), 2.26 (s, 3H), 2.17-1.90 (m, 6H), 1.80-1.68 (m, 2H) | 527.3 |
| 207 | (S)-N-(1-(2-Methyl-4-((3-methyl-[1,1'-biphenyl]-4-yl)methyl)piperazine-1-carbonyl)-1H-pyrazol-3-yl)acetamide | δ 8.03 (d, J = 2.8 Hz, 1H), 7.74 (br, 1H), 7.63-7.61 (m, 2H), 7.48-7.44 (m, 3H), 7.41-7.28 (m, 3H), 6.89 (d, J = 2.8 Hz, 1H), 4.75 (br, 1H), 4.36-4.32 (m, 1H), 3.55-3.47 (m, 2H), 3.43-3.37 (m, 1H), 2.88-2.85 (m, 1H), 2.75-2.72 (m, 1H), 2.48 (s, 3H), 2.39-2.32 (m, 1H), 2.23-2.13 (m, 4H), 1.44 (d, J = 6.8 Hz, 3H) | 432.3 |
| 208 | (R)-N-(1-(2-Methyl-4-((3-methyl-[1,1'-biphenyl]-4-yl)methyl)piperazine-1-carbonyl)-1H-pyrazol-3-yl)acetamide | δ 8.03 (d, J = 2.4 Hz, 1H), 7.78 (br, 1H), 7.63-7.61 (m, 2H), 7.48-7.41 (m, 3H), 7.39-7.28 (m, 3H), 6.89 (d, J = 2.4 Hz, 1H), 4.75 (br, 1H), 4.35-4.32 (m, 1H), 3.54-3.50 (m, 2H), 3.47-3.36 (m, 1H), 2.87-2.85 (m, 1H), 2.75-2.72 (m, 1H), 2.48 (s, 3H), 2.39-2.32 (m, 1H), 2.23-2.18 (m, 4H), 1.44 (d, J = 6.8 Hz, 3H) | 432.2 |

| Ex | Name | Structure | NMR (¹H NMR, 300 MHz or 400 MHz, chloroform-d) | MS [M + H]⁺ |
|---|---|---|---|---|
| 209 | N-(1-(4-((4-Chloro-3-(4-fluoro-piperidin-1-yl)benzyl)oxy)piperidine-1-carbonyl)-1H-pyrazol-3-yl)methane-sulfonamide | 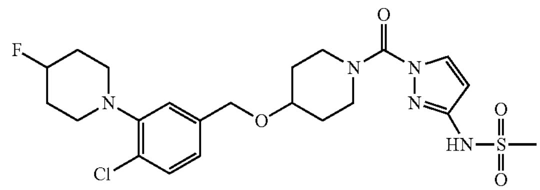 [SMILES: CS(=O)(=O)Nc1ccn(C(=O)N2CCC(OCc3ccc(Cl)c(N4CCC(F)CC4)c3)CC2)n1] | (Methanol-d4) δ 8.04 (d, J = 2.4 Hz, 1H), 7.35 (d, J = 8.0 Hz, 1H), 7.17 (s, 1H), 7.04 (d, J = 8.0 Hz, 1H), 6.25 (d, J = 2.4 Hz, 1H), 4.75-4.74 (m, 1H), 4.58-4.53 (m, 2H), 4.08 (br, 2H), 3.79-3.75 (m, 1H), 3.62-3.58 (m, 2H), 3.20-3.15 (m, 5H), 3.01-2.96 (m, 2H), 2.15-1.98 (m, 6H), 1.80-1.72 (m, 2H) | 514.1 |
| 210 | N-(1-((3S,4S)-3-Fluoro-4-(3-(4-fluoro-piperidin-1-yl)-4-(trifluoromethyl)phenoxy)piperidine-1-carbonyl)-1H-pyrazol-3-yl)methane-sulfonamide | 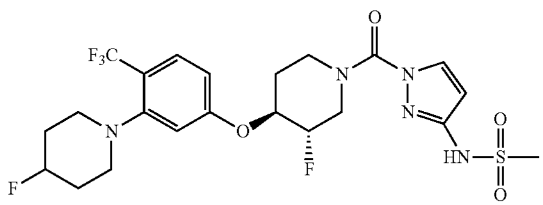 [SMILES: CS(=O)(=O)Nc1ccn(C(=O)N2CC[C@H](Oc3ccc(C(F)(F)F)c(N4CCC(F)CC4)c3)[C@@H](F)C2)n1] | (Methanol-d4) δ 8.10 (d, J = 2.8 Hz, 1H), 7.58 (d, J = 8.8 Hz, 1H), 7.08 (d, J = 2.0 Hz, 1H), 6.99-6.90 (m, 1H), 6.28 (d, J = 2.8 Hz, 1H), 4.88-4.80 (m, 2H), 4.79-4.69 (m, 1H), 4.37-4.20 (m, 1H), 4.20-4.09 (m, 1H), 4.04-3.91 (m, 1H), 3.91-3.80 (m, 1H), 3.16 (s, 3H), 3.12-3.02 (m, 2H), 2.90-2.80 (m, 2H), 2.39-2.26 (m, 1H), 2.12-2.01 (m, 1H), 2.01-1.84 (m, 4H) | 552.2 |
| 211 | N-(1-(4-(4-Chloro-3-(4-cyano-piperidin-1-yl)benzyl)piperazine-1-carbonyl)-1H-pyrazol-3-yl)methane-sulfonamide | 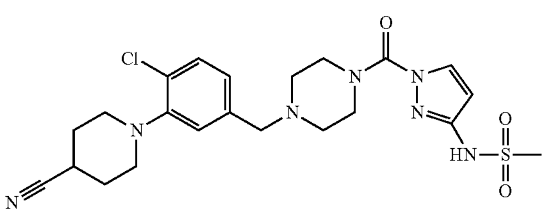 [SMILES: CS(=O)(=O)Nc1ccn(C(=O)N2CCN(Cc3ccc(Cl)c(N4CCC(C#N)CC4)c3)CC2)n1] | δ 8.01 (s, 1H), 7.39-7.24 (m, 1H), 7.03 (s, 1H), 7.01-6.90 (m, 1H), 6.29 (s, 1H), 4.90 (s, 1H), 3.94-3.73 (m, 4H), 3.50 (s, 2H), 3.27-3.18 (m, 2H), 3.13 (s, 3H), 3.00 (s, 2H), 2.91-2.81 (m, 1H), 2.57-2.46 (m, 4H), 2.18-2.00 (m, 4H) | 506.2 |
| 212 | N-(1-(4-(4-Chloro-3-fluorobenzyl)piperazine-1-carbonyl)-1H-pyrazol-3-yl)methane-sulfonamide | 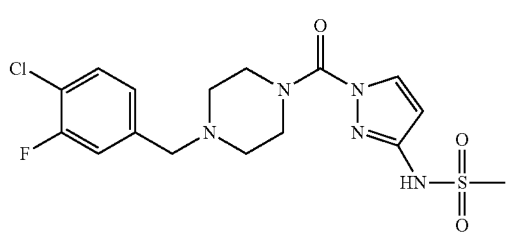 [SMILES: CS(=O)(=O)Nc1ccn(C(=O)N2CCN(Cc3ccc(Cl)c(F)c3)CC2)n1] | δ 7.91 (s, 1H), 7.28-7.19 (m, 1H), 7.11-7.04 (m, 1H), 6.99-6.89 (m, 1H), 6.45 (s, 1H), 6.17 (s, 1H), 3.73 (s, 4H), 3.41 (s, 2H), 3.04 (s, 3H), 2.42 (s, 4H) | 416.1 |
| 213 | N-(1-(4-(4-Chloro-3-(4-isopropyl-piperidin-1-yl)benzyl)piperazine-1-carbonyl)-1H-pyrazol-3-yl)methane-sulfonamide | 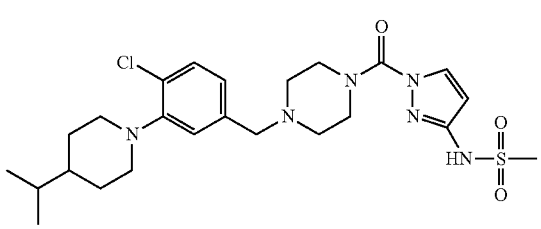 [SMILES: CC(C)C1CCN(c2cc(CN3CCN(C(=O)n4ccc(NS(C)(=O)=O)n4)CC3)ccc2Cl)CC1] | δ 7.93 (s, 1H), 7.23-7.10 (m, 1H), 6.91 (s, 1H), 6.85-6.72 (m, 1H), 6.19 (s, 1H), 3.74 (s, 4H), 3.41 (s, 2H), 3.39-3.24 (m, 2H), 3.03 (s, 3H), 2.55-2.35 (m, 6H), 1.75-1.62 (m, 2H), 1.50-1.30 (m, 3H), | 523.2 |

| Ex | Name | Structure | NMR (¹H NMR, 300 MHz or 400 MHz, chloroform-d) | MS [M + H]+ |
|---|---|---|---|---|
| | | | 1.13-0.99 (m, 1H), 0.93-0.77 (m, 6H) | |
| 214 | N-(1-(4-(4-Chloro-3-(trifluoromethyl)benzyl)piperazine-1-carbonyl)-1H-pyrazol-3-yl)methanesulfonamide | 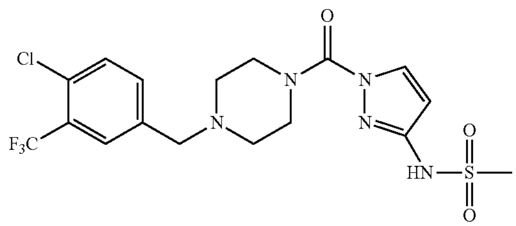 [SMILES: CS(=O)(=O)Nc1ccn(C(=O)N2CCN(Cc3ccc(Cl)c(C(F)(F)F)c3)CC2)n1] | δ 7.95 (s, 1H), 7.58 (s, 1H), 7.38 (s, 2H), 6.22 (s, 1H), 3.76 (s, 4H), 3.47 (s, 2H), 3.05 (s, 3H), 2.50-2.39 (m, 4H) | 466.1 |
| 215 | (R)-N-(1-(4-(4-Chloro-3-cyclopentyl-benzyl)-3-methyl-piperazine-1-carbonyl)-1H-pyrazol-3-yl)methanesulfonamide | 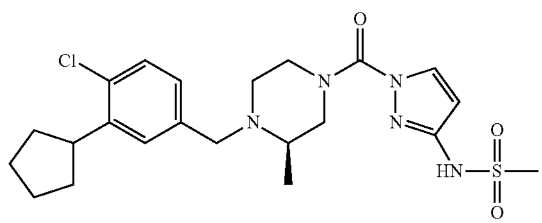 [SMILES: C[C@@H]1CN(C(=O)n2ccc(NS(C)(=O)=O)n2)CCN1Cc1ccc(Cl)c(C2CCCC2)c1] | δ 8.10-8.04 (m, 1H), 7.35-7.28 (m, 1H), 7.24 (s, 1H), 7.19-7.04 (m, 1H), 7.03-6.79 (m, 1H), 6.36-6.30 (m, 1H), 4.28-4.06 (m, 2H), 4.03-3.93 (m, 1H), 3.53-3.35 (m, 2H), 3.32-3.17 (m, 2H), 3.15 (s, 3H), 2.83-2.70 (m, 1H), 2.68-2.54 (m, 1H), 2.32-2.18 (m, 1H), 2.17-2.05 (m, 2H), 1.90-1.67 (m, 4H), 1.60-1.53 (m, 2H), 1.19 (d, J = 4.8 Hz, 3H) | 480.2 |
| 216 | (S)-N-(1-(4-(4-Chloro-3-cyclopentyl-benzyl)-3-methyl-piperazine-1-carbonyl)-1H-pyrazol-3-yl)methanesulfonamide | 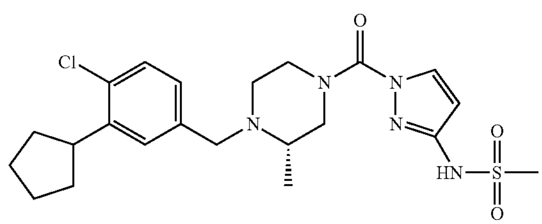 [SMILES: C[C@H]1CN(C(=O)n2ccc(NS(C)(=O)=O)n2)CCN1Cc1ccc(Cl)c(C2CCCC2)c1] | δ 8.10-8.04 (m, 1H), 7.35-7.28 (m, 1H), 7.24 (s, 1H), 7.19-7.04 (m, 1H), 7.03-6.79 (m, 1H), 6.36-6.30 (m, 1H), 4.28-4.06 (m, 2H), 4.03-3.93 (m, 1H), 3.53-3.35 (m, 2H), 3.32-3.17 (m, 2H), 3.15 (s, 3H), 2.83-2.70 (m, 1H), 2.68-2.54 (m, 1H), 2.32-2.18 (m, 1H), 2.17-2.05 (m, 2H), 1.90-1.67 (m, 4H), 1.60-1.53 (m, 2H), 1.19 (d, J = 3.2 Hz, 3H) | 480.2 |
| 217 | N-(1-(4-((4-Chloro-3-methylbenzyl)(methyl)amino)-4-methyl-piperidine-1-carbonyl)-1H-pyrazol-3-yl)acetamide | 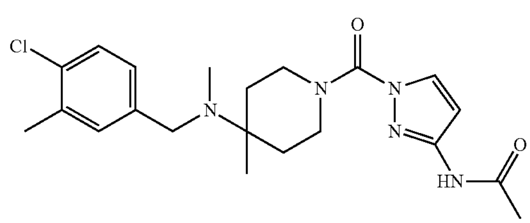 [SMILES: CC(=O)Nc1ccn(C(=O)N2CCC(C)(N(C)Cc3ccc(Cl)c(C)c3)CC2)n1] | δ 8.02 (d, J = 2.8 Hz, 1H), 7.76 (br, 1H), 7.28 (s, 1H), 7.26-7.16 (m, 2H), 6.90 (d, J = 2.8 Hz, 1H), 3.97 (br, 2H), 3.79 (br, 2H), 3.51 (br, 2H), 2.39 (br, 3H), 2.20 (br, 3H), 2.10 (s, 3H), 2.04 (br, 2H), 1.61 (br, 2H), 1.07 (br, 3H) | 418.2 |

-continued

| Ex | Name | Structure | NMR (¹H NMR, 300 MHz or 400 MHz, chloroform-d) | MS [M + H]⁺ |
|---|---|---|---|---|
| 218 | N-(1-(4-(4-Fluoro-3-(trifluoromethoxy)benzyl)piperazine-1-carbonyl)-1H-pyrazol-3-yl)methanesulfonamide | 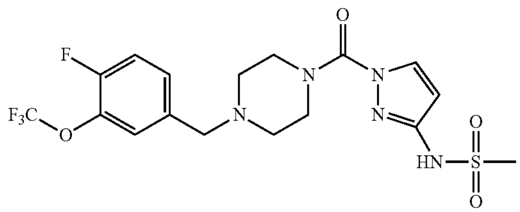 [SMILES: CS(=O)(=O)Nc1ccn(C(=O)N2CCN(Cc3ccc(F)c(OC(F)(F)F)c3)CC2)n1] | δ 7.96 (s, 1H), 7.27-7.22 (m, 1H), 7.19-7.14 (m, 1H), 7.12-7.05 (m, 1H), 6.24 (s, 1H), 3.83-3.70 (m, 4H), 3.44 (s, 2H), 3.06 (s, 3H), 2.49-2.40 (m, 4H) | 466.1 |
| 219 | N-(1-(4-(2-Chloro-3-(trifluoromethyl)benzyl)piperazine-1-carbonyl)-1H-pyrazol-3-yl)methanesulfonamide | 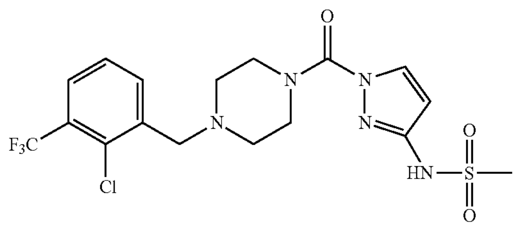 [SMILES: CS(=O)(=O)Nc1ccn(C(=O)N2CCN(Cc3cccc(C(F)(F)F)c3Cl)CC2)n1] | δ 8.03 (s, 1H), 7.77-7.69 (m, 1H), 7.69-7.63 (m, 1H), 7.43-7.33 (m, 1H), 6.42 (s, 1H), 6.29 (s, 1H), 3.86 (s, 4H), 3.72 (s, 2H), 3.16 (s, 3H), 2.70-2.54 (m, 4H) | 466.1 |
| 220 | N-(1-(4-(2-Methyl-3-(trifluoromethyl)benzyl)piperazine-1-carbonyl)-1H-pyrazol-3-yl)methanesulfonamide | 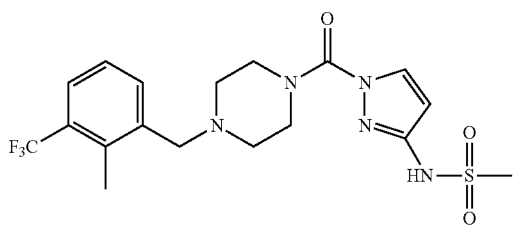 [SMILES: Cc1c(CN2CCN(C(=O)n3ccc(NS(C)(=O)=O)n3)CC2)cccc1C(F)(F)F] | δ 8.01 (s, 1H), 7.58 (s, 1H), 7.44 (s, 1H), 7.25 (s, 1H), 6.28 (s, 1H), 5.65 (s, 1H), 3.82 (s, 4H), 3.55 (s, 2H), 3.15 (s, 3H), 2.57-2.51 (m, 4H), 2.50 (s, 3H) | 446.1 |
| 221 | N-(1-(4-(3-(Cyclopropylmethoxy)-4-(difluoromethoxy)benzyl)piperazine-1-carbonyl)-1H-pyrazol-3-yl)methanesulfonamide | 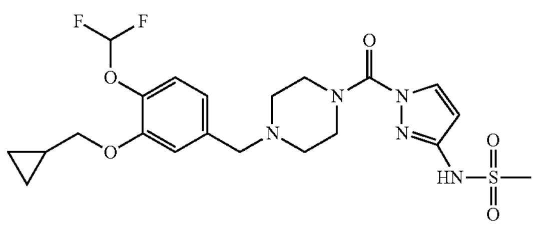 [SMILES: CS(=O)(=O)Nc1ccn(C(=O)N2CCN(Cc3ccc(OC(F)F)c(OCC4CC4)c3)CC2)n1] | δ 7.85 (s, 1H), 7.03-6.88 (m, 1H), 6.81 (s, 1H), 6.76-6.65 (m, 1H), 7.2-7.1, 6.50-6.40, 6.3-6.2 (m, 1H), 6.20-6.06 (m, 1H), 5.23 (s, 1H), 3.79-3.59 (m, 6H), 3.35 (s, 2H), 2.98 (s, 3H), 2.37 (s, 4H), 1.23-1.02 (m, 1H), 0.58-0.44 (m, 2H), 0.28-0.13 (m, 2H) | 500.2 |
| 222 | N-(1-(4-(4-Fluoro-3-phenoxybenzyl)piperazine-1-carbonyl)-1H-pyrazol-3-yl)methanesulfonamide | 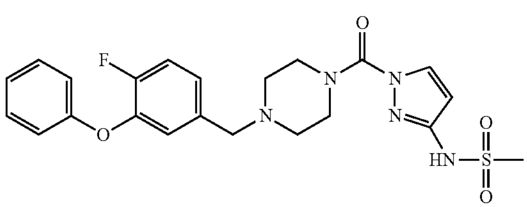 [SMILES: CS(=O)(=O)Nc1ccn(C(=O)N2CCN(Cc3ccc(F)c(Oc4ccccc4)c3)CC2)n1] | δ 8.00 (s, 1H), 7.41-7.31 (m, 2H), 7.21-7.05 (m, 4H), 7.04-6.94 (m, 2H), 6.28 (s, 1H), 5.77 (s, 1H), 3.87-3.70 (m, 4H), 3.48 (s, 2H), 3.12 (s, 3H), 2.60-2.44 (m, 4H) | 474.2 |
| 223 | (S)-N-(1-(4-((5-Chloro-4-(4-fluoropiperidin-1-yl)pyridin-2-yl)methyl)-3-methylpiperazine-1-carbonyl)-1H-pyrazol-3-yl)methanesulfonamide | 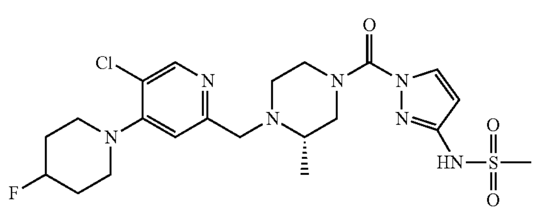 [SMILES: C[C@H]1CN(C(=O)n2ccc(NS(C)(=O)=O)n2)CCN1Cc1cc(N2CCC(F)CC2)c(Cl)cn1] | (Methanol-d4) δ 8.28 (s, 1H), 8.06 (d, J = 2.8 Hz, 1H), 7.22 (s, 1H), 6.24 (d, J = 2.8 Hz, 1H), 4.97-4.78 (m, 1H), 4.33-4.12 (m, 2H), 4.04-4.01 (m, 1H), 3.49-3.44 (m, 2H), 3.41-3.35 (m, 2H), 3.29-3.24 (m, 3H), 3.15 (s, 3H), 2.85-2.82 (m, 1H), 2.71-2.68 (m, 1H), 2.44-2.39 (m, 1H), 2.21-1.99 (m, | 514.3 |

| Ex | Name | Structure | NMR (¹H NMR, 300 MHz or 400 MHz, chloroform-d) | MS [M + H]⁺ |
|---|---|---|---|---|
| | | | 4H), 1.19 (d, J = 6.4 Hz, 3H) | |
| 224 | (R)-N-(1-(4-(4-Chloro-3-(pyrrolidin-1-yl)benzyl)-3-methyl-piperazine-1-carbonyl)-1H-pyrazol-3-yl)methane-sulfonamide | 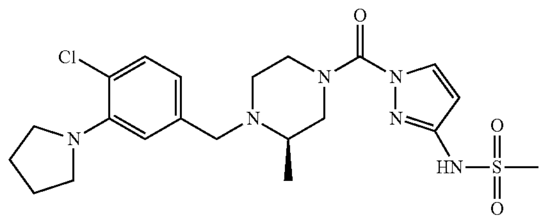 [SMILES: C[C@@H]1CN(C(=O)n2ccc(NS(C)(=O)=O)n2)CCN1Cc1ccc(Cl)c(N2CCCC2)c1] | δ 8.05 (d, J = 2.8 Hz, 1H), 7.25 (d, J = 7.6 Hz, 1H), 6.85 (s, 1H), 6.76 (d, J = 8.0 Hz, 1H), 6.32 (d, J = 2.8 Hz, 1H), 4.27-4.08 (m, 2H), 4.02-3.93 (m, 1H), 3.50-3.35 (m, 5H), 3.29-3.11 (m, 5H), 2.84-2.75 (m, 1H), 2.67-2.56 (m, 1H), 2.30-2.20 (m, 1H), 2.04-1.92 (m, 4H), 1.19 (d, J = 6.4 Hz, 3H) | 481.1 |

II. Biological Evaluation

In Vitro Competitive Activity-Based Protein Profiling.

Proteomes (mouse brain membrane fraction or cell lysates for mouse assays; human prefrontal cortex or PC3 cell membrane fractions for human assays) (50 µL, 1.0 or 2.0 mg/mL total protein concentration) were preincubated with varying concentrations of inhibitors at 37° C. After 30 min, FP-Rh or JW912 or HT-01 (1.0 µL, 50 µM in DMSO) was added and the mixture was incubated for another 30 min at 37° C. Reactions were quenched with SDS loading buffer (15 µL-4×) and run on SDS-PAGE. Following gel imaging, serine hydrolase activity was determined by measuring fluorescent intensity of gel bands corresponding to MAGL and FAAH using ImageJ 1.43u software. $IC_{50}$ data from this assay is shown in Table 1. All compounds in Table 1 were more potent inhibitors of MAGL than FAAH.

Preparation of Mouse Brain Proteomes from Inhibitor Treated Mice.

Inhibitors were administered to wild-type C57B1/6J by oral gavage in a vehicle of polyethylene glycol. Each animal was sacrificed 4 h following administration and brain proteomes were prepared and analyzed according to previously established methods (See Niphakis, M. J., et al. (2011) ACS Chem. Neurosci. and Long, J. Z., et al. Nat. Chem. Biol. 5:37-44).

Compounds demonstrated activity in the assays described herein as indicated in Table 1.

TABLE 1

| Ex | MAGL % inh. 1 µM (human) | FAAH % inh. 1 µM (human) | MAGL % inh. 1 µM (mouse) | FAAH % inh. 1 µM (mouse) | MAGL $IC_{50}$ (µM) (human) | FAAH $IC_{50}$ (µM) (human) | MAGL % inh. 5 mg/kg (mouse) | FAAH % inh. 5 mg/kg (mouse) |
|---|---|---|---|---|---|---|---|---|
| 1 | A @ 10 µM | D | D | D | | | | |
| 2 | A | D | A | D | | | | |
| 3 | A | D | A | D | | | | |
| 4 | A | D | A | D | | | D | D |
| 5 | A | D | A | D | | | | |
| 6 | A | D | A | D | | | | |
| 7 | A | D | A | D | | | | |
| 8 | A | D | A | D | | | | |
| 9 | A | D | A | D | | | | |
| 10 | B @ 10 µM | D | D | D | | | | |
| 11 | A | D | A | D | *** | * | C | D |
| 12 | A | D | A | D | | | D | D |
| 13 | | | A | C | *** | * | | |
| 14 | A | D | B | D | *** | * | D | D |
| 15 | A | D | A | C | | | | |
| 16 | A | C | A | C | | | | |
| 17 | A | A | A | A | | | | |
| 18 | A | A | A | A | *** | ** | | |
| 19 | A | D | A | D | | | | |
| 20 | A | D | A | A | *** | * | | |
| 21 | A | D | A | D | | | | |
| 22 | A | B | A | A | *** | ** | C | C |
| 23 | A | A | A | A | *** | ** | | |
| 24 | A | D | A | D | | | | |

TABLE 1-continued

| Ex | MAGL % inh. 1 μM (human) | FAAH % inh. 1 μM (human) | MAGL % inh. 1 μM (mouse) | FAAH % inh. 1 μM (mouse) | MAGL IC$_{50}$ (μM) (human) | FAAH IC$_{50}$ (μM) (human) | MAGL % inh. 5 mg/kg (mouse) | FAAH % inh. 5 mg/kg (mouse) |
|---|---|---|---|---|---|---|---|---|
| 25 | A | D | A | D | *** | * | | |
| 26 | A | D | D | D | | | | |
| 27 | D @ 10 μM | | D | D | | | | |
| 28 | A | A | A | A | | | | |
| 29 | B @ 10 μM | D | D | D | | | | |
| 30 | A | | A | A | | | | |
| 31 | A | D | A | D | | | | |
| 32 | A | D | A | D | | | A | D |
| 33 | A | | A | D | | | | |
| 34 | A | A | A | A | *** | ** | | |
| 35 | A | D | A | D | | | | |
| 36 | | | A | A | | | | |
| 37 | | | A | A | | | | |
| 38 | | | A | C | *** | * | | |
| 39 | | | A | B | *** | * | A | D |
| 40 | C | B | C | A | | | | |
| 41 | | | D | A | | | | |
| 42 | A | | A | | | | | |
| 43 | A | D | A | D | *** | * | | |
| 44 | | | A | A | | | | |
| 45 | D @ 10 μM | D | D | D | | | | |
| 46 | C @ 10 μM | D | D | D | | | | |
| 47 | C @ 50 μM | D | D | D | | | | |
| 48 | C @ 50 μM | D | D | D | | | | |
| 49 | C | D | B | D | | | | |
| 50 | B | D | B | A | | | | |
| 51 | A | A | A | A | *** | ** | | |
| 52 | A | D | A | D | *** | * | | |
| 53 | A @ 10 μM | D | D | D | | | | |
| 54 | A | D | A | D | | | | |
| 55 | A | D | A | D | | | | |
| 56 | A | D | A | D | | | | |
| 57 | A | D | A | D | | | | |
| 58 | A | D | A | D | | | A | D |
| 59 | A | D | A | D | | | | |
| 60 | A | D | A | D | | | | |
| 61 | C | D | B | D | | | | |
| 62 | A | D | A | D | | | | |
| 63 | A | D | A | D | *** | * | C | D |
| 64 | A | D | A | D | | | | |
| 65 | A | D | A | D | | | | |
| 66 | A | D | A | D | | | | |
| 67 | A | C | A | C | | | | |
| 68 | A | D | A | D | | | | |
| 69 | A @ 10 μM | D | D | D | | | | |
| 70 | A | D | A | D | | | | |
| 71 | A | D | A | D | | | A | D |
| 72 | A | D | C | B | | | | |
| 73 | A | D | A | B | | | | |
| 74 | A | D | A | D | *** | * | | |
| 75 | A | D | A | D | | | A | D |
| 76 | A | D | A | D | | | D | D |
| 77 | B | D | D | D | | | | |
| 78 | A | D | A | D | | | | |
| 79 | A | D | A | D | | | D | D |
| 80 | A | D | A | D | | | A | D |
| 81 | A | D | B | D | | | | |
| 82 | A | D | B | D | | | | |
| 83 | A | D | A | D | | | | |
| 84 | A | D | A | D | | | | |
| 85 | A | D | A | D | | | | |
| 86 | C | D | C | D | | | | |
| 87 | A | D | A | D | | | D | D |
| 88 | A | D | A | D | | | | |
| 89 | A | D | A | D | | | | |
| 90 | A | D | A | D | | | C | D |
| 91 | A | C | A | B | | | | |

TABLE 1-continued

| Ex | MAGL % inh. 1 μM (human) | FAAH % inh. 1 μM (human) | MAGL % inh. 1 μM (mouse) | FAAH % inh. 1 μM (mouse) | MAGL IC$_{50}$ (μM) (human) | FAAH IC$_{50}$ (μM) (human) | MAGL % inh. 5 mg/kg (mouse) | FAAH % inh. 5 mg/kg (mouse) |
|---|---|---|---|---|---|---|---|---|
| 92 | A | D | A | D | | | | |
| 93 | A | D | A | D | | | D | D |
| 94 | A | D | A | D | | | A | D |
| 95 | A | D | A | D | | | | |
| 96 | A | D | A | D | | | D | D |
| 97 | C | D | C | D | | | | |
| 98 | A | D | A | D | | | D | D |
| 99 | A | D | A | D | | | | |
| 100 | B | D | B | D | | | | |
| 101 | A | D | B | D | | | | |
| 102 | B | D | D | D | | | | |
| 103 | A | D | A | D | | | D | D |
| 104 | A | D | A | D | | | D | D |
| 105 | A | D | A | D | | | | |
| 106 | A | D | A | D | | | D | D |
| 107 | A | D | A | D | | | | |
| 108 | A | D | A | D | | | D | D |
| 109 | A | D | A | D | | | | |
| 110 | A | D | A | D | | | | |
| 111 | A | D | A | D | | | | |
| 112 | A | C | A | A | | | A | A |
| 113 | A | C | A | A | | | | |
| 114 | A | C | C | A | | | | |
| 115 | A | C | C | A | | | | |
| 116 | A | D | B | D | | | | |
| 117 | A | D | A | D | | | B | D |
| 118 | A | D | A | D | | | D | D |
| 119 | A | D | A | D | | | A | D |
| 120 | A | D | A | D | | | | |
| 121 | A | A | A | A | *** | ** | | |
| 122 | A | D | A | D | | | | |
| 123 | A | D | A | D | | | | |
| 124 | A | D | A | D | | | | |
| 125 | A | D | A | D | | | D | D |
| 126 | A | D | A | D | | | | |
| 127 | A | D | A | D | | | | |
| 128 | A | D | A | D | | | | |
| 129 | A | D | A | D | | | | |
| 130 | A | D | A | D | | | | |
| 131 | A | A | A | A | *** | * | A | A |
| 132 | A | D | A | D | *** | * | D | D |
| 133 | A | D | A | D | | | D | D |
| 134 | A | D | A | D | | | C | D |
| 135 | A | D | A | D | | | D | D |
| 136 | A | D | A | D | | | A | D |
| 137 | A | D | A | D | | | D | D |
| 138 | A | D | A | D | | | A | D |
| 139 | A | D | A | D | *** | * | D | D |
| 140 | C | D | D | D | | | | |
| 141 | A | D | A | D | | | A | D |
| 142 | A | D | A | D | | | | |
| 143 | A | D | A | D | | | D | D |
| 144 | A | D | A | D | | | | |
| 145 | A | A | A | A | *** | ** | | |
| 146 | A | A | A | A | *** | * | | |
| 147 | A | D | A | D | | | | |
| 148 | A | D | A | D | | | A | D |
| 149 | A | A | A | A | *** | ** | | |
| 150 | A | C | A | D | *** | * | D | D |
| 151 | A | D | A | D | | | | |
| 152 | A @ 10 μM | | | | | | | |
| 153 | A | D | B | D | | | | |
| 154 | A | C | A | A | *** | * | B | C |
| 155 | A | D | A | A | | | | |
| 156 | A | D | A | D | | | A | D |
| 157 | A | D | A | D | | | D | D |
| 158 | A | D | A | D | | | D | D |
| 159 | A | D | A | D | | | D | D |
| 160 | B | C | D | D | | | | |
| 161 | | | A | D | | | | |
| 162 | A | D | D | D | | | | |
| 163 | A | D | D | D | | | | |

TABLE 1-continued

| Ex | MAGL % inh. 1 μM (human) | FAAH % inh. 1 μM (human) | MAGL % inh. 1 μM (mouse) | FAAH % inh. 1 μM (mouse) | MAGL IC$_{50}$ (μM) (human) | FAAH IC$_{50}$ (μM) (human) | MAGL % inh. 5 mg/kg (mouse) | FAAH % inh. 5 mg/kg (mouse) |
|---|---|---|---|---|---|---|---|---|
| 164 | A | D | D | D | | | | |
| 165 | A @ 10 μM | | | | | | | |
| 166 | A | D | A | A | | | | |
| 167 | A | C | A | A | | | | |
| 168 | A | B | A | A | | | A | A |
| 169 | A | B | A | A | | | B | B |
| 170 | | | A | B | | | | |
| 171 | | | A | B | | | | |
| 172 | | | A | A | *** | ** | | |
| 173 | | | A | A | *** | ** | | |
| 174 | | | A | B | | | | |
| 175 | A | | A | | *** | | | |
| 176 | A | | A | | *** | | A | |
| 177 | A | | A | | | | | |
| 178 | A | | A | | *** | | | |
| 179 | A | | A | | *** | | | |
| 180 | A | | A | | *** | | | |
| 181 | A | | A | | *** | | | |
| 182 | A | | A | | *** | | D | |
| 183 | A | | A | | | | | |
| 184 | A | | A | | *** | | | |
| 185 | A | | A | | | | A | |
| 186 | A | | A | | | | A | |
| 187 | A | | A | | *** | | | |
| 188 | A | | A | | | | A | |
| 189 | A | | A | | | | A | |
| 190 | A | | A | | | | D | |
| 191 | A | | A | | | | | |
| 192 | A | | A | | | | | |
| 193 | A | | A | | | | | |
| 194 | B @ 10 μM | | D | | | | | |
| 195 | A | | A | | | | | |
| 196 | A | | A | | | | | |
| 197 | A | | A | | | | D | |
| 198 | A | | B | | | | | |
| 199 | A | | A | | | | | |
| 200 | A | | A | | | | | |
| 201 | A | | A | | | | | |
| 202 | A | | A | | | | | |
| 203 | A | | | | | | | |
| 204 | A | | | | | | | |
| 205 | A | | | | | | | |
| 206 | A | | | | | | | |
| 207 | A | | | | | | | |
| 208 | A | | | | *** | | | |
| 209 | A | | A | | | | | |
| 210 | A | | A | | | | | |
| 211 | A | | | | | | | |
| 212 | A | | | | | | | |
| 213 | A | | | | | | | |
| 214 | A | | | | | | | |
| 215 | A | | | | | | | |
| 216 | A | | | | | | | |
| 217 | A | | | | | | | |
| 218 | A | | | | | | | |
| 219 | A | | | | | | | |
| 220 | A | | | | | | | |
| 221 | A | | | | | | | |
| 222 | A | | | | | | | |
| 223 | A | | A | | | | | |
| 224 | A | | A | | | | | |

*** IC$_{50}$ is less than or equal to 100 nM;
** IC$_{50}$ is greater than 100 nM and less than 1 μM;
* IC$_{50}$ is greater than or equal to 1 μM and less or equal to 10 μM.
A = % inhibition is greater than or equal to 75%;
B = % inhibition is greater than or equal to 50% and less than 75%;
C = % inhibition is greater than or equal to 25% and less than 50%;
D = % inhibition is greater than or equal to 0% and less than 25%.

What is claimed is:

1. A compound of Formula (I):

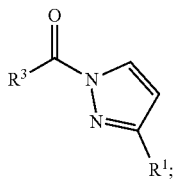

Formula (I)

wherein:

R¹ is —N(R²)C(O)R¹⁵ or —N(H)SO₂R¹⁵;
R is H or $C_{1-6}$alkyl;
R³ is

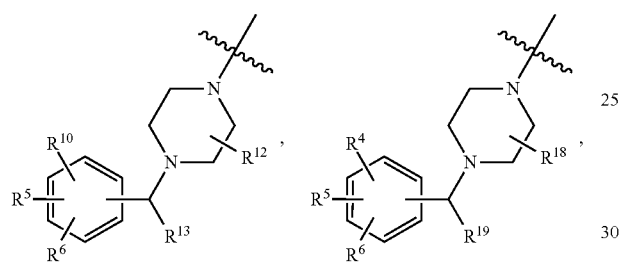

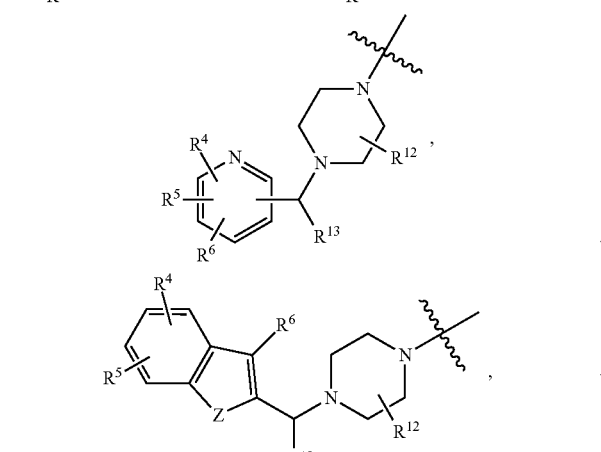

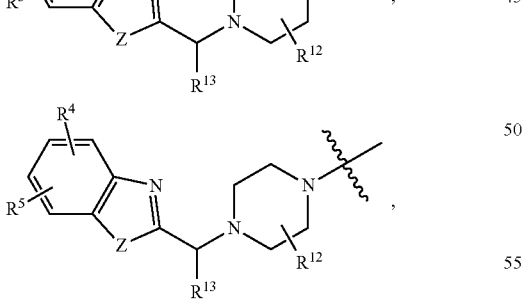

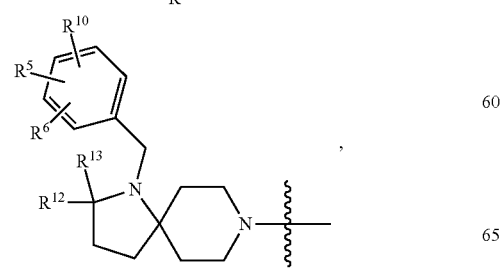

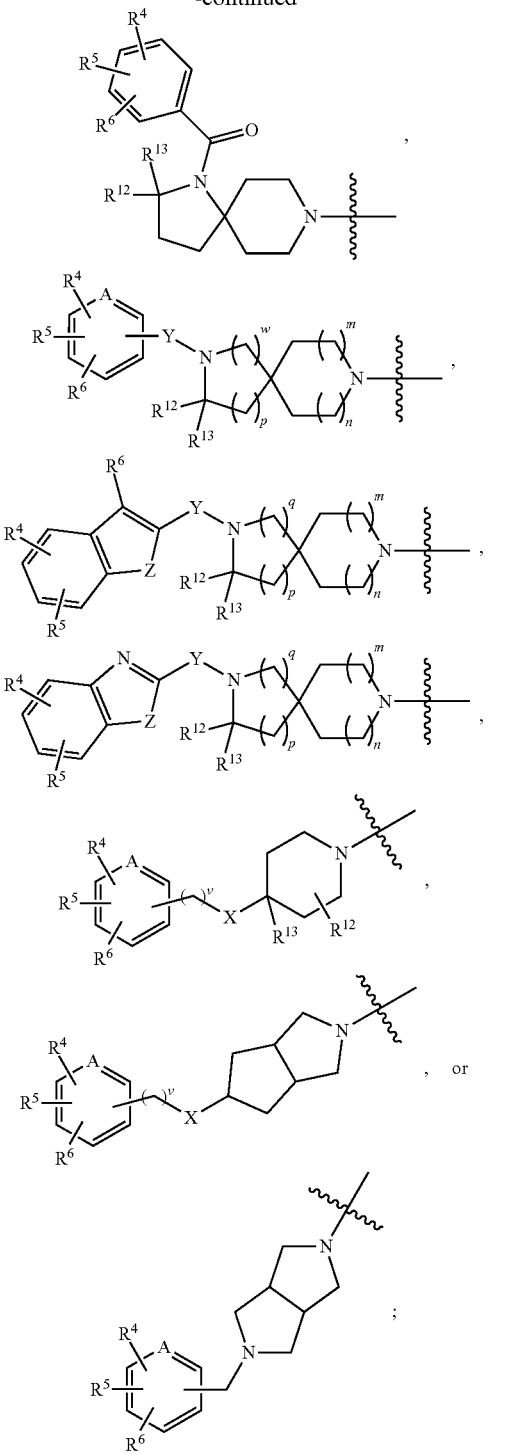

A is N or C(H);
X is —O—, —N(R¹⁶)—, or —CH₂N(R¹⁶)CH₂—;
Y is —CH₂— or —C(O)—;
Z is —S—, —O—, or —N(R²⁰)—;
R⁴ is H, halogen, —OR⁷, $C_{1-6}$alkyl, $C_{1-6}$alkyl-OH, $C_{2-6}$alkenyl, $C_{2-6}$alkynyl, $C_{1-6}$haloalkyl, —O—$C_{3-8}$cycloalkyl, —O—$C_{3-8}$cycloalkyl-OH, —N(H)—$C_{1-6}$alkyl-CO₂H, —SO₂R¹⁷, —CO₂R⁸, —C(O)NR⁸R⁹, $C_{3-8}$cycloalkyl, $C_{2-9}$heterocycloalkyl, —$C_{1-6}$alkyl-$C_{2-9}$heterocycloalkyl, $C_{6-10}$aryl, $C_{1-9}$heteroaryl, wherein $C_{3-8}$cycloalkyl, $C_{2-9}$heterocycloalkyl, —$C_{1-6}$alkyl-$C_{2-9}$heterocycloalkyl, $C_{6-10}$aryl, $C_{1-9}$heteroaryl are optionally substituted with 1 or 2 $R^{14}$;

$R^5$ is H, —CN, halogen, $C_{1-6}$alkyl, $C_{1-6}$haloalkyl, $C_{1-6}$haloalkoxy, or phenyl;

$R^6$ is H, halogen, or $C_{1-6}$alkyl;

$R^7$ is H, $C_{1-6}$alkyl, $C_{1-6}$haloalkyl, $C_{3-8}$cycloalkyl, $C_{2-9}$heterocycloalkyl, $C_{6-10}$aryl, or $C_{1-9}$heteroaryl, wherein $C_{2-9}$heterocycloalkyl, $C_{6-10}$aryl, or $C_{1-9}$heteroaryl are optionally substituted with 1 or 2 $R^{14}$;

each $R^8$ and each $R^9$ are independently selected from H and $C_{1-6}$alkyl; or $R^8$ and $R^9$ together with the nitrogen to which they are attached are combined to form a heterocycloalkyl ring;

$R^{10}$ is —O—$C_{1-6}$haloalkyl, —O—$C_{1-6}$alkyl-$CO_2H$, —O—$C_{3-8}$cycloalkyl, —O—$C_{3-8}$cycloalkyl-$CO_2H$, —N(H)—$C_{1-6}$alkyl-$CO_2H$, or —$SO_2R^{17}$;

$R^{12}$ is H, halogen, or $C_{1-6}$alkyl;

$R^{13}$ is H or $C_{1-6}$alkyl;

each $R^{14}$ is independently selected from halogen, —OH, oxo, $C_{1-6}$alkyl, $C_{1-6}$haloalkyl, $C_{1-6}$alkoxy, —$C_{1-6}$alkyl-OH, $C_{3-8}$cycloalkyl, —$CO_2R^8$, —C(O)NR$^8$R$^9$, —C(O)—$C_{1-6}$alkyl, —C(O)—$C_{1-6}$alkyl-OH, —$SO_2$—$C_{1-6}$alkyl, —N(R$^8$)$SO_2$—$C_{1-6}$alkyl, and —N(R$^8$)C(O)—$C_{1-6}$alkyl;

$R^{15}$ is $C_{1-6}$alkyl or $C_{3-8}$cycloalkyl;

$R^{16}$ is H, $C_{1-6}$alkyl, —C(O)—$C_{1-6}$alkyl, or —$CH_2CO_2H$;

$R^{17}$ is $C_{1-6}$alkyl or $C_{3-8}$cycloalkyl;

$R^{18}$ and $R^{19}$ are independently selected from H and $C_{1-6}$alkyl, wherein $R^{18}$ and $R^{19}$ are not both H;

$R^{20}$ is H or $C_{1-6}$alkyl;

v is 0 or 1;
n is 0 or 1;
m is 0 or 1;
p is 0, 1, or 2;
q is 0, 1, or 2; and
w is 1 or 2;

or a tautomer, N-oxide, stereoisomer, or pharmaceutically acceptable salt thereof.

2. The compound of claim 1, or a tautomer, N-oxide, stereoisomer, or pharmaceutically acceptable salt thereof, wherein $R^3$ is 3. The compound of claim 2, or a tautomer, N-oxide, stereoisomer, or pharmaceutically acceptable salt thereof, wherein m is 1, n is 1, p is 1, and w is 1.

4. The compound of claim 1, or a tautomer, N-oxide, stereoisomer, or pharmaceutically acceptable salt thereof, wherein A is C(H).

5. The compound of claim 1, or a tautomer, N-oxide, stereoisomer, or pharmaceutically acceptable salt thereof, wherein Y is —$CH_2$—.

6. The compound of claim 1, or a tautomer, N-oxide, stereoisomer, or pharmaceutically acceptable salt thereof, wherein $R^6$ is H.

7. The compound of claim 1, or a tautomer, N-oxide, stereoisomer, or pharmaceutically acceptable salt thereof, wherein $R^{13}$ is H.

8. The compound of claim 1, or a tautomer, N-oxide, stereoisomer, or pharmaceutically acceptable salt thereof, wherein $R^{12}$ is H.

9. The compound of claim 1, or a tautomer, N-oxide, stereoisomer, or pharmaceutically acceptable salt thereof, wherein $R^4$ is halogen, —$OR^7$, $C_{1-6}$alkyl-OH, —N(H)—$C_{1-6}$alkyl-$CO_2H$, $C_{1-6}$alkynyl, $C_{1-6}$haloalkyl, —$CO_2R^8$, —C(O)NR$^8$R$^9$, $C_{3-8}$cycloalkyl, $C_{2-9}$heterocycloalkyl, $C_{6-10}$aryl, or $C_{1-9}$heteroaryl, wherein $C_{3-8}$cycloalkyl, $C_{2-9}$heterocycloalkyl, $C_{6-10}$aryl, or $C_{1-9}$heteroaryl are optionally substituted with 1 or 2 $R^{14}$.

10. The compound of claim 1, or a tautomer, N-oxide, stereoisomer, or pharmaceutically acceptable salt thereof, wherein $R^4$ is halogen, —$OR^7$, —N(H)—$C_{1-6}$alkyl-$CO_2H$, $C_{1-6}$haloalkyl, —C(O)NR$^8$R$^9$, $C_{3-8}$cycloalkyl, $C_{2-9}$heterocycloalkyl, or $C_{1-9}$heteroaryl, wherein $C_{2-9}$heterocycloalkyl or $C_{1-9}$heteroaryl are optionally substituted with 1 or 2 $R^{14}$.

11. The compound of claim 1, or a tautomer, N-oxide, stereoisomer, or pharmaceutically acceptable salt thereof, wherein $R^4$ is $C_{1-6}$haloalkyl.

12. The compound of claim 1, or a tautomer, N-oxide, stereoisomer, or pharmaceutically acceptable salt thereof, wherein $R^4$ is —$CF_3$.

13. The compound of claim 1, or a tautomer, N-oxide, stereoisomer, or pharmaceutically acceptable salt thereof, wherein $R^4$ is —N(H)—$C_{1-6}$alkyl-$CO_2H$.

14. The compound of claim 1, or a tautomer, N-oxide, stereoisomer, or pharmaceutically acceptable salt thereof, wherein $R^4$ is —C(O)$NH_2$.

15. The compound of claim 1, or a tautomer, N-oxide, stereoisomer, or pharmaceutically acceptable salt thereof, wherein $R^5$ is H, —CN, halogen, $C_{1-6}$alkyl, $C_{1-6}$haloalkyl, or $C_{1-6}$haloalkoxy.

16. The compound of claim 1, or a tautomer, N-oxide, stereoisomer, or pharmaceutically acceptable salt thereof, wherein $R^5$ is $C_{1-6}$haloalkyl.

17. The compound of claim 1, or a tautomer, N-oxide, stereoisomer, or pharmaceutically acceptable salt thereof, wherein $R^5$ is —$CF_3$.

18. The compound of claim 1, or a tautomer, N-oxide, stereoisomer, or pharmaceutically acceptable salt thereof, wherein $R^1$ is —N(R$^2$)C(O)$R^{15}$.

19. The compound of claim 1, or a tautomer, N-oxide, stereoisomer, or pharmaceutically acceptable salt thereof, wherein $R^2$ is H.

20. The compound of claim 1, or a tautomer, N-oxide, stereoisomer, or pharmaceutically acceptable salt thereof, wherein $R^{15}$ is —$CH_3$.

21. A compound selected from:
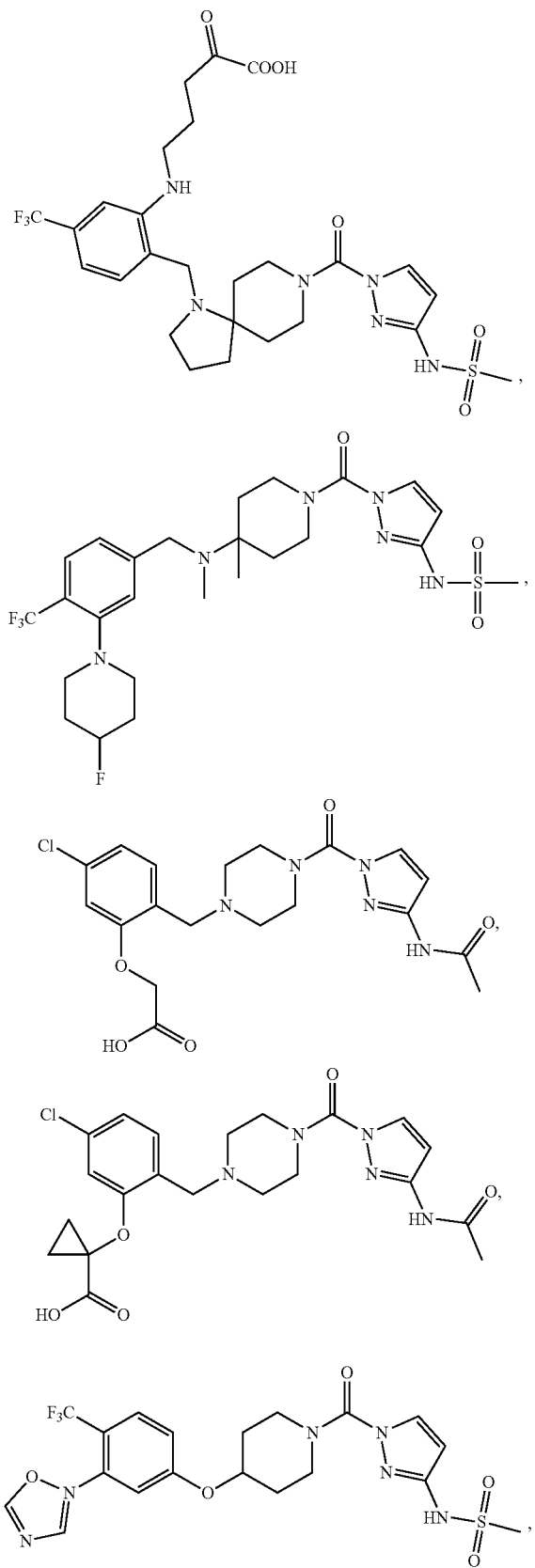
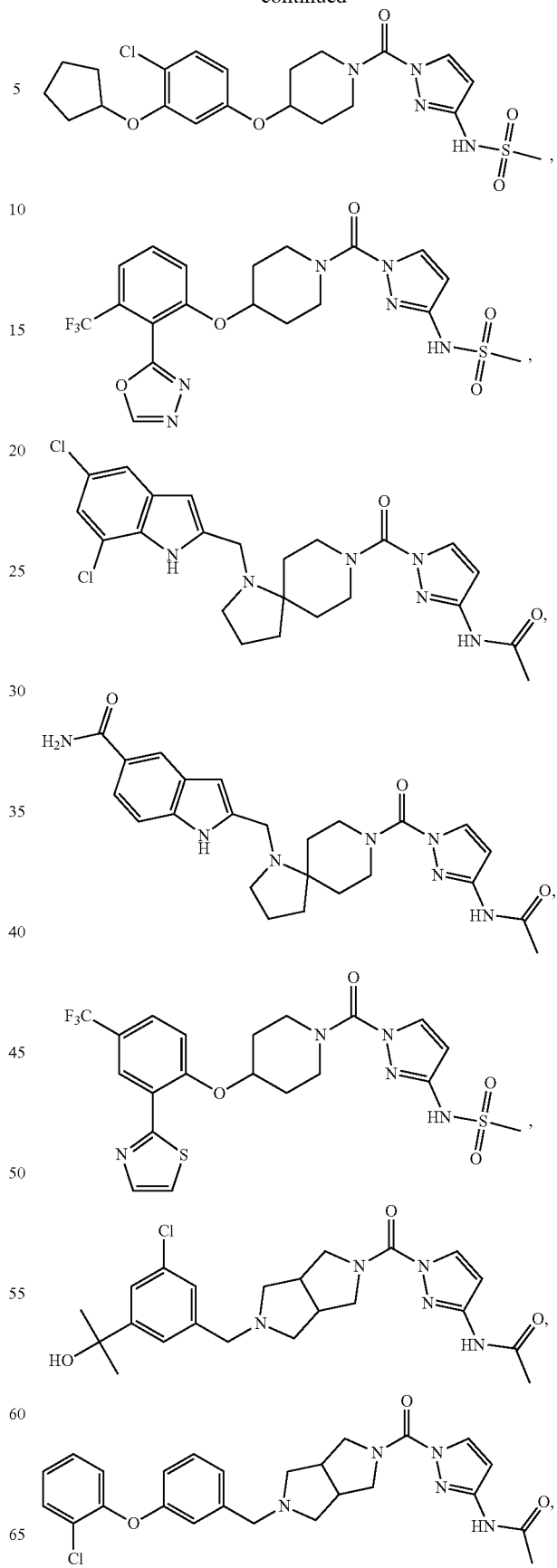

369
-continued
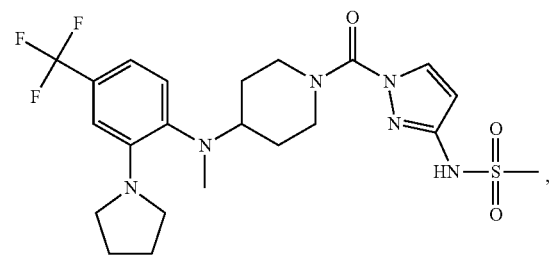
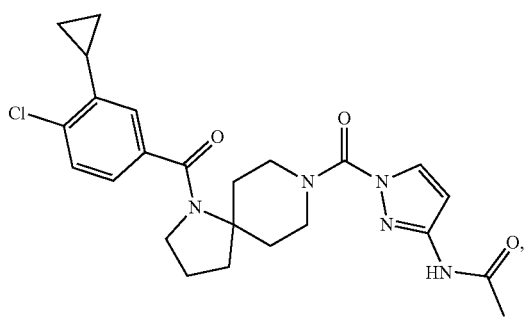
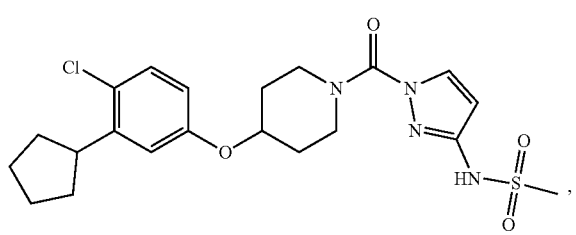
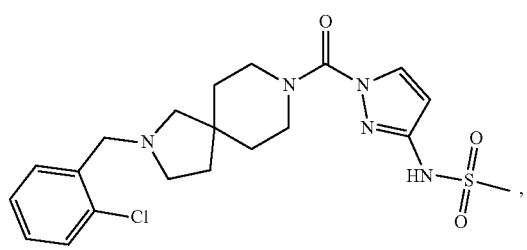
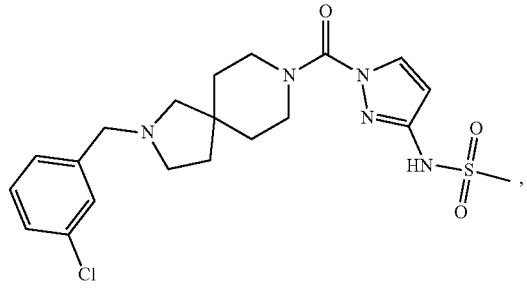
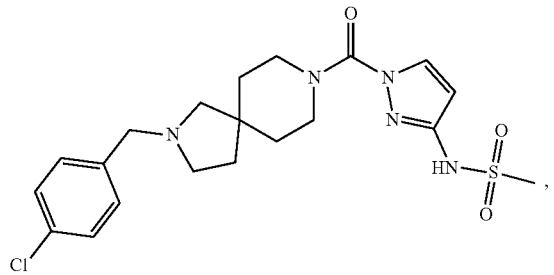
370
-continued
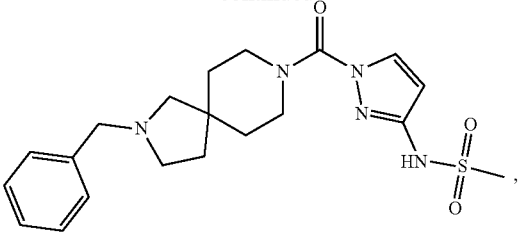
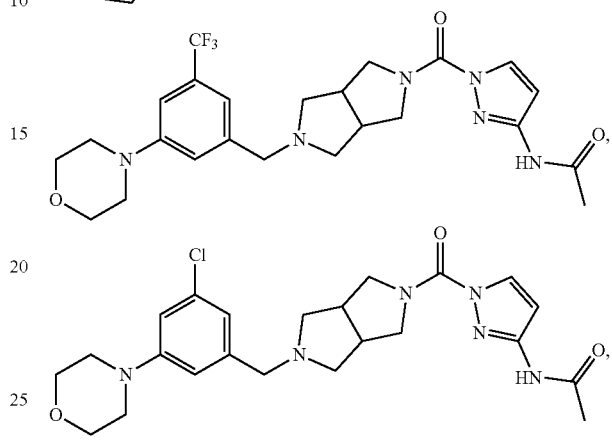
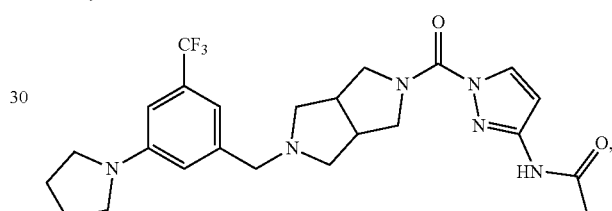
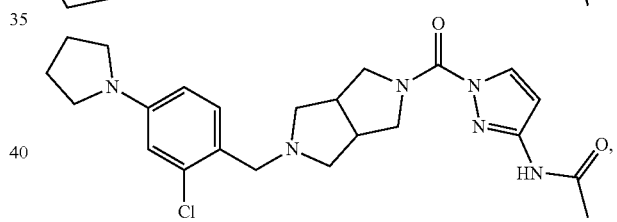
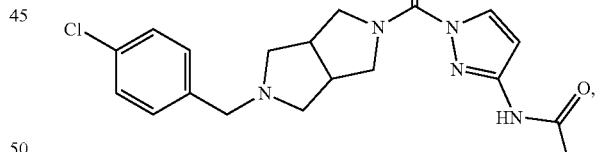
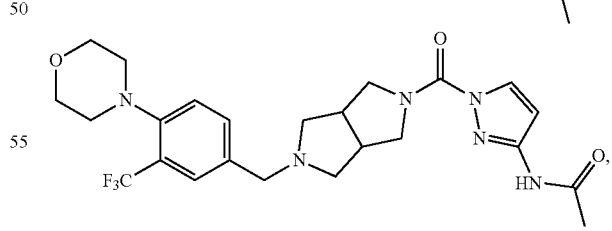
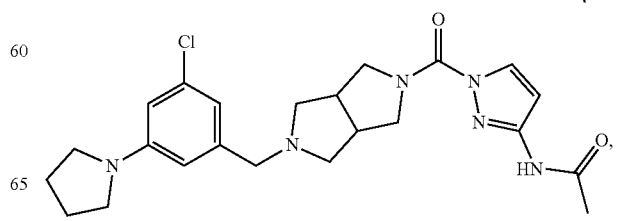

371
-continued
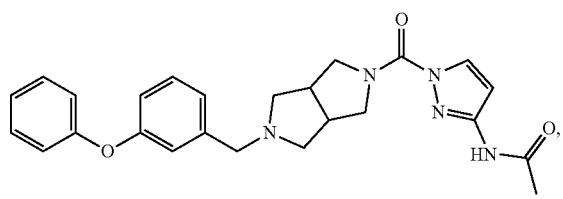
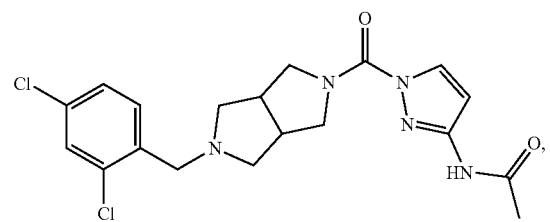
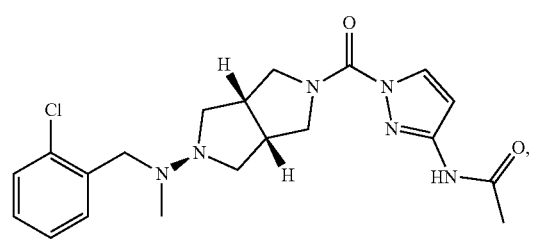
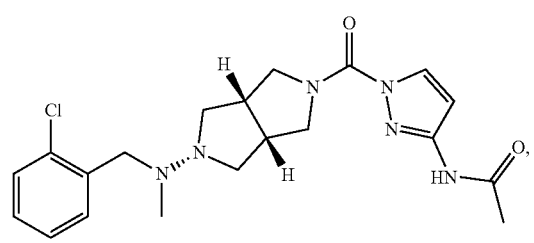
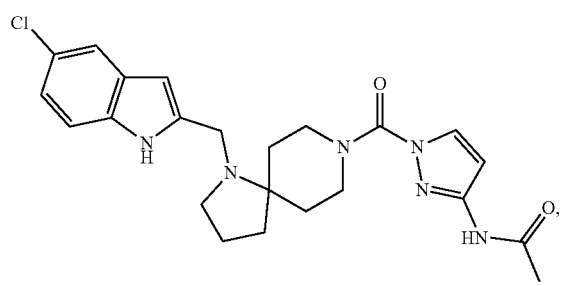
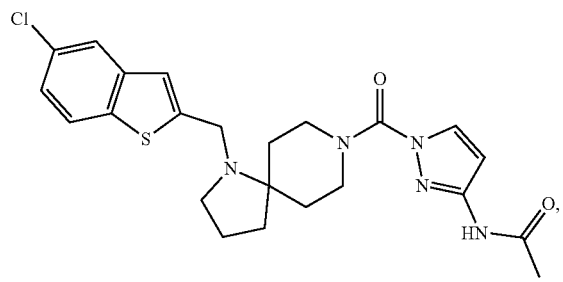
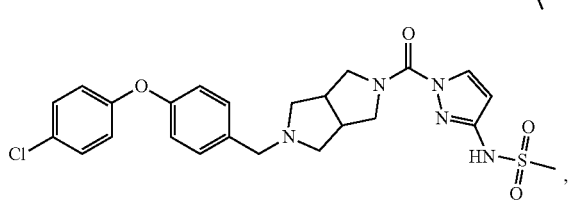
372
-continued
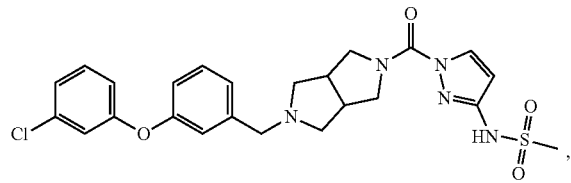
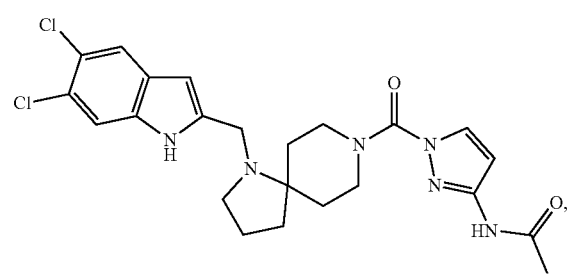
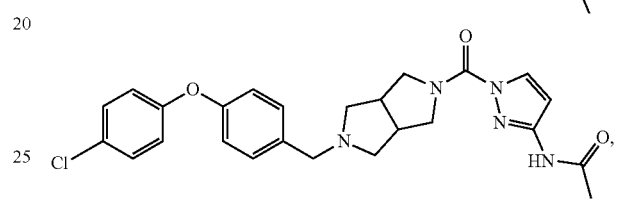
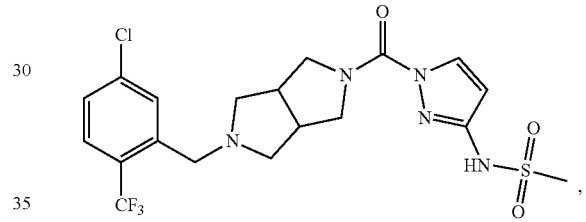
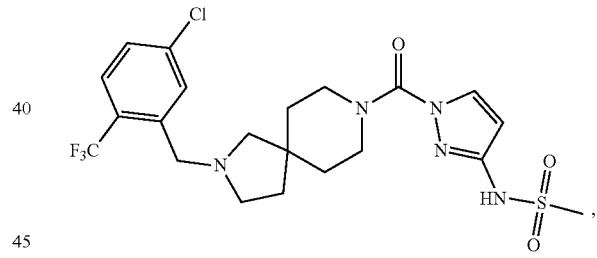
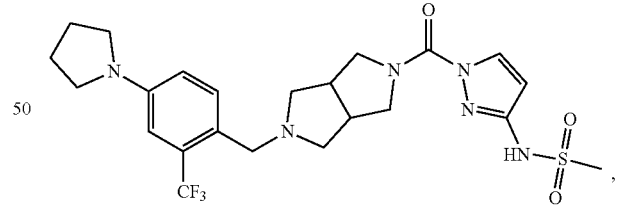
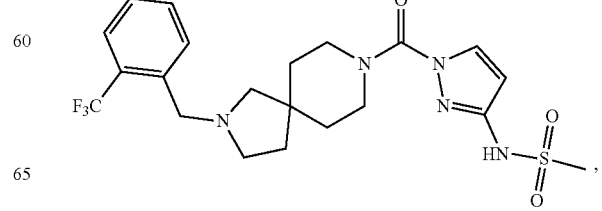

373
-continued
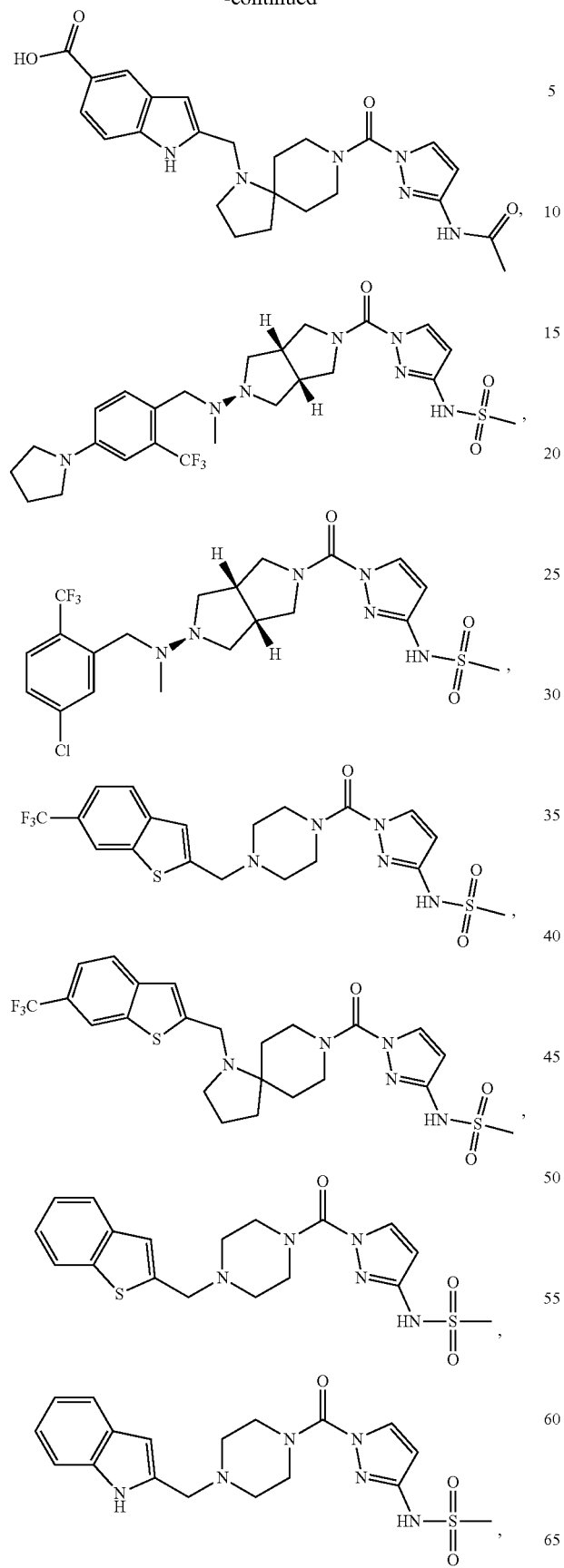
374
-continued
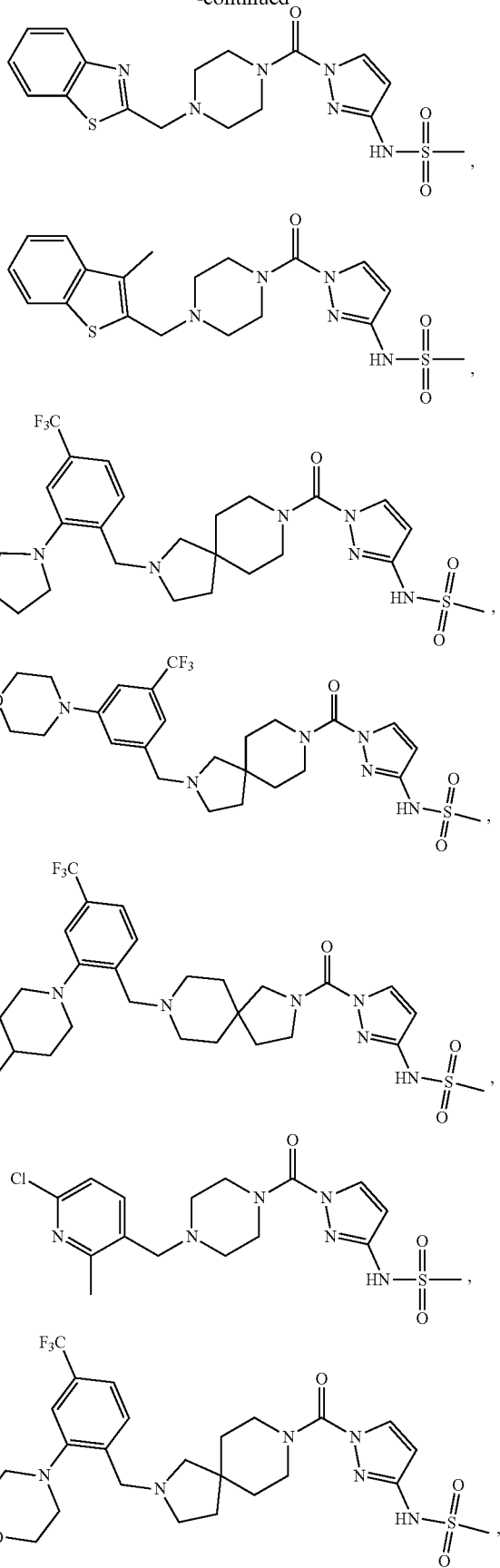

375
-continued
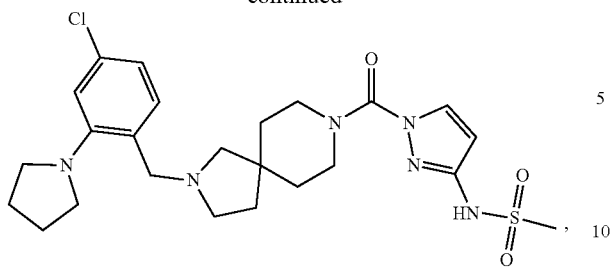
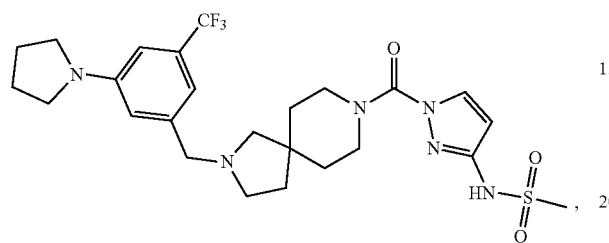
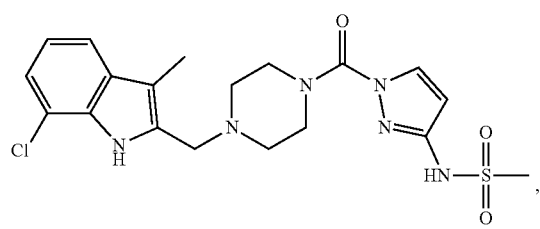
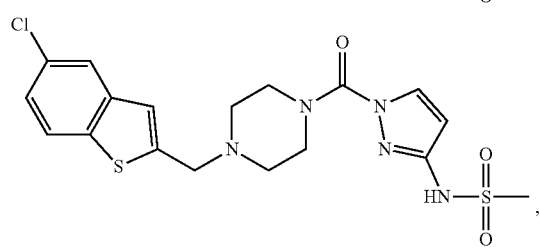
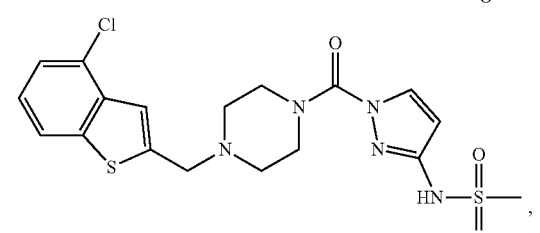
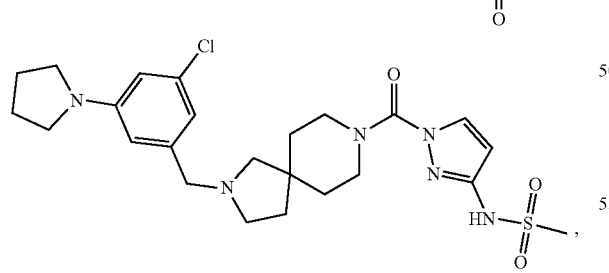
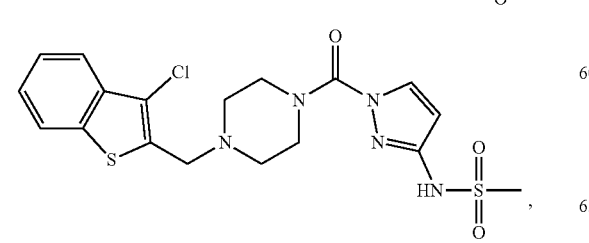
376
-continued
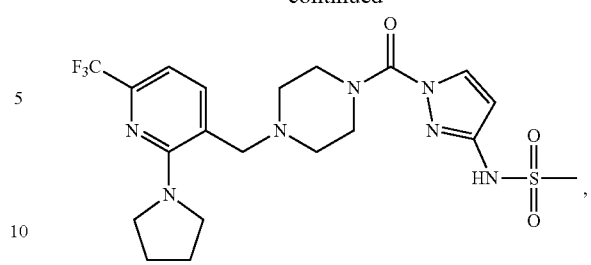
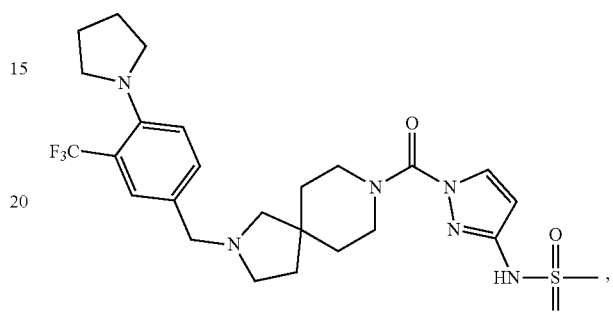
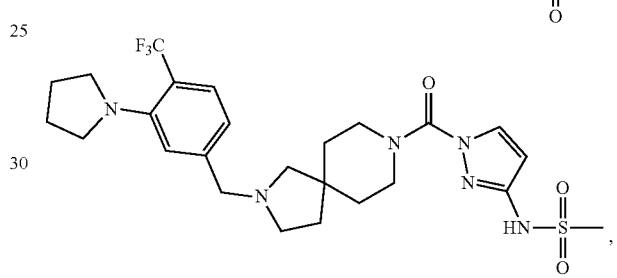
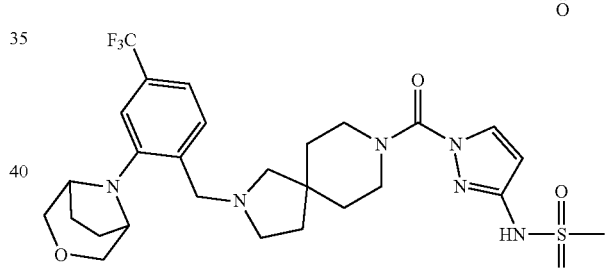
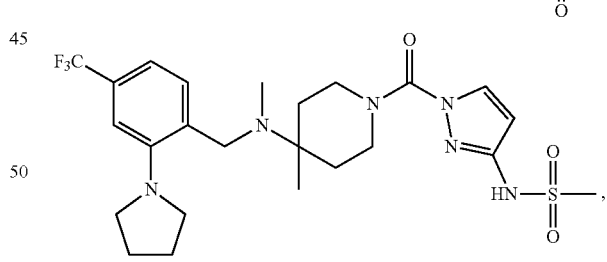
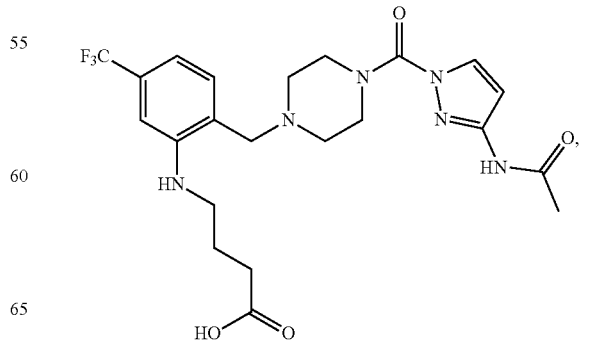

377
-continued
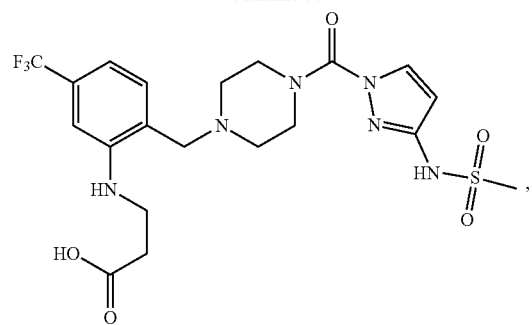
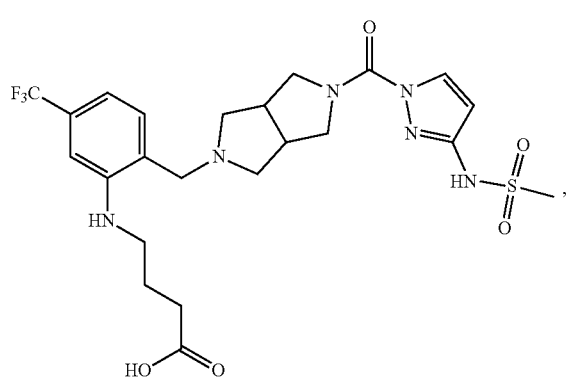
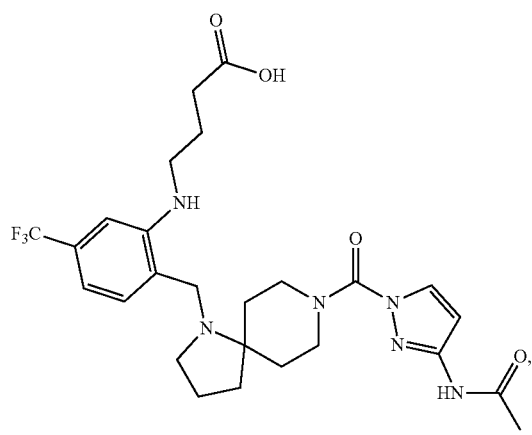
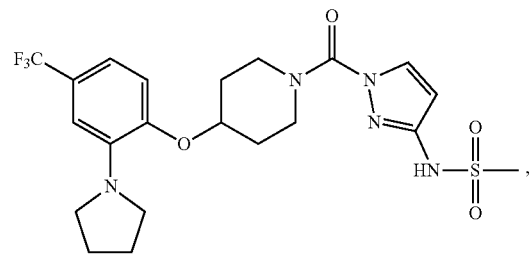
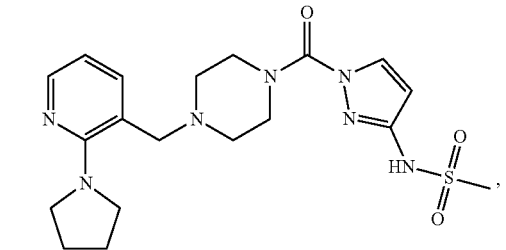
378
-continued
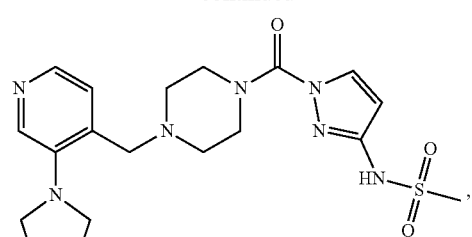
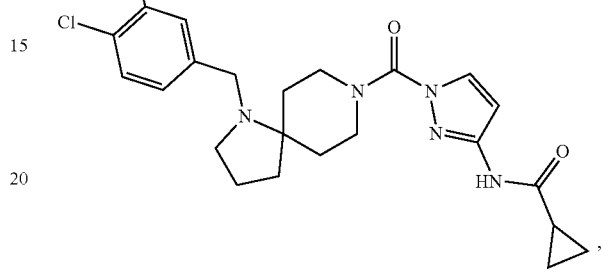
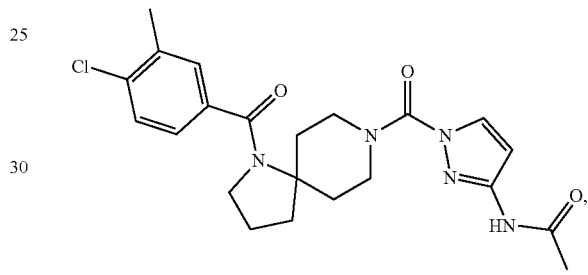
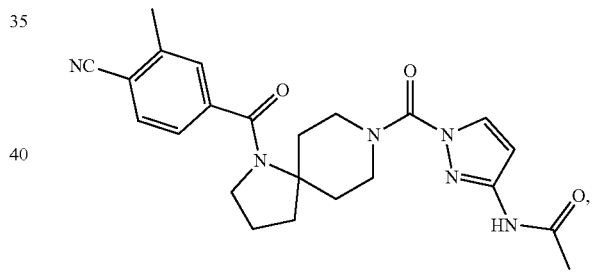
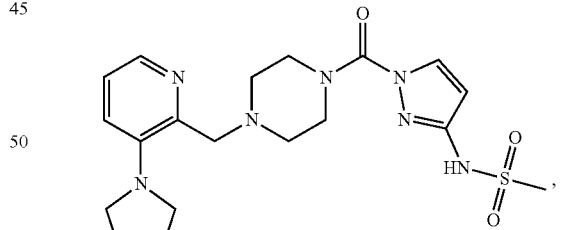
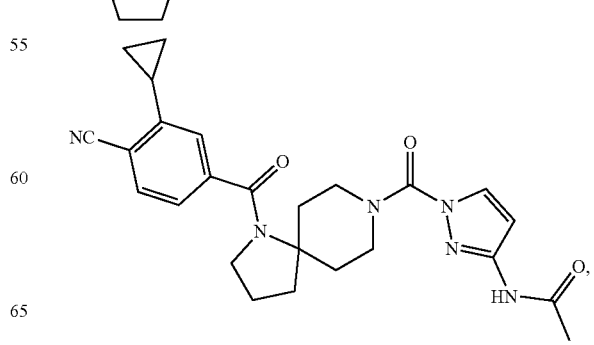

379
-continued
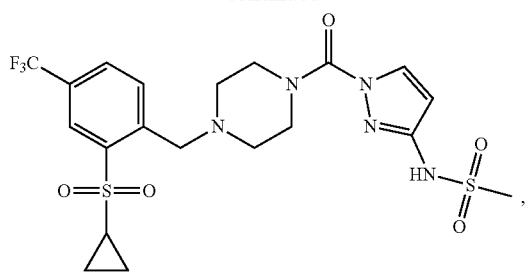
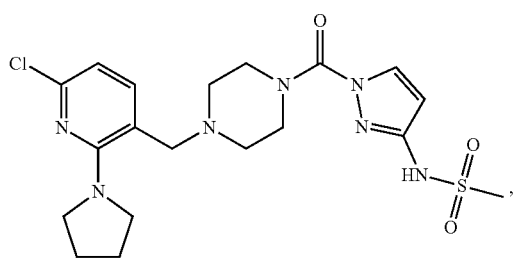
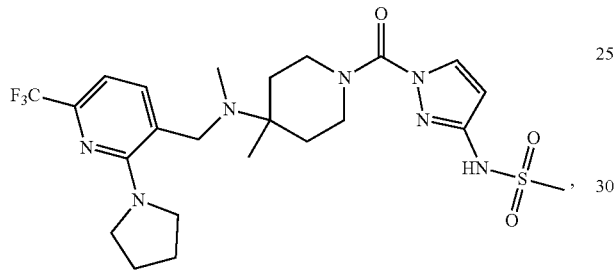
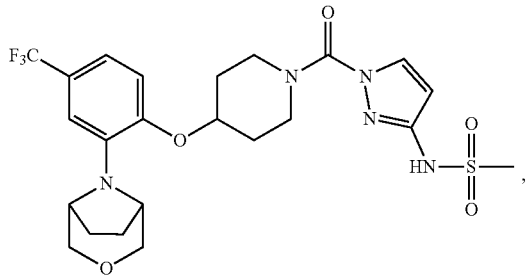
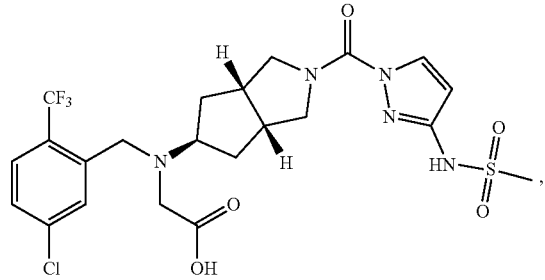
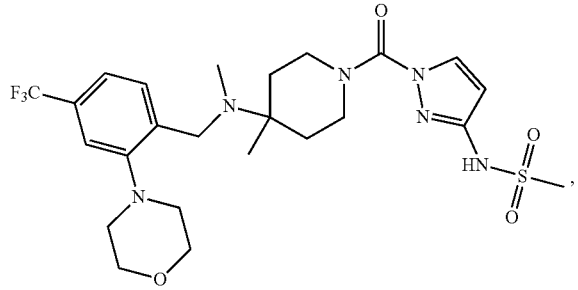
380
-continued
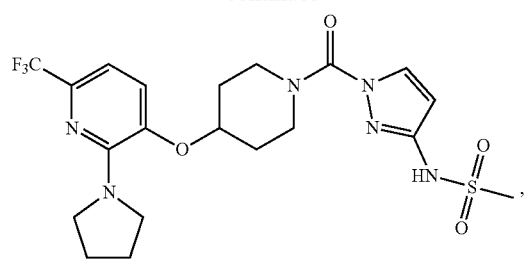
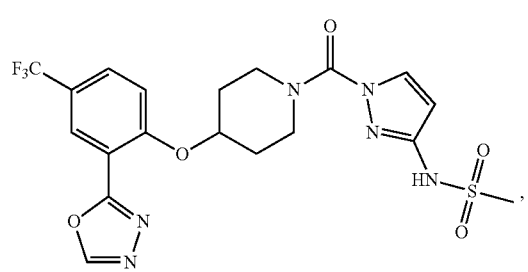
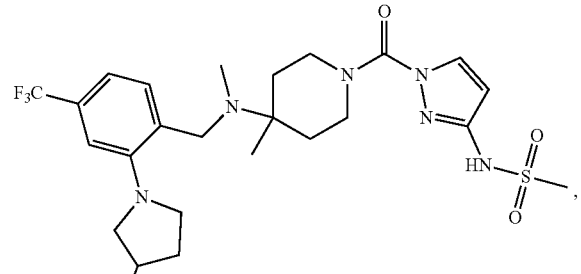
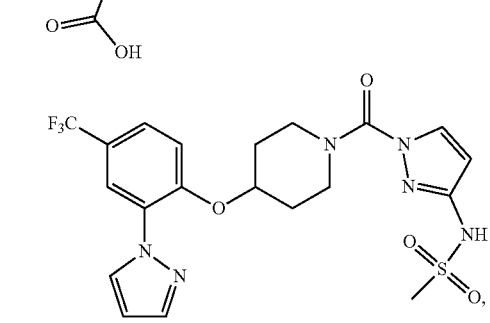
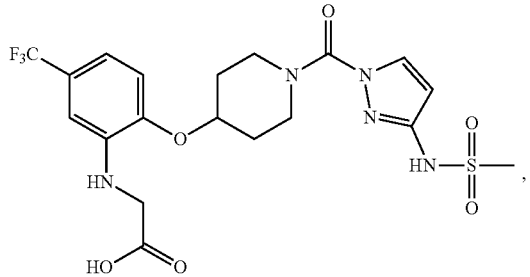
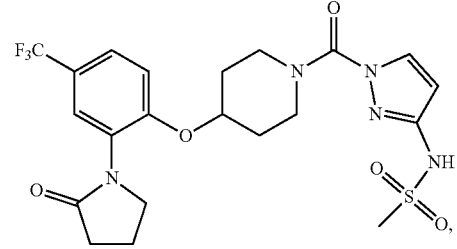

381
-continued
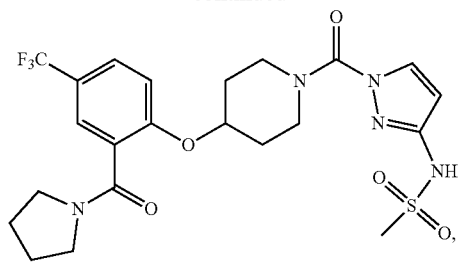
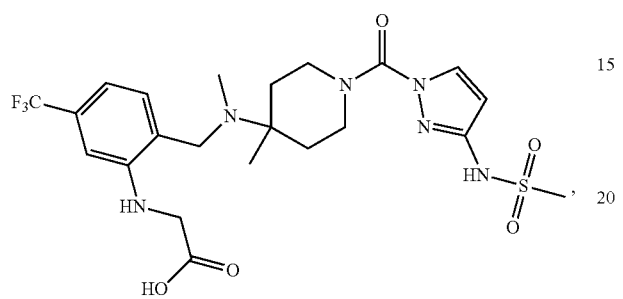
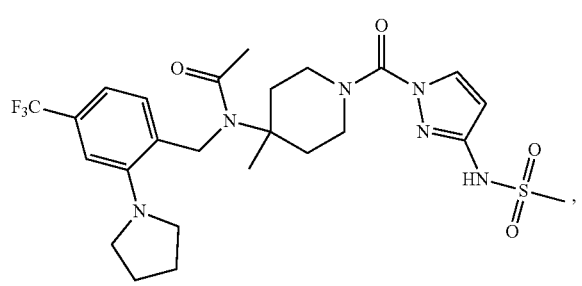
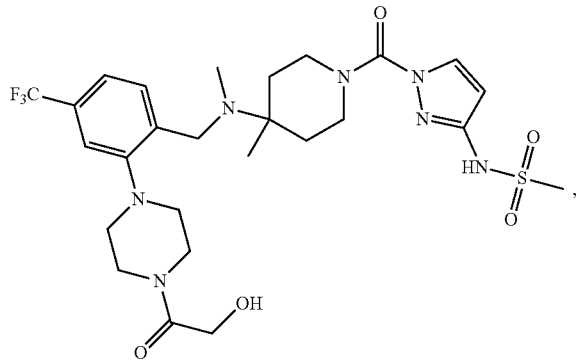
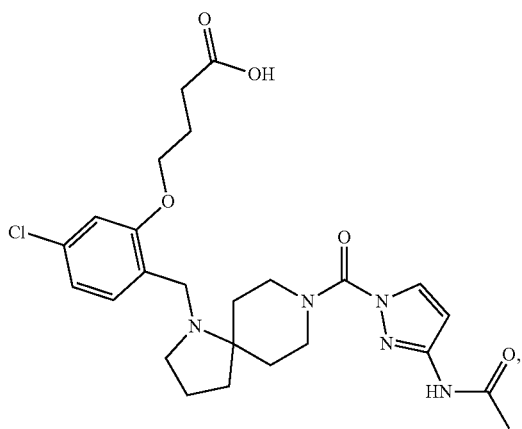
382
-continued
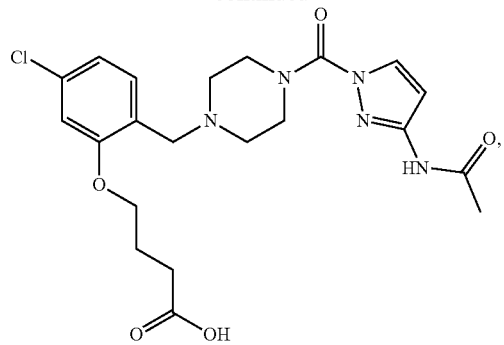
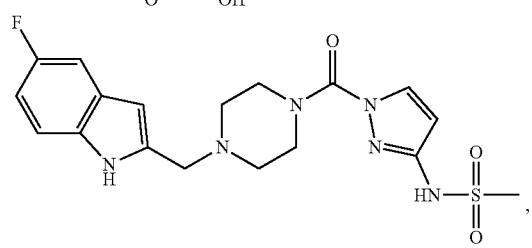
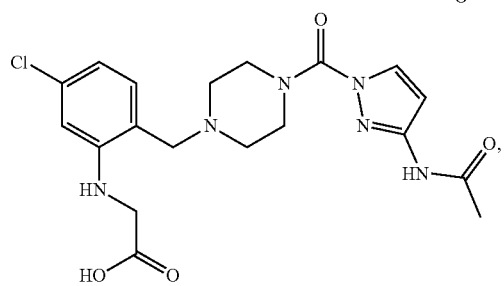
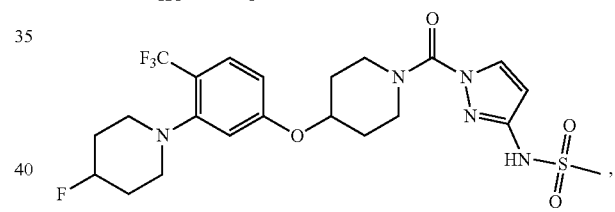
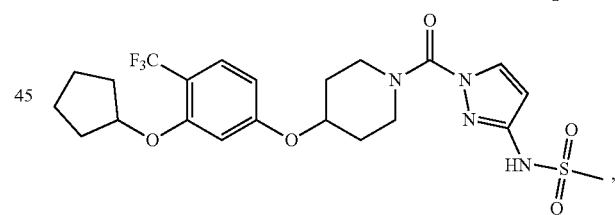
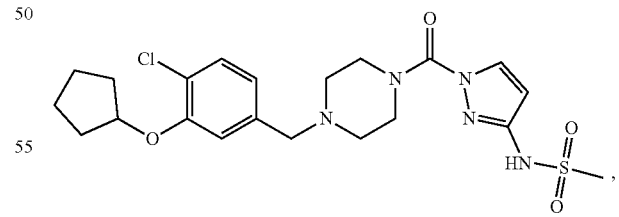
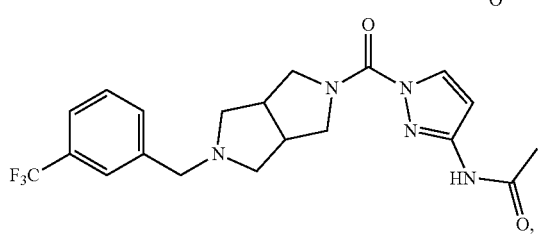

383
-continued
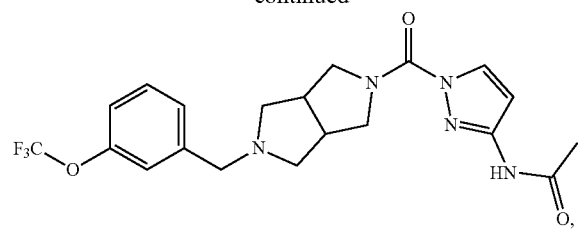
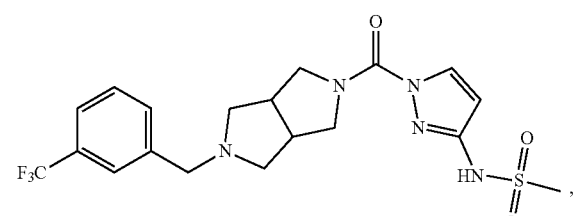
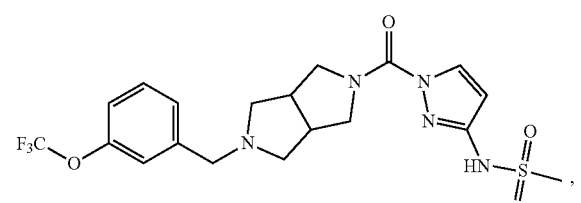
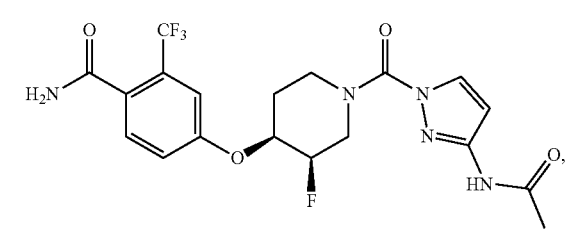
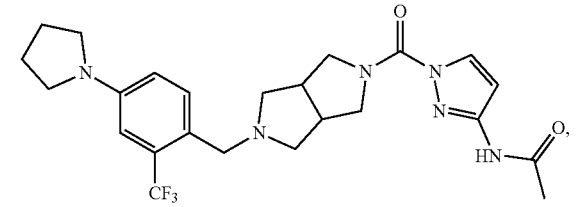
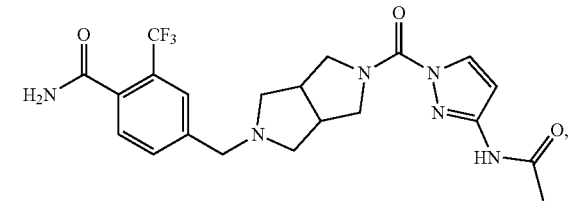
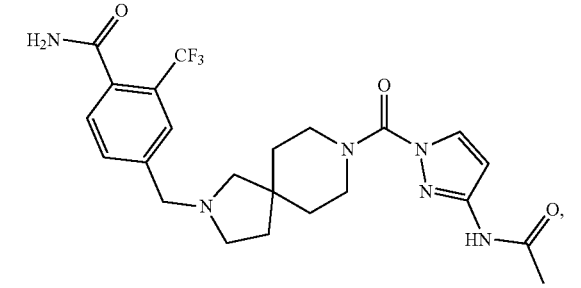
384
-continued
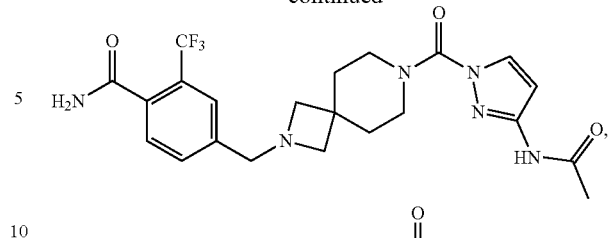
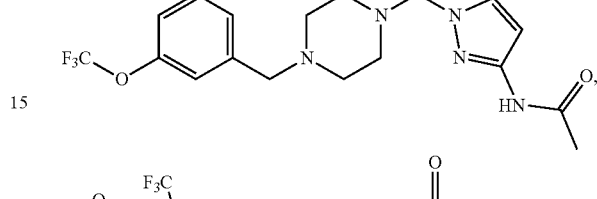
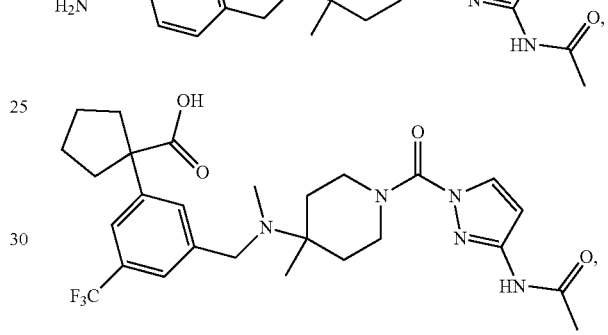
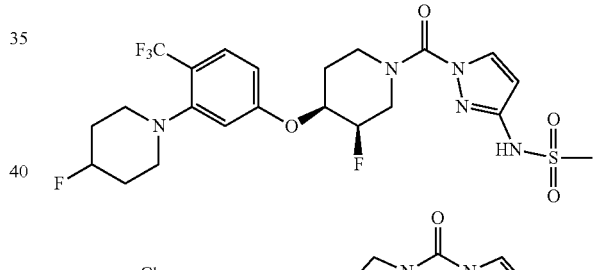
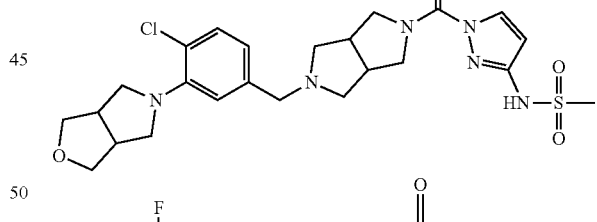
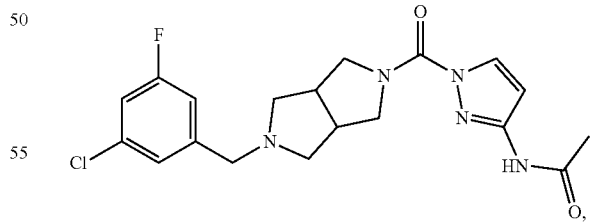
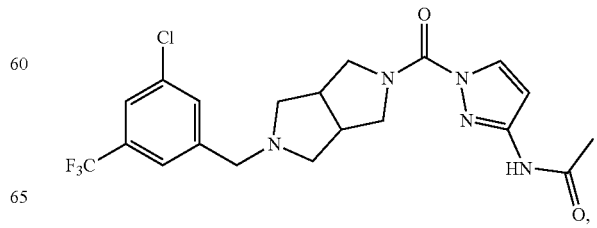

385
-continued
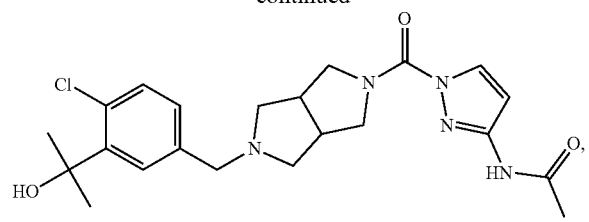
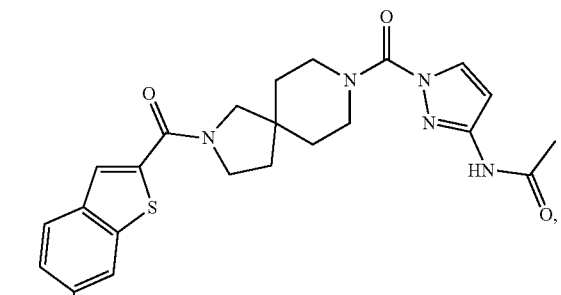
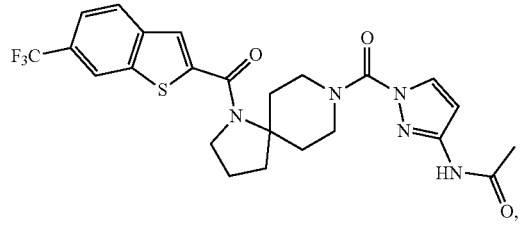
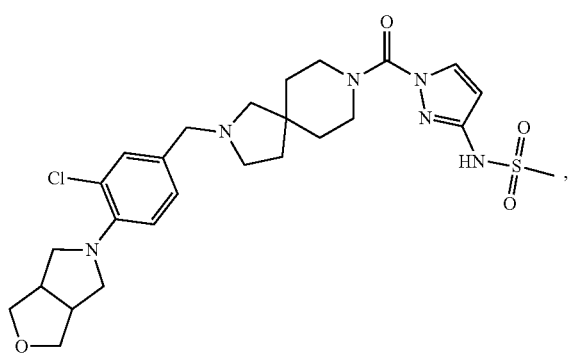
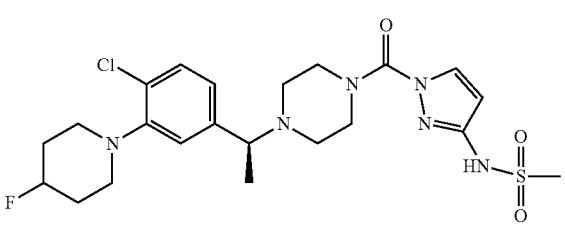
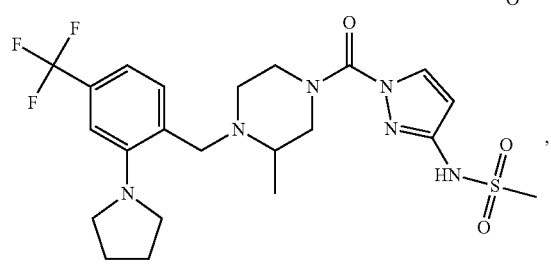
386
-continued
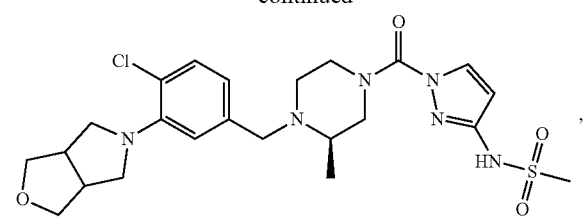
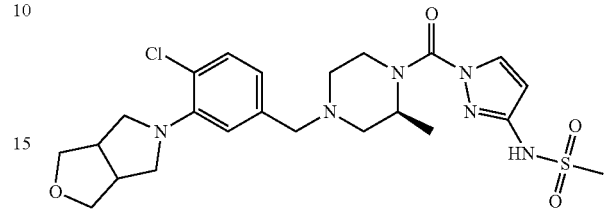
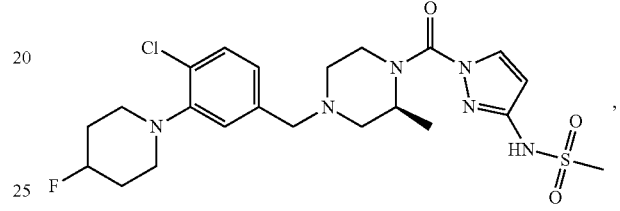
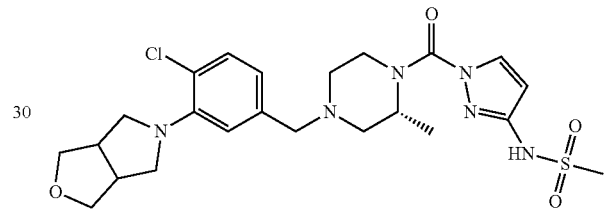
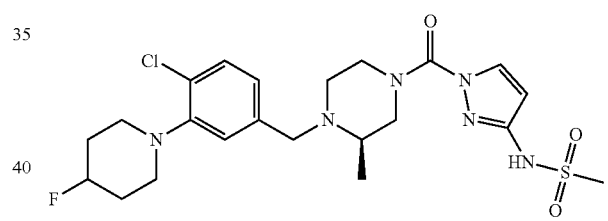
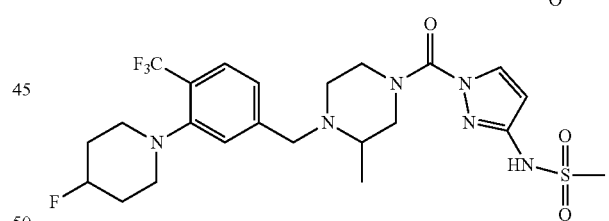
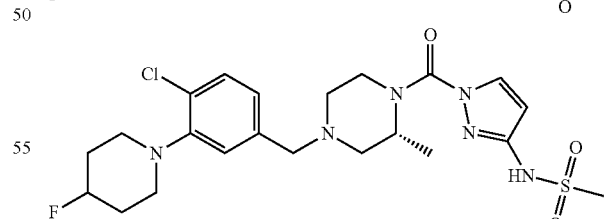
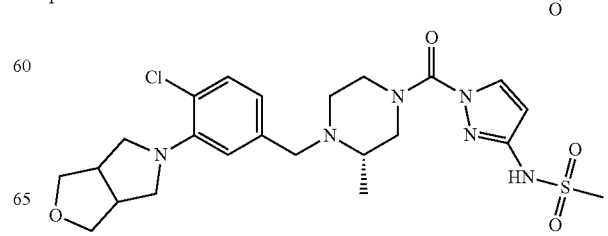

387
-continued
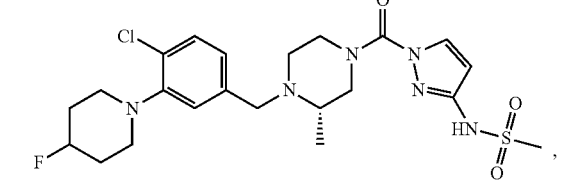
,
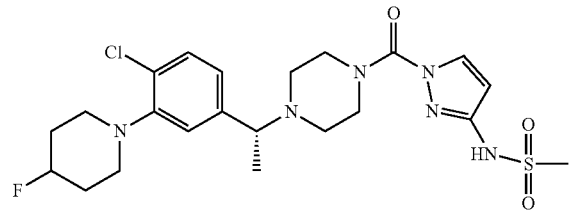
,
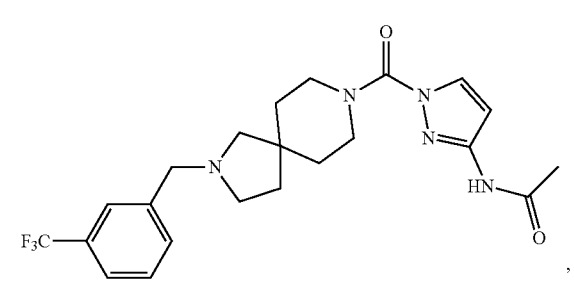
,
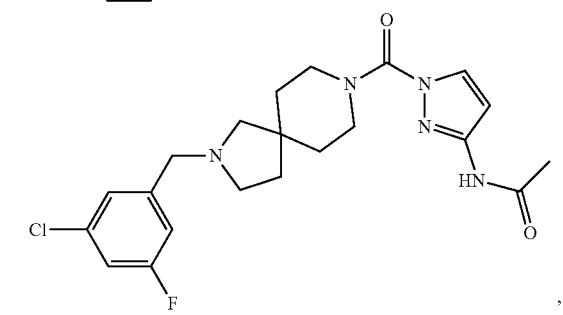
,
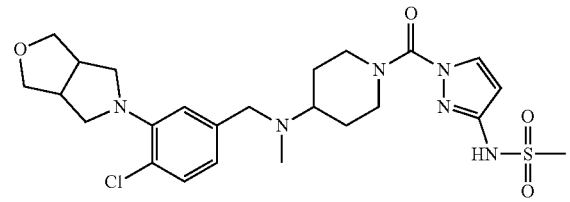
,
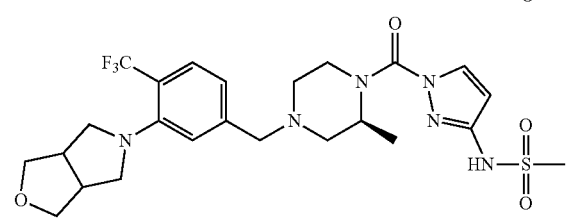
,
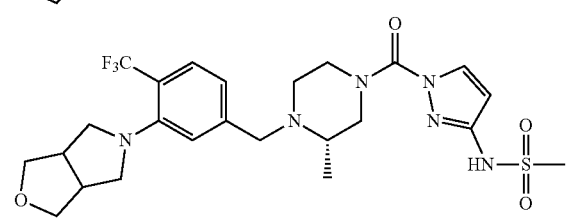
,
388
-continued
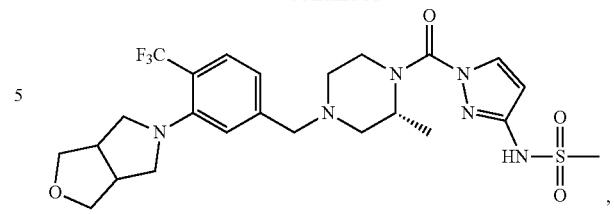
,
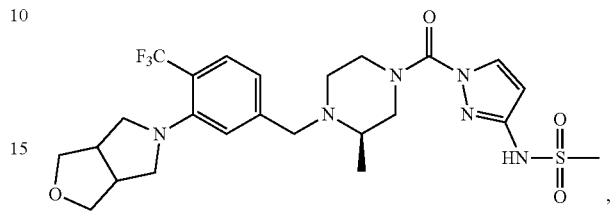
,
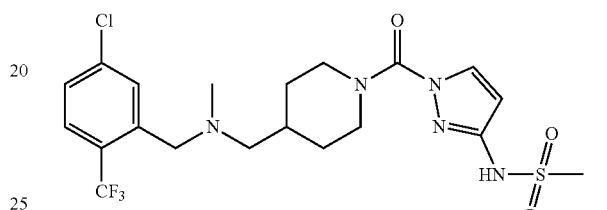
,
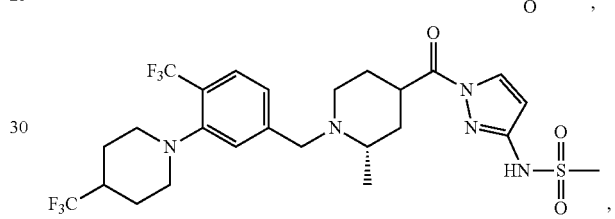
,
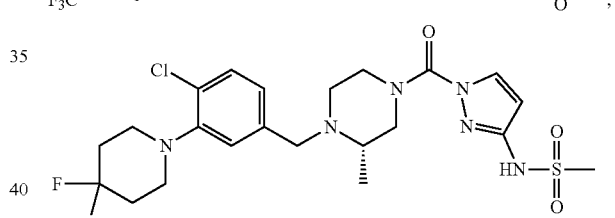
,
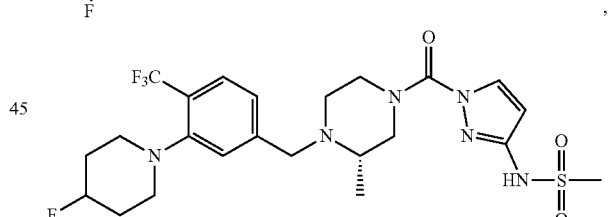
,
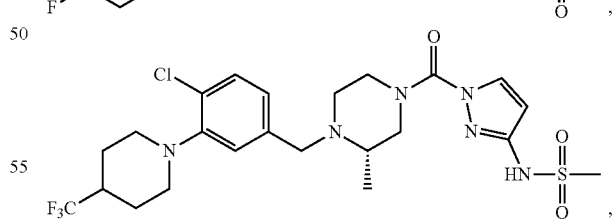
,
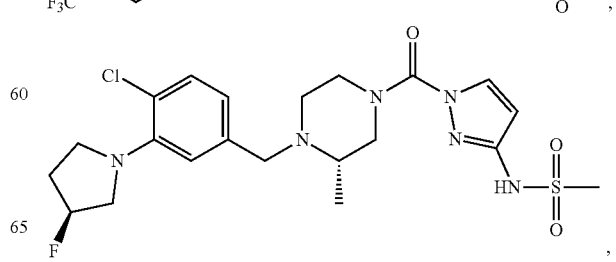
, 389
-continued
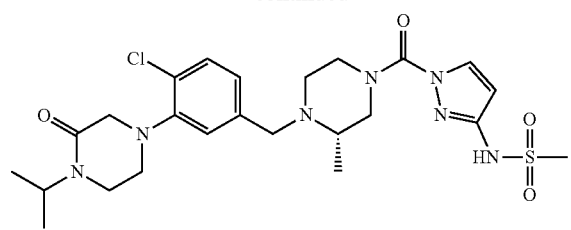
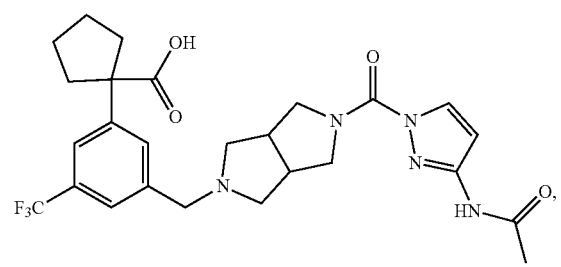
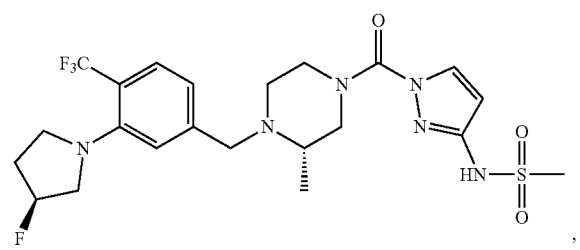
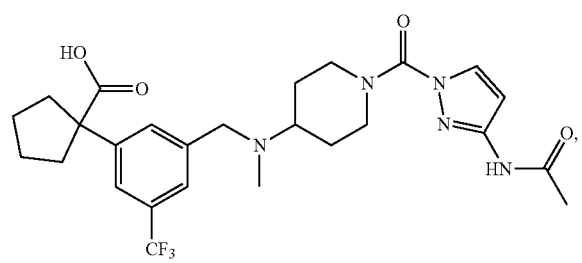
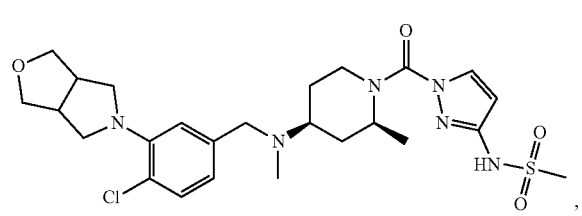
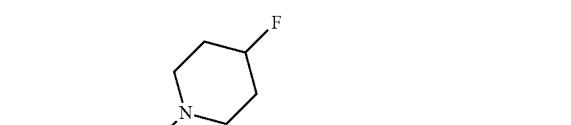
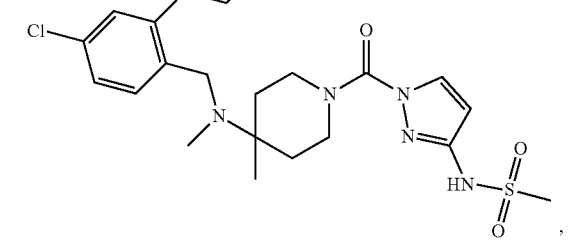
390
-continued
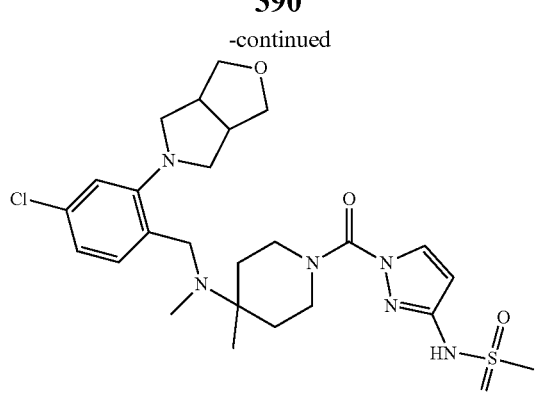
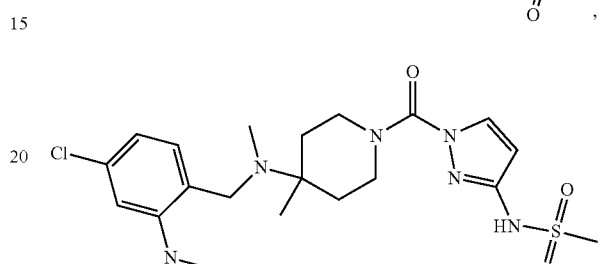
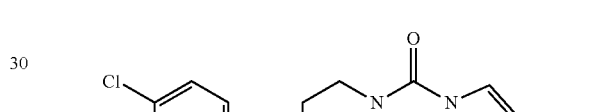
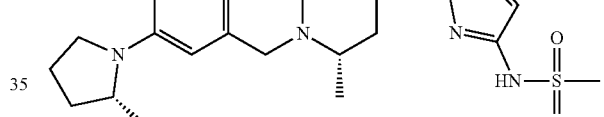
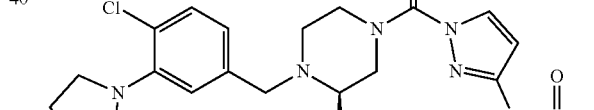
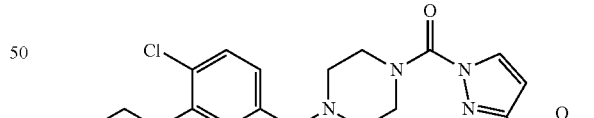
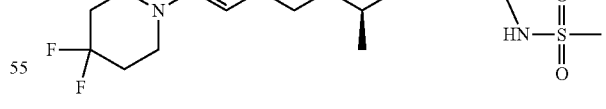
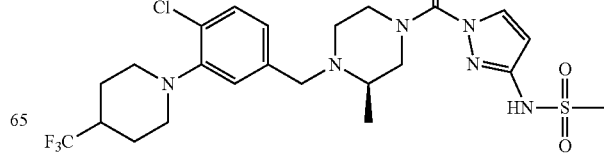

391
-continued
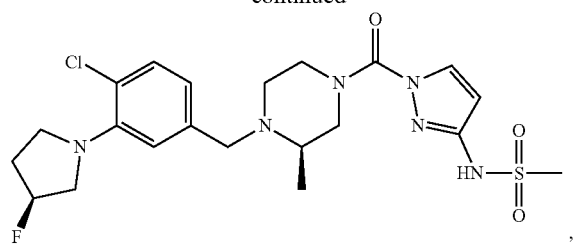,
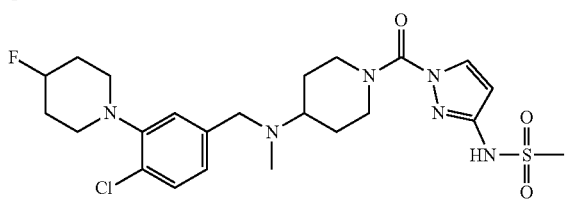,
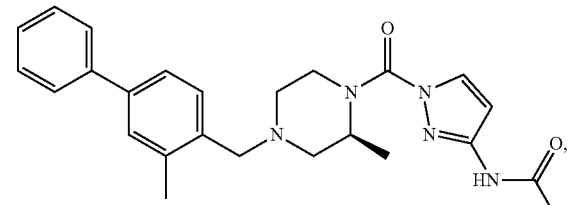,
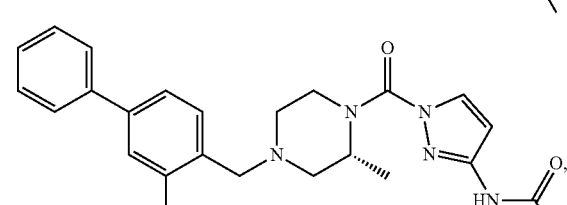,
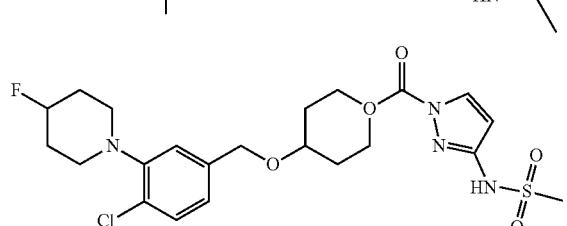,
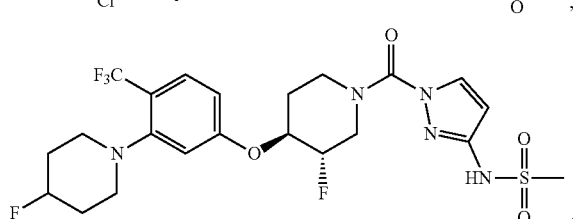,
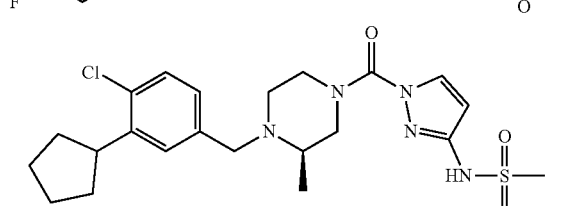,
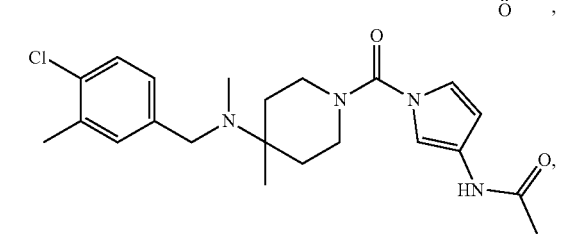,
392
-continued
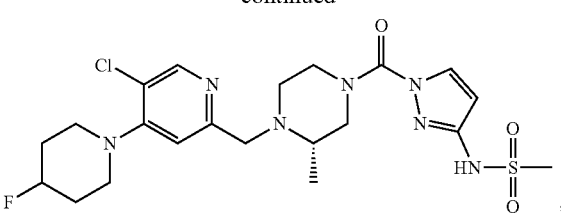,
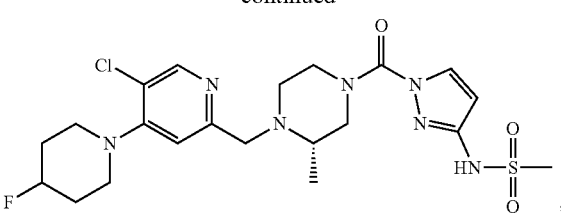,
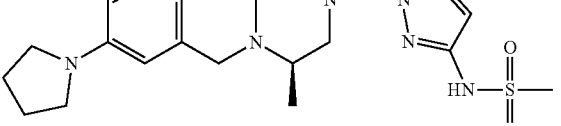,
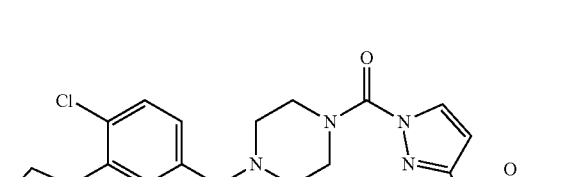,
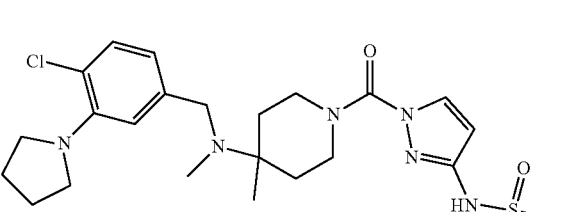,
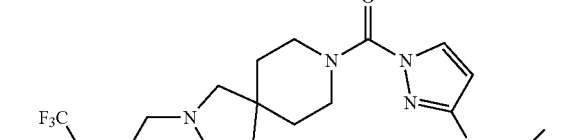,
,
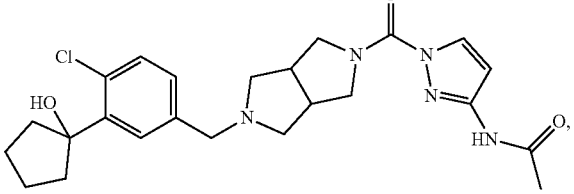, -continued

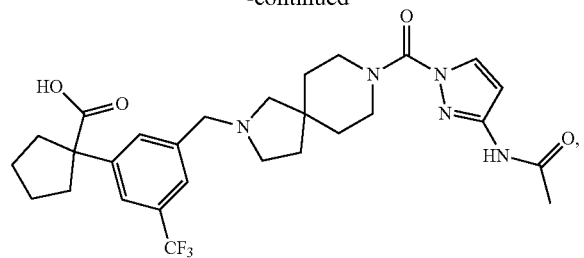
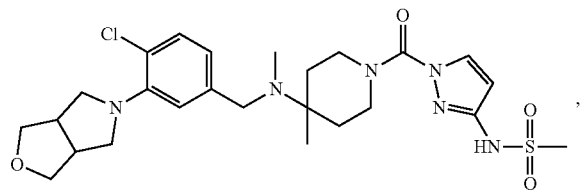
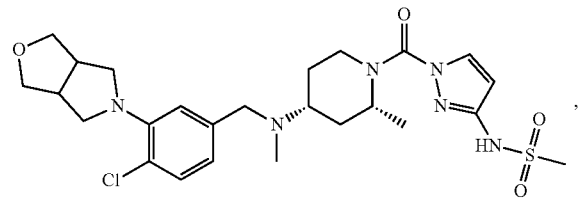
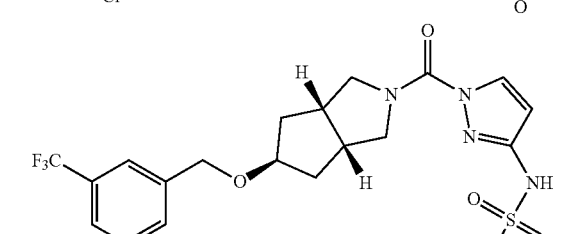
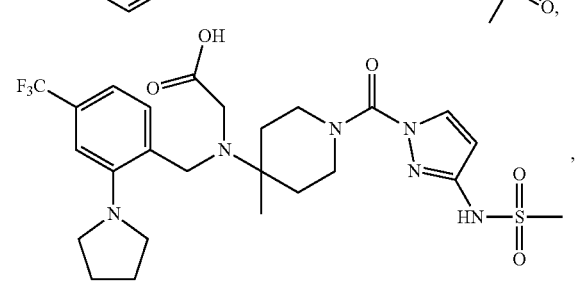
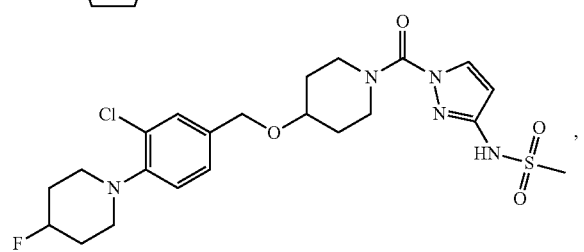
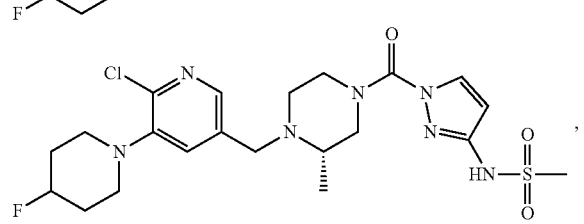

-continued

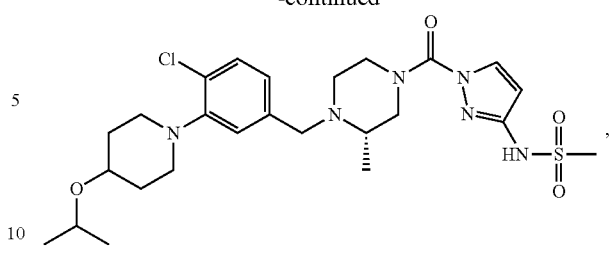
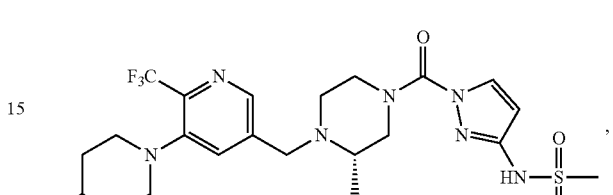
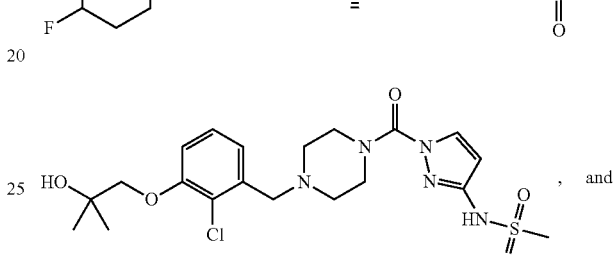
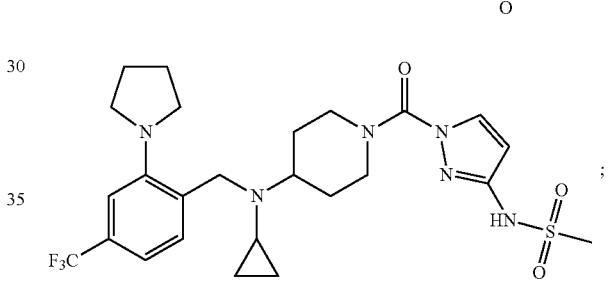

or a tautomer, N-oxide, stereoisomer, or pharmaceutically acceptable salt thereof.

22. A pharmaceutical composition comprising a compound of claim 1, or a tautomer, A-oxide, or a pharmaceutically acceptable salt thereof, and at least one pharmaceutically acceptable excipient.

23. A method of treating pain in a patient in need thereof, comprising administering to the patient a therapeutically effective amount of a compound of claim 1, or a tautomer, A-oxide, or a pharmaceutically acceptable salt thereof.

24. A method of treating a disease or disorder in a patient comprising administering to the patient in need thereof a therapeutically effective amount of a compound of claim 1, or a pharmaceutically acceptable salt thereof, wherein the disease or disorder is selected from migraine, epilepsy/seizure disorder, neuromyelitis optica (NMO), Tourette syndrome, persistent motor tic disorder, persistent vocal tic disorder, and abdominal pain associated with irritable bowel syndrome.

* * * * *

UNITED STATES PATENT AND TRADEMARK OFFICE
CERTIFICATE OF CORRECTION

PATENT NO. : 11,149,037 B2
APPLICATION NO. : 16/615746
DATED : October 19, 2021
INVENTOR(S) : Grice et al.

Page 1 of 1

It is certified that error appears in the above-identified patent and that said Letters Patent is hereby corrected as shown below:

In the Claims

• Columns 394, Line 44:
In Claim 22, the term, "A-oxide," should read, "N-oxide."

• Columns 394, Line 51:
In Claim 23, the term, "A-oxide," should read, "N-oxide."

Signed and Sealed this
Fifteenth Day of February, 2022

Drew Hirshfeld
*Performing the Functions and Duties of the
Under Secretary of Commerce for Intellectual Property and
Director of the United States Patent and Trademark Office*